(12) United States Patent
Aronhalt et al.

(10) Patent No.: US 9,700,317 B2
(45) Date of Patent: Jul. 11, 2017

(54) FASTENER CARTRIDGE COMPRISING A RELEASABLE TISSUE THICKNESS COMPENSATOR

(71) Applicant: Ethicon Endo-Surgery, Inc., Cincinnati, OH (US)

(72) Inventors: Taylor W. Aronhalt, Loveland, OH (US); Michael J. Vendely, Lebanon, OH (US); Lauren S. Weaner, Cincinnati, OH (US); Brandon J. Lloyd, Maineville, OH (US); Frederick E. Shelton, IV, Hillsboro, OH (US); Michael J. Miller, Mason, OH (US); Michael T. Isaacs, Burlington, KY (US); Emily A. Schellin, Cincinnati, OH (US); John V. Hunt, Cincinnati, OH (US); John E. Feds, Milford, OH (US)

(73) Assignee: Ethicon Endo-Surgery, LLC, Los Frailes Industrial Park, Guaynabo, PR (US)

( * ) Notice: Subject to any disclaimer, the term of this patent is extended or adjusted under 35 U.S.C. 154(b) by 676 days.

(21) Appl. No.: 13/763,048

(22) Filed: Feb. 8, 2013

(65) Prior Publication Data
US 2013/0221064 A1 Aug. 29, 2013

Related U.S. Application Data

(63) Continuation-in-part of application No. 13/097,907, filed on Apr. 29, 2011, now Pat. No. 9,301,755, (Continued)

(51) Int. Cl.
*A61B 17/068* (2006.01)
*A61B 17/072* (2006.01)
(Continued)

(52) U.S. Cl.
CPC ...... *A61B 17/07207* (2013.01); *A61B 17/068* (2013.01); *A61B 17/0644* (2013.01);
(Continued)

(58) Field of Classification Search
CPC ............... A61B 17/068; A61B 17/072; A61B 17/07207; A61B 17/07292;
(Continued)

(56) References Cited

U.S. PATENT DOCUMENTS

| 66,052 A | 6/1867 | Smith |
| 662,587 A | 11/1900 | Blake |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

International Search Report for PCT/US2011/053546, dated Nov. 30, 2011 (5 pages).

(Continued)

*Primary Examiner* — Stephen F Gerrity
*Assistant Examiner* — Joshua Kotis

(57) ABSTRACT

A fastener cartridge can comprise, one, a cartridge body configured to at least partially store a plurality of fasteners therein and, two, a layer of material attached to the cartridge body by a retention member. The retention member can be deactivated to release the layer from the cartridge body when a firing member is moved through the cartridge body to eject the fasteners from the cartridge body. The retention member can be deactivated at the beginning, the end, and/or at any suitable time during a firing stroke of the firing member. Certain fastener cartridges can comprise a plurality of retention members configured to releasably hold the layer (Continued)

to the cartridge body. In certain circumstances, the retention members can be sequentially released in order to progressively release the layer.

14 Claims, 177 Drawing Sheets

Related U.S. Application Data which is a continuation-in-part of application No. 12/894,360, filed on Sep. 30, 2010, now Pat. No. 9,113,862.

(51) Int. Cl.

| | |
|---|---|
| A61B 90/00 | (2016.01) |
| A61B 17/00 | (2006.01) |
| B25C 5/16 | (2006.01) |
| A61B 17/064 | (2006.01) |
| A61B 17/115 | (2006.01) |
| A61B 17/29 | (2006.01) |
| A61B 17/32 | (2006.01) |
| A61B 17/10 | (2006.01) |

(52) U.S. Cl.
CPC ...... *A61B 17/072* (2013.01); *A61B 17/07292* (2013.01); *A61B 17/00491* (2013.01); *A61B 17/0643* (2013.01); *A61B 17/0686* (2013.01); *A61B 17/105* (2013.01); *A61B 17/1155* (2013.01); *A61B 17/2909* (2013.01); *A61B 2017/00004* (2013.01); *A61B 2017/0053* (2013.01); *A61B 2017/00314* (2013.01); *A61B 2017/00327* (2013.01); *A61B 2017/00477* (2013.01); *A61B 2017/00526* (2013.01); *A61B 2017/00818* (2013.01); *A61B 2017/00862* (2013.01); *A61B 2017/00884* (2013.01); *A61B 2017/00893* (2013.01); *A61B 2017/00951* (2013.01); *A61B 2017/0641* (2013.01); *A61B 2017/0725* (2013.01); *A61B 2017/07228* (2013.01); *A61B 2017/07235* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2017/2908* (2013.01); *A61B 2017/2916* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/2946* (2013.01); *A61B 2017/320052* (2013.01); *A61B 2090/037* (2016.02); *B25C 5/1686* (2013.01)

(58) Field of Classification Search
CPC A61B 2017/07271; A61B 2017/07278; A61B 2017/07242
See application file for complete search history.

(56) References Cited

U.S. PATENT DOCUMENTS

| | | | |
|---|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |

(56) References Cited

U.S. PATENT DOCUMENTS

| | | |
|---|---|---|
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |

(56) References Cited

U.S. PATENT DOCUMENTS

| | | |
|---|---|---|
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |

(56) References Cited

U.S. PATENT DOCUMENTS

| | | |
|---|---|---|
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A * | 8/1996 | McKean ........... A61B 17/07207 227/178.1 |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,627 A | 8/1996 | Kieturakis |
| 5,549,628 A | 8/1996 | Cooper et al. |

(56) References Cited

U.S. PATENT DOCUMENTS

| | | |
|---|---|---|
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |

(56) References Cited

U.S. PATENT DOCUMENTS

| | | |
|---|---|---|
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |

(56) References Cited

U.S. PATENT DOCUMENTS

| | | |
|---|---|---|
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |

(56) References Cited

U.S. PATENT DOCUMENTS

| | | |
|---|---|---|
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |

(56) References Cited

U.S. PATENT DOCUMENTS

| | | |
|---|---|---|
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nakamura et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |

(56) References Cited

U.S. PATENT DOCUMENTS

| | | |
|---|---|---|
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 * | 12/2006 | Shelton, IV ..... A61B 17/07207 227/176.1 |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |

(56) References Cited

U.S. PATENT DOCUMENTS

| | | |
|---|---|---|
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |

(56) References Cited

U.S. PATENT DOCUMENTS

| | | |
|---|---|---|
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |

(56) References Cited

U.S. PATENT DOCUMENTS

| | | | |
|---|---|---|---|
| 7,828,794 | B2 | 11/2010 | Sartor |
| 7,828,808 | B2 | 11/2010 | Hinman et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,694 | B2 | 11/2010 | Tethrake et al. |
| 7,838,789 | B2 | 11/2010 | Stoffers et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,846,149 | B2 | 12/2010 | Jankowski |
| 7,850,642 | B2 | 12/2010 | Moll et al. |
| 7,850,982 | B2 | 12/2010 | Stopek et al. |
| 7,854,736 | B2 | 12/2010 | Ryan |
| 7,857,183 | B2 | 12/2010 | Shelton, IV |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,879,070 | B2 | 2/2011 | Ortiz et al. |
| 7,883,465 | B2 | 2/2011 | Donofrio et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,891,531 | B1 | 2/2011 | Ward |
| 7,891,532 | B2 | 2/2011 | Mastri et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,877 | B2 | 3/2011 | Hall et al. |
| 7,896,895 | B2 | 3/2011 | Boudreaux et al. |
| 7,900,805 | B2 | 3/2011 | Shelton, IV et al. |
| 7,905,380 | B2 | 3/2011 | Shelton, IV et al. |
| 7,905,381 | B2 | 3/2011 | Baxter, III et al. |
| 7,905,889 | B2 | 3/2011 | Catanese, III et al. |
| 7,905,902 | B2 | 3/2011 | Huitema et al. |
| 7,909,191 | B2 | 3/2011 | Baker et al. |
| 7,909,220 | B2 | 3/2011 | Viola |
| 7,909,221 | B2 | 3/2011 | Viola et al. |
| 7,913,891 | B2 | 3/2011 | Doll et al. |
| 7,913,893 | B2 | 3/2011 | Mastri et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,848 | B2 | 4/2011 | Lau et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,926,691 | B2 | 4/2011 | Viola et al. |
| 7,927,328 | B2 | 4/2011 | Orszulak et al. |
| 7,928,281 | B2 | 4/2011 | Augustine |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,934,630 | B2 | 5/2011 | Shelton, IV et al. |
| 7,934,631 | B2 | 5/2011 | Balbierz et al. |
| 7,935,773 | B2 | 5/2011 | Hadba et al. |
| 7,938,307 | B2 | 5/2011 | Bettuchi |
| 7,941,865 | B2 | 5/2011 | Seman, Jr. et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,950,560 | B2 | 5/2011 | Zemlok et al. |
| 7,950,561 | B2 * | 5/2011 | Aranyi ............ A61B 17/07207 227/175.1 |
| 7,951,071 | B2 | 5/2011 | Whitman et al. |
| 7,951,166 | B2 | 5/2011 | Orban et al. |
| 7,954,682 | B2 | 6/2011 | Giordano et al. |
| 7,954,684 | B2 | 6/2011 | Boudreaux |
| 7,954,686 | B2 | 6/2011 | Baxter, III et al. |
| 7,954,687 | B2 | 6/2011 | Zemlok et al. |
| 7,955,257 | B2 | 6/2011 | Frasier et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,963 | B2 | 6/2011 | Francischelli et al. |
| 7,963,964 | B2 | 6/2011 | Santilli et al. |
| 7,966,799 | B2 | 6/2011 | Morgan et al. |
| 7,967,178 | B2 | 6/2011 | Scirica et al. |
| 7,967,179 | B2 * | 6/2011 | Olson ............ A61B 17/07207 227/175.1 |
| 7,967,180 | B2 | 6/2011 | Scirica |
| 7,967,181 | B2 | 6/2011 | Viola et al. |
| 7,967,839 | B2 | 6/2011 | Flock et al. |
| 7,972,298 | B2 | 7/2011 | Wallace et al. |
| 7,980,443 | B2 | 7/2011 | Scheib et al. |
| 7,988,026 | B2 | 8/2011 | Knodel et al. |
| 7,988,027 | B2 * | 8/2011 | Olson ............ A61B 17/07207 227/175.1 |
| 7,988,028 | B2 | 8/2011 | Farascioni et al. |
| 7,992,757 | B2 | 8/2011 | Wheeler et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,511 | B2 | 8/2011 | Brock et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 * | 9/2011 | Tarinelli ........... A61B 17/07207 227/175.1 |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,855 | B2 | 9/2011 | Whitman et al. |
| 8,016,858 | B2 | 9/2011 | Whitman |
| 8,016,881 | B2 | 9/2011 | Furst |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,028,883 | B2 * | 10/2011 | Stopek ................ A61B 17/072 227/175.1 |
| 8,028,884 | B2 | 10/2011 | Sniffin et al. |
| 8,028,885 | B2 | 10/2011 | Smith et al. |
| 8,034,077 | B2 | 10/2011 | Smith et al. |
| 8,034,363 | B2 | 10/2011 | Li et al. |
| 8,037,591 | B2 | 10/2011 | Spivey et al. |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,047,236 | B2 | 11/2011 | Perry |
| 8,048,503 | B2 | 11/2011 | Farnsworth et al. |
| 8,056,787 | B2 | 11/2011 | Boudreaux et al. |
| 8,056,788 | B2 | 11/2011 | Mastri et al. |
| 8,057,508 | B2 | 11/2011 | Shelton, IV |

(56) References Cited

U.S. PATENT DOCUMENTS

| | | |
|---|---|---|
| 8,058,771 B2 | 11/2011 | Giordano et al. |
| 8,061,576 B2 | 11/2011 | Cappola |
| 8,066,167 B2 | 11/2011 | Measamer et al. |
| 8,066,168 B2 | 11/2011 | Vidal et al. |
| D650,074 S | 12/2011 | Hunt et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |

(56) References Cited

U.S. PATENT DOCUMENTS

| | | |
|---|---|---|
| 8,333,764 B2 | 12/2012 | Francischelli et al. |
| 8,336,753 B2 | 12/2012 | Olson et al. |
| 8,336,754 B2 | 12/2012 | Cappola et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |

(56) References Cited

U.S. PATENT DOCUMENTS

| | | |
|---|---|---|
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,808,294 B2 | 8/2014 | Fox et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,858,571 B2 | 10/2014 | Shelton, IV et al. |
| 8,858,590 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |
| 8,968,337 B2 | 3/2015 | Whitfield et al. |
| 8,973,803 B2 | 3/2015 | Hall et al. |
| 8,973,804 B2 | 3/2015 | Hess et al. |
| 8,978,955 B2 | 3/2015 | Aronhalt et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,017,331 B2 | 4/2015 | Fox |
| 9,023,014 B2 | 5/2015 | Chowaniec et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,204 B2 | 5/2015 | Shelton, IV et al. |
| 9,038,881 B1 | 5/2015 | Schaller et al. |
| 9,043,027 B2 | 5/2015 | Durant et al. |
| 9,044,230 B2 | 6/2015 | Morgan et al. |
| 9,050,083 B2 | 6/2015 | Yates et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,330 B2 | 7/2015 | Widenhouse et al. |
| 9,095,339 B2 | 8/2015 | Moore et al. |
| 9,096,033 B2 | 8/2015 | Holop et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Sharbnik et al. |
| 9,138,225 B2 | 9/2015 | Huang et al. |
| 9,149,274 B2 | 10/2015 | Spivey et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,192,380 B2 | 11/2015 | (Tarinelli) Racenet et al. |

(56) References Cited

U.S. PATENT DOCUMENTS

| | | |
|---|---|---|
| 9,192,384 B2 | 11/2015 | Bettuchi |
| 9,198,661 B2 | 12/2015 | Swensgard |
| 9,204,878 B2 | 12/2015 | Hall et al. |
| 9,204,879 B2 | 12/2015 | Shelton, IV |
| 9,211,121 B2 | 12/2015 | Hall et al. |
| 9,211,122 B2 | 12/2015 | Hagerty et al. |
| 9,226,751 B2 | 1/2016 | Shelton, IV et al. |
| 9,232,945 B2 | 1/2016 | Zingman |
| 2001/0025183 A1 | 9/2001 | Shahidi |
| 2001/0044637 A1 | 11/2001 | Jacobs et al. |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0165541 A1 | 11/2002 | Whitman |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |

(56) References Cited

U.S. PATENT DOCUMENTS

| | | |
|---|---|---|
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton IV, et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078801 A1* | 4/2008 | Shelton ............ A61B 17/07207 227/175.1 |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |

(56) References Cited

U.S. PATENT DOCUMENTS

| | | |
|---|---|---|
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1* | 12/2008 | Marczyk ........... A61B 17/07207 227/178.1 |
| 2008/0315829 A1 | 12/2008 | Jones et al. |
| 2009/0001121 A1 | 1/2009 | Hess et al. |
| 2009/0001122 A1* | 1/2009 | Prommersberger A61B 17/07207 227/176.1 |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1* | 8/2009 | Huitema ........... A61B 17/07207 227/175.1 |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206134 A1* | 8/2009 | Swayze ........... A61B 17/07207 227/176.1 |
| 2009/0206137 A1 | 8/2009 | Hall et al. |
| 2009/0206139 A1* | 8/2009 | Hall ........... A61B 17/07207 227/176.1 |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247901 A1 | 10/2009 | Zimmer |
| 2009/0248038 A1 | 10/2009 | Blumenkranz et al. |
| 2009/0253959 A1 | 10/2009 | Yoshie et al. |
| 2009/0255974 A1* | 10/2009 | Viola ........... A61B 17/07207 227/176.1 |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0270895 A1 | 10/2009 | Churchill et al. |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1* | 1/2010 | Tarinelli Racenet ........... A61B 17/07207 227/180.1 |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0186219 A1 | 7/2010 | Smith |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1* | 9/2010 | Aranyi ........... A61B 17/07207 227/176.1 |
| 2010/0249497 A1 | 9/2010 | Peine et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Castro et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0017801 A1 | 1/2011 | Zemlok et al. |
| 2011/0022032 A1 | 1/2011 | Zemlok et al. |

(56) References Cited

U.S. PATENT DOCUMENTS

| | | |
|---|---|---|
| 2011/0024477 A1 | 2/2011 | Hall et al. |
| 2011/0024478 A1 | 2/2011 | Shelton, IV |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0290851 A1 | 12/2011 | Shelton, IV |
| 2011/0290856 A1 | 12/2011 | Shelton, IV et al. |
| 2011/0293690 A1 | 12/2011 | Griffin et al. |
| 2011/0295269 A1 | 12/2011 | Swensgard et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0080332 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080502 A1 | 4/2012 | Morgan et al. |
| 2012/0083835 A1 | 4/2012 | Shelton, IV et al. |
| 2012/0083836 A1 | 4/2012 | Shelton, IV et al. |
| 2012/0089131 A1 | 4/2012 | Zemlok et al. |
| 2012/0110810 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0150192 A1 | 6/2012 | Dachs, II et al. |
| 2012/0160721 A1 | 6/2012 | Shelton, IV et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0209289 A1 | 8/2012 | Duque et al. |
| 2012/0223123 A1 | 9/2012 | Baxter, III et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248167 A1 | 10/2012 | Flanagan et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126582 A1 | 5/2013 | Shelton, IV et al. |
| 2013/0131651 A1 | 5/2013 | Strobl et al. |

(56) References Cited

U.S. PATENT DOCUMENTS

| | | |
|---|---|---|
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek (nee Prommersberger) et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0042205 A1 | 2/2014 | Baxter, III et al. |
| 2014/0048580 A1 | 2/2014 | Merchant et al. |
| 2014/0048582 A1 | 2/2014 | Shelton, IV et al. |
| 2014/0061279 A1 | 3/2014 | Laurent et al. |
| 2014/0061280 A1 | 3/2014 | Ingmanson et al. |
| 2014/0097227 A1 | 4/2014 | Aronhalt et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0151431 A1 | 6/2014 | Hodgkinson et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |

(56) References Cited

U.S. PATENT DOCUMENTS

| | | |
|---|---|---|
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0090765 A1 | 4/2015 | Hess et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |

(56) References Cited

U.S. PATENT DOCUMENTS

| | | |
|---|---|---|
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0351755 A1 | 12/2015 | Shelton, IV et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 101683280 A | 3/2010 |
| CN | 102188270 A | 9/2011 |
| CN | 101534723 B | 1/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |

(56) References Cited

FOREIGN PATENT DOCUMENTS

| | | |
|---|---|---|
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |

(56) References Cited

FOREIGN PATENT DOCUMENTS

| | | |
|---|---|---|
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |

(56) References Cited

FOREIGN PATENT DOCUMENTS

| | | |
|---|---|---|
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 1884206 B1 | 3/2013 |
| EP | 2090238 B1 | 4/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2759267 A2 | 7/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 47-11908 Y1 | 5/1972 |
| JP | 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 A | 1/2000 |
| JP | 2000033071 | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 A | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |

(56) References Cited

FOREIGN PATENT DOCUMENTS

| | | |
|---|---|---|
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 1009439 A | 4/1983 |
| RU | 1022703 A1 | 6/1983 |
| RU | 1814161 A1 | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |

(56) References Cited

FOREIGN PATENT DOCUMENTS

| | | |
|---|---|---|
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |

(56) References Cited

FOREIGN PATENT DOCUMENTS

| | | |
|---|---|---|
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/143913 A2 | 10/2012 |
| WO | WO 2012/148667 A2 | 11/2012 |
| WO | WO 2012/148703 A2 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/148762 A2 | 10/2013 |
| WO | WO 2013/167427 A1 | 11/2013 |
| WO | WO 2014/004199 A1 | 1/2014 |

OTHER PUBLICATIONS

International Search Report for PCT/US2012/032979, dated Oct. 18, 2013 (7 pages).
International Preliminary Report on Patentability for PCT/US2011/053546, dated Apr. 2, 2013 (7 pages).
Written Opinion for PCT/US2011/053546, dated Nov. 30, 2011 (7 pages).
International Preliminary Report on Patentability for PCT/US2012/032979, dated Oct. 29, 2013 (9 pages).
European Search Report for 12166181.3, dated Oct. 18, 2013 (8 pages).
International Search Report for PCT/US2014/014826, Jul. 15, 2014 (8 pages).
International Search Report for PCT/US2014/014853, May 23, 2014 (4 pages).
International Search Report for PCT/US2014/014864, May 9, 2014 (3 pages).
International Search Report for PCT/US2014/014874, Jul. 1, 2014 (7 pages).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
International Search Report for PCT/US2014/014838, dated Sep. 23, 2014 (8 pages).
International Preliminary Report on Patentability for PCT/US2014/014838, dated Aug. 11, 2015 (12 pages).
European Search Report for Application No. 14154563.2, dated May 20, 2014 (8 pages).
European Search Report for Application No. 14154560.8, dated Sep. 2, 2014 (13 pages).
Partial European Search Report for Application No. 14154560.8, dated May 14, 2014 (8 pages.).
European Examination Report for Application No. 14154560.8, dated Sep. 30, 2015 (4 pages).
European Search Report for Application No. 14154542.6, dated May 12, 2014 (5 pages).
Partial European Search Report for Application No. 14154559.0, dated Jun. 11, 2014 (7 pages).
European Search Report for Application No. 14154559.0, dated Oct. 21, 2014 (12 pages).
European Search Report for Application No. 14154561.6, dated Sep. 11, 2014 (12 pages).
Disclosed Anonymously, "Motor-Driven Surgical Stapler Improvements," Research Disclosure Database No. 526041, Published: Feb. 2008.

(56) References Cited

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
U.S. Appl. No. 12/031,573, filed Feb. 14, 2008.
U.S. Appl. No. 14/498,070, filed Sep. 26, 2014.
U.S. Appl. No. 14/498,087, filed Sep. 26, 2014.
U.S. Appl. No. 14/498,105, filed Sep. 26, 2014.
U.S. Appl. No. 14/498,107, filed Sep. 26, 2014.
U.S. Appl. No. 14/498,121, filed Sep. 26, 2014.
U.S. Appl. No. 14/498,145, filed Sep. 26, 2014.
U.S. Appl. No. 14/633,555, filed Feb. 27, 2015.
U.S. Appl. No. 14/633,562, filed Feb. 27, 2015.
U.S. Appl. No. 14/633,576, filed Feb. 27, 2015.
U.S. Appl. No. 14/633,546, filed Feb. 27, 2015.
U.S. Appl. No. 14/633,560, filed Feb. 27, 2015.
U.S. Appl. No. 14/633,566, filed Feb. 27, 2015.
U.S. Appl. No. 14/633,542, filed Feb. 27, 2015.
U.S. Appl. No. 14/633,548, filed Feb. 27, 2015.
U.S. Appl. No. 14/633,526, filed Feb. 27, 2015.
U.S. Appl. No. 14/574,478, filed Dec. 18, 2014.
U.S. Appl. No. 14/574,483, filed Dec. 18, 2014.
U.S. Appl. No. 14/575,139, filed Dec. 18, 2014.
U.S. Appl. No. 14/575,148, filed Dec. 18, 2014.
U.S. Appl. No. 14/575,130, filed Dec. 18, 2014.
U.S. Appl. No. 14/575,143, filed Dec. 18, 2014.
U.S. Appl. No. 14/575,117, filed Dec. 18, 2014.
U.S. Appl. No. 14/575,154, filed Dec. 18, 2014.
U.S. Appl. No. 14/574,493, filed Dec. 18, 2014.
U.S. Appl. No. 14/574,500, filed Dec. 18, 2014.
U.S. Appl. No. 14/479,103, filed Sep. 5, 2014.
U.S. Appl. No. 14/479,119, filed Sep. 5, 2014.
U.S. Appl. No. 14/478,908, filed Sep. 5, 2014.
U.S. Appl. No. 14/478,895, filed Sep. 5, 2014.
U.S. Appl. No. 14/479,110, filed Sep. 5, 2014.
U.S. Appl. No. 14/479,098, filed Sep. 5, 2014.
U.S. Appl. No. 14/479,115, filed Sep. 5, 2014.
U.S. Appl. No. 14/479,108, filed Sep. 5, 2014.
U.S. Appl. No. 14/952,486, filed Nov. 25, 2015.
U.S. Appl. No. 14/640,837, filed Mar. 6, 2015.

* cited by examiner

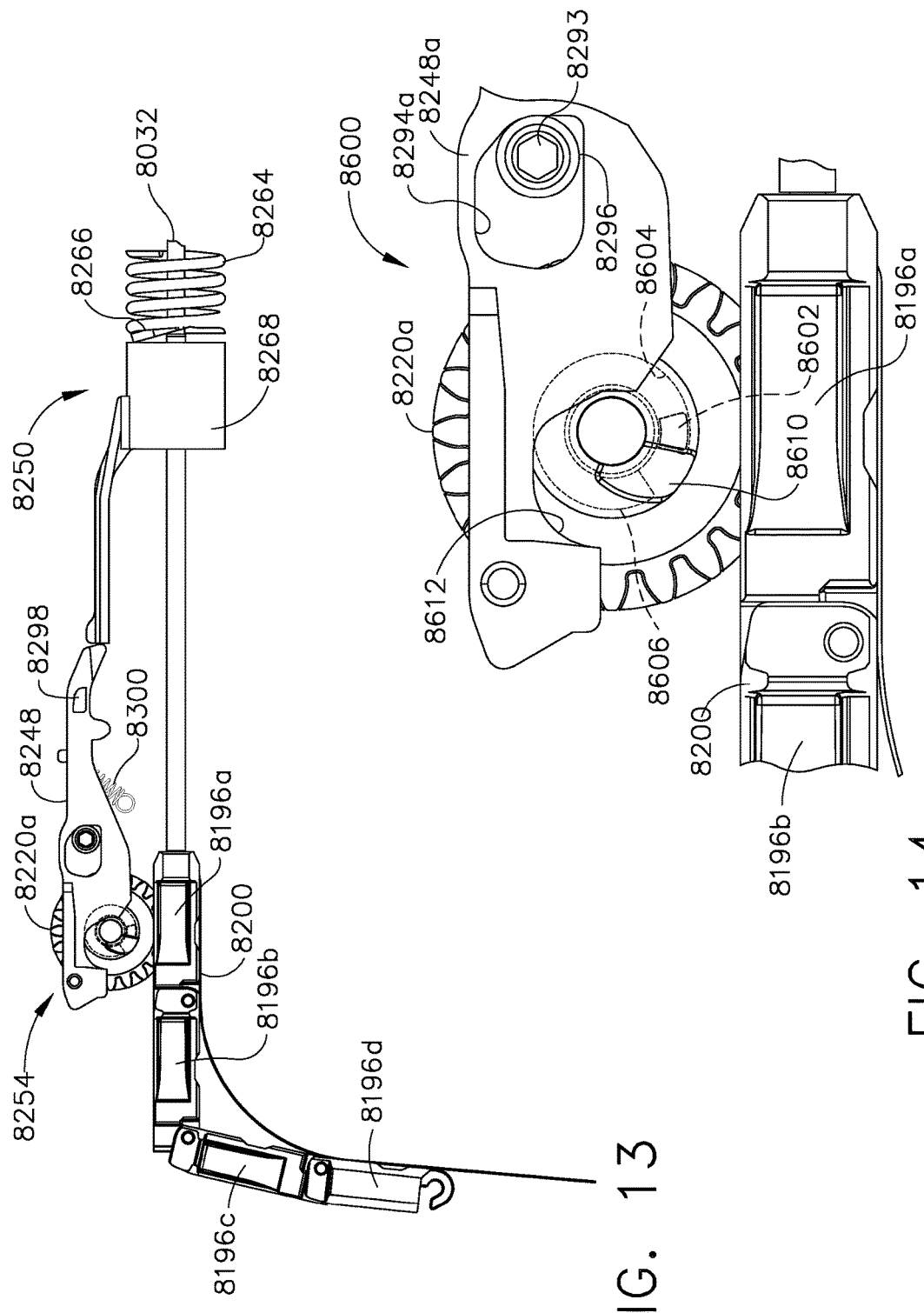

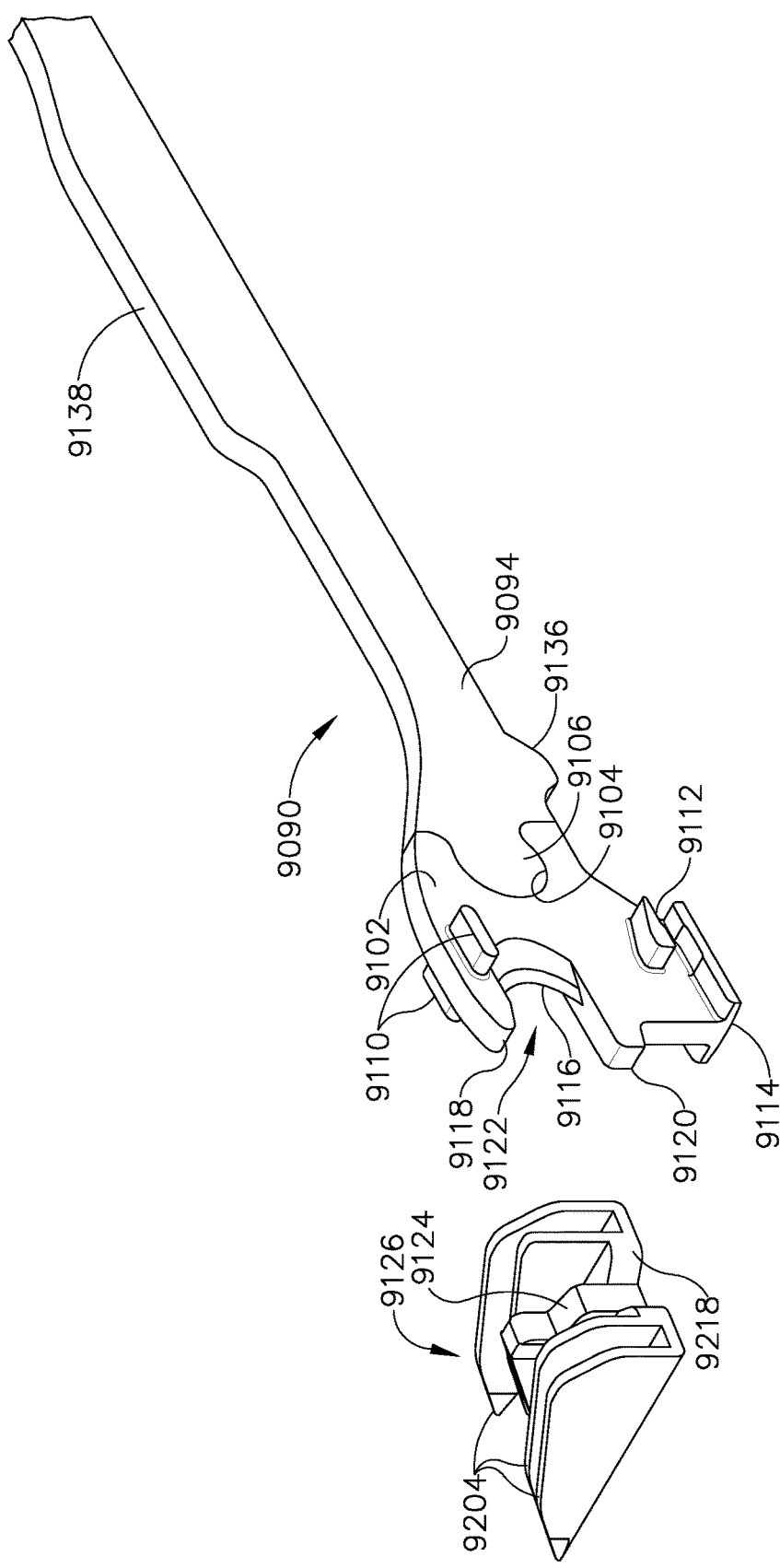

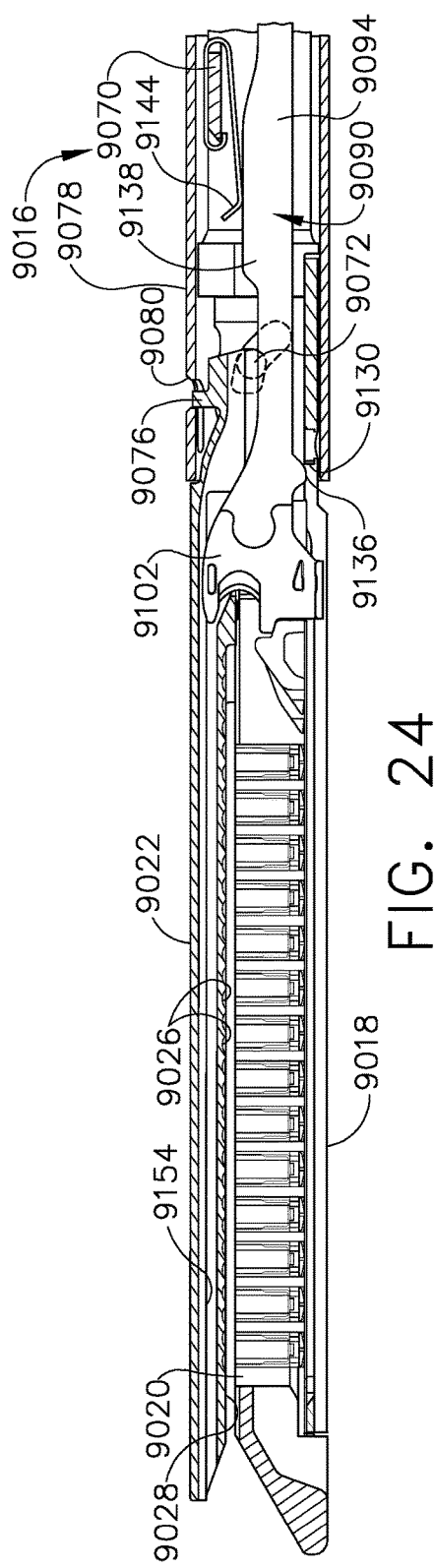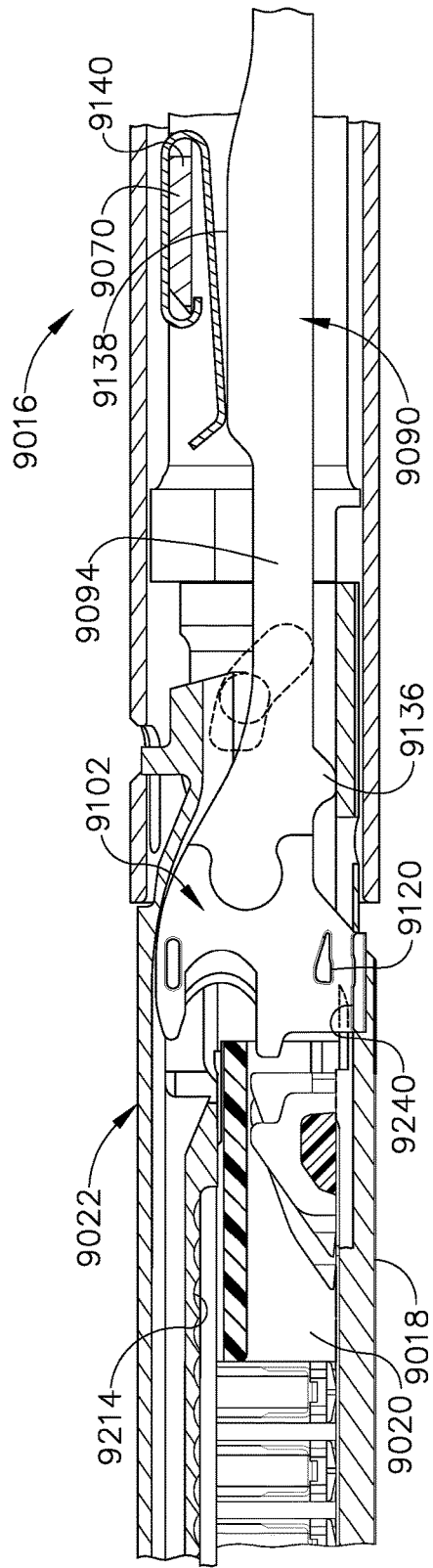

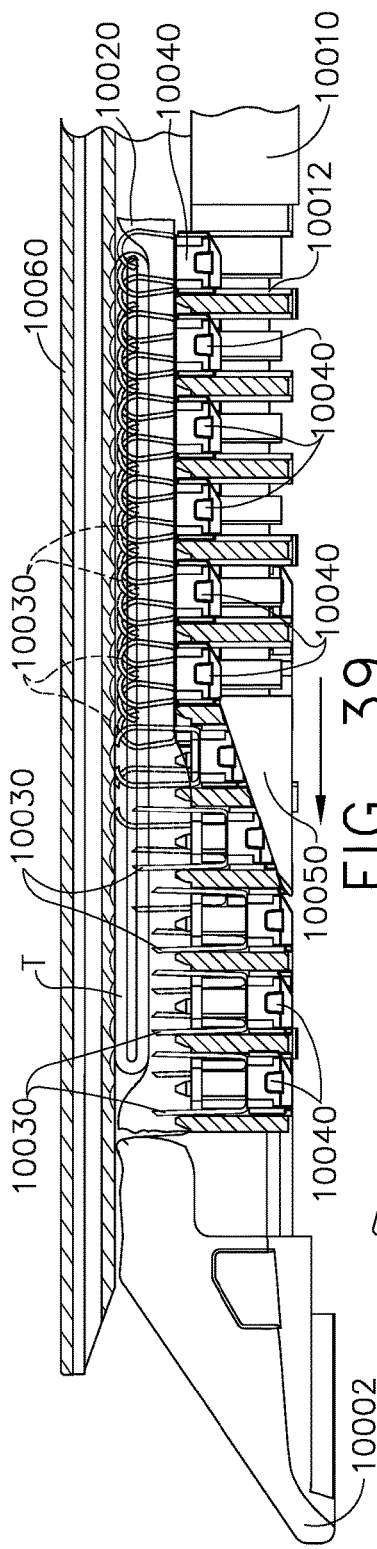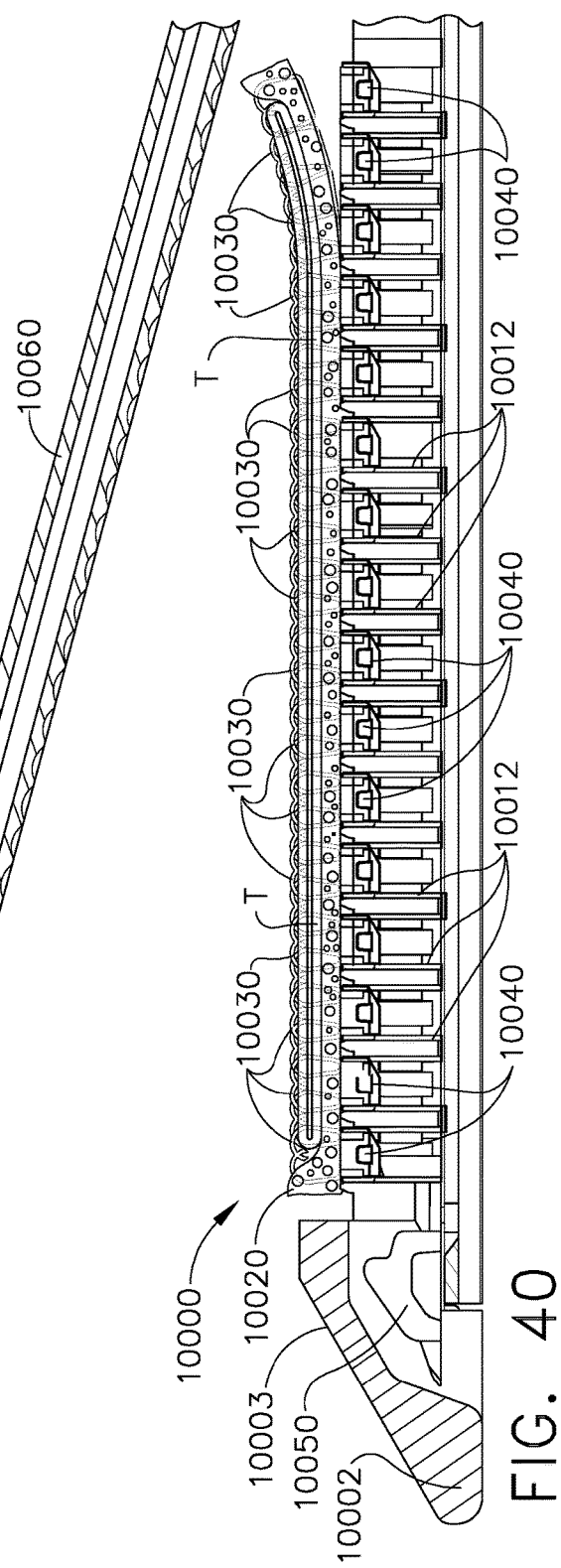

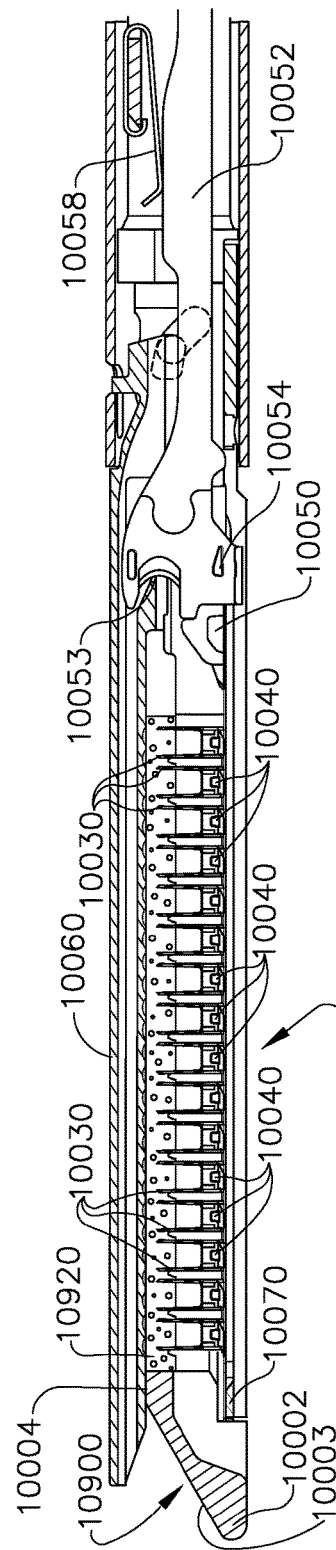
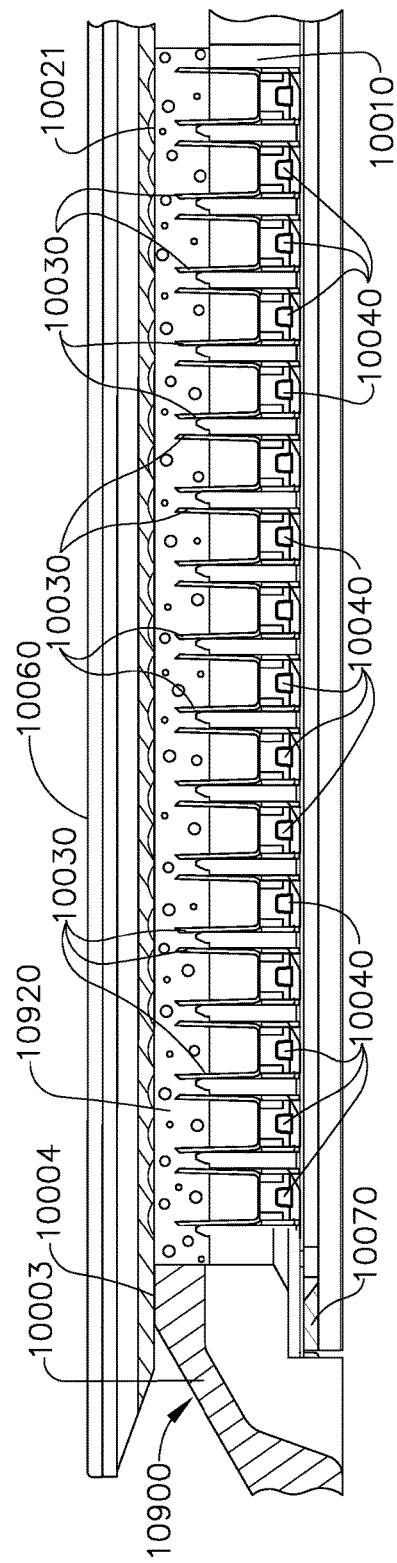

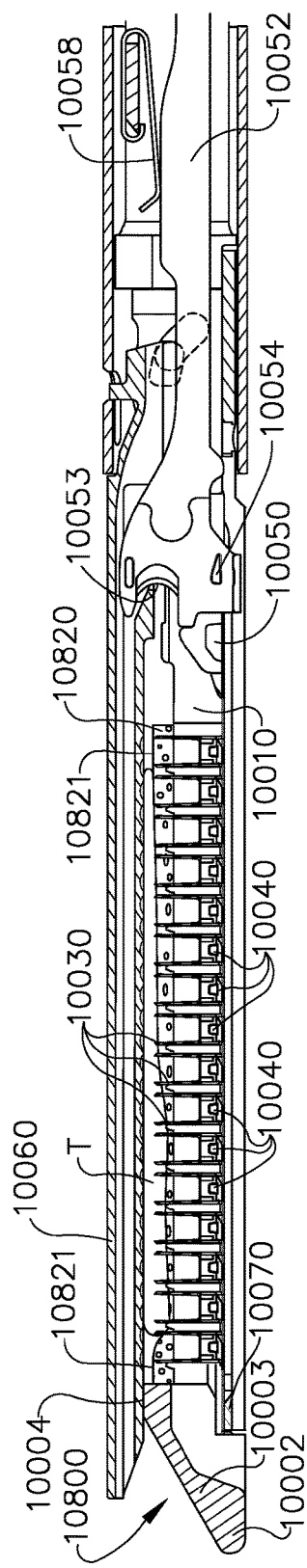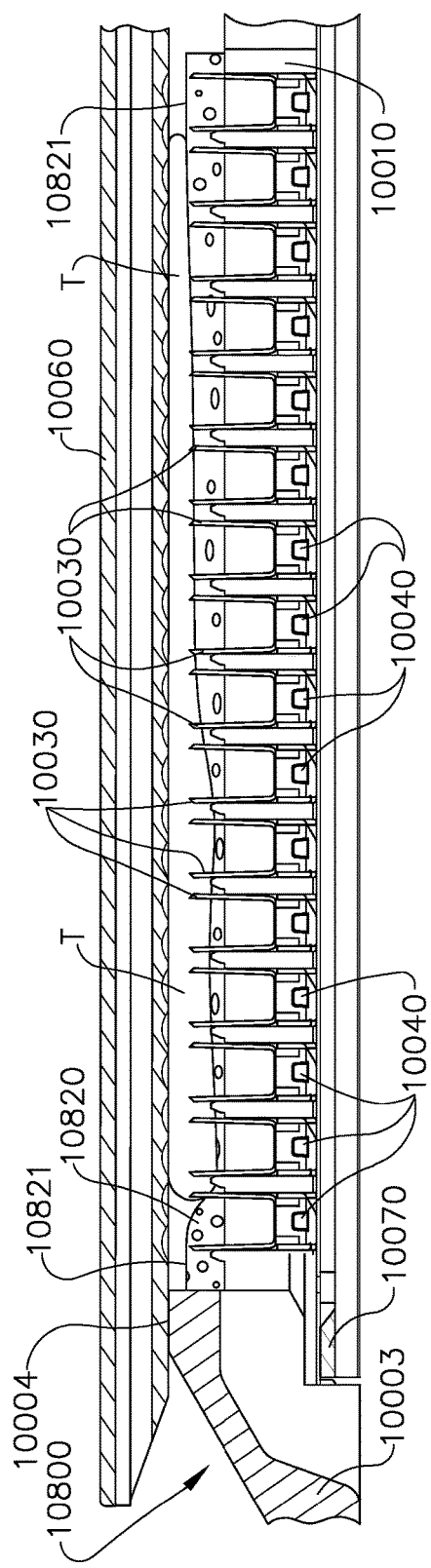

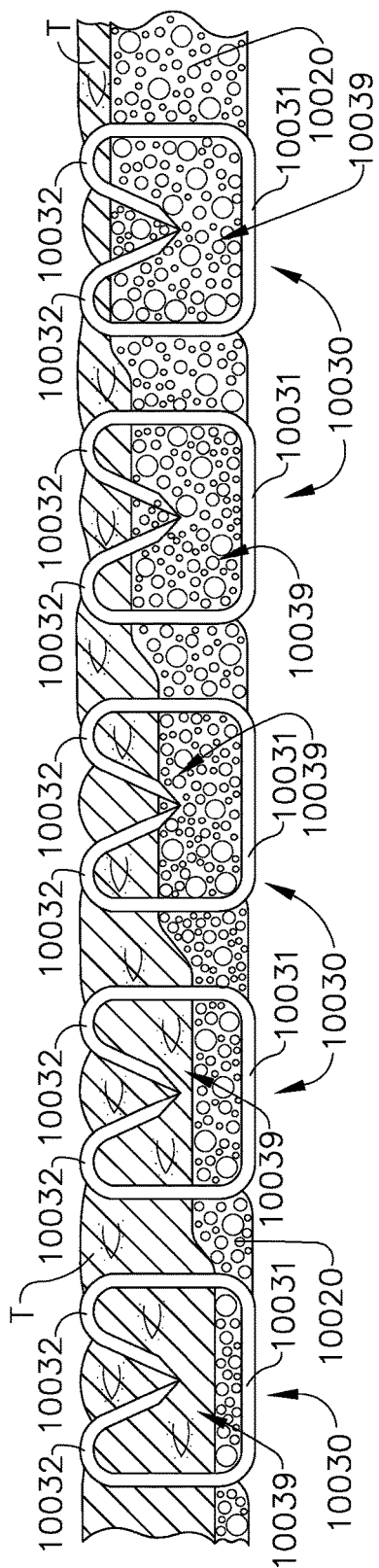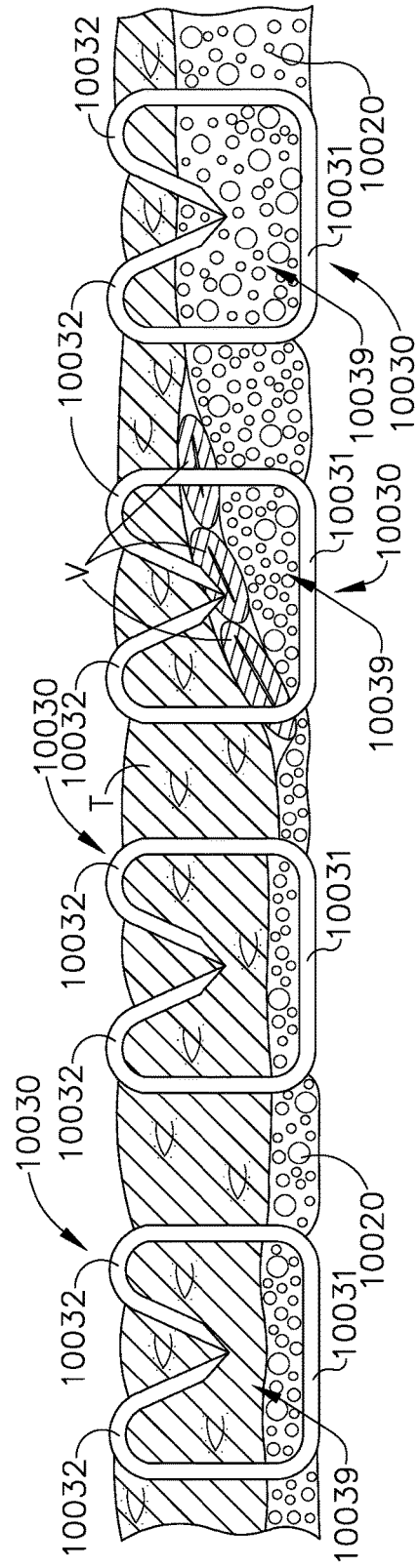

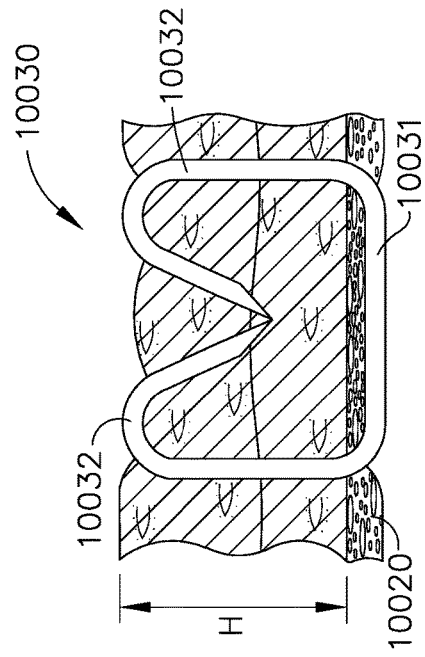
FIG. 51
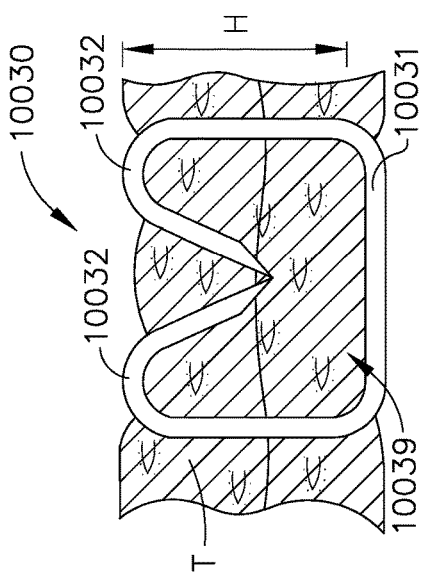
FIG. 53
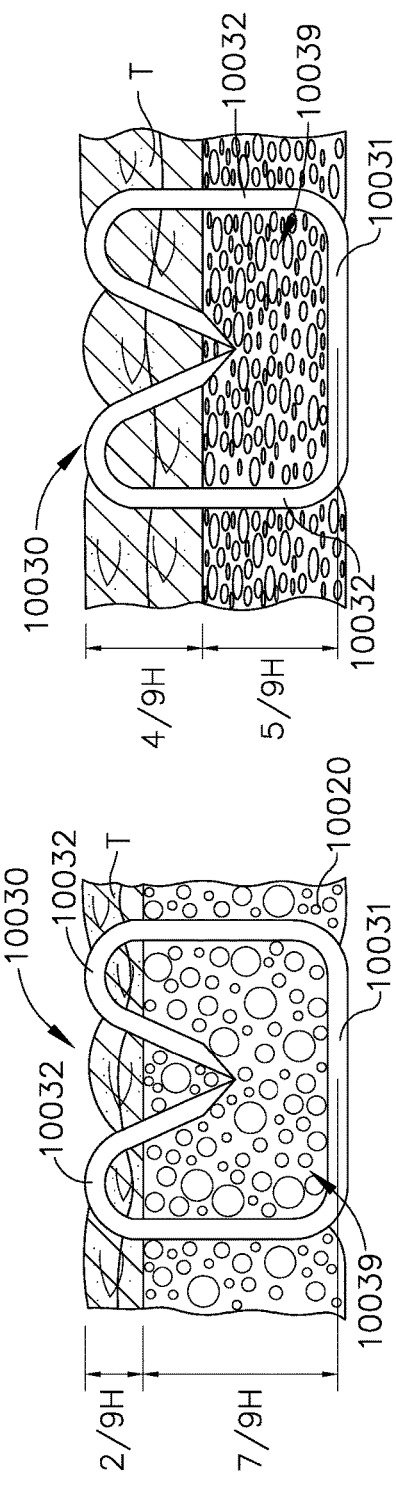
FIG. 52
FIG. 54

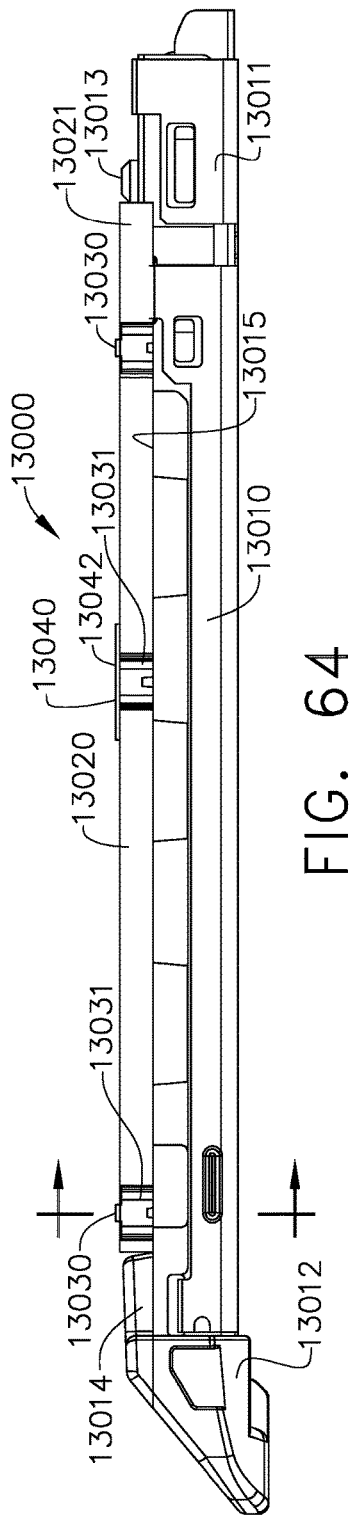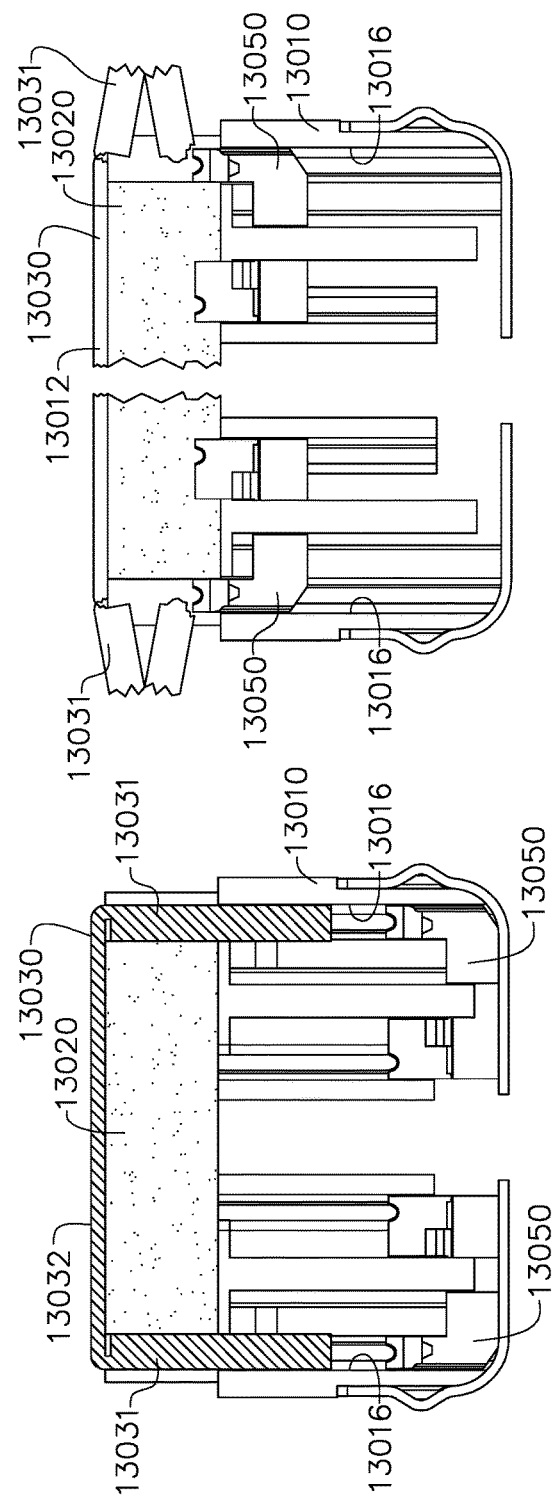

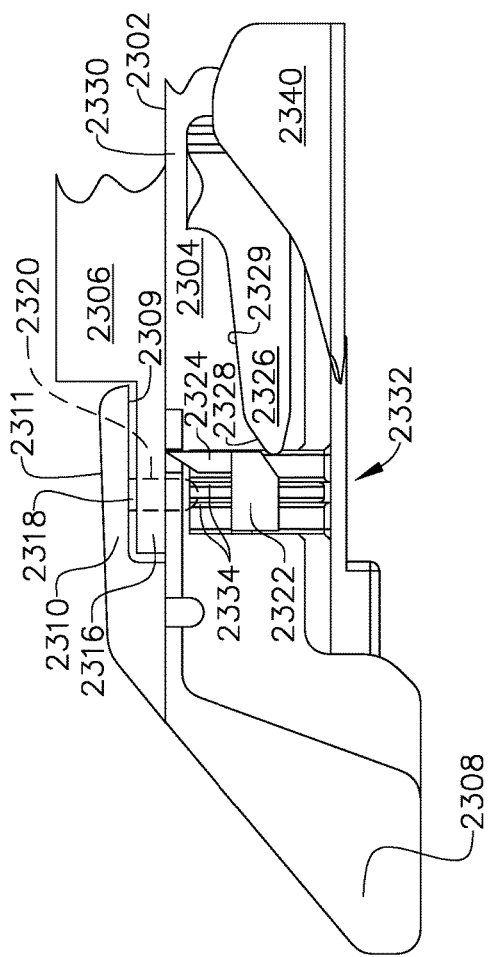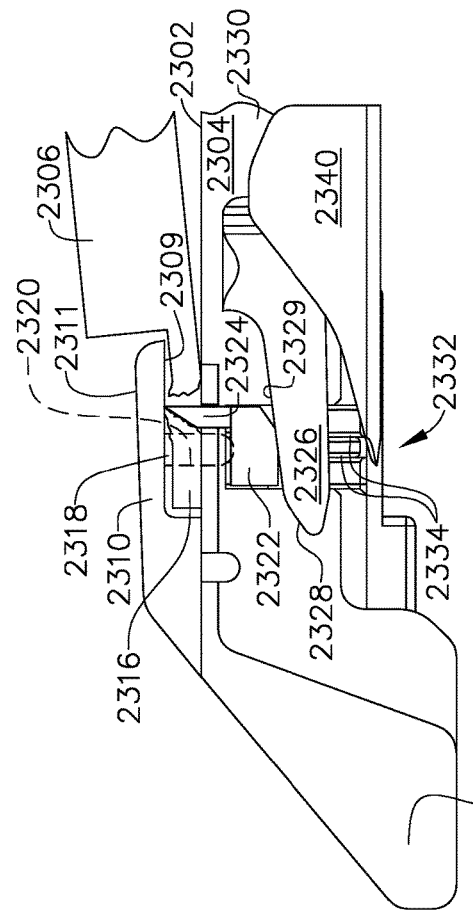

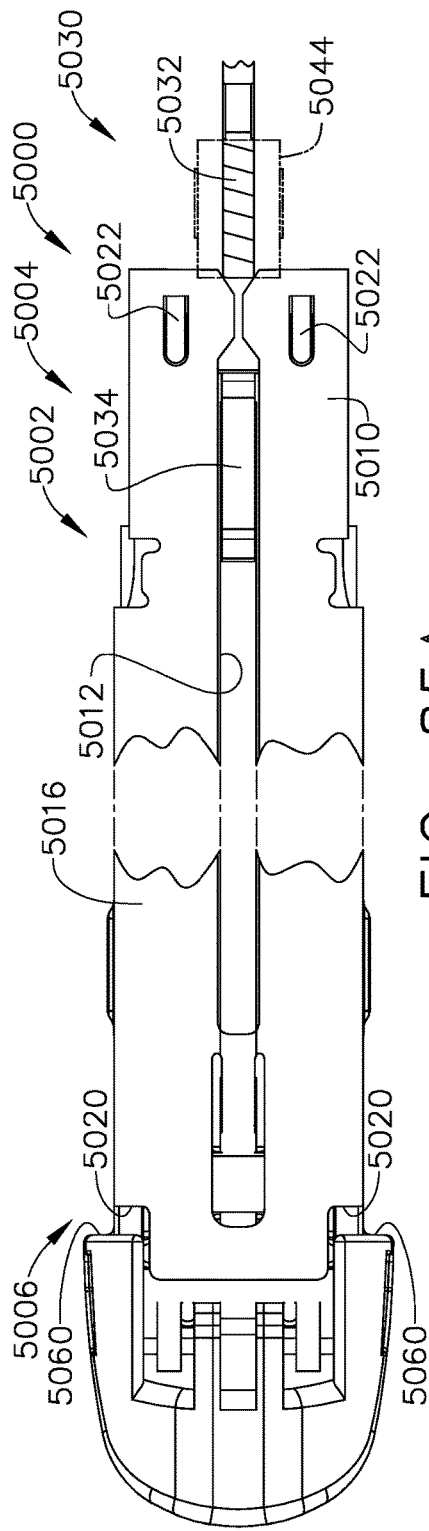
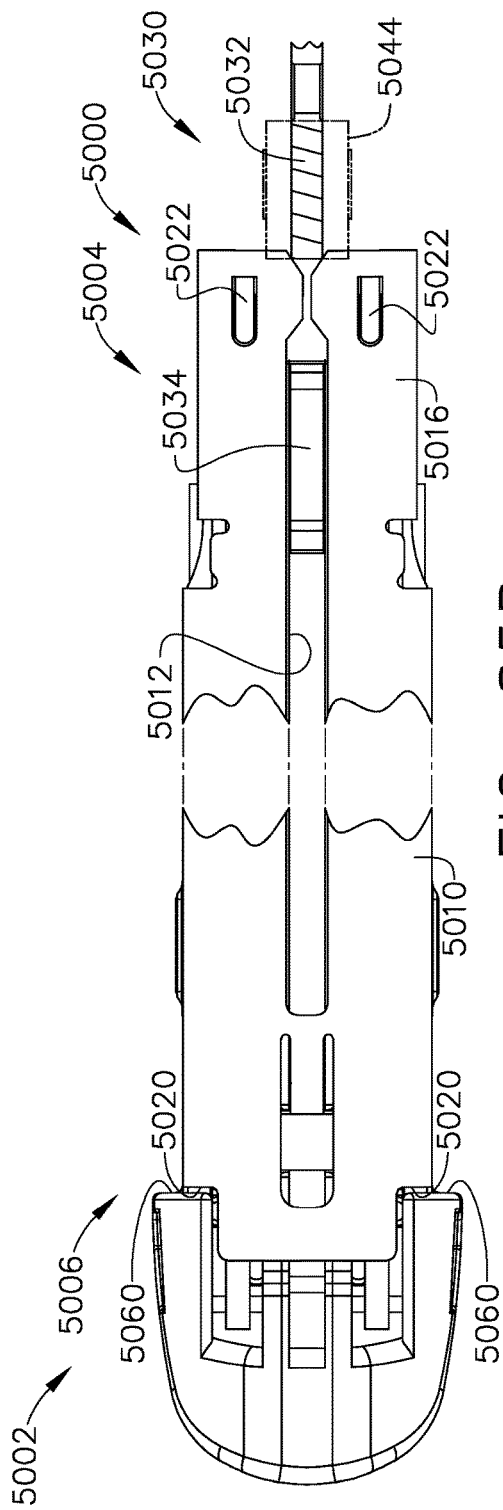

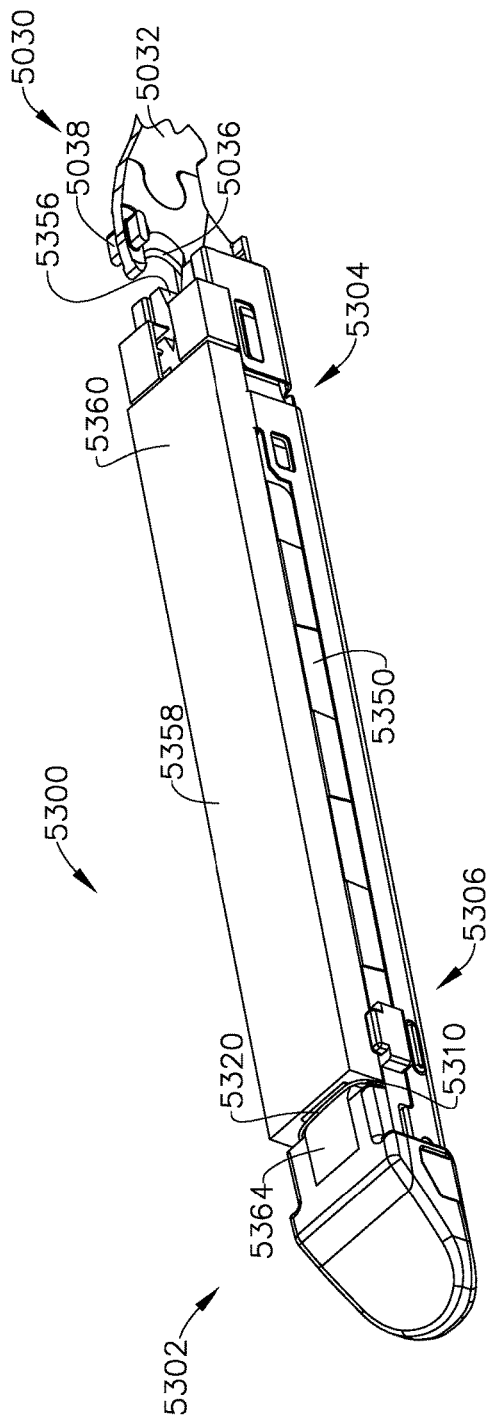
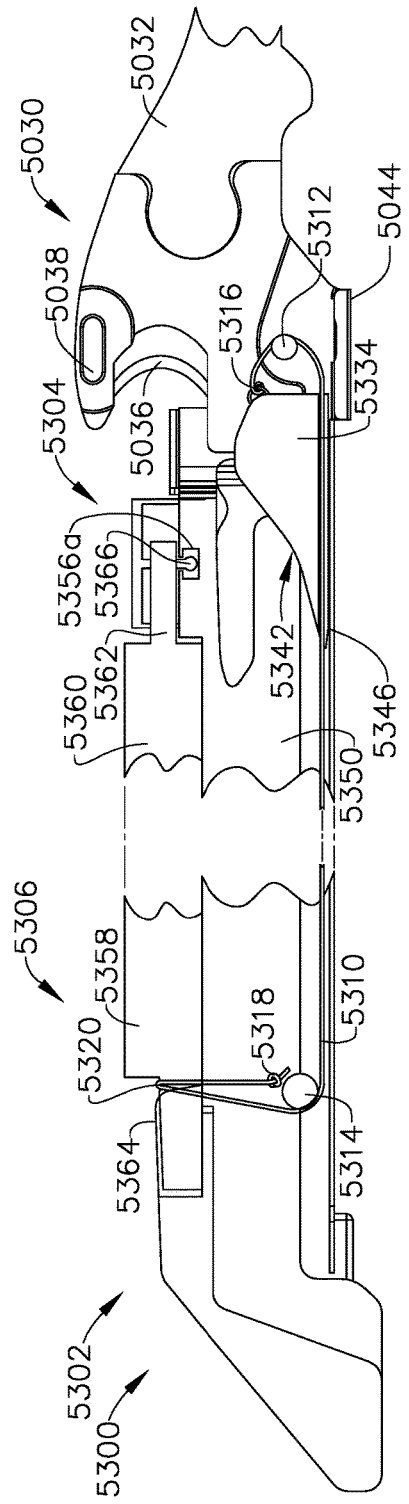
FIG. 88
FIG. 89

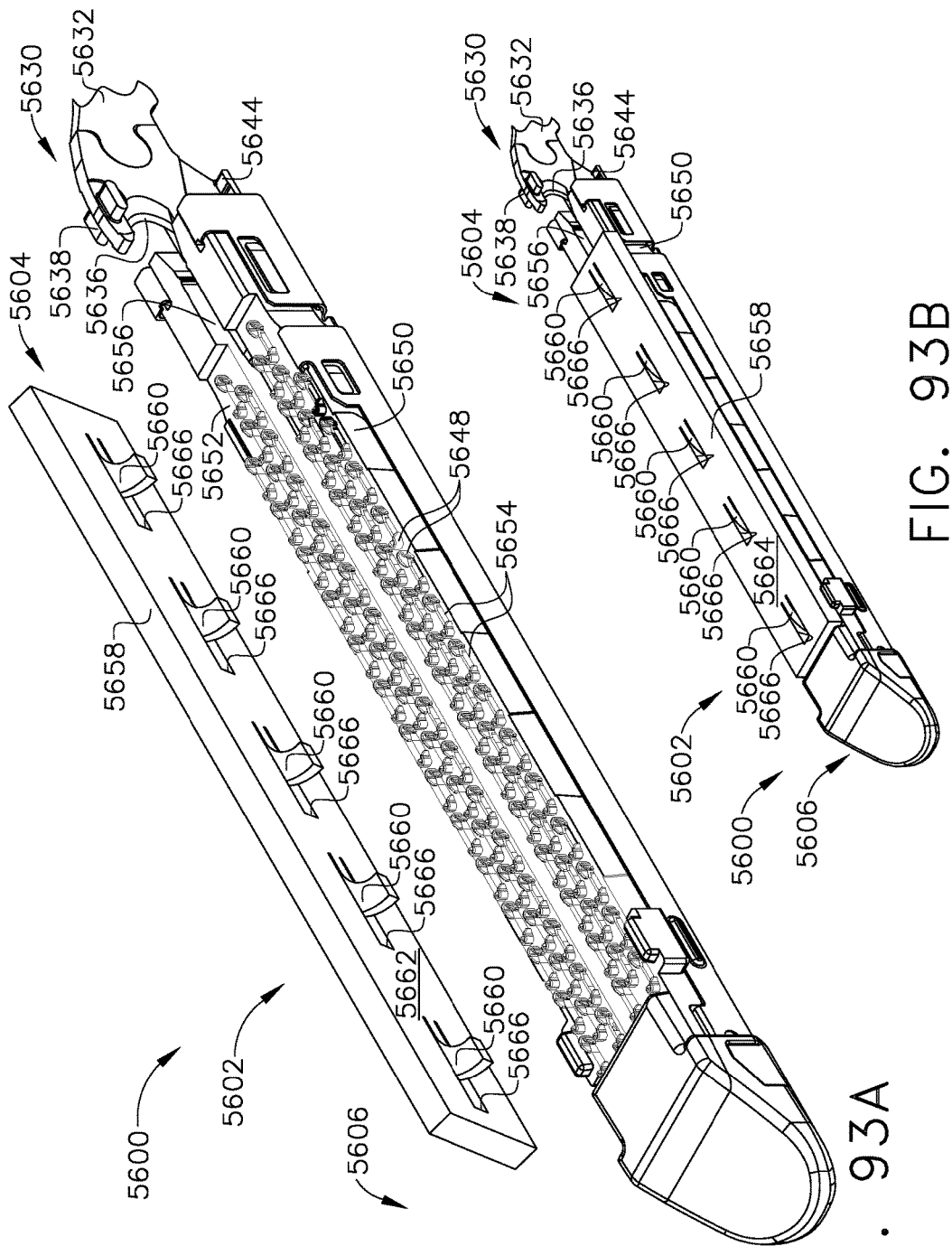

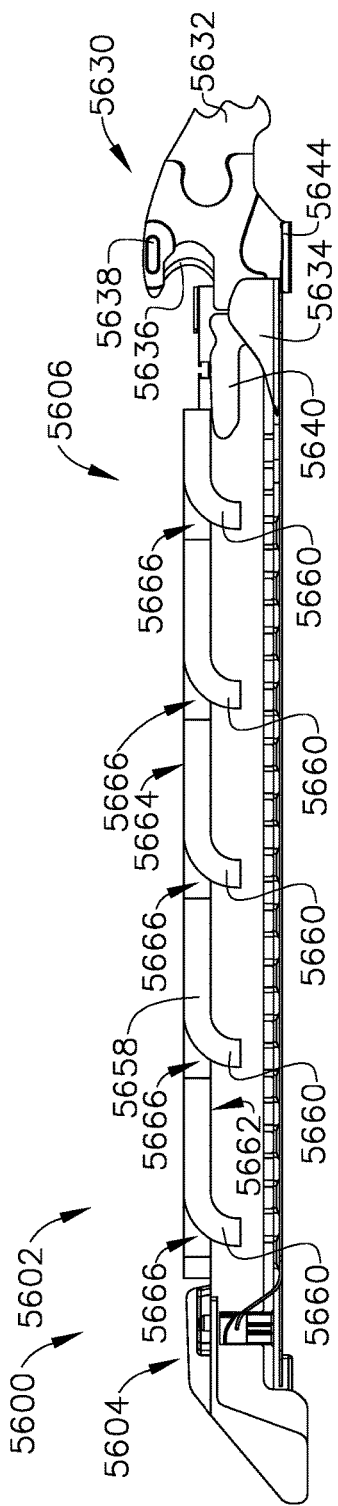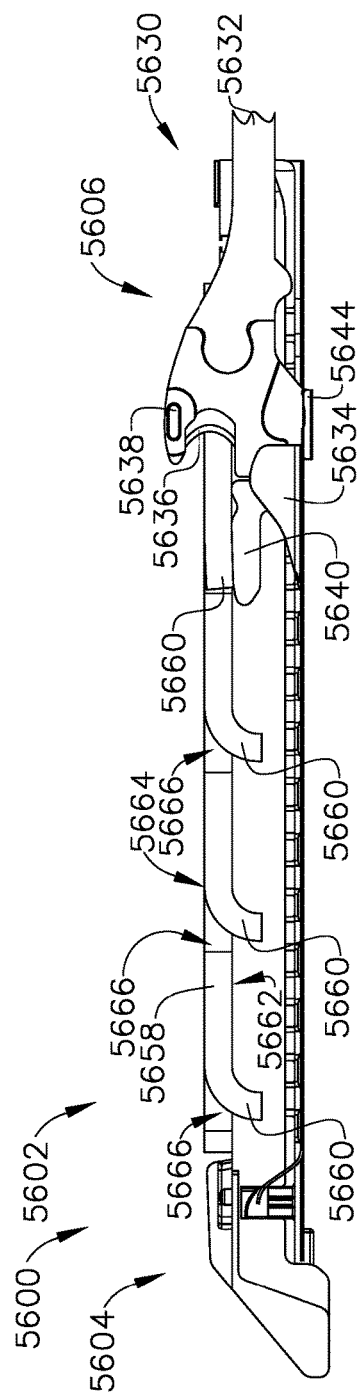

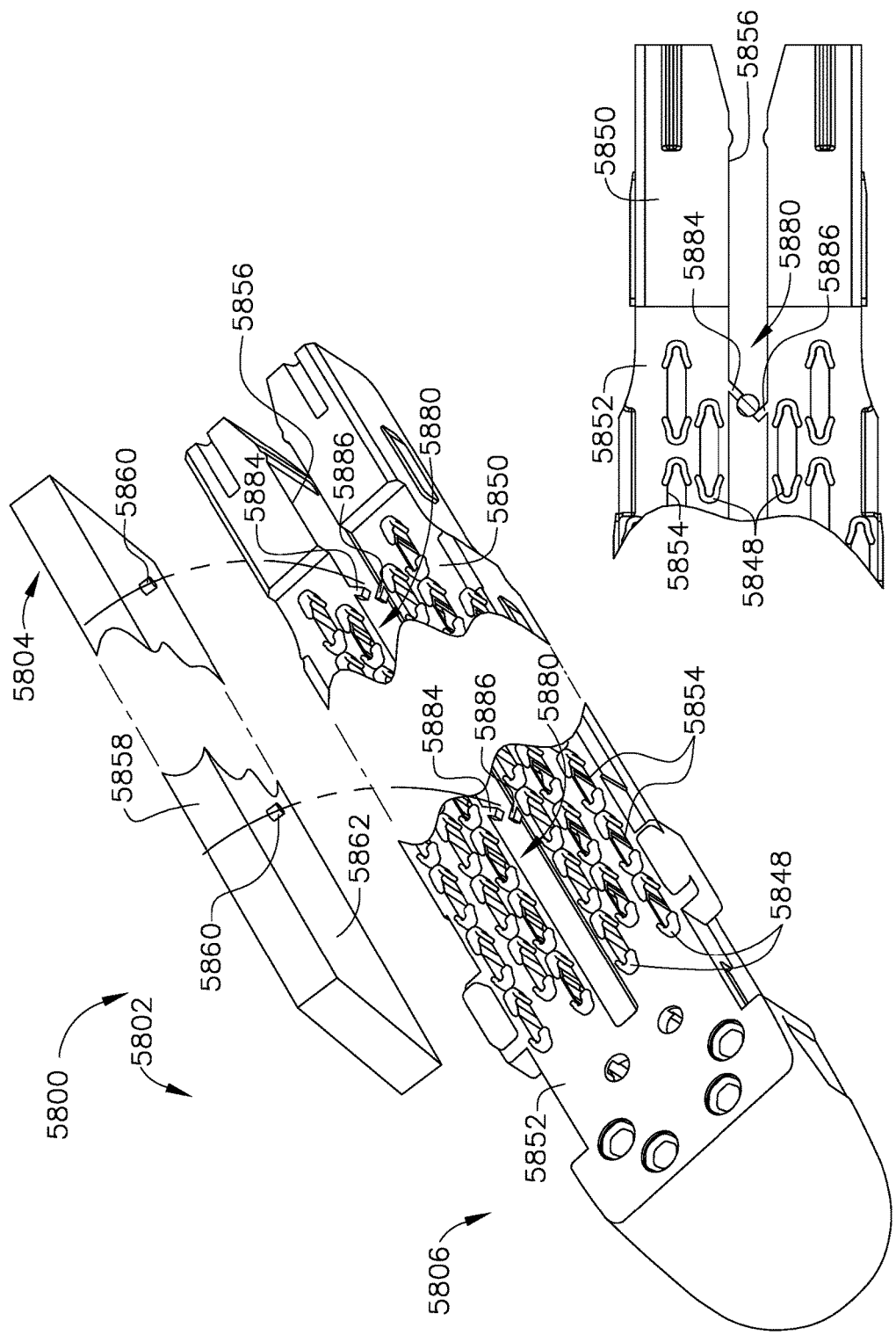

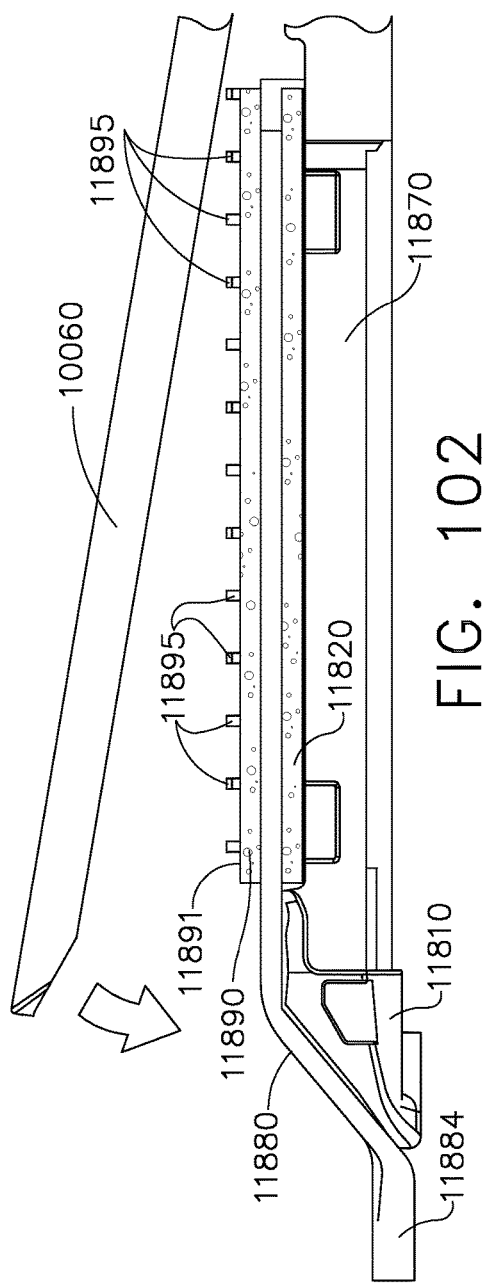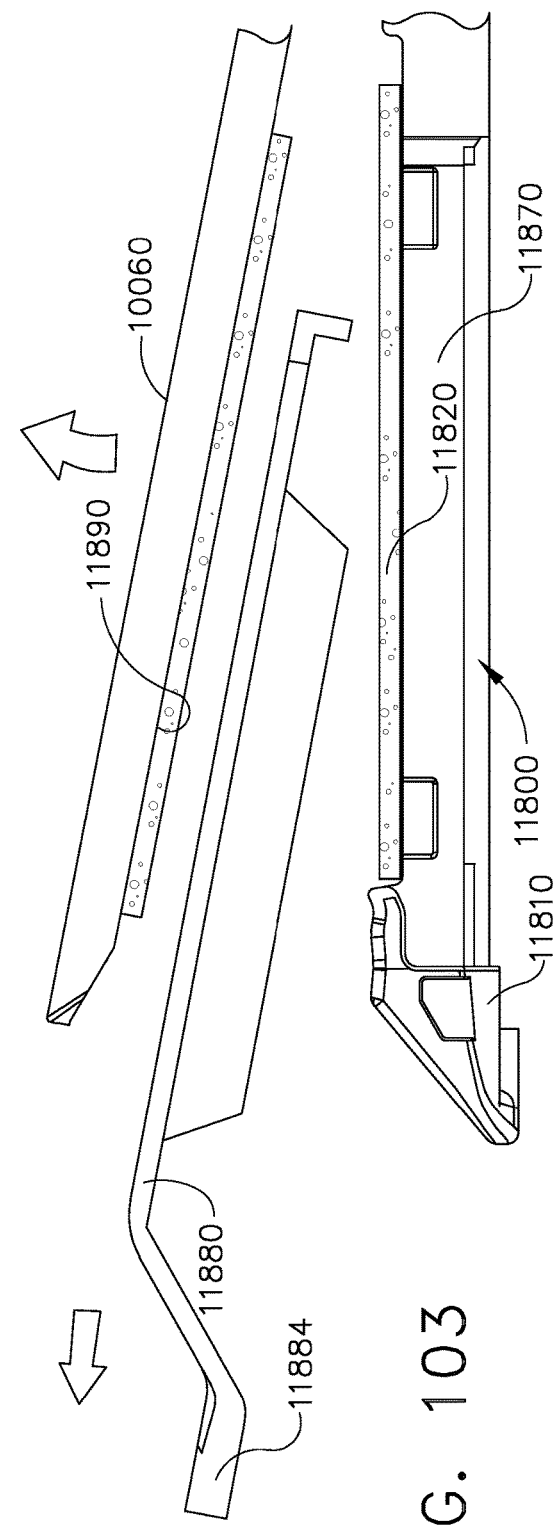

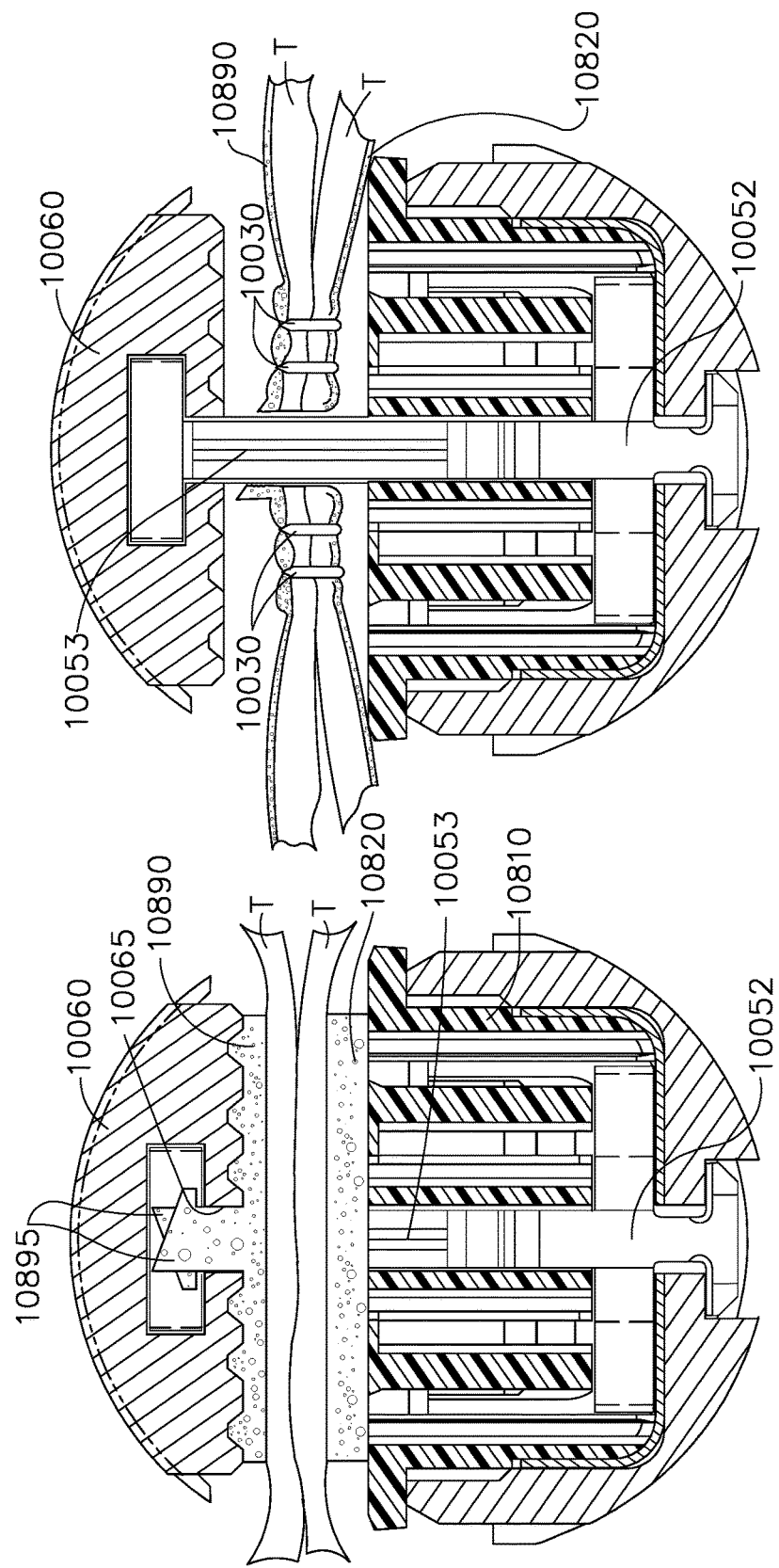

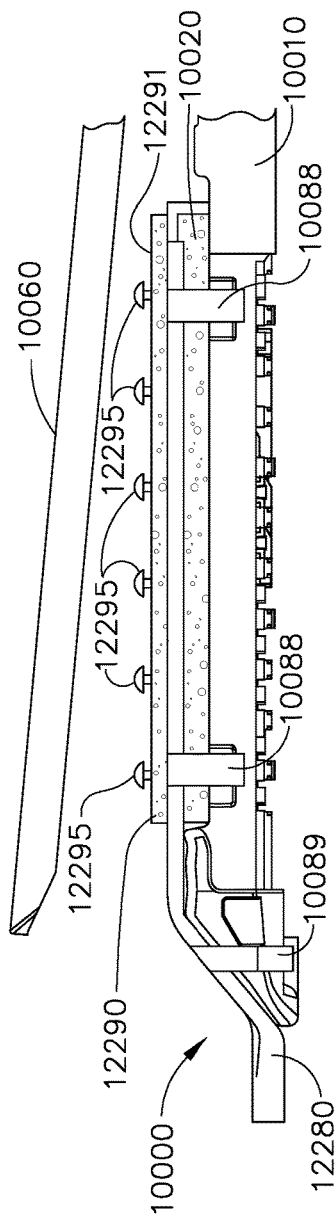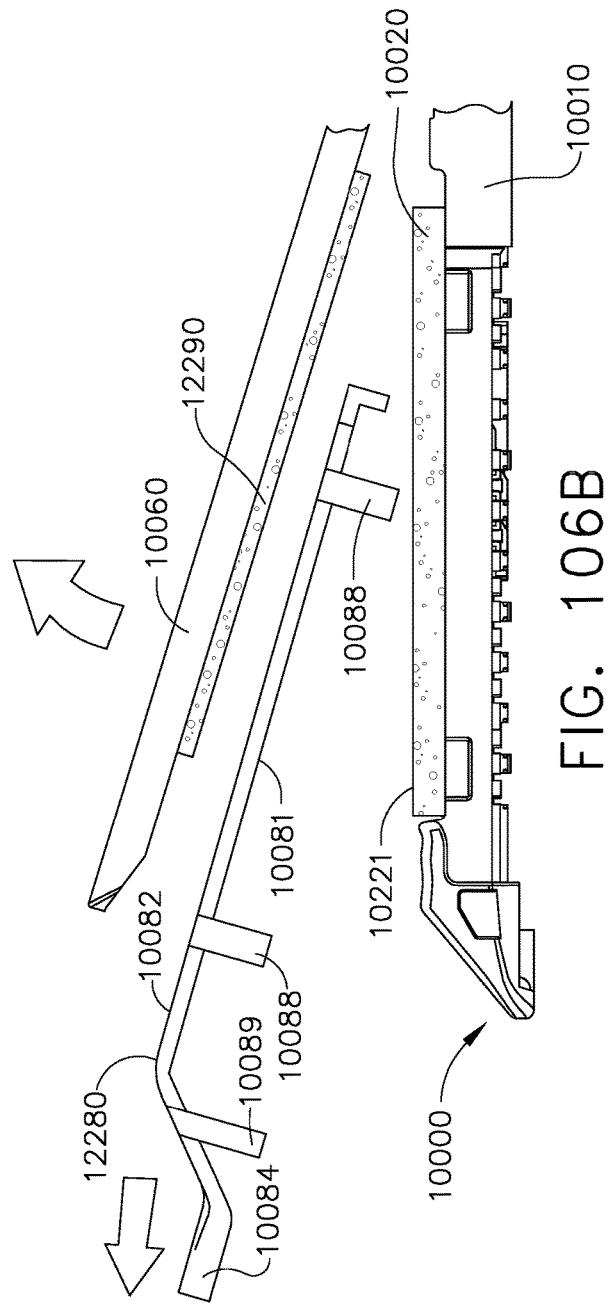

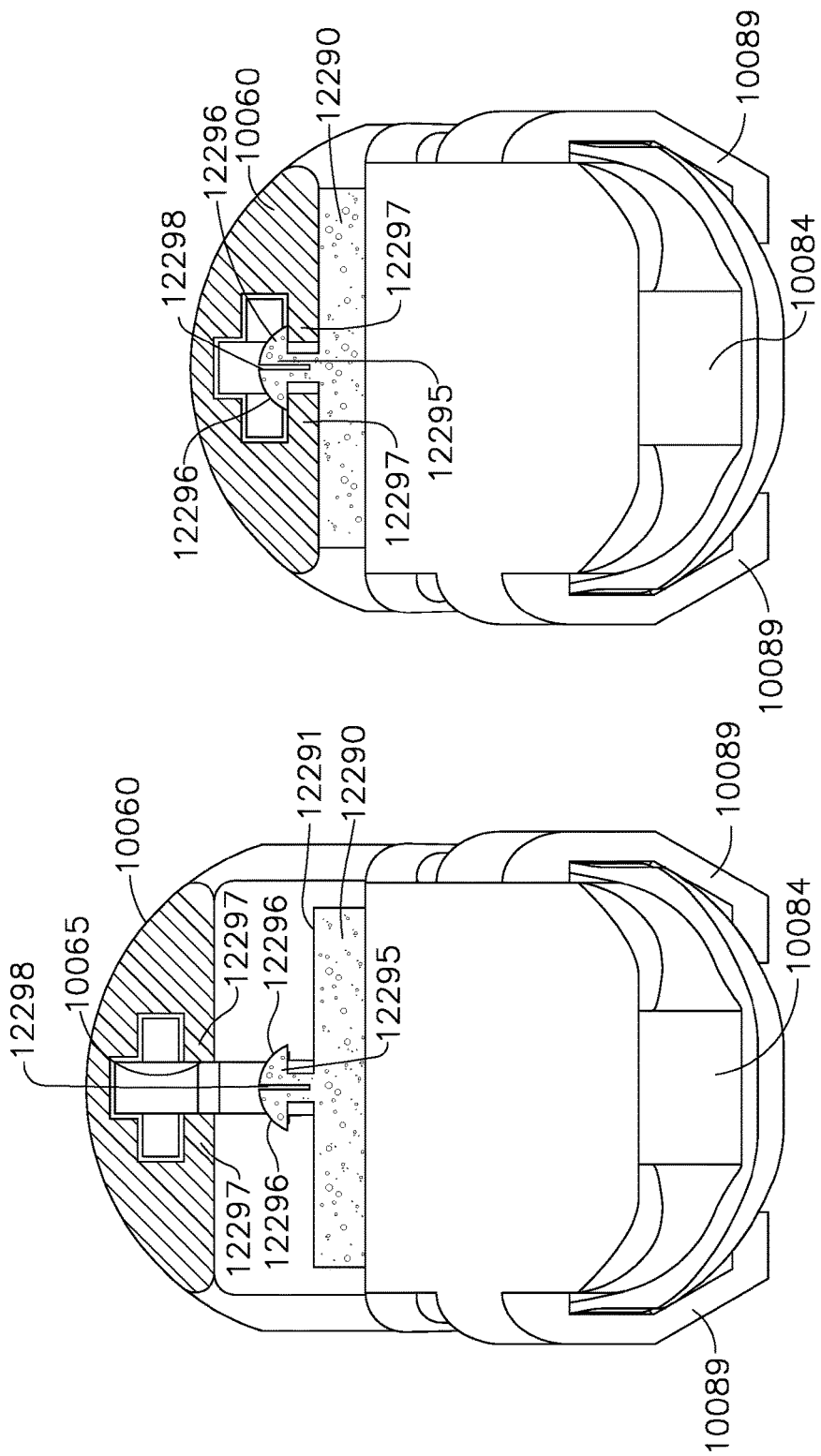

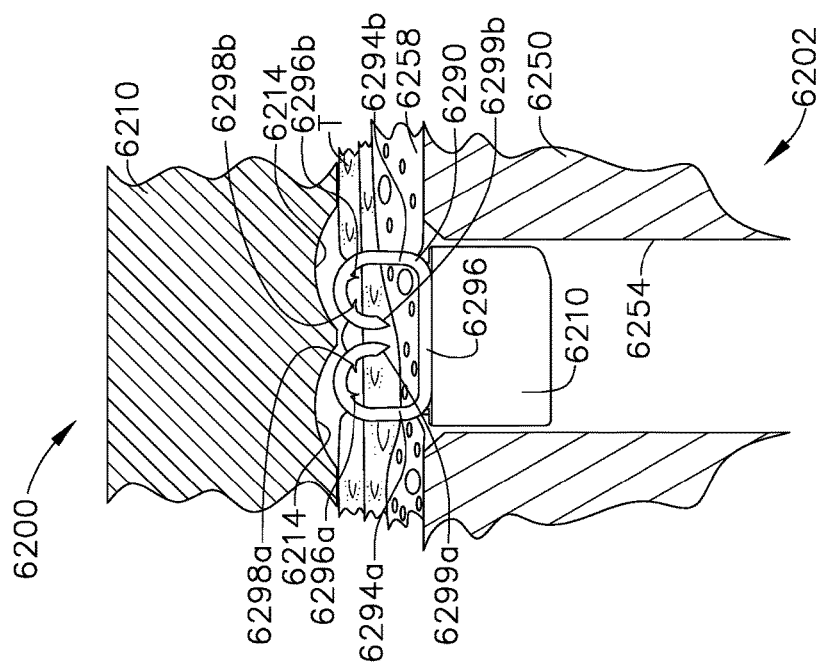
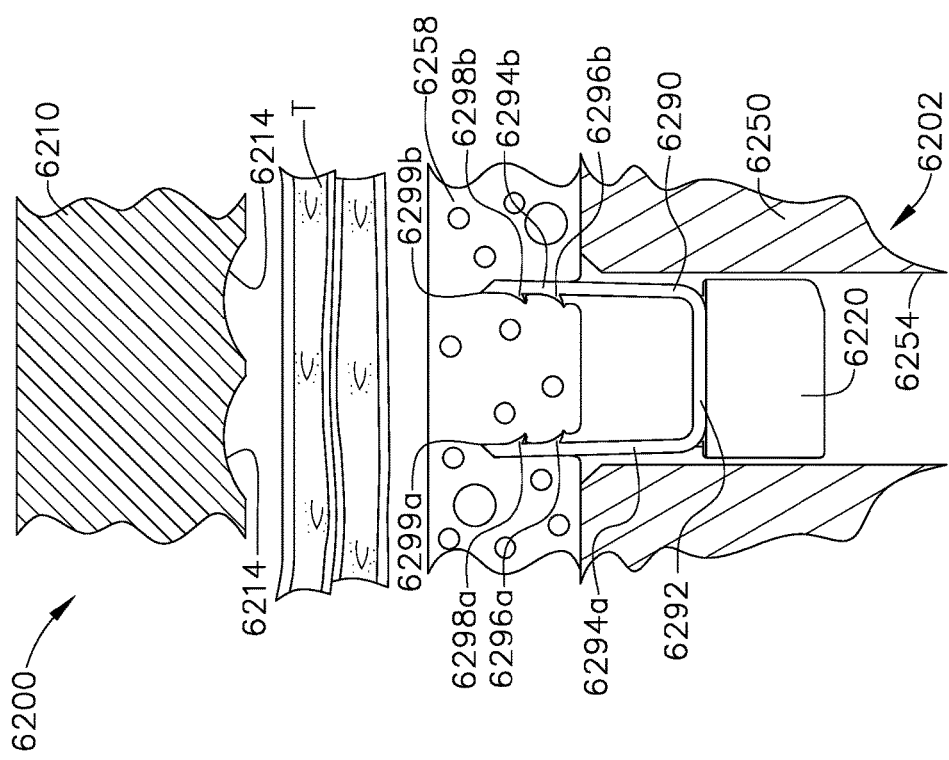

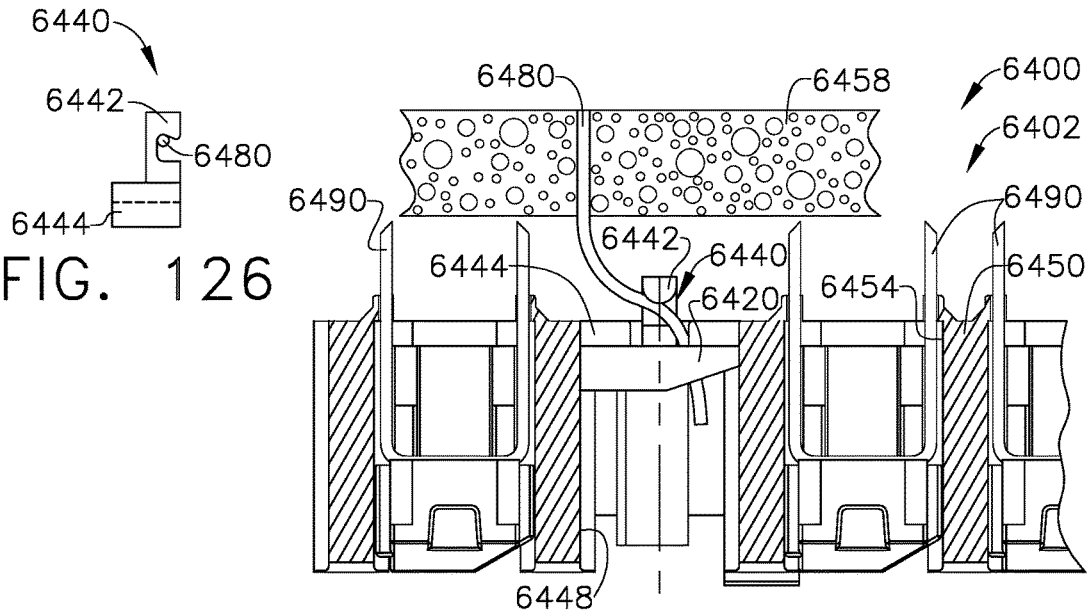
FIG. 126
FIG. 126A
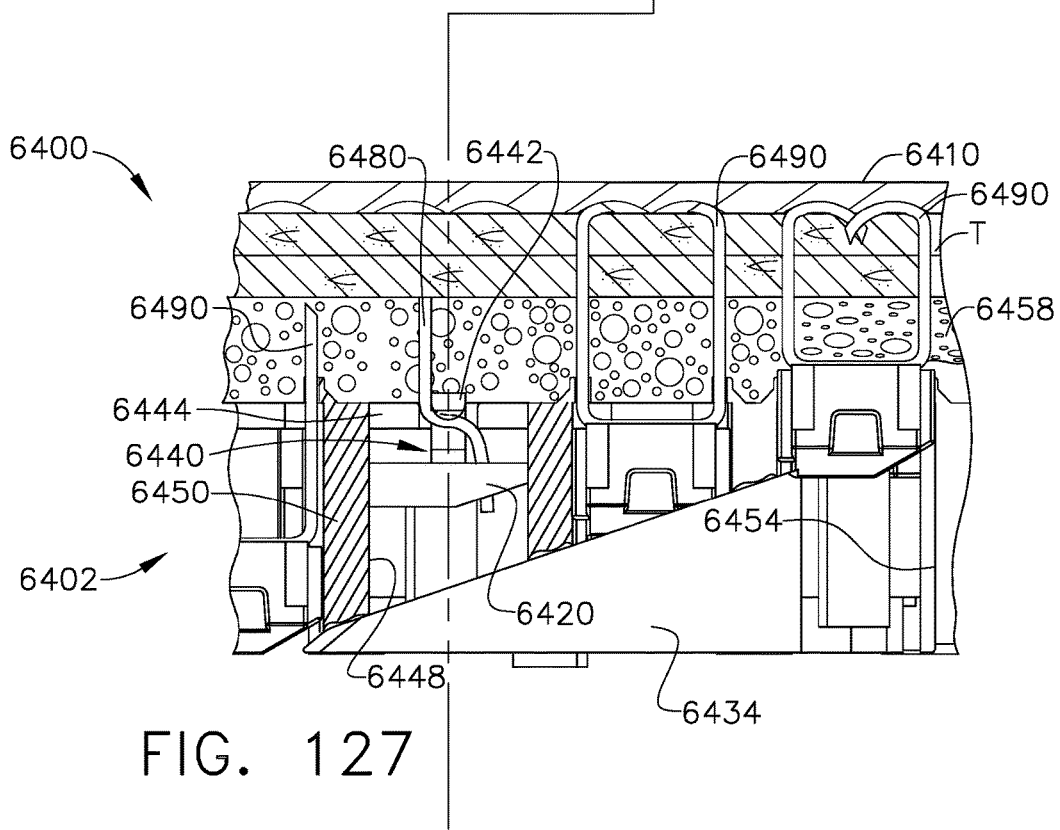
FIG. 127

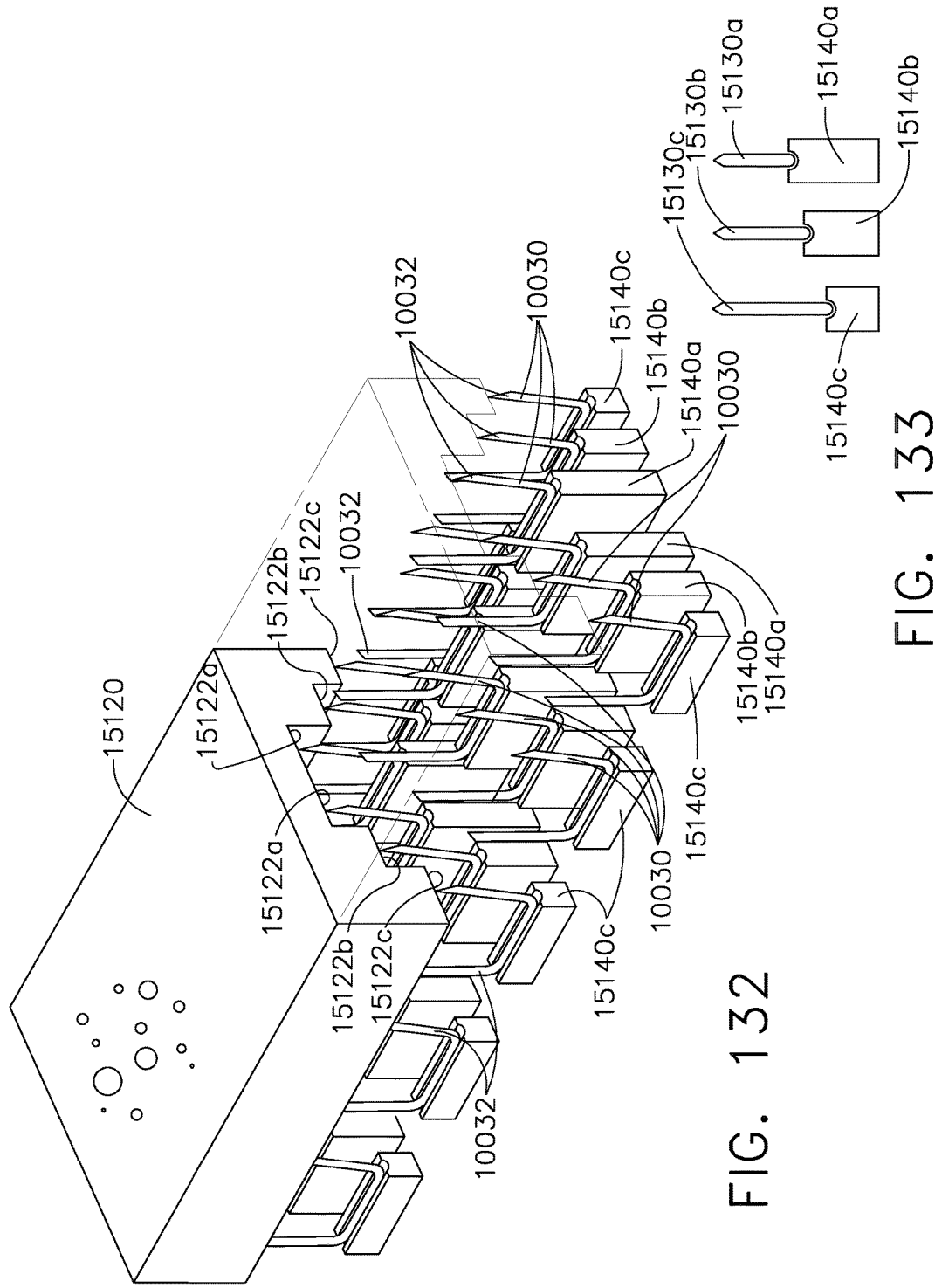

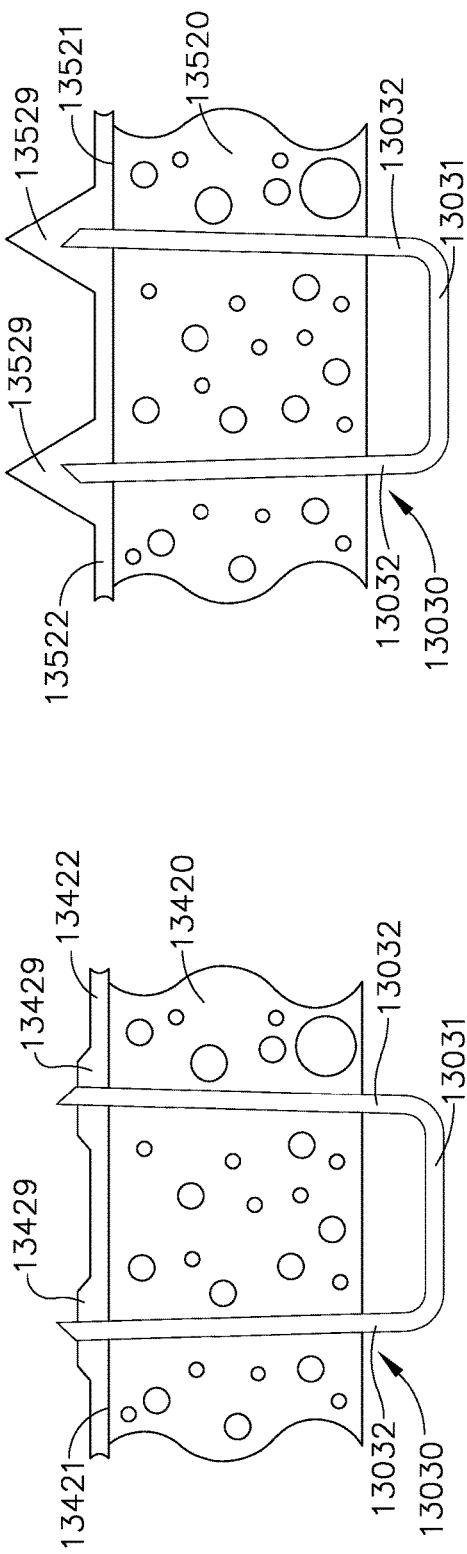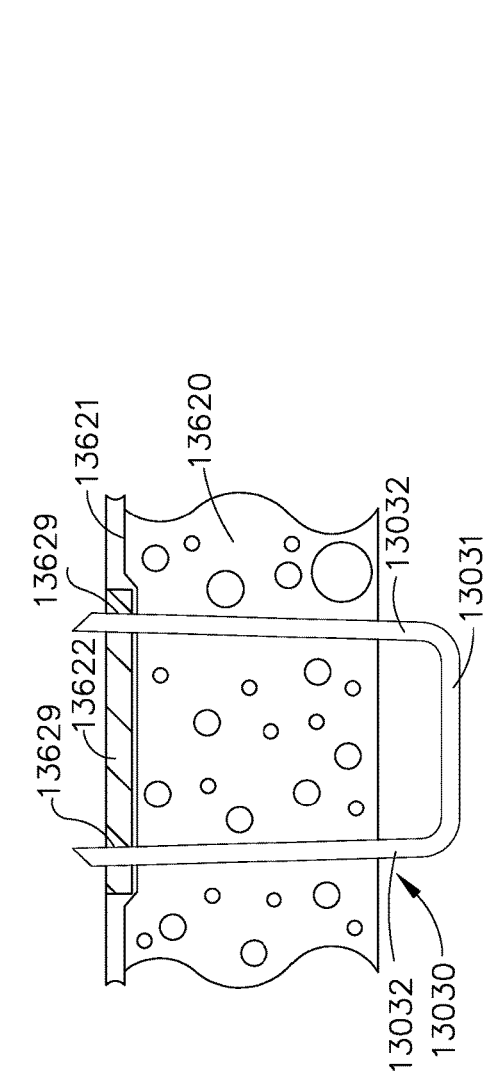

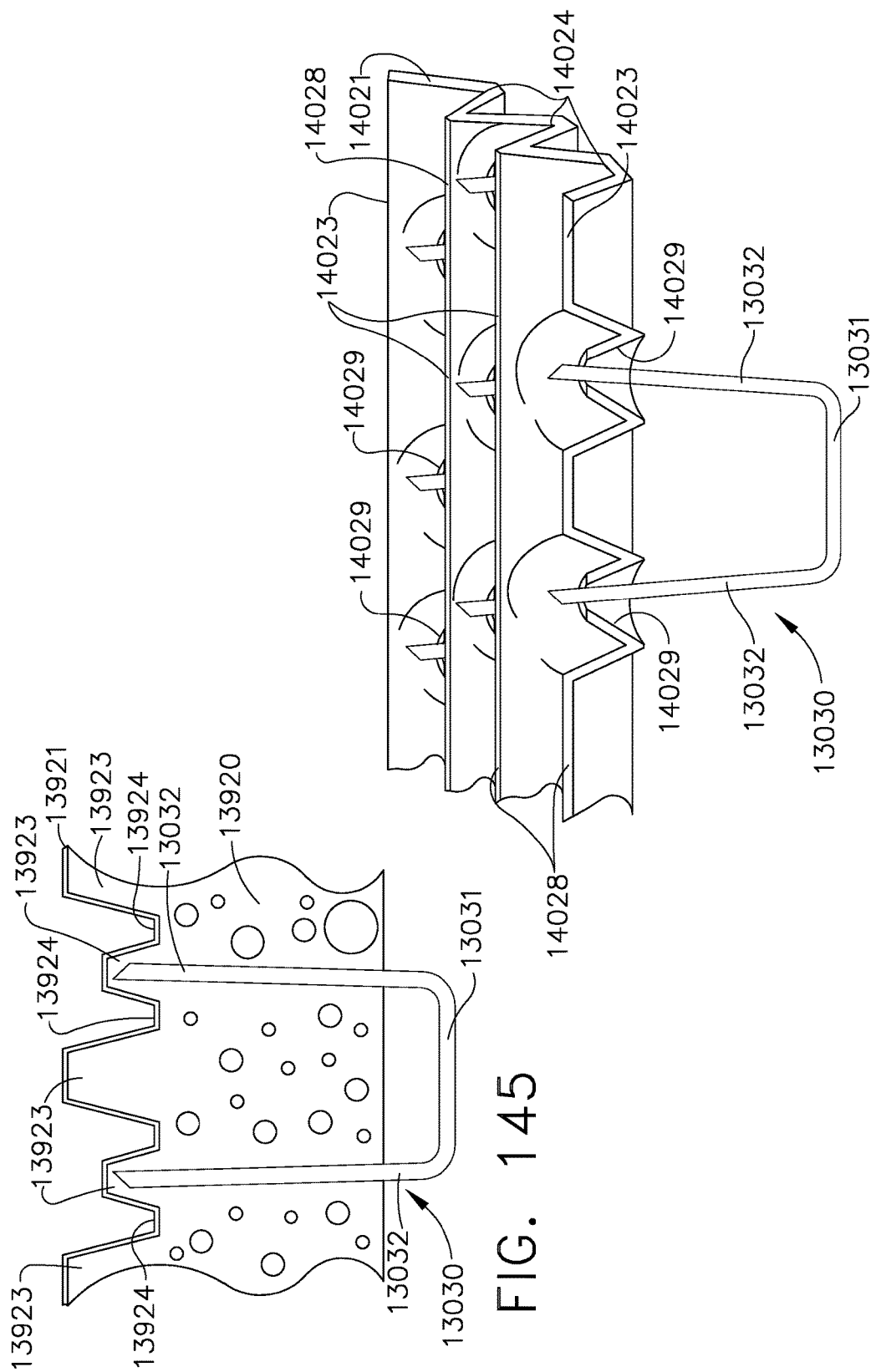

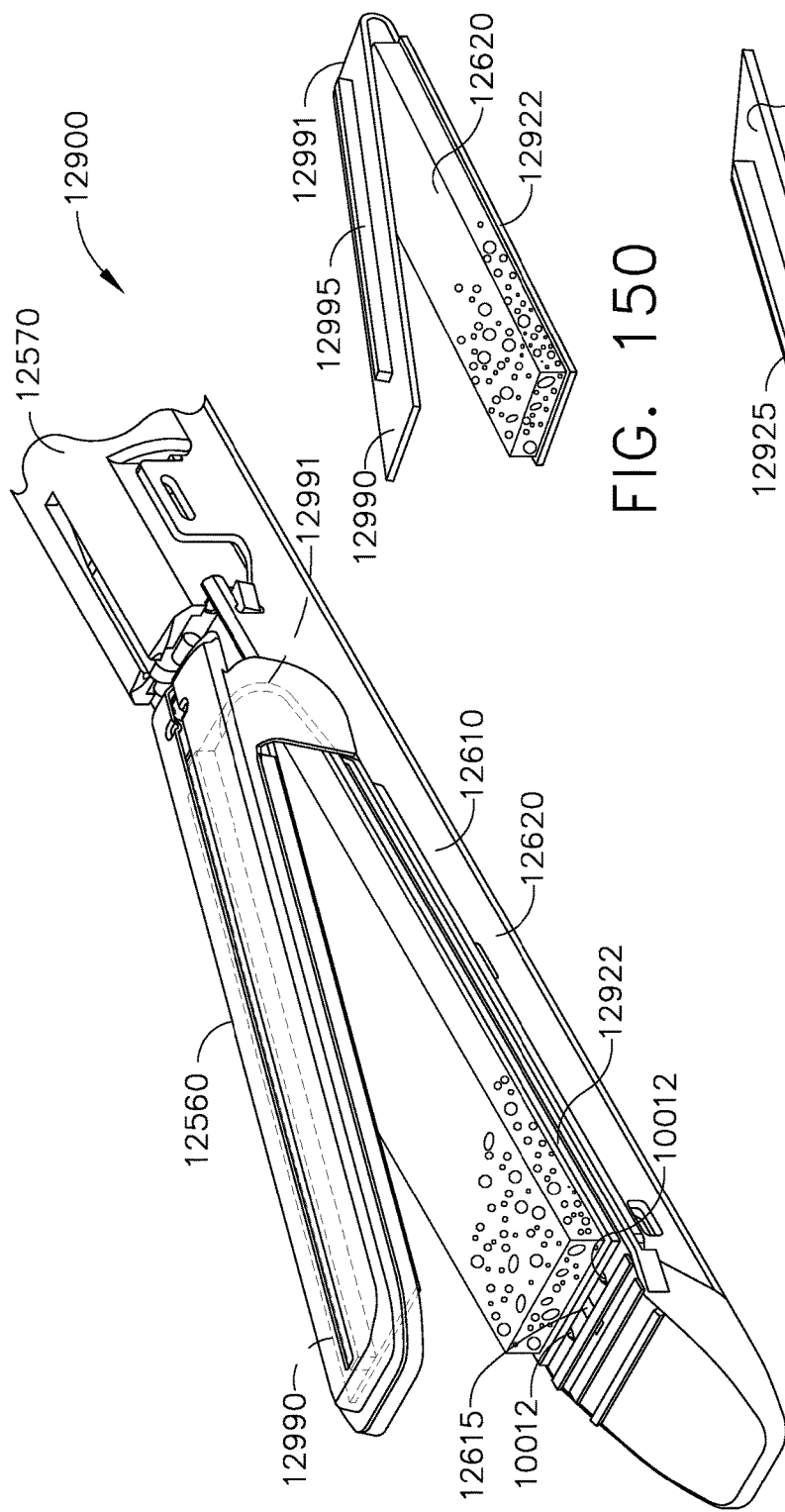
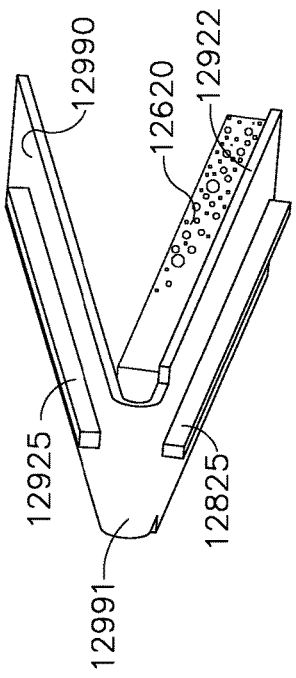
FIG. 149
FIG. 150
FIG. 151

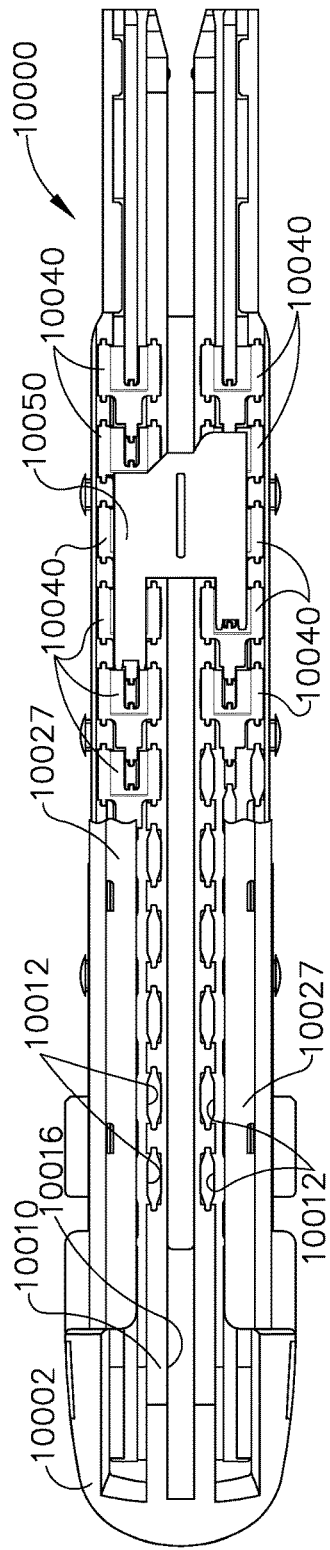
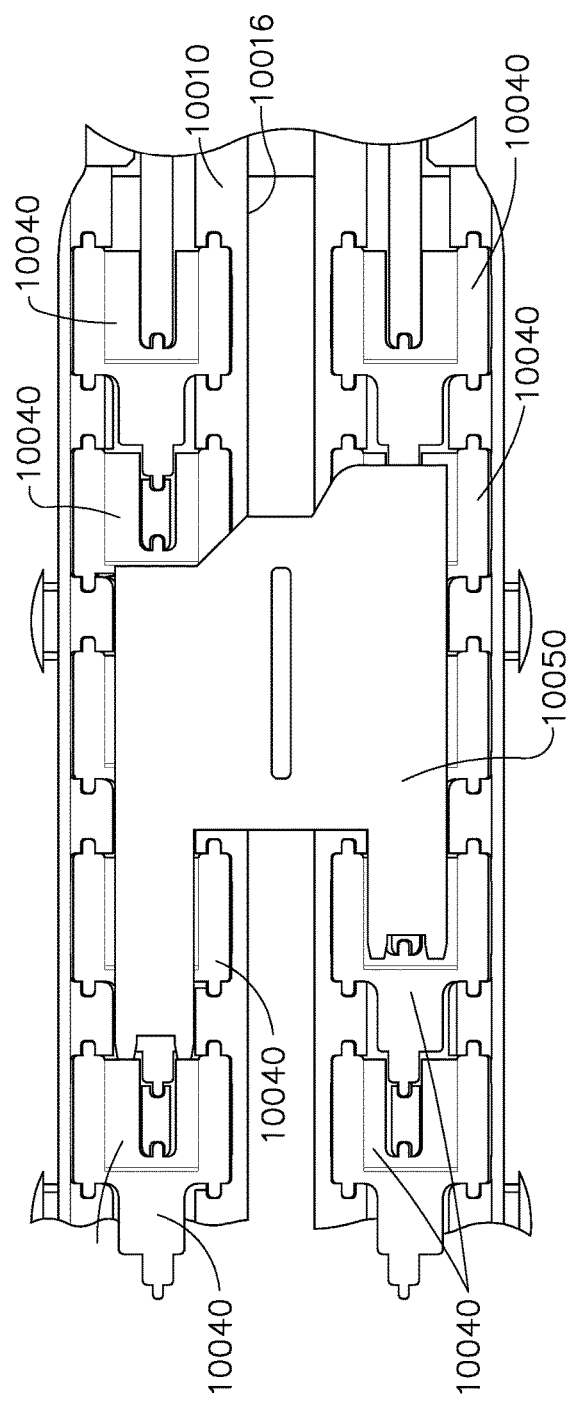
FIG. 161
FIG. 162

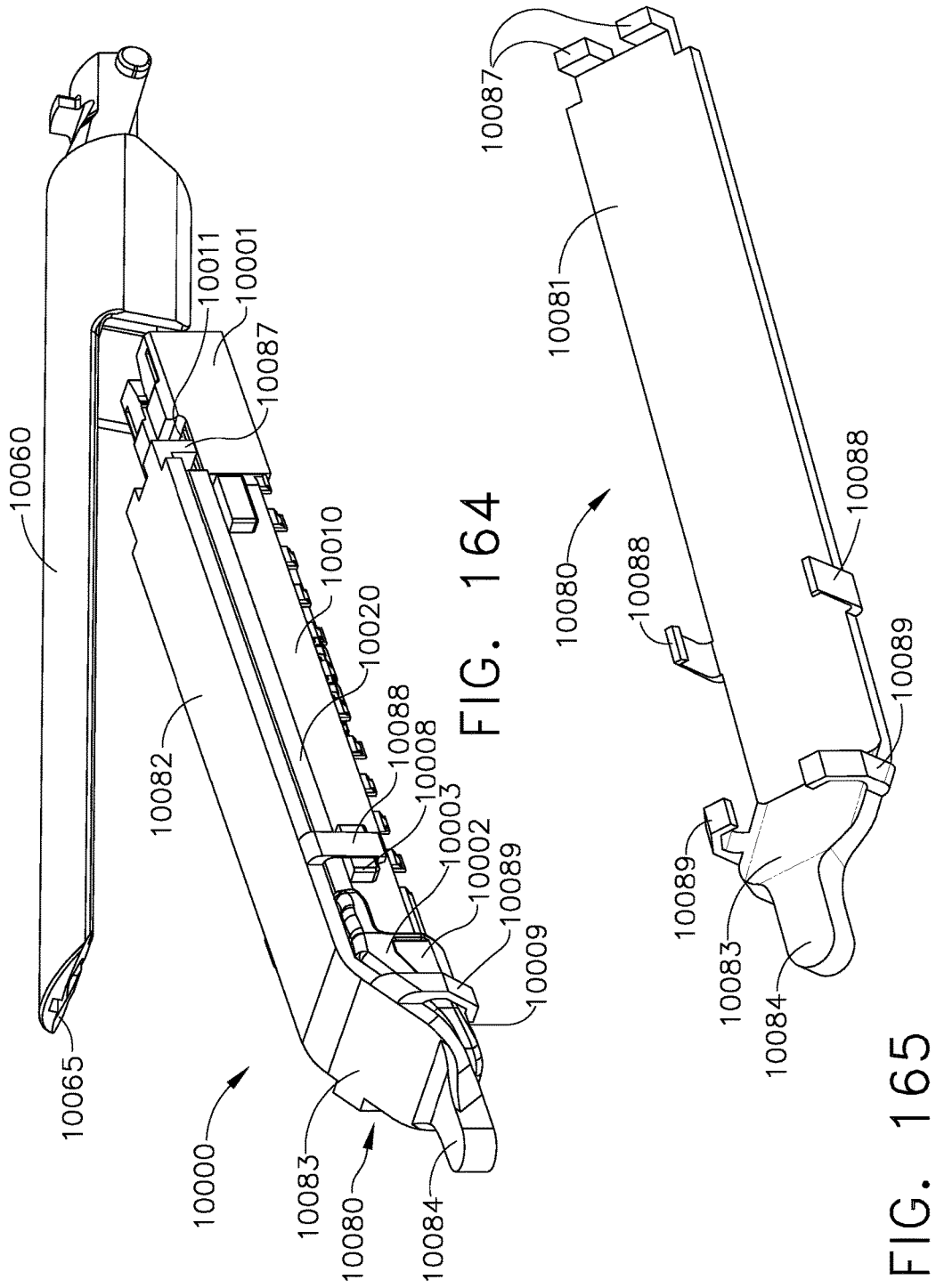

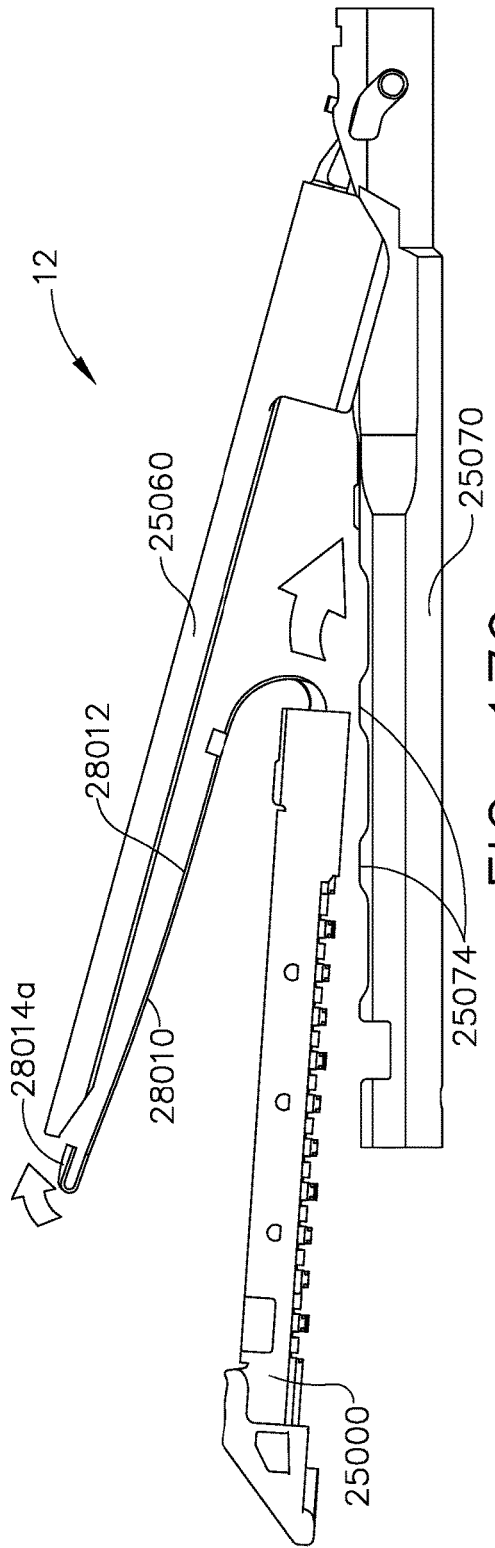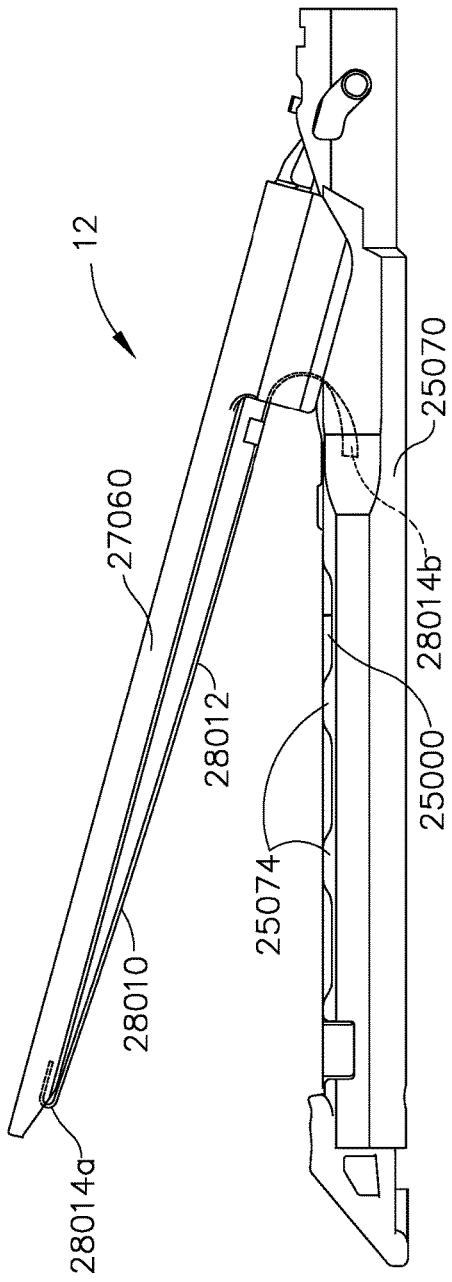

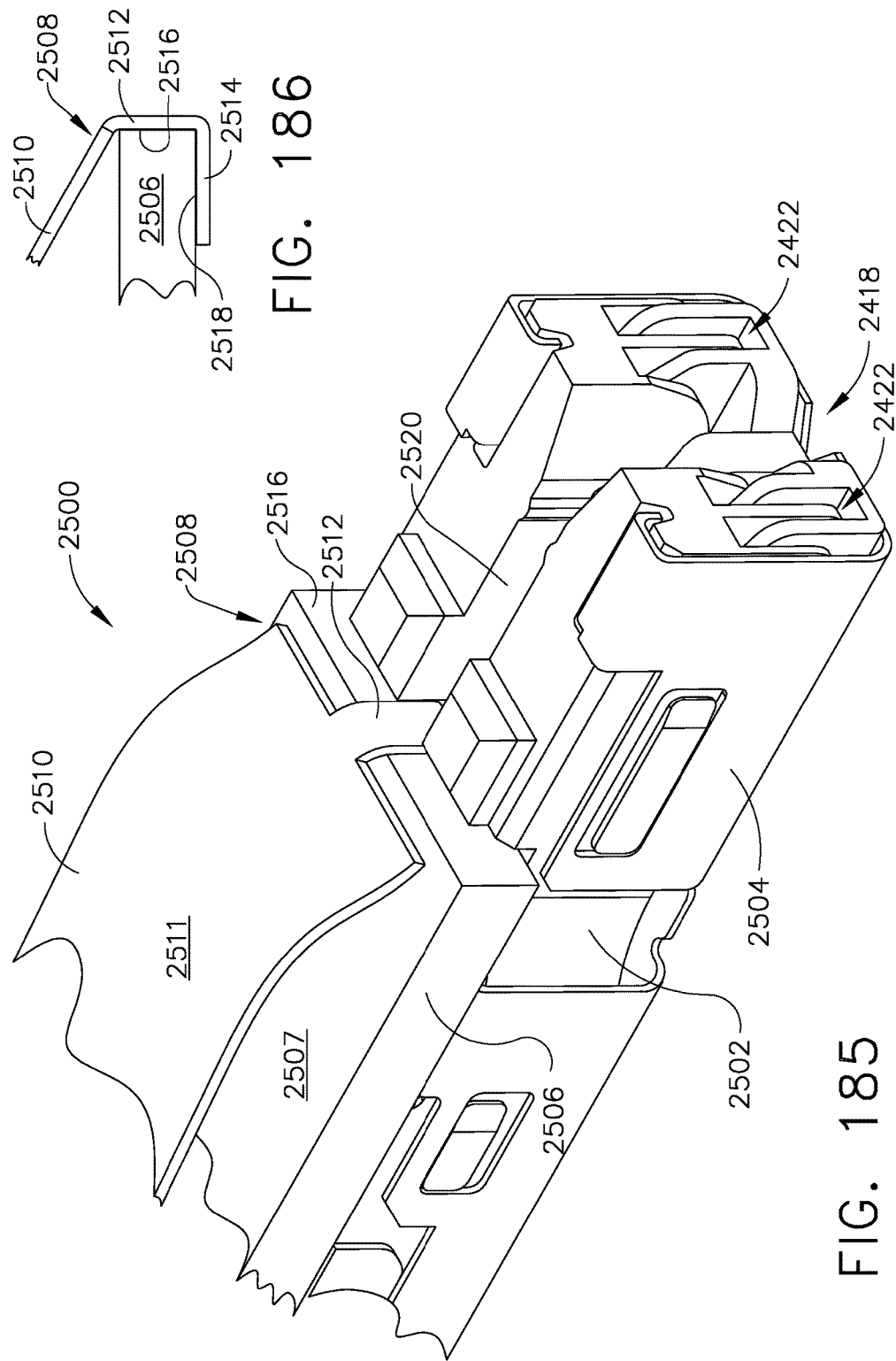

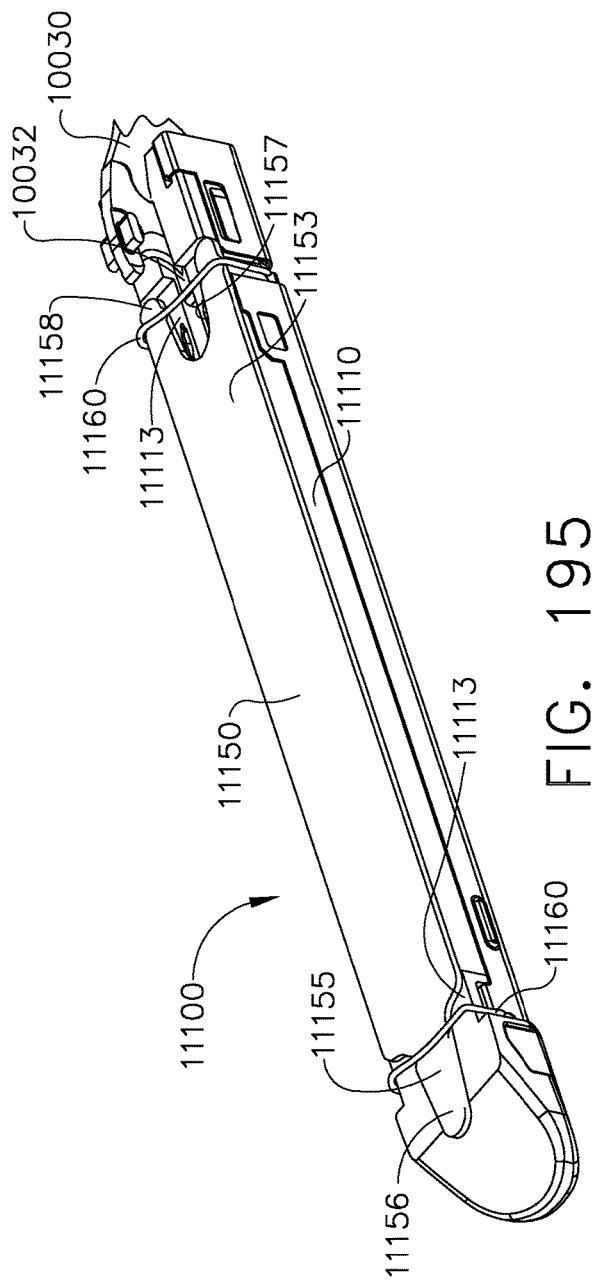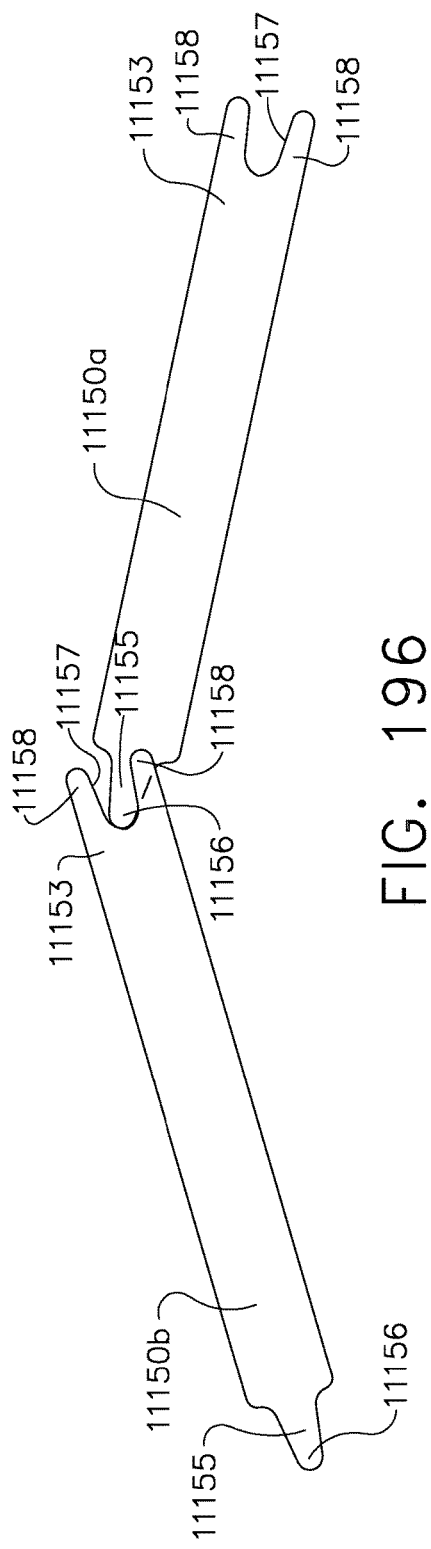

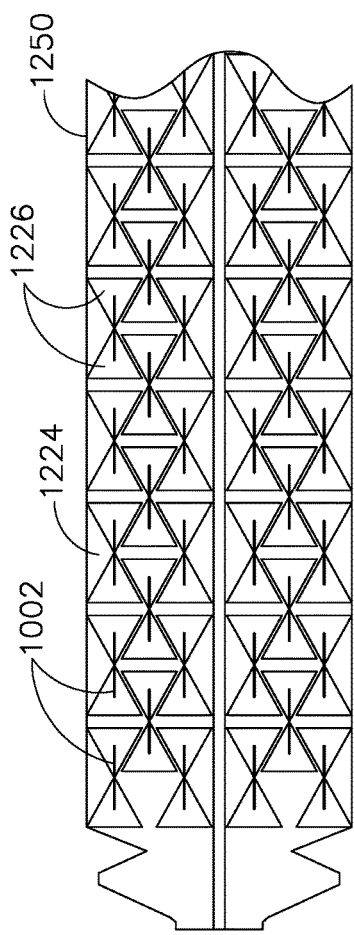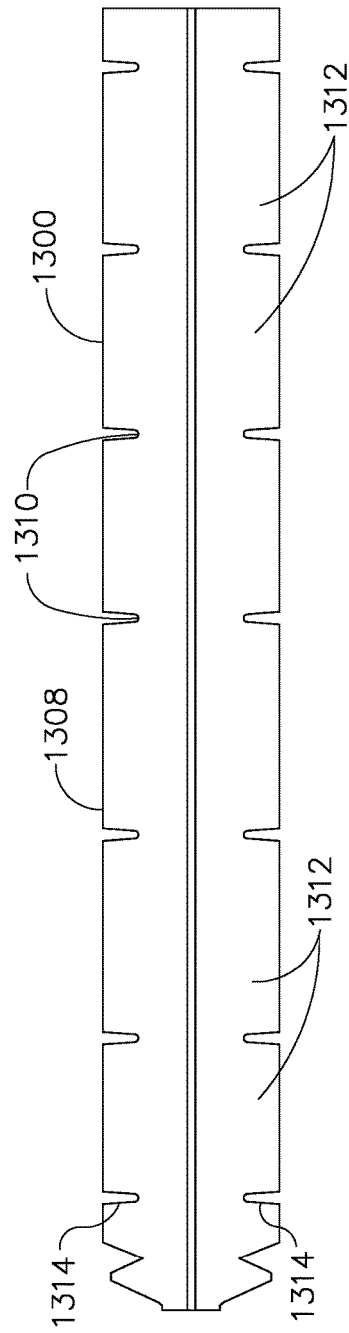

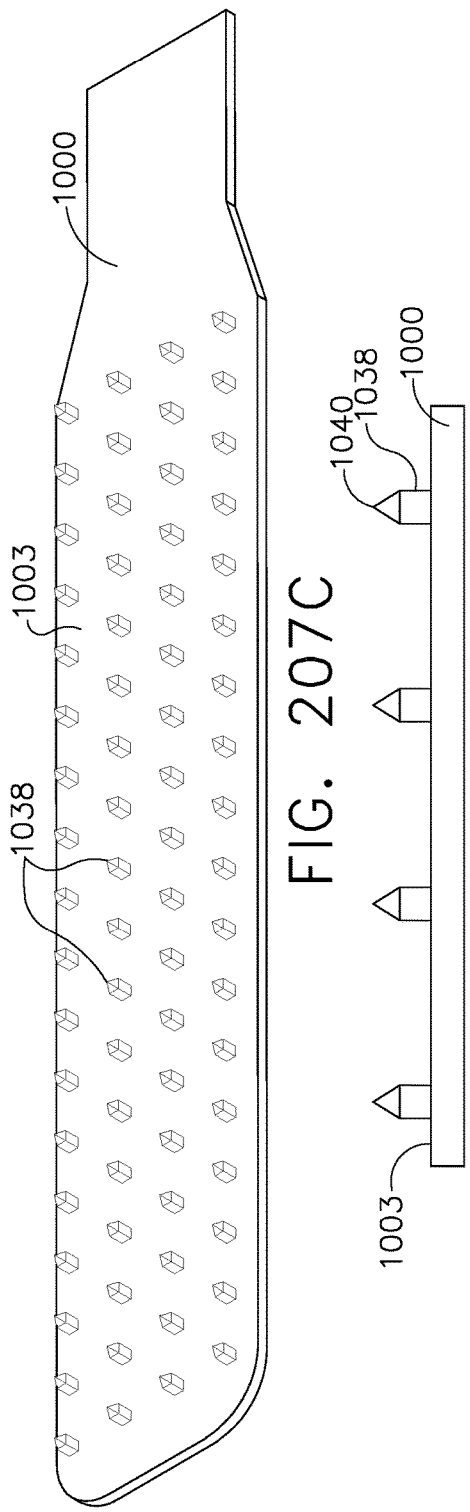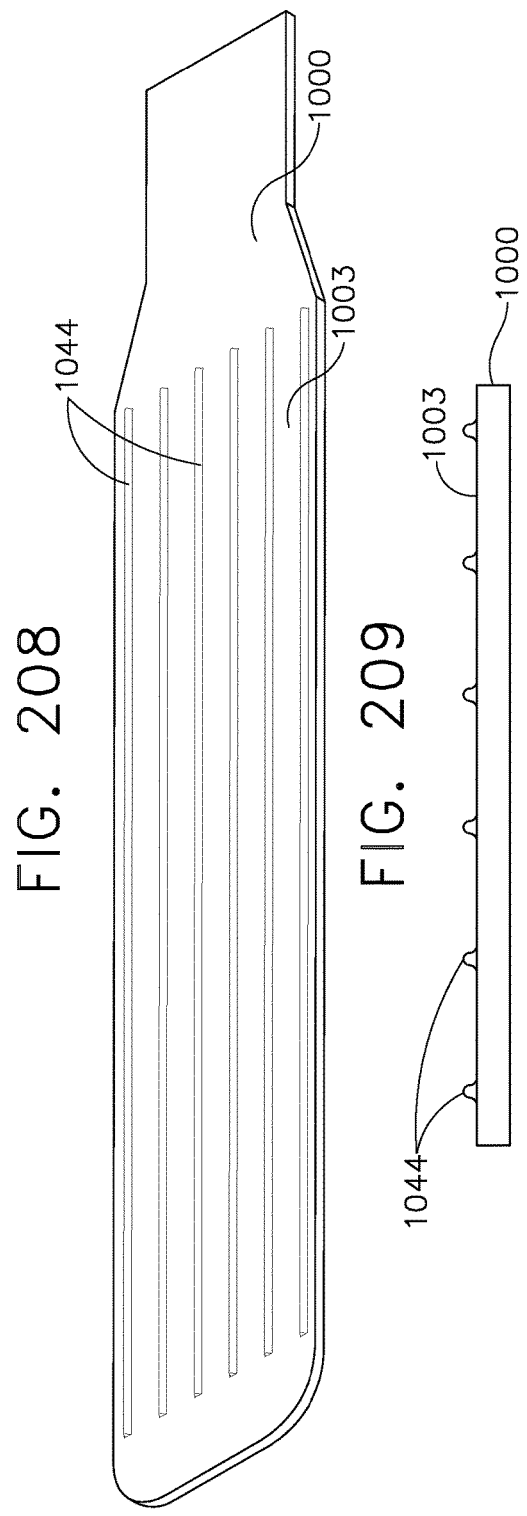
FIG. 207C  FIG. 208  FIG. 209  FIG. 210

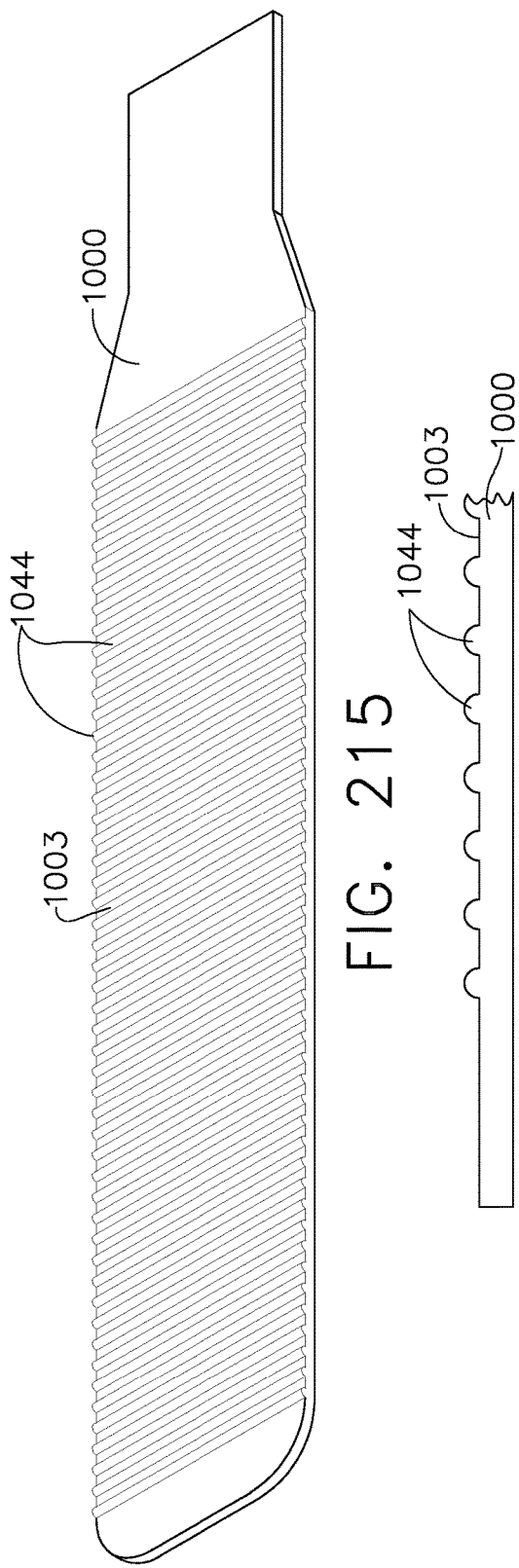
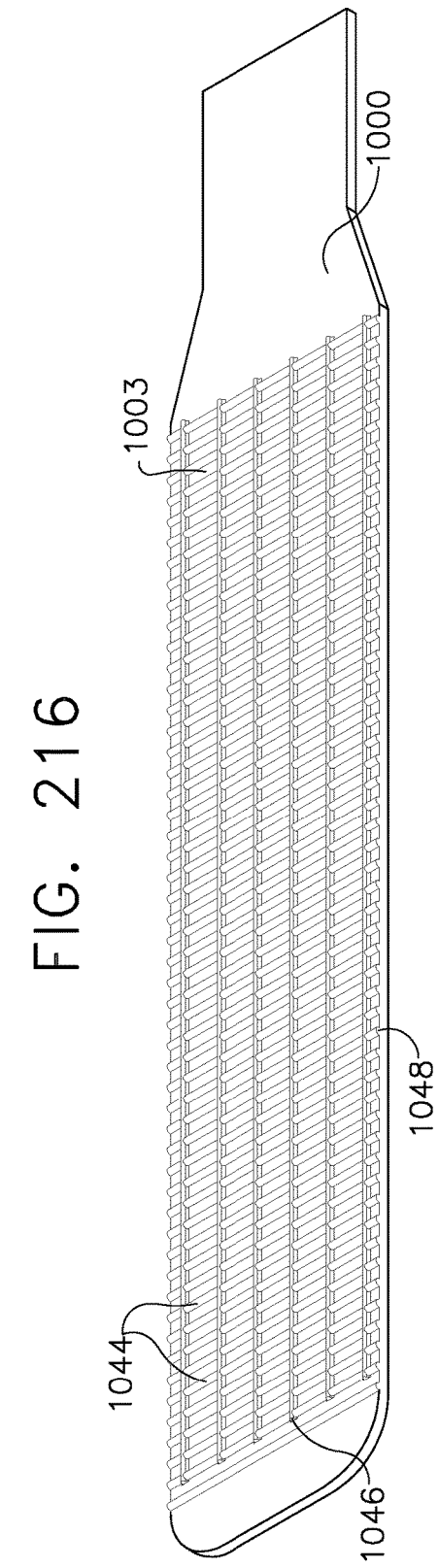
FIG. 215  FIG. 216  FIG. 217

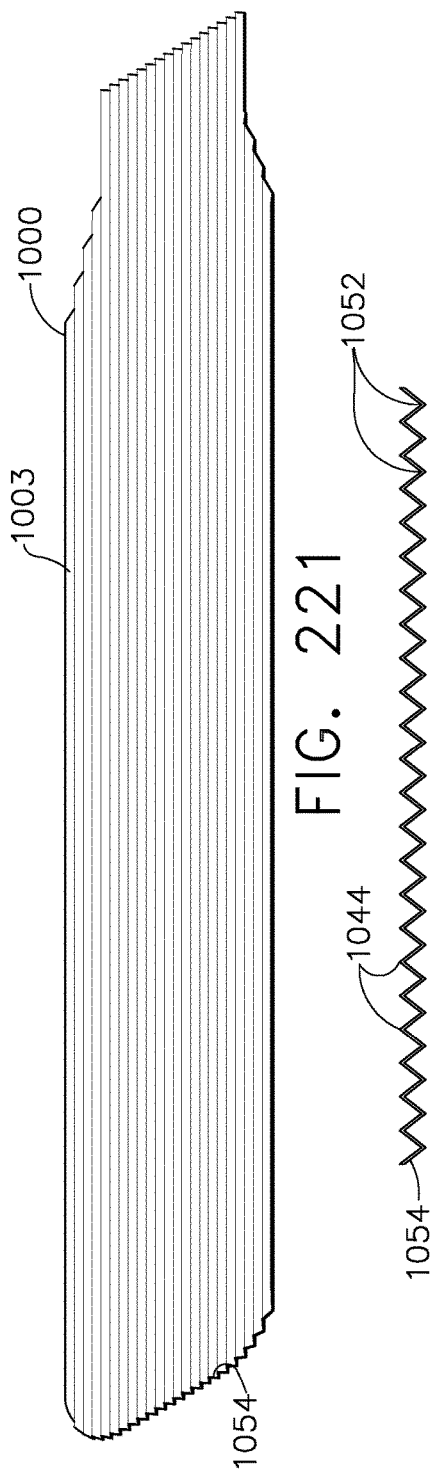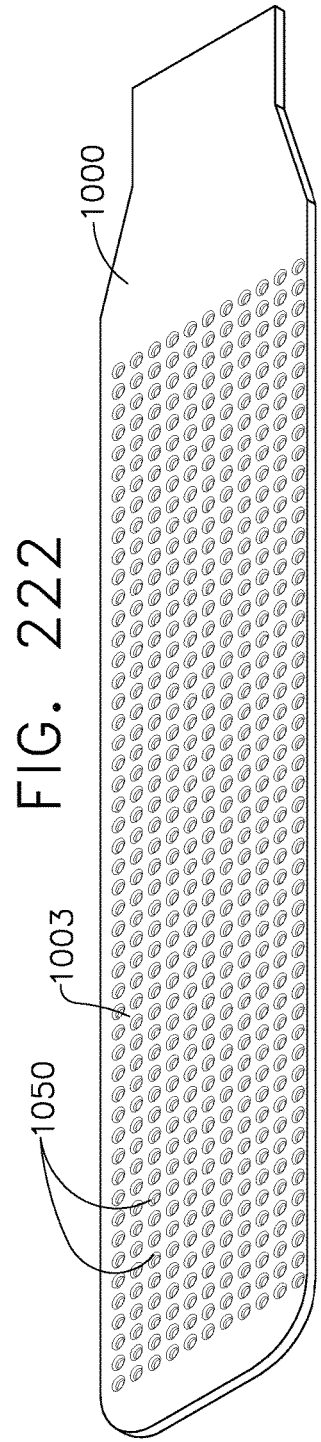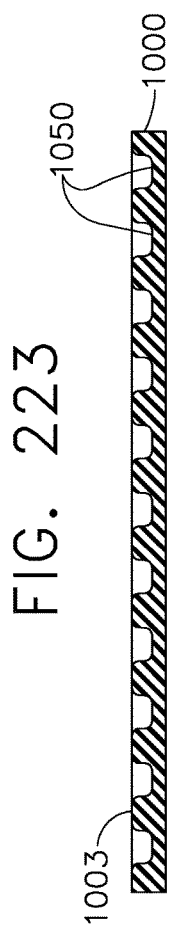
FIG. 221  FIG. 222  FIG. 223  FIG. 224

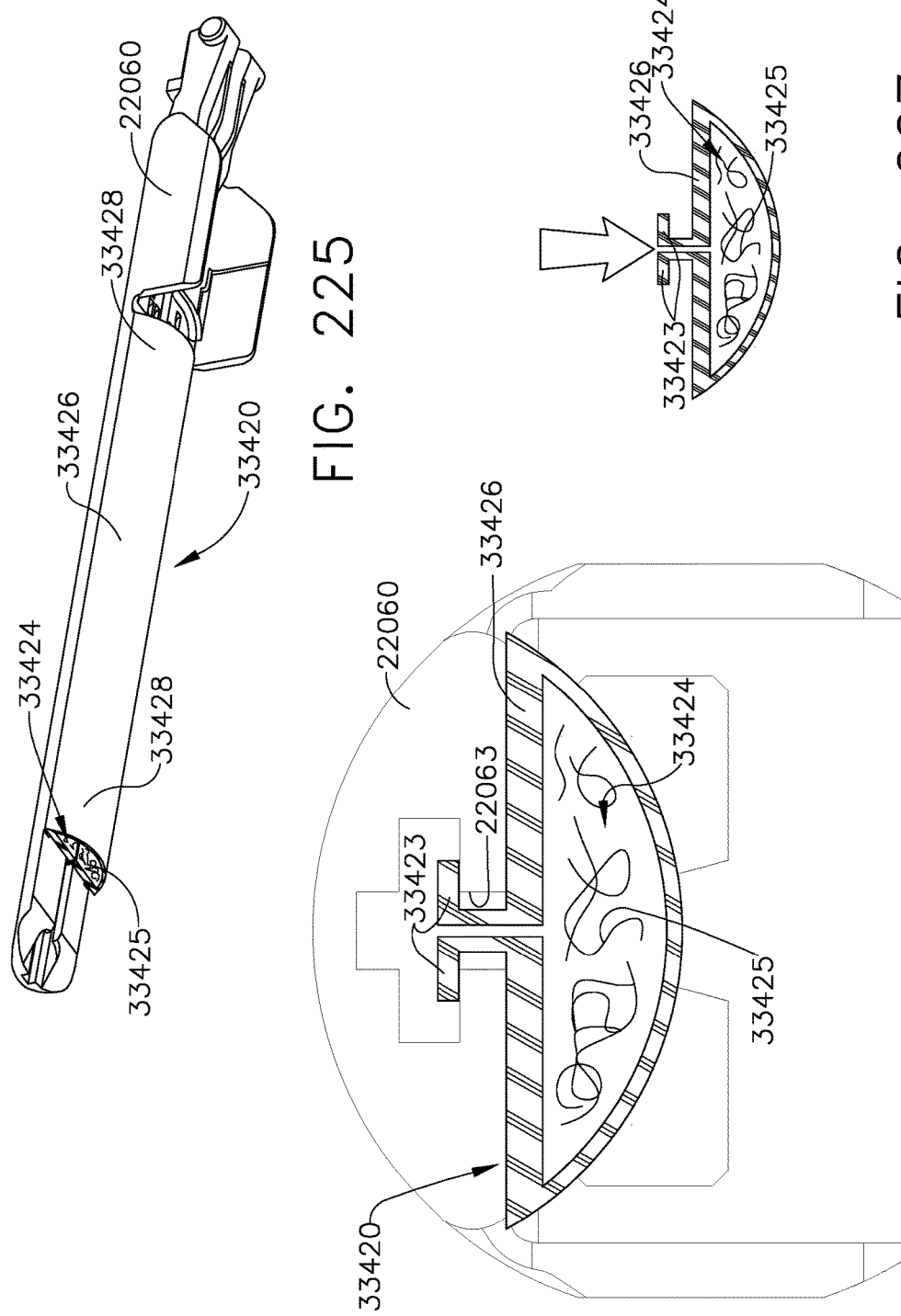

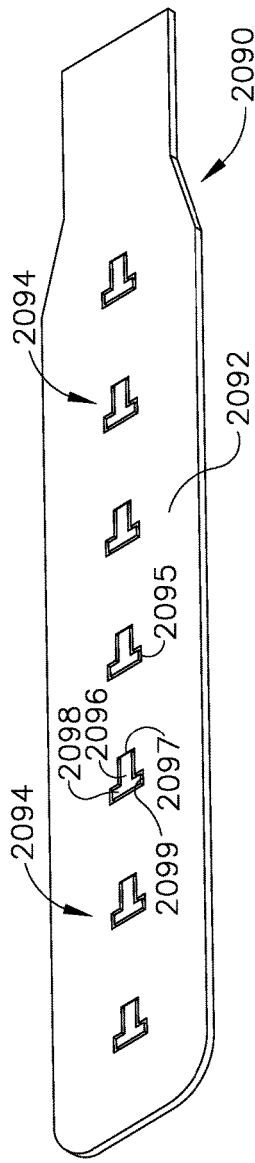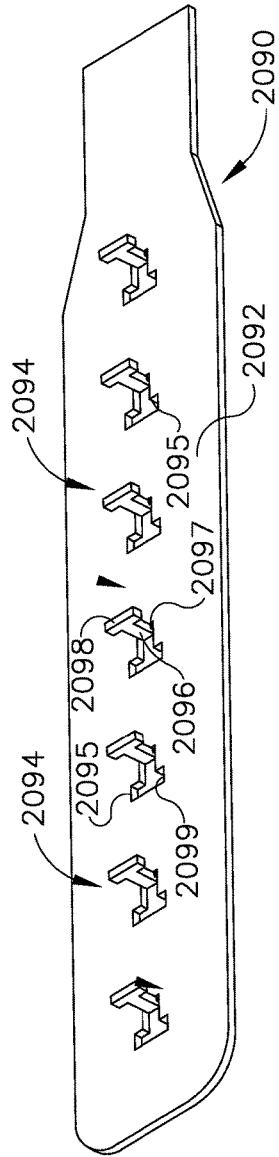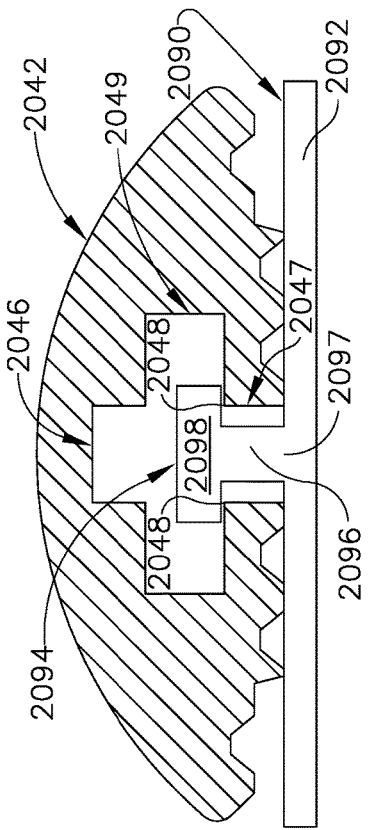

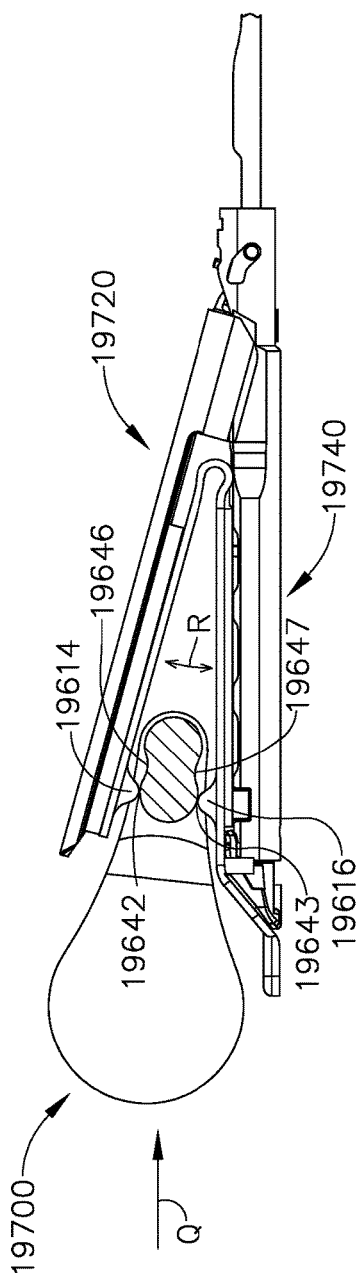
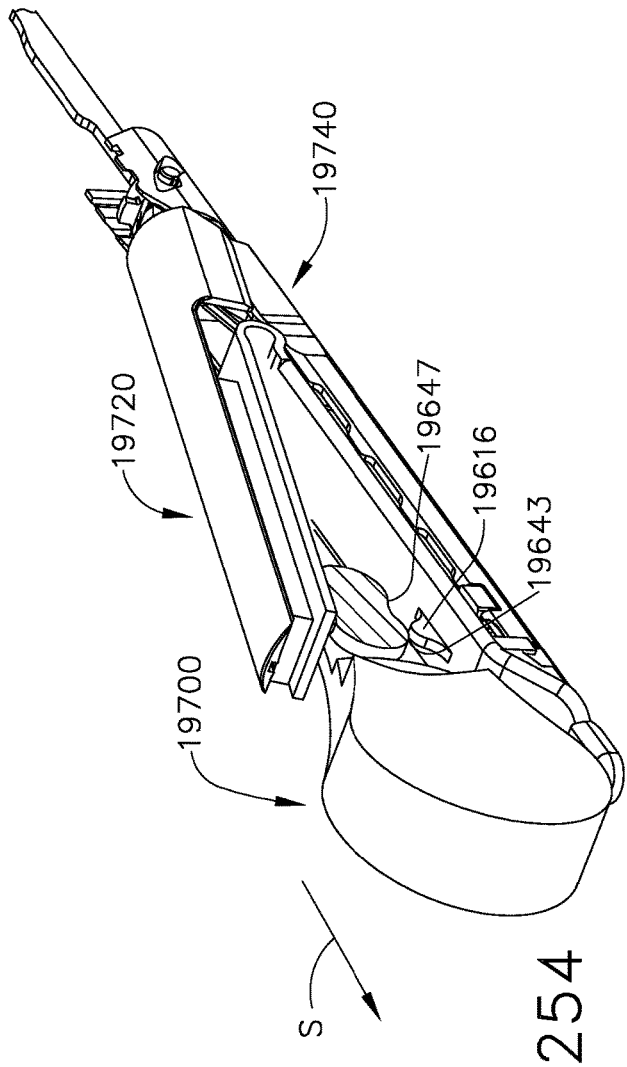
FIG. 253
FIG. 254

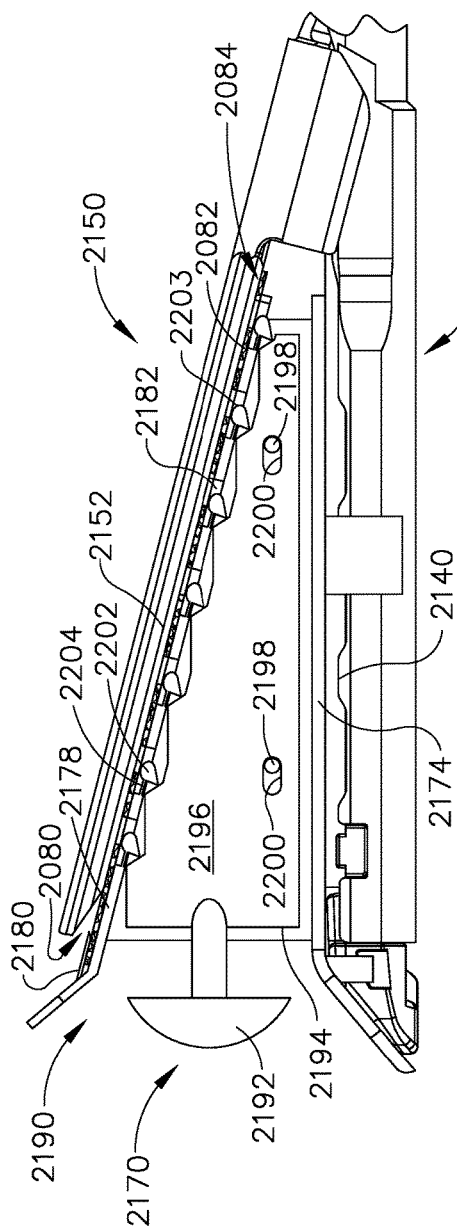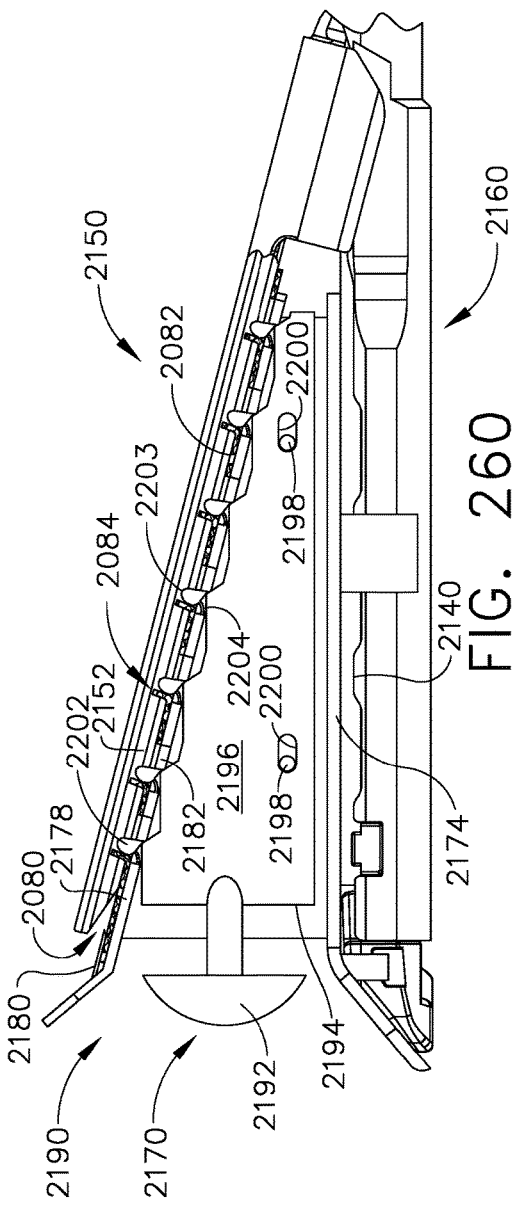

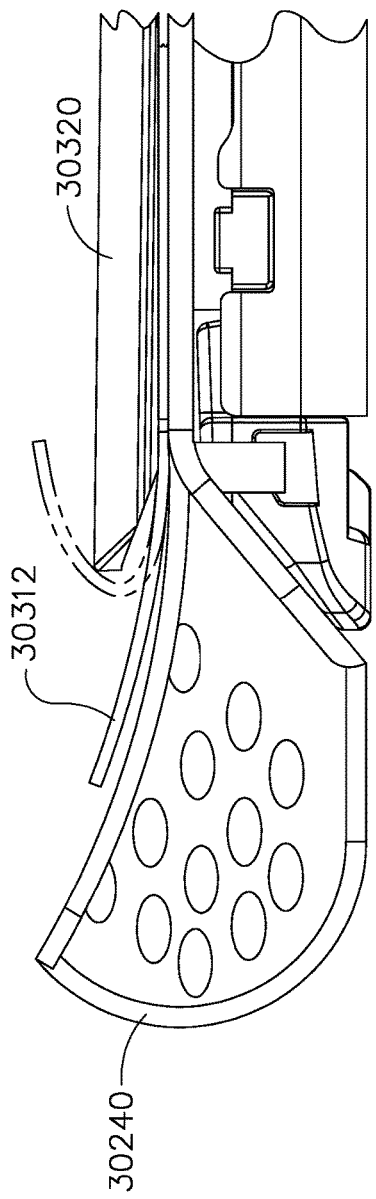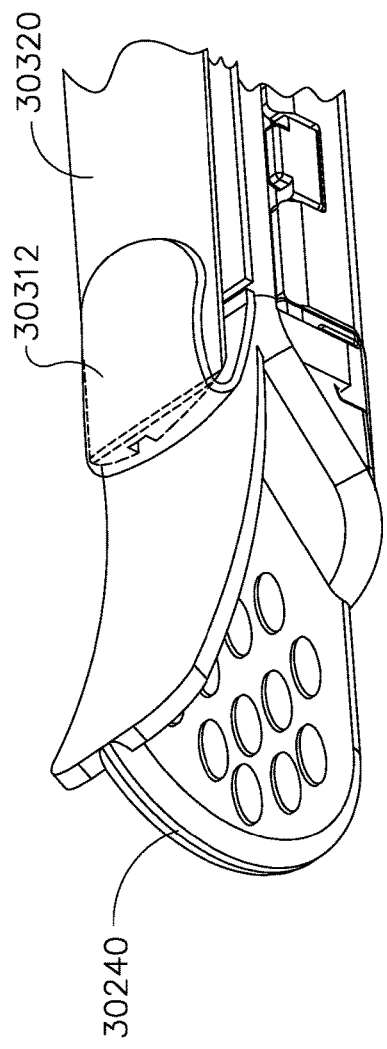

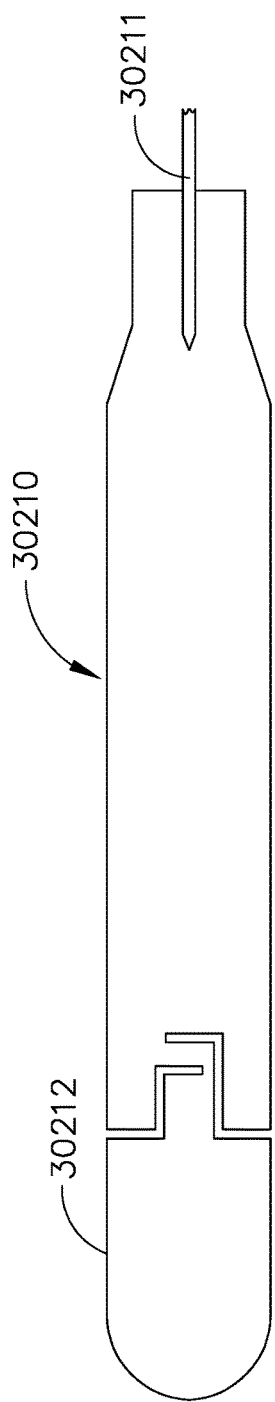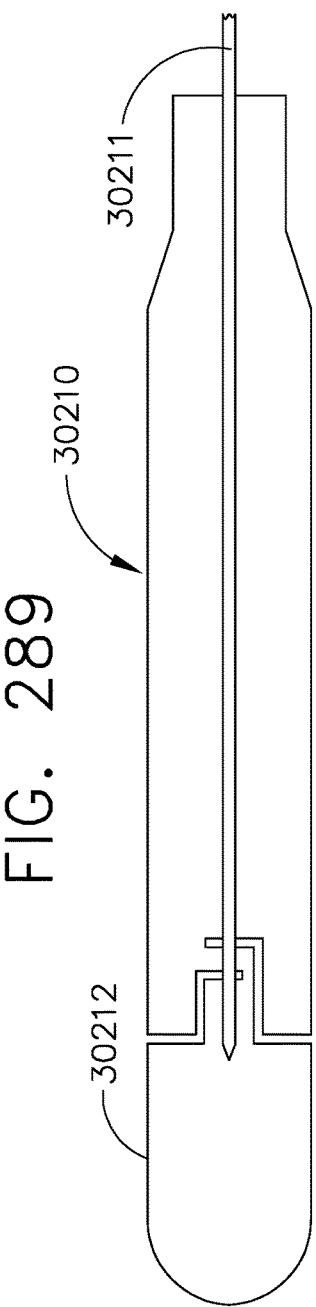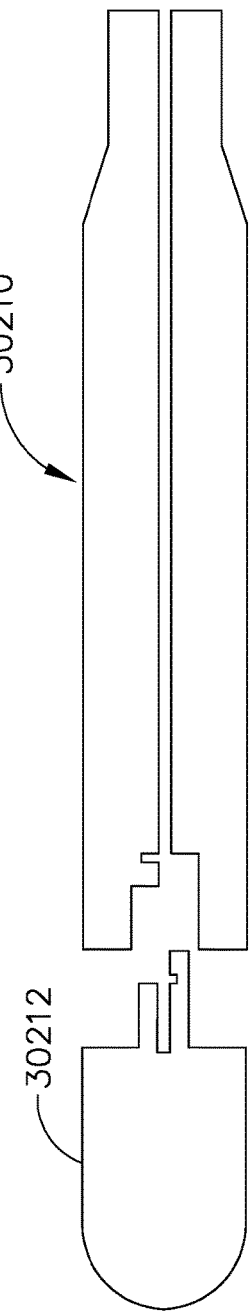

FASTENER CARTRIDGE COMPRISING A RELEASABLE TISSUE THICKNESS COMPENSATOR

CROSS REFERENCE TO RELATED APPLICATIONS

This non-provisional patent application is a continuation-in-part application under 35 U.S.C. §120 of U.S. patent application Ser. No. 13/097,907, entitled COMPRESSIBLE STAPLE CARTRIDGE ASSEMBLY, filed on Apr. 29, 2011, now U.S. Patent Application Publication No. 2012/0080338, which is a continuation-in-part application under 35 U.S.C. §120 of U.S. patent application Ser. No. 12/894,360, entitled SURGICAL STAPLING INSTRUMENT WITH A VARIABLE STAPLE FORMING SYSTEM, filed on Sep. 30, 2010, now U.S. Pat. No. 9,113,862, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 13 is a right side view in elevation of an alternative anti-backup release mechanism with the linked rack in a retracted position and the anti-backup release lever proximally positioned with the anti-backup plate engaged to the firing rod;

FIG. 14 is a right detail side view in elevation of the aft gear, automatic retraction cam wheel and distal-most link of FIG. 13;

FIG. 19 is a perspective view of a two-piece knife and firing bar ("E-beam") of the staple applying assembly of FIG. 16;

FIG. 20 is a perspective view of a wedge sled of a staple cartridge of a staple applying assembly;

FIG. 24 is a left side view in elevation taken generally along the longitudinal axis of line 24-24 of a closed staple applying assembly of FIG. 16 to include center contact points between the two-piece knife and wedge sled but also laterally offset to show staples and staple drivers within the staple cartridge;

FIG. 25 is a left side detail view in elevation of the staple applying assembly of FIG. 24 with the two-piece knife retracted slightly more as typical for staple cartridge replacement;

FIG. 39 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 40 is another cross-sectional view of the anvil and the staple cartridge of FIG. 39 illustrating the anvil in an open position after the firing sequence has been completed;

FIG. 42 is a cross-sectional elevational view of a staple cartridge comprising a rigid support portion and a compressible tissue thickness compensator illustrating the staples in an unfired position;

FIG. 43 is a detail view of the staple cartridge of FIG. 42;

FIG. 47 is an elevational view of the anvil and staple cartridge of FIG. 45 illustrating tissue having different thicknesses positioned between the anvil and the staple cartridge;

FIG. 48 is a detail view of the anvil and staple cartridge of FIG. 45 as illustrated in FIG. 47;

FIG. 49 is a diagram illustrating a tissue thickness compensator which is compensating for different tissue thickness captured within different staples;

FIG. 50 is a diagram illustrating a tissue thickness compensator applying a compressive pressure to one or more vessels that have been transected by a staple line;

FIG. 51 is a diagram illustrating tissue captured within a staple;

FIG. 52 is a diagram illustrating thick tissue and a tissue thickness compensator captured within a staple;

FIG. 53 is a diagram illustrating thin tissue and a tissue thickness compensator captured within a staple;

FIG. 54 is a diagram illustrating tissue having an intermediate thickness and a tissue thickness compensator captured within a staple;

FIG. 64 is an elevational view of the staple cartridge of FIG. 62;

FIG. 65 is a cross-sectional view of the staple cartridge of FIG. 62 taken along a cross-sectional line in FIG. 64 illustrating the firable attachment members in an unfired position;

FIG. 66 is a cross-sectional view of the staple cartridge of FIG. 62 taken along the cross-sectional line in FIG. 64 illustrating the firable attachment members in a fired, broken, position;

FIG. 82 is a cross-sectional plan view of the staple cartridge of FIG. 81A, showing a cutting blade for severing the distal end of the layer arranged in a distal cavity in the staple cartridge, wherein the cutting blade is undeployed, and wherein staples are omitted for purposes of clarity;

FIG. 83 is a cross-sectional plan view of the staple cartridge of FIG. 81A, wherein the cutting blade for severing the distal end of the layer is deployed, and wherein staples are omitted for purposes of clarity;

FIG. 85A is a partial, plan view of the jaw of FIG. 84, depicting the actuator in a pre-actuated position;

FIG. 85B is a partial, plan view of the jaw of FIG. 84, depicting the actuator in an actuated position;

FIG. 88 is a perspective view of a jaw of an end effector assembly according to various embodiments of the present disclosure, depicting a tissue thickness compensator secured to a cartridge body, and further depicting a firing assembly in an unfired position;

FIG. 89 is a partial, elevation view of the jaw of FIG. 88 with various elements shown in transparency, depicting an actuator extending through the jaw, and further depicting the firing assembly in an unfired position;

FIG. 93A is a perspective view of a fastener cartridge assembly of an end effector assembly according to various embodiments of the present disclosure, depicting a tissue thickness compensator released from a cartridge body of the fastener cartridge assembly;

FIG. 93B is a perspective view of the fastener cartridge assembly of FIG. 93A, depicting the tissue thickness compensator secured to the cartridge body of the staple cartridge assembly;

FIG. 93C is an elevational view of the fastener cartridge assembly of FIG. 93A with various elements removed therefrom, depicting a firing assembly in a pre-fired position;

FIG. 93D is an elevational view of the fastener cartridge assembly of FIG. 93A with various elements removed therefrom, depicting the firing assembly in a partially-fired position;

FIG. 95 is a partial, perspective view of a fastener cartridge assembly of an end effector assembly according to various embodiments of the present disclosure, depicting a tissue thickness compensator released from a cartridge body of the fastener cartridge assembly;

FIG. 96 is a partial, cross-sectional view of the fastener cartridge assembly of FIG. 95, depicting a mount of the tissue thickness compensator held in a bridge of the cartridge body;

FIG. 102 is an elevational view of the staple cartridge applicator assembly of FIG. 101 positioned within a staple cartridge channel and an anvil being closed onto the staple cartridge applicator assembly;

FIG. 103 is an elevational view of the anvil of FIG. 102 in a re-opened position and the staple cartridge applicator of FIG. 101 being removed from the end effector;

FIG. 104 is a cross-sectional view of tissue positioned intermediate the upper tissue thickness compensator and the lower tissue thickness compensator of FIG. 101;

FIG. 105 is a cross-sectional view illustrating the upper tissue thickness compensator and the lower tissue thickness compensator stapled to the tissue and severed by a cutting member;

FIG. 106A is an elevational view of the staple cartridge applicator assembly of FIG. 106 positioned within a staple cartridge channel and an anvil being moved toward the upper tissue thickness compensator;

FIG. 106B illustrates the staple cartridge applicator of FIG. 106 being removed from the end effector after the upper tissue thickness compensator has been engaged with the anvil;

FIG. 107 is a cross-sectional end view of the anvil being moved toward the upper tissue thickness compensator of FIG. 106;

FIG. 108 is a cross-sectional end view of the anvil engaged with the upper tissue thickness compensator;

FIG. 109 is a perspective view of a staple cartridge having a piece of buttress material releasably retained thereto in accordance with one non-limiting embodiment of the present invention;

FIG. 110 is an exploded, perspective view of the staple cartridge and the piece of buttress material of FIG. 109, wherein the piece of buttress material includes a plurality of members extending therefrom;

FIG. 111 is a cross-sectional view taken along line 111-111 in FIG. 109 illustrating the members of FIG. 110 engaged with staple cavities in accordance with one non-limiting embodiment of the present invention;

FIG. 112 is a cross-sectional view of a piece of buttress material including members engaged with staple cavities of a staple cartridge in accordance with one non-limiting embodiment of the present invention;

FIG. 113 is an exploded view of FIG. 112 illustrating the members separated from the staple cavities of the staple cartridge in accordance with one non-limiting embodiment of the present invention;

FIG. 114 is a partial, perspective view of a support portion of a staple cartridge comprising detachable and/or displaceable staple leg guides;

FIG. 115 is a partial, cross-sectional view of the staple cartridge of FIG. 114 illustrating staples being deployed from the staple cartridge;

FIG. 116 is a detail view of the cross-sectional view of FIG. 114 after the staple cartridge has been fired;

Figure 117:
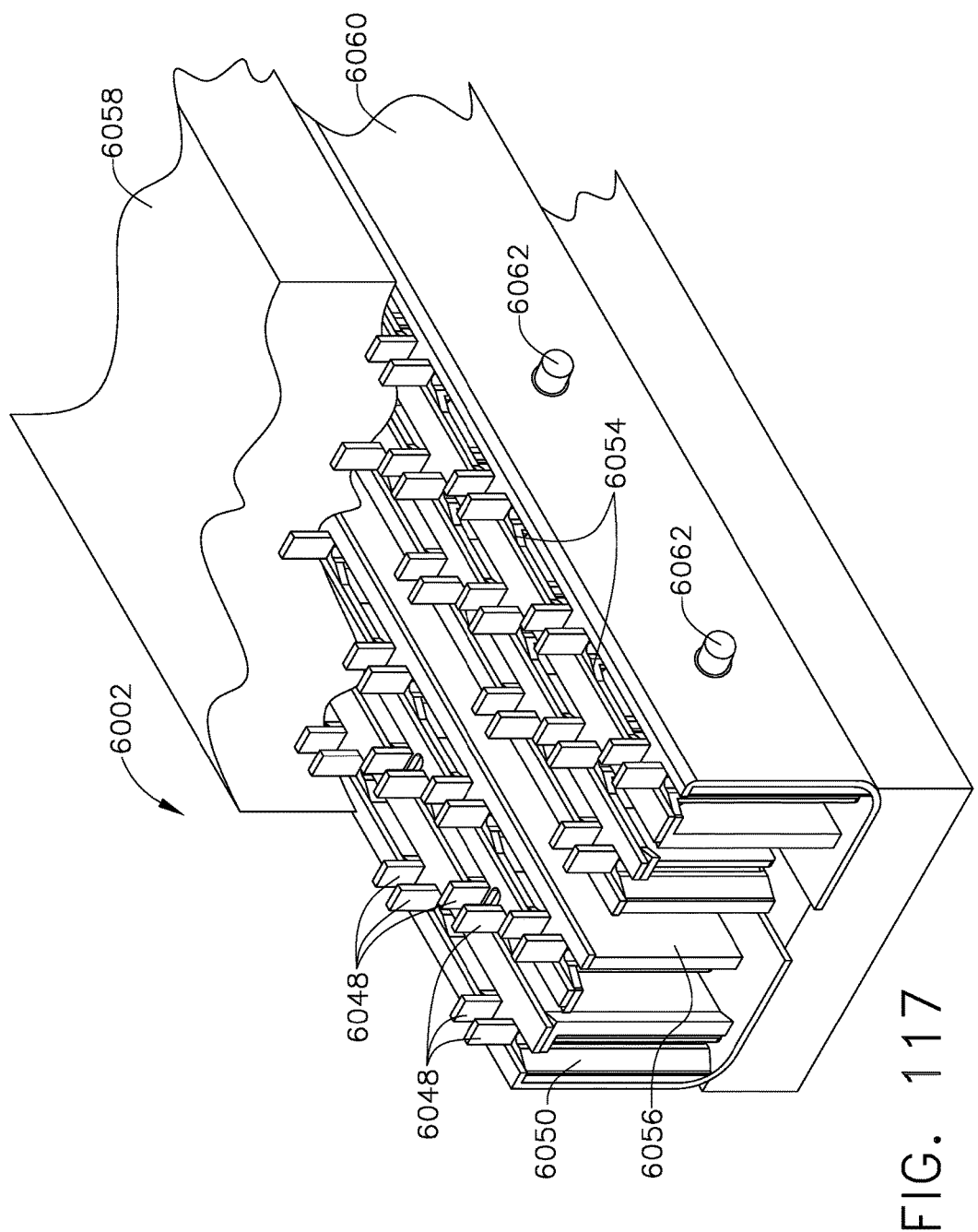
Figure 118:
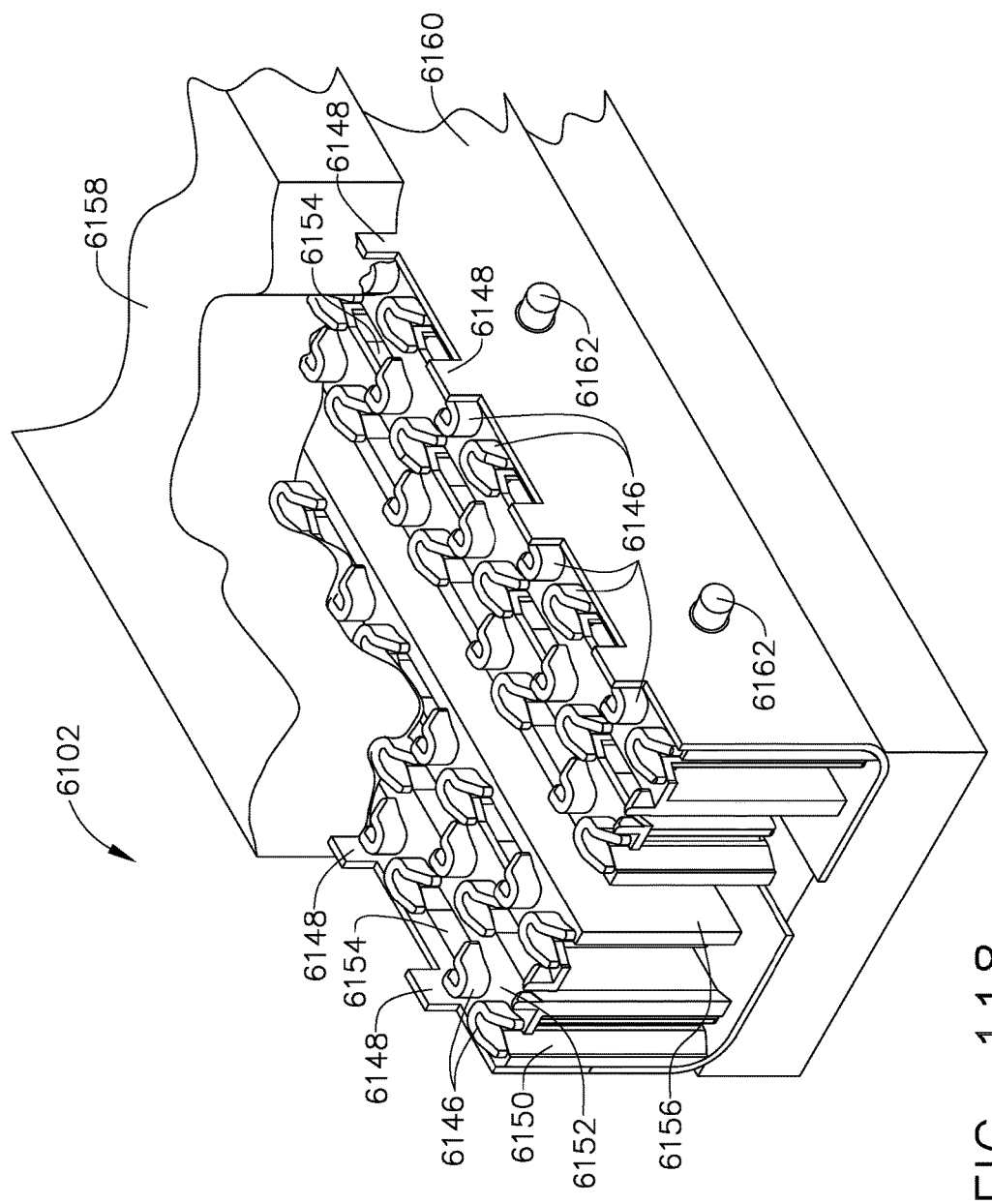
Figure 122:
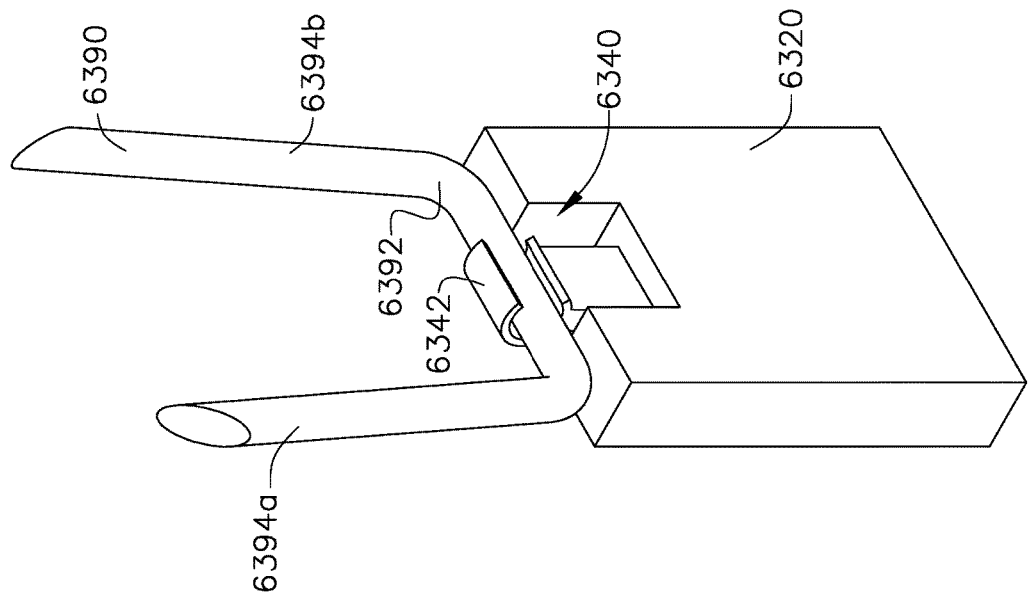
Figure 121:
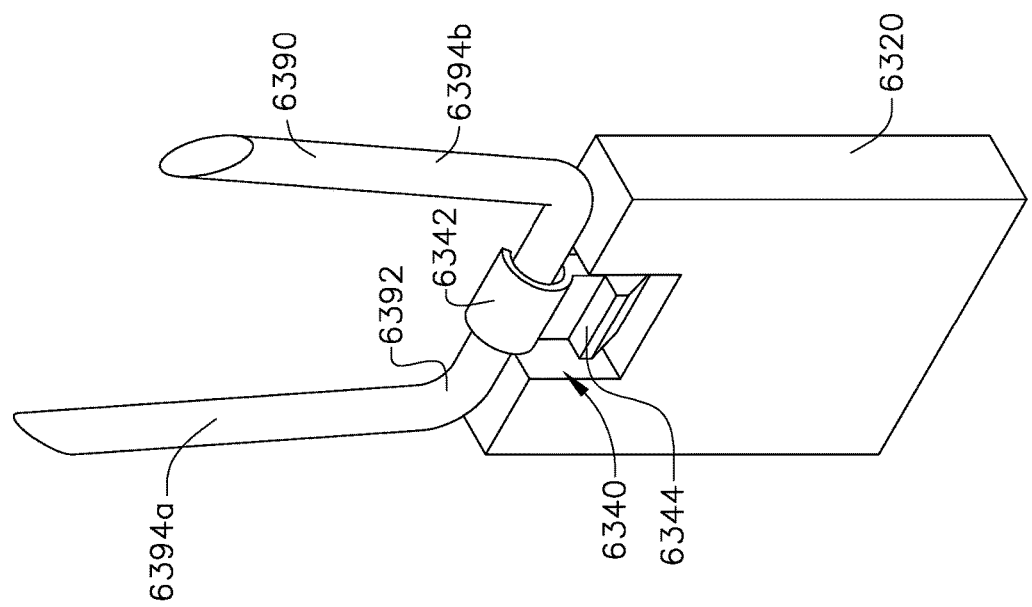
Figure 123:
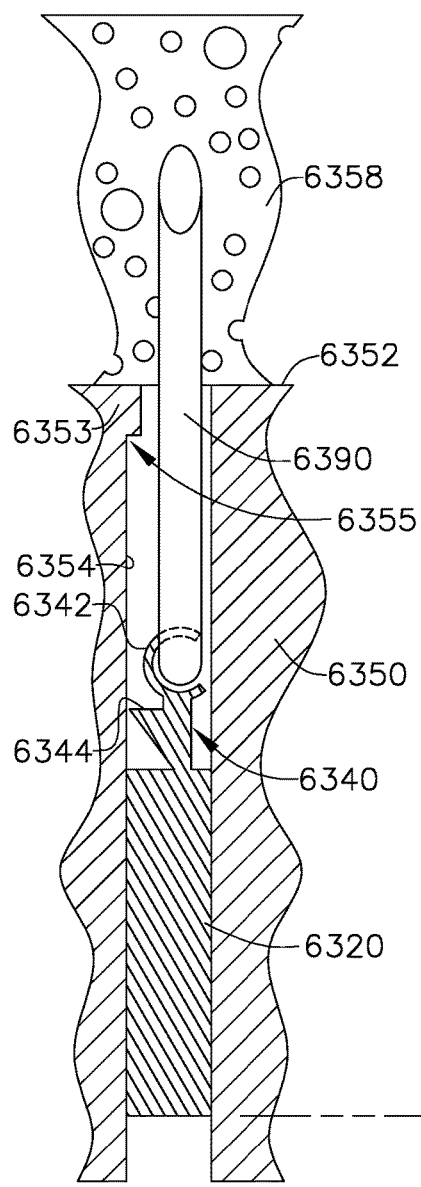
Figure 124:
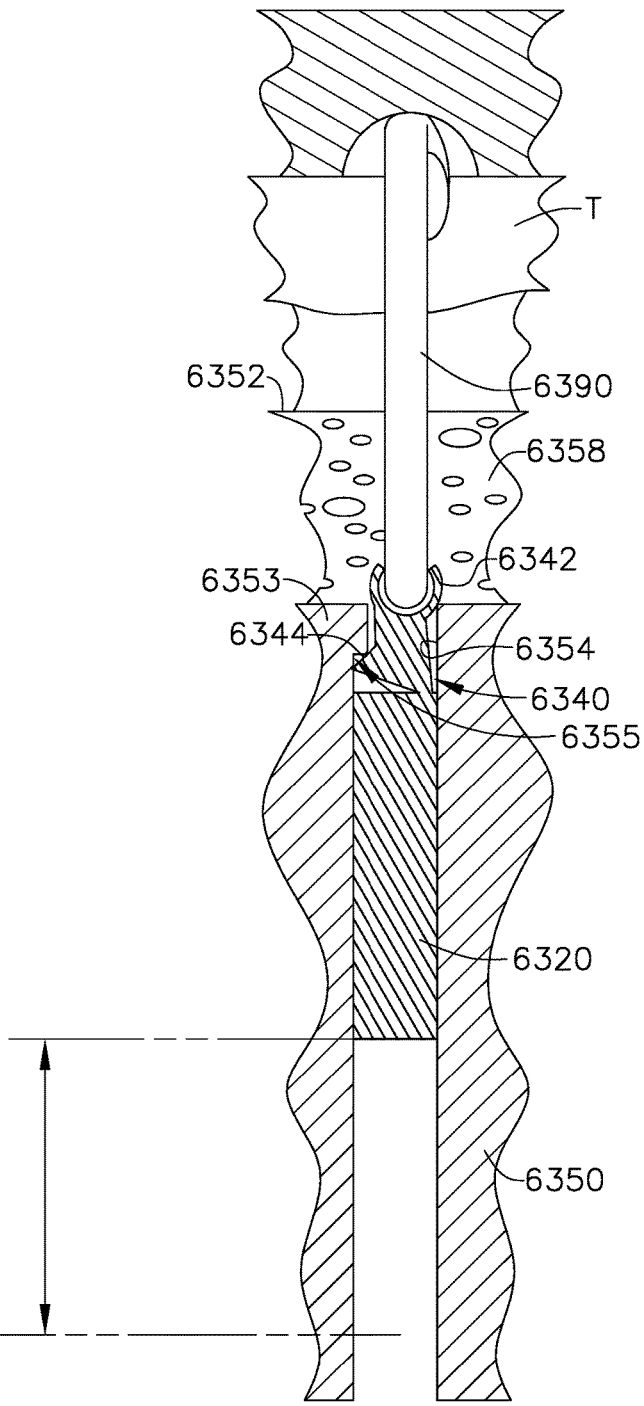
Figure 125:
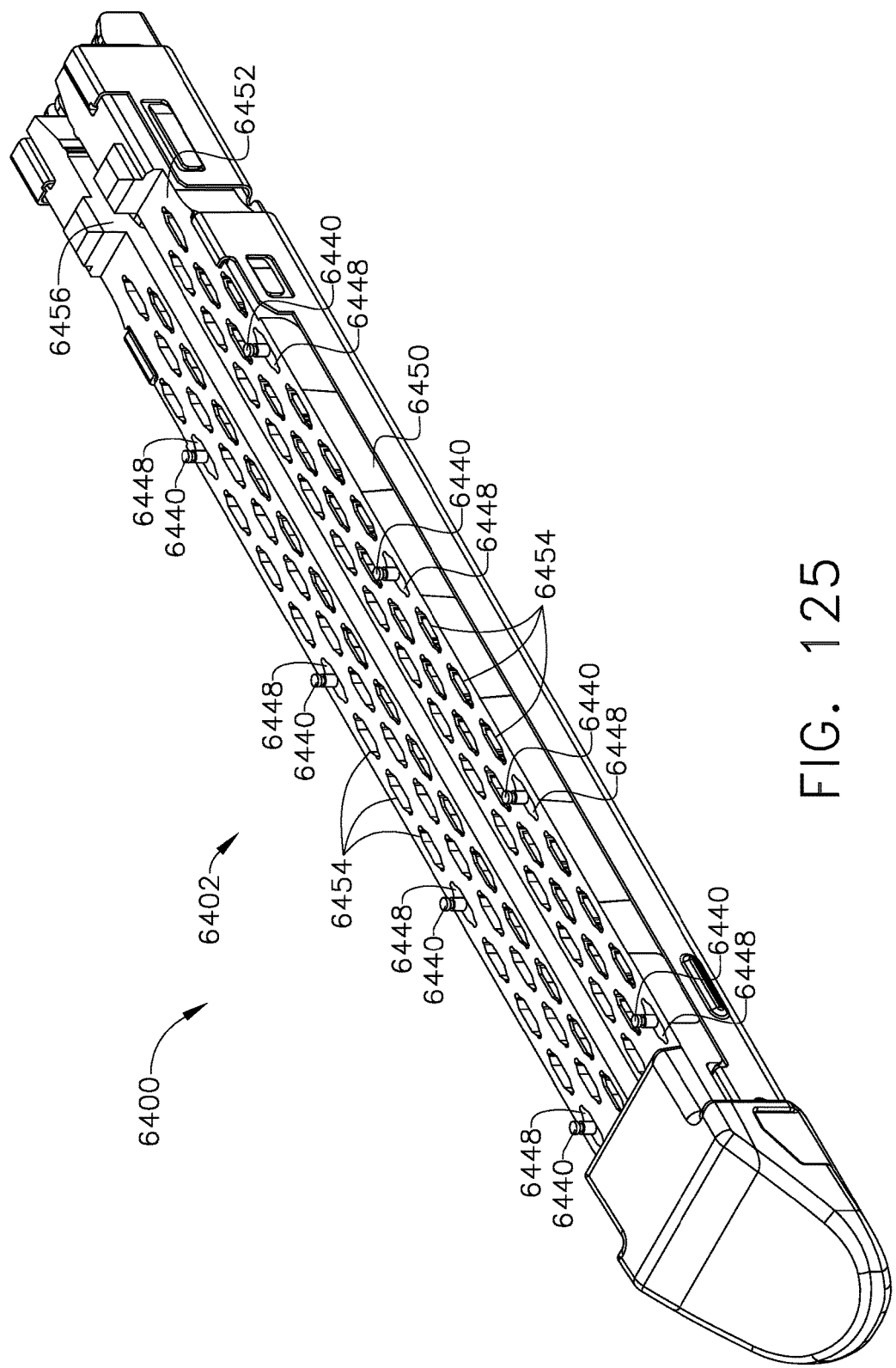
Figure 128:
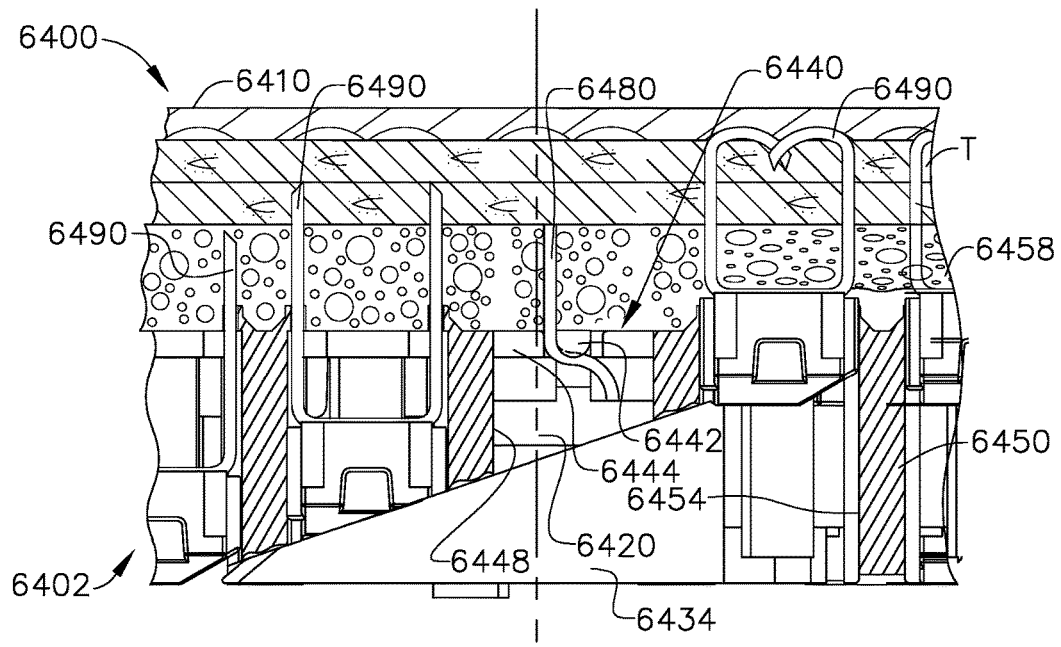
Figure 129:
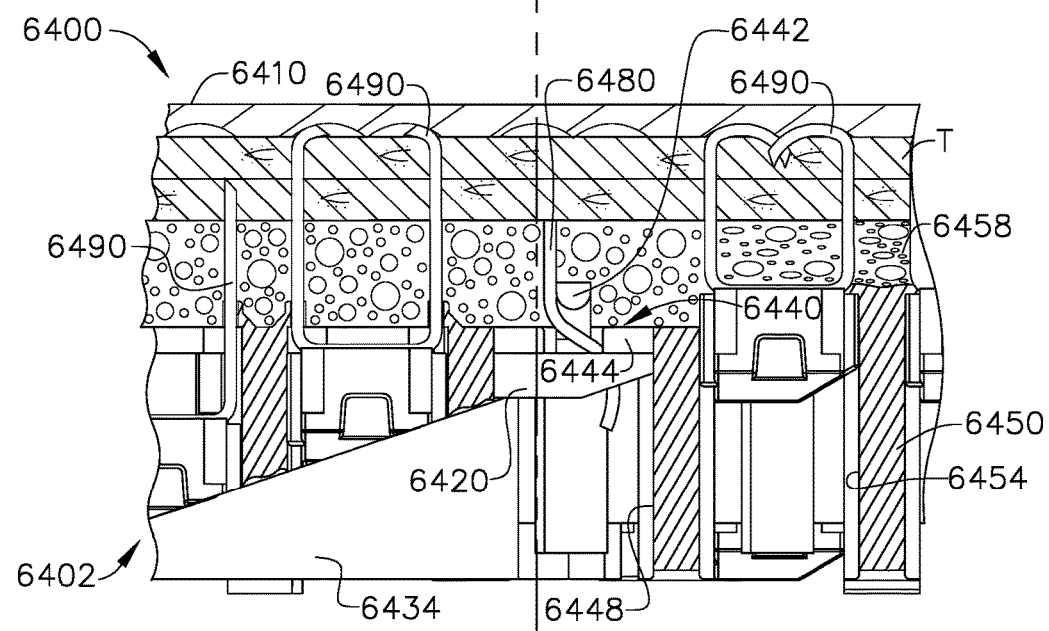
Figure 130:
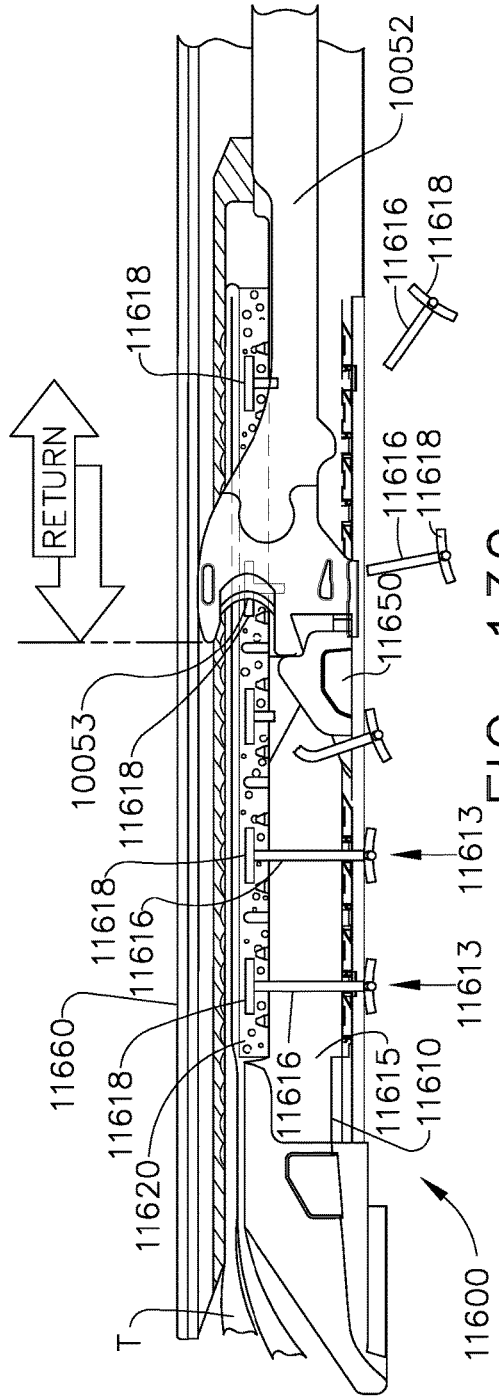
Figure 131:
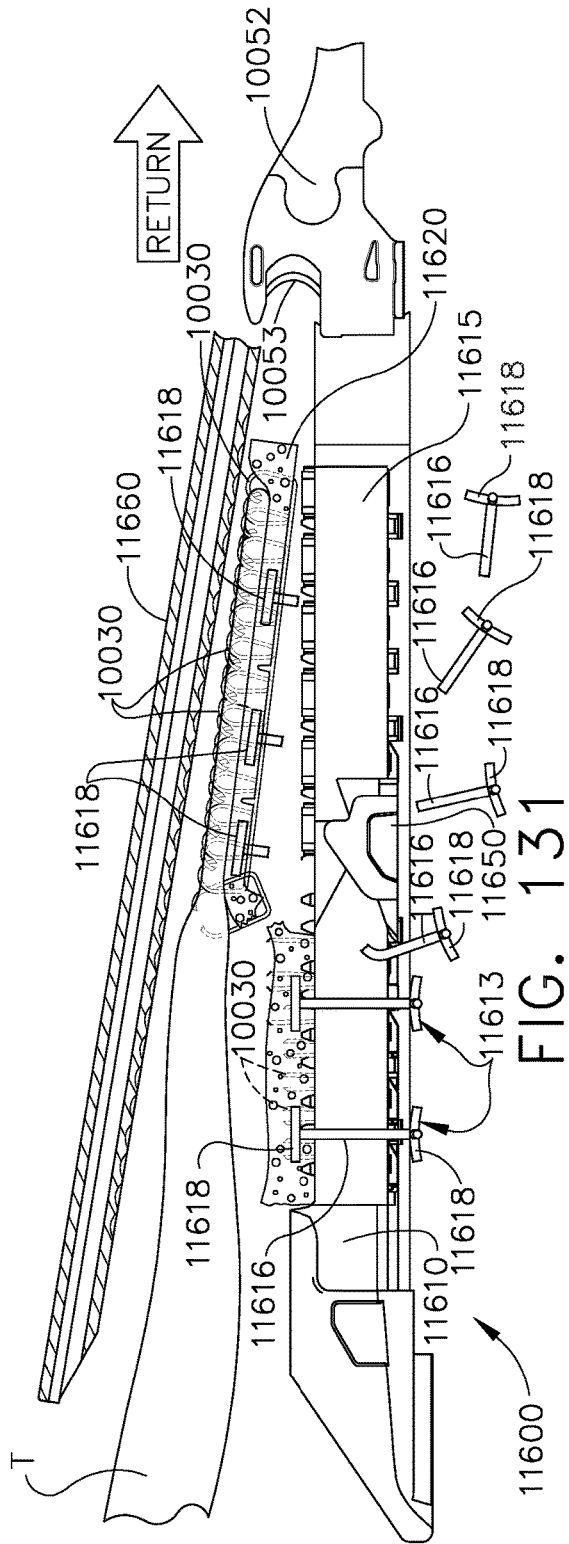
Figure 134:
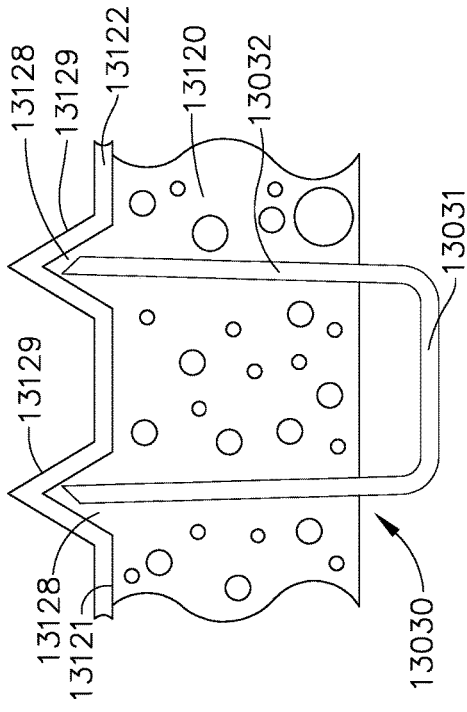
Figure 135:
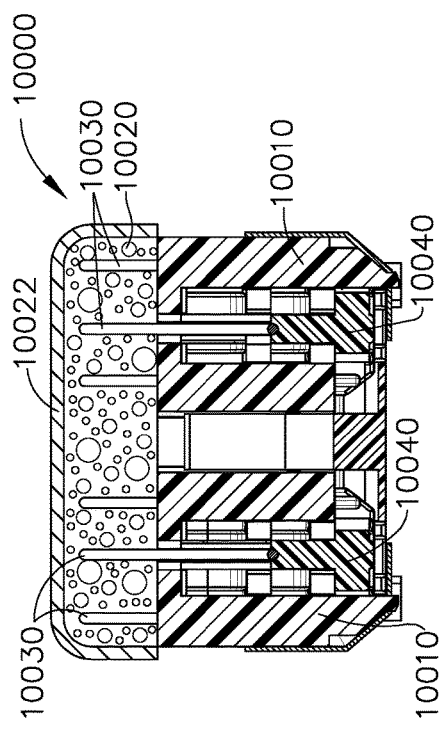
Figure 136:
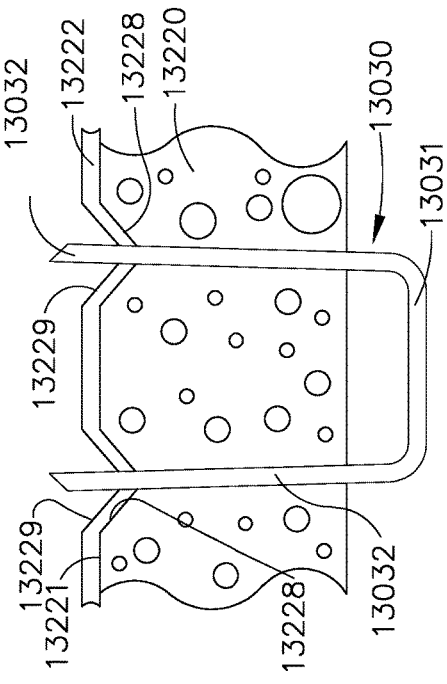
Figure 137:
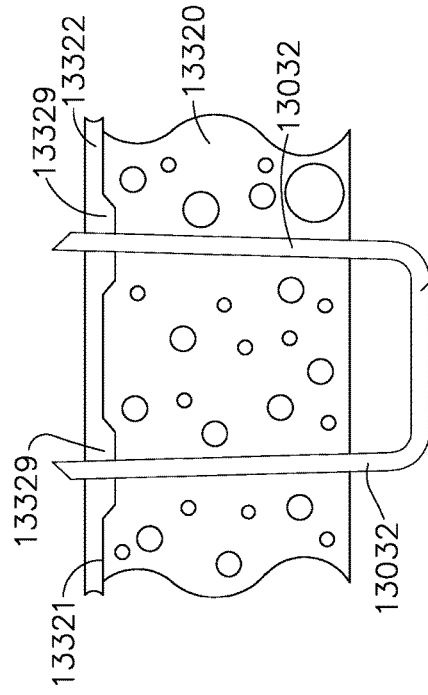
Figure 142:
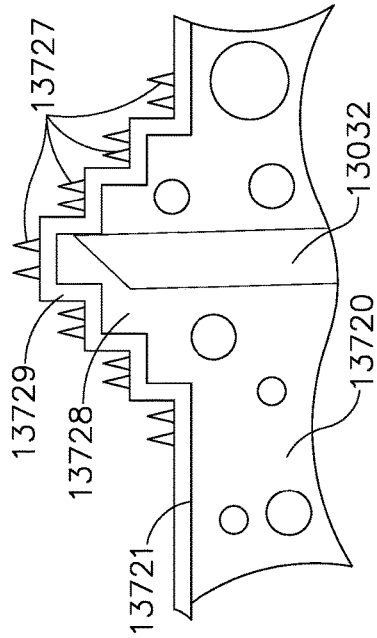
Figure 144:
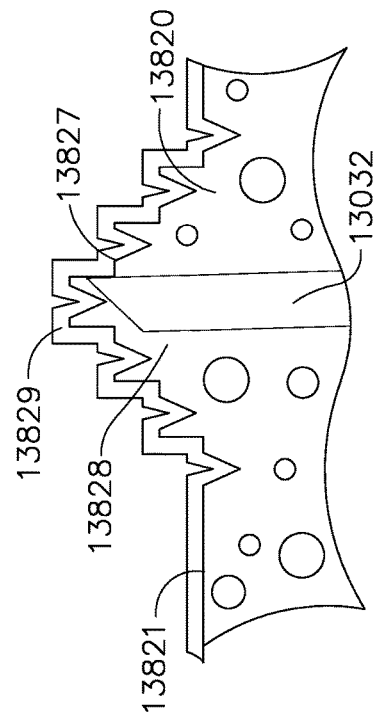
Figure 141:
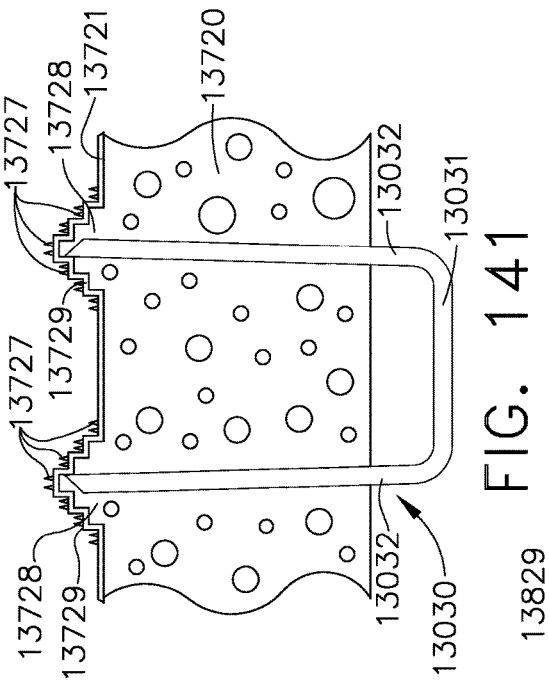
Figure 143:
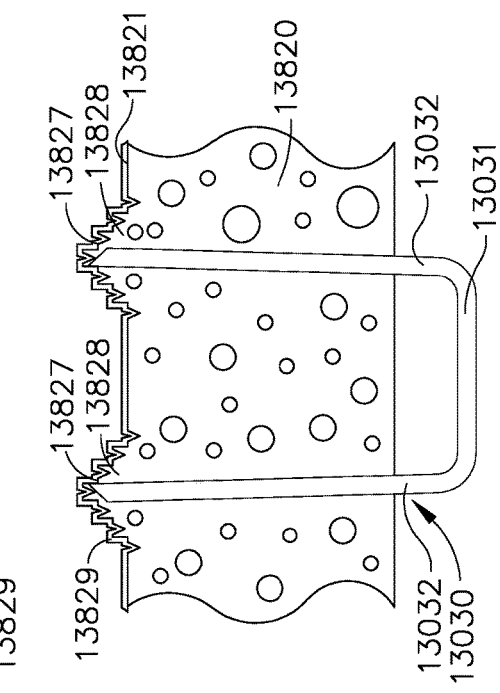
Figure 147:
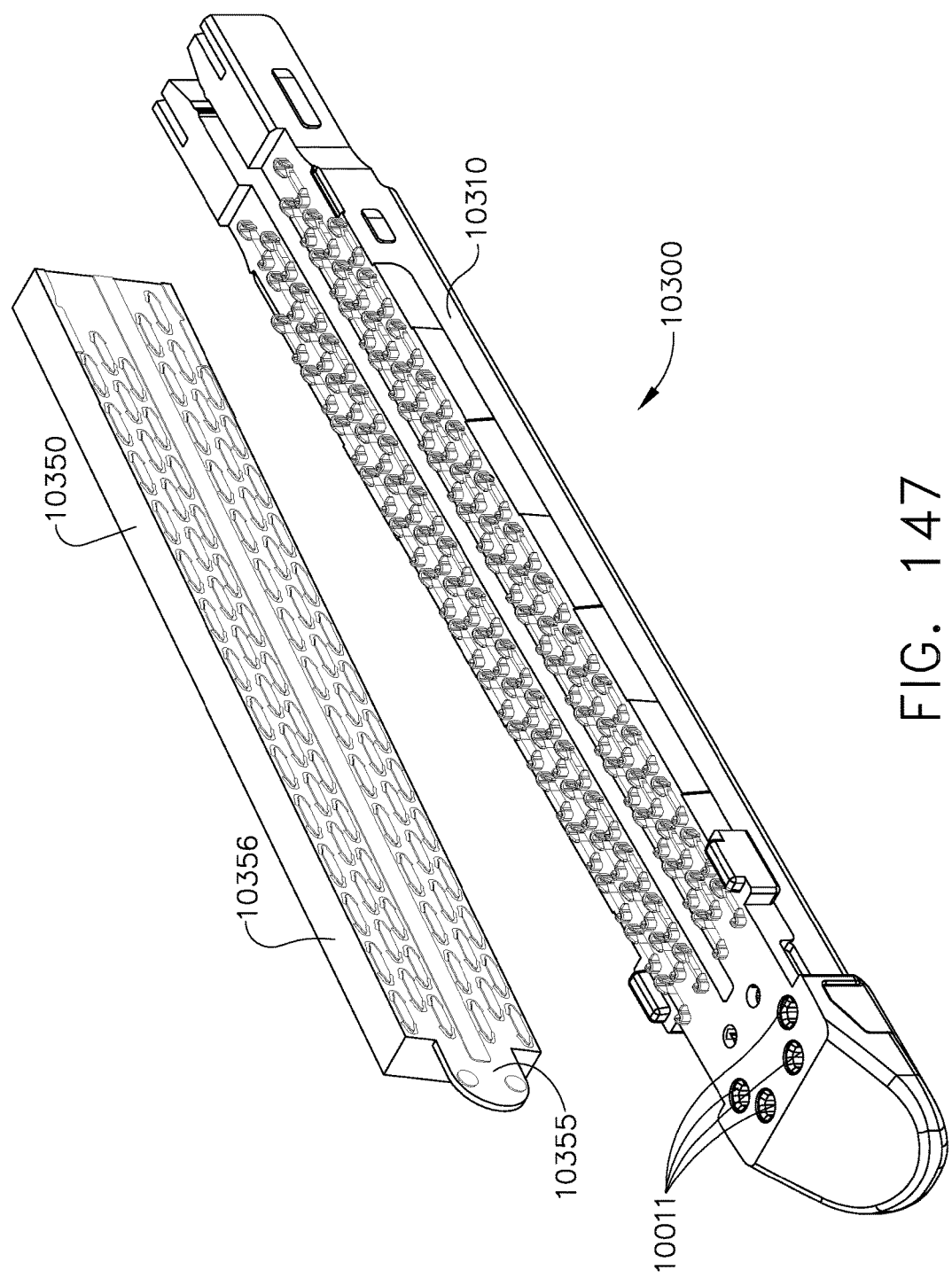
Figure 148:
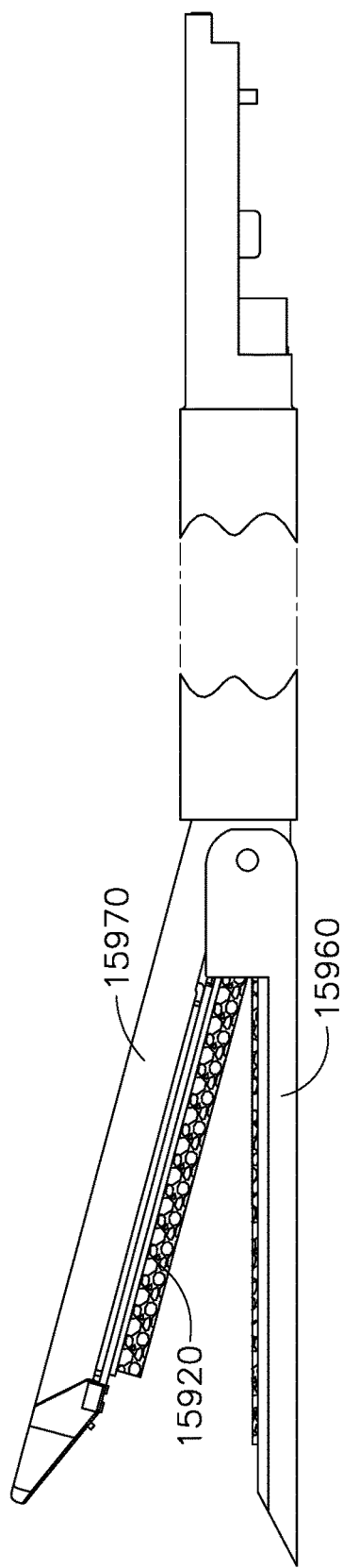
Figures 152, 153:
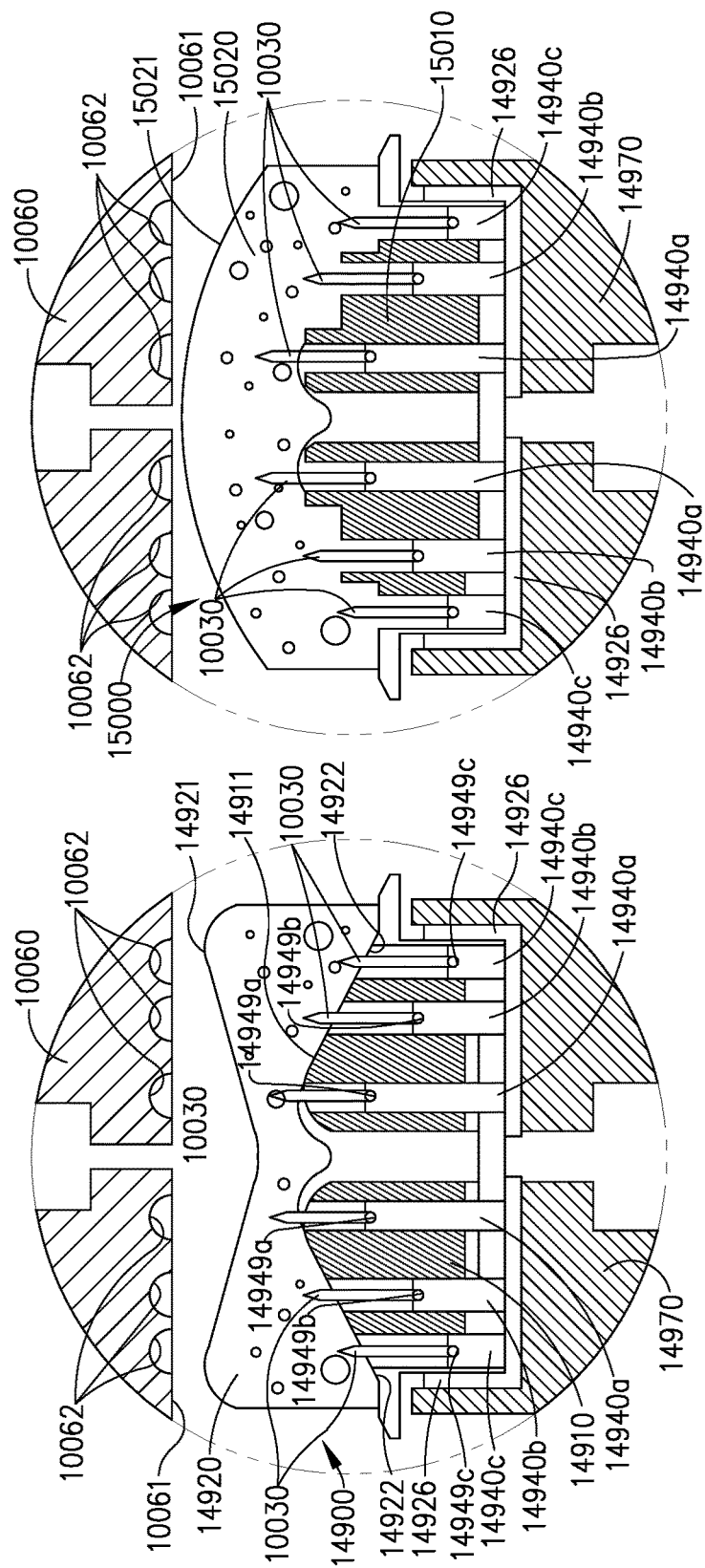
Figure 154:
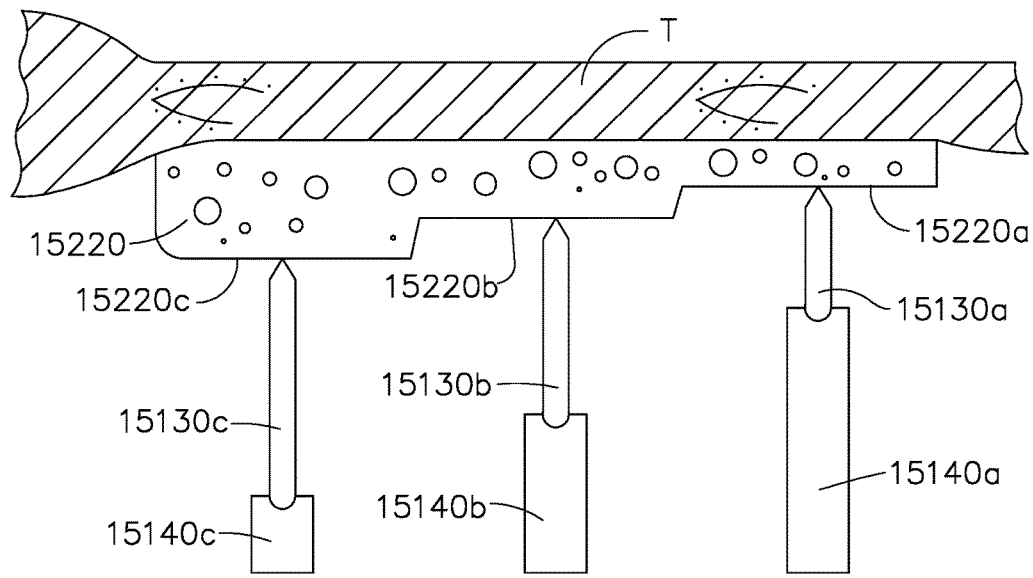
Figure 155:
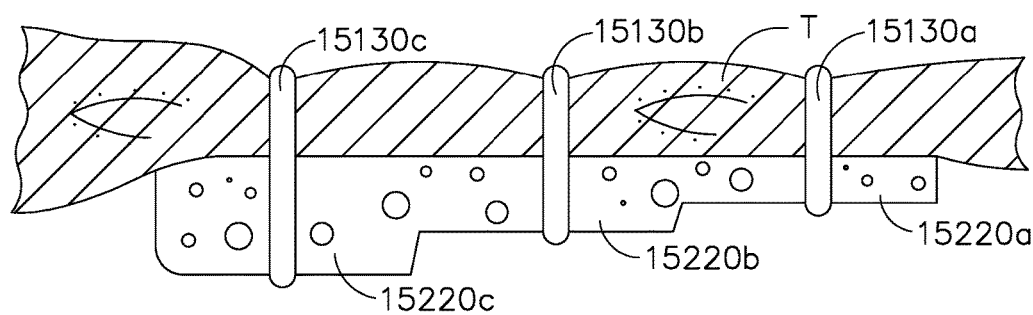
Figure 156:
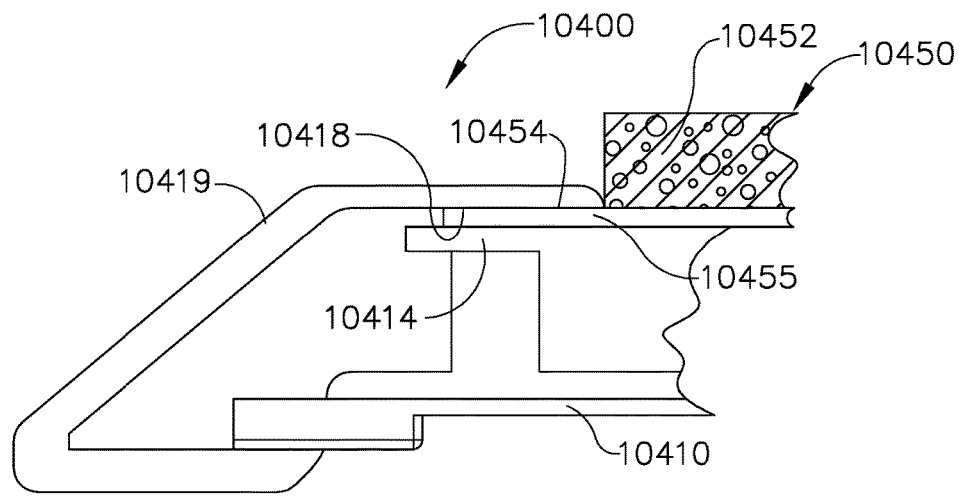
Figure 157:
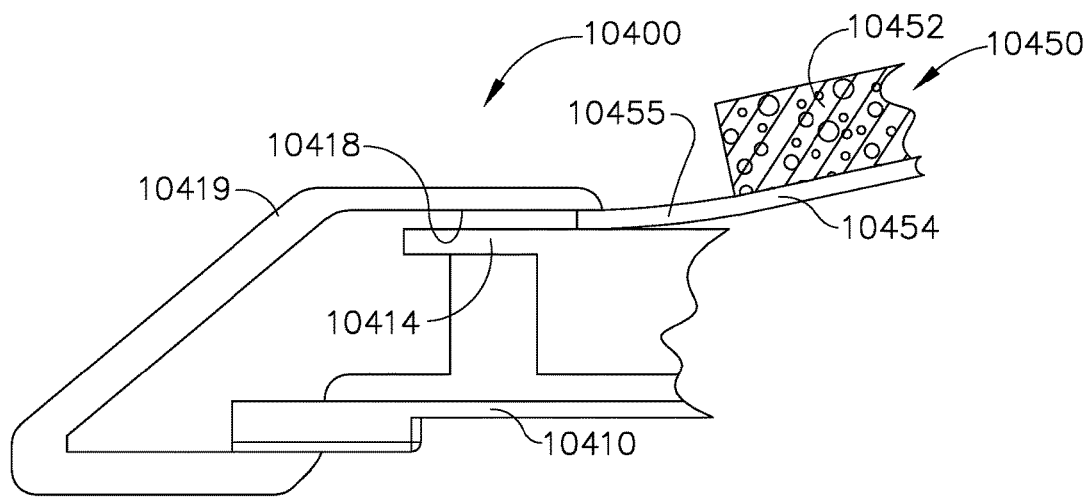
Figure 158:
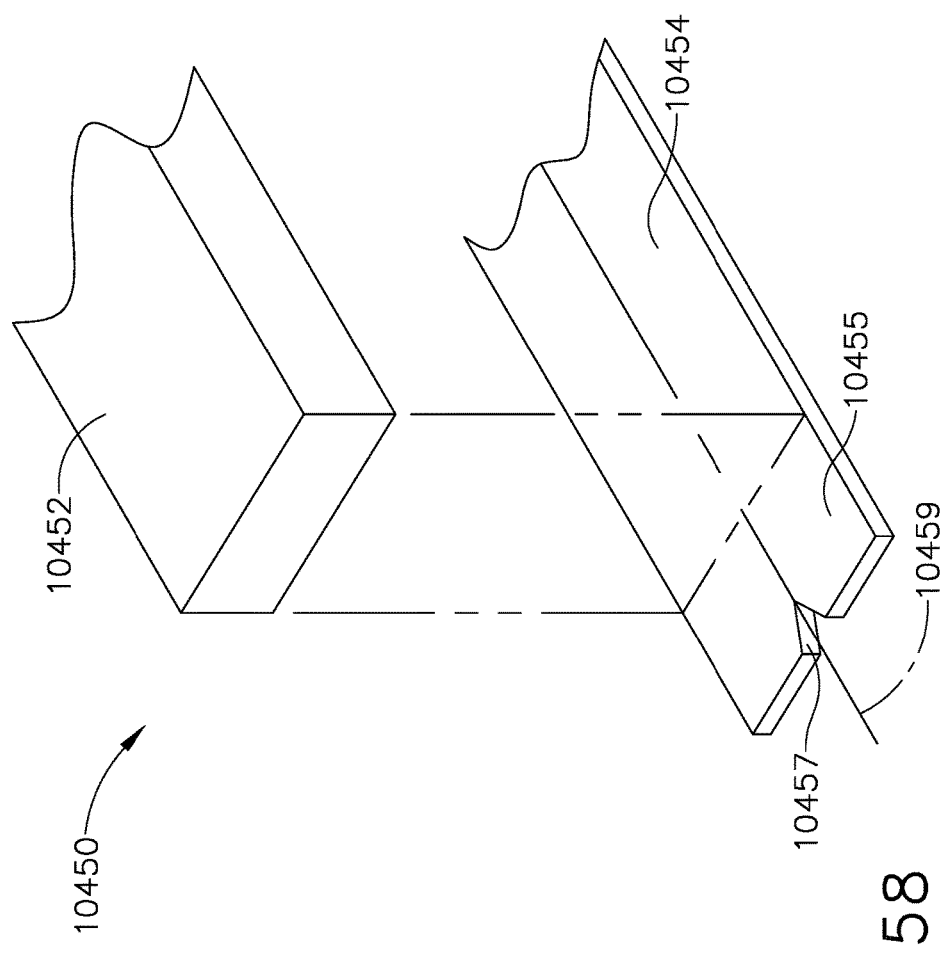
Figure 159:
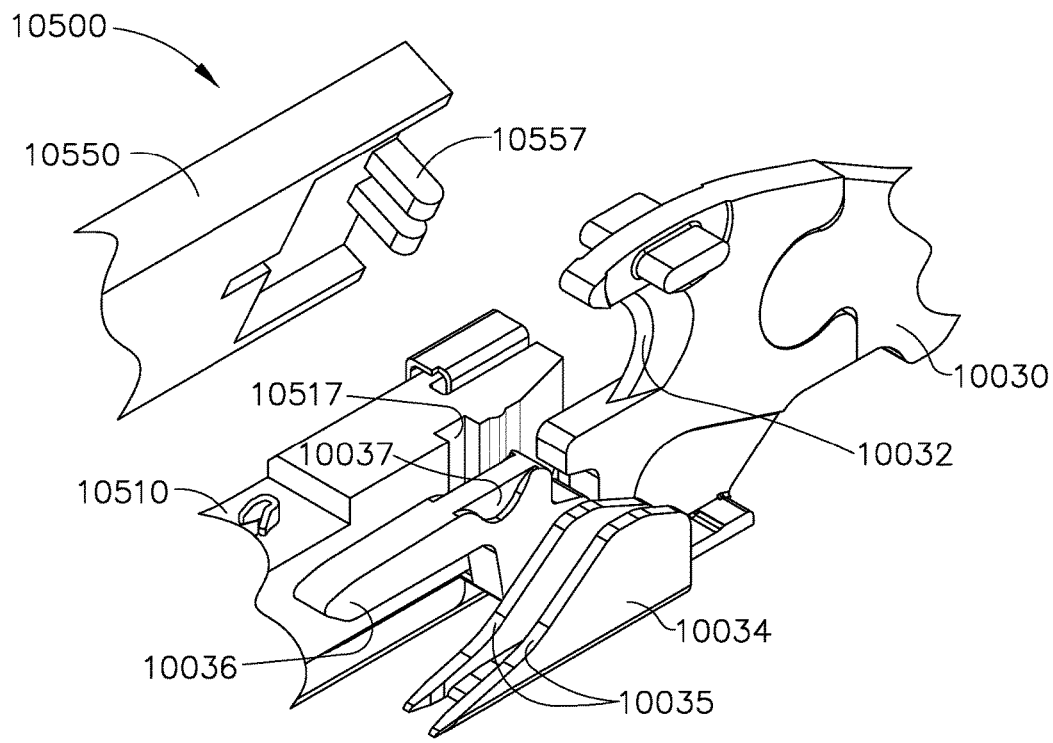
Figure 160:
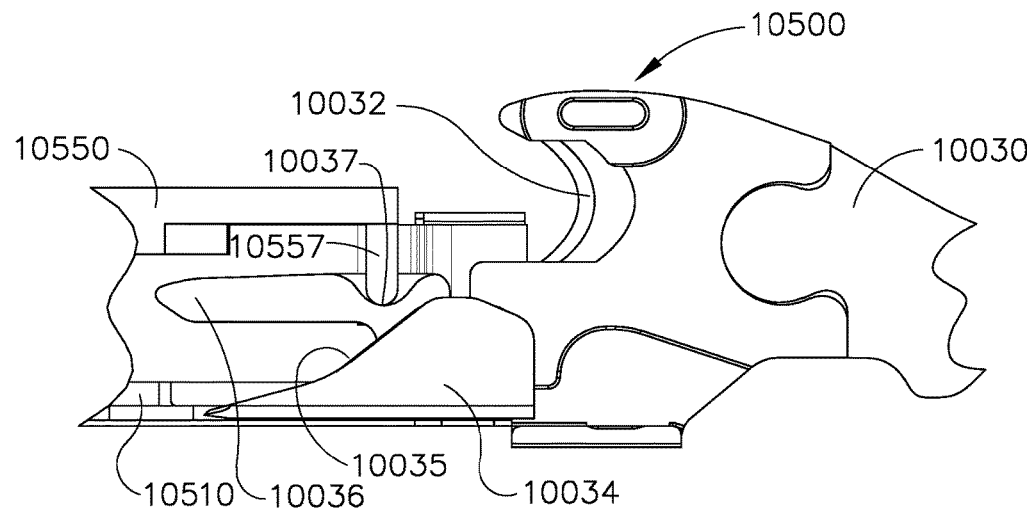
Figure 163:
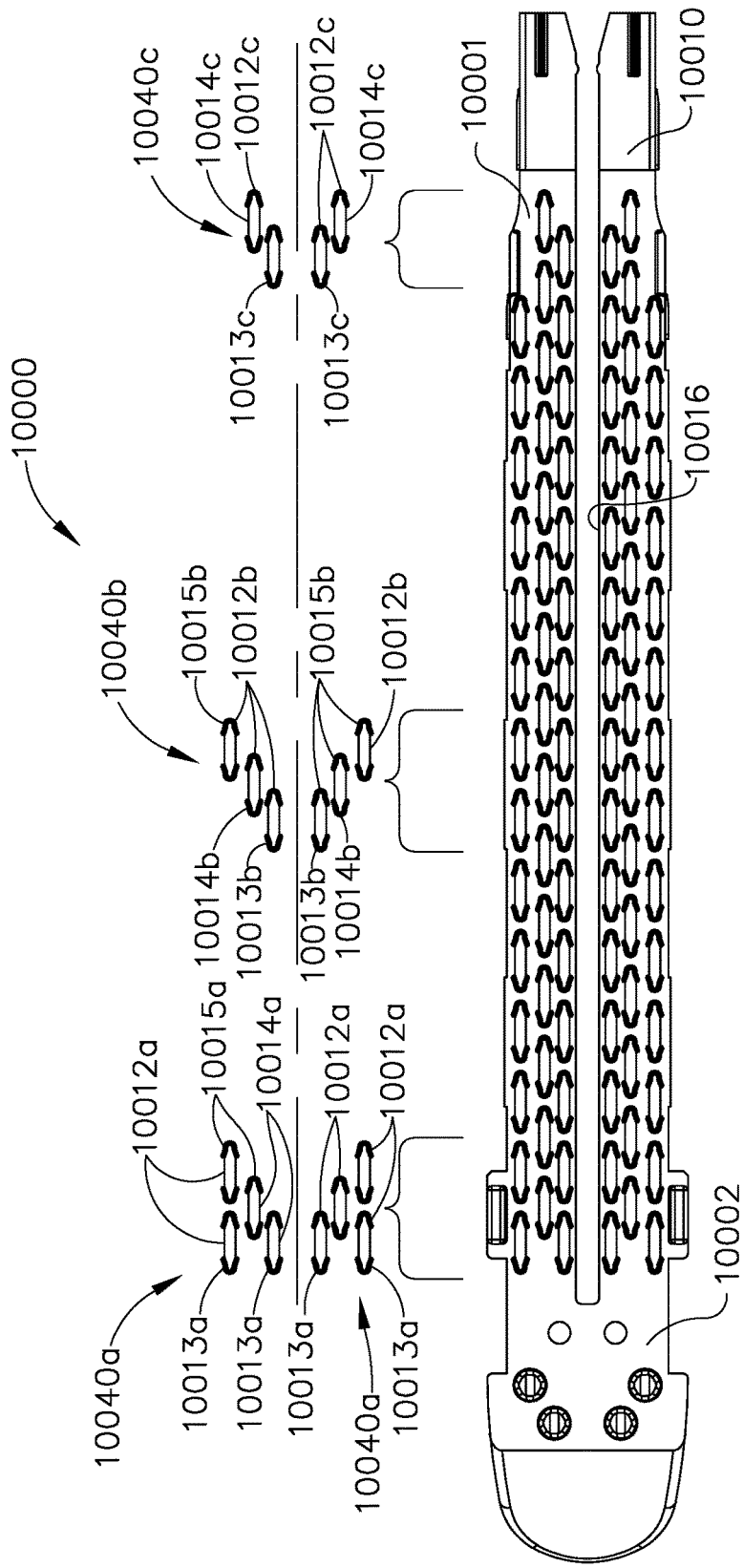
Figure 166:
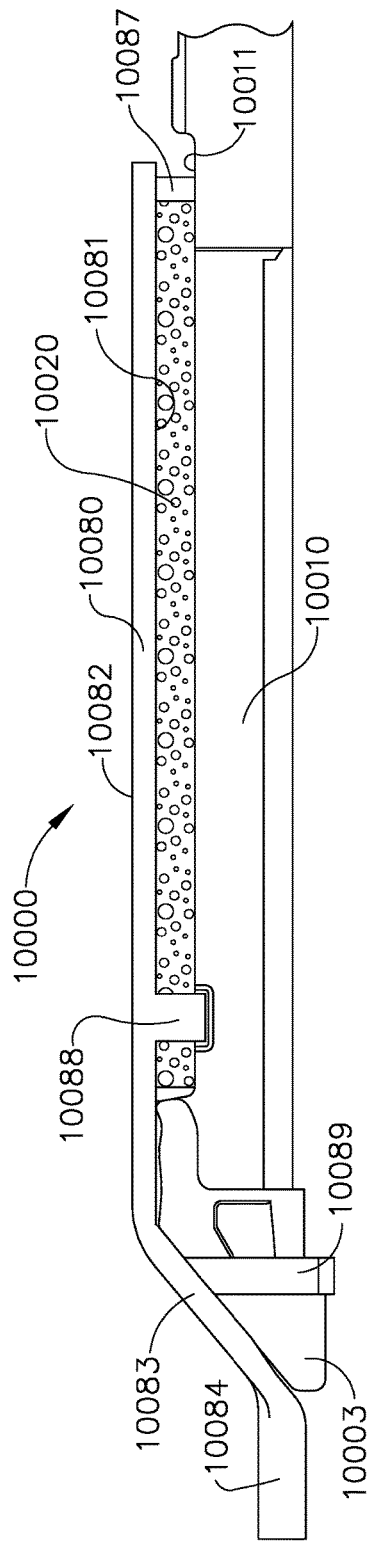
Figure 167:
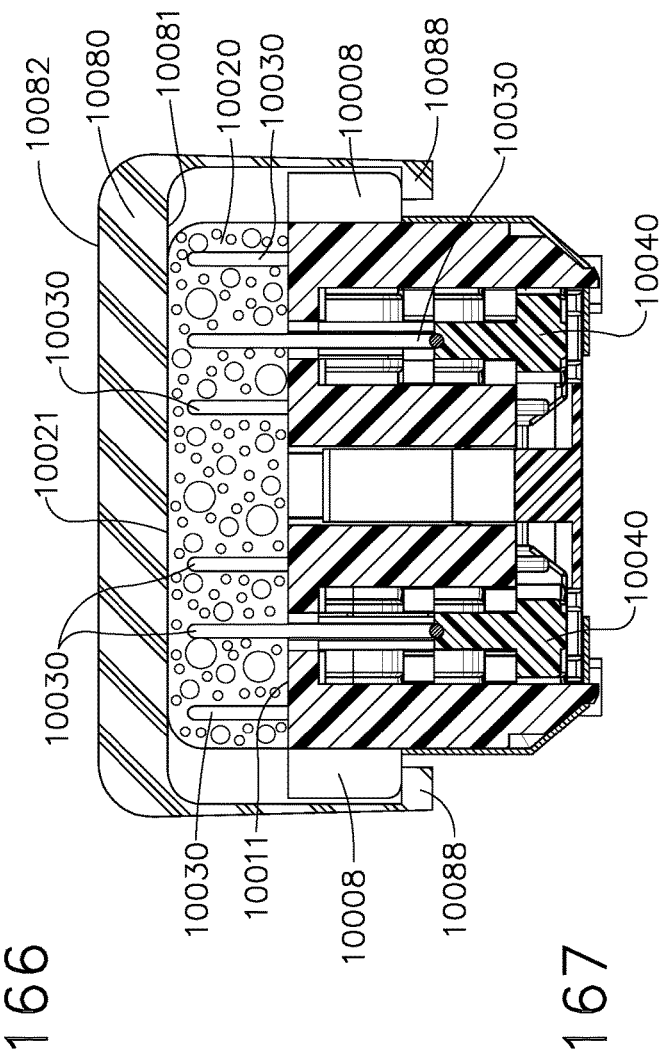
Figure 168:
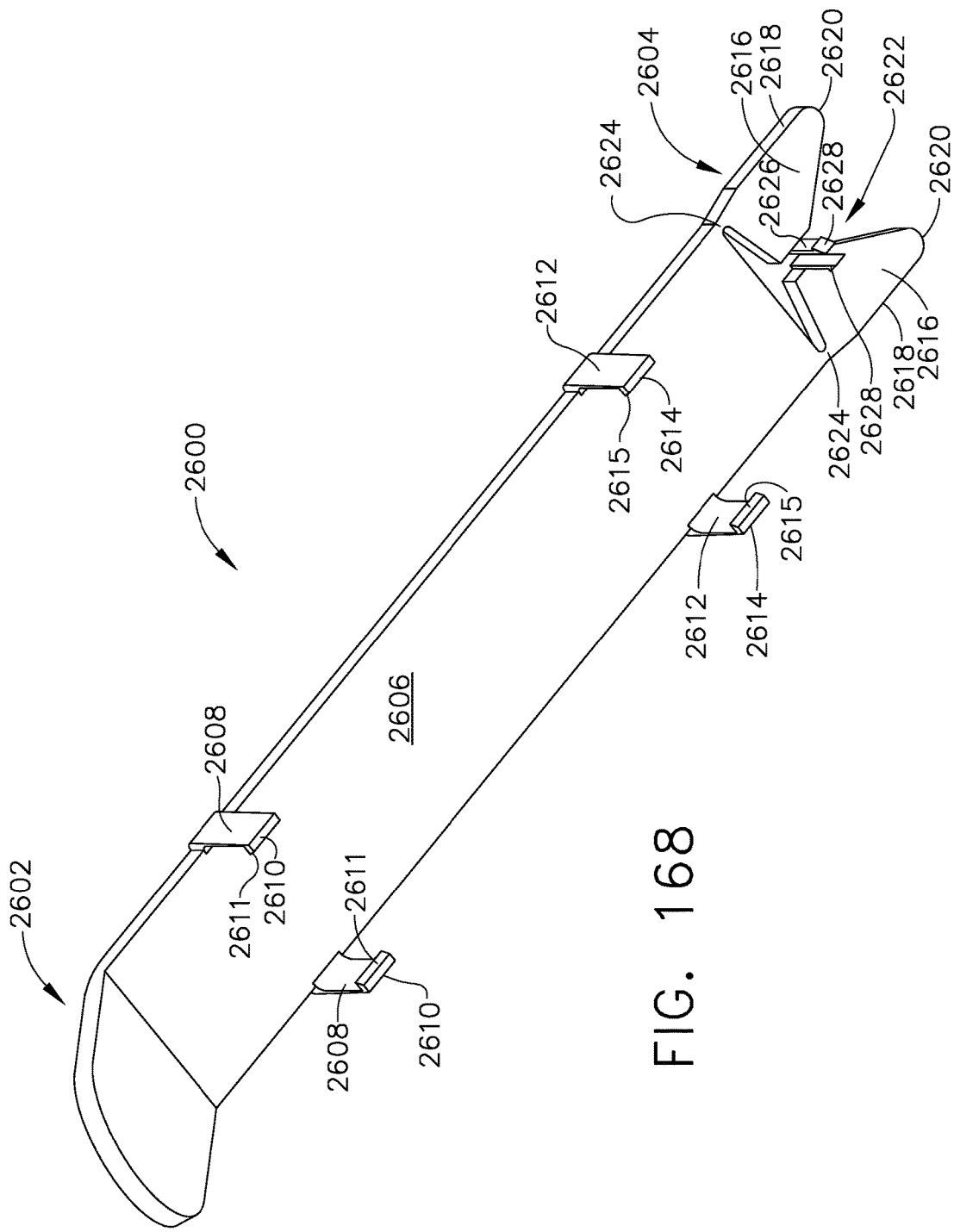
Figure 169:
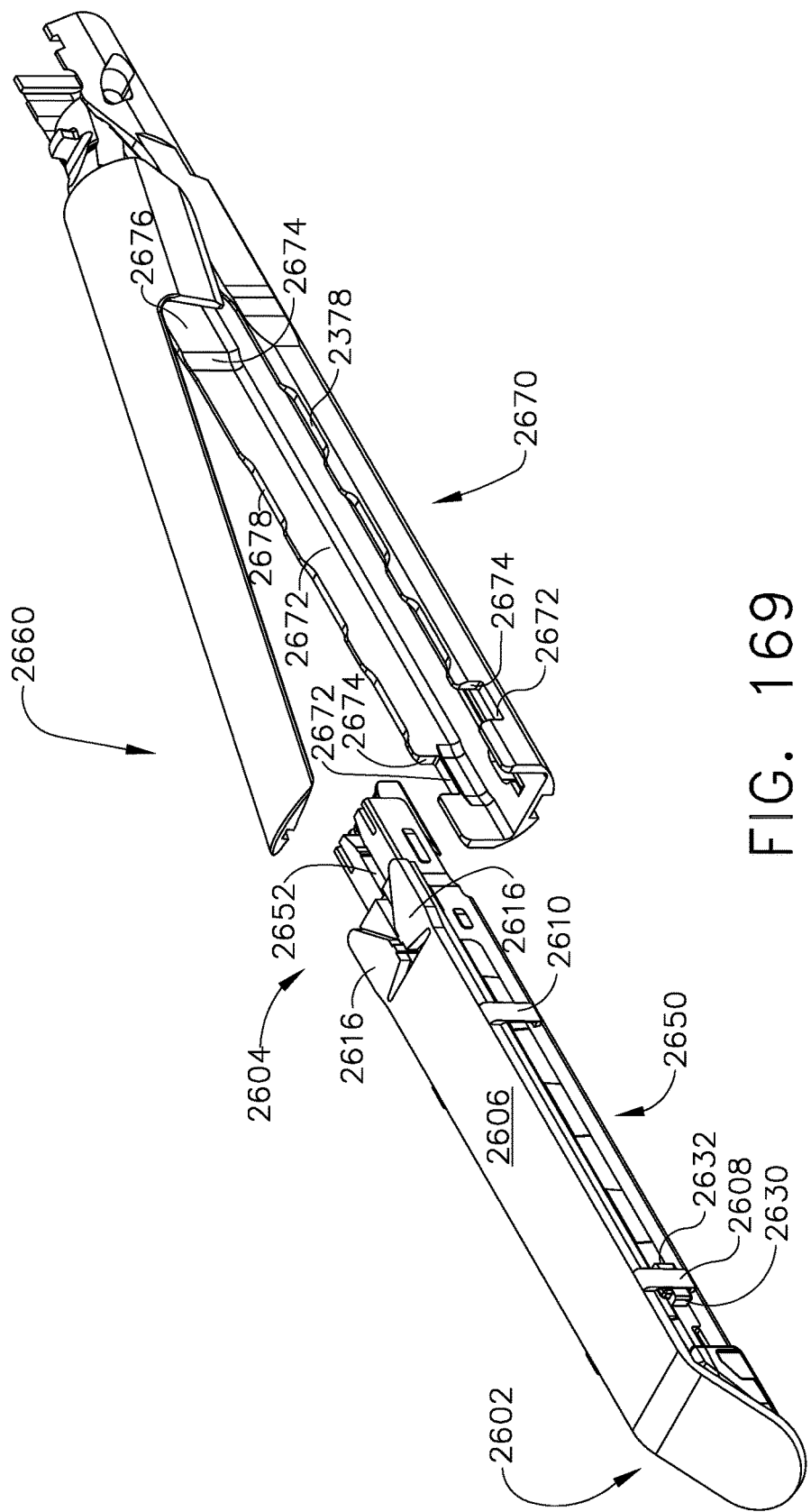
Figure 170:
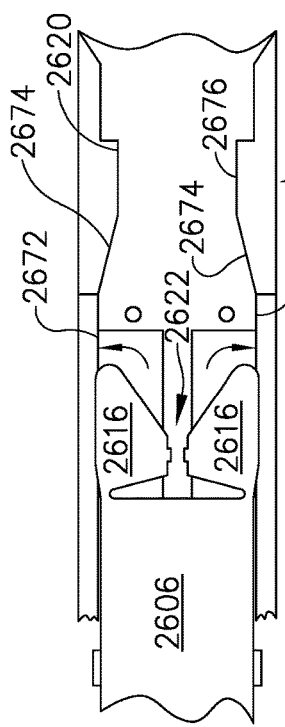
Figure 172:
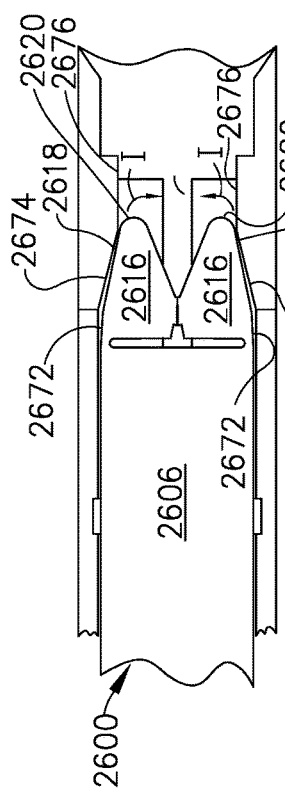
Figure 171:
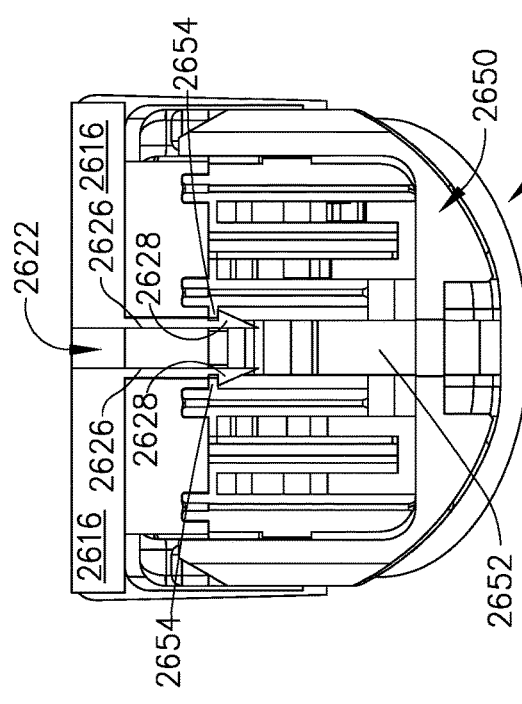
Figure 173:
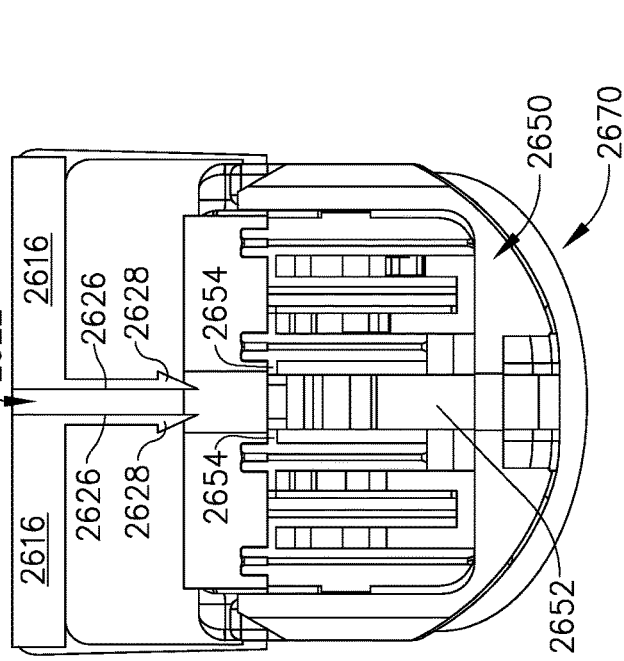
Figure 174:
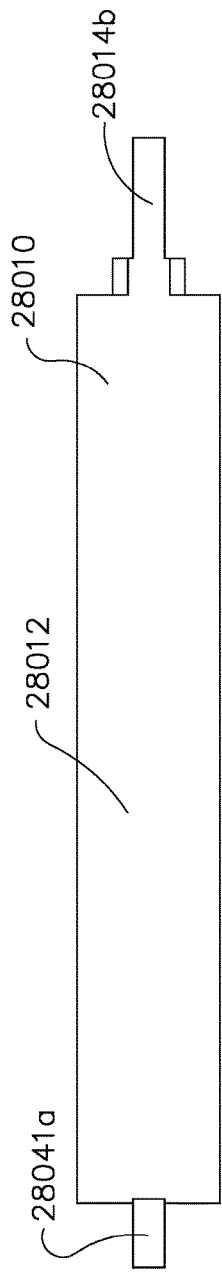
Figure 175:
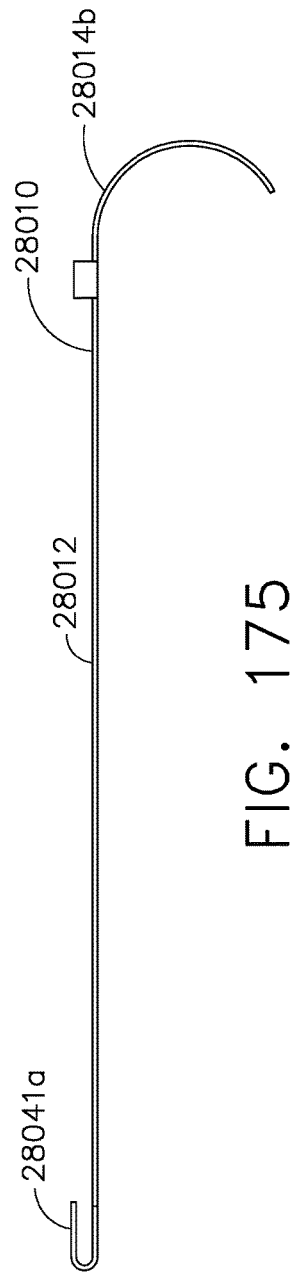
Figure 176:
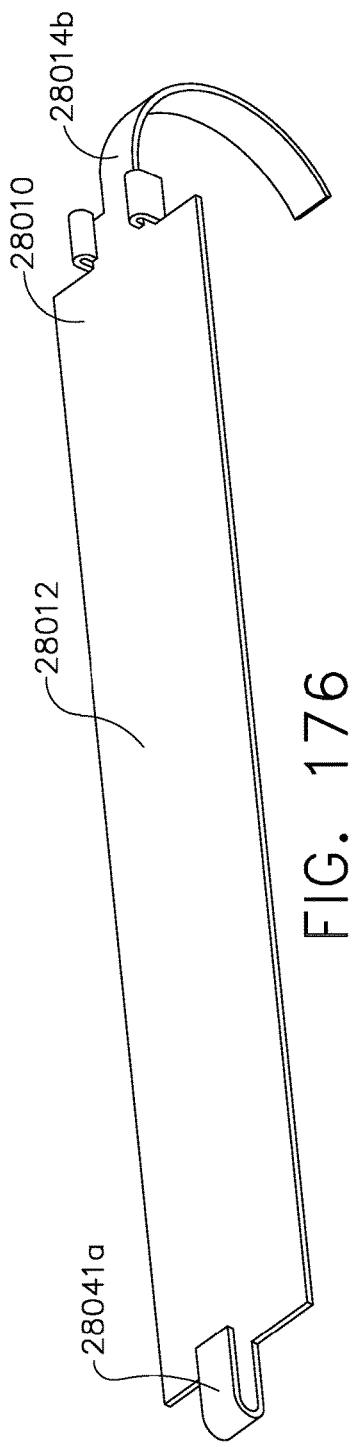
Figure 177:
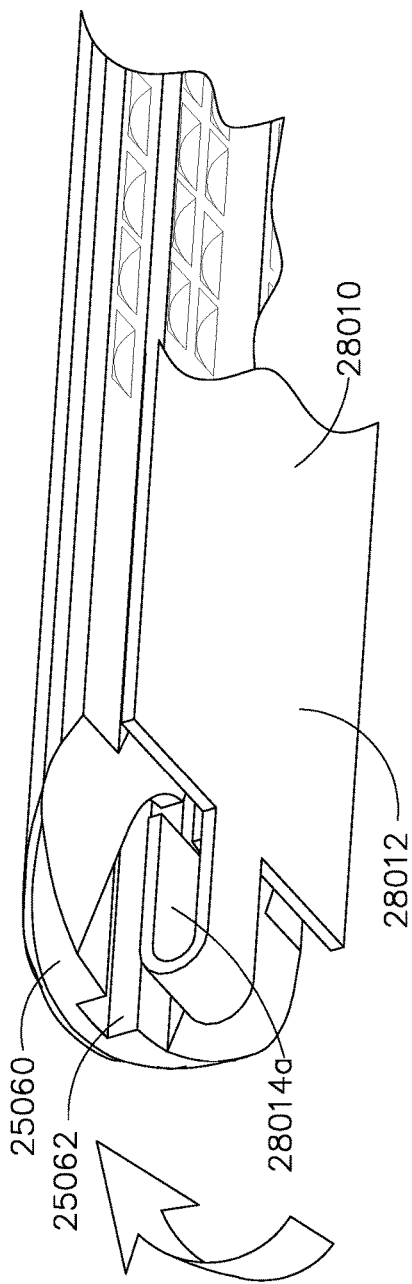
Figure 178:
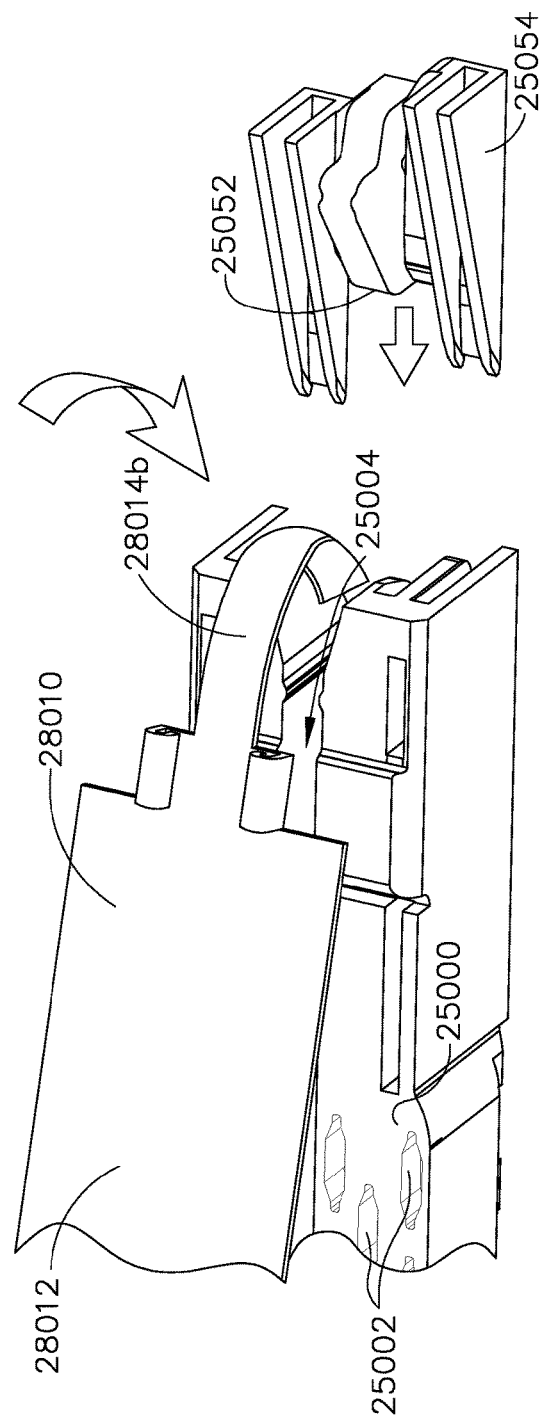
Figure 181:
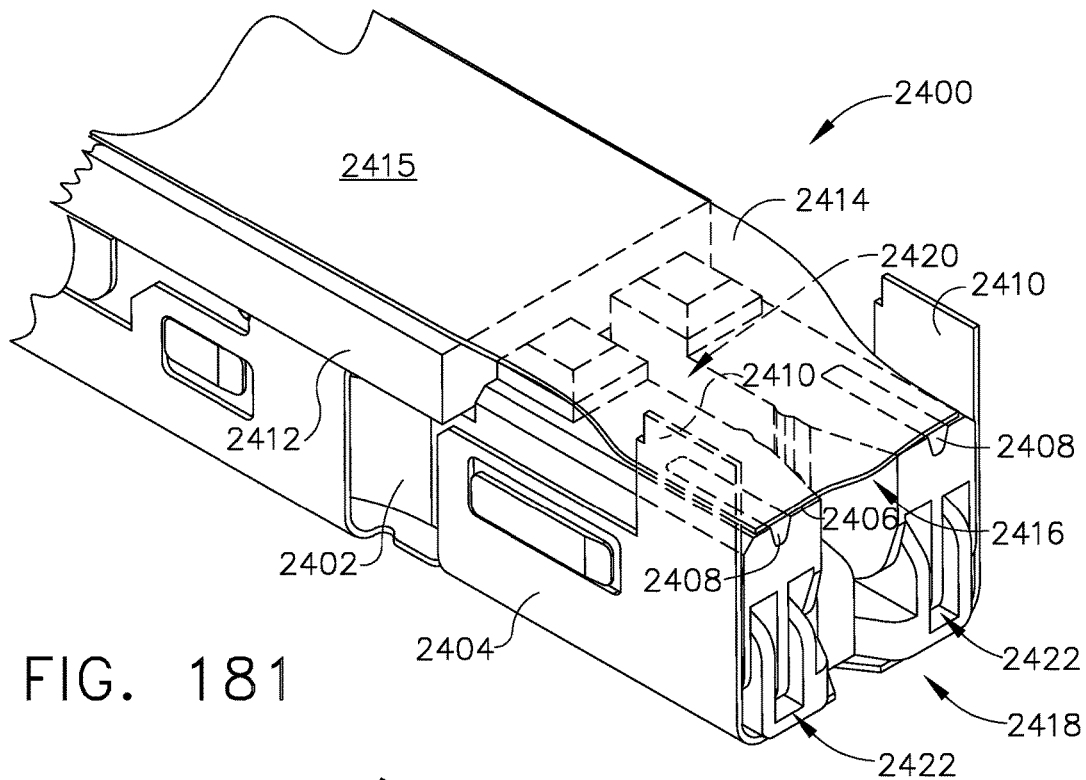
Figure 182:
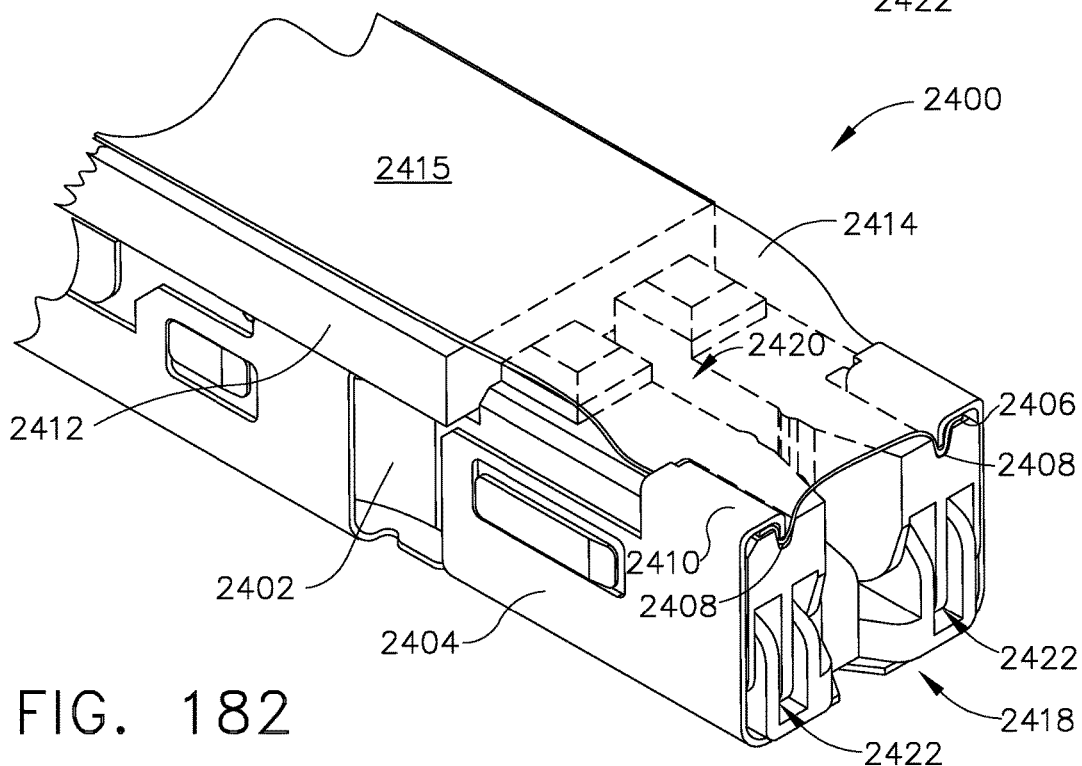
Figure 183:
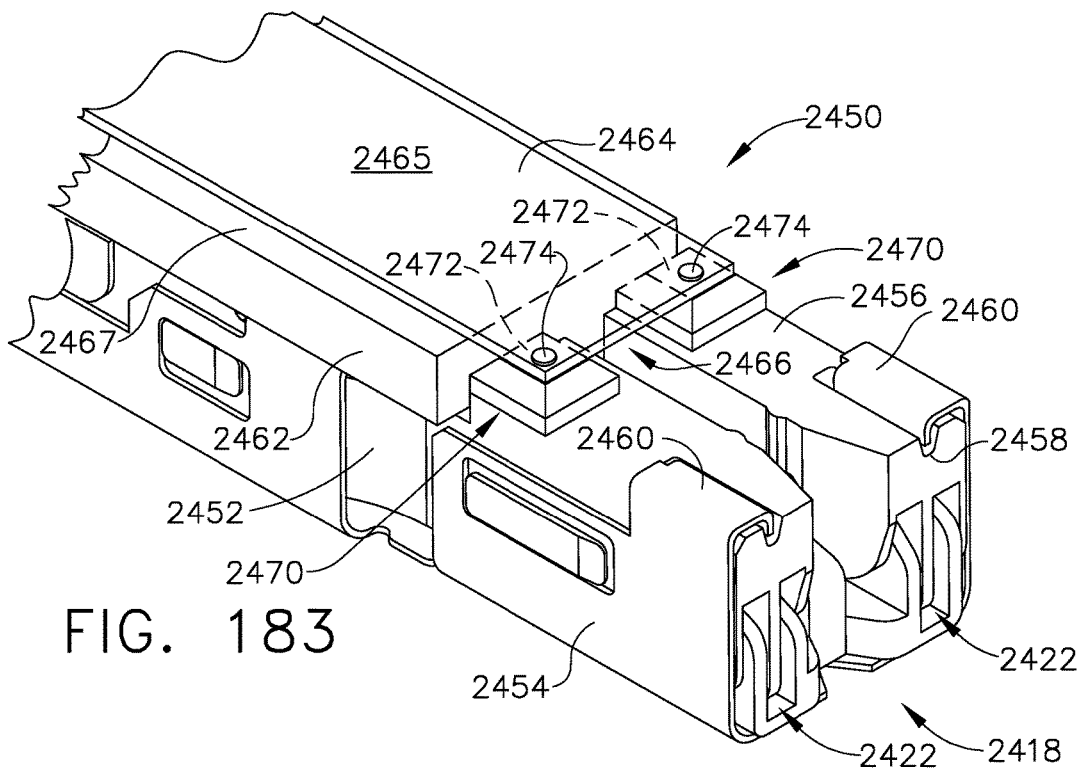
Figure 184:
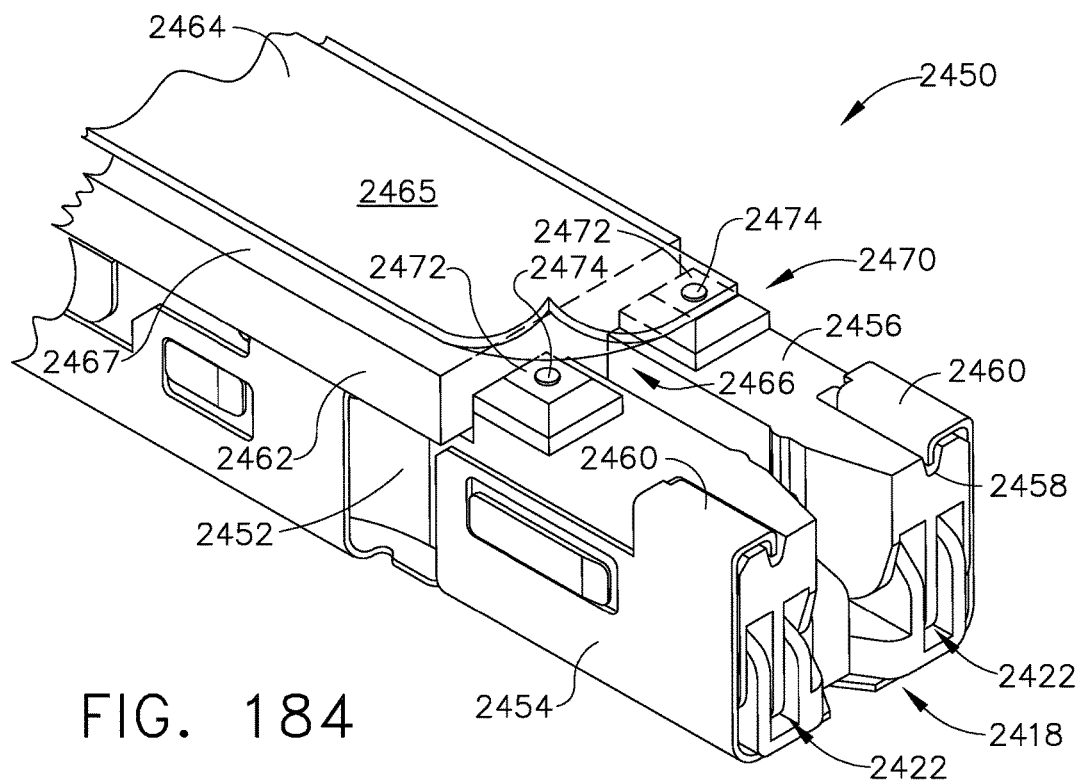
Figure 187:
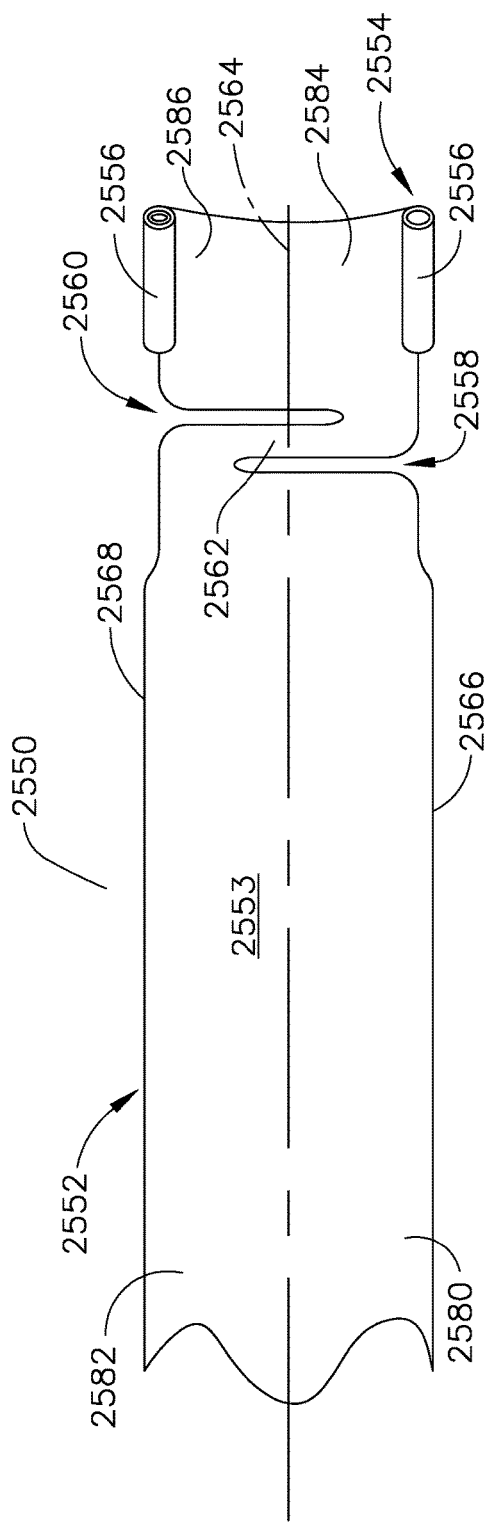
Figure 188:
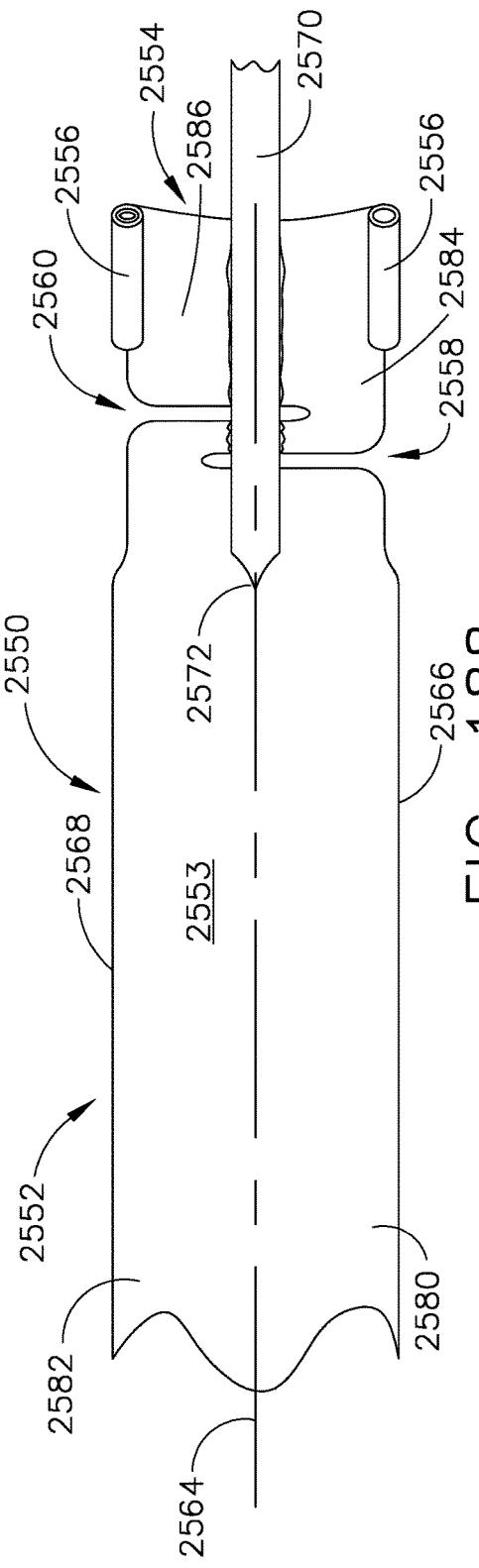
Figure 190:
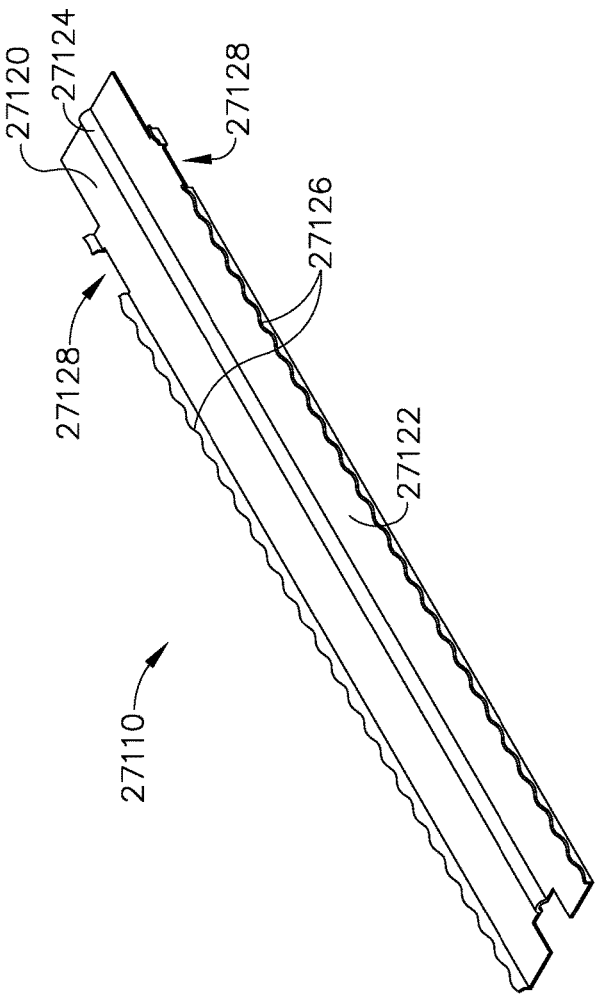
Figure 191:
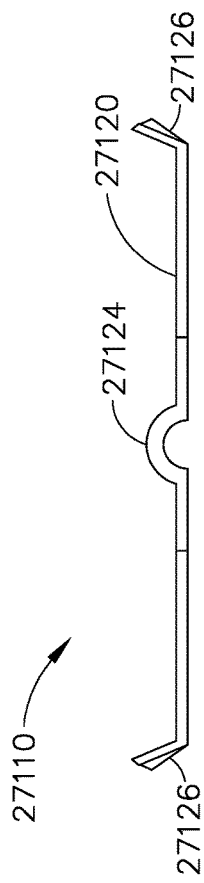
Figure 189:
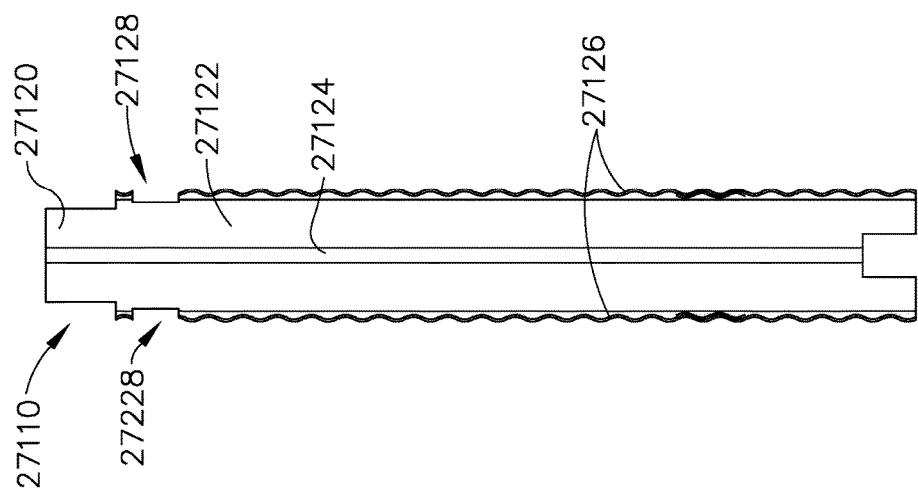
Figure 192:
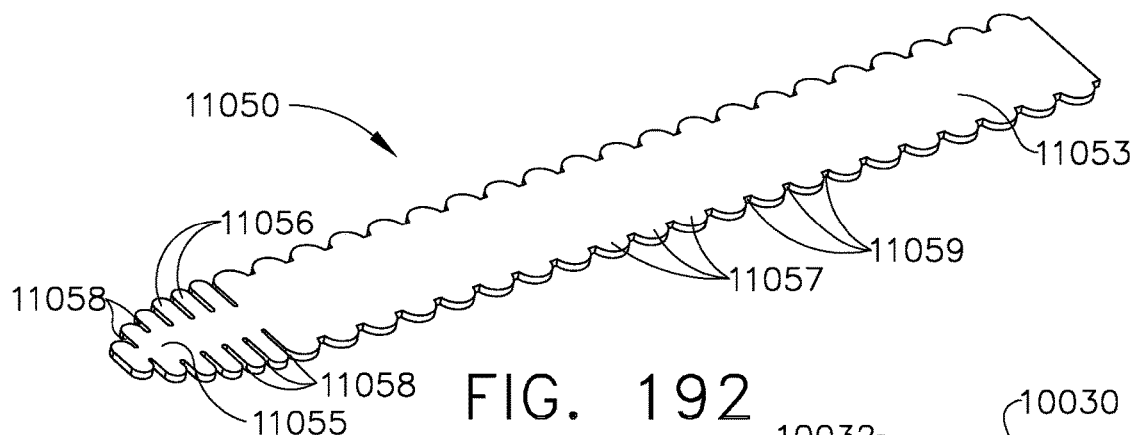
Figure 193:
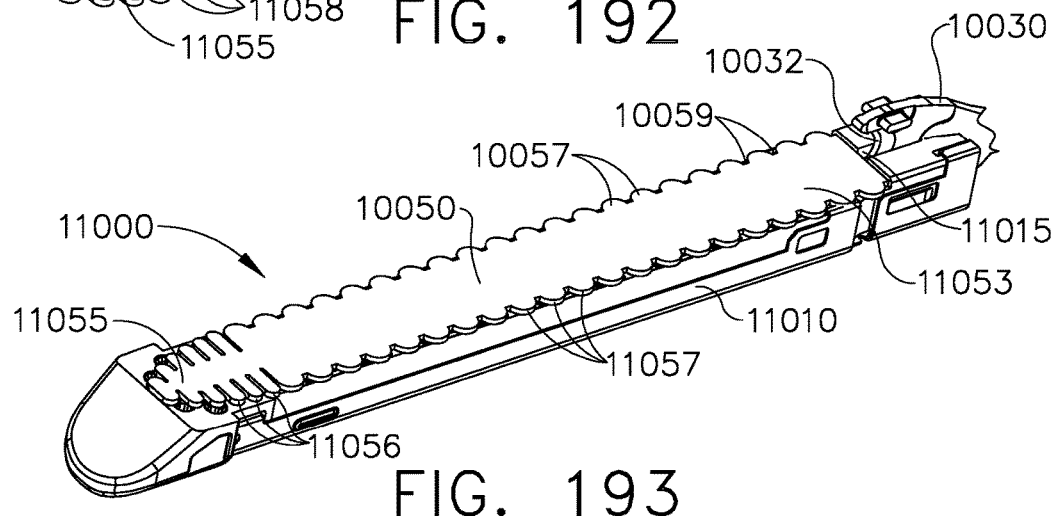
Figure 194:
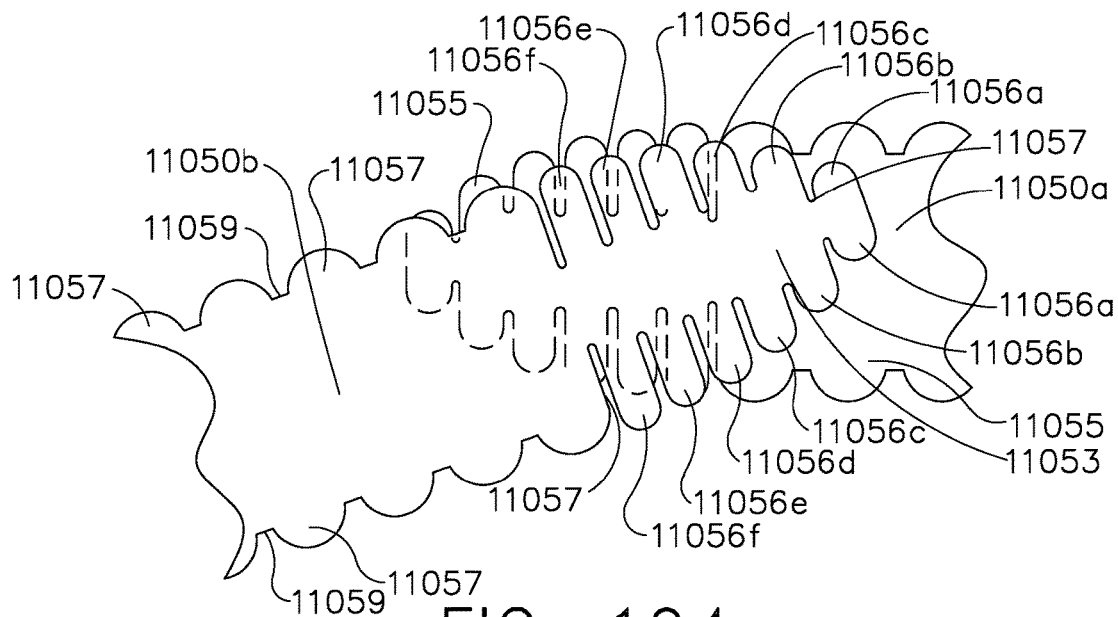
Figure 197:
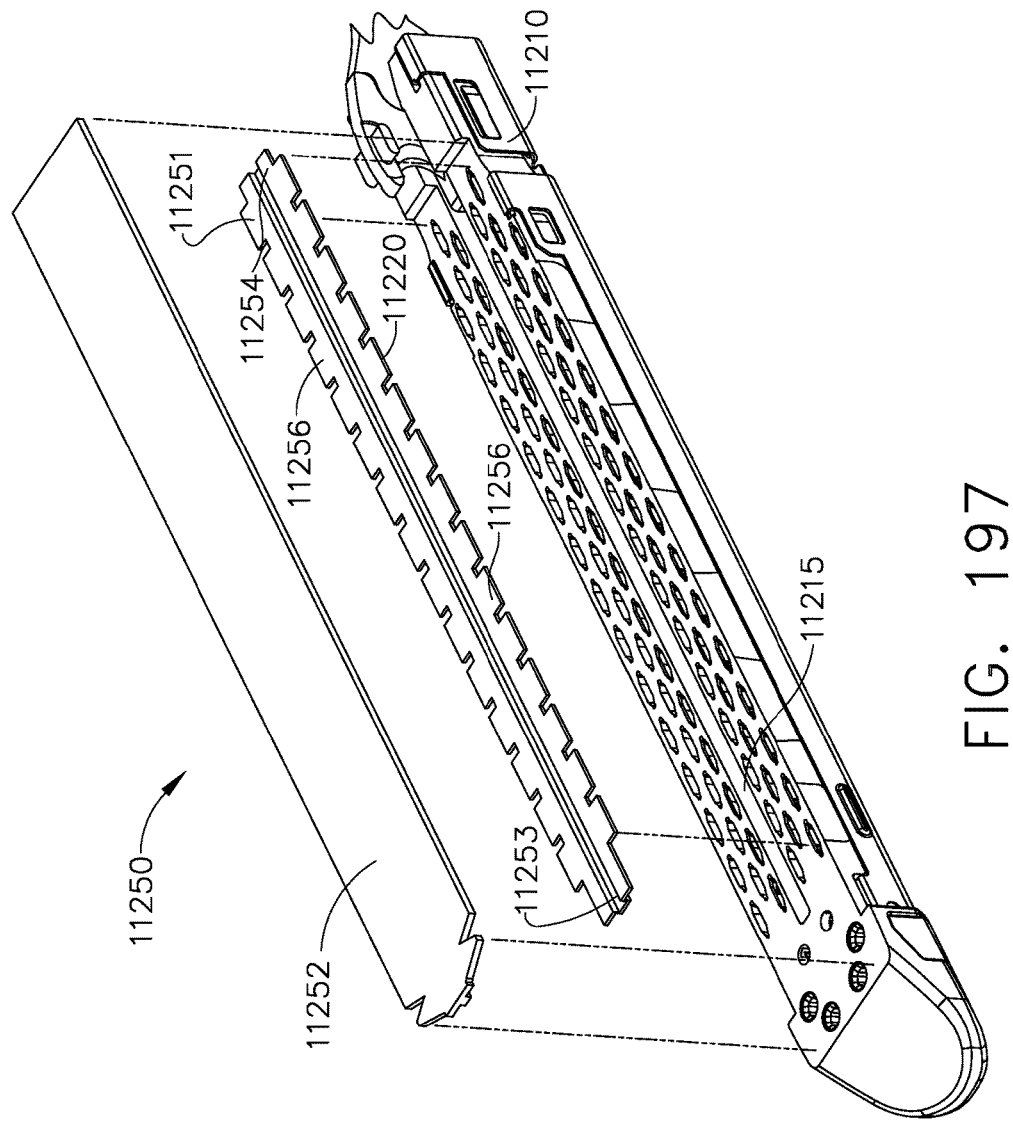
Figure 198:
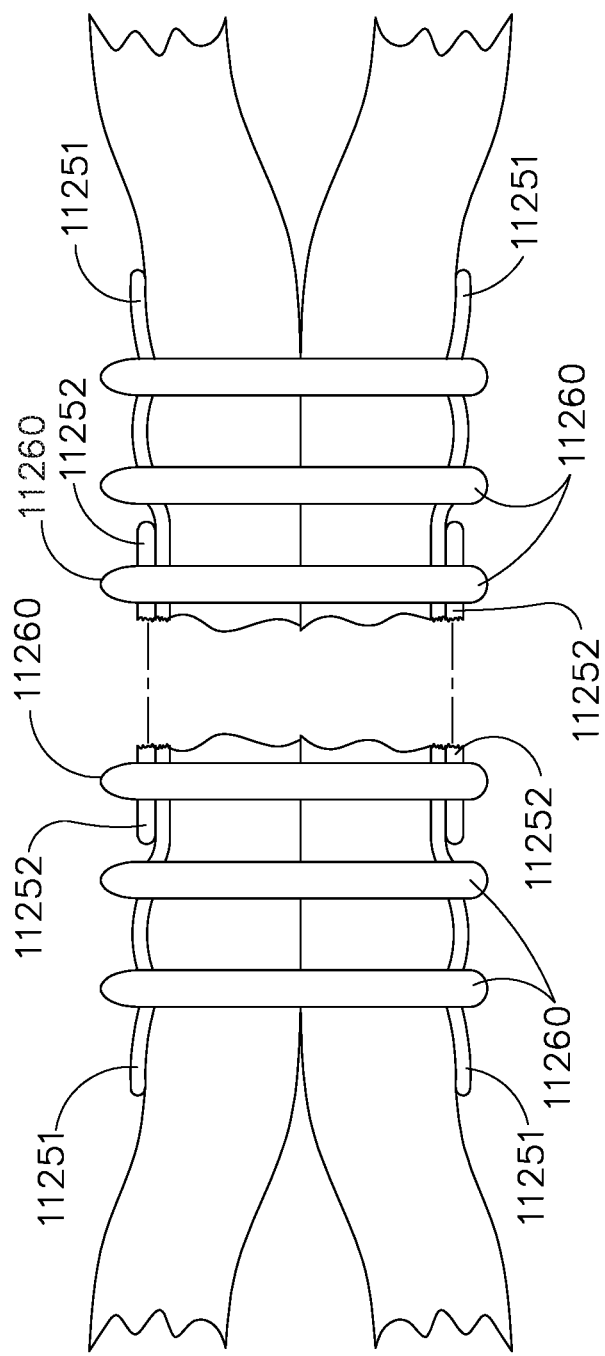
Figure 199:
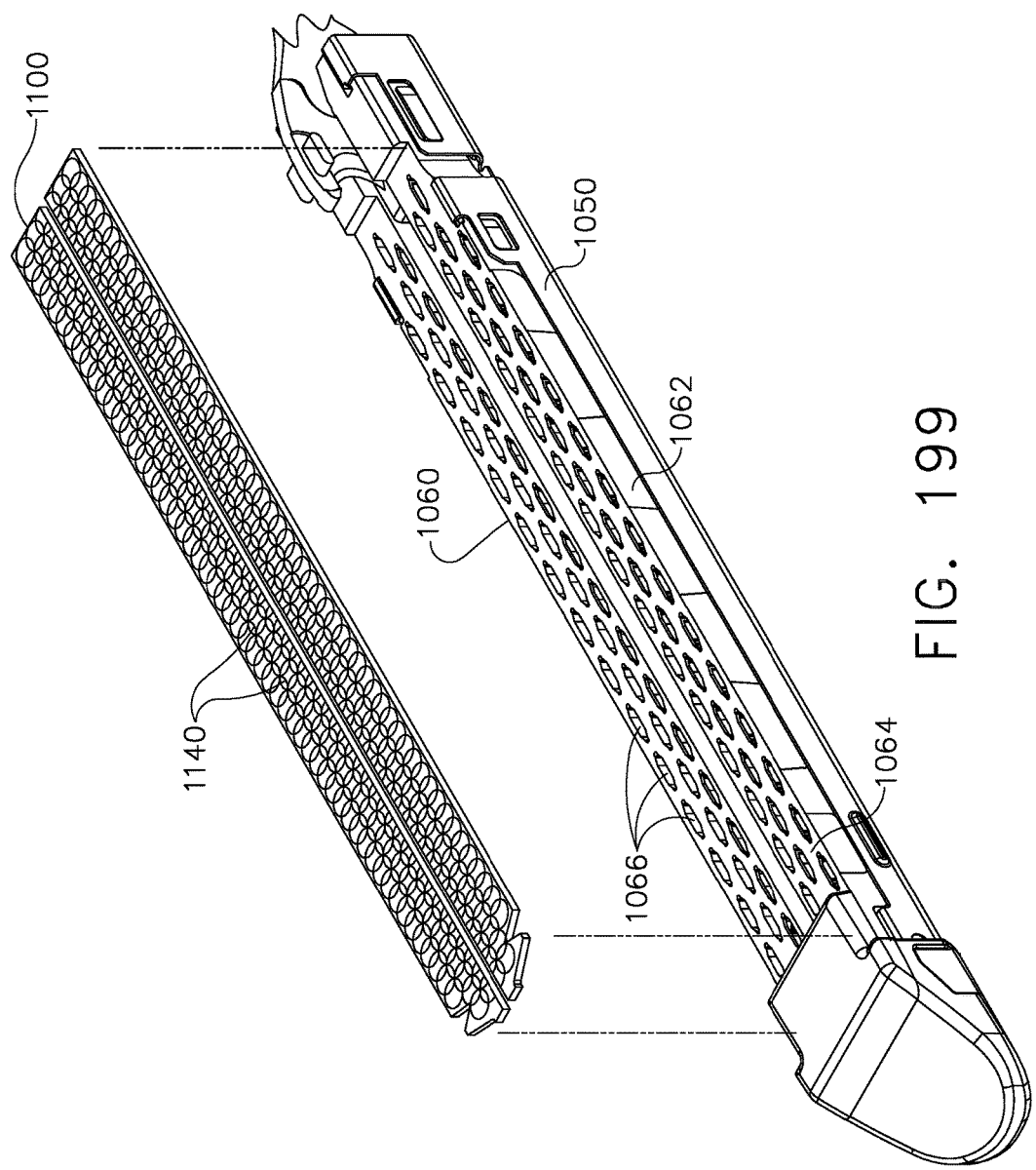
Figure 200:
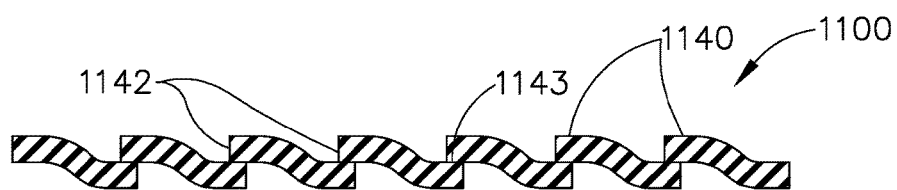
Figure 201:
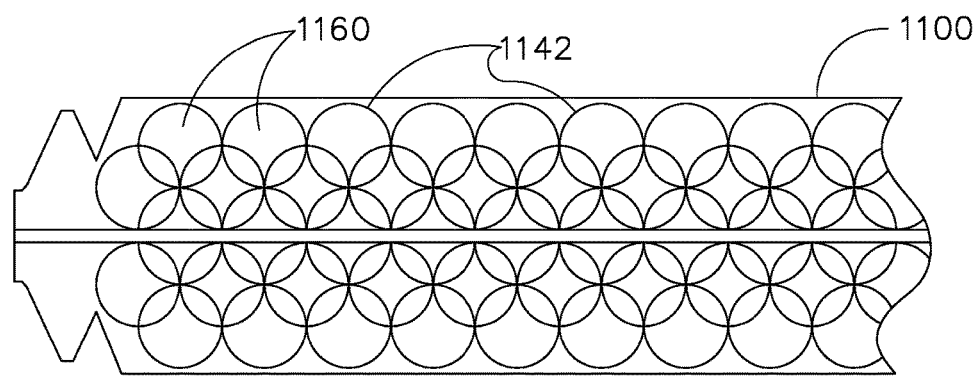
Figure 202:
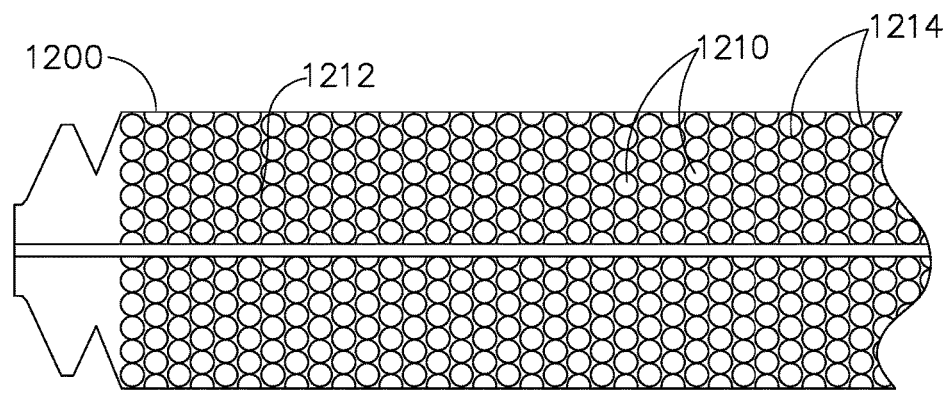
Figure 202A:
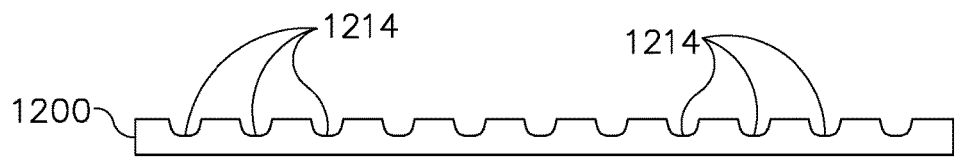
Figure 203:
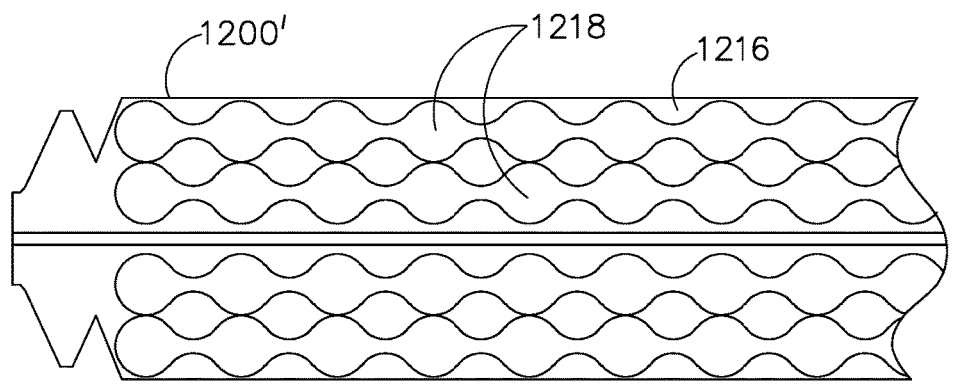
Figure 204:
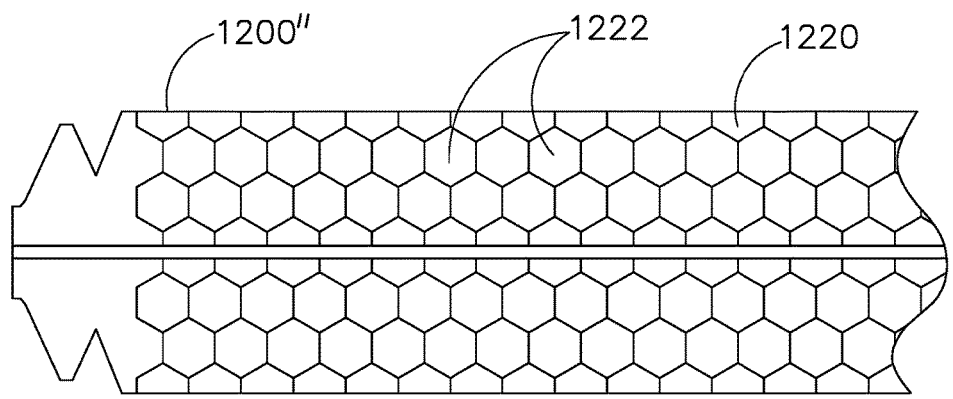
Figure 207A:
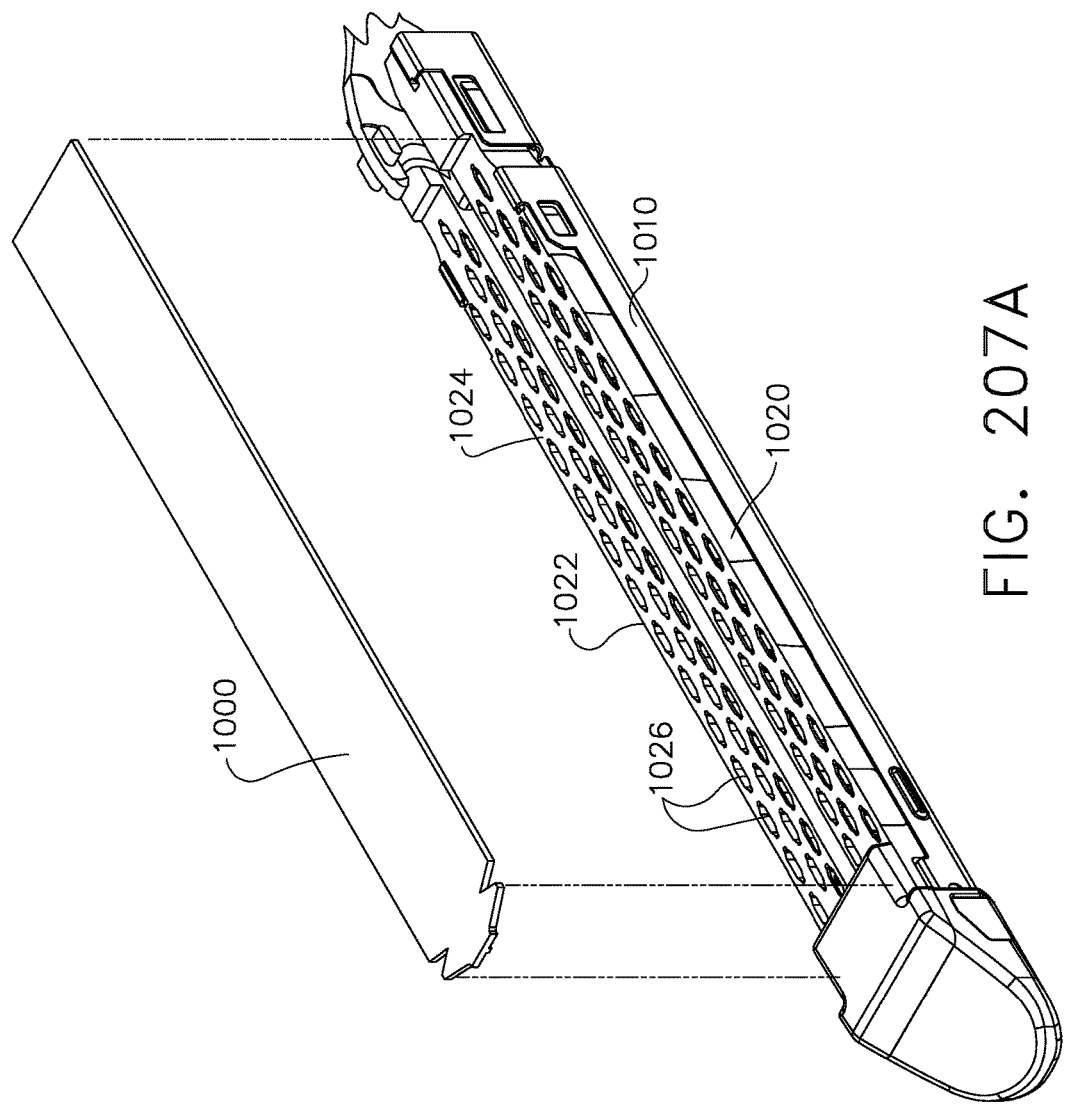
Figure 207B:
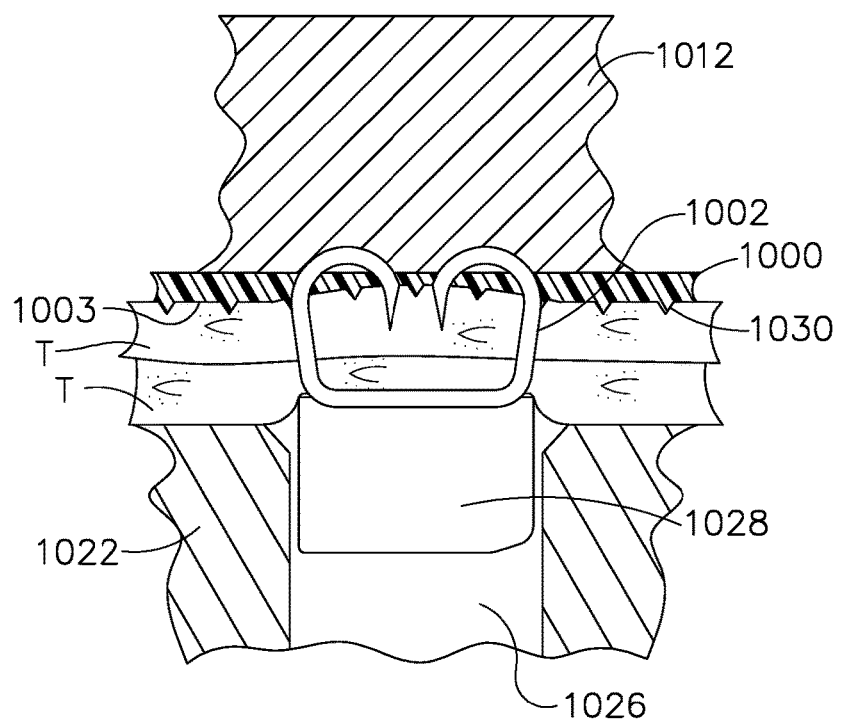
Figure 211:
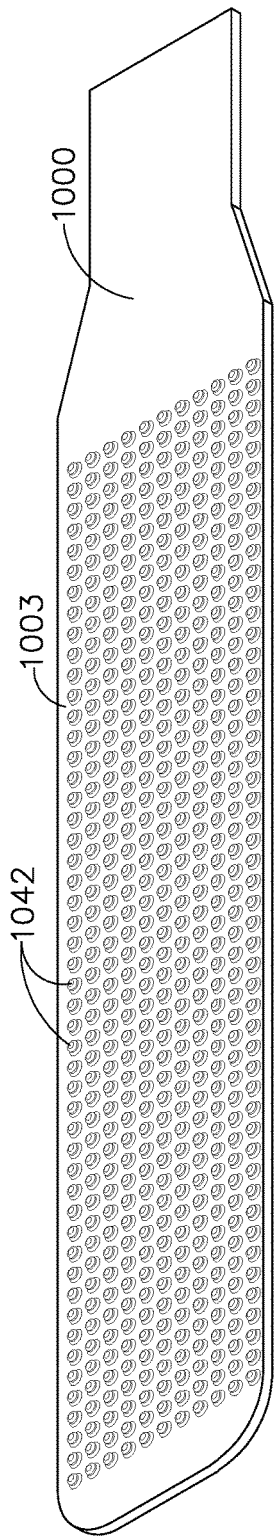
Figure 212:
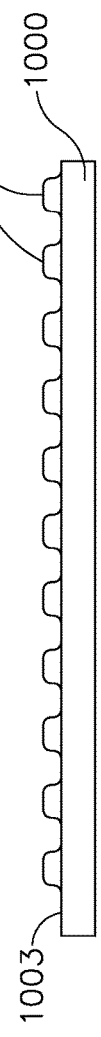
Figure 213:
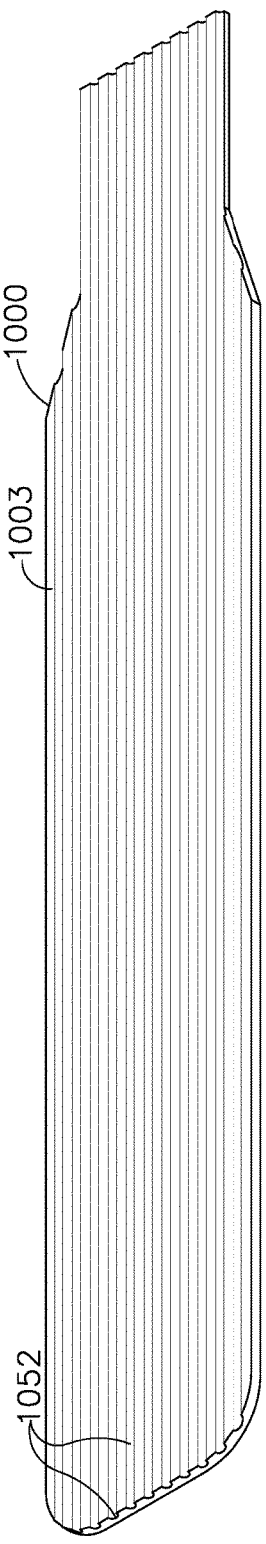
Figure 214:
Figure 218:
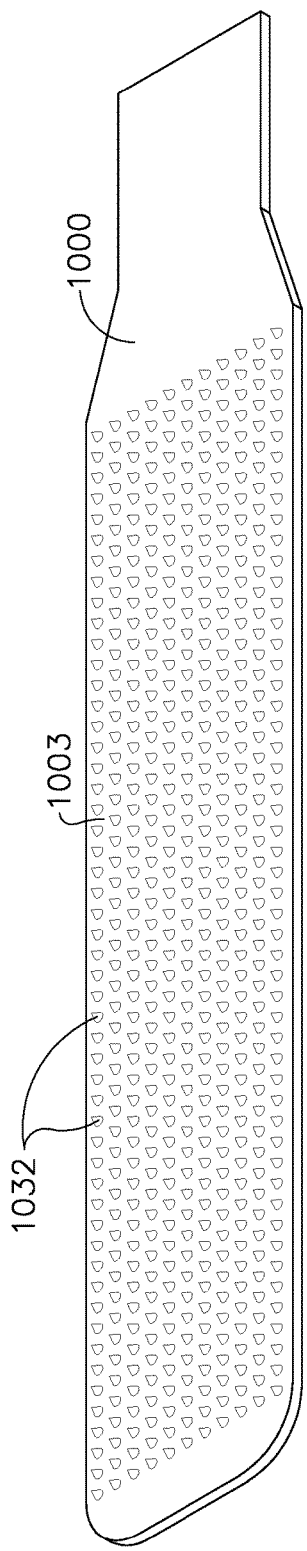
Figure 219:
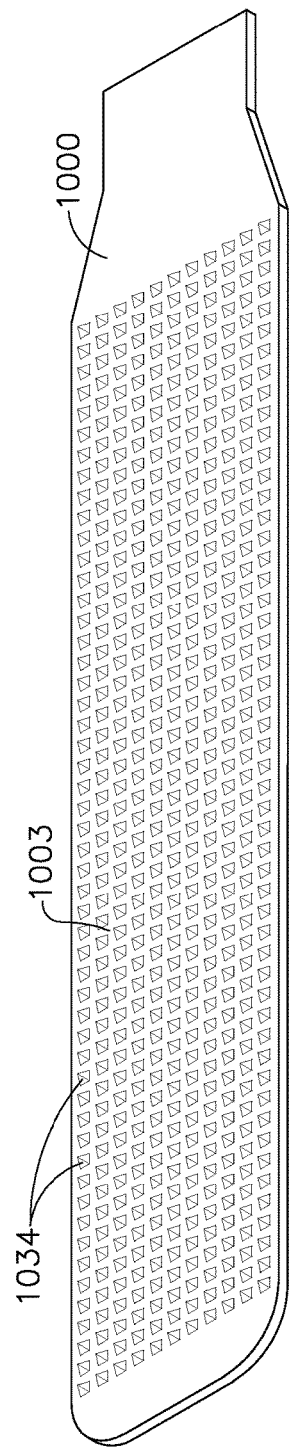
Figure 220:
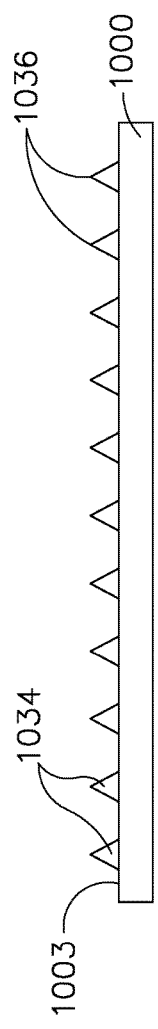
Figure 224A:
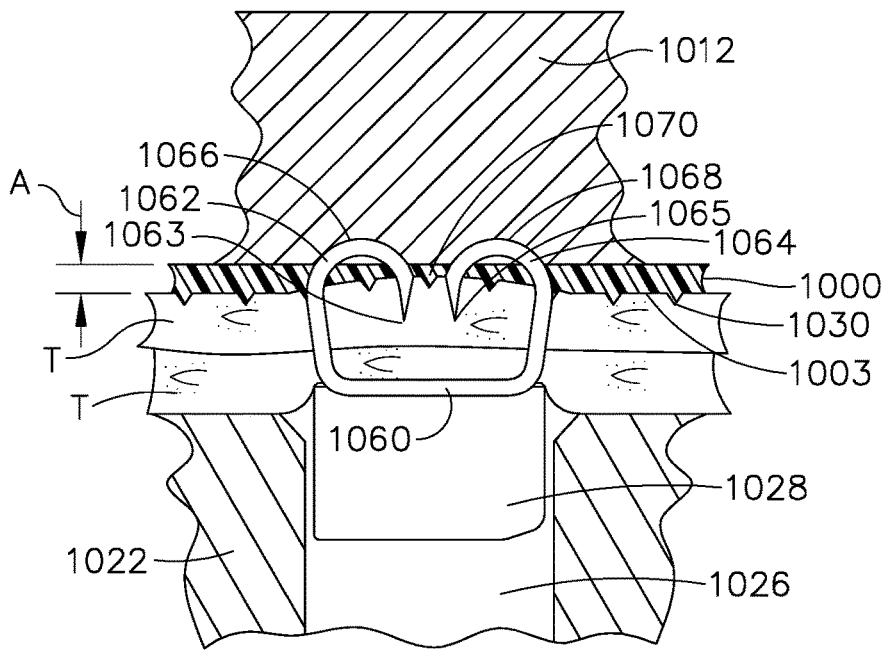
Figure 224B:
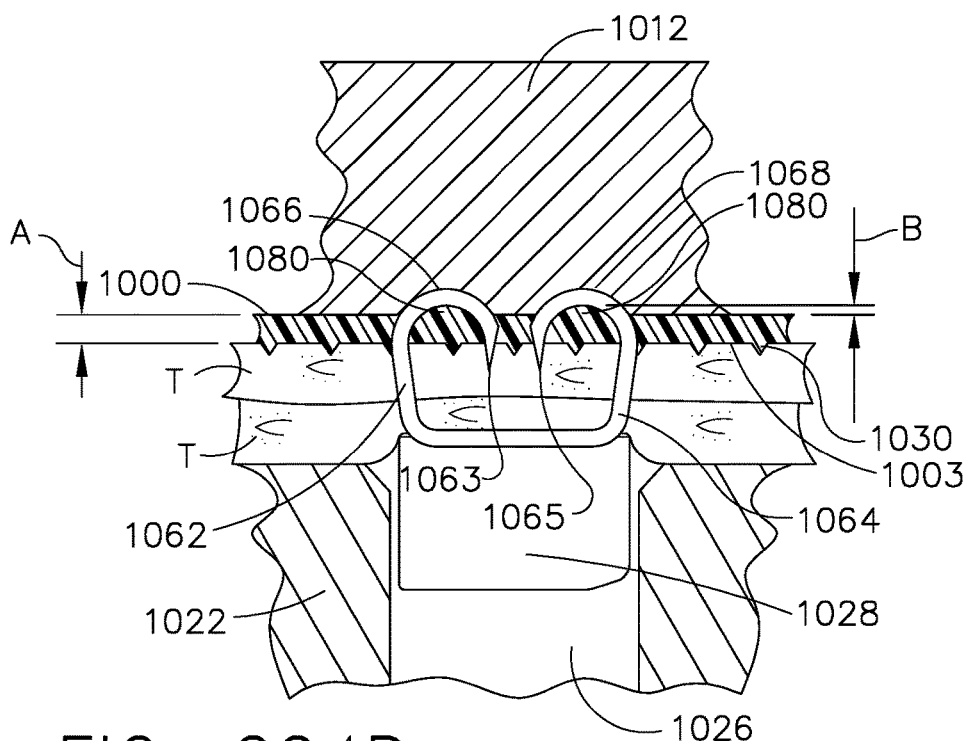
Figure 228:
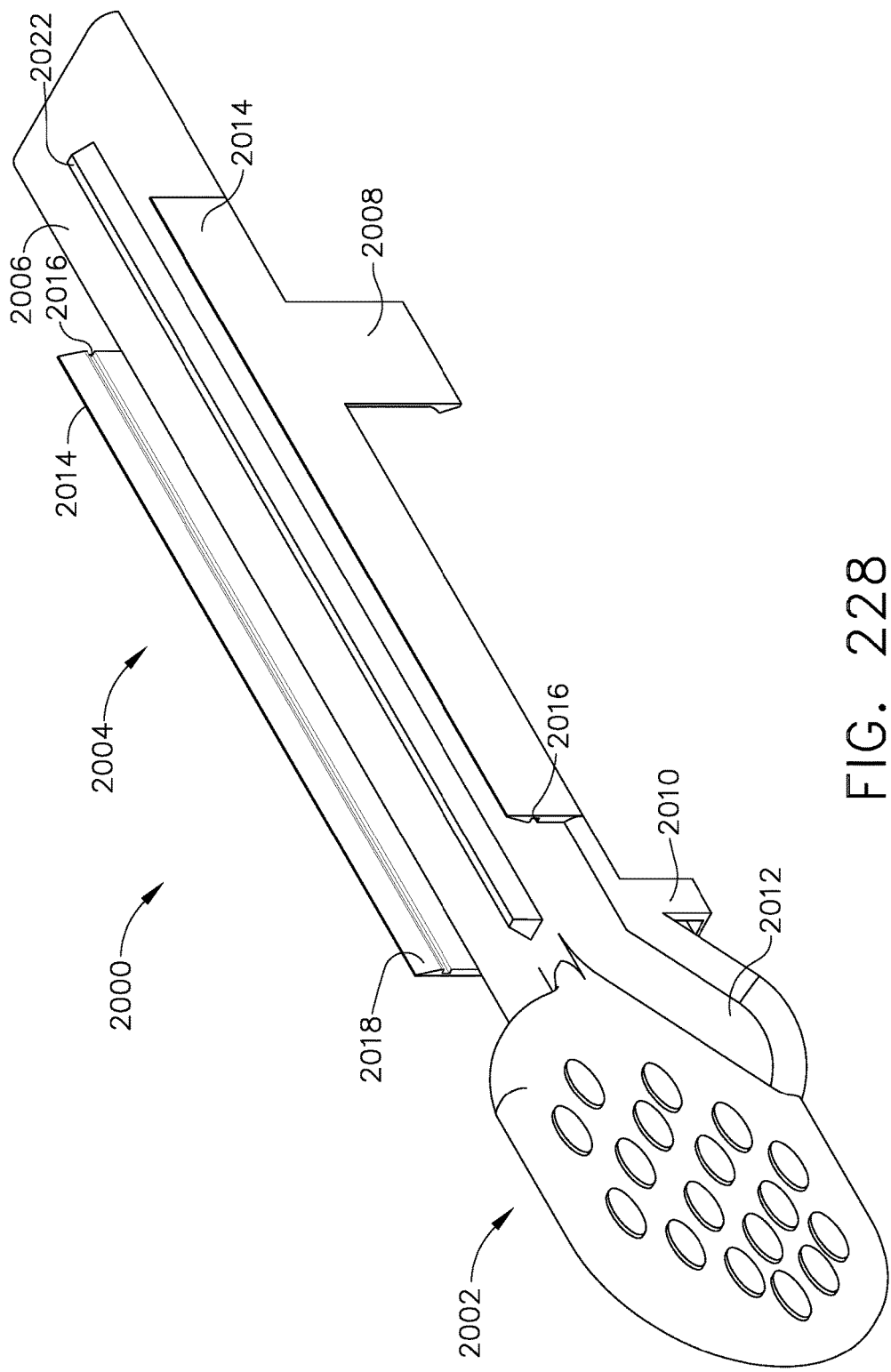
Figures 229, 230:
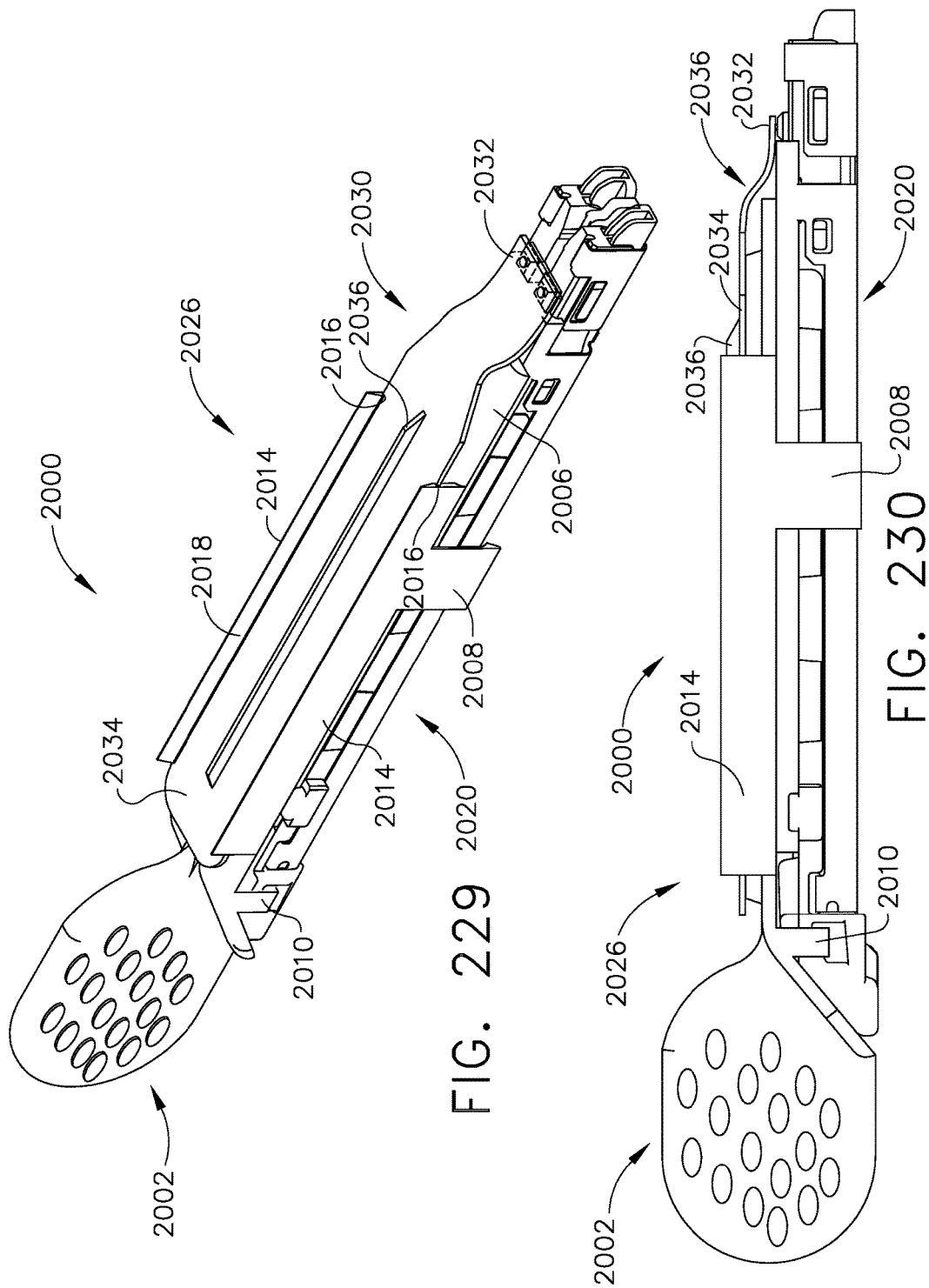
Figures 231, 232:
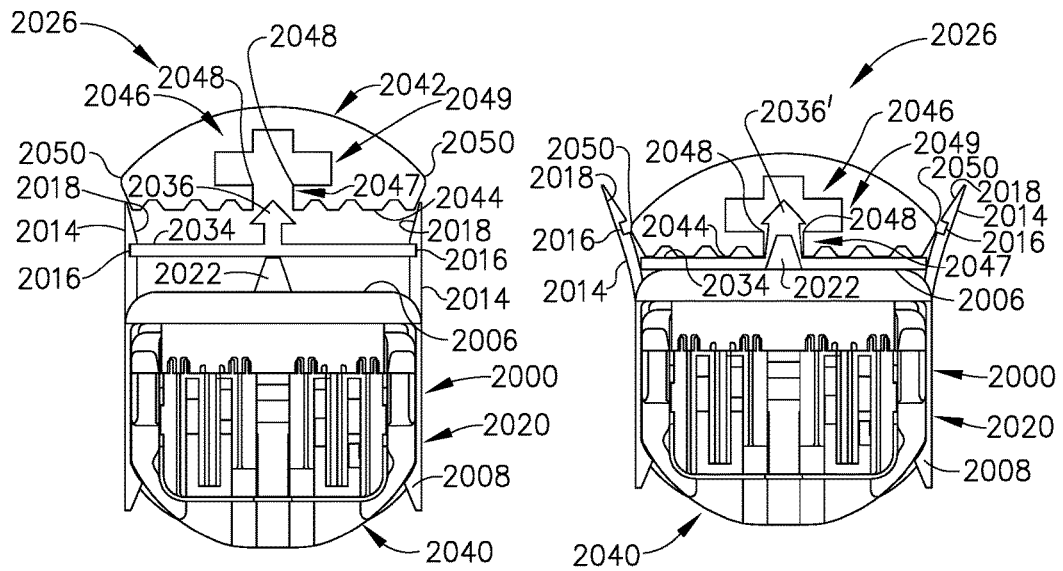
Figures 233, 234:
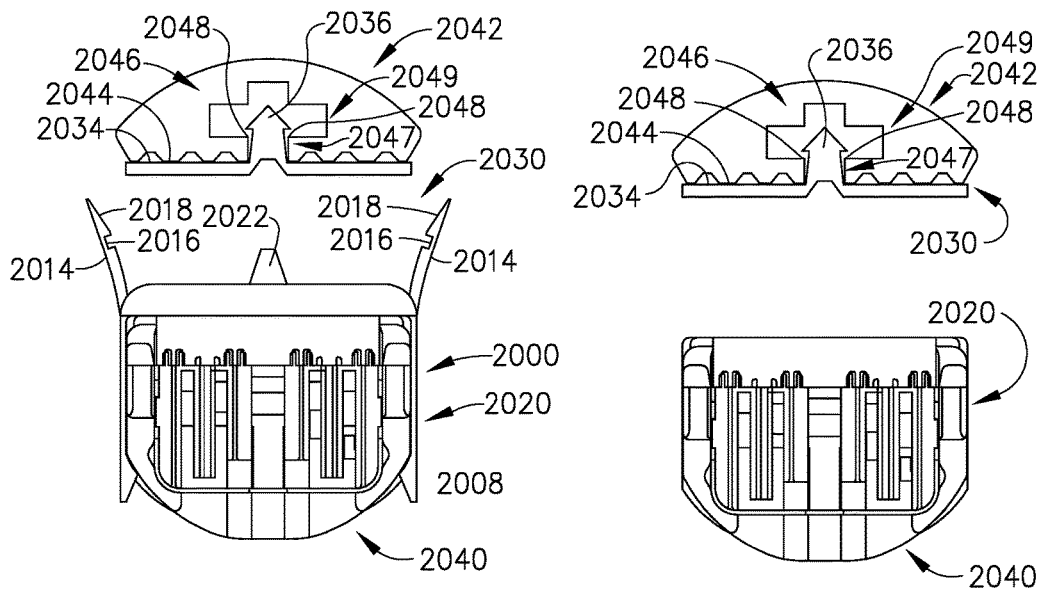
Figure 235:
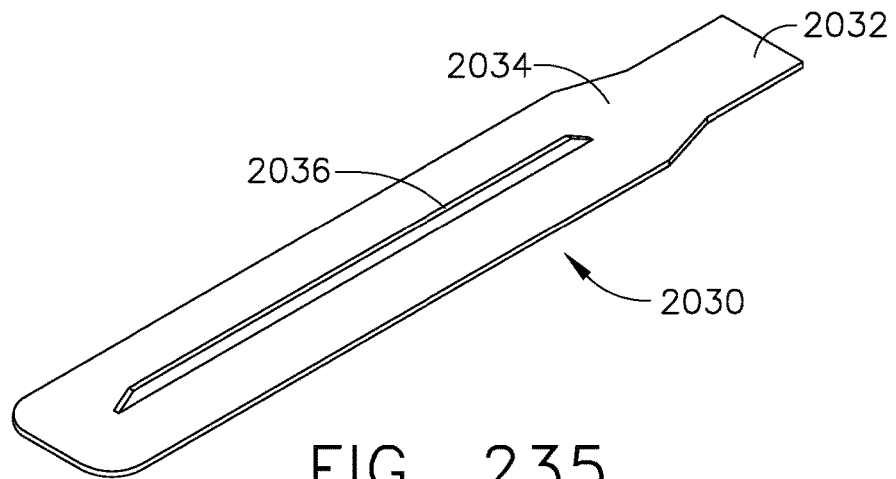
Figure 236:
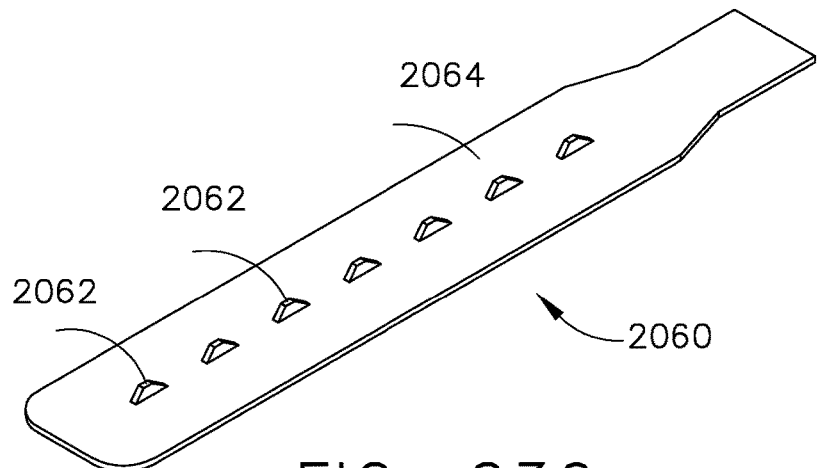
Figure 237:
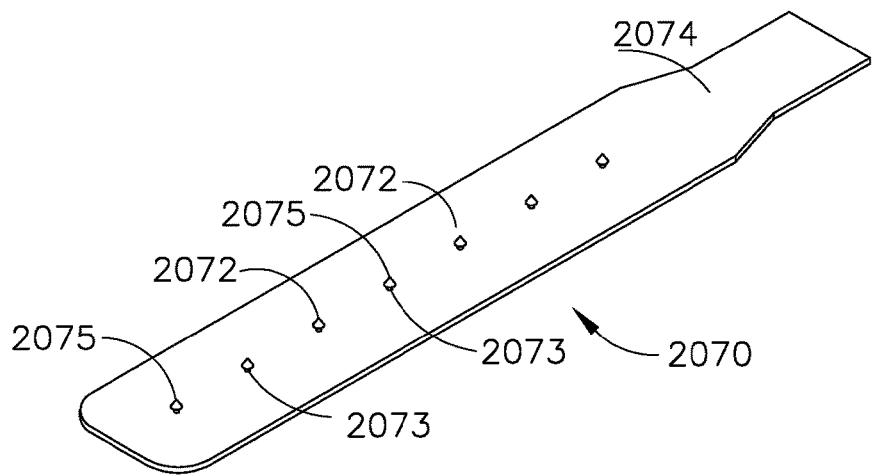
Figure 238:
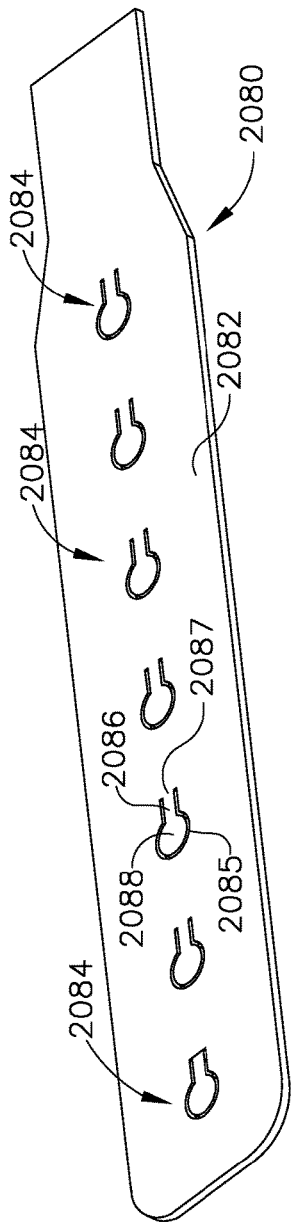
Figure 239:
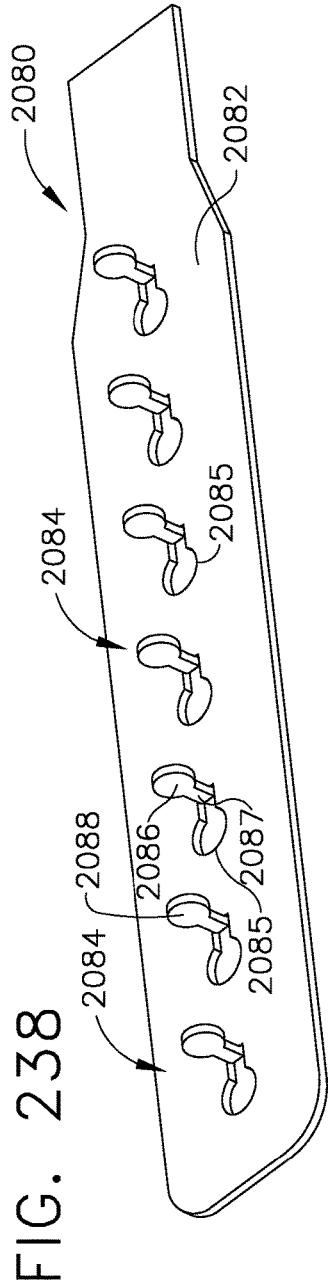
Figure 240:
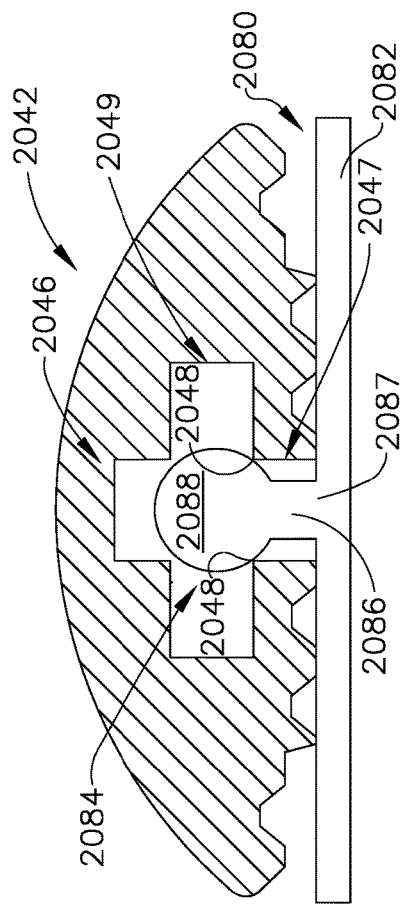
Figure 244:
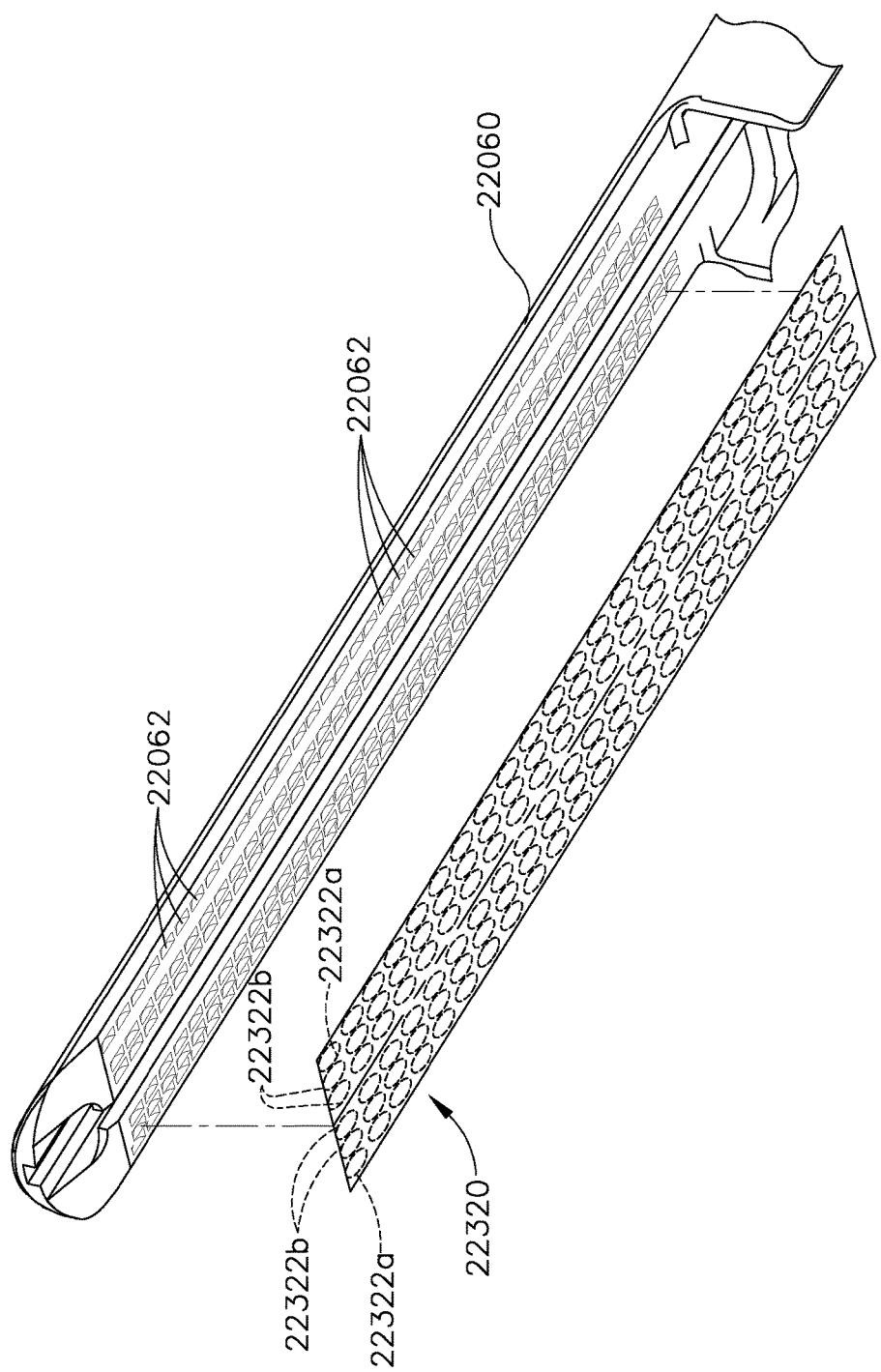
Figure 245:
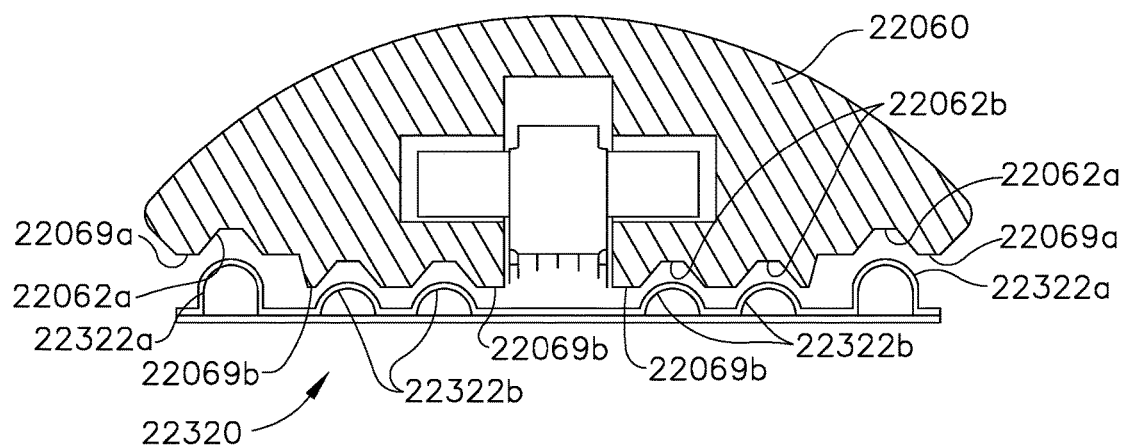
Figure 246:
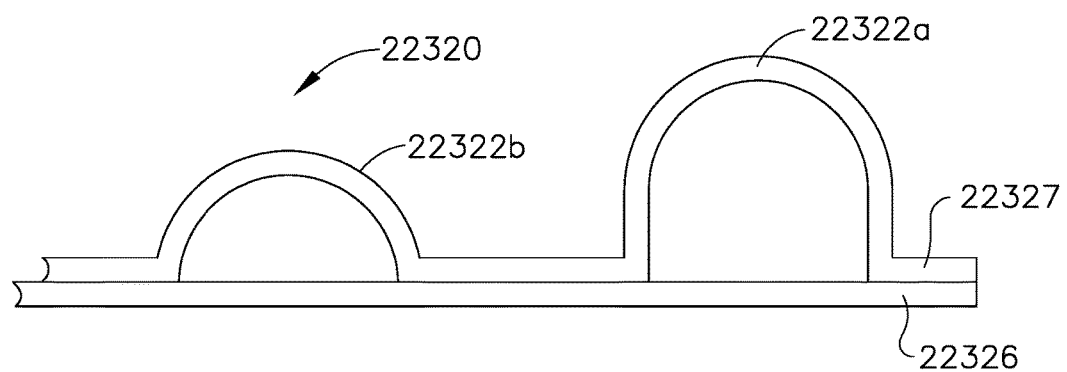
Figures 247, 248:
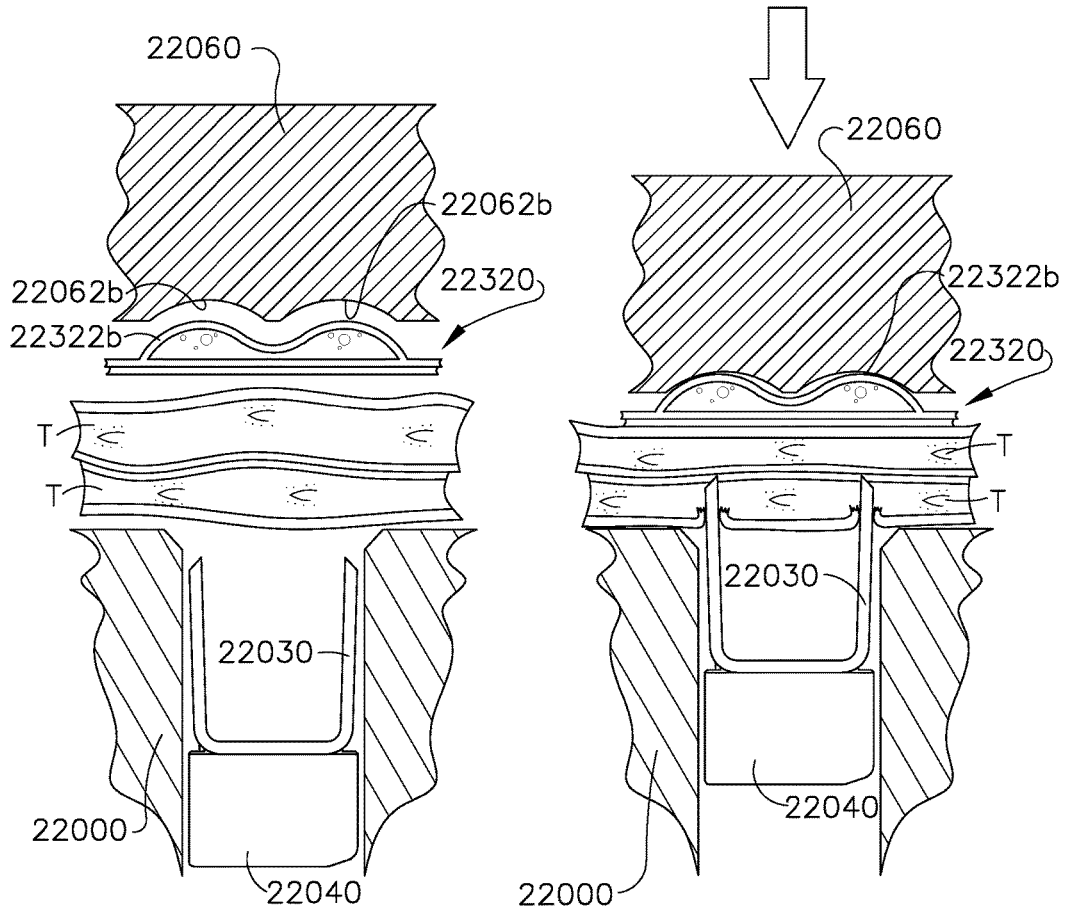
Figure 249:
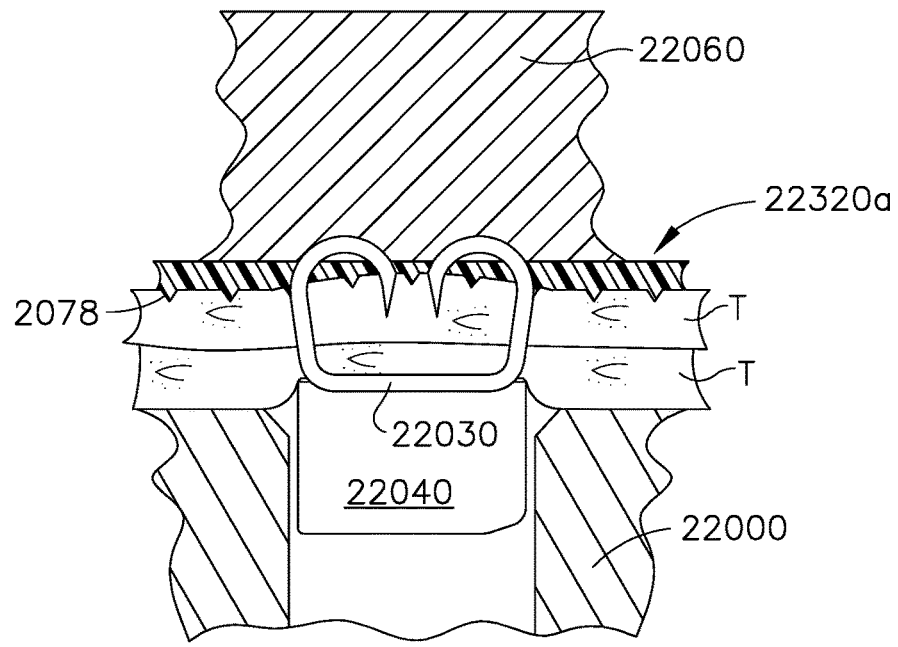
Figure 250:
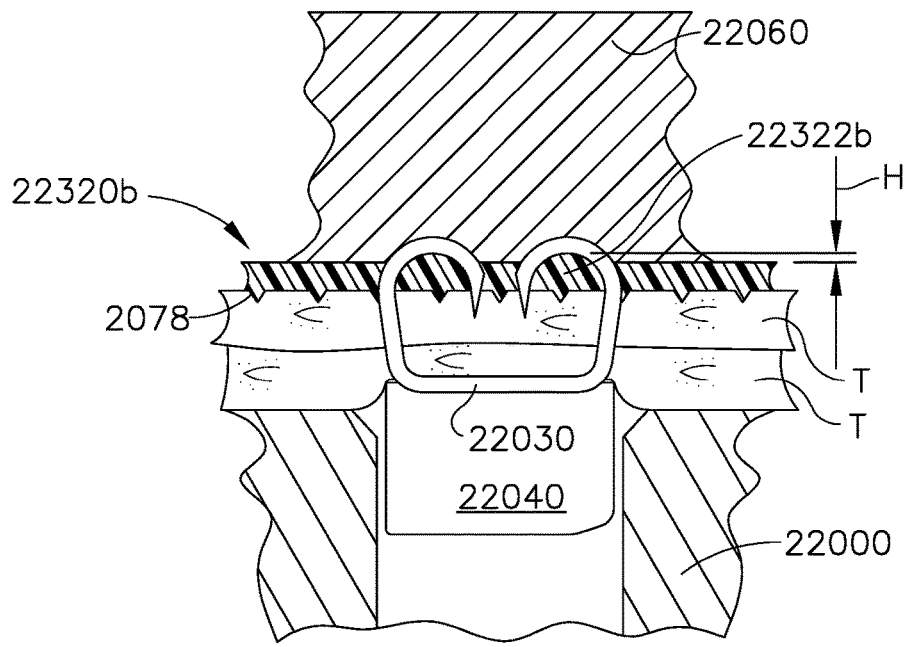
Figure 251:
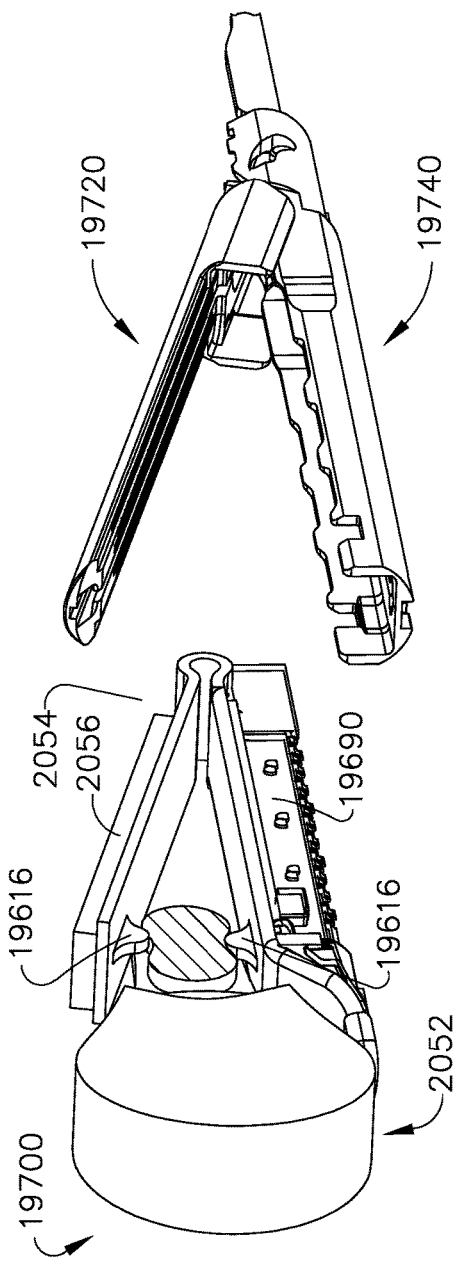
Figure 252:
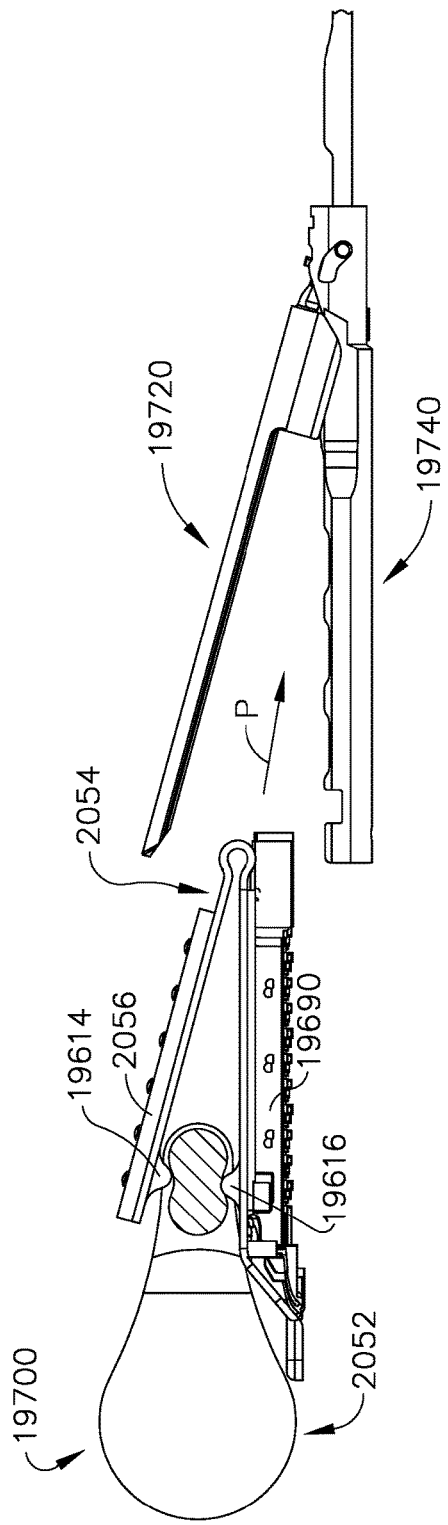
Figure 255:
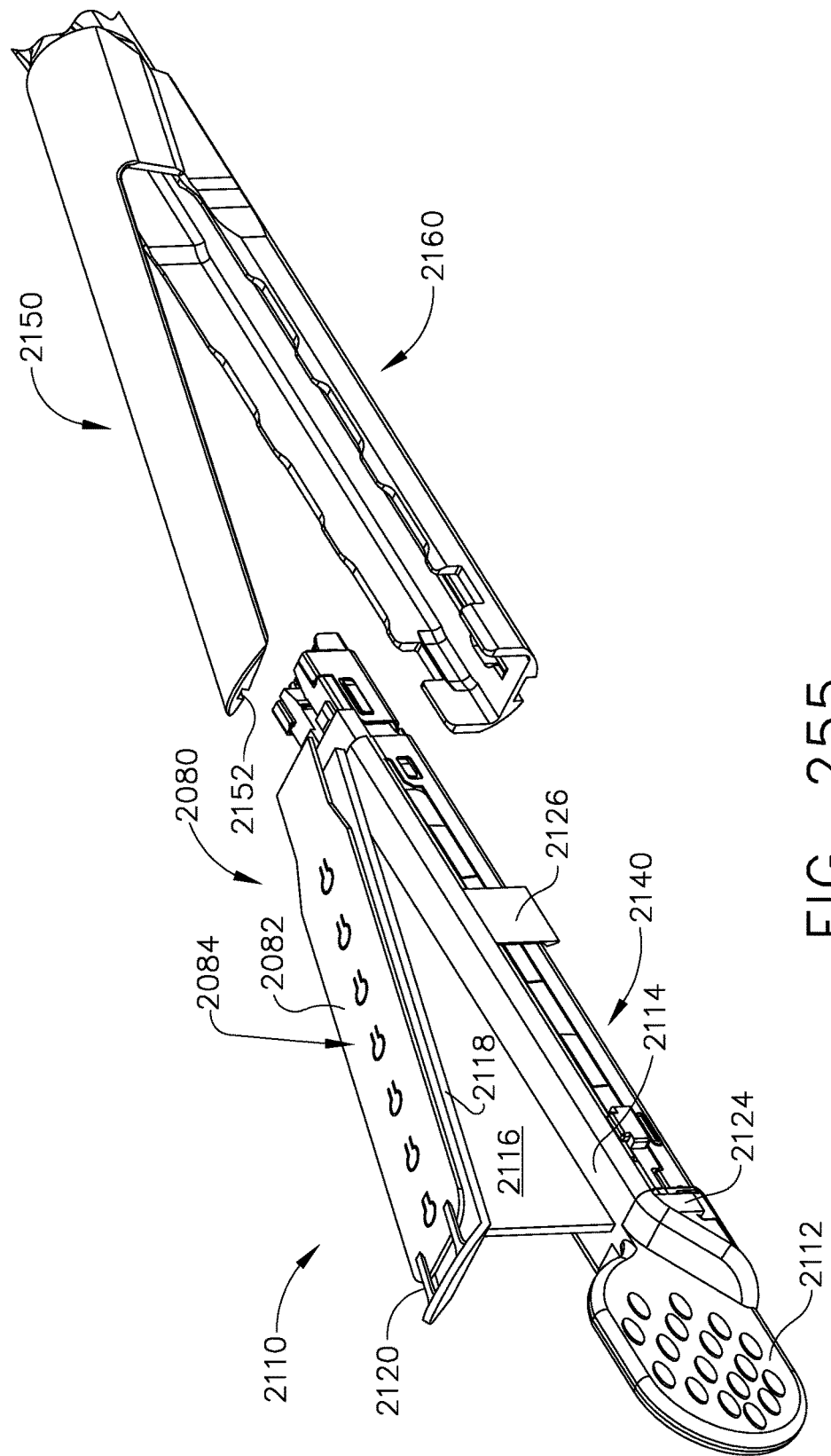
Figure 256:
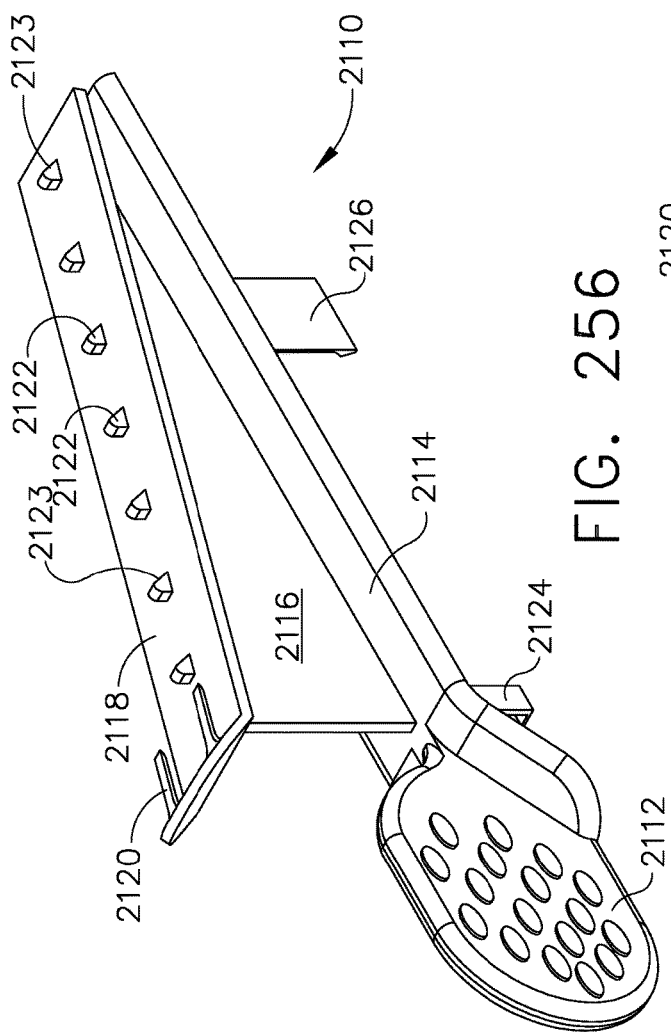
Figure 257:
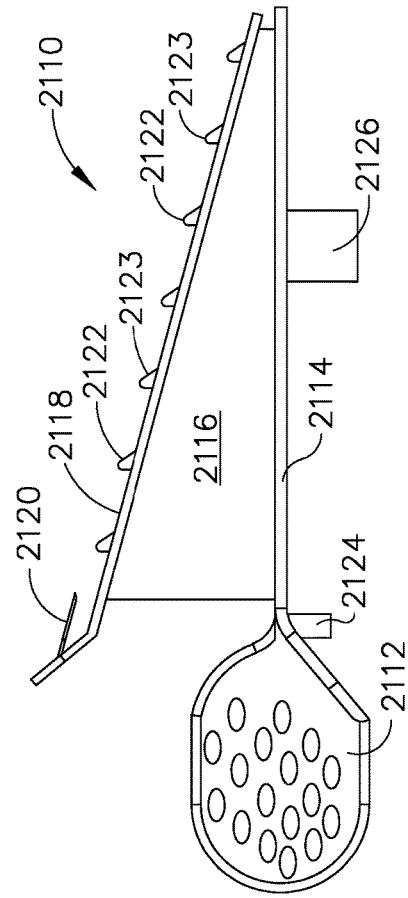
Figure 258:
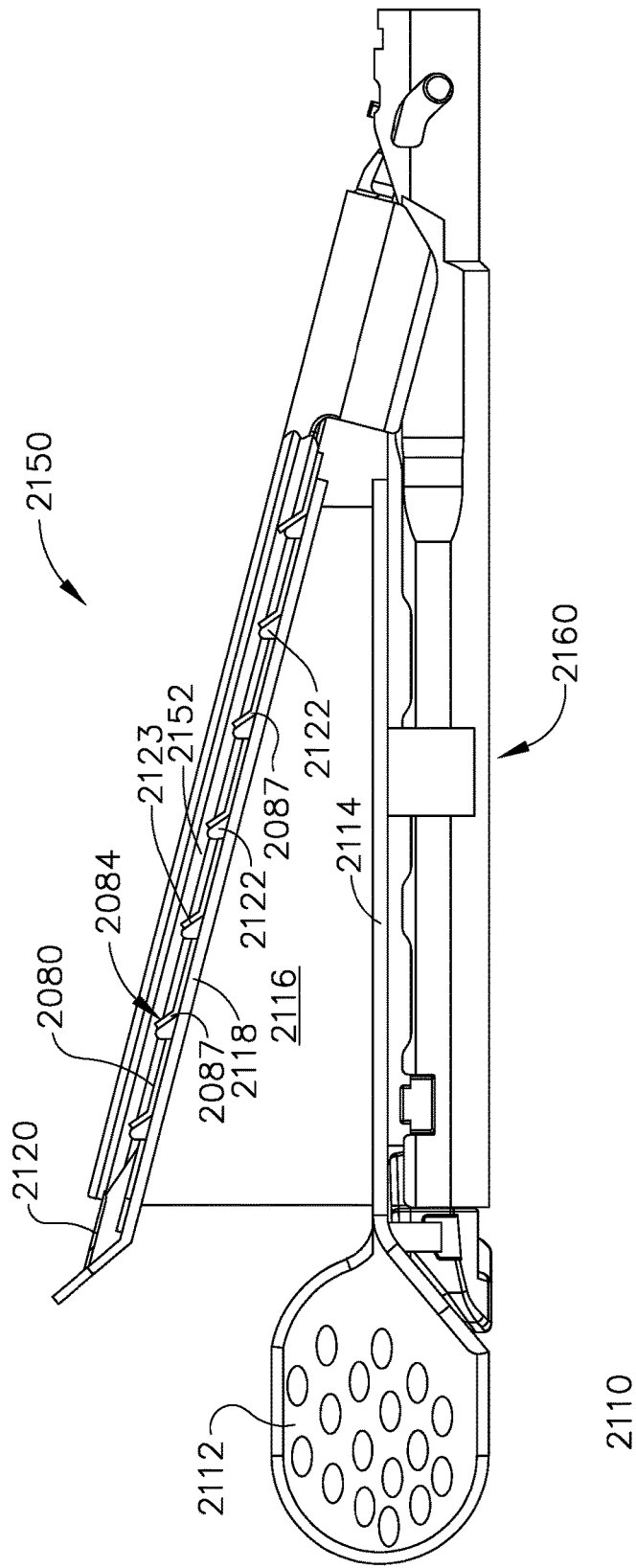
Figure 261:
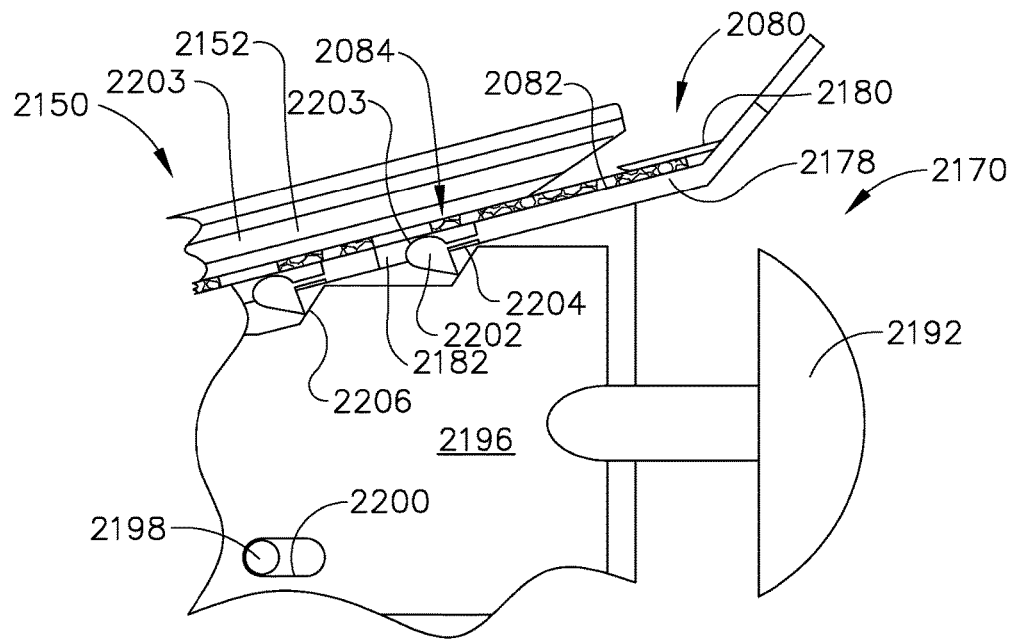
Figure 262:
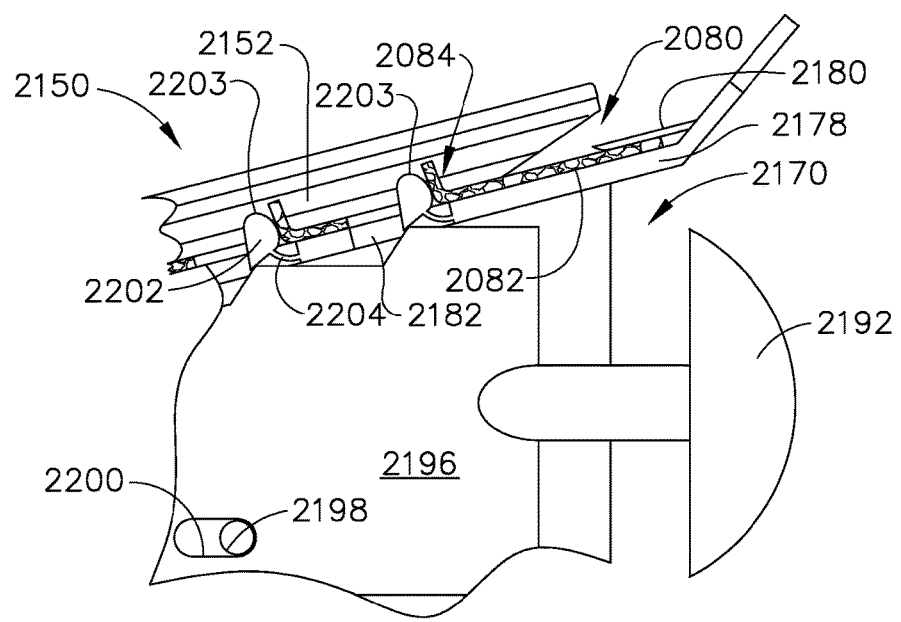
Figure 263:
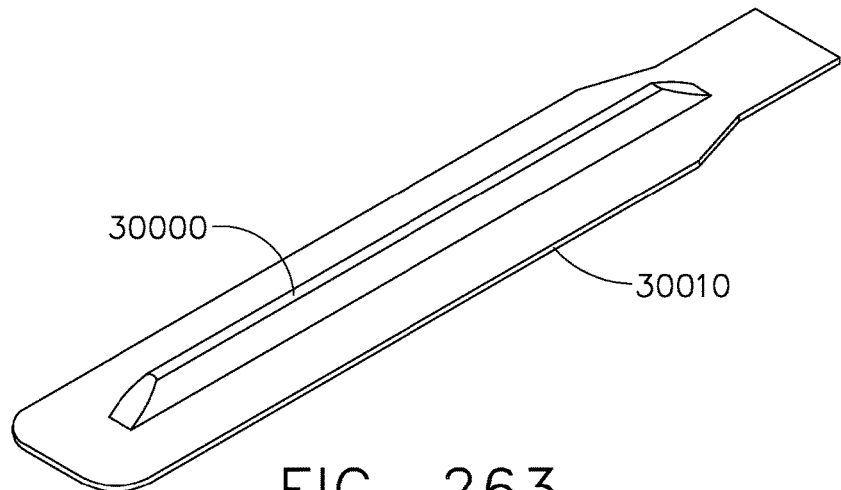
Figure 264:
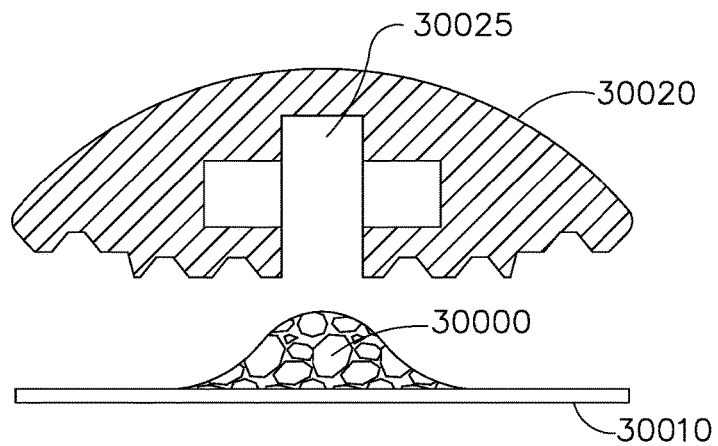
Figure 265:
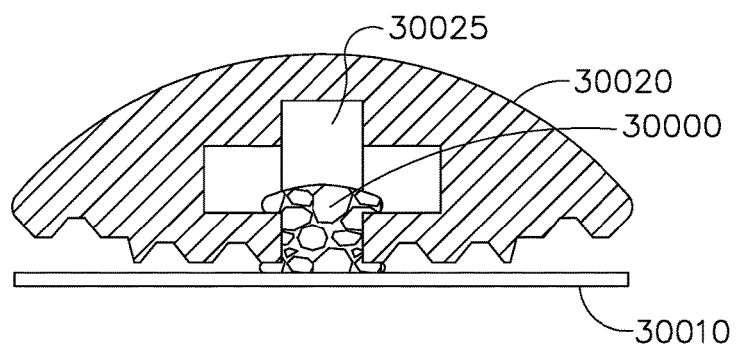
Figure 266:
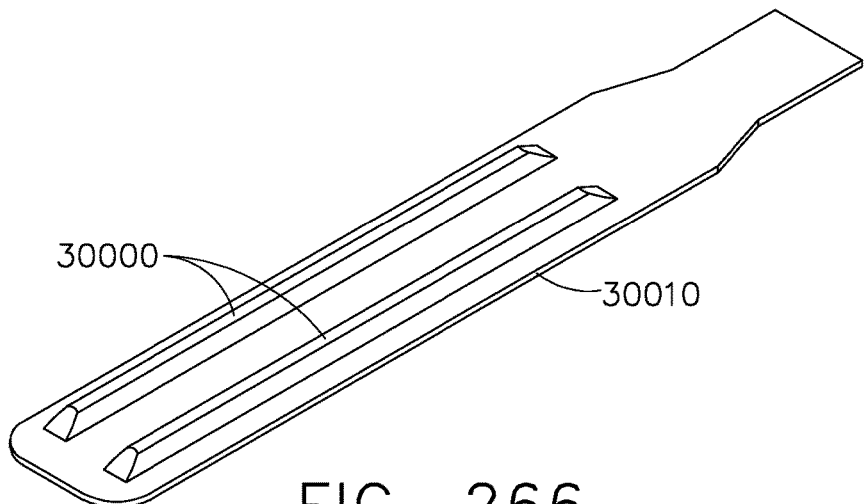
Figure 267:
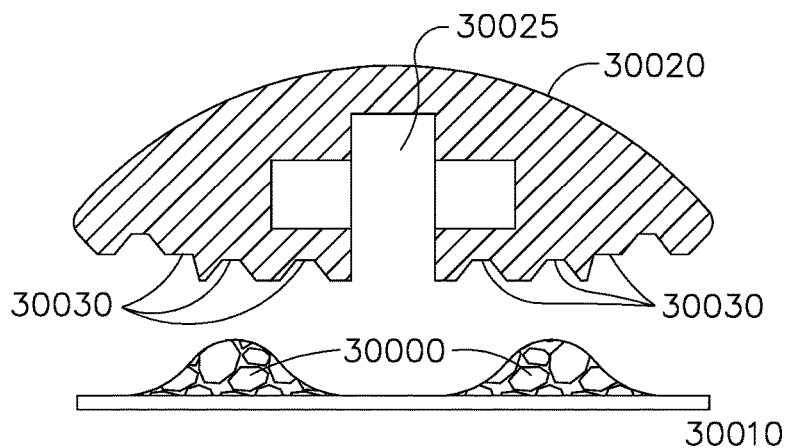
Figure 268:
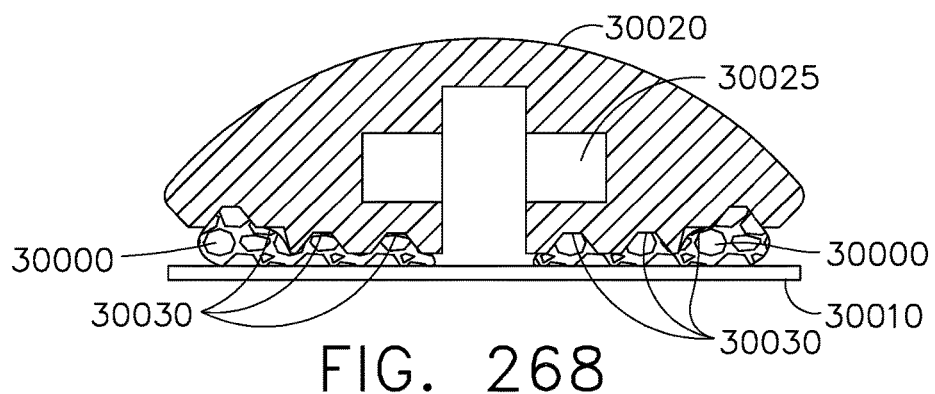
Figure 269:
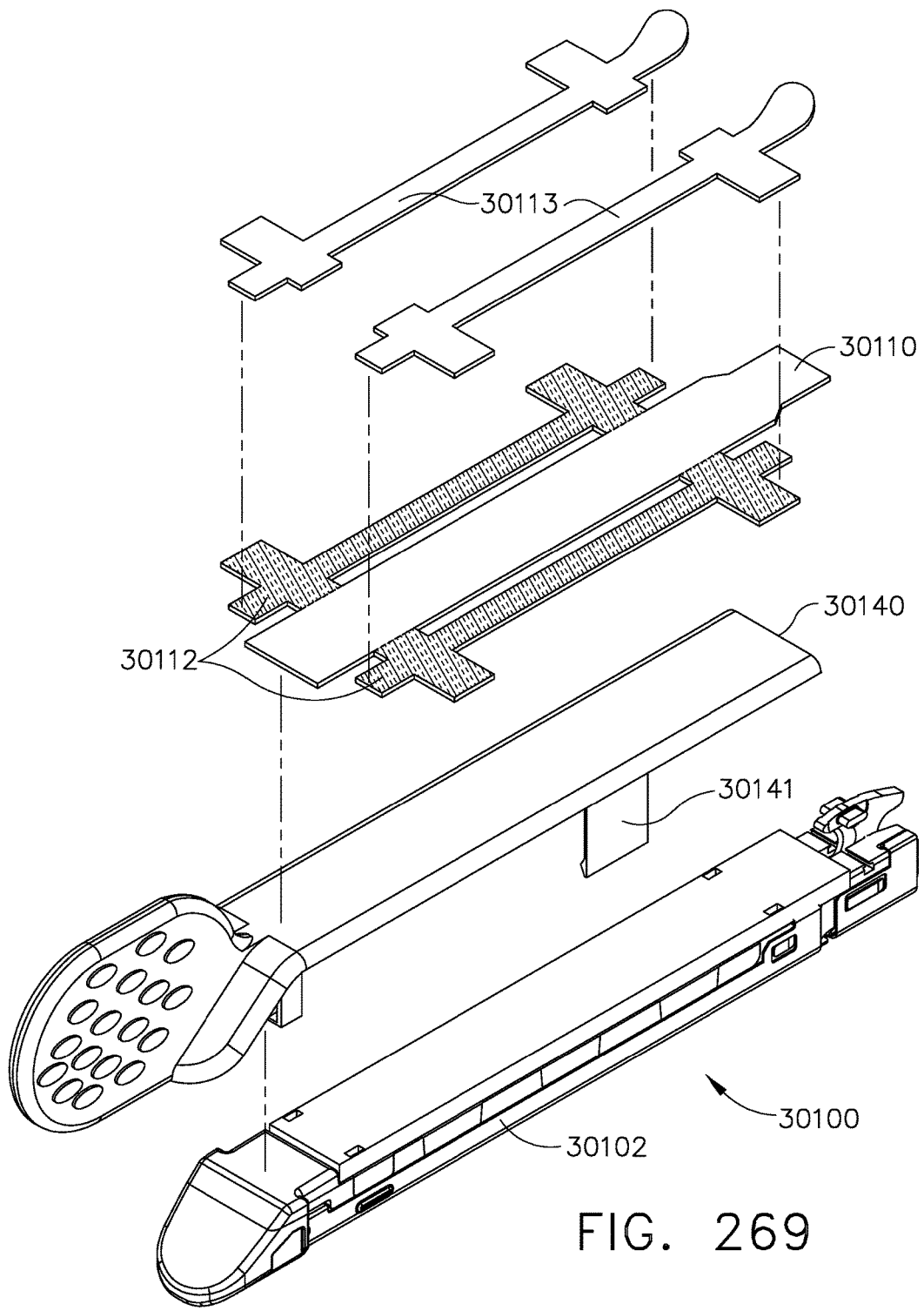
Figure 270:
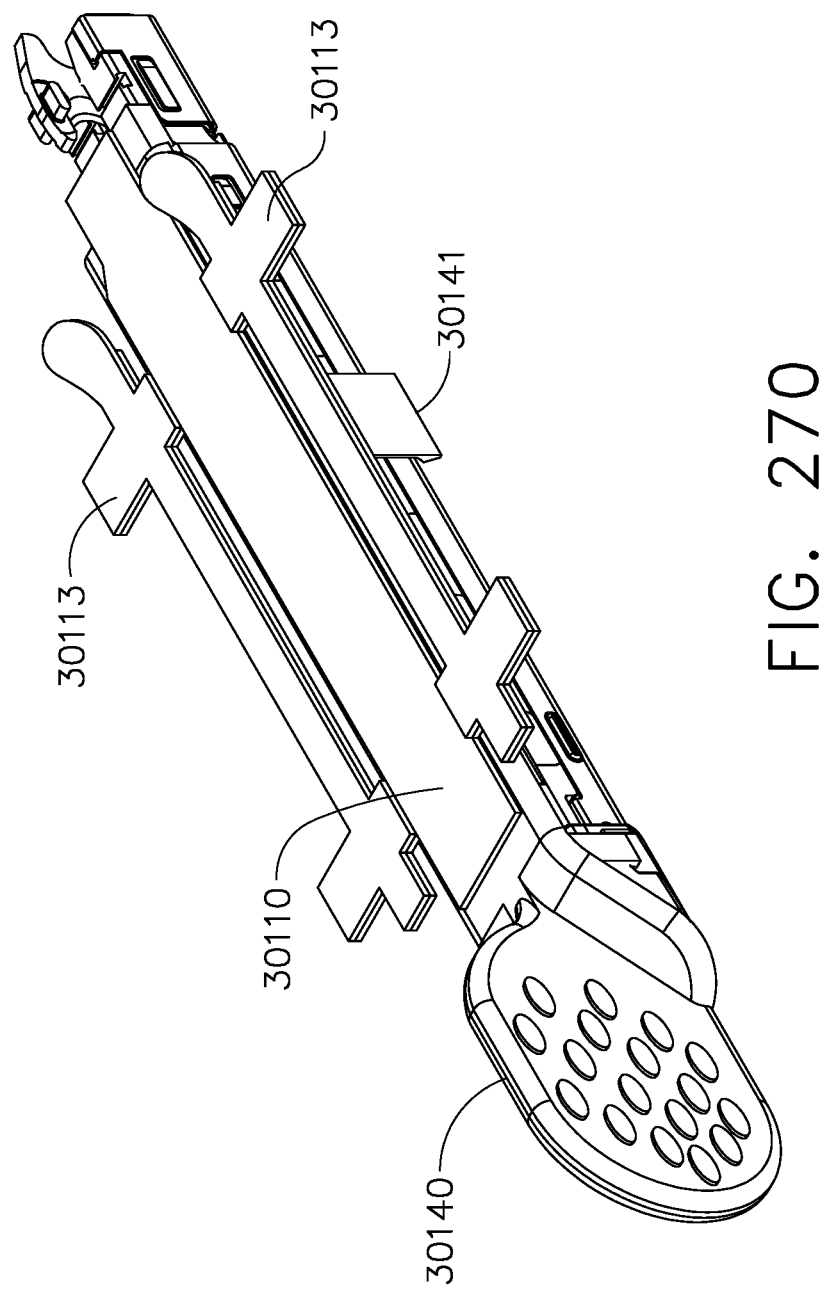
Figure 293:
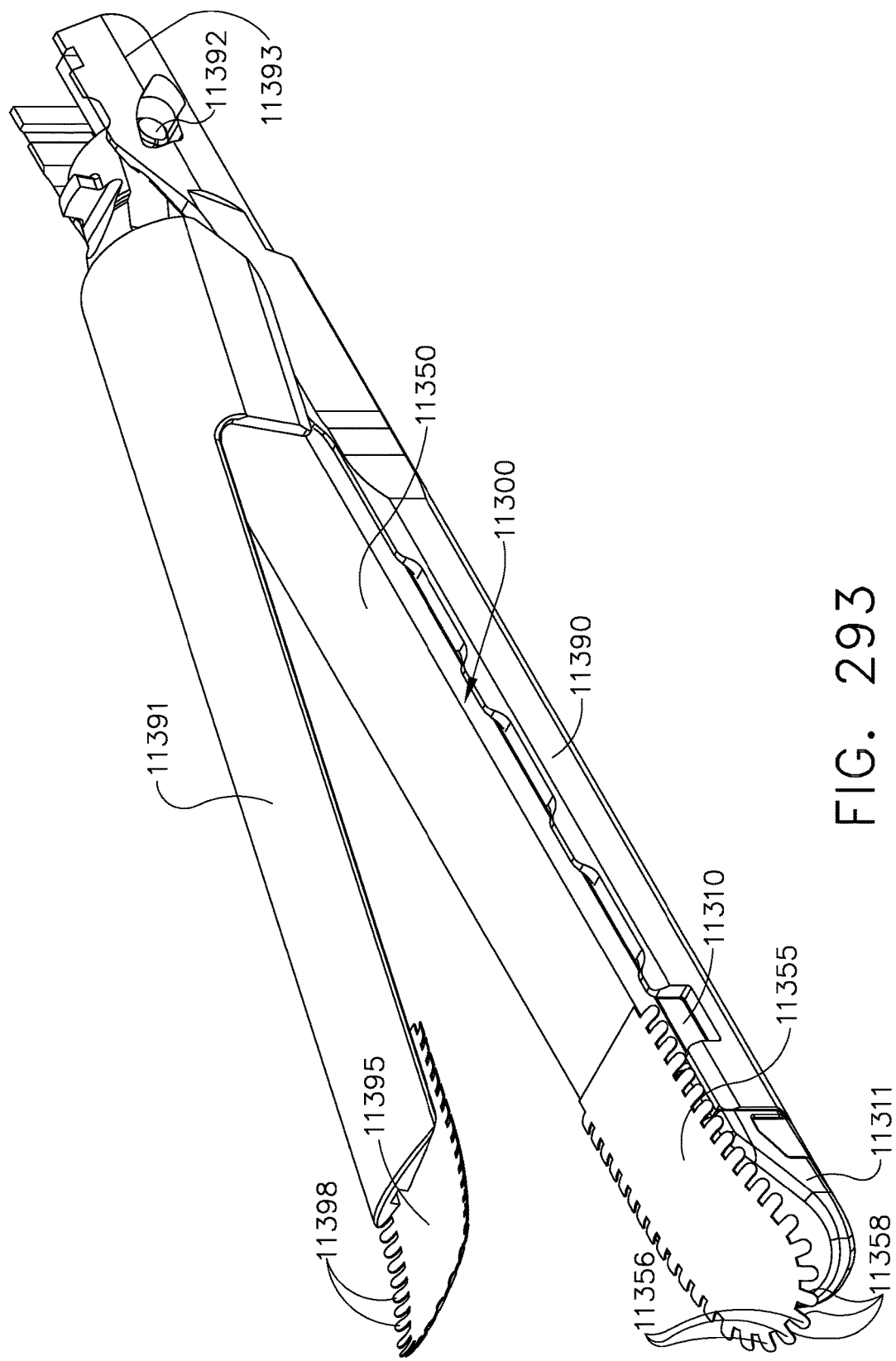
Figure 294:
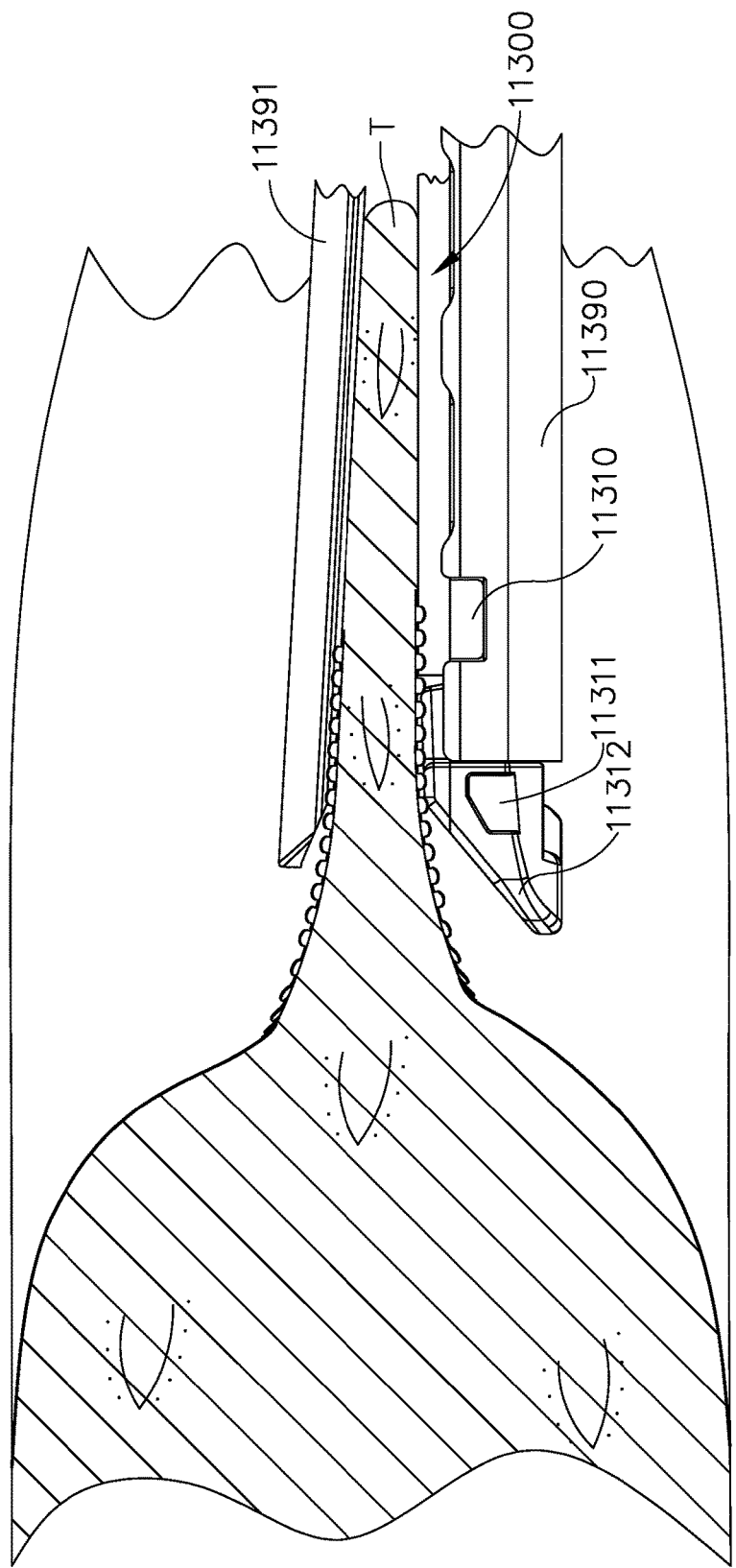

FIG. 117 is a partial, perspective view of a cartridge body, a shell, and a tissue thickness compensator according to various embodiments to the present disclosure, depicting projections extending from the cartridge body;

FIG. 118 is a partial, perspective view of a cartridge body, a shell, and a tissue thickness compensator according to various embodiments of the present disclosure, depicting projections extending from the shell;

FIG. 119 is a partial, cross-sectional view of an end effector assembly according to various embodiments of the present disclosure, depicting a staple positioned in a staple cavity of a cartridge body of the end effector assembly, and further depicting the staple in an unformed configuration;

FIG. 120 is a partial, cross-sectional view of the end effector assembly of FIG. 119, depicting the staple ejected from the staple cavity, and further depicting the staple in a formed configuration;

FIG. 121 is perspective view of a staple and a lock according to various embodiments of the present disclosure, depicting the lock in a locked configuration;

FIG. 122 is a perspective view of the staple and the lock of FIG. 121, depicting the lock in the locked configuration;

FIG. 123 is a perspective view of the staple and the lock of FIG. 121, depicting the lock in a pre-fired position in a staple cavity, and further depicting the lock in the locked configuration;

FIG. 124 is a perspective view of the staple and lock of FIG. 121, depicting the lock in a fired position in the staple cavity, and further depicting the lock in an unlocked configuration;

FIG. 125 is a perspective view of a fastener cartridge assembly of an end effector assembly according to various embodiments to the present disclosure, depicting locks extending from lock cavities in a cartridge body of the fastener cartridge assembly;

FIG. 126 is a cross-sectional view of a lock of FIG. 125, depicting the lock in an unlocked configuration and a connector unsecured to the lock;

FIG. 126A is a partial, cross-sectional view of the fastener cartridge assembly of FIG. 125, depicting the cartridge body, a connector, a tissue thickness compensator, and a lock in a partially assembled position;

FIG. 127 is a partial, cross-sectional view of the fastener cartridge assembly of FIG. 125, depicting the lock in a locked configuration, depicting an anvil in a clamped position, and depicting a driver key in an unfired position;

FIG. 128 is a partial, cross-sectional view of the fastener cartridge assembly of FIG. 125, depicting the lock in a locked configuration, depicting the anvil in the clamped position, and further depicting the driver key in a partially-fired position;

FIG. 129 is a partial, cross-sectional view of the fastener cartridge assembly of FIG. 125, depicting the lock in the unlocked configuration, depicting the anvil in the clamped position, and further depicting the driver key in the fired position;

FIG. 130 is a cross-sectional view of an end effector of illustrating a firing member in a partially-fired position;

FIG. 131 is a cross-sectional view of the end effector of FIG. 130 illustrating the support portion being moved away from the partially-implanted tissue thickness compensator;

FIG. 132 is partial cut-away view of a staple cartridge comprising staple drivers having different heights in accordance with at least one embodiment;

FIG. 133 is a diagram illustrating the staple drivers of FIG. 132 and staples having different unfired heights supported thereon;

FIG. 134 is a cross-sectional view of a staple cartridge comprising a tissue thickness compensator and a support portion in accordance with at least one embodiment;

FIG. 135 is a partial cross-sectional view of a tissue thickness compensator, a staple guide layer, and a staple in an unfired position;

FIG. 136 is a partial cross-sectional view of a tissue thickness compensator, a staple guide layer, and a staple in an unfired position in accordance with at least one alternative embodiment;

FIG. 137 is a partial cross-sectional view of a tissue thickness compensator, a staple guide layer, and a staple in an unfired position in accordance with at least one alternative embodiment;

FIG. 138 is a partial cross-sectional view of a tissue thickness compensator, a staple guide layer, and a staple in an unfired position in accordance with at least one alternative embodiment;

FIG. 139 is a partial cross-sectional view of a tissue thickness compensator, a staple guide layer, and a staple in an unfired position in accordance with at least one alternative embodiment;

FIG. 140 is a partial cross-sectional view of a tissue thickness compensator, a staple guide layer, and a staple in an unfired position in accordance with at least one alternative embodiment;

FIG. 141 is a partial cross-sectional view of a tissue thickness compensator, a staple guide layer, and a staple in an unfired position in accordance with at least one alternative embodiment;

FIG. 142 is a detail view of a region surrounding a tip of the staple of FIG. 141;

FIG. 143 is a partial cross-sectional view of a tissue thickness compensator, a staple guide layer, and a staple in an unfired position in accordance with at least one alternative embodiment;

FIG. 144 is a detail view of a region surrounding a tip of the staple of FIG. 143;

FIG. 145 is a partial cross-sectional view of a tissue thickness compensator, a staple guide layer, and a staple in an unfired position in accordance with at least one alternative embodiment;

FIG. 146 is a perspective view of a staple guide layer and a plurality of staples in an unfired position in accordance with at least one alternative embodiment;

FIG. 147 is an exploded view of a tissue thickness compensator and a staple cartridge body;

FIG. 148 is an elevational view of a disposable loading unit including a pivotable jaw configured to support a staple cartridge;

FIG. 149 is a perspective view of a tissue thickness compensator applicator positioned within an effector of a disposable loading unit;

FIG. 150 is a top perspective view of the tissue thickness compensator applicator of FIG. 149;

FIG. 151 is a bottom perspective view of the tissue thickness compensator applicator of FIG. 149;

FIG. 152 is a cross-sectional view of an end effector of a surgical stapling instrument comprising staple drivers having different heights and a contoured deck surface in accordance with at least one embodiment;

FIG. 153 is a cross-sectional view of an end effector of a surgical stapling instrument comprising staple drivers having different heights and a stepped deck surface in accordance with at least one embodiment;

FIG. 154 is a diagram illustrating a tissue thickness compensator comprising a varying thickness, staple drivers having different heights, and staples having different unformed heights;

FIG. 155 is a diagram illustrating the staples and the tissue thickness compensator of FIG. 154 implanted to tissue;

FIG. 156 is a partial cross-sectional view of a tissue thickness compensator attached to a staple cartridge body;

FIG. 157 is a partial cross-sectional view of a the tissue thickness compensator and the staple cartridge body of FIG. 156;

FIG. 158 is a partial exploded view of the tissue thickness compensator of FIG. 156;

FIG. 159 is a partial exploded view of a tissue thickness compensator, a staple cartridge body, and a firing member;

FIG. 160 is a partial elevational view of the embodiment of FIG. 159;

FIG. 161 is a bottom view of a staple cartridge;

FIG. 162 is a detail bottom view of the staple cartridge of FIG. 161;

FIG. 163 is an exploded view of a staple cartridge illustrating a staple driver arrangement;

FIG. 164 is a perspective view of an embodiment of a retainer attached to a staple cartridge and with a layer, such as a tissue thickness compensator, arranged intermediate the retainer and the staple cartridge, wherein the retainer, layer, and staple cartridge are arranged relative to a surgical stapler, and wherein a staple cartridge channel is removed for purposes of illustration;

FIG. 165 is a perspective view of the retainer of FIG. 164;

FIG. 166 is a plan view of the retainer, layer, and staple cartridge of FIG. 164;

FIG. 167 is a cross-sectional view of the retainer, layer, and staple cartridge of FIG. 164, wherein tips of staples extend from staple cavities in the staple cartridge and into the layer;

FIG. 168 is a perspective view of an embodiment of a retainer, wherein the retainer includes moveable cam portions and locking tabs;

FIG. 169 is a perspective view of the retainer of FIG. 168 attached to a staple cartridge, wherein the staple cartridge and retainer are positioned for insertion into a staple cartridge channel of an end effector of a surgical stapler;

FIG. 170 is a plan view of the retainer of FIG. 168 positioned, but not fully inserted, into a cartridge channel of the end effector of the surgical stapler;

FIG. 171 is a cross-sectional end view of the retainer of FIG. 168 positioned, but not fully inserted, into the staple cartridge channel of FIG. 170;

FIG. 172 is a plan view of the retainer of FIG. 168 fully inserted in the staple cartridge channel of FIG. 170;

FIG. 173 is a cross-sectional end view of the retainer of FIG. 168 fully inserted in the staple cartridge channel of FIG. 170, wherein the retainer is unlocked and is being removed from the staple cartridge;

FIG. 174 is a plan view of an end effector insert in accordance with at least one embodiment;

FIG. 175 is an elevational view of the end effector insert of FIG. 174;

FIG. 176 is a perspective view of the end effector insert of FIG. 174;

FIG. 177 is a partial perspective view of the end effector insert of FIG. 174 depicting the end effector insert engaging the anvil of the end effector of a surgical instrument;

FIG. 178 is a partial perspective view of the end effector insert of FIG. 174 depicting the end effector insert engaging the staple cartridge of the end effector of a surgical instrument;

FIG. 179 is an elevational view of the end effector insert of FIG. 174 depicting the end effector insert engaging the end effector of a surgical instrument;

FIG. 180 is an elevational view of the end effector insert of FIG. 174 positioned in the end effector of a surgical instrument;

FIG. 181 is a partial perspective view of an embodiment of a staple cartridge assembly that includes a staple-cartridge layer and an anvil-attachable layer positioned relative to a staple cartridge;

FIG. 182 is a partial perspective view of the staple cartridge assembly of FIG. 181, wherein the anvil-attachable layer is fastened to the staple cartridge;

FIG. 183 is a partial perspective view of an embodiment of a staple cartridge assembly that includes a staple-cartridge layer and an anvil-attachable layer positioned relative to a staple cartridge, wherein a proximal end portion of the anvil-attachable layer is attached to attachment features of the staple cartridge by an adhesive or by a weld, and wherein a portion of the anvil-attachable layer is shown as being transparent for purposes of illustration;

FIG. 184 is a partial perspective view of the staple cartridge assembly of FIG. 183, wherein a corner of the proximal end portion of the anvil-attachable layer is shown detached and lifted away from the staple cartridge;

FIG. 185 is a partial perspective view of an embodiment of a staple cartridge assembly, that includes a staple cartridge layer and an anvil-attachable layer positioned relative to a staple cartridge, wherein the anvil-attachable layer is attached to the staple cartridge layer;

FIG. 186 is a detail view of the staple cartridge layer of FIG. 185 and the anvil-attachable layer attached thereto;

FIG. 187 is a partial plan view of an embodiment of an anvil-attachable layer;

FIG. 188 is a partial plan view of the anvil-attachable layer of FIG. 187 being cut by a cutting blade;

FIG. 189 is a plan view of a tissue compensator of a sleeve in accordance with at least one embodiment;

FIG. 190 is a perspective view of the tissue compensator of FIG. 189;

FIG. 191 is an elevational view of the tissue compensator of FIG. 189;

FIG. 192 is a perspective view of a tissue thickness compensator;

FIG. 193 is a perspective view of the tissue thickness compensator of FIG. 192 attached to a staple cartridge;

FIG. 194 is a detail view of one tissue thickness compensator of FIG. 192 at least partially overlapped with another tissue thickness compensator of FIG. 192;

FIG. 195 is a perspective view of a staple cartridge including a tissue thickness compensator attached thereto;

FIG. 196 is a detail view of one tissue thickness compensator of FIG. 195 at least partially overlapped with another tissue thickness compensator of FIG. 195;

FIG. 197 is an exploded view of a staple cartridge including a tissue thickness compensator including a plurality of layers;

FIG. 198 is a cross-sectional diagram illustrating a tissue thickness compensator of FIG. 197 implanted on one side of patient tissue and another tissue thickness compensator of FIG. 197 implanted on the other side of the tissue;

FIG. 199 is an exploded perspective view of an end effector of a stapling instrument comprising a staple cartridge and a tissue thickness compensator according to various embodiments;

FIG. 200 is a cross sectional view of the tissue thickness compensator in FIG. 199 according to various embodiments;

FIG. 201 is a top view of a tissue thickness compensator including a plurality of circular pieces according to various embodiments;

FIG. 202 is a top view of a tissue thickness compensator including a plurality of circular pieces according to various embodiments;

FIG. 202A is a cross sectional view of a tissue thickness compensator according to various embodiments;

FIG. 203 is a top view of a tissue thickness compensator according to various embodiments;

FIG. 204 is a top view of a tissue thickness compensator including a plurality of hexagonal pieces according to various embodiments;

FIG. 205 is a top view of a fastened tissue thickness compensator including a plurality of pieces according to various embodiments;

FIG. 206 is a top view of a tissue thickness compensator including a plurality of slits according to various embodiments;

FIG. 207A is an exploded view of a staple cartridge and a layer in accordance with at least one embodiment;

FIG. 207B is a cross-sectional view of a layer and tissue T captured between a staple cartridge and an anvil in accordance with at least one embodiment;

FIG. 207C is a perspective view of a layer comprising pillar-shaped cleats in accordance with at least one embodiment;

FIG. 208 is a cross-sectional view of the layer in FIG. 207C;

FIG. 209 is a perspective view of a layer comprising linear protrusions in accordance with at least one embodiment;

FIG. 210 is a cross-sectional view of the layer in FIG. 209;

FIG. 211 is a perspective view of a layer comprising dome-shaped protrusions in accordance with at least one embodiment;

FIG. 212 is a cross-sectional view of the layer in FIG. 211;

FIG. 213 is a perspective view of a layer comprising linear depressions in accordance with at least one embodiment;

FIG. 214 is a cross-sectional view of the layer in FIG. 213;

FIG. 215 is a perspective view of a layer comprising linear protrusions in accordance with at least one embodiment;

FIG. 216 is a cross-sectional view of the layer in FIG. 215;

FIG. 217 is a perspective view of a layer comprising linear protrusions in accordance with at least one embodiment;

FIG. 218 is a perspective view of a layer comprising cone-shaped protrusions in accordance with at least one embodiment;

FIG. 219 is a perspective view of a layer comprising pyramid-shaped protrusions in accordance with at least one embodiment;

FIG. 220 is a cross-sectional view of the layer in FIG. 219 in accordance with at least one embodiment;

FIG. 221 is a perspective view of a layer in accordance with at least one embodiment;

FIG. 222 is a cross-sectional view of the layer in FIG. 221;

FIG. 223 is a perspective view of a layer comprising depressions in accordance with at least one embodiment;

FIG. 224 is a cross-sectional view of the layer in FIG. 223;

FIG. 224A is a cross-sectional view of a layer comprising portions with reduced thickness and tissue T captured between an anvil comprising a plurality of staple forming pockets and a staple cartridge in accordance with at least one embodiment;

FIG. 224B is a cross-sectional view of a layer comprising a plurality of protrusions and tissue T captured between an anvil comprising a plurality of staple forming pockets and a staple cartridge in accordance with at least one embodiment;

FIG. 225 is a perspective cross-sectional view of a layer, such as a tissue thickness compensator, secured to an anvil of an end effector of a surgical instrument in accordance with at least one embodiment;

FIG. 226 is a cross-sectional view of the layer of FIG. 225 secured to the anvil;

FIG. 227 is a cross-sectional view of the layer of FIG. 225;

FIG. 228 is a perspective view of an embodiment of a retainer for use with a staple cartridge;

FIG. 229 is a perspective view of a staple cartridge assembly that includes the retainer of FIG. 228 engaged with a staple cartridge and an anvil-attachable layer;

FIG. 230 is a plan view of the staple cartridge assembly of FIG. 229;

FIG. 231 is a cross-sectional end view of the staple cartridge assembly of FIG. 229, wherein the staple cartridge assembly is inserted into a staple cartridge channel of an end effector and an anvil of the end effector is positioned relative thereto;

FIG. 232 is a cross-sectional end view of the staple cartridge assembly and end effector shown in FIG. 231, wherein the anvil is pressed against the anvil-attachable layer and the retainer;

FIG. 233 is a cross-sectional plan view of the staple cartridge assembly and end effector shown in FIG. 231, wherein the anvil has been lifted from the retainer, removing the attached anvil-attachable layer from the retainer;

FIG. 234 is a cross-sectional plan view of the end effector shown in FIG. 231, wherein the anvil-attachable layer is attached to the anvil and the retainer has been removed;

FIG. 235 is a perspective view of an embodiment of an anvil-attachable layer in accordance with at least one embodiment;

FIG. 236 is a perspective view of an embodiment of an anvil-attachable layer in accordance with at least one embodiment;

FIG. 237 is a perspective view of an embodiment of an anvil-attachable layer in accordance with at least one embodiment;

FIG. 238 is a perspective view of an embodiment of an anvil-attachable layer with deployable attachment features, wherein the deployable attachment features are in an undeployed configuration;

FIG. 239 is a perspective view of the anvil-attachable layer of FIG. 238, wherein the deployable attachment features are shown in a deployed configuration;

FIG. 240 is a cross-sectional plan view of the anvil-attachable layer of FIG. 238 positioned relative to an anvil of an end effector, wherein the deployable attachment features are deployed in a slot of the anvil;

FIG. 241 is a perspective view of an embodiment of an anvil-attachable layer with deployable attachment features, wherein the deployable attachment features are in an undeployed configuration;

FIG. 242 is a perspective view of the anvil-attachable layer of FIG. 241, wherein the deployable attachment features are shown in a deployed configuration;

FIG. 243 is a cross-sectional plan view of the anvil-attachable layer of FIG. 241 positioned relative to an anvil of an end effector, wherein the deployable attachment features are deployed in a slot of the anvil;

FIG. 244 is an exploded perspective view of an anvil and a tissue thickness compensator in accordance with at least one embodiment;

FIG. 245 is a cross-sectional plan view of an anvil comprising a plurality of staple forming pockets and an anvil-attachable layer, such as a tissue thickness compensator, comprising a plurality of capsules aligned with the forming pockets in accordance with at least one embodiment;

FIG. 246 is a detail view of the capsules of the anvil-attachable layer of FIG. 245;

FIG. 247 is a diagram illustrating the anvil and the anvil-attachable layer of FIG. 245 positioned relative to tissue which is to be stapled by staples from a staple cartridge positioned on the opposite side of the tissue;

FIG. 248 is a diagram illustrating the anvil of FIG. 245 moved toward the staple cartridge of FIG. 247 and staples partially fired from the staple cartridge;

FIG. 249 is a cross-sectional view of an embodiment of an anvil-attachable layer arranged relative to an anvil and patient tissue, wherein staples of a staple cartridge are fired through the layer and the patient tissue;

FIG. 250 is a cross-sectional view of an embodiment of an anvil-attachable layer positioned relative to an anvil and patient tissue, wherein staples of a staple cartridge are fired through the layer and the patient tissue;

FIG. 251 illustrates a retainer assembly being inserted into a surgical instrument, wherein the surgical instrument comprises an anvil and a staple cartridge channel, and wherein a portion of the insertion tool is removed for the purposes of illustration;

FIG. 252 illustrates the retainer assembly of FIG. 251 being inserted into the surgical instrument, wherein a portion of the insertion tool is removed for the purposes of illustration;

FIG. 253 illustrates the insertion tool of FIG. 251 being moved relative to the retainer to engage the staple cartridge in the staple cartridge channel and to engage an anvil-attachable layer, such as a tissue thickness compensator, with the anvil, wherein a portion of the insertion tool is removed for the purposes of illustration;

FIG. 254 illustrates the insertion tool of FIG. 251 being moved relative to the retainer to disengage the retainer from the anvil-attachable layer and from the staple cartridge, wherein a portion of the insertion tool is removed for the purposes of illustration;

FIG. 255 is a perspective view of an embodiment of a retainer engaged with a staple cartridge, wherein an anvil-attachable layer having deployable attachment features engaged with the retainer, and wherein the retainer is positioned for insertion into an end effector;

FIG. 256 is a perspective view of the retainer of FIG. 255;

FIG. 257 is an elevational view of the retainer of FIG. 255;

FIG. 258 is an elevational view of the retainer, staple cartridge and anvil-attachable layer of FIG. 255 inserted into an end effector, wherein the deployable attachment features of the anvil-attachable layer are deployed, and wherein portions of the anvil and the anvil-attachable layer are removed for purposes of illustration;

FIG. 259 is an elevational view of an embodiment of a retainer inserted in an end effector, wherein an anvil-attachable layer with deployable attachment features is arranged on the retainer, and wherein portions of the retainer, the anvil-attachable layer, and the anvil are removed for purposes of illustration;

FIG. 260 is an elevational view of the retainer of FIG. 259, wherein the retainer has deployed the deployable attachment features of the anvil-attachable layer, and wherein portions of the retainer, the anvil-attachable layer, and the anvil are removed for purposes of illustration;

FIG. 261 is a detail elevational view of the retainer, anvil-attachable layer, and anvil of FIG. 259, wherein the deployable attachment features are not deployed, and wherein portions of the retainer, anvil-attachable layer, and anvil are removed for purposes of illustration;

FIG. 262 is a detail elevational view of the retainer, anvil-attachable layer, and anvil of FIG. 259, wherein the deployable attachment features are deployed into a slot in the anvil, and wherein portions of the retainer, anvil-attachable layer, and anvil are removed for purposes of illustration;

FIG. 263 illustrates a tissue thickness compensator comprising a flowable attachment portion according to certain non-limiting embodiments;

FIG. 264 illustrates a pressure sensitive adhesive laminate in an unstressed position aligned with a slot in the staple cartridge according to certain non-limiting embodiments;

FIG. 265 illustrates the pressure sensitive adhesive laminate in FIG. 264 releasably attached to a staple cartridge according to certain non-limiting embodiments;

FIG. 266 illustrates a tissue thickness compensator comprising a flowable attachment portion according to certain non-limiting embodiments;

FIG. 267 illustrates a pressure sensitive adhesive laminate in an unstressed position aligned with staple cavities in the staple cartridge according to certain non-limiting embodiments;

FIG. 268 illustrates the pressure sensitive adhesive laminate in FIG. 267 releasably attached to a staple cartridge according to certain non-limiting embodiments;

FIGS. 269-273 illustrate a pressure sensitive adhesive laminate comprising an adhesive tab according to certain non-limiting embodiments;

FIGS. 274-279 illustrate a pressure sensitive adhesive laminate comprising an adhesive tab according to certain non-limiting embodiments;

FIGS. 280-283 illustrate a pressure sensitive adhesive laminate comprising tabs to releasably attach to an anvil according to certain non-limiting embodiments;

FIGS. 284-288 illustrate a pressure sensitive adhesive laminate releasably attached to an anvil using an applicator according to certain non-limiting embodiments;

FIGS. 289-292 illustrate a pressure sensitive adhesive laminate releasably attached to an anvil according to certain non-limiting embodiments;

FIG. 293 is a perspective view of an end effector of a surgical stapling instrument including an implantable transition portion extending from the anvil and an implantable transition portion extending from the staple cartridge; and FIG. 294 is a diagram depicting tissue positioned between the anvil and the staple cartridge of the surgical stapling instrument of FIG. 293.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PRE- VENTING ACTUATION MOTIONS WHEN A CARTRIDGE IS NOT PRESENT, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Patent Application Publication No. 2012/0080488;

U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Patent Application Publication No. 2012/0080338;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084;

U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741;

U.S. patent application Ser. No. 13/241,629, entitled SURGICAL INSTRUMENT WITH SELECTIVELY ARTICULATABLE END EFFECTOR, now U.S. Patent Application Publication No. 2012/0074200;

U.S. application Ser. No. 13/433,096, entitled TISSUE THICKNESS COMPENSATOR COMPRISING A PLURALITY OF CAPSULES, now U.S. Patent Application Publication No. 2012/0241496;

U.S. application Ser. No. 13/433,103, entitled TISSUE THICKNESS COMPENSATOR COMPRISING A PLURALITY OF LAYERS, now U.S. Patent Application Publication No. 2012/0241498;

U.S. application Ser. No. 13/433,098, entitled EXPANDABLE TISSUE THICKNESS COMPENSATOR, now U.S. Patent Application Publication No. 2012/0241491;

U.S. application Ser. No. 13/433,102, entitled TISSUE THICKNESS COMPENSATOR COMPRISING A RESERVOIR, now U.S. Pat. No. 9,232,941;

U.S. application Ser. No. 13/433,114, entitled RETAINER ASSEMBLY INCLUDING A TISSUE THICKNESS COMPENSATOR, now U.S. Patent Application Publication No. 2012/0241499;

U.S. application Ser. No. 13/433,136, entitled TISSUE THICKNESS COMPENSATOR COMPRISING AT LEAST ONE MEDICAMENT, now U.S. Patent Application Publication No. 2012/0241492;

U.S. application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. application Ser. No. 13/433,144, entitled TISSUE THICKNESS COMPENSATOR COMPRISING FIBERS TO PRODUCE A RESILIENT LOAD, now U.S. Patent Application Publication No. 2012/0241500;

U.S. application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. application Ser. No. 13/433,155, entitled TISSUE THICKNESS COMPENSATOR COMPRISING RESILIENT MEMBERS, now U.S. Patent Application Publication No. 2012/0241502;

U.S. application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. application Ser. No. 13/433,167, entitled TISSUE THICKNESS COMPENSATORS, now U.S. Pat. No. 9,220,501;

U.S. application Ser. No. 13/433,175, entitled LAYERED TISSUE THICKNESS COMPENSATOR, now U.S. Patent Application Publication No. 2012/0253298;

U.S. application Ser. No. 13/433,179, entitled TISSUE THICKNESS COMPENSATORS FOR CIRCULAR SURGICAL STAPLERS, now U.S. Patent Application Publication No. 2012/0241505;

U.S. application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. application Ser. No. 13/433,118, entitled TISSUE THICKNESS COMPENSATOR COMPRISED OF A PLURALITY OF MATERIALS, now U.S. Patent Application Publication No. 2013/0256365;

U.S. application Ser. No. 13/433,135, entitled MOVABLE MEMBER FOR USE WITH A TISSUE THICKNESS COMPENSATOR, now U.S. Patent Application Publication No. 2013/0256382;

U.S. application Ser. No. 13/433,140, entitled TISSUE THICKNESS COMPENSATOR AND METHOD FOR MAKING THE SAME, now U.S. Pat. No. 9,241,714;

U.S. application Ser. No. 13/433,147, entitled TISSUE THICKNESS COMPENSATOR COMPRISING CHANNELS, now U.S. Patent Application Publication No. 2013/0256369;

U.S. application Ser. No. 13/433,126, entitled TISSUE THICKNESS COMPENSATOR COMPRISING TISSUE INGROWTH FEATURES, now U.S. Patent Application Publication No. 2013/0256366;

U.S. application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373; and U.S. application Ser. No. 13/433,129, entitled TISSUE THICKNESS COMPENSATOR COMPRISING A PLURALITY OF MEDICAMENTS, now U.S. Pat. No. 9,211,120.

The Applicant of the present application also owns the U.S. Patent Applications identified below which are each herein incorporated by reference in their respective entirety:

U.S. application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. application Ser. No. 11/714,049, entitled SURGICAL STAPLING DEVICE WITH ANVIL HAVING STAPLE FORMING POCKETS OF VARYING DEPTHS, now U.S. Patent Publication No. 2007/0194082;

U.S. application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. application Ser. No. 11/711,975, entitled SURGICAL STAPLING DEVICE WITH STAPLE DRIVERS OF DIFFERENT HEIGHT, now U.S. Patent Publication No. 2007/0194079;

U.S. application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. application Ser. No. 13/020,263, entitled SURGICAL STAPLING SYSTEMS THAT PRODUCE FORMED STAPLES HAVING DIFFERENT LENGTHS, now U.S. Patent Publication No. 2011/0147434;

U.S. application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Patent Publication No. 2011/0290851;

U.S. application Ser. No. 13/369,629, entitled ROBOTICALLY-CONTROLLED CABLE-BASED SURGICAL END EFFECTORS, now U.S. Patent Publication No. 2012/0138660;

U.S. application Ser. No. 12/695,359, entitled SURGICAL STAPLING DEVICES FOR FORMING STAPLES WITH DIFFERENT FORMED HEIGHTS, now U.S. Patent Publication No. 2010/0127042; and U.S. application Ser. No. 13/072,923, entitled STAPLE CARTRIDGES FOR FORMING STAPLES HAVING DIFFERING FORMED STAPLE HEIGHTS, now U.S. Patent Publication No. 2011/0174863.

The Applicant of the present application also owns the U.S. Patent Applications identified below which were filed on Feb. 8, 2013 and which are each herein incorporated by reference in their respective entirety:

U.S. patent application Ser. No. 13/763,112, entitled SURGICAL STAPLING CARTRIDGE WITH LAYER RETENTION FEATURES, now U.S. Patent Application Publication No. 2013/0256379;

U.S. patent application Ser. No. 13/763,028, entitled ADHESIVE FILM LAMINATE, now U.S. Patent Application Publication No. 2013/0146643;

U.S. patent application Ser. No. 13/763,035, entitled ACTUATOR FOR RELEASING A TISSUE THICKNESS COMPENSATOR FROM A FASTENER CARTRIDGE, now U.S. Patent Application Publication No. 2013/0214030;

U.S. patent application Ser. No. 13/763,042, entitled RELEASABLE TISSUE THICKNESS COMPENSATOR AND FASTENER CARTRIDGE HAVING THE SAME, now U.S. Patent Application Publication No. 2013/0221063;

U.S. patent application Ser. No. 13/763,054, entitled FASTENER CARTRIDGE COMPRISING A CUTTING MEMBER FOR RELEASING A TISSUE THICKNESS COMPENSATOR, now U.S. Patent Application Publication No. 2014/0097227;

U.S. patent application Ser. No. 13/763,065, entitled FASTENER CARTRIDGE COMPRISING A RELEASABLY ATTACHED TISSUE THICKNESS COMPENSATOR, now U.S. Patent Application Publication No. 2013/0221065;

U.S. patent application Ser. No. 13/763,021, entitled STAPLE CARTRIDGE COMPRISING A RELEASABLE COVER, now U.S. Patent Application Publication No. 2014/0224686;

U.S. patent application Ser. No. 13/763,078, entitled ANVIL LAYER ATTACHED TO A PROXIMAL END OF AN END EFFECTOR, now U.S. Patent Application Publication No. 2013/0256383;

U.S. patent application Ser. No. 13/763,094, entitled LAYER COMPRISING DEPLOYABLE ATTACHMENT MEMBERS, now U.S. Patent Application Publication No. 2013/0256377;

U.S. patent application Ser. No. 13/763,106, entitled END EFFECTOR COMPRISING A DISTAL TISSUE ABUTMENT MEMBER, now U.S. Patent Application Publication No. 2013/0256378;

U.S. patent application Ser. No. 13/763,095, entitled LAYER ARRANGEMENTS FOR SURGICAL STAPLE CARTRIDGES, now U.S. Patent Application Publication No. 2013/0161374;

U.S. patent application Ser. No. 13/763,147, entitled IMPLANTABLE ARRANGEMENTS FOR SURGICAL STAPLE CARTRIDGES, now U.S. Patent Application Publication No. 2013/0153636;

U.S. patent application Ser. No. 13/763,192, entitled MULTIPLE THICKNESS IMPLANTABLE LAYERS FOR SURGICAL STAPLING DEVICES, now U.S. Patent Application Publication No. 2013/0146642;

U.S. patent application Ser. No. 13/763,161, entitled RELEASABLE LAYER OF MATERIAL AND SURGICAL END EFFECTOR HAVING THE SAME, now U.S. Patent Application Publication No. 2013/0153641;

U.S. patent application Ser. No. 13/763,177, entitled ACTUATOR FOR RELEASING A LAYER OF MATERIAL FROM A SURGICAL END EFFECTOR, now U.S. Patent Application Publication No. 2013/0146641; and U.S. patent application Ser. No. 13/763,037, entitled STAPLE CARTRIDGE COMPRISING A COMPRESSIBLE PORTION, now U.S. Patent Application Publication No. 2014/0224857.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
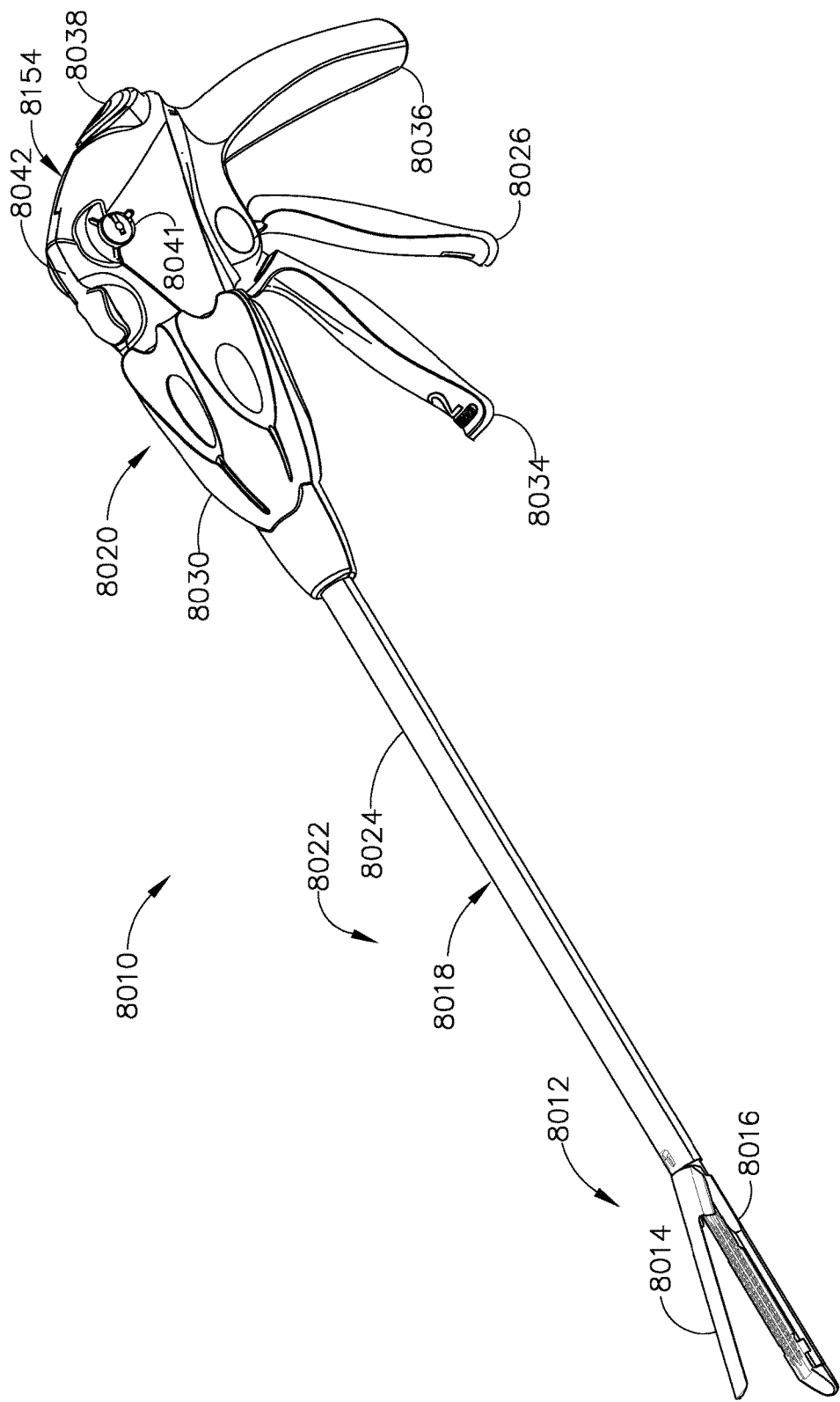
FIG. 1 is a left front perspective view of a surgical stapling and severing instrument with a handle portion including a link triggered automatic retraction and a ratcheting manual retraction mechanism.
Figure 2:
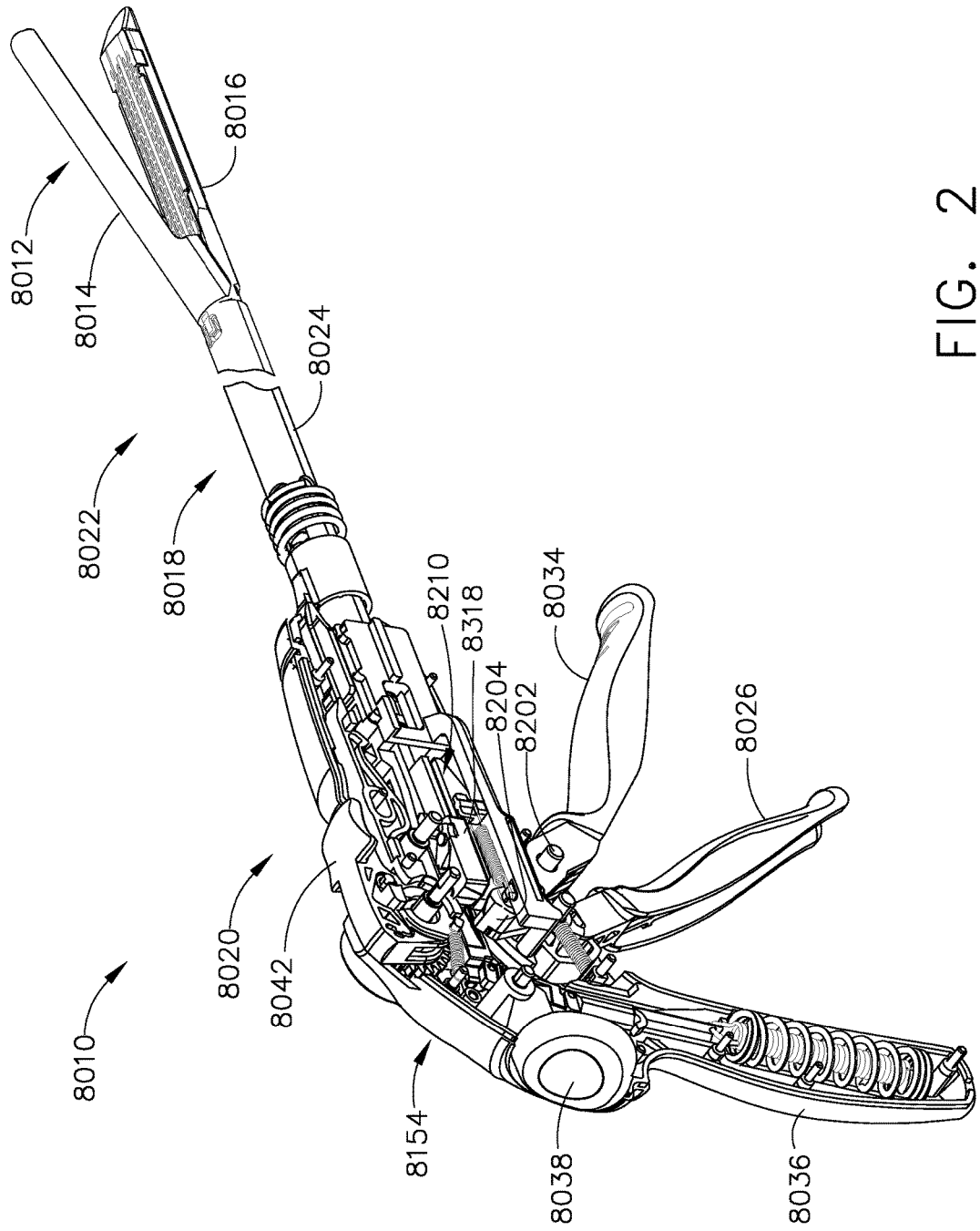
FIG. 2 is a right aft perspective view of the surgical stapling and severing instrument of FIG. 1 with a portion of an elongate shaft cut away and a right half shell of a handle housing removed to expose an automatic end-of-firing travel retraction mechanism and a manual firing retraction mechanism.

In FIGS. 1 and 2, a surgical stapling and severing instrument 8010 can comprise an anvil 8014 which may be repeatably opened and closed about its pivotal attachment to an elongate staple channel 8016. A staple applying assembly 8012 can comprise the anvil 8014 and the channel 8016, wherein the assembly 8012 can be proximally attached to the elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar. In various embodiments, the assembly 8012 can be manipulated by a handle 8020 connected to the shaft 8018. The handle 8020 can comprise user controls such as a rotation knob 8030 that rotates the elongate shaft 8018 and staple applying assembly 8012 about a longitudinal axis of the shaft 8018. A closure trigger 8026, which can pivot in front of a pistol grip 8036 about a closure trigger pin 8152 (FIG. 3) engaged laterally across the handle housing 8154, can be depressed to close the staple applying assembly 8012. In various embodiments, a closure release button 8038 can be outwardly presented on the handle 8020 when the closure trigger 8026 is clamped such that the release button 8038 can be depressed to unclamp the closure trigger 8026 and open the staple applying assembly 8012, as described in greater detail below. A firing trigger 8034, which can pivot in front of the closure trigger 8026, can cause the staple applying assembly 8012 to simultaneously sever and staple tissue clamped therein. In various circumstances, as described in greater detail below, multiple firing strokes can be employed using the firing trigger 8034 to reduce the amount of force required to be applied by the surgeon's hand per stroke. In certain embodiments, the handle 8020 can comprise rotatable right and/or left indicator wheels 8040, 8041 (FIG. 3) which can indicate the firing progress. For instance, full firing travel may require three full firing strokes of firing trigger 8034 and thus the indicator wheels 8040, 8041 can rotate up to one-third of a revolution each per stroke of firing trigger 8034. As described in greater detail below, a manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails.

Figure 3:
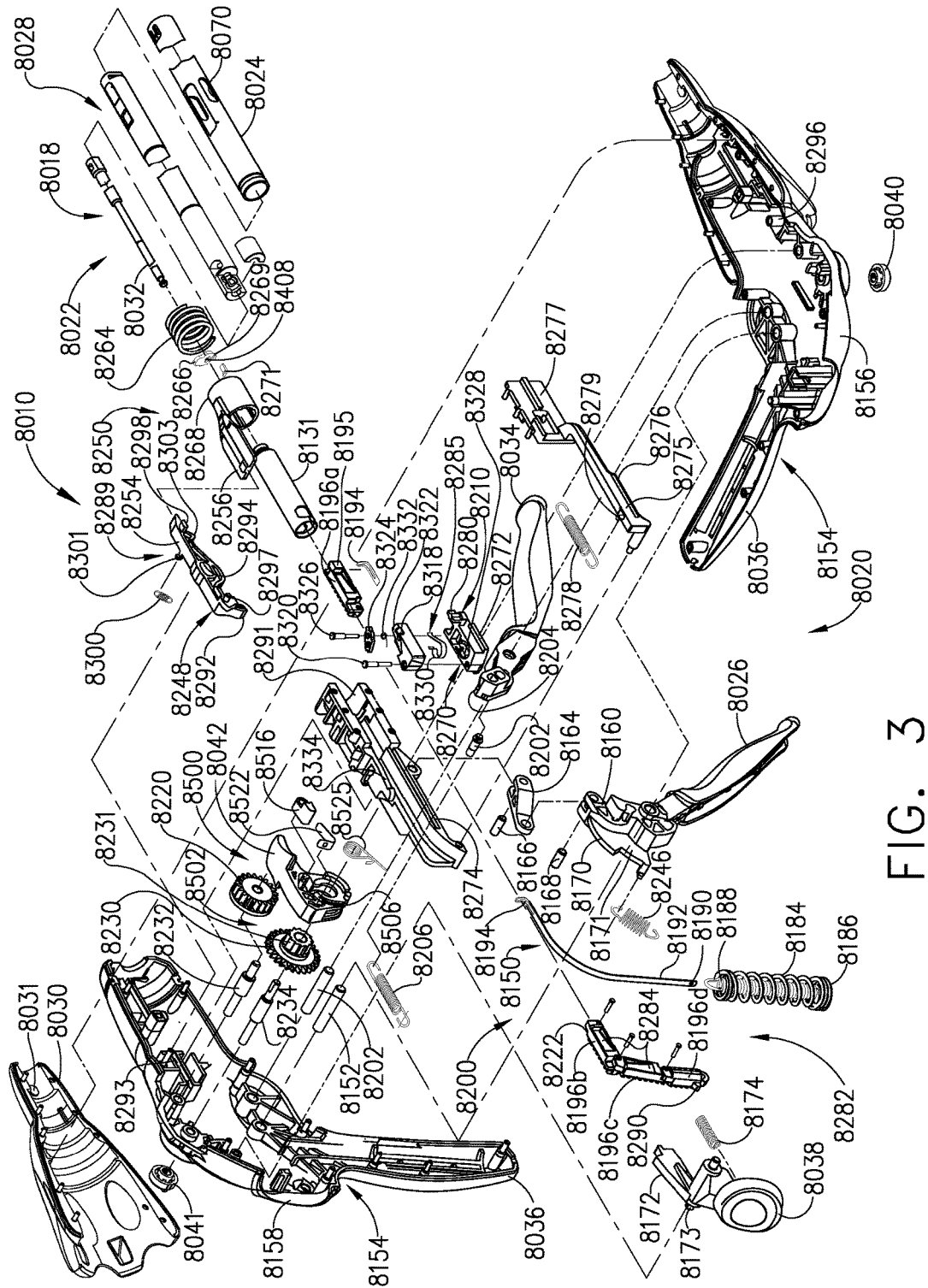
FIG. 3 is a right aft perspective disassembled view of the handle portion and an elongate shaft of the surgical stapling and severing instrument of FIG. 1.

With reference to FIGS. 1 and 3, the elongate shaft 8018 can comprise an outer structure including a longitudinally reciprocating closure tube 8024 that pivots the anvil 8014 toward its close position in response to the proximal depression of the closure trigger 8026 of handle 8020. The elongate channel 8018 can be connected to the handle 8020 by a frame 8028 (FIG. 3) that is internal to the closure tube 8024. The frame 8028 can be rotatably engaged to the handle 8020 so that the rotation of the rotation knob 8030 (FIG. 1) can rotate the implement portion 8022. With particular reference to FIG. 3, the rotation knob 8030 can be comprised of two half-shells which can include one or more inward projections 8031 that can extend through one or more elongate side openings 8070 in the closure tube 8024 and engage the frame 8028. As a result of the above, the rotation knob 8030 and the frame 8028 can be rotated together, or synchronously, such that the rotated position of knob 8030 determines the rotated position of the implement portion 8022. In various embodiments, the longitudinal length of the longer opening 8070 is sufficiently long to allow the longitudinal closure motion, and opening motion, of the closure tube 8024. With regard to generating the closure motion of closure tube 8024, referring primarily to FIGS. 3 and 5, an upper portion 8160 of the closure trigger 8026 can push forward a closure yoke 8162 (FIG. 4) via a closure link 8164. The closure link 8164 is pivotally attached at its distal end by a closure yoke pin 8166 to the closure yoke 8162 and is pivotally attached at its proximal end by a closure link pin 8168. In various embodiments, the closure trigger 8026 can be urged to an open position by a closure trigger tension spring 8246 that is connected proximally to the upper portion 8160 of the closure trigger 8026 and a handle housing 8154 formed by right and left half shells 8156, 8158. The tension force applied by the tension spring 8246 can be overcome by a closing force applied to the closure trigger 8026 in order to advance the yoke 8162, closure link 8164, and the closure tube 8024 distally.

As the closure trigger 8026 is actuated, or depressed, as described above, the closure release button 8038 can be positioned such that the surgeon, or other clinician, can push the closure release button 8038, if desired, and allow the closure trigger 8026, and the rest of the surgical instrument, to return to an unactuated state. In various embodiments, the closure release button 8038 can be connected to a pivoting locking arm 8172 by a central lateral pivot 8173 such that motion can be transferred between the release button 8038 and the locking arm 8172. Referring again to FIG. 3, a compression spring 8174 can bias the closure release button 8038 proximally, i.e., clockwise about the central lateral pivot 8173 as viewed from the right and the upper portion 8160 of the closure trigger 8026 can include a proximal crest 8170 with an aft notch 8171. As the closure trigger 8026 is depressed, the pivoting locking arm 8172 can ride upon the proximal crest 8170 and when the closure trigger 8026 reaches its fully depressed position, it should be appreciated that the aft notch 8171 is presented below the pivoting locking arm 8172 which drops into and locks against the aft notch 8171 under the urging of the compression spring 8174. At such point, manual depression of the closure release button 8038 rotates the pivoting locking arm 8172 upward and out of aft notch 8171 thereby unlocking the closure trigger 8026 and allowing the closure trigger 8026 to be returned to its unclamped position.

Once the closure trigger 8026 is proximally clamped, as discussed above, the firing trigger 8034 can be drawn toward the pistol grip 8036 in order to advance a firing rod 8032 distally from the handle 8020. In various embodiments, the firing trigger 8034 can pivot about a firing trigger pin 8202 that laterally traverses and is engaged with the right and left half shells 8156, 8158 of the handle 8020. The firing trigger 8034, when actuated, can advance a linked transmission firing mechanism 8150. The linked transmission firing mechanism 8150 can be urged into a retracted, unfired, position by a spring 8184 that is, one, attached to the pistol grip 8036 of the handle 8020 and, two, attached to one of the links, for example, of the linked transmission firing mechanism 8150 as described in greater detail below. The spring 8184 can comprise a nonmoving end 8186 connected to the housing 8154 and a moving end 8188 connected to a proximal end 8190 of a steel band 8192. A distally-disposed end 8194 of the steel band 8192 can be attached to an attachment feature 8195 on a front link 8196a of a plurality of links 8196a-8196d that form a linked rack 8200. Linked rack 8200 can be flexible such that it can readily retract into the pistol grip 8036 and minimize the length of the handle 8020 and yet form a straight rigid rack assembly that may transfer a significant firing force to and/or through the firing rod 8032. As described in greater detail below, the firing trigger 8034 can be engaged with a first link 8196a during a first actuation of the firing trigger 8034, engaged with a second link 8196b during a second actuation of the firing trigger 8034, engaged with a third link 8196c during a third actuation of the firing trigger 8034, and engaged with a fourth link 8196d during a fourth actuation of the firing trigger 8034, wherein each actuation of the firing trigger 8034 can advance the linked rack 8200 distally an incremental amount. In various embodiments, further to the above, the multiple strokes of firing trigger 8034 can rotate the right and left indicator gauge wheels 8040, 8041 to indicate the distance in which the linked rack 8200 has been advanced.

Figure 5:
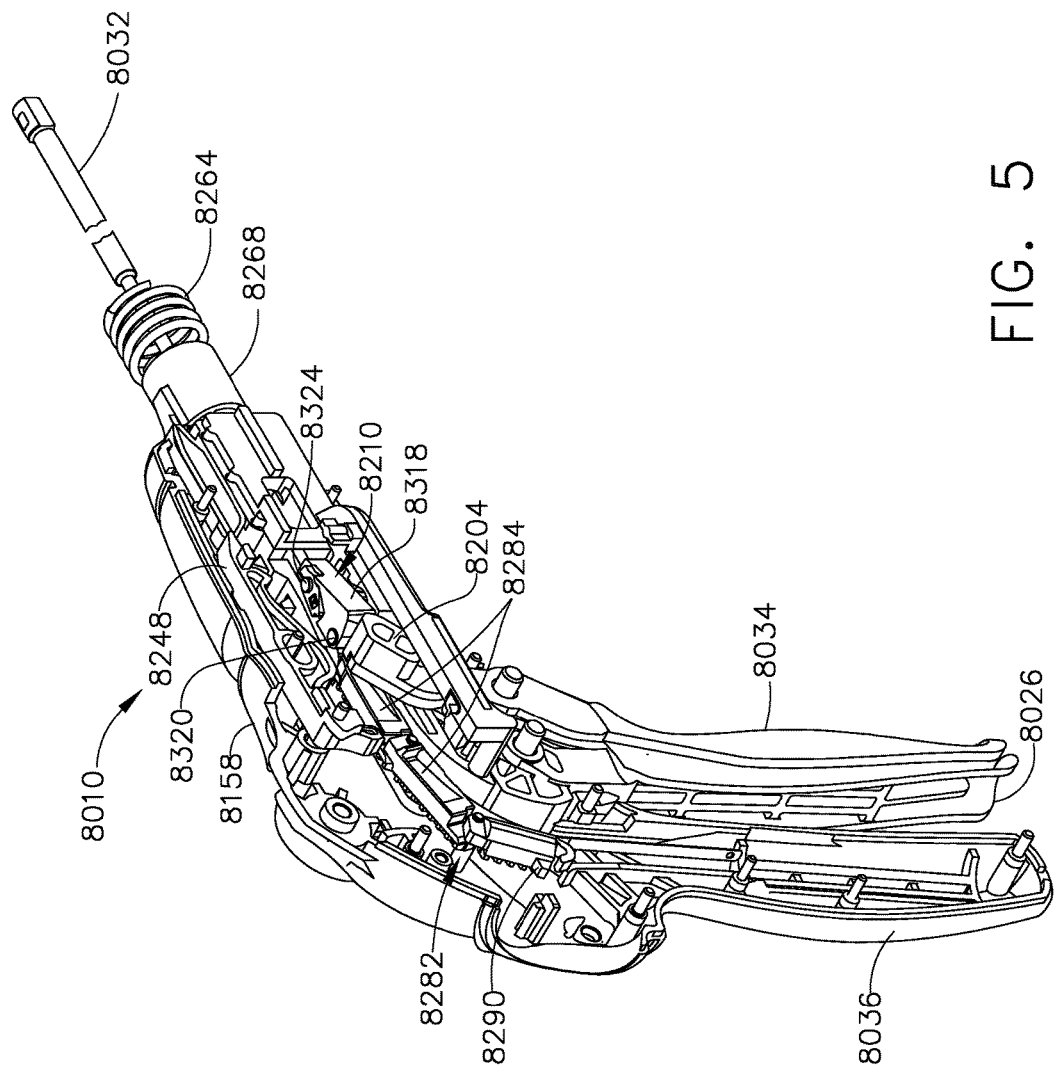
FIG. 5 is a right aft perspective view of the partially disassembled surgical stapling and severing instrument of FIG. 1 with a closure mechanism closed and clamped and the side pawl firing mechanism completing a first stroke and with a manual retraction mechanism removed to expose a distal link of the linked rack that triggers automatic retraction of the firing mechanism.

Referring now to FIGS. 3 and 5, an anti-backup mechanism 8250 can prevent the combination tension/compression spring 8184 from retracting the linked rack 8200 between firing strokes. In various embodiments, a coupling slide tube 8131 abuts the first link 8196a and connects to the firing rod 8032 to communicate the firing motion. The firing rod 8032 extends proximally out of a proximal end of the frame 8028 and through a through hole 8408 of an anti-backup plate 8266. The through hole 8408 is sized to slidingly receive the firing rod 8032 when perpendicularly aligned but to bind when tipped. A lower tab attachment 8271 extends proximally from a lower lip of the proximal end of the frame 8028, extending through an aperture 8269 on a lower edge of the anti-backup plate 8266. This lower tab attachment 8271 draws the lower portion of the anti-backup plate 8266 proximate to the frame 8028 so that the anti-backup plate 8266 is perpendicular when the firing rod 8032 is distally advanced and allowed to tip top aft into a binding state when the firing rod 8032 attempts to retract. An anti-backup compression spring 8264 is distally constrained by the proximal end of the frame 8028 and proximally abuts a top portion of the anti-backup plate 8266, biasing the anti-backup plate 8266 to a locking state. Opposing the spring bias, an anti-backup cam tube 8268 slidingly encompasses the coupling slide tube 8131 and abuts the anti-backup plate 8266. A proximally projecting anti-backup yoke 8256 attached to the anti-backup cam tube 8268 extends overtop of the closure yoke 8162.

Figure 6:
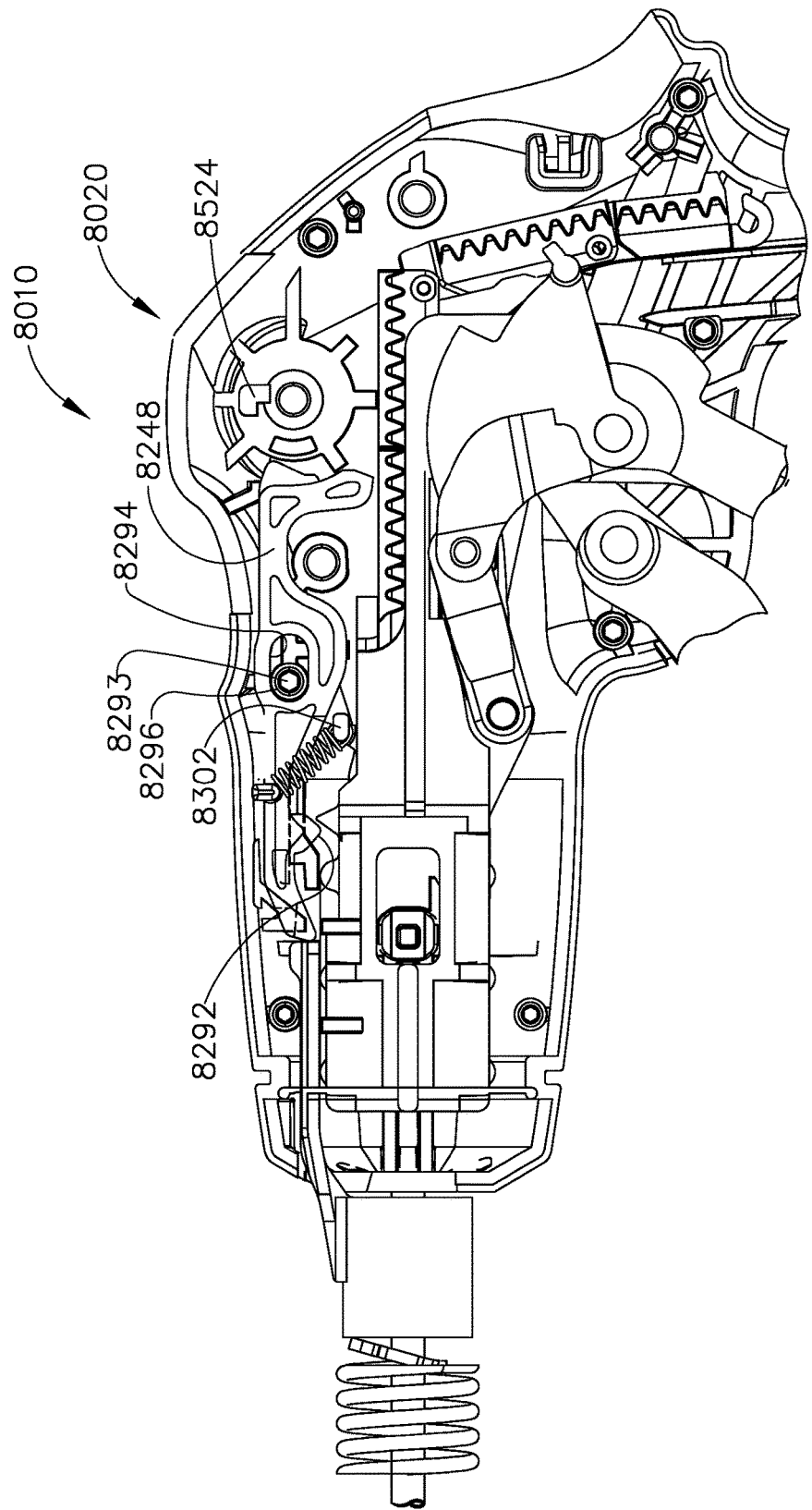
FIG. 6 is a left side view in elevation of the partially disassembled surgical stapling and severing instrument of FIG. 4 in an initial state of end effector open and anti-backup mechanism engaged.

Referring to FIG. 3, a link triggered automatic retraction mechanism 8289 is incorporated into the surgical stapling and severing instrument 8010 to cause knife retraction at the end of full firing travel. To that end, the distal link 8196*d* includes a tang 8290 that projects upwardly when the distal link 8196*d* is advanced into rack channel 8291 (FIG. 3) formed in the closure yoke 8162. This tang 8290 is aligned to activate a bottom proximal cam 8292 on an anti-backup release lever 8248 (FIG. 6). With particular reference to FIG. 6, structures formed in the right and left half shells 8156, 8158 constrain movement of the anti-backup release lever 8248. A pin receptacle 8296 and circular pin 8293 formed respectively between right and left half shells 8156, 8158 is received through a longitudinally elongate aperture 8294 formed in the anti-backup release lever 8248 distal to the bottom proximal cam 8292, thus allowing longitudinal translation as well as rotation about the circular pin 8293. In the right half shell 8156, a proximally open channel includes a proximal horizontal portion that communicates with an upwardly and distally angled portion that receives a rightward aft pin 8297 near the proximal end of the anti-backup release lever 8248, thus imparting an upward rotation as the anti-backup release lever 8248 reaches the distal most portion of its translation. A blocking structure formed in the right half shell 8156 proximal to the anti-backup release lever 8248 prevents proximal movement thereof once assembled to maintain rightward aft pin 8297 in the proximally open channel, discussed above.

Figure 7:
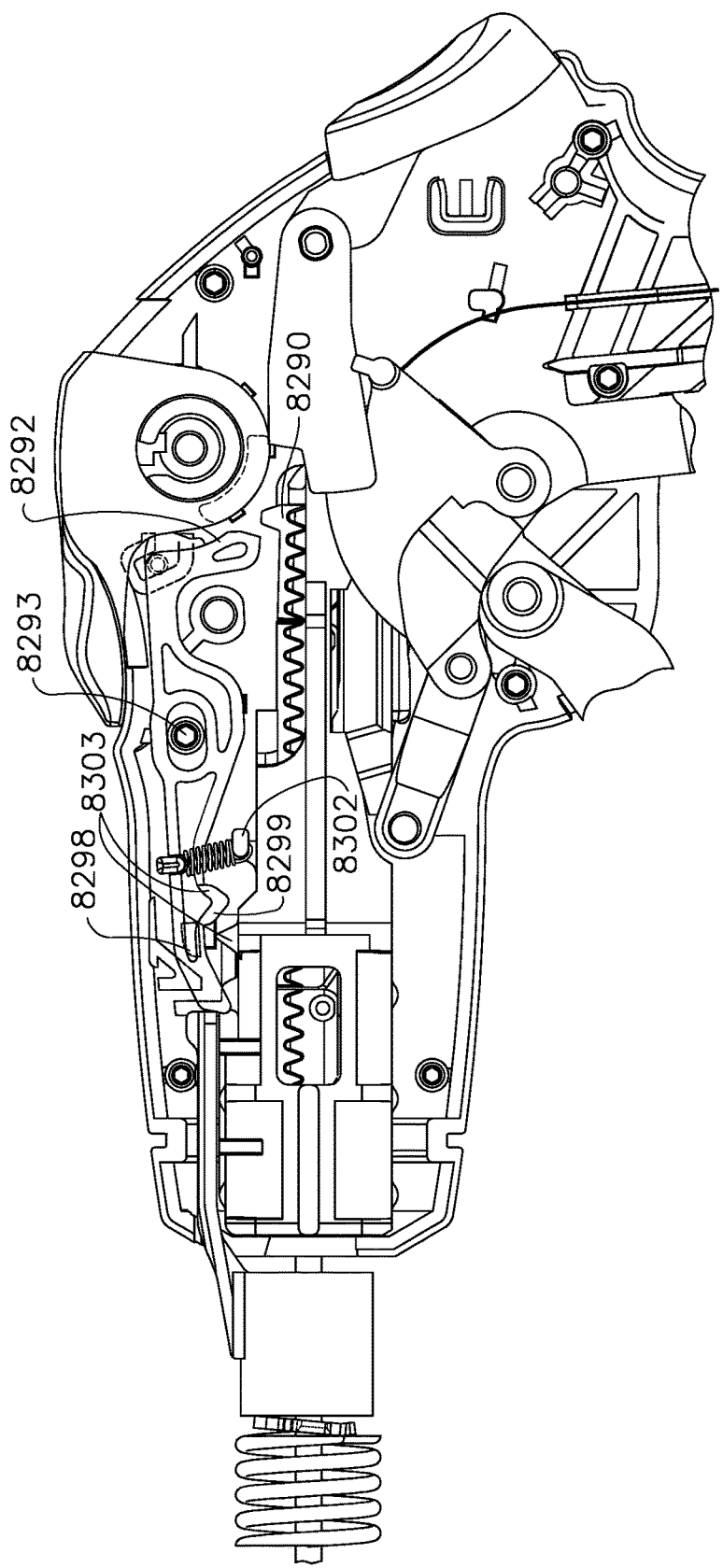
FIG. 7 is a left side detail in elevation of the disassembled surgical stapling and severing instrument of FIG. 1 immediately after the distal link has actuated and locked forward the anti-backup release lever, allowing the linked rack to retract.

Further to the above, referencing now FIGS. 3 and 7, a distal end 8254 of the anti-backup release lever 8248 thus is urged distally and downwardly, causing a rightward front pin 8298 to drop into distally open step structure 8299 formed in the right half shell 8156, which is urged into this engagement by a compression spring 8300 (FIG. 3) hooked to a leftward hook 8301 on the anti-backup release lever 8248 between the rightward front pin 8298 and the longitudinally elongate aperture 8294. The other end of the compression spring 8300 is attached to a hook 8302 (FIG. 6) formed in the right half shell 8156 in a more proximal and lower position just above the closure yoke 8266. The compression spring 8300 thus pulls the distal end 8254 of the anti-backup release lever 8248 down and aft, which results in the rightward front pin 8298 locking into the distally open step structure 8299 when distally advanced. Thus, once tripped, referring to FIG. 7, the anti-backup release lever 8248 remains forward holding the anti-backup plate 8266 perpendicularly and thus allowing the linked rack 8200 to be retracted. When the closure yoke 8266 is subsequently retracted when unclamping the end effector 8012, an upwardly projecting reset tang 8303 on the closure yoke 8266 contacts a bottom distal cam 8305 of the anti-backup release lever 8248, lifting the rightward front pin 8298 out of the distally open step structure 8299 so that the anti-backup compression spring 8264 can proximally push the anti-backup cam tube 8268 and the anti-backup release lever 8248 to their retracted positions (FIG. 6).

Figure 4:
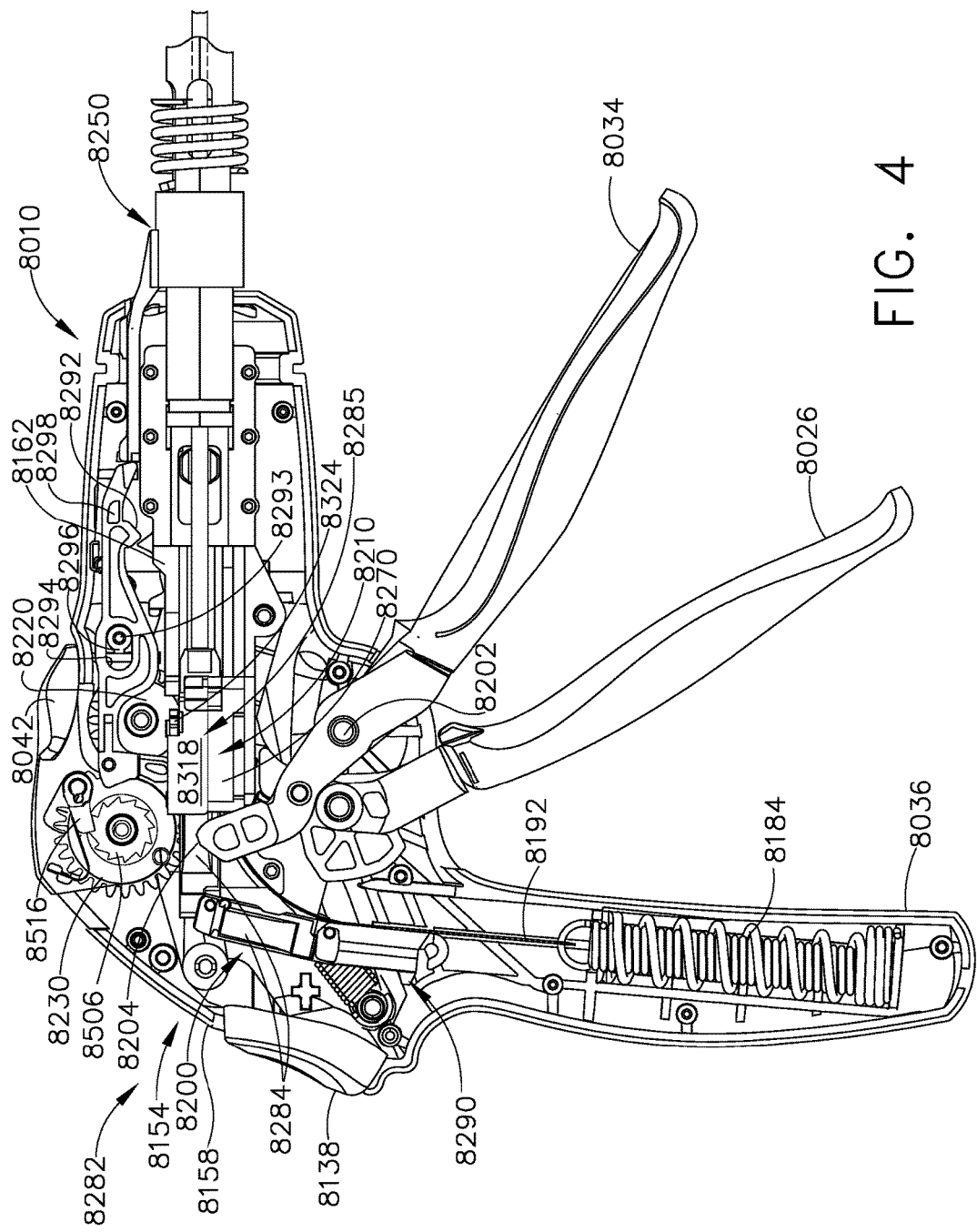
FIG. 4 is a right side view in elevation of the partially disassembled surgical stapling and severing instrument of FIG. 1.

In various embodiments, referring to FIGS. 1-3, the firing trigger 8034 can be operably engaged to the linked rack 8200 in any suitable manner. With particular reference to FIGS. 2 and 3, the firing trigger 8034 pivots about a firing trigger pin 8202 that is connected to the housing 8154. An upper portion 8204 of the firing trigger 8034 moves distally about the firing trigger pin 8202 as the firing trigger 8034 is depressed towards pistol grip 8036, stretching a proximally placed firing trigger tension spring 8206 (FIG. 3) proximally connected between the upper portion 8204 of the firing trigger 8034 and the housing 8154. The upper portion 8204 of the firing trigger 8034 engages the linked rack 8200 during each firing trigger depression via a spring biased side pawl mechanism 8210. When the firing trigger is released, the side pawl mechanism is disengaged from the linked rack 8200 and the firing trigger can be returned to an undepressed, or unfired, position. In use, a ramped right-side track formed by a proximally and rightwardly facing beveled surface 8284 in each of the links 8196*a*-8196*d* is engaged by a side pawl assembly 8285. In particular, a pawl slide 8270 (FIGS. 3 and 4) has right and left lower guides 8272 that slide respectively in a left track 8274 (FIG. 3) formed in the closure yoke 8266 below the rack channel 8291 and a right track 8275 in a closure yoke rail 8276 that parallels rack channel 8291 and is attached to a rack channel cover 8277 that closes a rightwardly open portion of the rack channel 8291 in the closure yoke 8266 that is distal to the travel of the pawl slide 8270. In FIGS. 3-5, a compression spring 8278 is attached between a hook 8279 on a top proximal position on the closure yoke rail 8276 and a hook 8280 on a distal right-side of the pawl slide 8270, which keeps the pawl slide 8270 drawn proximally into contact with the upper portion 8204 of the firing trigger 8034.

With particular reference to FIG. 3, a pawl block 8318 sits on the pawl slide 8270 pivoting about a vertical aft pin 8320 that passes through a left proximal corner of pawl block 8318 and pawl slide 8270. A kick-out block recess 8322 is formed on a distal portion of a top surface of the block 8318 to receive a kick-out block 8324 pivotally pinned therein by a vertical pin 8326 whose bottom tip extends into a pawl spring recess 8328 on a top surface of the pawl slide 8270. A pawl spring 8330 in the pawl spring recess 8328 extends to the right of the vertical front pin 8326 urging the pawl block 8318 to rotate counterclockwise when viewed from above into engagement with the ramped right-side track 8282. A small coil spring 8332 in the kick-out block recess 8322 urges the kick-out block 8324 to rotate clockwise when viewed from above, its proximal end urged into contact with a contoured lip 8334 formed in the closure yoke 8266 above the rack channel 8291. As shown in FIG. 5, the stronger mechanical advantage of the pawl spring 8330 over the small coil spring 8332 means that the pawl block 8318 tends toward engagement with the kick-out block 8324 rotated clockwise. In FIG. 3, as the firing trigger 8034 is fully depressed and begins to be release, the kick-out block 8324 encounters a ridge 8336 in the contoured lip 8334 as the pawl slide 8270 retracts, forcing the kick-out block 8324 to rotate clockwise when viewed from above and thereby kicking out the pawl block 8318 from engagement with the linked rack 8200. The shape of the kick-out block recess 8322 stops the clockwise rotation of the kick-out block 8324 to a perpendicular orientation to the contoured lip 8334 maintaining this disengagement during the full retraction and thereby eliminating a ratcheting noise.

Figure 8:
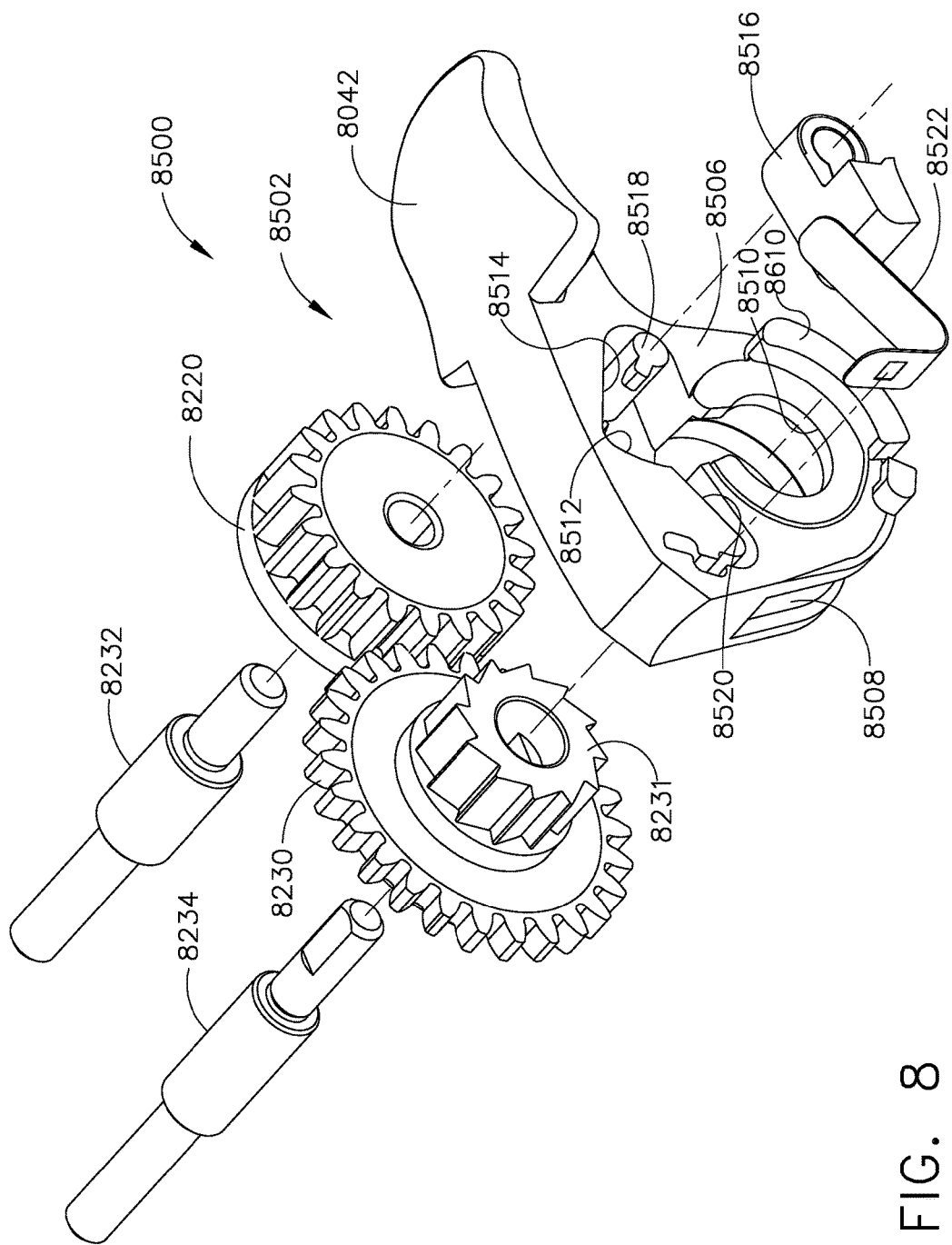
FIG. 8 is a right disassembled perspective view of the idler and aft gears and manual retraction lever and ratcheting pawl of a manual retraction mechanism of the surgical stapling and severing instrument of FIG. 1.
Figure 10:
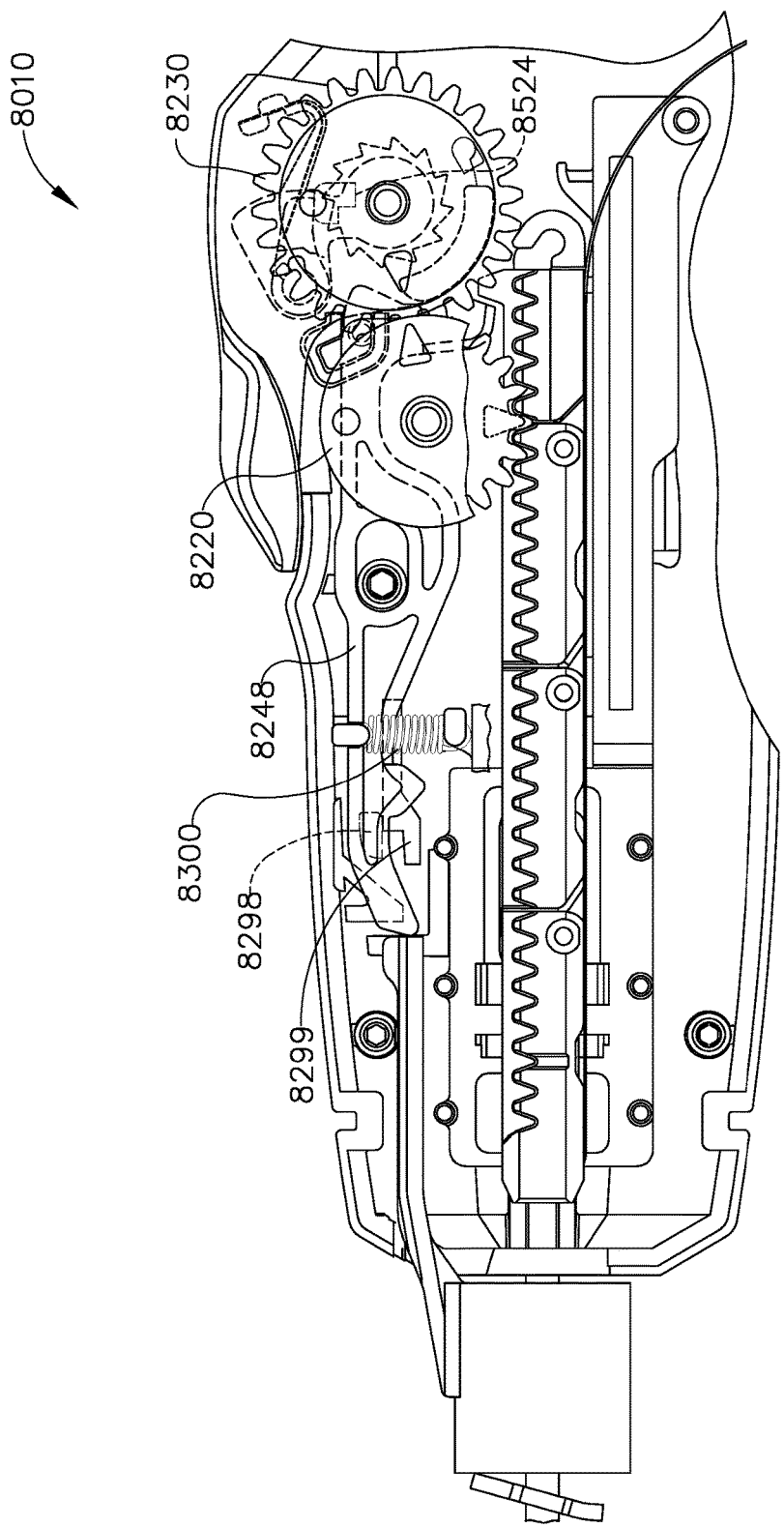
FIG. 10 is a partially disassembled left side view in elevation of the surgical stapling and severing instrument of FIG. 9 with hidden portions of the anti-backup release lever, aft gear, and manual firing release lever shown in phantom.

In FIGS. 3, 4, 8, and 12, the surgical stapling and severing instrument 8010 can include a manual retraction mechanism 8500 that provides for a manual release of the firing mechanism, manual retraction, and in one version (FIGS. 13-15) further performs automatic retraction at the end of full firing travel. Referring now to FIGS. 3 and 8, in particular, a front idler gear 8220 is engaged with a toothed upper, left surface 8222 of the linked rack 8200 wherein the front idler gear 8220 also engages an aft idler gear 8230 having a smaller right-side ratchet gear 8231. Both the front idler gear 8220 and aft idler gear 8230 are rotatably connected to the handle housing 8154 respectively on front idler axle 8232 and aft idler axle 8234. Each end of the aft axle 8232 extend through the respective right and left housing half shells 8156, 8158 and are attached to the left and right indicator gauge wheels 8040, 8041 and, since the aft axle 8234 is free spinning in the handle housing 8154 and has a keyed engagement to the aft gear 8230, the indicator gauge wheels 8040, 8041 rotate with the aft gear 8230. The gear relationship between the linked rack 8200, idler gear 8220 and aft gear 8230 may be advantageously selected so that the toothed upper surface 8222 has tooth dimensions that are suitably strong and that the aft gear 8230 makes no more than one revolution during the full firing travel of the linked transmission firing mechanism 8150. In addition to gear mechanism 8502 visually indicating the firing travel, or progress, the gear mechanism 8502 can also be used to manual retract the knife. In various embodiments, the smaller right-side ratchet gear 8231 of the aft idler gear 8230 extends into a hub 8506 of the manual retraction lever 8042, specifically aligned with a vertical longitudinally-aligned slot 8508 (FIG. 8) bisecting the hub 8506. A lateral through hole 8510 of the hub 8506 communicates with an upper recess 8512. A front portion 8514 is shaped to receive a proximally directed locking pawl 8516 that pivots about a rightward lateral pin 8518 formed in a distal end of the upper recess 8512. An aft portion 8520 is shaped to receive an L-shaped spring tab 8522 that urges the locking pawl 8516 downward into engagement with the right-side smaller ratchet gear 8231. A hold-up structure 8524 (FIG. 6) projects from the right half shell 8156 into the upper recess 8512 holding up the locking pawl 8516 from engaging the smaller right-side ratchet gear 8231 when the manual retraction lever 8042 is down (FIG. 10). A coil spring 8525 (FIG. 3) urges the manual retraction lever 8042 down.

Figure 9:
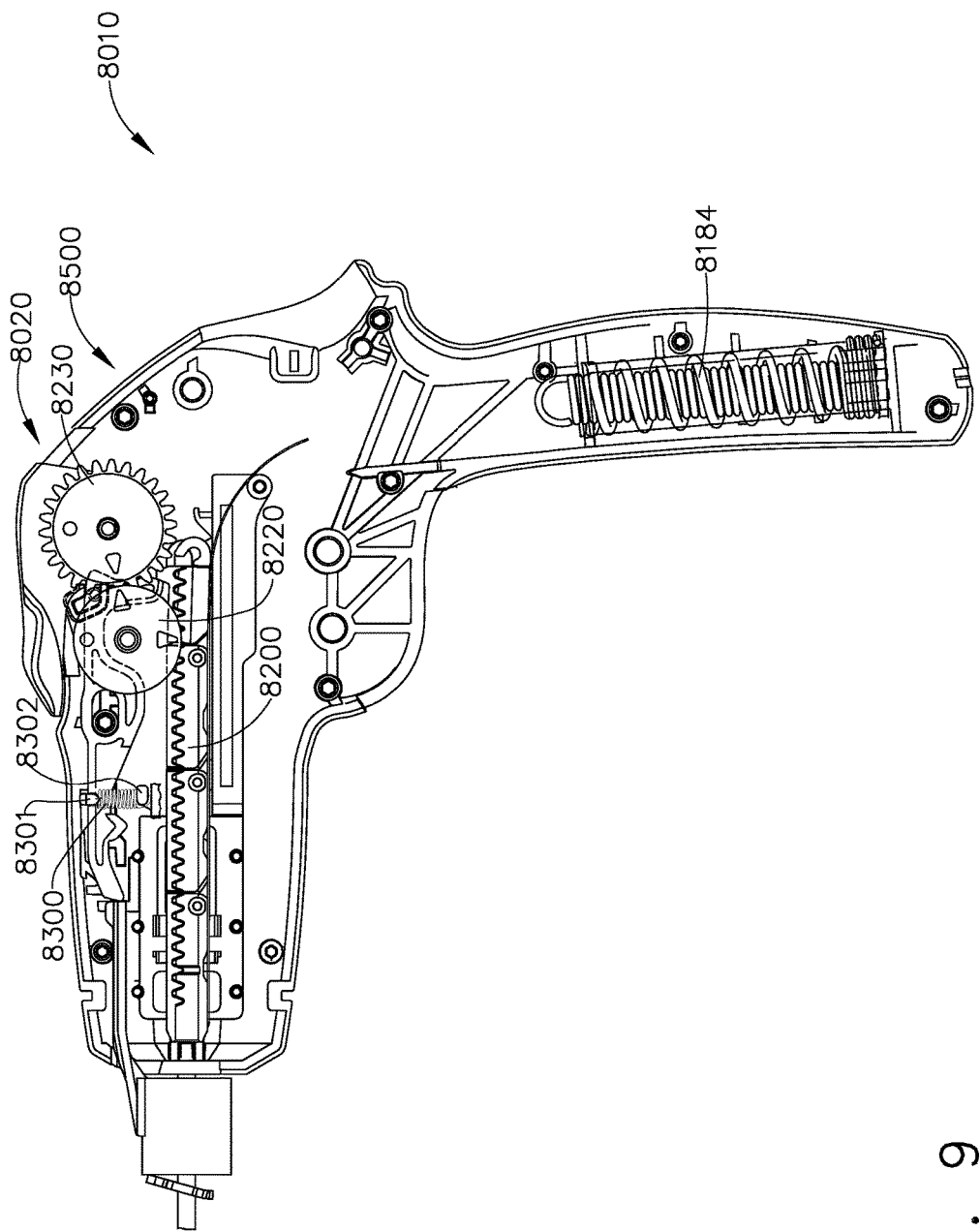
FIG. 9 is a partially disassembled left side view in elevation of a surgical stapling and severing instrument of FIG. 1 with the anti-backup mechanism engaged to a fully fired linked rack that is disconnected from a combination tension/compression spring prior to actuation of the manual retraction lever of FIG. 8.
Figure 11:
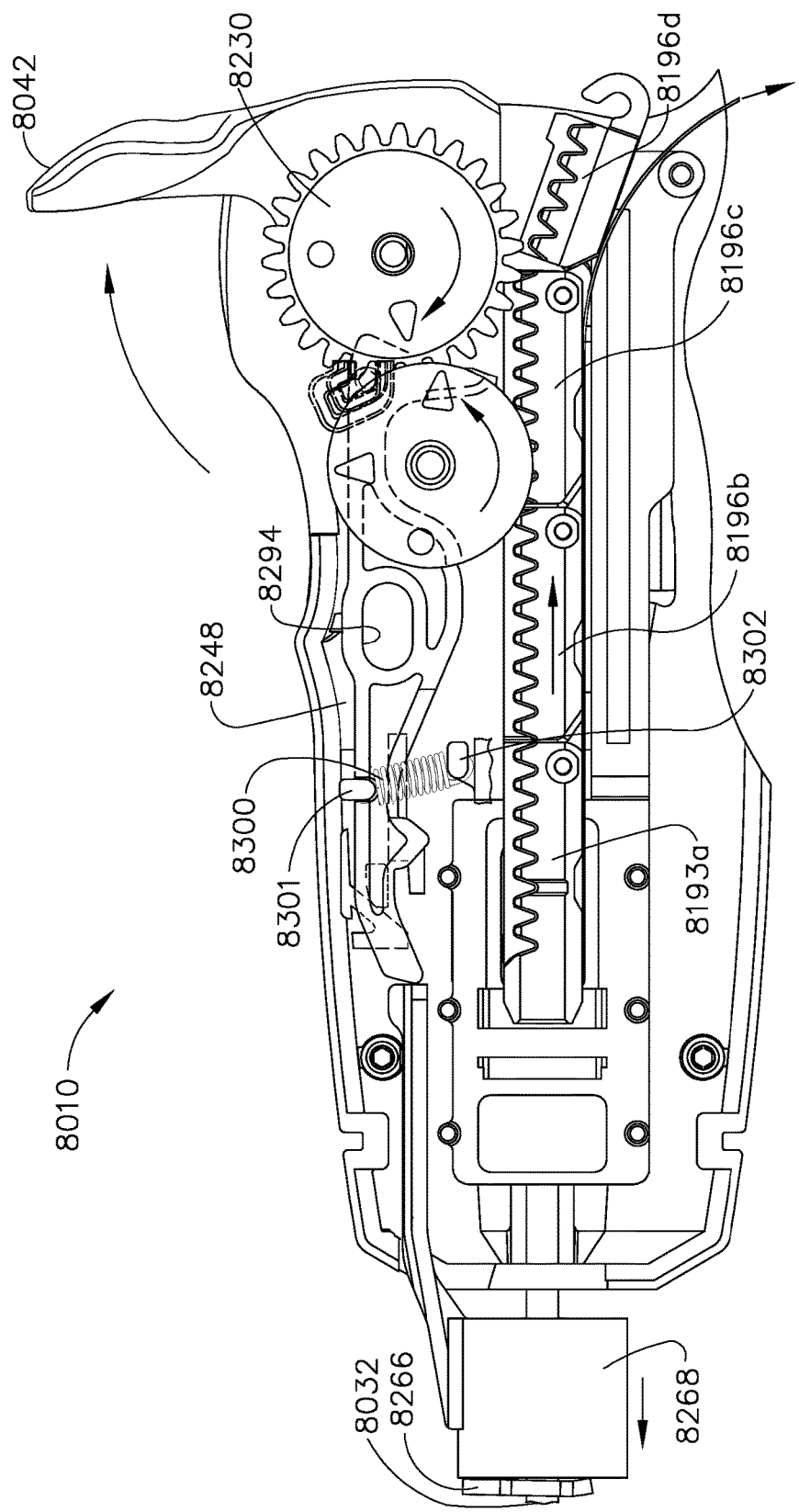
FIG. 11 is a partially disassembled left side view in elevation of the surgical stapling and severing instrument of FIG. 10 after actuation of the manual firing release lever has manually retracted the link rack.
Figure 12:
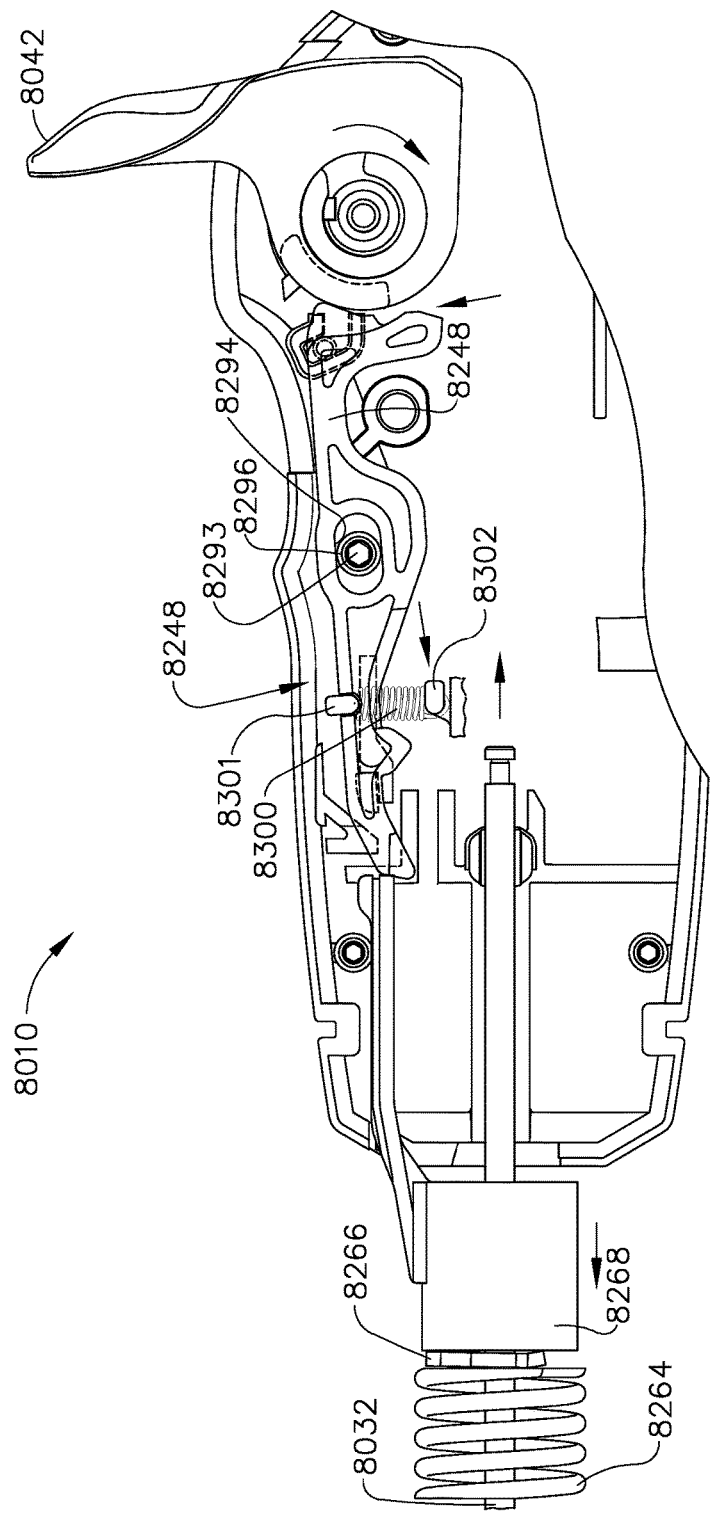
FIG. 12 is a partially disassembled left side view in elevation of the surgical stapling and severing instrument of FIG. 11 with the linked rack omitted depicting the manual firing release lever disengaging the anti-backup mechanism.

In use, as depicted in FIGS. 9 and 10, the combination tension/compression spring 8184 may become disconnected with the linked rack distally positioned. In FIGS. 11 and 12, as the manual retraction lever 8042 is raised, the locking pawl 8516 rotates clockwise and no longer is held up by the hold-up structure 8524 and engages the smaller right-side ratcheting gear 8231, rotating the aft idler gear 8230 clockwise when viewed from the left. Thus, the forward idler gear 8220 responds counterclockwise retracting the linked rack 8200. In addition, a rightward curved ridge 8510 projects out from the hub 8506, sized to contact and distally move the anti-backup release lever 8248 to release the anti-backup mechanism 8250 as the manual retraction lever 8042 is rotated.

Figure 15:
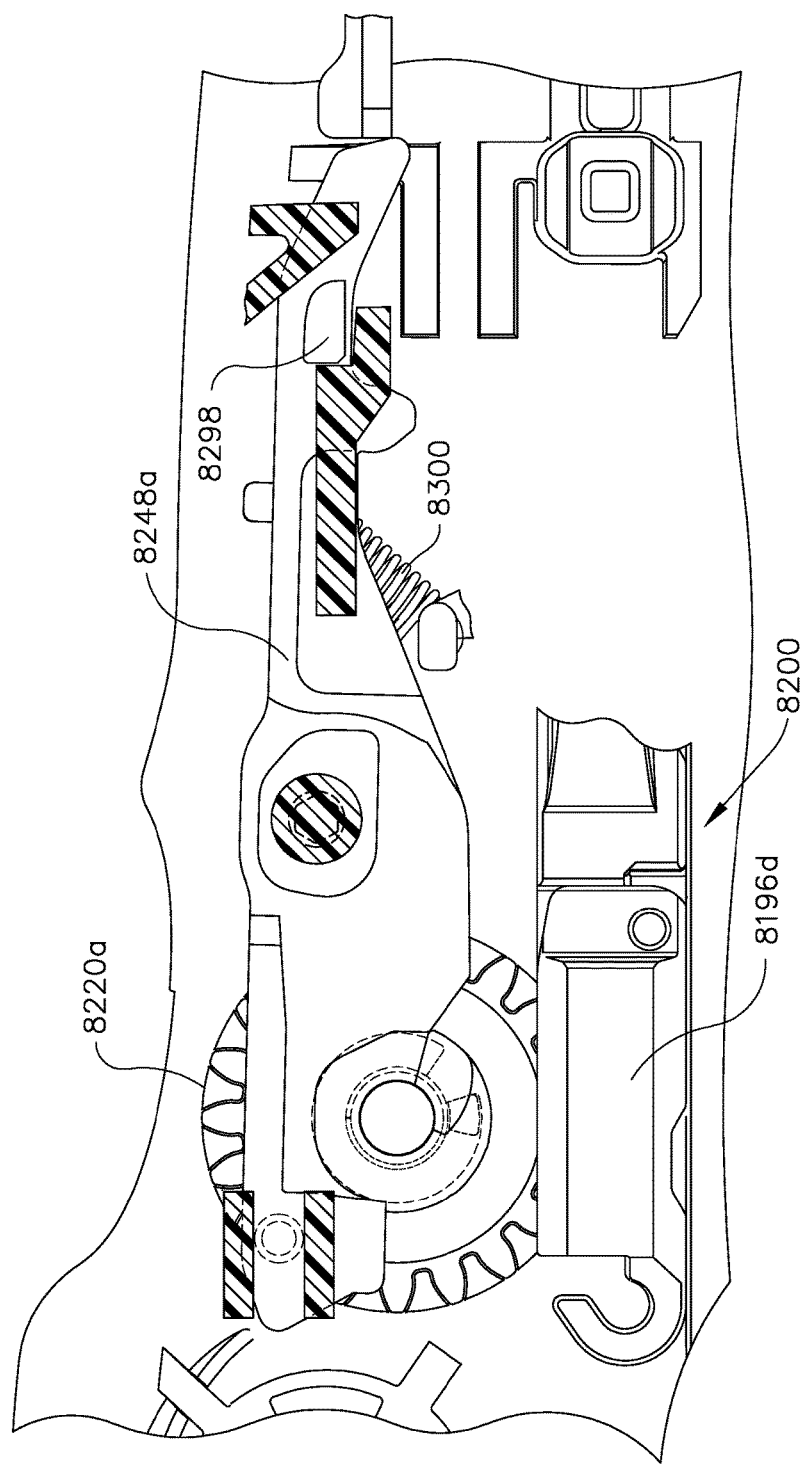
FIG. 15 is a right side view in elevation of an automatic release mechanism after a further firing stroke causes the automatic retraction cam wheel to distally slide and lock the anti-backup release lever, disengaging the anti-backup mechanism.

In FIGS. 13-15, an automatic retraction mechanism 8600 for a surgical stapling and severing instrument can incorporate automatic retraction at the end of full firing travel into a front idler gear 8220a having a tooth 8602 that moves within a circular groove 8604 in a cam wheel 8606 until encountering a blockage after nearly a full rotation corresponding to three firing strokes. In such circumstances, rightward ridge 8610 is rotated upward into contact a bottom cam recess 8612 to distally move an anti-backup release lever 8248a. With particular reference to FIG. 13, the anti-backup release lever 8248a includes the distal end 8254 that operates as previously described. The circular pin 8293 and pin receptacle 8296 formed between right and left half shells 8156, 8158 is received through a generally rectangular aperture 8294a formed in the anti-backup release lever 8248a aft of the bottom cam 8192, thus allowing longitudinal translation as well as downward locking motion of the distal end 8254 of the anti-backup release lever 8248a. In the right half shell 8156, a horizontal proximally open channel receives the rightward aft pin near the proximal end of the anti-backup release lever 8248a.

In operation, before firing in FIGS. 13, 14, the linked rack 8200 and the anti-backup cam tube 8268 are in a retracted position, locking the anti-backup mechanism 8250 as the anti-backup compression spring 8264 proximally tips the anti-backup plate 8266. The automatic retraction mechanism 8600 is at an initial state with the anti-backup release lever 8248a retracted with link 8196a in contact with the forward idler gear 8220a. The tooth 8602 is at a six o'clock position with full travel of the circular groove 8604 progressing counterclockwise thereof with the rightward ridge 8610 just proximal to the tooth 8602. After one firing stroke, the linked rack 8200 has moved up one distal link 8196b into contact with the forward idler gear 8220a. The tooth 8602 has progressed one third of a turn through the circular groove 8604 of the immobile cam wheel 8606. After a second firing stroke, the linked rack has moved up one more link 8196c into contact with the forward idler gear 8220a. The tooth 8602 has progressed two thirds of a turn through the circular groove 8604 of the immobile cam wheel 8606. After a third firing stroke, the linked rack 8200 has moved up one distal link 8196d into contact with the forward idler gear 8220a. The tooth 8602 has progressed fully around the circular groove 8604 into contact with the blockage, mentioned above, initiating counterclockwise rotation (when viewed from the right) of the cam wheel 8606 bringing the rightward ridge into contact with the anti-backup release lever 8248a. In FIG. 15, the anti-backup release lever 8248a has moved distally in response thereto, locking the rightward front pin 8298 into the distally open step structure 8299 and releasing the anti-backup mechanism 8250. Similar surgical stapling instruments are disclosed in U.S. Pat. No. 7,083,075, which issued on Aug. 1, 2006, the entire disclosure of which is incorporated by reference herein.

Figure 16:
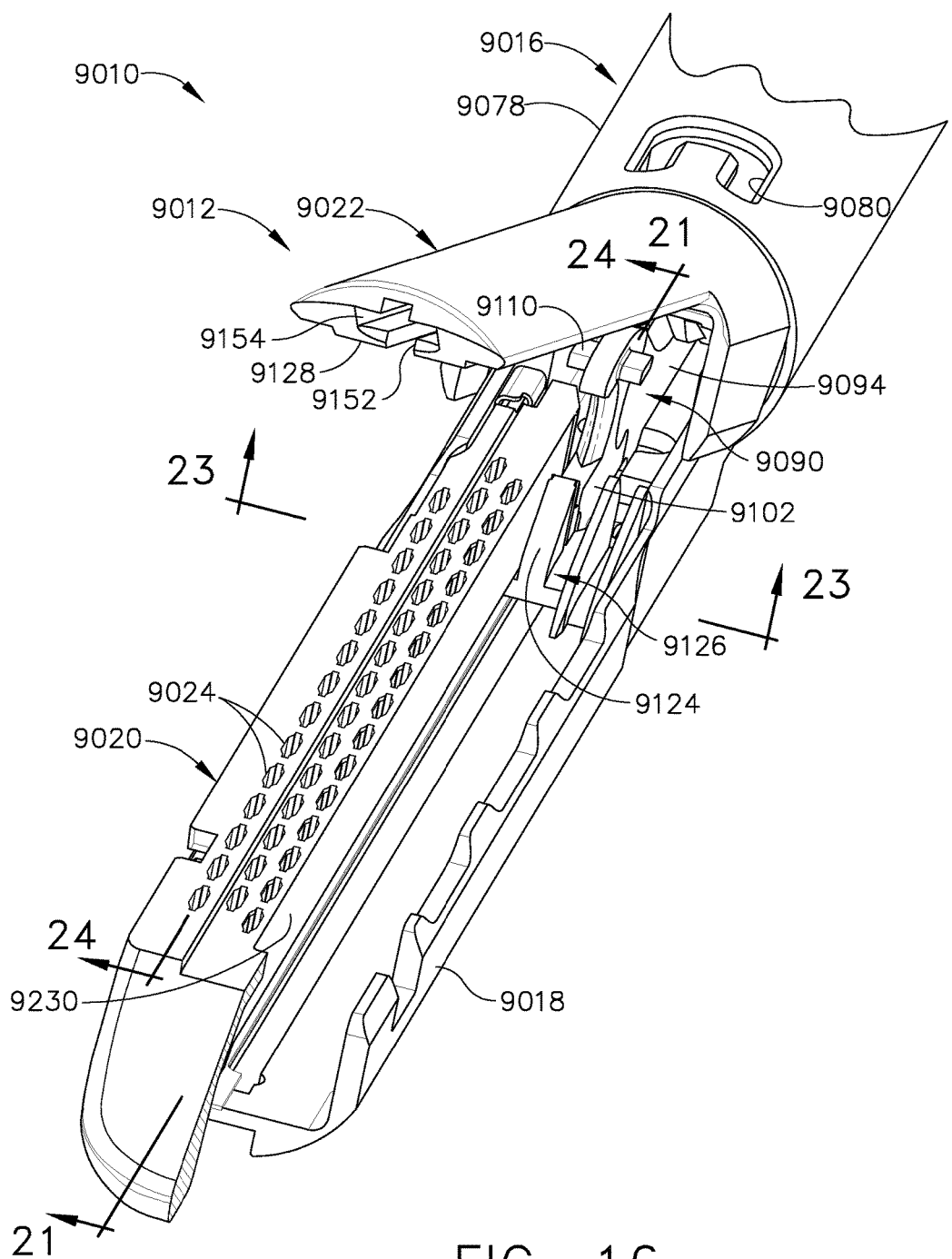
FIG. 16 is a left, front perspective view of an open staple applying assembly with a right half portion of a replaceable staple cartridge included in a staple channel.

Referring to FIG. 16, the staple applying assembly 9012 of a surgical stapling instrument 9010 accomplishes the functions of clamping onto tissue, driving staples and severing tissue by two distinct motions transferred longitudinally down the shaft 9016 relative to a shaft frame 9070. This shaft frame 9070 is proximally attached to a handle of a surgical stapling instrument and is coupled thereto for rotation about a longitudinal axis. An illustrative multistroke handle for the surgical stapling and severing instrument is described in greater detail in the co owned U.S. patent application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in commonly owned U.S. patent application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

Figure 17:
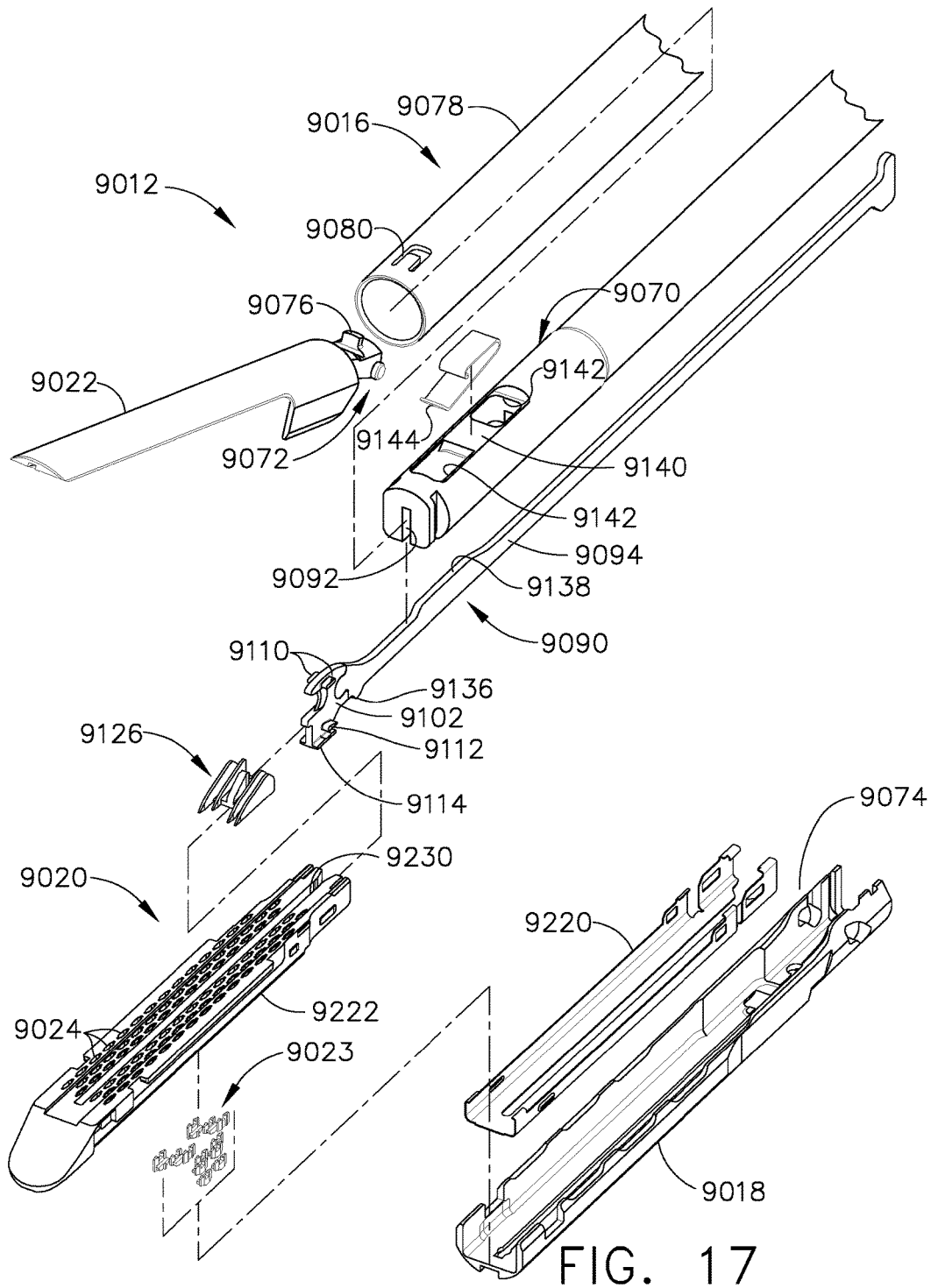
FIG. 17 is an exploded perspective view of the staple applying assembly of FIG. 16 with a complete replaceable staple cartridge and an nonarticulating shaft configuration.

With particular reference to FIG. 17, the distal end of the shaft frame 9070 is attached to the staple channel 9018. The anvil 9022 has a proximal pivoting end 9072 that is pivotally received within a proximal end 9074 of the staple channel 9018, just distal to its engagement to the shaft frame 9070. When the anvil 9022 is pivoted downwardly, the anvil 9022 moves a tissue contacting surface 9028 and forming pockets 9026 toward an opposing staple cartridge, described in greater detail further below. The pivoting end 9072 of the anvil 9022 includes a closure feature 9076 proximate but distal to its pivotal attachment with the staple channel 9018. Thus, a closure tube 9078, whose distal end includes a horseshoe aperture 9080 that engages this closure feature 9076, selectively imparts an opening motion to the anvil 9022 during proximal longitudinal motion and a closing motion to the anvil 9022 during distal longitudinal motion of the closure tube 9078 sliding over the shaft frame 9070 in response to a closure trigger, similar to the above. The shaft frame 9070 encompasses and guides a firing motion from the handle through a longitudinally reciprocating, two-piece knife and firing bar 9090. In particular, the shaft frame 9070 includes a longitudinal firing bar slot 9092 that receives a proximal portion of the two-piece knife and firing bar 9090, specifically a laminate tapered firing bar 9094. It should be appreciated that the laminated tapered firing bar 9094 may be substituted with a solid firing bar and/or any other suitable materials.

An E-beam 9102 is the distal portion of the two-piece knife and firing bar 9090, which facilitates separate closure and firing as well as spacing of the anvil 9022 from the elongate staple channel 9018 during firing. With particular reference to FIGS. 17 and 19, in addition to any attachment treatment such as brazing or an adhesive, the knife and firing bar 9090 are formed of a female vertical attachment aperture 9104 proximally formed in the E-beam 9102 that receives a corresponding male attachment member 9106 distally presented by the laminated tapered firing bar 9094, allowing each portion to be formed of a selected material and process suitable for their disparate functions (e.g., strength, flexibility, friction). The E-beam 9102 may be advantageously formed of a material having suitable material properties for forming a pair of top pins 9110, a pair of middle pins 9112 and a bottom pin or foot 9114, as well as being able to acquire a sharp cutting edge 9116. In addition, integrally formed and proximally projecting top guide 9118 and middle guide 9120 bracketing each vertical end of the cutting edge 9116 further define a tissue staging area 9122 assisting in guiding tissue to the sharp cutting edge 9116 prior to being severed. The middle guide 9120 also serves to engage and fire the staple applying apparatus 9012 by abutting a stepped central member 9124 of a wedge sled 9126 (FIG. 20) that effects staple formation by the staple applying assembly 9012, as described in greater detail below. Forming these features (e.g., top pins 9110, middle pins 9112, and bottom foot 9114) integrally with the E-beam 9102 facilitates manufacturing at tighter tolerances relative to one another as compared to being assembled from a plurality of parts, ensuring desired operation during firing and/or effective interaction with various lockout features of the staple applying assembly 9012.

Figure 21:
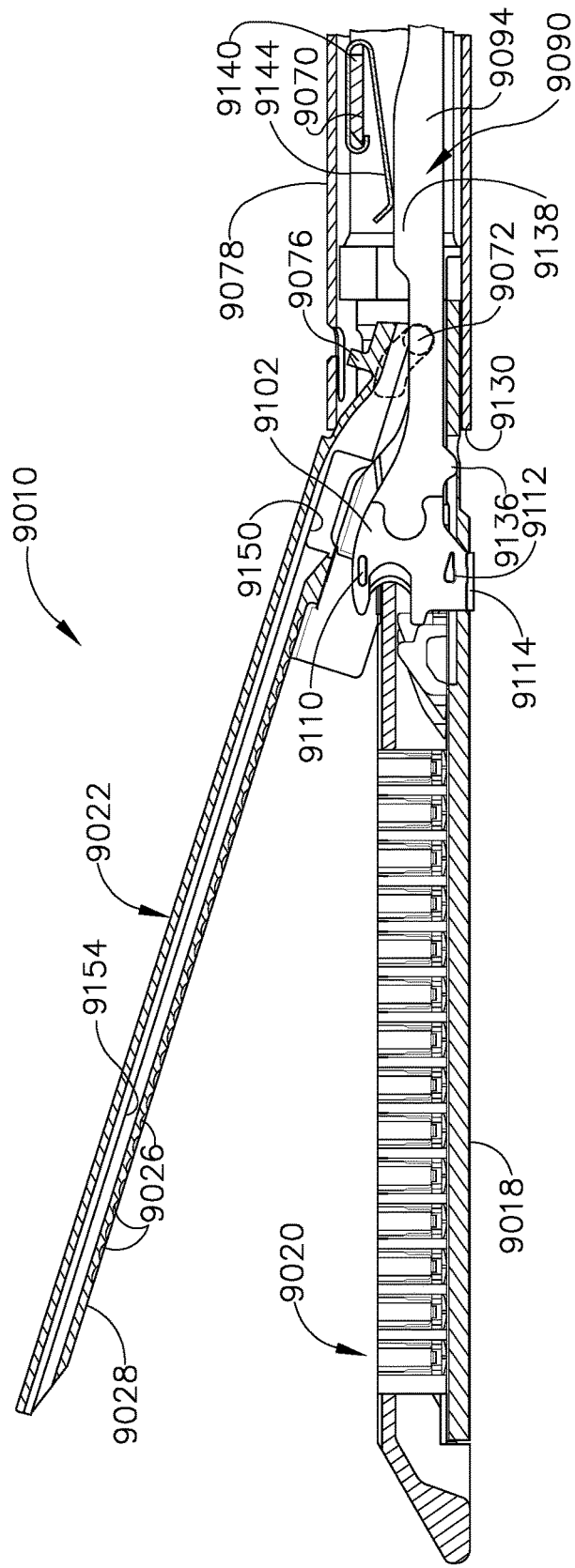
FIG. 21 is a left side view in elevation taken in longitudinal cross section along a centerline line 21-21 of the staple applying assembly of FIG. 16.
Figure 22:
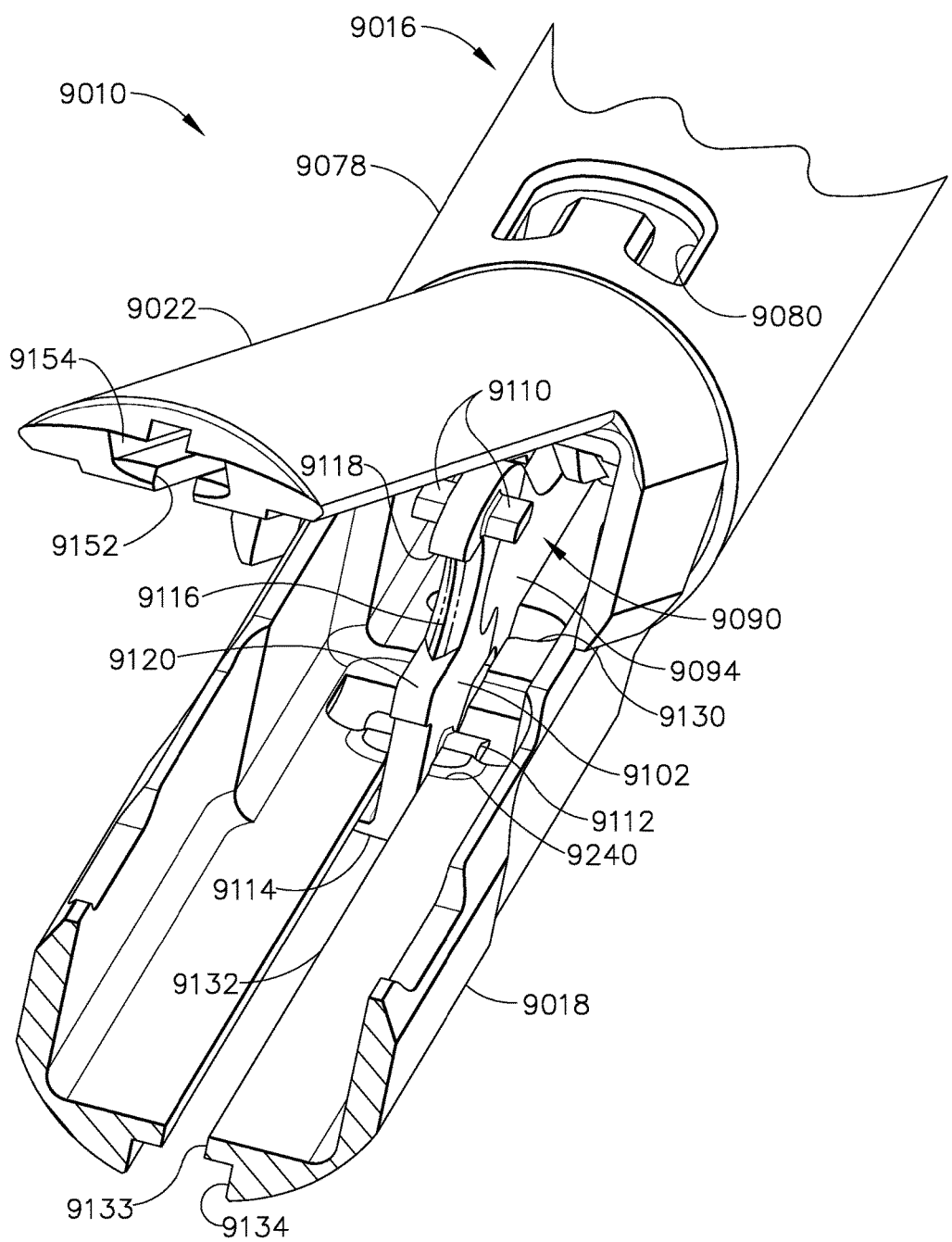
FIG. 22 is a perspective view of the open staple applying assembly of FIG. 16 without the replaceable staple cartridge and without a distal portion of a staple channel.

In FIGS. 21 and 22, the staple applying assembly 9012 is shown open, with the E-beam 9102 fully retracted. During assembly, the lower foot 9114 of the E-beam 9102 is dropped through a widened hole 9130 in the staple channel 9018 and the E-beam 9102 is then advanced such that the E-beam 9102 slides distally along a lower track 9132 formed in the staple channel 9018. In particular, the lower track 9132 includes a narrow slot 9133 that opens up as a widened slot 9134 on an undersurface of the staple channel 9018 to form an inverted T-shape in lateral cross section, as depicted particularly in FIGS. 22 and 23, which communicates with the widened hole 9130. Once assembled, the components proximally coupled to the laminate tapered firing bar 9094 do not allow the lower foot 9114 to proximally travel again to the widened hole 9130 to permit disengagement. Referring to FIG. 24, the laminate tapered firing bar 9094 facilitates insertion of the staple applying assembly 9012 through a trocar. In particular, a more distal, downward projection 9136 raises the E-beam 9102 when fully retracted. This is accomplished by placement of the downward projection 9136 at a point where it cams upwardly on a proximal edge of the widened hole 9130 in the staple channel 9018. Referring now to FIG. 25, the laminate tapered firing bar 9094 also enhances operation of certain lockout features that may be incorporated into the staple channel 9018 by including a more proximal upward projection 9138 that is urged downwardly by the shaft frame 9070 during an initial portion of the firing travel. In particular, a lateral bar 9140 is defined between a pair of square apertures 9142 in the shaft frame 9070 (FIG. 17). A clip spring 9144 that encompasses the lateral bar 9140 downwardly urges a portion of the laminate tapered firing bar 9094 projecting distally out of the longitudinal firing bar slot 9092, which ensures certain advantageous lockout features are engaged when appropriate. This urging is more pronounced or confined solely to that portion of the firing travel when the upward projection 9138 contacts the clip spring 9144.

Figure 23:
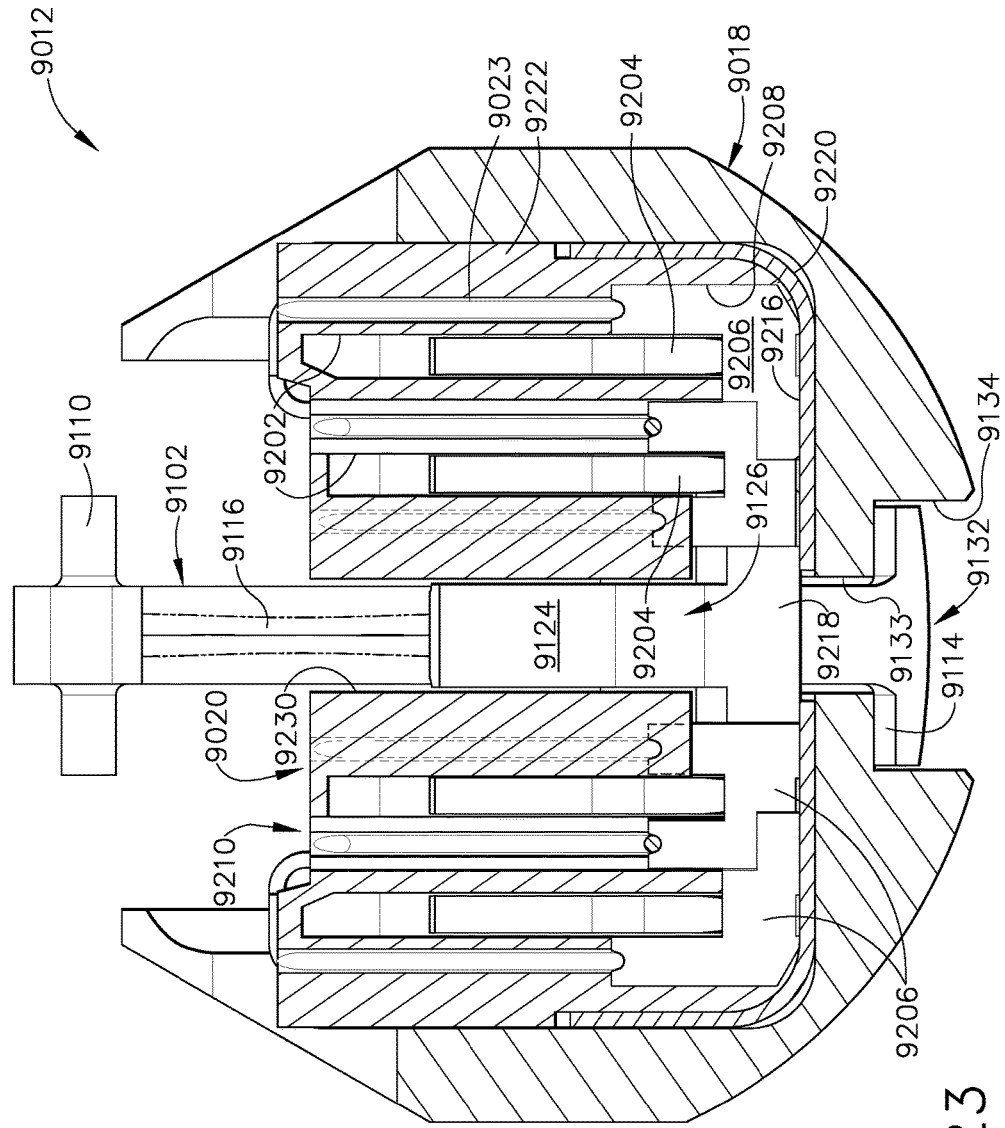
FIG. 23 is a front view in elevation taken in cross section along line 23-23 of the staple applying assembly of FIG. 16 depicting internal staple drivers of the staple cartridge and portions of the two-piece knife and firing bar.

In FIGS. 21 and 22, the E-beam 9102 is retracted with the top pins 9110 thereof residing within an anvil pocket 9150 near the pivoting proximal end of the anvil 9022. A downwardly open vertical anvil slot 9152 (FIG. 16) laterally widens in the anvil 9022 into an anvil internal track 9154 that captures the top pins 9110 of the E-beam 9102 as they distally advance during firing, as depicted in FIGS. 24 and 25, affirmatively spacing the anvil 9022 from the staple channel 9018. Thus, with the E-beam 9102 retracted, the surgeon is able to repeatably open and close the staple applying assembly 9012 until satisfied with the placement and orientation of tissue captured therein for stapling and severing, yet the E-beam 9102 assists in proper positioning of tissue even for a staple applying assembly 9012 of reduced diameter and correspondingly reduced rigidity. In FIGS. 16, 17, 20, 21, 23, and 29, the staple applying assembly 9012 is shown with the replaceable staple cartridge 9020 that includes the wedge sled 9126. Longitudinally aligned and parallel plurality of downwardly open wedge slots 9202 (FIG. 23) receive respective wedges 9204 integral to the wedge sled 9126. In FIGS. 23-25, the wedge sled 9126 thus cams upwardly a plurality of staple drivers 9206 that are vertically slidable within staple driver recesses 9208. In this illustrative version, each staple driver 9206 includes two vertical prongs, each translating upwardly into a respective staple hole 9210, or cavity 9024, to upwardly force out and deform a staple 9023 resting thereupon against a staple forming surface 9214 (FIG. 25) of the anvil 9022. A central firing recess 9216 (FIG. 17) defined within the staple cartridge 9020 proximate to the staple channel 9018 allows the passage of the bottom, horizontal portion 9218 (FIG. 20) of the wedge sled 9126 as well as the middle pins 9112 of the E-beam 9102. Specifically, a staple cartridge tray 9220 (FIGS. 17, 23) attaches to and underlies a polymer staple cartridge body 9222 that has the staple driver recesses 9208, staple holes 9210, and central firing recess 9216 formed therein. As staples 9023 are thus formed to either side, the sharp cutting edge 9116 enters a vertical through slot 9230 passing through the longitudinal axis of the staple cartridge 9020, excepting only a most distal end thereof.

Figure 26:
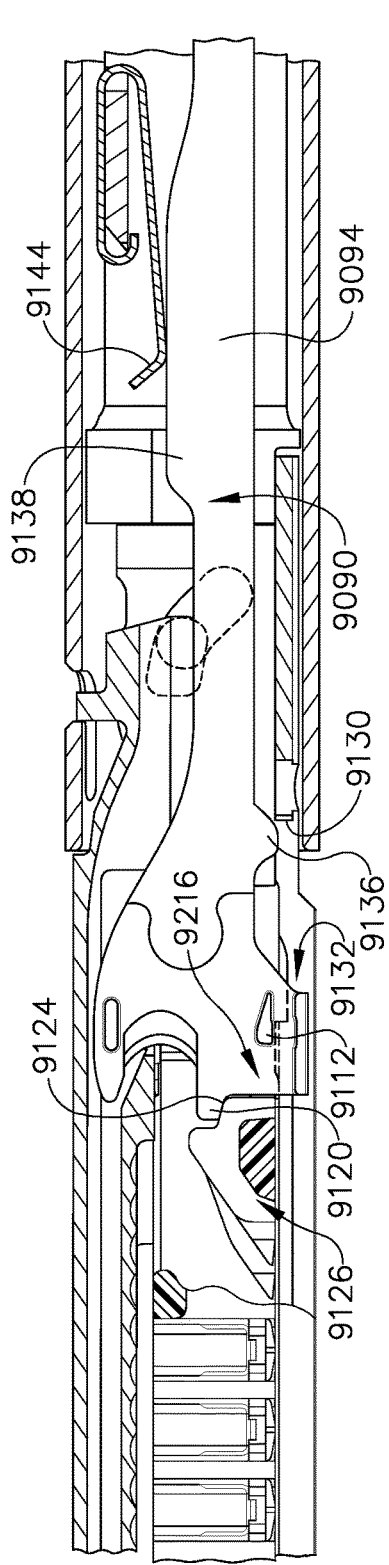
FIG. 26 is a left side detail view in elevation of the staple applying assembly of FIG. 25 with the two-piece knife beginning to fire, corresponding to the configuration depicted in FIG. 24.
Figure 27:
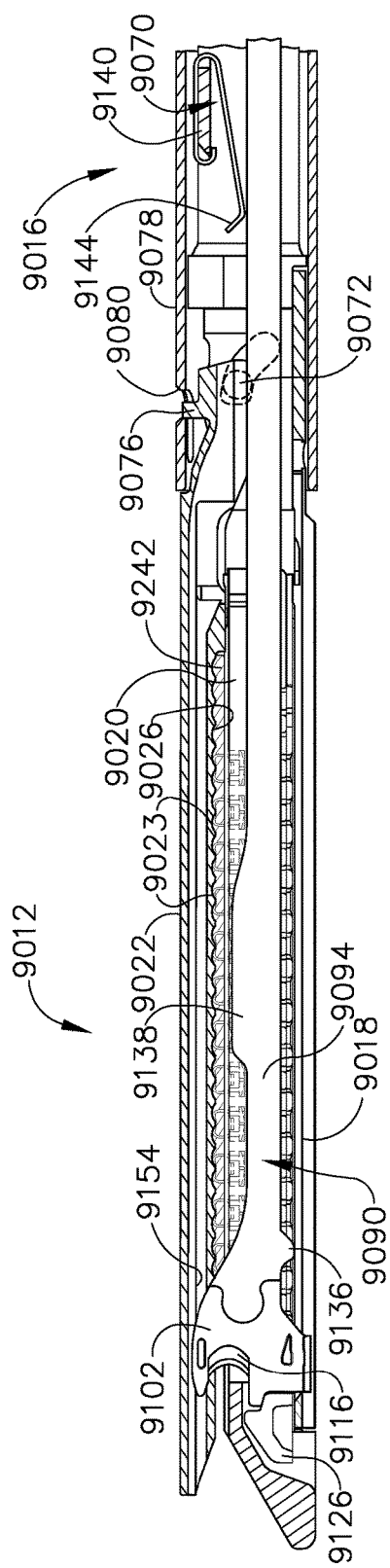
FIG. 27 is a left side cross-sectional view in elevation of the closed staple applying assembly of FIG. 24 after the two-piece knife and firing bar has distally fired.
Figure 28:
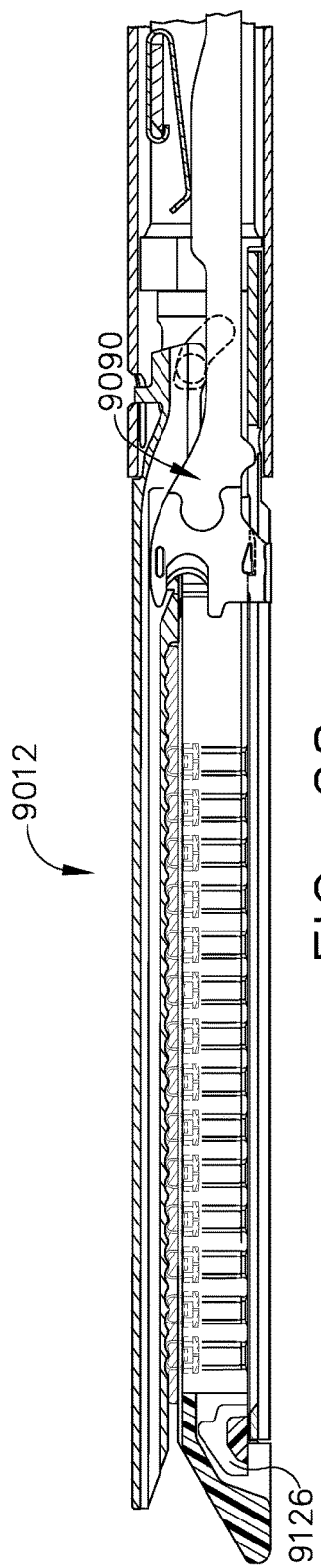
FIG. 28 is a left side cross-sectional view in elevation of the closed staple applying assembly of FIG. 27 after firing of the staple cartridge and retraction of the two-piece knife.
Figure 29:
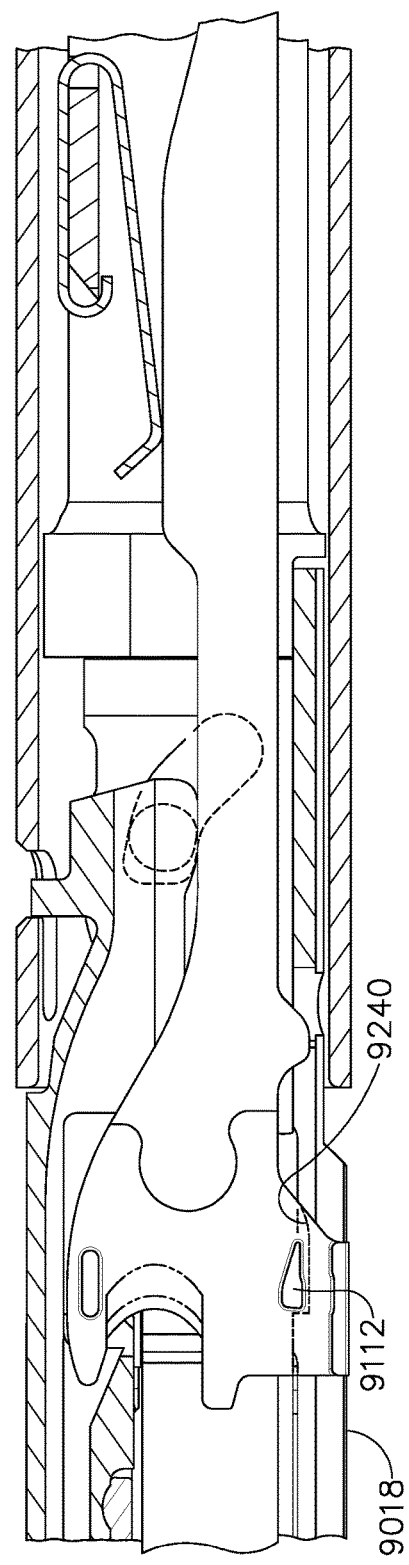
FIG. 29 is a left side cross-sectional detail view in elevation of the staple applying assembly of FIG. 28 with the two-piece knife allowed to drop into a lockout position.

Firing the staple applying assembly 9012 begins as depicted in FIG. 25 with the two-piece knife and firing bar 9090 proximally drawn until the downward projection 9136 cams the middle guide 9120 on the E-beam 9102 upward and aft, allowing a new staple cartridge 9020 to be inserted into the staple channel 9018 when the anvil 9022 is open as depicted in FIGS. 16 and 21. In FIG. 26, the two-piece knife and firing bar 9090 has been distally advanced a small distance, allowing the downward projection 9136 to drop into the widened hole 9130 of the lower track 9132 under the urging of the clip spring 9144 against the upward projection 9138 of the laminate tapered firing bar 9094. The middle guide 9120 prevents further downward rotation by resting upon the stepped central member 9124 of the wedge sled 9126, thus maintaining the middle pin 9112 of the E-beam within the central firing recess 9216. In FIG. 27, the two-piece knife and firing bar 9090 has been distally fired, advancing the wedge sled 9126 to cause formation of staples 9023 while severing tissue 9242 clamped between the anvil 9022 and staple cartridge 9020 with the sharp cutting edge 9116. Thereafter, in FIG. 28, the two-piece knife and firing bar 9090 is retracted, leaving the wedge sled 9126 distally positioned. In FIG. 29, the middle pin 9112 is allowed to translate down into a lockout recess 9240 formed in the staple channel 9018 (also see FIGS. 22 and 25). Thus, the operator would receive a tactile indication as the middle pin 9112 encounters the distal edge of the lockout recess 9240 when the wedge sled 9126 (not shown in FIG. 29) is not proximally positioned (i.e., missing staple cartridge 9020 or spent staple cartridge 9020). Similar surgical stapling instruments are disclosed in U.S. Pat. No. 7,380,696, which issued on Jun. 3, 2008, the entire disclosure of which is incorporated by reference herein.

Figure 36:
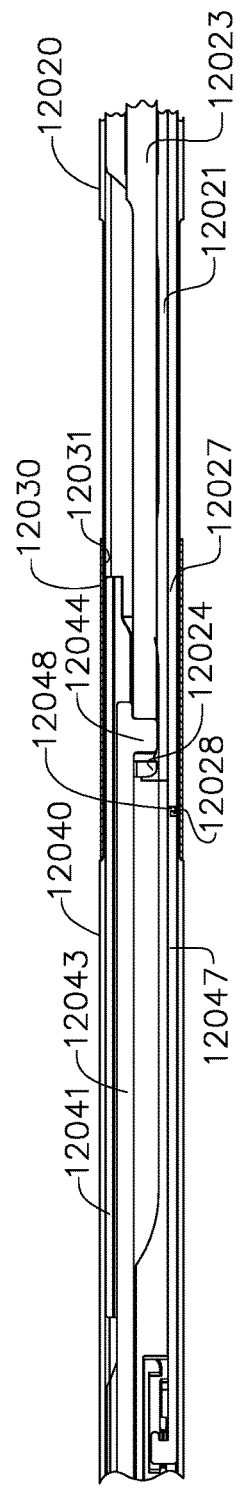
FIG. 36 is a partial cross-sectional elevational view illustrating the end effector coupled to the shaft of the surgical stapling instrument of FIG. 30, and further illustrating the slide collar in a closed, locked position.
Figure 37:
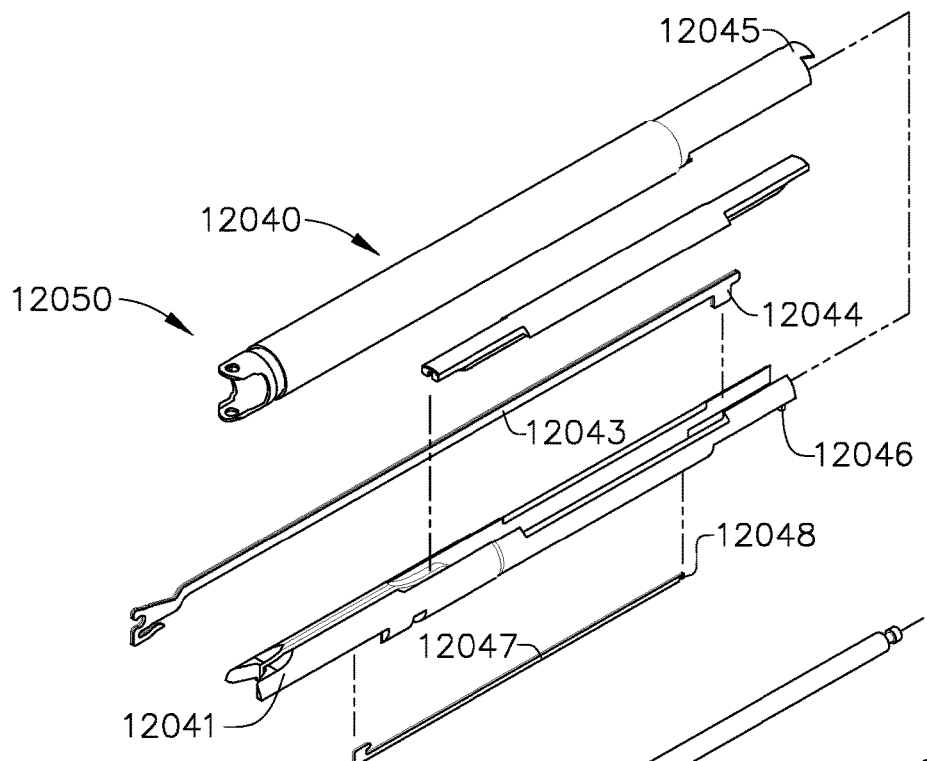
FIG. 37 is an exploded view of the end effector of FIG. 30 illustrated with components removed.
Figure 38:
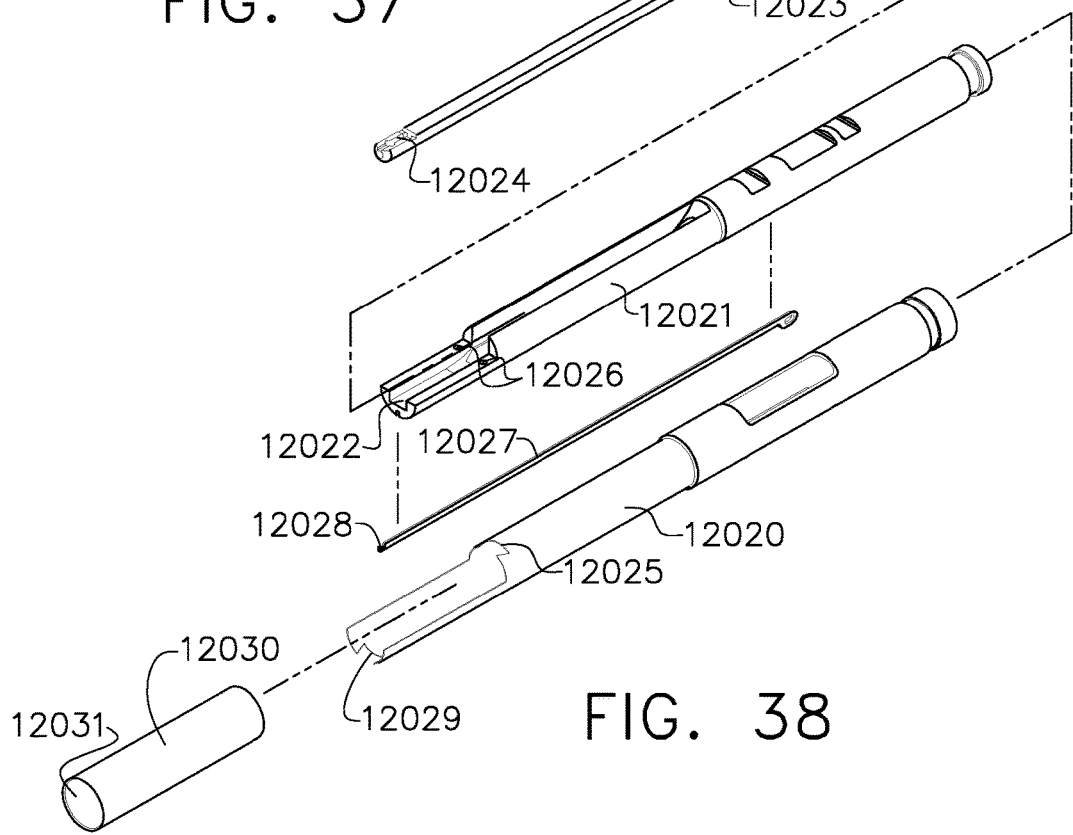
FIG. 38 is an exploded view of the shaft of FIG. 30.

In various embodiments, turning now to FIGS. 30-38, a surgical instrument 12000 can comprise a handle 12010, a shaft 12020 extending from the handle 12010, and an end effector 12040 removably attachable to the shaft 12020, as described in greater detail further below. The handle 12010 can comprise a trigger 12014 which can be actuated to, one, close the end effector 12040 and, two, advance a firing member 12043 distally through the end effector 12040. Although not illustrated in FIGS. 30-38, the handle 12010 can include any suitable drive train configured to transfer and convert the rotational motion of the trigger 12014 to linear motion of a firing member 12023 extending through the shaft 12010. In use, the trigger 12014 can be actuated toward a pistol grip 12012 of the handle 12010 in order to advance the firing member 12023 distally within the shaft 12020 along a longitudinal axis 12039 and, when the shaft firing member 12023 is operably coupled with the end effector firing member 12043, as discussed in greater detail further below, the distal movement of the shaft firing member 12023 can be transferred to the end effector firing member 12043. When the end effector firing member 12043 is advanced distally, the end effector firing member 12043 can be configured to engage a first jaw 12040*a* including an anvil and/or a second jaw 12040*b* including a staple cartridge channel and move at least one of the first jaw 12040*a* and the second jaw 12040*b* toward the other. Further to the above, and referring primarily to FIGS. 30-32, the end effector 12040 can be assembled to the shaft 12010 in a direction which is transverse to the longitudinal axis 12039. For instance, the end effector 12040 can be assembled to the shaft 12010 in a direction which is perpendicular to the longitudinal axis 12039, for example. In such circumstances, the end effector 12040 can be moved toward the shaft 12010 such that the frame 12041 of the end effector 12040 engages and connects to the frame 12021 and such that the proximal end 12044 of the firing member 12043 engages and couples to the distal end 12024 of the firing member 12023. The shaft frame 12021 can include a channel 12022 defined therein which can be configured to slidably receive the shaft firing member 12023 and define the longitudinal axis 12039. To align the end effector frame 12041 with the shaft frame 12021, in various embodiments, the proximal end 12045 of the end effector frame 12041 and the distal end 12025 of the shaft frame 12021 can include co-operating dovetail features, for example, which can orient the end effector 12040 relative to the shaft 12020. The shaft frame 12021 can further include mounting apertures 12026 defined therein which can be configured to receive mounting projections 12046 extending from the end effector frame 12041. As a result of the co-operating dovetail features of the ends 12025, 12045 and/or the mounting features 12026, 12046, in various circumstances, can securely mount the end effector 12040 to the shaft 12020. In various embodiments, the surgical instrument 12000 can further comprise a lock collar 12030 which can be configured to lock the end effector 12040 to the shaft 12020. Primarily referring now to FIGS. 34-36, the lock collar 12030 can be moved between an unlocked position (FIGS. 34 and 35) and a locked position (FIG. 36). When the lock collar 12030 is in its unlocked position, referring to FIG. 34, the end effector 12040 can be assembled to the shaft 12020. Once end effector 12040 has been engaged with the shaft 12020, the lock collar 12030 can be slid over the interconnection between the end effector 12040 and the shaft 12020 to lock the end effector 12040 in place. More specifically, in at least one embodiment, the lock collar 12030 can define an inner aperture 12031 which can be configured to closely receive the outside perimeters of the end effector 12040 and the shaft 12020. In certain embodiments, the surgical instrument 12000 can comprise a spring or biasing member configured to bias the lock collar 12030 into its locked position. In such embodiments, a clinician can pull the lock collar 12030 proximally against the biasing force of the spring and, thereafter, release the lock collar 12030 and allow the spring to return the lock collar 12030 to its locked position.

Referring again to FIGS. 30-38, and primarily to FIGS. 32 and 33, the surgical instrument 12000 can comprise an articulation joint 12050. The articulation joint 12050, in various embodiments, can be configured to permit a distal portion of the end effector 12040 to pivot about an axis defined by the articulation joint 12050. In such and embodiment, the end effector 12040 can comprise a proximal portion securely mounted to the shaft 12020 and the distal portion which can rotate relative to the proximal portion about the articulation joint 12050. In certain embodiments, the surgical instrument 12000 can comprise a lock configured to engage and disengage the distal portion of the end effector 12040. For instance, the end effector 12040 can include an end effector lock portion 12047 which can be pushed distally to lock the distal portion of the end effector 12040 in position and/or pulled proximally to unlock the distal portion of the end effector 12040. The surgical instrument 12000 can further comprise a lock actuator 12060 adjacent the handle 12010, for example, which can be pulled proximally in order to pull the end effector lock portion 12047 proximally. In such an embodiment, the lock actuator 12060 can be operably coupled with a lock portion 12027 extending through the shaft 12020 which is operably coupled, or operably couplable, to the end effector lock portion 12047. In at least one such embodiment, the proximal end 12048 of the end effector lock portion 12047 can be assembled to the distal end 12028 of the lock portion 12027 when the end effector 12040 is assembled to the shaft 12020. In at least one such embodiment, the end effector lock portion 12047 can be assembled to the lock portion 12027 at the same time that the end effector firing member 12043 is assembled to shaft firing member 12023.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist.

Figure 41:
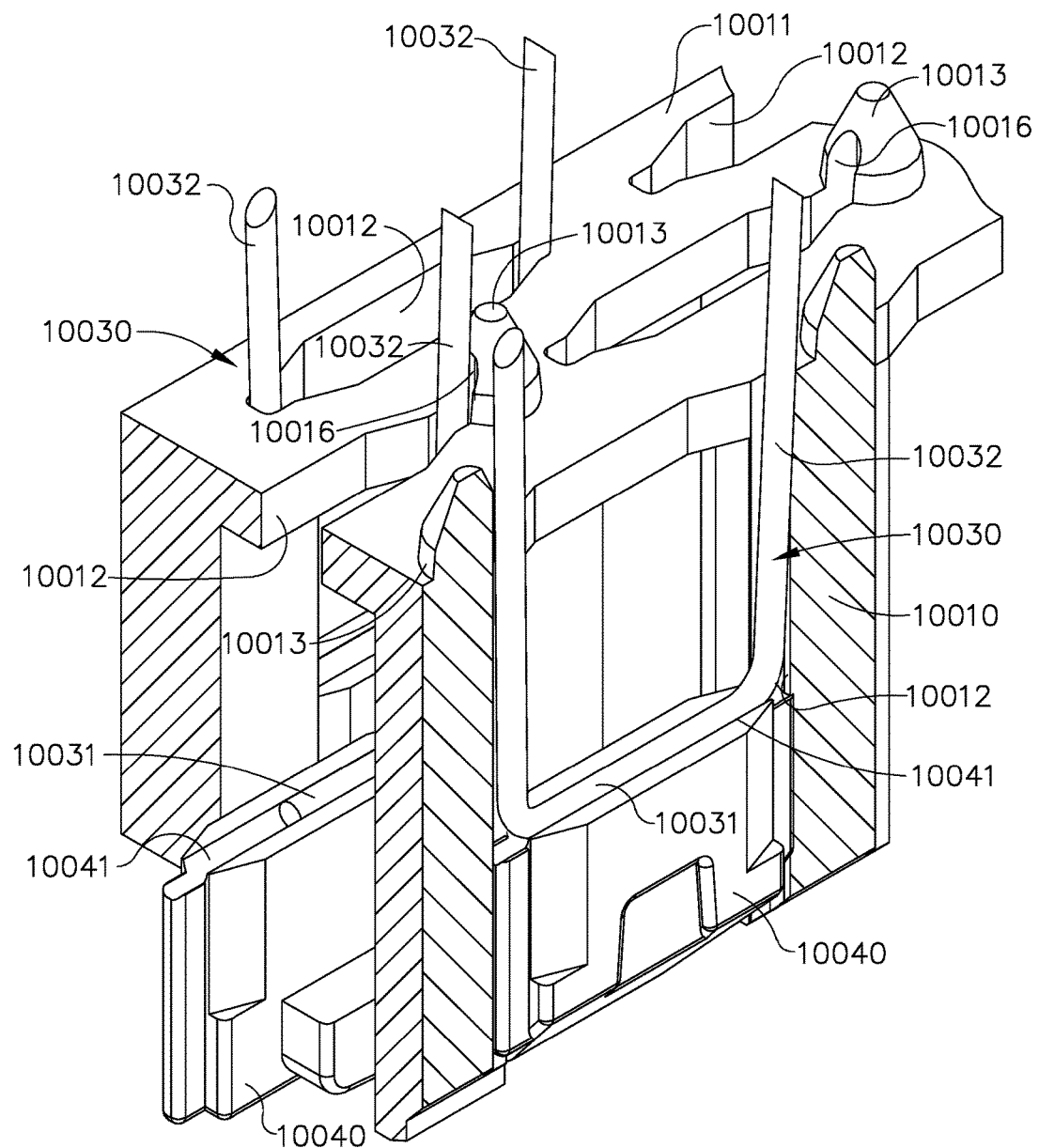
FIG. 41 is a partial detail view of the staple cartridge of FIG. 39 illustrating the staples in an unfired position.

In use, further to the above and referring primarily to FIG. 39, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 39. In various embodiments, as mentioned above, the staple-firing sled 10050 can be moved from the proximal end 10001 of the staple cartridge 10000 toward the distal end 10002, as illustrated in FIG. 40. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, each staple driver 10040 can comprise at least one inclined surface and the sled 10050 can comprise one or more inclined surfaces which can be configured such that the sled inclined surfaces can slide under the driver inclined surface as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011 (FIG. 41). During an exemplary firing sequence, the sled 10050 can contact a first staple 10030 and begin to lift the first staple 10030 upwardly. As the sled 10050 is advanced further distally, the sled 10050 can begin to lift additional staples 10030, and any other subsequent staples, in a sequential order. The sled 10050 can drive the staples 10030 upwardly such that the legs 10032 of the staples contact the opposing anvil, are deformed to a desired shape, and ejected therefrom the support portion 10010. In various circumstances, the sled 10050 can move several staples upwardly at the same time as part of a firing sequence.

With reference to FIGS. 49-54, each staple 10030 can be deformed such that a compression zone 10039 is defined therein. For instance, each staple 10030 can comprise a base 10031 and one or more legs 10032 extending from the base 10031 which, when deformed, can co-operatively define an area with the base 10031 within which the tissue T and the tissue thickness compensator 10020 can be captured. Within the compression zone 10039, the tissue thickness compensator 10020 can apply pressure to the tissue T and, in certain circumstances, assume different compressed heights depending on the thickness of the tissue T. In some circumstances, the tissue thickness compensator 10020 can resiliently fill gaps, or free spaces, present within the compression zones 10039 defined by the staples 10030.

As discussed above, and referring to FIG. 41, the staple legs 10032 of the staples 10030 can extend above the deck surface 10011 of the support portion 10010 when the staples 10030 are in their unfired positions. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, the tips of the staple legs can protrude through the tissue-contacting surface. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 (FIG. 41) extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013 can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 41, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, a tissue thickness compensator can comprise a compressible core and a wrap surrounding the compressible core.

In various embodiments, a tissue thickness compensator can comprise a wrap for releasably holding a compressible core to the support portion 10010. In at least one such embodiment, a staple cartridge can further comprise retainer clips which can be configured to inhibit the wrap, and the compressible core, from prematurely detaching from the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

Figure 44:
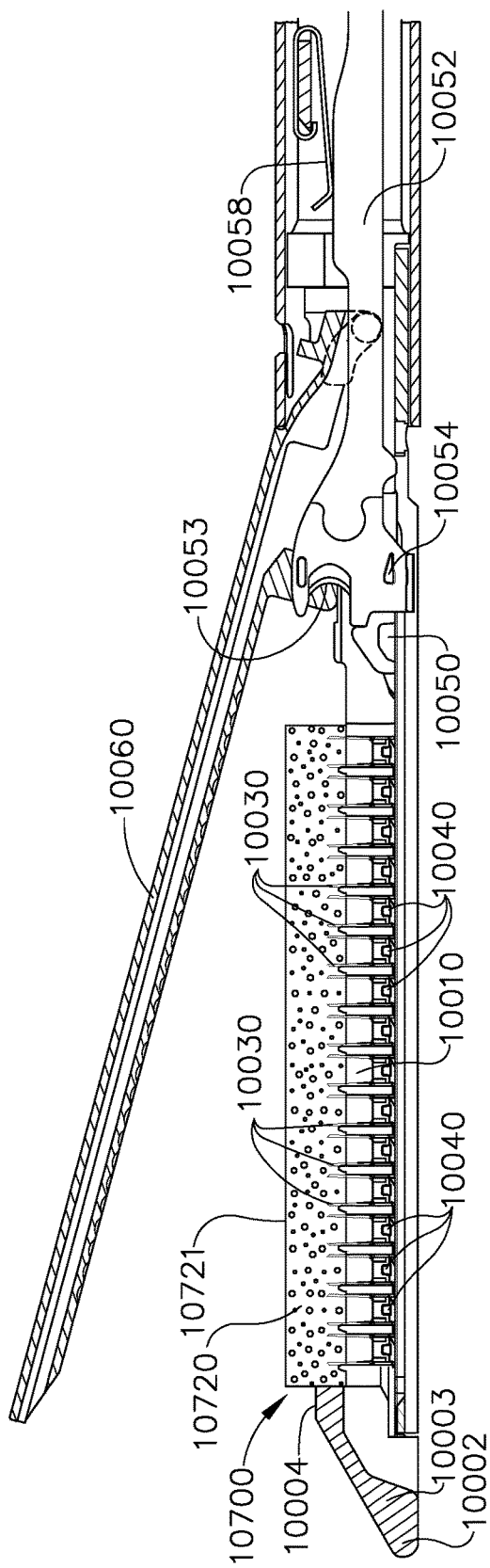
FIG. 44 is an elevational view of an anvil in an open position and a staple cartridge comprising a rigid support portion and a compressible tissue thickness compensator illustrating the staples in an unfired position.

In various embodiments, further to the above, the sled 10050 can be advanced from a proximal end to a distal end to fully deploy all of the staples 10030 contained within the staple cartridge 10000. In at least one embodiment, referring now to FIG. 44, the sled 10050 can be advanced distally within a longitudinal cavity within the support portion 10010 by a firing member, or knife bar, 10052 of a surgical stapler. In use, the staple cartridge 10000 can be inserted into a staple cartridge channel in a jaw of the surgical stapler and the firing member 10052 can be advanced into contact with the sled 10050, as illustrated in FIG. 44. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 44, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end of the staple cartridge 10000. At such point, the firing member 10052 can be retracted proximally. In some embodiments, the sled 10050 can be retracted proximally with the firing member 10052 but, in various embodiments, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel.

After the expended staple cartridge 10000 has been removed from the staple cartridge channel, further to the above, a new staple cartridge 10000, or any other suitable staple cartridge, can be inserted into the staple cartridge channel. In various embodiments, further to the above, the staple cartridge channel, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, as the firing member 10052 is advanced into contact with the sled 10050 and, when the sled 10050 is in its proximal unfired position, a support nose of the firing member 10052 can be positioned on and/or over a support ledge on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall of the lock recess as the firing member 10052 is advanced. As the firing member 10052 pushes the sled 10050 distally, the firing member 10052 can be supported in its upward firing position owing to the support nose resting on the support ledge. When the firing member 10052 is retracted relative to the sled 10050, as discussed above, the firing member 10052 can drop downwardly from its upward position as the support nose is no longer resting on the support ledge of the sled 10050. In at least one such embodiment, the surgical stapler can comprise a spring, and/or any other suitable biasing element, which can be configured to bias the firing member 10052 into its downward position. Once the firing member 10052 has been completely retracted, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, is hereby incorporated by reference in its entirety.

In various circumstances, further to the above, a compressible tissue thickness compensator can move, twist, and/or deflect relative to the underlying rigid support portion of a staple cartridge. In various embodiments, the support portion, and/or any other suitable portion of the staple cartridge, can comprise one or more features configured to limit relative movement between the tissue thickness compensator and the support portion. As described above, at least a portion of the staples 10030 can extend above the deck surface 10011 of the support portion 10010 wherein, in certain circumstances, lateral forces applied to a tissue thickness compensator can be resisted by the staples 10030 and/or the cleats 10013 extending from the support portion 10010, for example. In various circumstances, the staples 10030 may tilt and/or bend within the staple cavities 10012 while resisting the lateral movement of the tissue thickness compensator wherein, in various embodiments, the staple cavities 10012 and the staples 10030 can be sized and configured to maintain the relative alignment between the legs 10032 of the staples 10030 and the forming pockets in the opposing anvil 10060 such that the staples 10000 are properly formed during the staple forming process. In various embodiments, the staples 10030 and/or the cleats 10013 can be configured to prevent or at least limit lateral distortion within the tissue thickness compensator 10020. In at least one such embodiment, the staples 10030 and/or cleats 10013, for example, can be configured to stiffen, or limit the lateral and/or longitudinal movement of, a first, or tissue-contacting, surface of the tissue thickness compensator relative to a second, or bottom, surface. In various embodiments, a staple cartridge, and/or a staple cartridge channel in which the staple cartridge is positioned, can comprise at least one distortion minimizing member which can extend upwardly to limit the lateral and/or longitudinal movement, or distortion, of a tissue thickness compensator. A wrap at least partially surrounding a tissue thickness compensator, as discussed above, may also prevent, or at least limit, the lateral and/or longitudinal movement, or distortion, of the tissue thickness compensator.

In various embodiments, a staple cartridge can comprise a plurality of staple cavities each containing a staple positioned therein wherein the staple cavities can be arranged in a plurality of rows, and wherein an anvil positioned opposite the staple cartridge can comprise a plurality of forming pockets which correspond to the staple cavities in the staple cartridge. Stated another way, the anvil can comprise a plurality of forming pocket rows wherein each forming pocket can be positioned opposite a staple cavity in the staple cartridge. In various embodiments, each forming pocket can comprise two forming cups configured to receive the staple legs 10032 of a staple 10030 wherein each forming cup is configured to receive a staple leg 10032 and form or curl the staple leg 10032 toward the other staple leg 10032, for example. In various circumstances, the legs 10032 may miss or not properly enter into the forming cups and, as a result, the staple legs 10032 may become malformed during the firing sequence. In various embodiments described herein, an anvil can comprise an array, or grid, of forming pockets which are each configured to receive and form a staple leg. In at least one such embodiment, the array of forming pockets can comprise a quantity of forming pockets that exceeds the quantity of staples contained within the staple cartridge. In at least one embodiment, a staple cartridge can comprise six longitudinal rows of staple cavities, for example, wherein the anvil can comprise six rows of forming pockets aligned with the six rows of staple cavities and, in addition, forming pockets positioned intermediate the rows of forming pockets. For example, on one side of the anvil, the anvil can comprise a first row of forming pockets which can be positioned over a first row of staple cavities, a second row of forming pockets which can be positioned over a second row of staple cavities that is adjacent to the first row of staple cavities, and, in addition, a row of forming pockets positioned intermediate the first row of forming pockets and the second row of forming pockets.

Figure 55:
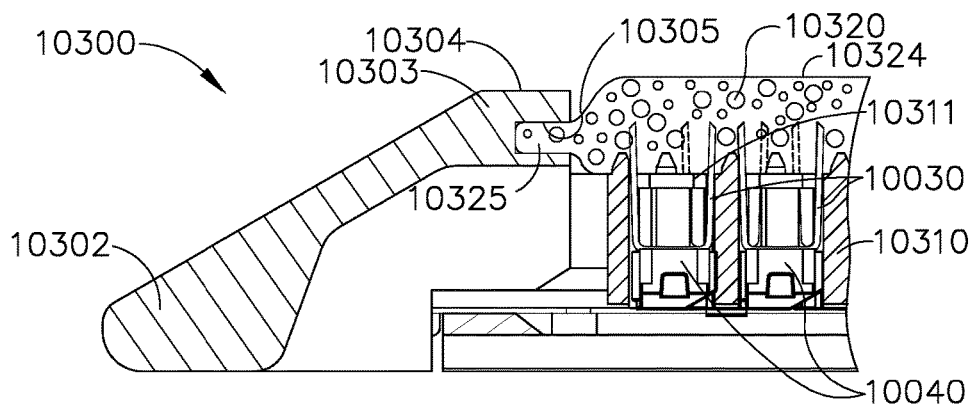
FIG. 55 is a partial cross-sectional view of an end effector of a surgical stapling instrument in accordance with at least one embodiment.
Figure 56:
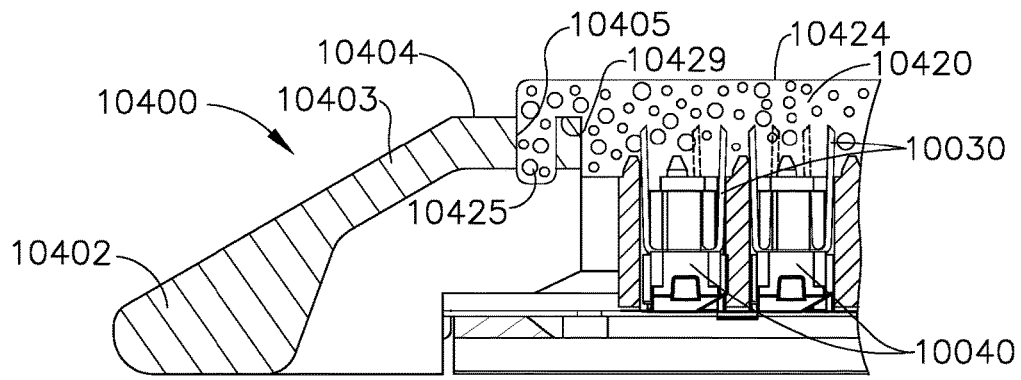
FIG. 56 is a partial cross-sectional view of an end effector in accordance with at least one alternative embodiment.
Figure 57:
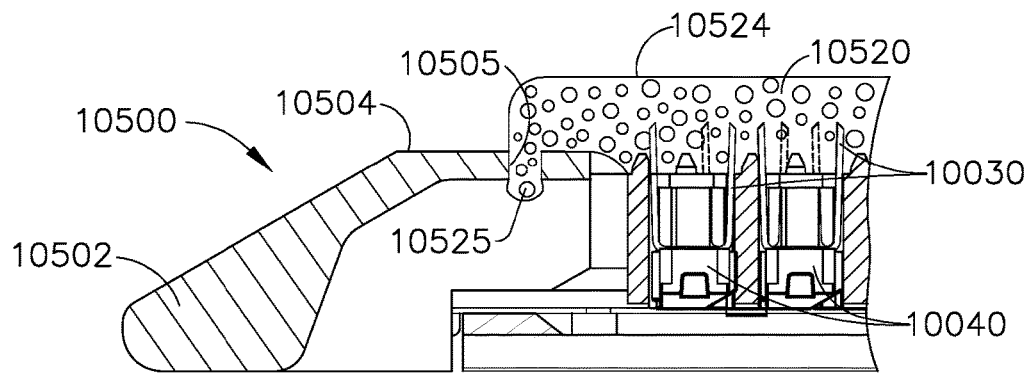
FIG. 57 is a partial cross-sectional view of an end effector in accordance with another alternative embodiment.

In various embodiments, as described above, an anvil can be moved from an open position to a closed position in order to compress tissue against the tissue thickness compensator of a staple cartridge, such as tissue thickness compensator 10020, for example. In various circumstances, the tissue thickness compensator can be positioned adjacent to the support portion of the staple cartridge prior to the tissue thickness compensator being positioned relative to the tissue. In certain embodiments, the tissue thickness compensator 10020 can be in a position in which it abuts the support portion 10018 prior to the anvil being moved into its closed position. In certain other embodiments, the tissue thickness compensator 10020 can be in a position in which a gap is present between the tissue thickness compensator 10020 and the support portion 10018. In at least one such embodiment, the anvil can displace the tissue and the tissue thickness compensator 10020 downwardly until the tissue thickness compensator 10020 abuts the support portion 10018 wherein, at such point, the anvil can be moved into is closed position and generate compression within the tissue. In the event that a surgeon is not satisfied with the positioning of the tissue between the anvil and the staple cartridge, the surgeon can open the anvil, adjust the position of the anvil and the staple cartridge, and close the anvil once again. Owing to such positioning and re-positioning of the staple cartridge relative to the tissue, in various circumstances, the distal end of the tissue thickness compensator 10020 may become dislodged from the support portion 10010, for example. In some such circumstances, the distal end of the tissue thickness compensator 10020 can contact the tissue and peel away from, or roll relative to, the support portion 10010. In various embodiments, as described in greater detail below, a staple cartridge can comprise one or more features configured to releasably retain a tissue thickness compensator to an underlying support portion of the staple cartridge In various embodiments, referring now to FIG. 55, a staple cartridge 10300 can comprise a support portion 10310, a tissue thickness compensator 10320 supported by the support portion 10310, and a distal end 10302 which includes a nose 10303 configured to releasably hold a distal end 10325 of the tissue thickness compensator 10320 in position. In at least one embodiment, the nose 10303 can comprise a slot 10305 configured to receive the distal end 10325 of the tissue thickness compensator 10320. In various embodiments, the distal end 10325 can be compressed, or wedged, within the slot 10305 such that the distal end 10325 can be held in place as the staple cartridge 10300 is positioned relative to the tissue. In at least one such embodiment, the slot 10305 can be oriented in a direction which is parallel, or at least substantially parallel, to the deck surface 10311 of the support portion 10310. In various embodiments, the slot 10305 can be horizontal with respect to the deck surface 10311. In various other embodiments, referring now to FIG. 56, a staple cartridge 10400 can comprise a support portion, a tissue thickness compensator 10420 supported by support portion, and a distal end 10402 which includes a nose 10403 configured to releasably hold the distal end 10425 of the tissue thickness compensator 10420 in position. In at least one embodiment, the distal end 10425 can comprise a projection extending therefrom and the nose 10403 can comprise a vertical slot 10405 configured to receive the projection of the distal end 10425. In various embodiments, the distal end 10425, and/or the projection extending therefrom, can be compressed, or wedged, within the slot 10405 such that the distal end 10425 can be held in place as the staple cartridge 10400 is positioned relative to the tissue. In certain embodiments, the tissue thickness compensator 10420 can comprise a slot, such as slot 10429, for example, which can be configured to receive at least a portion of the nose 10403 therein. In at least one embodiment, the slot 10405 can be oriented in a direction which is perpendicular, or at least substantially perpendicular, to the deck surface 10411 of the support portion. In various embodiments, referring now to FIG. 57, a staple cartridge 10500 can comprise a support portion, a tissue thickness compensator 10520 supported by the support portion, and a distal end 10502 which includes a nose configured to releasably hold the distal end 10525 of the tissue thickness compensator 10520 in position. In at least one embodiment, the nose can comprise a vertical slot 10505 configured to receive the distal end 10525 of the tissue thickness compensator 10520. In various embodiments, the distal end 10525 can be compressed, or wedged, within the slot 10505 such that the distal end 10525 can be held in place as the staple cartridge 10500 is positioned relative to the tissue.

In various embodiments, referring again to FIG. 55, the tissue thickness compensator 10320 can comprise a top surface 10324 which can be positioned above the top surface 10304 of the nose 10303. Another exemplary embodiment in which the top surface of a tissue thickness compensator is positioned above the nose of the staple cartridge is illustrated in FIG. 44, wherein the top surface 10721 of the tissue thickness compensator 10720 is positioned above the top surface 10004 of the nose 10003, for example. In use, referring once again to FIG. 55, tissue can slide over the top surface 10304 of the nose 10303 and, in some circumstance, the tissue can contact the distal end 10325 of the tissue thickness compensator 10320 and can apply a force to the tissue thickness compensator 10320 tending to peel the tissue thickness compensator 10320 away from the support portion 10310. In the embodiments described herein, this peel force can be resisted by the portion of the distal end 10325 wedged within the nose 10303. In any event, once the tissue has been suitably positioned relative to the staple cartridge 13000, an anvil can be rotated into a closed position to compress the tissue and the tissue thickness compensator 10320 against the support portion 10310. In at least one such embodiment, the anvil can be rotated into a position in which the anvil contacts the top surface 10304 of the nose 10303 and, as a result, the anvil can be prevented from rotating further. In various circumstances, owing to the top surface 10324 of the tissue thickness compensator 10320 being positioned above the top surface 10304 of the nose 10303, the top surface 10324 can be pushed downwardly toward the support portion 10310 as the anvil is being closed and, in some circumstances, the top surface 10324 can be pushed below the top surface 10304 of the nose 10303, for example. After the staples contained within the staple cartridge 10300 have been deployed and the tissue thickness compensator 10320 has been incised, as described herein, the support portion 10310 and the nose 10303 can be moved away from the tissue thickness compensator 10320 such that the distal end 10325 of the tissue thickness compensator 10320 can slide out of the slot 10305.

Figure 45:
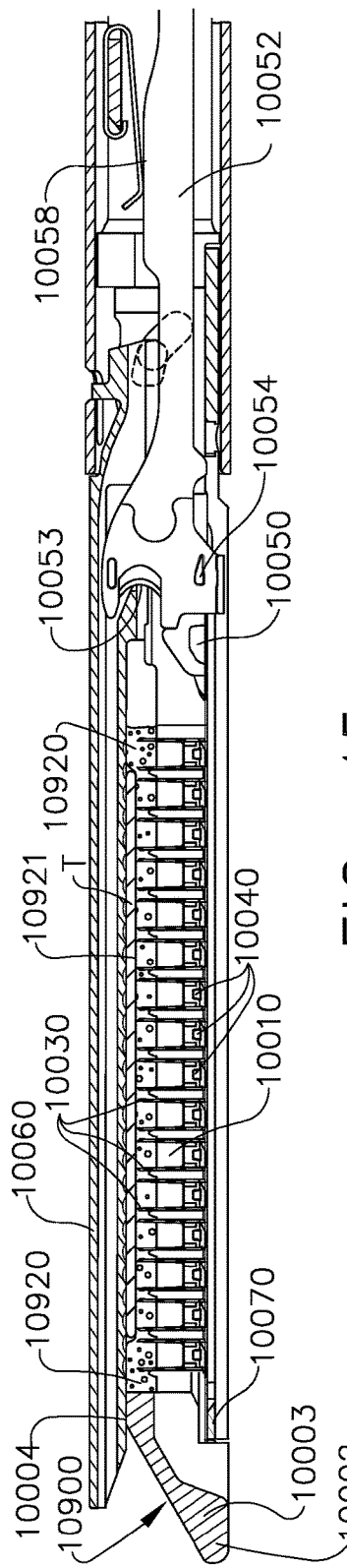
FIG. 45 is an elevational view of an anvil in a closed position and a staple cartridge comprising a rigid support portion and a compressible tissue thickness compensator illustrating the staples in an unfired position and tissue captured between the anvil and the tissue thickness compensator.
Figure 46:
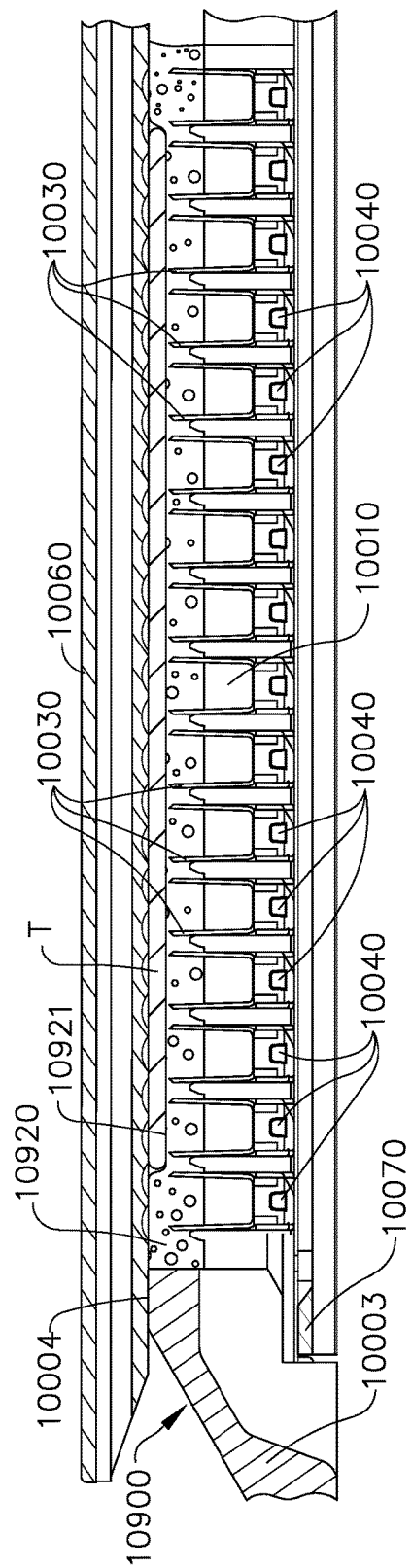
FIG. 46 is a detail view of the anvil and staple cartridge of FIG. 45.

As described above, an anvil, such as anvil 10060, for example, can be rotated into a closed position in which the anvil 10060 contacts the top nose surface 10004 of a staple cartridge, such as staple cartridge 10000, for example. Once the anvil has reached its closed position, the amount in which a tissue thickness compensator, such as tissue thickness compensator 10020, for example, is compressed will depend on, among other things, the uncompressed thickness, or height, of the tissue thickness compensator and the thickness of the tissue. Referring now to FIGS. 42 and 43, a tissue thickness compensator 10920 can comprise a top surface which is flush, or at least substantially flush, with the top surface 10004 of the nose 10003. In such embodiments, the top surface of the tissue thickness compensator 10920 can be pushed below the top surface 10004 of the nose 10003. Referring now to FIGS. 47 and 48, a tissue thickness compensator, such as tissue thickness compensator 10820, for example, can comprise a top surface 10821 which is positioned below the top nose surface 10004 prior to the tissue thickness compensator 10820 being compressed by the tissue T and anvil 10060. In the circumstances where the tissue T is relatively thin, as illustrated in FIGS. 45 and 46, the tissue thickness compensator 10920 may undergo relatively little compression. Referring now to FIGS. 47 and 48, the tissue thickness compensator 10820 may undergo a larger compression when the tissue T is relatively thicker. In the circumstances where the tissue T has both thin sections and thicker sections, as illustrated in FIGS. 47 and 48, the tissue thickness compensator 10820 may be compressed a larger amount when it is positioned under the thicker tissue T and a lesser amount when it is positioned under the thinner tissue T, for example. In this way, as described above, the tissue thickness compensator can compensate for different tissue thicknesses.

Figure 58:
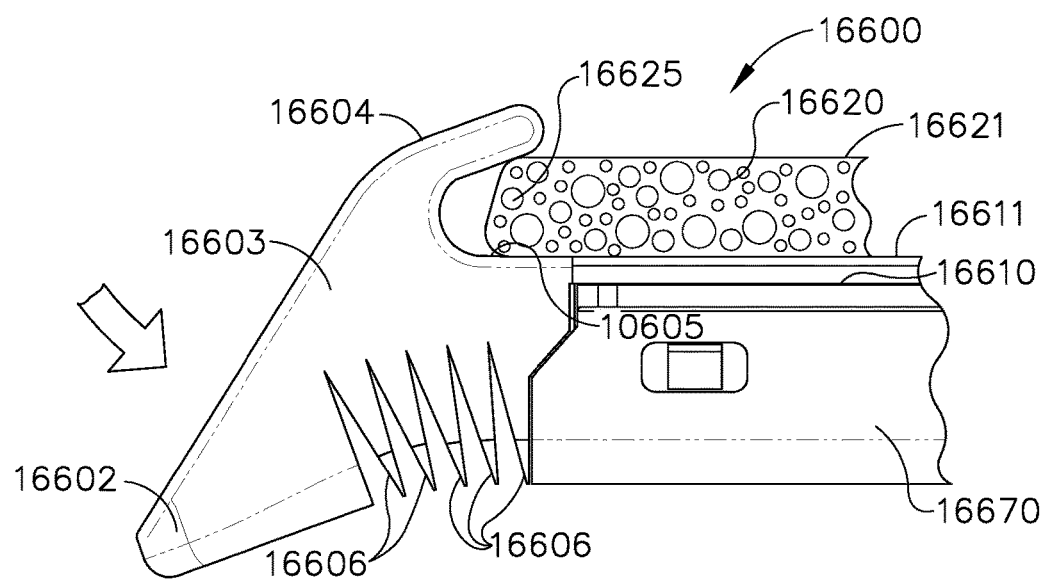
FIG. 58 is a partial cross-sectional view of an end effector illustrated in a flexed condition.
Figure 59:
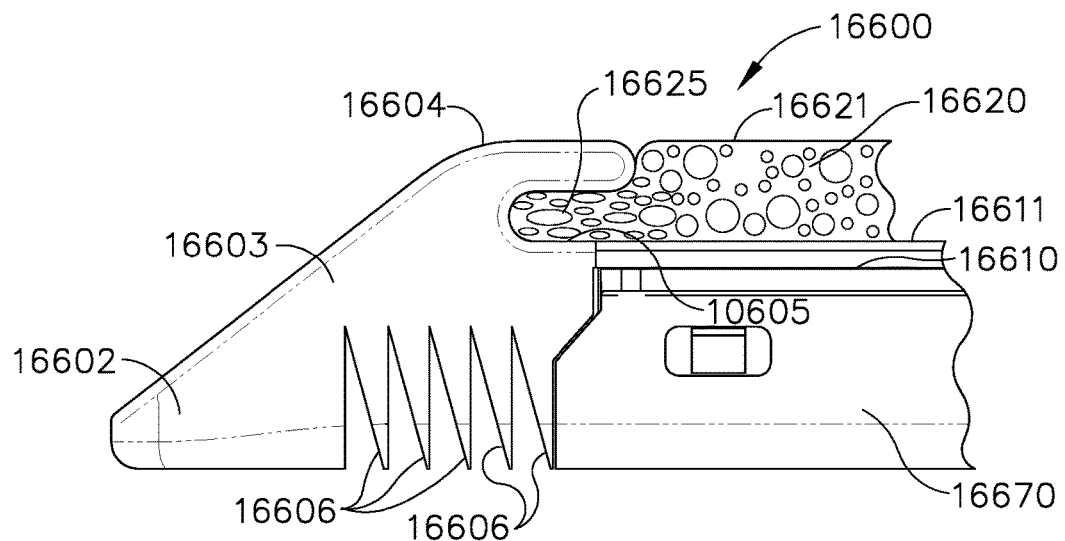
FIG. 59 is a partial cross-sectional view of the end effector of FIG. 58 in a released condition.

In various embodiments, referring now to FIGS. 58 and 59, a surgical stapling instrument can comprise, one, a cartridge channel 16670 configured to receive a staple cartridge 16600 and, two, an anvil 16660 pivotably coupled to the cartridge channel 16670. The staple cartridge 16600 can comprise a support portion 16610 and a tissue thickness compensator 16620 wherein a distal end 16625 of the tissue thickness compensator 16620 can be releasably held to the support portion 16610 by a nose 16603 at the distal end 16602 of the staple cartridge 16600. In at least one embodiment, the nose 16603 can comprise a slot 16605 and can be comprised of a flexible material. In use, referring primarily to FIG. 58, the nose 16603 can be flexed downwardly in order to expand the opening of slot 16605. In certain embodiments, the nose 16603 can comprise notches or cut-outs 16606 which can be configured to permit the nose 16603 to flex downwardly. In any event, in various circumstances, the expanded opening of the slot 16605 can facilitate the insertion of the distal end 16625 of the tissue thickness compensator 16620 into the slot 16605. Once the tissue thickness compensator 16620 has been suitably positioned, the nose 16603 can be released and, owing to the resiliency of the material comprising the nose 16603, the nose 16603 can return, or at least substantially return, to its unflexed condition and trap the distal end 16625 of the tissue thickness compensator 16620 against the deck surface 16611, as illustrated in FIG. 59. In use, similar to the above, the distal end 16625 can be pulled out of the slot 16605 when the support portion 16610 is moved away from the stapled tissue. In various circumstances, the flexible nose 16603 can be configured to deflect as the tissue thickness compensator 16620 is detached from the support portion 16610. In various embodiments, referring again to FIG. 59, the tissue thickness compensator 16620 can comprise a top surface 16621 which is aligned, or at least substantially aligned, with a top surface 16604 of the nose 16603.

Figure 60:
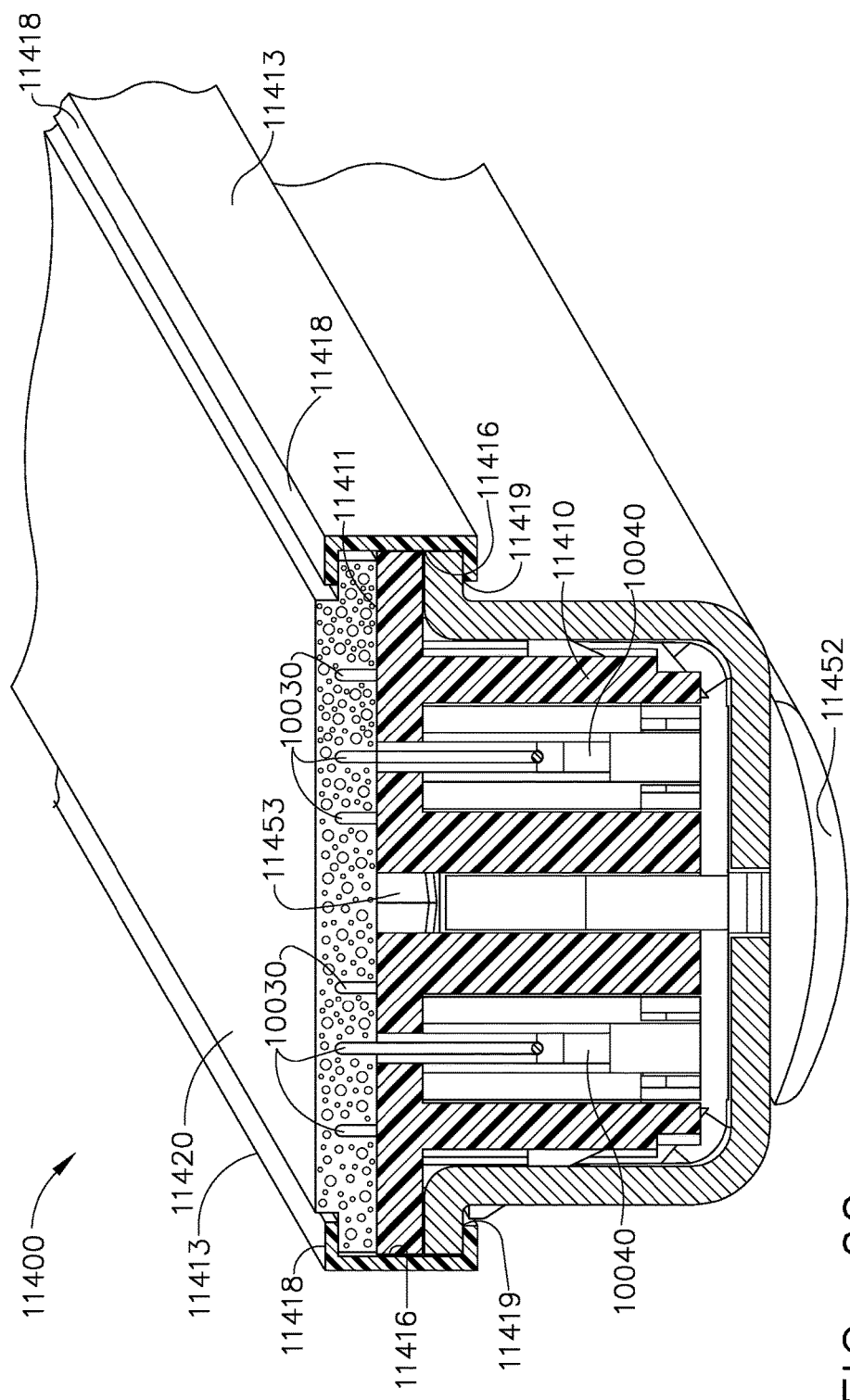
FIG. 60 is a cross-sectional perspective view of a staple cartridge comprising lateral retention members configured to hold a tissue thickness compensator to a support portion.
Figure 61:
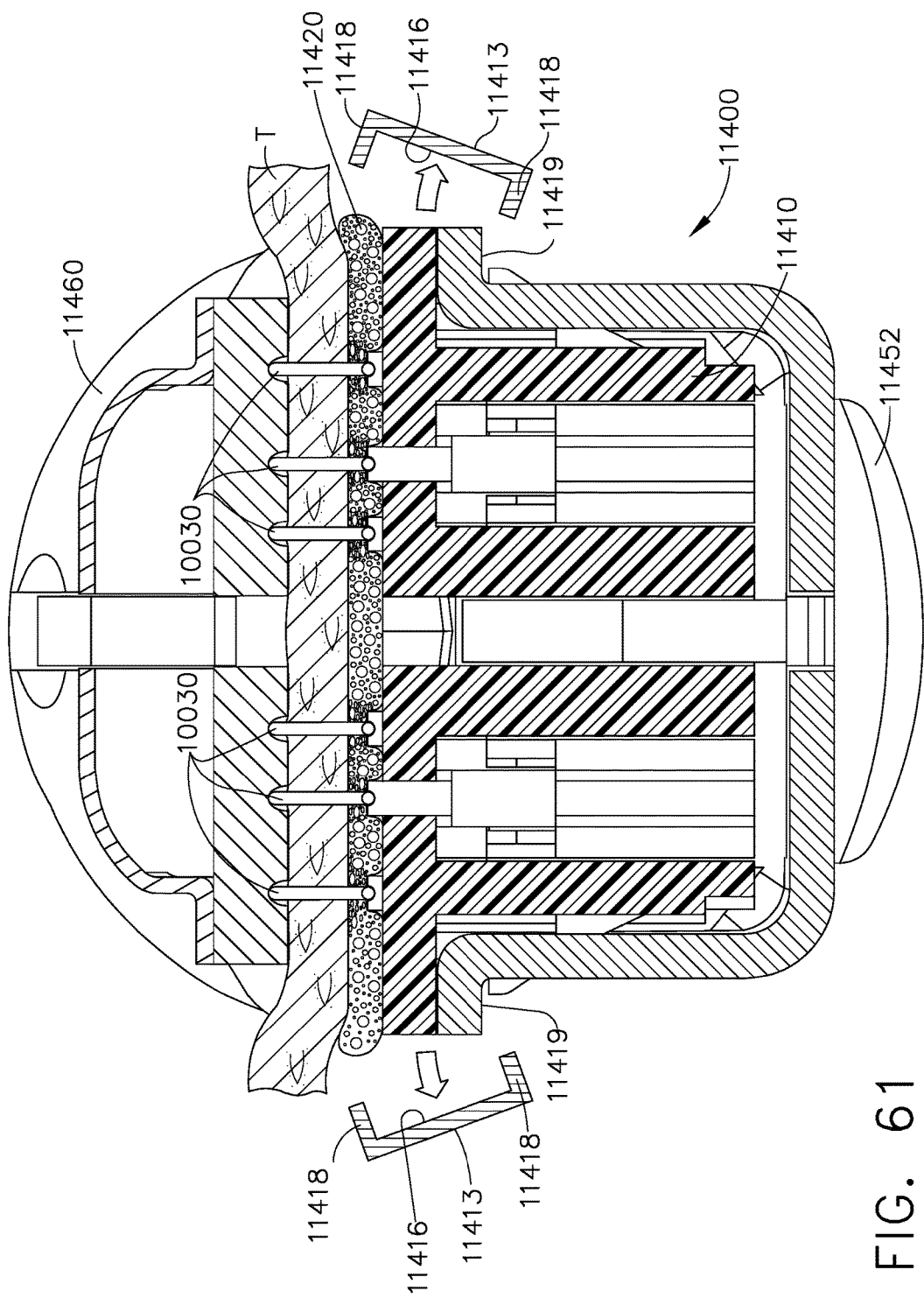
FIG. 61 is a cross-sectional view of the staple cartridge of FIG. 60 being utilized to staple tissue.
Figure 62:
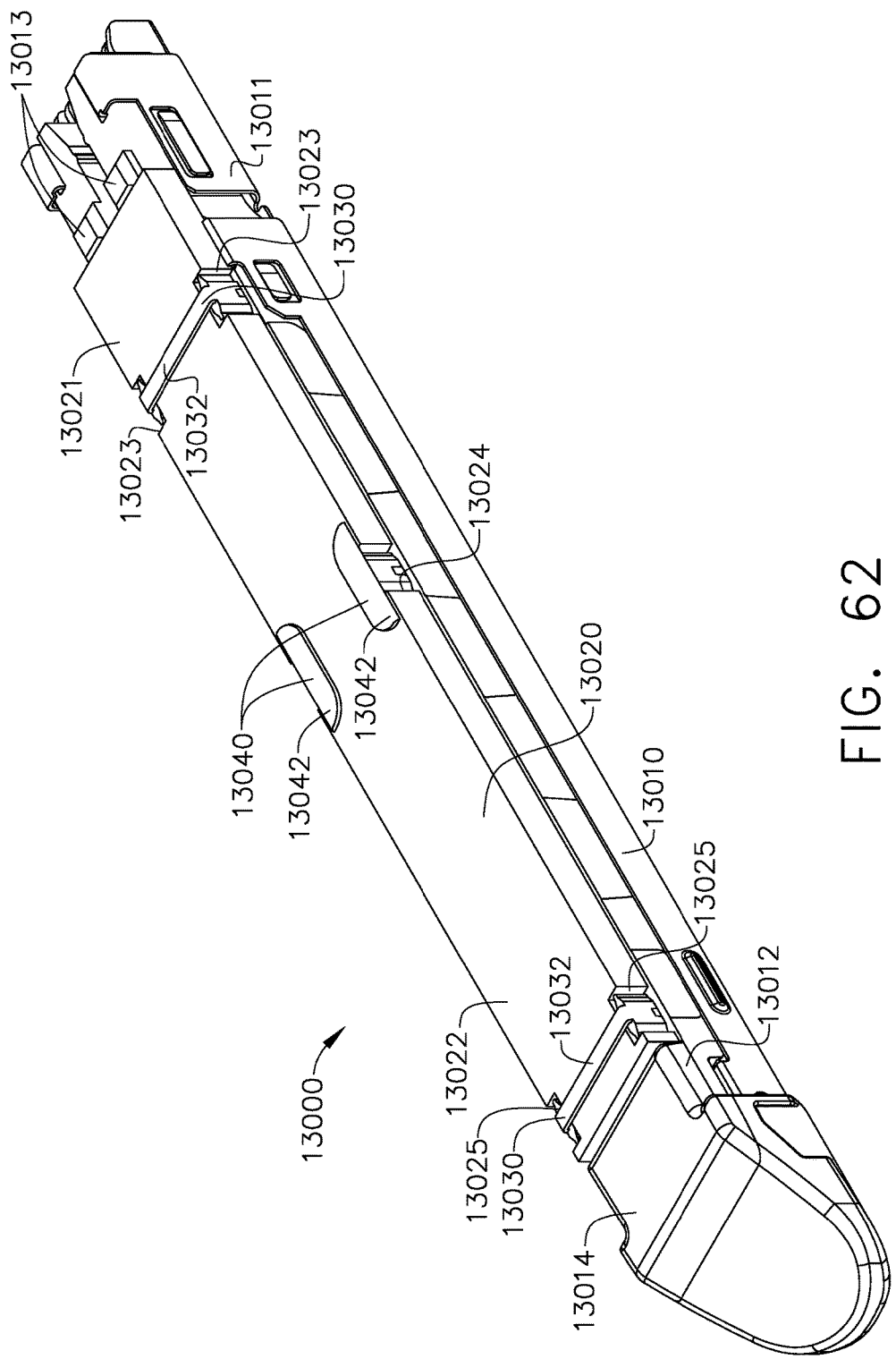
FIG. 62 is a perspective view of a staple cartridge including a cartridge body and a tissue thickness compensator attached to the cartridge body by a plurality of firable attachment members.

In various embodiments, referring now to FIGS. 60-61, a staple cartridge, such as staple cartridge 11400, for example, can comprise a tissue thickness compensator 11420 removably attached to a support portion 11410. In at least one embodiment, the staple cartridge 11400 can comprise one or more retainer bars 11413 which can be configured to hold the longitudinal sides of the tissue thickness compensator 11420 to the deck surface 11411. In at least one such embodiment, each retainer bar 11413 can comprise opposing arms 11418 which can define a channel 11416 therebetween. In such embodiments, one of the arms 11418 can be configured to extend over the tissue thickness compensator 11420 and the other arm 11418 can be configured to extend under a lip 11419 extending from the support portion 11410. Referring primarily to FIG. 60, the channel 11416 of each retainer bar 11413 can be sized and configured to apply a compressive force to the longitudinal sides of the tissue thickness compensator 11420 prior to the staple cartridge 11400 being used. During use, referring primarily to FIG. 61, the staple cartridge 11400 can be positioned within a staple cartridge channel and, once the staple cartridge 11400 has been suitably positioned, an anvil, such as anvil 11460, for example, can be moved into a position in which it can compress the tissue thickness compensator 11420. Similar to the above, the thickness tissue compensator 11420, when compressed, can expand laterally, or outwardly, and, as a result, detach the retainer bars 11413 from the staple cartridge 11400. In certain other embodiments, the closing of the anvil 11460 may not detach, or may not completely detach, the retainer bars 11413 from the staple cartridge. In at least one such embodiment, the advancement of a firing bar, described above, through the staple cartridge 11400 can deploy the staples 10030 from the support portion 11410 and, simultaneously, squeeze the anvil 11460 and the staple cartridge 11400 closer together to apply a compressive force to the tissue thickness compensator 11420 that is sufficient to cause the tissue thickness compensator 11420 to expand laterally and detach the retainer bars 11413 from the staple cartridge 11400. Once the retainer bars 11413 have been detached from the staple cartridge 11400, the support portion 11410 can be moved away from the implanted tissue thickness compensator 11420 and removed from the surgical site.

In various embodiments, further to the above, a staple cartridge can comprise a plurality of fasteners configured to releasably hold a tissue thickness compensator to a support portion of the staple cartridge. In certain embodiments, the support portion can comprise a plurality of apertures defined in the deck surface, for example, wherein the fasteners can extend through the tissue thickness compensator and can be releasably retained in the support portion apertures. In use, the fasteners can be progressively released from the support portion as the staples are progressively ejected from the support portion. In at least one such embodiment, the fasteners can be implanted with the tissue thickness compensator and, in at least one embodiment, the fasteners can be comprised of at least one bioabsorbable material, for example. In certain embodiments, the fasteners can detach from the support portion after the tissue thickness compensator has been at least partially implanted and as the support portion is moved away from the implanted tissue thickness compensator. In various embodiments, referring now to FIGS. 130-131, a staple cartridge, such as staple cartridge 11600, for example, can comprise a tissue thickness compensator 11620 releasably mounted to a support portion 11610 by a plurality of fasteners 11613. Each fastener 11613 can comprise a first end 11618 embedded within and/or otherwise engaged with the tissue thickness compensator 11620, a second end 11618 engaged with the support portion 11610, and a connector 11616 which connects the first end 11618 to the second end 11618. In various embodiments, the fasteners 11613 can extend through a knife slot 11615 defined in the support portion 11610. In use, a firing member 10052 can move a knife edge through the knife slot 11615 in the support portion 11610 and incise the fasteners 11613 in order to release the tissue thickness compensator 11620 from the support portion 11610. In at least one such embodiment, the firing bar 10052 can be advanced from a proximal end of the staple cartridge 11600 to a distal end of the staple cartridge 11600 in order to, one, advance the sled 10050 distally and progressively fire the staples 10030, as discussed above, and, two, progressively incise and/or break the fasteners 11613 to progressively release the tissue thickness compensator 11620 from the support portion 11610. In certain embodiments, similar to the above, the tissue thickness compensator 11620 can comprise a plurality of detachable segments which can each be held to support portion 11610 by one or more fasteners 11613, for example. In the event that the firing member 10052 is stopped intermediate the proximal end and the distal end of the staple cartridge 11600, as illustrated in FIG. 130, the fasteners 11613 can assist in holding the unimplanted portion of the tissue thickness compensator 11620 to the support portion 11610 after the anvil 11660 is opened and the support portion 11610 is moved away from the tissue T, as illustrated in FIG. 131. In various embodiments, further to the above, the cutting edge 10053 of the firing member 10052 can be configured to incise and/or break the fasteners 11613.

In various embodiments, referring now to FIG. 132, a staple cartridge can comprise a tissue thickness compensator, such as tissue thickness compensator 15120, for example, which can comprise a plurality of portions having different thicknesses. In at least one embodiment, the tissue thickness compensator 15120 can comprise a first, or inner, portion 15122a which can have a first thickness, second, or intermediate, portions 15122b extending from the first portion 15122b which can each have a second thickness, and third, or outer, portions 15122c extending from the second portions 15122b which can each have a third thickness. In at least one such embodiment, the third thickness can be thicker than the second thickness and the second thickness can be thicker than the first thickness, for example, although any suitable thicknesses could be utilized in various other embodiments. In various embodiments, the portions 15122a-15122c of the tissue thickness compensator 15120 can comprise steps having different thickness. In at least one embodiment, similar to the above, a staple cartridge can comprise several rows of staples 10030 and a plurality of staple drivers having different heights which can deform the staples 10030 to different formed heights. Also similar to the above, the staple cartridge can comprise first staple drivers 15140a which can drive the staples 10030 supported thereon to a first formed height, second staple drivers 15140b which can drive the staples 10030 supported thereon to a second formed height, and third staple drivers which can drive the staples 10030 supported thereon to a third formed height, wherein the first formed height can be shorter than the second formed height and the second formed height can be shorter than the third formed height, for example. In various embodiments, as illustrated in FIG. 132, each staple 10030 can comprise the same, or substantially the same, unformed, or unfired, height. In certain other embodiments, referring now to FIG. 133, the first drivers 15140a, the second drivers 15140b, and/or the third drivers 15140c can support staples having different unformed heights. In at least one such embodiment, the first staple drivers 15140a can support staples 15130a having a first unformed height, the second staple drivers 15140b can support staples 15130b having a second unformed height, and the third staple drivers 15140c can support staples 15130c having a third unformed height, wherein the first unformed height can be shorter than the second unformed height and the second unformed height can be shorter than the third unformed height, for example. In various embodiments, referring again to FIG. 133, the tips of the staples 15130a, 15130b, and/or 15130c can lie, or at least substantially lie, in the same plane while, in other embodiments, the tips of the staples 15130a, 15130b, and/or 15130c may not lie in same plane.

In certain embodiments, referring now to FIG. 154, a staple cartridge can include a tissue thickness compensator 15220 having a plurality of portions having different thickness which can be implanted against the tissue T by the staples 15130a, 15130b, and 15130c, as described above. In at least one embodiment, referring now to FIG. 155, the staples 15130a, 15130b, and/or 15130c can be deformed to different formed heights wherein the first staples 15130a can be formed to a first formed height, the second staples 15130b can be formed to a second formed height, and the third staples 15130c can be formed to a third formed height, and wherein the first formed height can be shorter than the second formed height and the second formed height can be shorter than the third formed height, for example. Other embodiments are envisioned in which the staples 15130a, 15130b, and 15130c can be formed to any suitable formed heights and/or any relative formed heights.

As discussed above and referring to FIG. 134, a staple cartridge, such as staple cartridge 10000, for example, can comprise a support portion 10010 and a tissue thickness compensator 10020 wherein a plurality of staples 10030 can be at least partially stored in the support portion 10010 and can extend into the tissue thickness compensator 10020 when the staples 10030 are in their unfired position. In various embodiments, the tips of the staples 10030 do not protrude from the tissue thickness compensator 10020 when the staples 10030 are in their unfired positions. As the staples 10030 are moved from their unfired positions to their fired positions by the staple drivers 10040, as discussed above, the tips of the staples 10030 can penetrate through the tissue thickness compensator 10020 and/or penetrate through the upper layer, or skin, 10022. In certain alternative embodiments, the tips of the staples 10030 can protrude through the top surface of the tissue thickness compensator 10020 and/or skin 10022 when the staples 10030 are in their unfired position. In either event, the staples 10030, as they extend upwardly out of the support portion 10010 prior to being deployed, may tilt and/or deflect relative to the support portion, as also discussed above.

In various embodiments, referring now to FIG. 140, a staple cartridge can comprise a tissue thickness compensator 13620 and a skin, or top layer, 13621, for example. In at least one such embodiment, one or more pledgets, or retainers, 13622, for example, can be embedded in the skin 13621. In certain embodiments, each retainer 13622 can comprise one or more apertures 13629 defined therein which can be configured to receive the staple legs 13032 of staples 13030 therein when the staples 13030 are in their unfired position, as illustrated in FIG. 140. In use, further to the above, the staple legs 10032 can slide through the apertures 13629 when the staples 13030 are moved from their unfired position to their fired position until the bases 13031 of the staples 13030 contact the tissue thickness compensator 13620 and compress at least a portion of the tissue thickness compensator 13620 against the bottom surfaces of the pledgets 13622, for example. In various embodiments, referring now to FIG. 135, a staple cartridge can comprise a tissue thickness compensator 13120 and a skin, or top layer, 13122, for example. In at least one such embodiment, the tissue thickness compensator 13120 can comprise conical bumps, projections, and/or protrusions 13128, for example, which can extend upwardly from the top surface 13121 of the tissue thickness compensator 13120. The projections 13128 can be configured to receive and envelop the tips of the staple legs 13032 of the staples 13030 when the staples 13030 are in their unfired position, as illustrated in FIG. 135. The top layer 13122 can also comprise conical bumps, projections, and/or protrusions 13129 which can be aligned, or at least substantially aligned, with the projections 13128. In use, the staple legs 10032 can penetrate the projections 13128 and 13129 and emerge from the tissue thickness compensator 13120. In various embodiments, referring now to FIG. 139, a staple cartridge can comprise a tissue thickness compensator 13520 and a skin, or top layer, 13522, for example. In at least one such embodiment, the skin 13522 can comprise conical bumps, projections, and/or protrusions 13529, for example, which can extend upwardly from the top surface 13521 of the tissue thickness compensator 13520. Similar to the above, the projections 13529 can be configured to receive and envelop the tips of the staple legs 13032 of the staples 13030 when the staples 13030 are in their unfired position, as illustrated in FIG. 139. In use, the staple legs 10032 can penetrate the projections 13529 and emerge from the skin 13522.

In various embodiments, referring now to FIG. 136, a staple cartridge can comprise a tissue thickness compensator 13220 and a skin, or top layer, 13222, for example. In at least one such embodiment, the tissue thickness compensator 13220 can comprise conical dimples and/or recesses 13128, for example, which can extend downwardly into the top surface 13221 of the tissue thickness compensator 13220. In various embodiments, the tips of the staple legs 13032 can extend through the recesses 13128 when the staples 13030 are in their unfired position, as illustrated in FIG. 136. In at least one embodiment, the top layer 13222 can also comprise conical dimples and/or recesses 13229 which can be aligned, or at least substantially aligned, with the recesses 13228. In various embodiments, referring now to FIG. 137, a staple cartridge can comprise a tissue thickness compensator 13320 and a skin, or top layer, 13322, for example. In at least one such embodiment, the skin 13320 can comprise thick portions 13329 which can extend downwardly into the top surface 13321 of the tissue thickness compensator 13320. In various circumstances, the thick portions 13329 can be configured to receive at least a portion of the staple legs 13032 of the staples 13030 therein when the staples 13030 are in their unfired position, as illustrated in FIG. 137. In such embodiments, the thick portions 13329 can hold the staple legs 13032 in position such that the legs 13032 are aligned, or at least substantially aligned, with the staple-forming pockets of an anvil positioned opposite the tissue thickness compensator 13320. In various embodiments, referring now to FIG. 138, a staple cartridge can comprise a tissue thickness compensator 13420 and a skin, or top layer, 13422, for example. In at least one such embodiment, the skin 13422 can comprise thick portions 13429 which can extend upwardly from the top surface 13421 of the tissue thickness compensator 13420. In various circumstances, the thick portions 13429 can be configured to receive at least a portion of the staple legs 13032 of the staples 13030 therein when the staples 13030 are in their unfired position, as illustrated in FIG. 138. In such embodiments, the thick portions 13429 can hold the staple legs 13032 in position such that the legs 13032 are aligned, or at least substantially aligned, with the staple-forming pockets of an anvil positioned opposite the tissue thickness compensator 13420.

In various embodiments, referring now to FIGS. 141 and 142, a staple cartridge can comprise a tissue thickness compensator 13720 and a skin, or top layer, 13721, for example. In at least one such embodiment, the tissue thickness compensator 13720 can comprise pyramidal and/or stepped bumps, projections, and/or protrusions 13728, for example, which can extend upwardly from the top surface 13721 of the tissue thickness compensator 13720. The projections 13728 can be configured to receive and envelop the tips of the staple legs 13032 of the staples 13030 when the staples 13030 are in their unfired position, as illustrated in FIG. 142. Similarly, the top layer 13721 can comprise pyramidal and/or stepped bumps, projections, and/or protrusions 13729 which can be aligned, or at least substantially aligned, with the projections 13728. In various embodiments, the skin 13721 can further comprise one or more teeth 13727 extending upwardly from the projections 13729 which can be configured to engage tissue positioned against the top layer 13721 and prevent, or at least limit, relative lateral and/or longitudinal movement between the tissue, the top layer 13721, and/or the tips of the staple legs 13032. In use, the staple legs 13032 can penetrate the projections 13728 and 13729 and emerge from the tissue thickness compensator 13720 when the staples 13030 are moved from their unfired positions to their fired positions. In various embodiments, referring now to FIGS. 143 and 144, a staple cartridge can comprise a tissue thickness compensator 13820 and a skin, or top layer, 13821, for example. In at least one such embodiment, the tissue thickness compensator 13820 can comprise pyramidal and/or stepped bumps, projections, and/or protrusions 13828, for example, which can extend upwardly from the top surface 13821 of the tissue thickness compensator 13820. The projections 13828 can be configured to receive and envelop the tips of the staple legs 13032 of the staples 13030 when the staples 13030 are in their unfired position, as illustrated in FIG. 144. Similarly, the top layer 13821 can comprise pyramidal and/or stepped bumps, projections, and/or protrusions 13829 which can be aligned, or at least substantially aligned, with the projections 13828. In various embodiments, the top layer 13821 can further comprise one or more teeth 13827 extending downwardly into the tissue thickness compensator 13820 which can be configured to prevent, or at least limit, relative lateral and/or longitudinal movement between the top layer 13821 and the tissue thickness compensator 13820, for example. In use, the staple legs 10032 can penetrate the projections 13828 and 13829 and emerge from the tissue thickness compensator 13820 when the staples 13030 are moved from their unfired positions and their fired positions.

In various embodiments, referring now to FIG. 145, a staple cartridge can comprise a tissue thickness compensator, such as tissue thickness compensator 13920, for example, which can include ridges 13923 and valleys 13924 defined therein wherein, in at least one embodiment, the valleys 13924 can be defined between the ridges 13923. In various embodiments, each ridge 13923 can comprise the same height, substantially the same height, or different heights. Similarly, each valley 13924 can comprise the same depth, substantially the same depth, or different depths. In various embodiments, a plurality of staples 13030 can be at least partially stored within the tissue thickness compensator 13920 such that the tips of the staples 13030 can be positioned within the ridges 13923. In at least one such embodiment, the staple legs 13032 of the staples 13030 may not protrude from the tissue thickness compensator 13920 and/or a skin, or top layer, 13921 attached to the tissue thickness compensator 13920, for example, when the staples 13030 are stored in their unfired position. In various embodiments, the ridges 13923 and/or the valleys 13924 can extend laterally across the staple cartridge. In at least one such embodiment, the staple cartridge can comprise a longitudinal knife slot wherein the ridges 13923 and the valleys 13924 can extend in a direction which is transverse and/or perpendicular to the knife slot. In various circumstances, the ridges 13923 can be configured to hold the tips of the staple legs 13032 in position until the staples 13030 are moved from their unfired position into their fired position. In various embodiments, referring now to FIG. 146, a tissue thickness compensator, and/or a skin covering a tissue thickness compensator, can comprise longitudinal ridges and/or valleys. In at least one such embodiment, a tissue thickness compensator can comprise a top surface defined by ridges 14023 and valleys 14024, wherein the valleys 14024 can be defined between the ridges 14023, for example. In various embodiments, the tissue thickness compensator can comprise a skin 14021 which can include a plurality of apertures 14029 defined therein which can each be configured to receive a staple leg 13032. In certain embodiments, the apertures 14029 can be defined in the ridges 14023 wherein the tips of the staple legs 13032 may be positioned below the peaks 14028 of the ridges 14029, positioned flush with the peaks 14028, and/or positioned above the peaks 14028. In certain embodiments, in addition to or in lieu of the above, the apertures 14029 can be defined in the valleys 14024, for example. In certain embodiments, each aperture can be surrounded, or at least partially surrounded, by an embossment, for example, which can strengthen the skin and/or tissue thickness compensator surrounding the apertures. In any event, further to the above, the skin 14021 can be attached to a tissue thickness compensator in any suitable manner, including using at least one adhesive, for example.

In various embodiments, referring now to FIG. 148, a disposable loading unit 15900, for example, can comprise an anvil 15960 and a staple cartridge channel 15970 wherein the staple cartridge channel 15970 can rotate relative to the anvil 15960. In at least one such embodiment, the anvil 15960 may not be able to rotate. In certain embodiments, tissue can be positioned between the anvil 15960 and the staple cartridge channel 15970 and, thereafter, the staple cartridge channel 15970 can be rotated toward the tissue to clamp the tissue against the anvil. In at least one such embodiment, the disposable loading unit 15900 can further comprise a tissue thickness compensator 15920 which can be configured to contact the tissue.

In various embodiments, referring now to FIGS. 149-151, a disposable loading unit 12900 can comprise a loading assembly including a bottom portion 12922 which can be removably attached to the support portion 12610, a top portion 12990 which can be removably attached to the anvil 12560, and a flexible joint 12991 connecting the bottom portion 12922 and the top portion 12990. Similar to the above, a longitudinal retention rail 12825 can extend downwardly from the bottom portion 12922 and into the knife slot 12615 defined in the support portion 12610 such that the bottom portion 12922 can be releasably retained to the support portion 12610. Similarly, a longitudinal retention rail 12995 can extend upwardly from the top portion 12990 into a knife slot defined in the anvil 12560 such that the top portion 12990 can be releasably retained to the anvil 12560.

As illustrated in FIGS. 150 and 151, a tissue thickness compensator 12620 can be mounted to the bottom portion 12922 of the loading assembly wherein, in order to position the tissue thickness compensator 12620 relative to the support portion 12610, a clinician could flex the top portion 12990 and the bottom portion 12922 toward one another, position the loading assembly between the anvil 12560 and the support portion 12610, and release the flexed loading assembly such that it can resiliently expand and bias the top portion 12990 against the anvil 12560 and the bottom portion 12922 against the support portion 12610.

In various embodiments, referring now to FIG. 152, a staple cartridge, such as staple cartridge 14900, for example, can comprise a support portion 14910 and, in addition, a tissue thickness compensator 14920 positioned against the support portion 14910. Similar to the above, the support portion 14910 can comprise staple drivers which can be lifted upwardly by a staple-deploying sled in order to lift staples, such as staples 10030, for example, at least partially positioned within the support portion 14910 toward an anvil, such as anvil 10060, for example, positioned opposite the staple cartridge 14900. In certain embodiments, the support portion 14910 can comprise six rows of staple cavities, such as two outer rows of staple cavities, two inner rows of staple cavities, and two intermediate rows of staple cavities positioned intermediate the inner rows and the outer rows, for example, wherein the anvil 10060 can comprise six rows of forming pockets 10062 aligned, or at least substantially aligned, with the staple cavities. In various embodiments, the inner rows of staple cavities can include staple drivers 14940a positioned therein, the intermediate rows of staple cavities can include staple drivers 14940b positioned therein, and the outer rows of staple cavities can include staple drivers 14940c positioned therein, wherein each of the staple drivers 14940a can include a cradle 14949a configured to support a staple 10030, wherein each of the staple drivers 14940b can include a cradle 14949b configured to support a staple 10030, and wherein each of the staple drivers 14940c can include a cradle 14949c configured to support a staple 10030. In their unfired positions, i.e., when the staple drivers 14940a-14940c are sitting on driver supports 14926 which extend underneath the support portion 14910, the cradles 14949a of the staple drivers 14940a can be positioned closer to the anvil 10060 than the cradles 14949b of the staple drivers 14940b and the cradles 14949c of the staple drivers 14940c. In such a position, a first forming distance can be defined between the cradles 14949a and the forming pockets 10062 positioned over the cradles 14949a, a second forming distance can be defined between the cradles 14949b and the forming pockets 10062 positioned over the cradles 14949b, and a third forming distance can be defined between the cradles 14949c and the forming pockets 10062 positioned over the cradles 14949c, wherein, in various embodiments, the first forming distance can be shorter than the second forming distance and the second forming distance can be shorter than the third forming distance, for example. When the staple drivers 14940a-14940c are moved from their unfired positions (FIG. 152) to their fired positions, each staple driver 14940a-14940c can be moved upwardly an equal, or an at least substantially equal, distance toward the anvil 10060 by the staple-deploying sled such that the first drivers 14940a drive their respective staples 10030 to a first formed height, the second drivers 14940b drive their respective staples 10030 to a second formed height, and the third drivers 14940c drive their respective staples 10030 to a third formed height, wherein the first formed height can be shorter than the second formed height and the second formed height can be shorter than the third formed height, for example. Various other embodiments are envisioned in which the first staple drivers 14940*a* are displaced upwardly a first distance, the second staple drivers 14940*b* are displaced upwardly a second distance, and the third staple drivers 14940*c* are displaced upwardly a third distance, wherein one or more of the first distance, the second distance, and the third distance can be different.

In various embodiments, referring again to FIG. 152, the deck surface 14911 of the support portion 14910 can vary in height with respect to the tissue-contacting surface 10061 of the anvil 10060. In certain embodiments, this height variation can occur laterally and, in at least one embodiment, the height of the deck surface 14911 surrounding the inner rows of staple cavities can be higher than the deck surface 14911 surrounding the outer rows of staple cavities, for example. In various embodiments, the bottom surface 14922 of the tissue thickness compensator 14920 can be configured to parallel, or at least substantially parallel, the deck surface 14911 of the support portion 14910. Further to the above, the tissue thickness compensator 14920 can also vary in thickness wherein, in at least one embodiment, the top, or tissue-contacting, surface 14921 of the tissue thickness compensator 14920 can slope inwardly from the outside or lateral edges thereof. In at least one such embodiment, as a result of the above, the tissue thickness compensator 14920 can be thinner in a region positioned over the inner rows of staple cavities and thicker in a region positioned over the outer rows of staple cavities, for example. In various embodiments, referring now to FIG. 153, the deck surface of a support portion 15010 can comprise a stepped deck surface, for example, wherein the highest steps of the stepped surface can surround the inner rows of staple cavities and the lowest steps of the stepped surface can surround the outer rows of staple cavities, for example. In at least one such embodiment, steps having an intermediate height can surround the intermediate rows of staple cavities. In certain embodiments, a tissue thickness compensator, such as tissue thickness compensator 15020, for example, can comprise a bottom surface which can parallel and abut the deck surface of the support portion 15010. In at least one embodiment, the top, or tissue-contacting, surface 15021 of the tissue thickness compensator can comprise an arcuate, parabolic, and/or curved surface, for example, which, in at least one such embodiment, can extend from a first lateral side of the tissue thickness compensator 15020 to a second lateral side of the tissue thickness compensator 15020 with an apex aligned, or at least substantially aligned, with the center of the staple cartridge 15000, for example.

In various embodiments, further to the above, a staple-firing sled 10050 of a staple cartridge 10000 can be moved from a proximal end of the staple cartridge 10000 toward a distal end 10002 of the staple cartridge, as illustrated in FIGS. 161 and 162, by a firing member, illustrated elsewhere. As the sled 10050 is advanced, the sled 10050 can contact the staple drivers 10040 and lift the staple drivers 10040 upwardly within the staple cavities 10012 defined in a cartridge body 10010 of the staple cartridge 10000. In at least one embodiment, the sled 10050 and the staple drivers 10040 can each comprise one or more ramps, or inclined surfaces, which can co-operate to move the staple drivers 10040, and the staples supported thereon, upwardly from their unfired positions. The staple cartridge 10000 can further comprise a pan 10027, for example, which can at least partially surround the bottom of the cartridge body 10010 and at least partially contain the staple drivers 10040 within the cartridge body 10010. The cartridge body 10010 can further comprise a longitudinal slot 10016 defined therein which can be configured to at least partially receive the firing member as it passes through the staple cartridge 10000.

Figure 18:
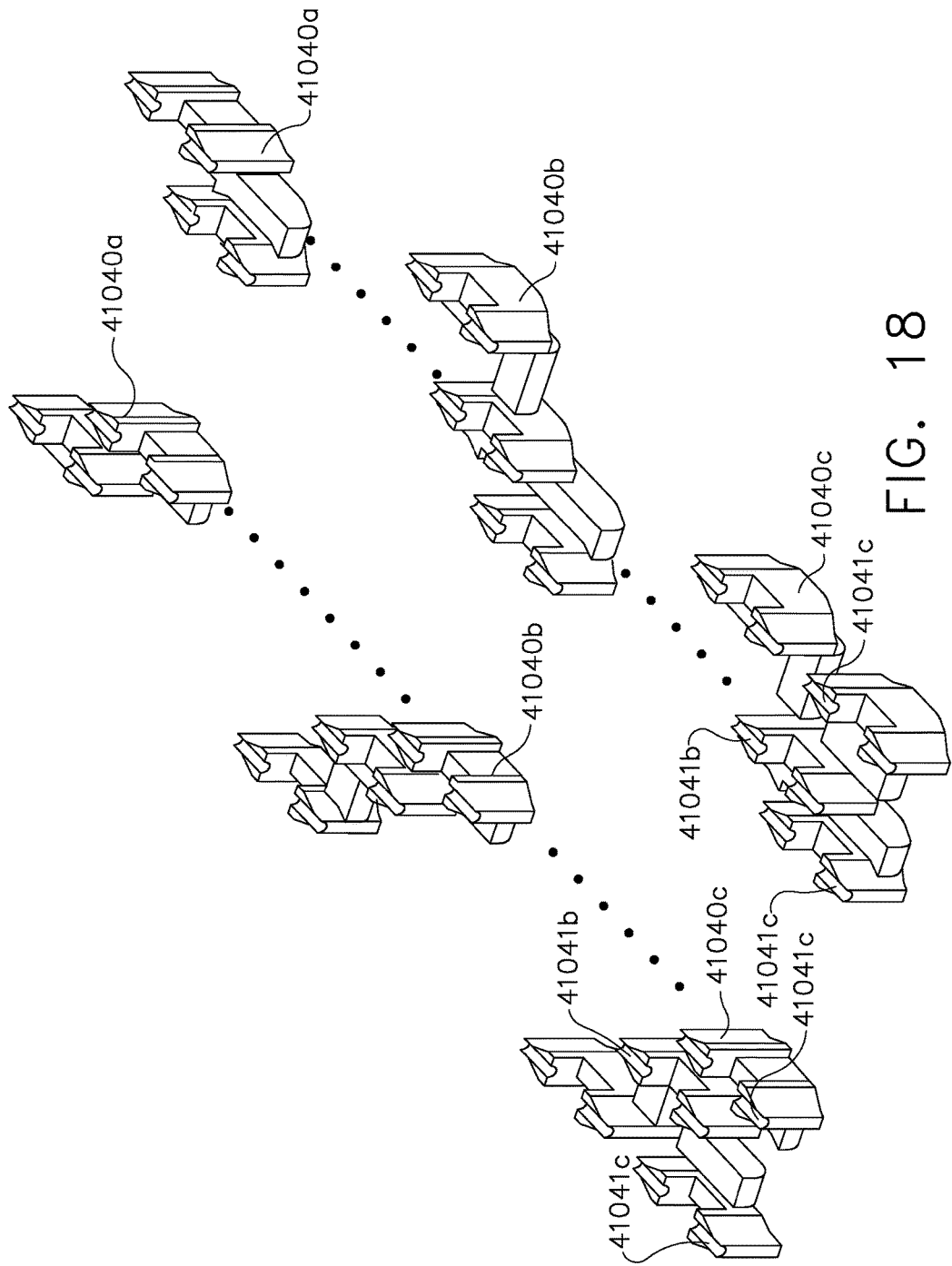
FIG. 18 is a perspective view of a plurality of staple drivers positionable within a cartridge body of a staple cartridge.

Turning now to FIG. 163, the staples contained within the staple cartridge body 10010 can be fired sequentially between a proximal end 10001 and a distal end 10002 of the staple cartridge 10000. In various embodiments, the staple cartridge 10000 can comprise staple drivers 10040*a*, 10040*b*, and 10040*c*, for example, which can fire the staples in a predetermined manner. For instance, the staple cartridge 10000 can comprise a proximal driver 10040*c* positioned on a first side of the longitudinal slot 10016 and a second proximal driver 10040*c* positioned on a second, or opposite, side of the slot 10016. Each driver 10040*c* can be configured to fire two staples, i.e., the two proximal-most staples, simultaneously. Such staples are positioned in the staple cavities designated 10012*c*. In fact, of the two staple cavities designated 10012*c* on each side of the slot 10016, such staple cavities 10012*c* can comprise a distal staple cavity designated 10013*c* and a proximal staple cavity 10014*c*. The reader will appreciate that the staple cavity 10013*c* is positioned in a different staple row than the staple cavity 10014*c*. In fact, the staple cavities 10013*c* and 10014*c* may be located in the two innermost rows of staples with the third, outermost, staple row not having a staple which is fired by a driver 10040*c*. Furthermore, the staple cartridge 10000 can comprise an intermediate driver 10040*b* positioned on a first side of the longitudinal slot 10016 and a second intermediate driver 10040*b* positioned on a second, or opposite, side of the slot 10016. Each driver 10040*b* can be configured to fire three staples simultaneously. Such staples are positioned in the staple cavities designated 10012*b*. In fact, of the three staple cavities designated 10012*b* on each side of the slot 10016, such staple cavities 10012*b* can comprise a distal staple cavity designated 10013*b*, an intermediate staple cavity 10014*b*, and a distal staple cavity 10015*b*. The reader will also appreciate that the staple cavities 10013*b*, 10014*b*, and 10015*b* are all positioned in different staple rows. In addition, the staple cartridge 10000 can comprise a distal driver 10040*a* positioned on a first side of the longitudinal slot 10015 and a second distal driver 10040*a* positioned on a second, or opposite, side of the slot 10015. Each driver 10040*a* can be configured to fire four staples simultaneously. Such staples are positioned in the staple cavities designated 10012*a*. In fact, of the four staple cavities designated 10012*a* on each side of the slot 10016, such staple cavities 10012*a* can comprise two distal staple cavities designated 10013*a*, an intermediate staple cavity 10014*a*, and a distal staple cavity 10015*a*. The reader will also appreciate that the staple cavities 10013*a*, 10014*a*, and 10015*a* are all positioned in an array extending across all three staple rows on a side of the longitudinal slot 10016. In fact, the distal-most staples positioned within the distal-most cavities 10013*a* within the cartridge body 10010 are positioned in the inner and outer staple rows and extend distally with respect to the distal-most staple cavity 10014*a* in the intermediate row positioned between the inner row and outer row of staple cavities. While only a few staple drivers 10040*a*, 10040*b*, and 10040*c* are discussed above, the staple cartridge 10000 can comprise any suitable number of staple drivers to eject the staples from the staple cavities. Such staple drivers can eject two, three, four, and/or more staples simultaneously. With particular reference to FIG. 18, a staple cartridge can comprise one or more staple drivers 41040*a*, for example, configured to support two staples thereon, one or more drivers 41040b, for example, configured to support three staples thereon, and/or one or more staple drivers 41040c configured to support four staples thereon. In various embodiments, the last, or distal-most, drivers contained within a cartridge can comprise drivers 41040c which can include two distal support cradles 41041c which can hold the last staples in a staple line. For instance, the drivers 41040a-c support staples in six staple lines and drivers 41040c support the last staples in four of those lines. Such staples can be aligned, or at least substantially aligned, along an axis which is perpendicular to a cut path which extends along a longitudinal axis. Such staples, owing to their arrangement, can provide various hemostatic advantages. The last staples in the other two staple lines can be supported by cradles 41041b.

In various embodiments, a staple cartridge for a surgical stapler can include a layer, such as a tissue thickness compensator and/or a buttress material, for example, arranged on a staple deck of a staple cartridge. In use, the layer and patient tissue can be captured by staples when the staples are fired. Then, the layer can be separated from the surgical stapler and can remain in the patient when the stapler is removed from the patient. In certain embodiments, a distal end of the layer can be attached to the staple cartridge to stabilize the layer relative to the staple cartridge while the staple cartridge and the layer are being positioned relative to patient tissue.

In certain embodiments in which a distal end of the layer is attached to the staple cartridge, the staple cartridge can include a distally-arranged cutting blade that cuts the layer free from the distal end that is attached to the staple cartridge. FIGS. 81A-83 illustrate a staple cartridge assembly 2300 that includes a staple cartridge 2330 and a distal cutting blade 2324 arranged in a distal cavity 2332 of the staple cartridge 2330. As described in greater detail below, the distal cutting blade 2324 can be moved from an undeployed position within the distal cavity 2332 to a deployed positioned in which the cutting blade 2324 extends out of the distal cavity 2332 to sever a distal end portion 2316 of a layer 2306 arranged on the staple cartridge.

Referring to FIGS. 82 and 83, in various embodiments, the distal portion 2316 of the layer 2306 can be attached to the staple cartridge 2300 by being captured between the staple cartridge 2300 and a panel 2310 extending proximally from a nose 2308 of the staple cartridge assembly 2300. In certain embodiments, the layer 2306 can be captured by being compressed between the staple cartridge 2330 and the panel 2310. Put differently, a gap between the staple cartridge 2330 and the panel 2310 can be smaller than a thickness of the distal portion 2316 of the layer 2306 positioned in the gap so that the distal portion 2316 is compressed between the staple cartridge 2330 and the panel 2310. In certain embodiments, referring to FIGS. 82 and 83, the distal portion 2316 of the layer 2306 can include one or more apertures 2320. One or more pegs 2318 can extend from the panel 2308 and pass through the apertures 2320 to capture the distal portion 2316 of the layer 2306. In certain embodiments, the distal portion 2316 of the layer 2306 can be attached to the staple cartridge 2330 by adhesives, welding, and/or heat staking, for example.

The distal cutting blade 2324 that severs the distal portion 2316 of the layer 2306 from the remainder of the layer 2306 can be arranged in a distal cavity 2332 of the staple cartridge 2330. The distal cavity 2332 and the distal cutting blade 2324 can be positioned such that the distal cutting blade 2324 can sever the distal portion 2316 of the layer 2306 at a proximal location relative to a location where the distal portion 2316 is attached to the staple cartridge 2330. For example, referring to FIGS. 82 and 83, the distal cutting blade 2324 can sever the distal portion 2316 of the layer 2306 at a proximal location relative to the pegs 2318 and apertures 2320 that attach the distal portion 2316 to the staple cartridge 2330. As a result, when the distal cutting blade 2324 severs the distal portion 2316 of the layer 2306, the remainder of the layer 2306 can be released from the staple cartridge.

The distal cutting blade 2324 can include a cam 2322 that can push the distal cutting blade 2324 out of the distal cavity 2332. The cam 2322 can engage rails and/or channels 2334 in the distal cavity 2332 that can constrain the movement of the cam 2322 and the distal cutting blade 2324 to a particular direction as the blade 2324 extends out of the distal cavity 2332. The rails and/or channels 2334 are illustrated in FIGS. 82 and 83 as being perpendicular to the staple deck 2302 of the staple cartridge 2330. In such an arrangement, when moved from an undeployed position (shown in FIG. 82) to a deployed position (shown in FIG. 83), the distal cutting blade 2324 can extend from the distal cavity 2332 in a direction that is perpendicular to the staple deck 2302 of the staple cartridge 2330. In various embodiments, the rails and/or channels 2334 can be arranged at any suitable angle relative to the staple deck 2302 of the staple cartridge 2330. For example, the rails or channels 2334 can be arranged at a 30° angle relative to the staple deck 2302 of the staple cartridge 2330 such that the distal cutting blade 2324 extends out of the distal cavity 2322 partially in a distal direction that is 30° from perpendicular relative to the staple deck 2302 of the staple cartridge 2330.

To deploy the distal cutting blade, the cam 2322 can be pushed by a firing member 2326. The firing member 2326 can be arranged in a slot in the staple cartridge 2330, such as the knife slot 2304, for example. The firing member 2326 can include cam surfaces 2328 and 2329 that can engage the cam 2322 to displace the cam 2322 and the distal cutting blade 2324 towards the layer 2306. The firing member 2326 can move distally relative to the cam 2322 and the distal cutting blade 2324 from an unactuated position to an actuated position to deploy the cutting blade 2324 and sever the distal portion 2316 of the layer 2306. FIG. 82 illustrates the firing member 2326 in an unactuated position in which the cam surfaces 2328 and 2329 have not engaged the cam 2322. In various embodiments, one or both of the surfaces 2328 and 2329 of the firing member 2326 can be in contact the cam in an unactuated position so long as the distal cutting blade 2324 is not pushed out of the distal cavity 2332. As the firing member 2326 moves distally to an actuated position illustrated in FIG. 83, the cam surfaces 2328 of the firing member 2326 engage the cam 2322 to progressively push the cam 2322 and the distal cutting blade 2324 to a deployed position such that the distal cutting blade severs the distal portion 2316 of the layer 2306.

As described above, the cam 2322 can engage rails and/or channels 2334 in the distal cavity 2332. Furthermore, the rails and/or channels 2334 can be arranged at an angle relative to the staple deck 2302 of the staple cartridge 2330. In various embodiments, the rails and/or channels 2334 can be arranged at an angle such that the cam 2322 and the distal cutting blade 2324 move distally as the blade 2324 deploys from the distal cavity. In various circumstances, arranging the rails at such an angle can reduce the amount of force required to actuate the firing member 2326 by aligning a component of the movement of the cam 2322 and the blade 2324 along a longitudinal axis along which the firing member 2326 moves. Arranging the rails at such an angle can also reduce the likelihood of binding between the cam 2322 and the firing member 2326 and/or between the cam 2322 and the rails and/or channels 2324 in the distal cavity 2332.

In various embodiments, the firing member 2326 can be moved distally from an unactuated position to an actuated position by the cutting blade 2312 and/or a staple driver 2340. In various embodiments, the firing member 2326 can be integral with the tissue-cutting blade 2312 and/or the staple driver 2340 such that the firing member 2326 travels through the staple cartridge 2330 and along a longitudinal axis of the staple cartridge 2330 with the tissue cutting blade 2312 and/or the staple driver 2340. In various other embodiments, the firing member 2326 can be separate from the tissue-cutting blade 2312 and/or the staple driver 2340. In such embodiments, the tissue-cutting blade 2312 and/or the staple driver 2340 can push the firing member 2326 through the staple cartridge 2330. Alternatively, in such embodiments in which the firing member 2326 is separate from the tissue-cutting blade 2312 and/or the staple driver 2340, the firing member 2326 can be positioned at a distal end of the staple cartridge 2330 in an unactuated position, as illustrated in FIG. 82. The cutting blade 2312 and/or the staple driver 2340 can travel through the staple cartridge 2330 and then push the firing member 2326 into the actuated position illustrated in FIG. 83 as the cutting blade 2312 and/or the staple driver 2340 reach the distal end of the staple cartridge 2330. In all of these embodiments, motion of the tissue-cutting blade 2312 and/or the staple driver 2340 in a direction along a longitudinal axis of the staple cartridge 2330 can cause the distal cutting blade 2324 to deploy in a direction different from the tissue-cutting blade and/or the staple driver 2340.

In various embodiments, the distal cutting blade 2324 is not deployed to sever the distal portion 2316 of the layer 2306 until the firing stroke of the tissue cutting blade 2312 and/or the staple driver 2340 have been completed or are almost completed. In such embodiments, the distal portion 2316 of the layer 2306 can remain attached to the staple cartridge 2330, thereby stabilizing the layer 2306 relative to the staple cartridge 2330, until most or all of the staples have been fired by the staple driver 2340 and/or until patient tissue and the layer 2306 have been severed by the tissue cutting blade 2312. In various other embodiments, the distal cutting blade 2324 can be deployed to sever the distal portion 2316 of the layer 2306 before the tissue cutting blade 2312 and/or the staple driver 2340 have begun their firing stroke. For example, the firing member 2326 can be moved from the unactuated position illustrated in FIG. 82 to the actuated position illustrated in FIG. 83 by a first actuation of a firing trigger of a surgical stapler. A subsequent actuation of the firing trigger can move the tissue cutting blade 2312 and/or the staple driver 2340. As a result, the distal portion 2316 of the layer 2306 can be detached from the staple cartridge 2330 before the tissue cutting blade 2312 severs patient tissue and/or before the staples capture the layer 2306 and patient tissue. As another example, the firing member 2326 can be actuated by a first trigger of the surgical instrument and the tissue-cutting blade 2312 and/or the staple driver 2340 can be actuated by a second trigger.

As described above, the nose 2308 of the staple cartridge assembly 2300 can include a panel 2310 that extends proximally from the nose 2308 and that at least partially covers the distal portion 2316 of the layer 2306. The panel 2310 can include an inward-facing surface 2309 that can face the distal portion 2316 of the layer 2306. In certain embodiments, the inward-facing surface 2309 of the panel 2310 can support the distal portion 2316 of the layer 2306 as the distal cutting blade 2324 severs the distal portion 2316. In various circumstances, when the distal cutting blade 2324 is deployed, the distal cutting blade 2324 can eventually make contact with the inward-facing surface 2309, thereby completely severing the distal portion 2316 of the layer 2306 from the remainder of the layer 2306.

The panel 2310 can also protect patient tissue from the distal cutting blade 2324. In various circumstances, unaffected patient tissue that is not severed by the tissue cutting blade 2312 and/or stapled by staples from the staple cartridge 2330 can pass over an outward-facing surface 2311 of the panel 2310. In such circumstances, the panel 2310 can shield the unaffected tissue from the distal cutting blade 2324. For example, as illustrated in FIG. 83, the panel 2310 can be positioned between the distal cutting blade 2324 extending out of the distal cavity 2332 and patient tissue proximate to the outward-facing surface 2311 of the panel 2310, such that the patient tissue is not exposed to the distal cutting blade 2324.

Figure 77:
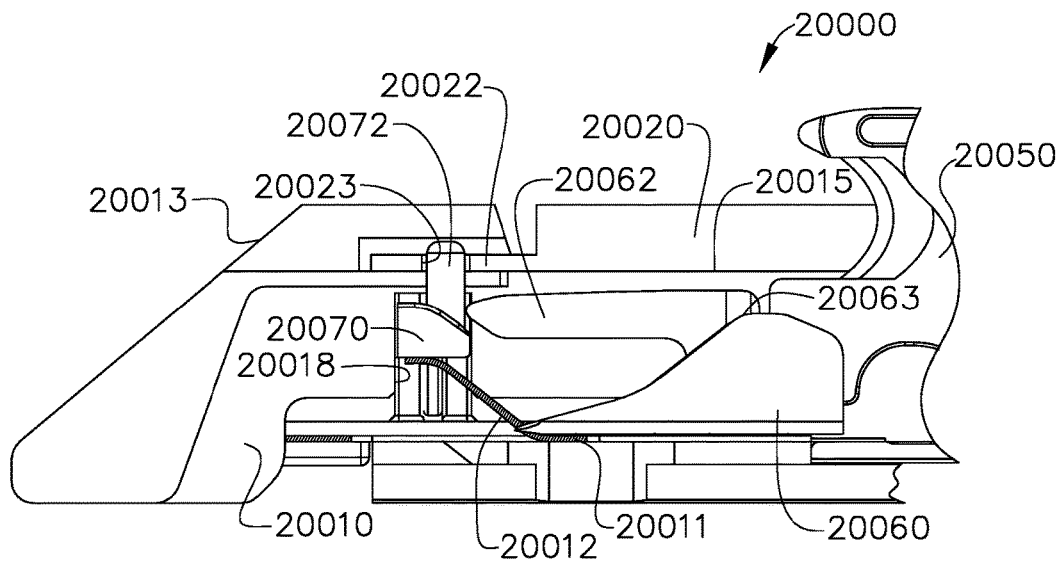
FIG. 77 is a partial cross-sectional view of a staple cartridge including a retention pin configured to releasably hold a tissue thickness compensator to a cartridge body of the staple cartridge.
Figure 77A:
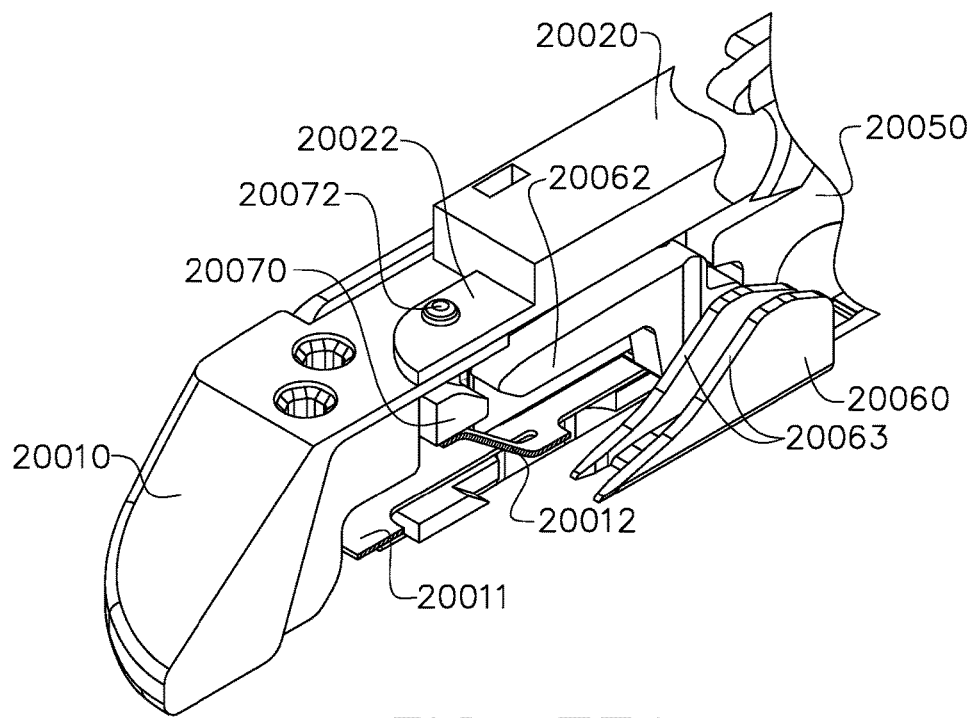
FIG. 77A is a partial cross-sectional perspective view of the staple cartridge of FIG. 77 with portions thereof removed for the purposes of illustration.
Figure 78:
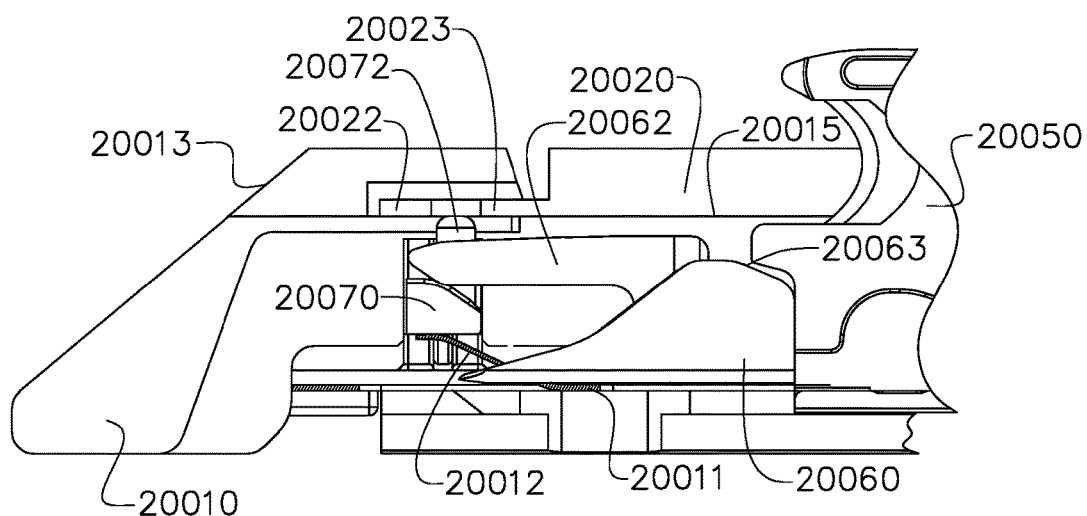
FIG. 78 is a partial cross-sectional view of the staple cartridge of FIG. 77 illustrating the retention pin in a defeated condition.
Figure 79:
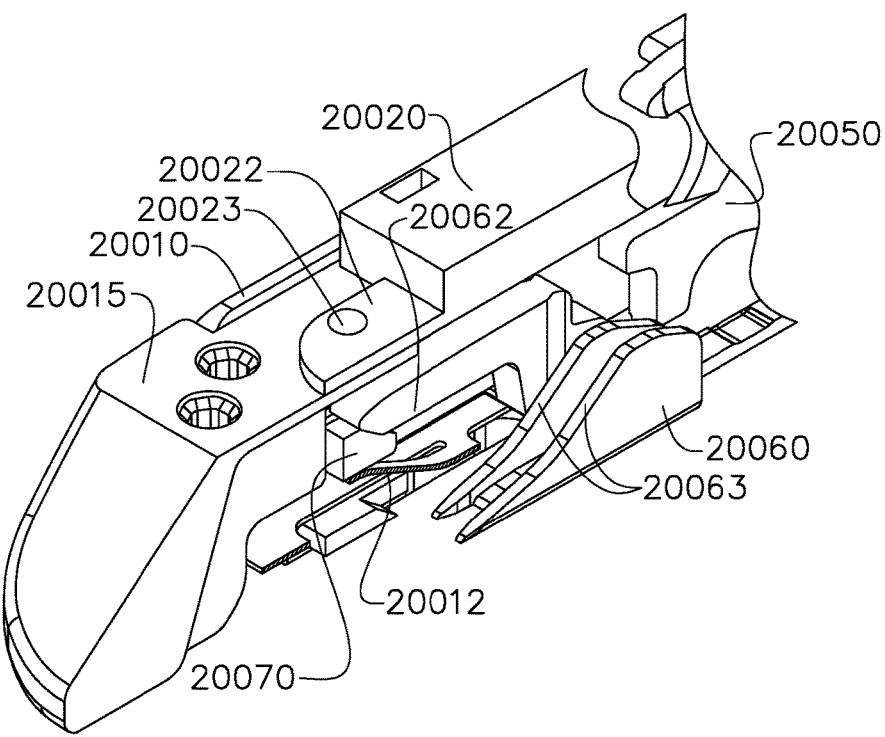
FIG. 79 is a partial cross-sectional perspective view of the staple cartridge of FIG. 77 also illustrating the retention pin in a defeated condition.

Referring now to FIGS. 77-79, a staple cartridge 20000 can comprise a cartridge body 20010 and a tissue thickness compensator 20020 releasably attached thereto. The staple cartridge 20000 can comprise any suitable arrangement of staples, staple cavities, and/or staple drivers which are fired by a sled, or firing member, passing distally through the staple cartridge 20000 to capture at least a portion of the tissue thickness compensator 20020 and at least a portion of the patient tissue within the staples, as described elsewhere herein. Such discussion of the staples, staple cavities, and staple drivers is not repeated here for the sake of brevity to the reader. Referring primarily now to FIGS. 77 and 77A, the staple cartridge 20000 can include a sled 20060 which is advanced distally by a firing member 20050. At a certain point during the distal progression of the firing member 20050 and the sled 20060, the sled 20060, for example, can be configured to release the tissue thickness compensator 20020 from the cartridge body 20010, as illustrated in FIGS. 78 and 79. For instance, the distal end 20022 of the tissue thickness compensator 20020 can be releasably retained to the distal end of the cartridge body 20010 by a flexible clamp 20013 and a retention pin 20072 wherein the sled 20060 can defeat, or withdraw, the retention pin 20072. The flexible clamp 20013 can be configured to securely hold the tissue thickness compensator 20020 against the deck 20015 of the cartridge body 20010. In such circumstances, the flexible clamp 20013 can provide a sufficient clamping force to the tissue thickness compensator 20020 in order to hold the tissue thickness compensator 20020 in place. The retention pin 20072 may also securely hold the tissue thickness compensator 20020 to the cartridge body 20010. For instance, referring to FIGS. 77 and 77A, the distal end 20022 of the tissue thickness compensator 20020 can comprise an aperture 20023 defined therein which can be configured to receive the retention pin 20072 and, owing to the interaction between the retention pin 20072 and the sidewalls of the aperture 20023, the retention pin 20072 can prevent the tissue thickness compensator 20020 from sliding out between the clamp 20013 and the cartridge deck 20015. Moreover, the retention pin 20072 and the clamp 20013 can co-operatively confine the movement of the tissue thickness compensator 20020 and, in various circumstances, the top of the retention pin 20072 can abut or can be positioned closely adjacent to the clamp 20013.

In use, further to the above, the retention pin 20072 can be lowered by the sled 20060, as illustrated in FIGS. 78 and 79. More specifically, the retention pin 20072 can extend from a cam 20070 wherein the cam 20070 can rest or sit upon a resilient member, or spring, 20012 extending from a pan 20011 attached to the cartridge body 20010 and, when the sled 20060 engages the cam 20070, the sled 20060 can push the cam 20070 and the retention pin 20072 downwardly thereby compressing the spring 20012. The cartridge body 20010 can include guides 20018 defined therein which confine the movement of the cam 20070 along a substantially vertical path, i.e., a path perpendicular to cartridge deck 20015. In various embodiments, the sled 20060 can include a cam actuator 20062 which extends distally with respect to the staple driver lift surfaces 20063. Once the pin 20072 has been sufficiently lowered, the tissue thickness compensator 20020 can slide relative to cartridge deck 20015 and slip out of the clamp 20013. In various circumstances, the pin 20072 can be lowered a sufficient amount while still at least partially protruding from the cartridge deck 20015. In other circumstances, the pin 20072 can be lowered beneath the cartridge deck 20015. In either event, the cam actuator 20062 and staple driver lift surfaces 20063 of the sled 20060 can be configured such that the retention pin 20072 is sufficiently lowered at the same time that the last, or distal-most, staple is fired by the sled 20060. In other circumstances, the cam actuator 20062 and staple driver lift surfaces 20063 of the sled 20060 can be configured such that the retention pin 20072 is sufficiently lowered before the last, or distal-most, staple is fired by the sled 20060. In yet other circumstances, the cam actuator 20062 and staple driver lift surfaces 20063 of the sled 20060 can be configured such that the retention pin 20072 is sufficiently lowered after the last, or distal-most, staple is fired by the sled 20060. Although cam 20070 is described herein as having one retention pin 20072, a plurality of retention pins 20072 can extend from the cam 20070 which can each be configured to releasably retain the tissue thickness compensator 20020 to the cartridge body 20010. Accordingly, the tissue thickness compensator 20020 can include a suitable number of apertures 20023 configured to receive the retention pins 20072.

Figure 80:
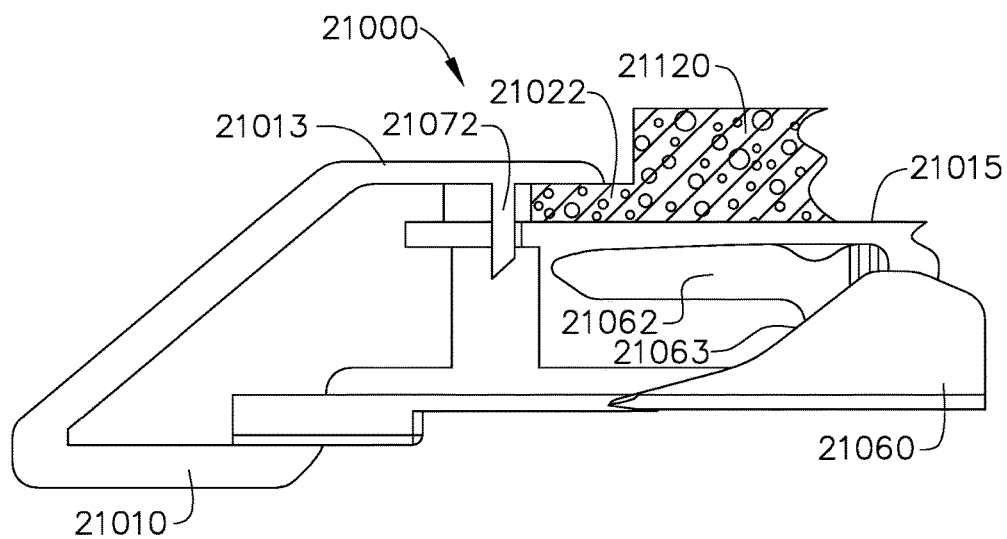
FIG. 80 is a partial cross-sectional view of a staple cartridge including a clamp configured to releasably hold a tissue thickness compensator to a cartridge body illustrating the clamp in a closed condition.
Figure 81:
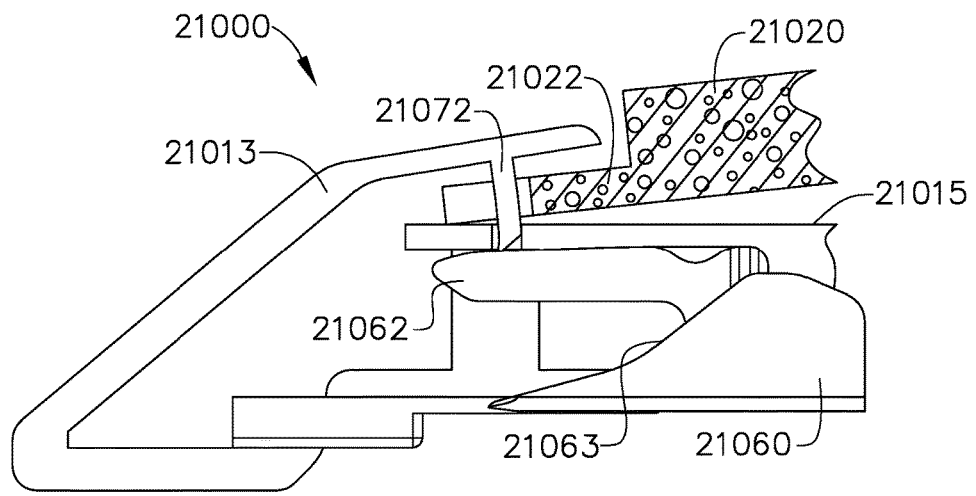
FIG. 81 is a partial cross-sectional view of the staple cartridge of FIG. 80 illustrating the clamp in an open condition.
Figure 81A:
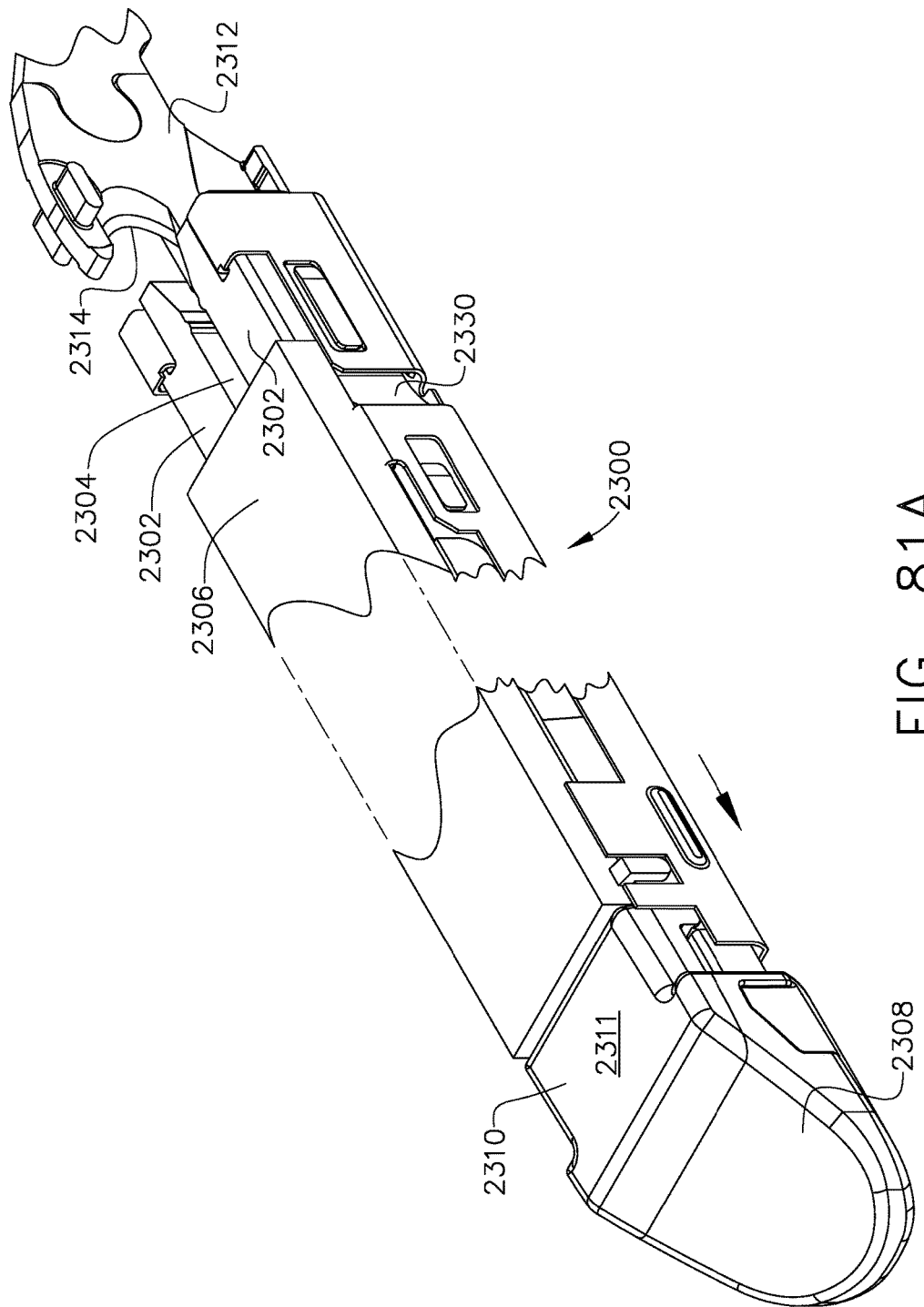
FIG. 81A is a perspective view of a staple cartridge with a layer, such as a tissue thickness compensator and/or a buttress material, arranged thereon, wherein the staple cartridge is arranged relative to an end effector cutting blade, and wherein remaining portions of the end effector are removed for purposes of illustration.

Referring now to FIGS. 80 and 81, a cartridge 21000, for example, can comprise a cartridge body 21010, a tissue thickness compensator 21020 releasably secured to the cartridge body 21010, and a sled 21060 which can be configured to release the tissue thickness compensator 21020 from the cartridge body 21010. Similar to the above, the sled 21060 can comprise staple driver lift surfaces 21063 which are configured to lift staple drivers, and staples supported thereon, toward an anvil positioned opposite the tissue thickness compensator 21020. Also similar to the above, the sled 21060 can further comprise a cam actuator 21062 which can be configured to deactivate a clamp 21013 holding a distal end 21022 of the tissue thickness compensator 21020 to the deck surface 21015 of the cartridge body 21010. More specifically, the clamp 21013 can include a cam 21072 extending downwardly into the cartridge body 21010 wherein the cam 21072 can be engaged by the cam actuator 21062 as the sled 21060 is advanced distally through the staple cartridge 21000. When the cam actuator 21062 engages the cam 21072, the cam actuator 21062 can lift the cam 21072 upwardly and flex the clamp 21013 away from the distal end 21022 of the tissue thickness compensator 21020, as illustrated in FIG. 81. At such point, the cartridge body 21010 can be moved away from the tissue thickness compensator 21020. Stated another way, by the time that the tissue thickness compensator 21020 is released from the cartridge body 21010, the tissue thickness compensator 21020 will have been implanted to the patient tissue by one or more staples wherein, after the tissue thickness compensator 21020 has been released, the cartridge body 21010 can be moved away from the implanted tissue thickness compensator 21020 and removed from the surgical site.

Further to the above, the cam actuator 21062 and staple driver lift surfaces 21063 of the sled 21060 can be configured such that the cam 20072 is sufficiently raised to sufficiently reduce the clamping force applied by the clamp 21013 at the same time that the last, or distal-most, staple is fired by the sled 20060. In other circumstances, the cam actuator 21062 and staple driver lift surfaces 21063 of the sled 21060 can be configured such that the cam 21072 is sufficiently raised to sufficiently reduce the clamping force applied by the clamp 21013 before the last, or distal-most, staple is fired by the sled 21060. In yet other circumstances, the cam actuator 21062 and staple driver lift surfaces 21063 of the sled 21060 can be configured such that the cam 20072 is sufficiently raised to sufficiently reduce the clamping force applied by the clamp 21013 after the last, or distal-most, staple is fired by the sled 21060. Although the clamp 21013 is described herein as having one cam 21072 extending therefrom, a plurality of cams 21072 can extend from the clamp 21013 which can each be configured to lift the clamp 21013 and release the tissue thickness compensator 20020 from the cartridge body 20010.

Figure 90:
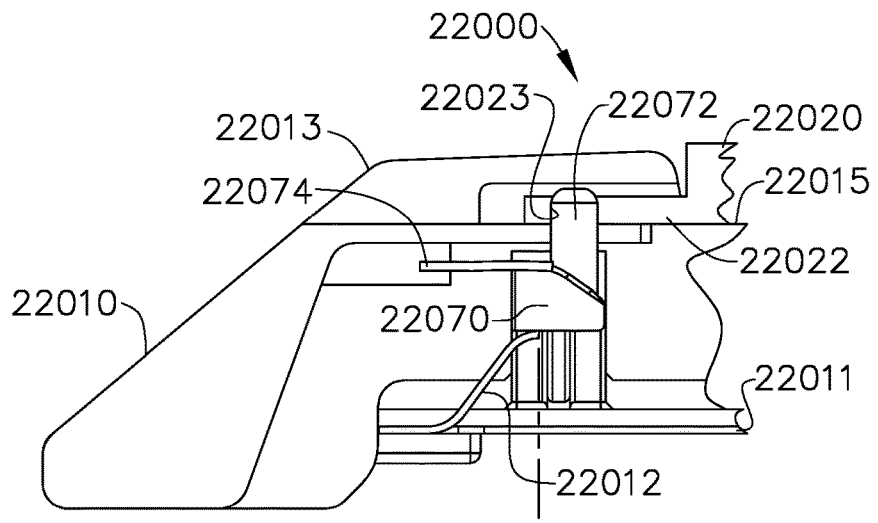
FIG. 90 is a partial cross-sectional view of a staple cartridge which includes a retention pin configured to releasably hold a tissue thickness compensator to a cartridge body illustrating the retention pin in an activated condition.
Figure 91:
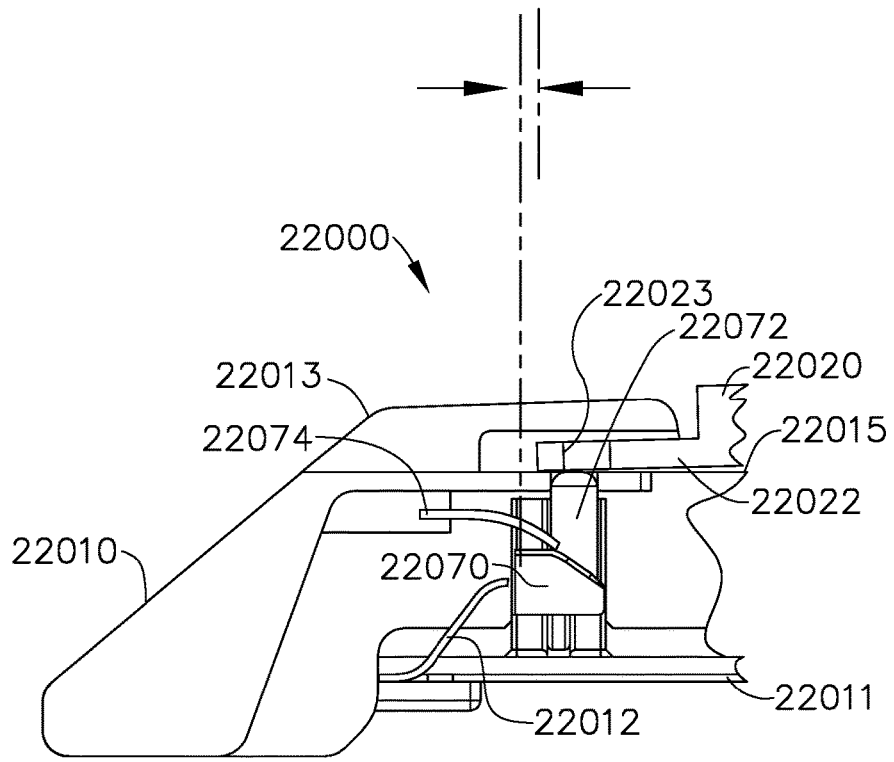
FIG. 91 is a partial cross-sectional view of the staple cartridge of FIG. 90 illustrating the retention pin in a deactivated condition.
Figure 92:
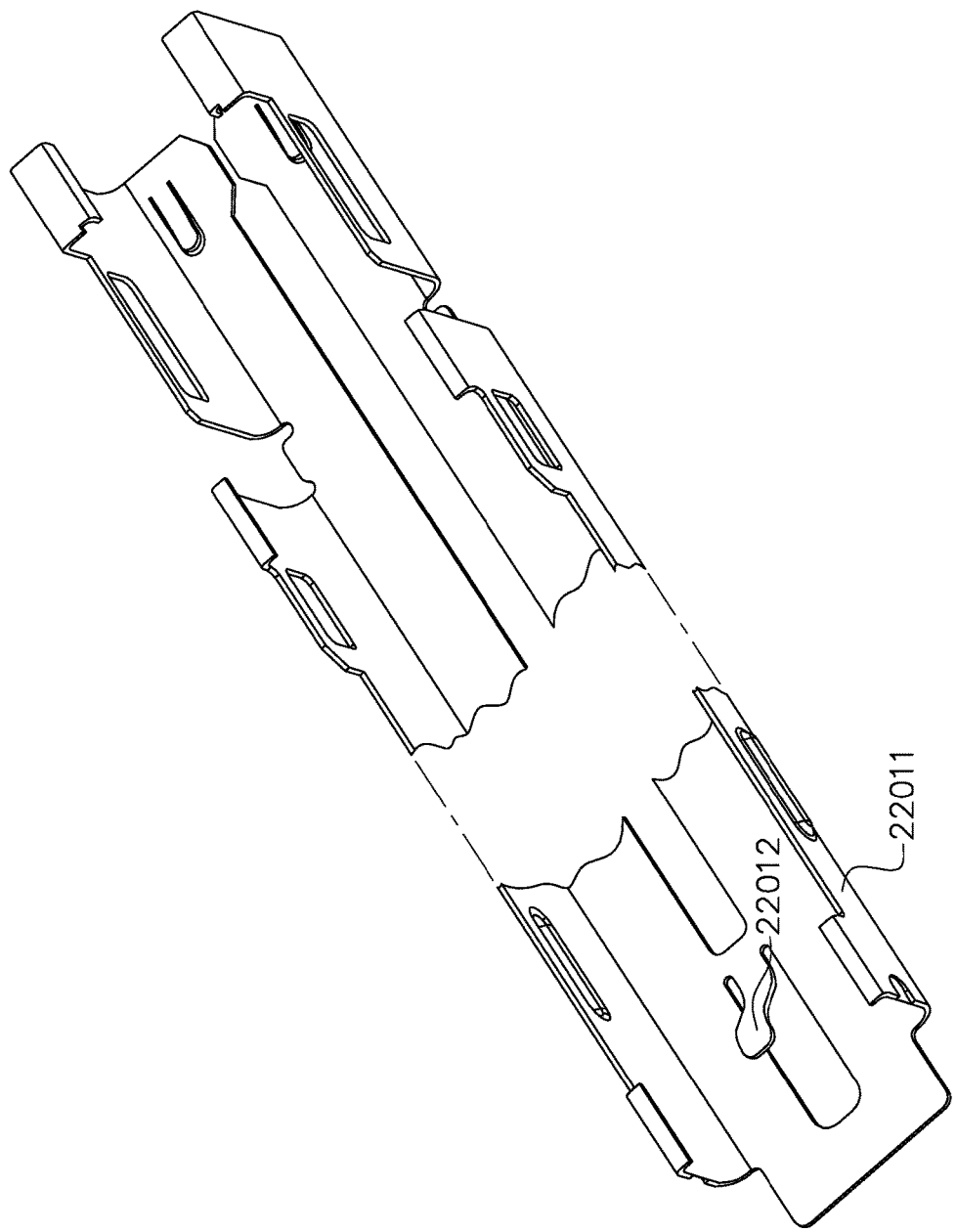
FIG. 92 is a perspective view of an actuator of the staple cartridge of FIG. 90 which is configured to deactivate the retention pin.

Further to the above, a sled, or firing member, passing through a staple cartridge can release a tissue thickness compensator from a cartridge body at the end, or near the end, of the distal movement of the sled and/or the end of the firing stroke of the firing member. Stated another way, the tissue thickness compensator can be released from the cartridge body at the same time, or nearly the same time, that all of the staples have been fired from the staple cartridge. In various other embodiments, the tissue thickness compensator can be released from the cartridge body at the same time, or before, the first, or proximal-most, staples have been fired from the staple cartridge. One such exemplary embodiment is depicted in FIGS. 90-92 which illustrate a staple cartridge 22000. Similar to the above, the staple cartridge 22000 can comprise a cartridge body 22010 and a tissue thickness compensator 22020 releasably secured thereto. Although the staple cartridge 22000 can further include a staple-firing sled as described above, the sled may not release the tissue thickness compensator 22020; rather, the staple cartridge 22000 may further comprise an actuator 22011 which can be advanced distally by the firing member at the beginning of the firing stroke thereof. Various other embodiments are disclosed herein which disclose means for advancing an actuator distally and are not repeated with regard to this embodiment for sake of brevity to the reader. In any event, the actuator 22011 can include a cam support 22012 extending therefrom which can be configured to support a cam 22070 when the actuator 22011 is in its unactuated position, as illustrated in FIG. 90. Moreover, the staple cartridge 22000 can further comprise a biasing member, or spring, 22074 which can be configured to hold or bias the cam 22070 against the cam support 22012 while, again, the actuator 22011 is in its unactuated position illustrated in FIG. 90. In such a position of the cam 22070, a retention pin 22072 extending from the cam 22070 can be engaged with and extend through an aperture 22023 defined in a distal end 22022 of the tissue thickness compensator 22020 such that, similar to the above, the retention pin 22072, and/or the retention pin 22072 in concert with a clamp 22013 extending from the cartridge body 22010, can hold the tissue thickness compensator 22020 in position.

When the actuator 22011 is advanced distally by the firing member, referring now to FIG. 91, the cam support 22012 can be advanced distally such that the cam support 22012 may no longer support the cam 22070. In such circumstances, the spring 22074 may bias the cam 22070 downwardly such that the retention pin 22072 is biased out of engagement, or at least partially out of engagement, with the tissue thickness compensator 22020. In at least one circumstance, the spring 22074 can bias the cam 22070 downwardly such that the retention pin 22072 is positioned below the deck 22015 of the cartridge 22010. In any event, the distal advancement of the actuator 22011 can release the tissue thickness compensator 22020 from the cartridge body 22010. Stated another way, once the retention pin 22072 has been lowered, the clamp 22013 may still provide a holding force to the tissue thickness compensator 22020 such that the tissue thickness compensator 22020 remains pinned against the staple deck 22015; however, the tissue thickness compensator 22020 can be slid out from underneath the clamp 22013 upon the application of a sufficient relative force between the tissue thickness compensator 22020 and the cartridge body 22010. Further to the above, the release of the tissue thickness compensator 22020 from the cartridge body 22010 can occur before, contemporaneous with, and/or immediately after the proximal-most staples are fired from the staple cartridge 22000. In such circumstances, the early release of the tissue thickness compensator 22020 may permit the tissue thickness compensator 22020 to be released from the cartridge body 22010 eventhough the staple cartridge 22000 has only been partially fired, for example.

Figure 84:
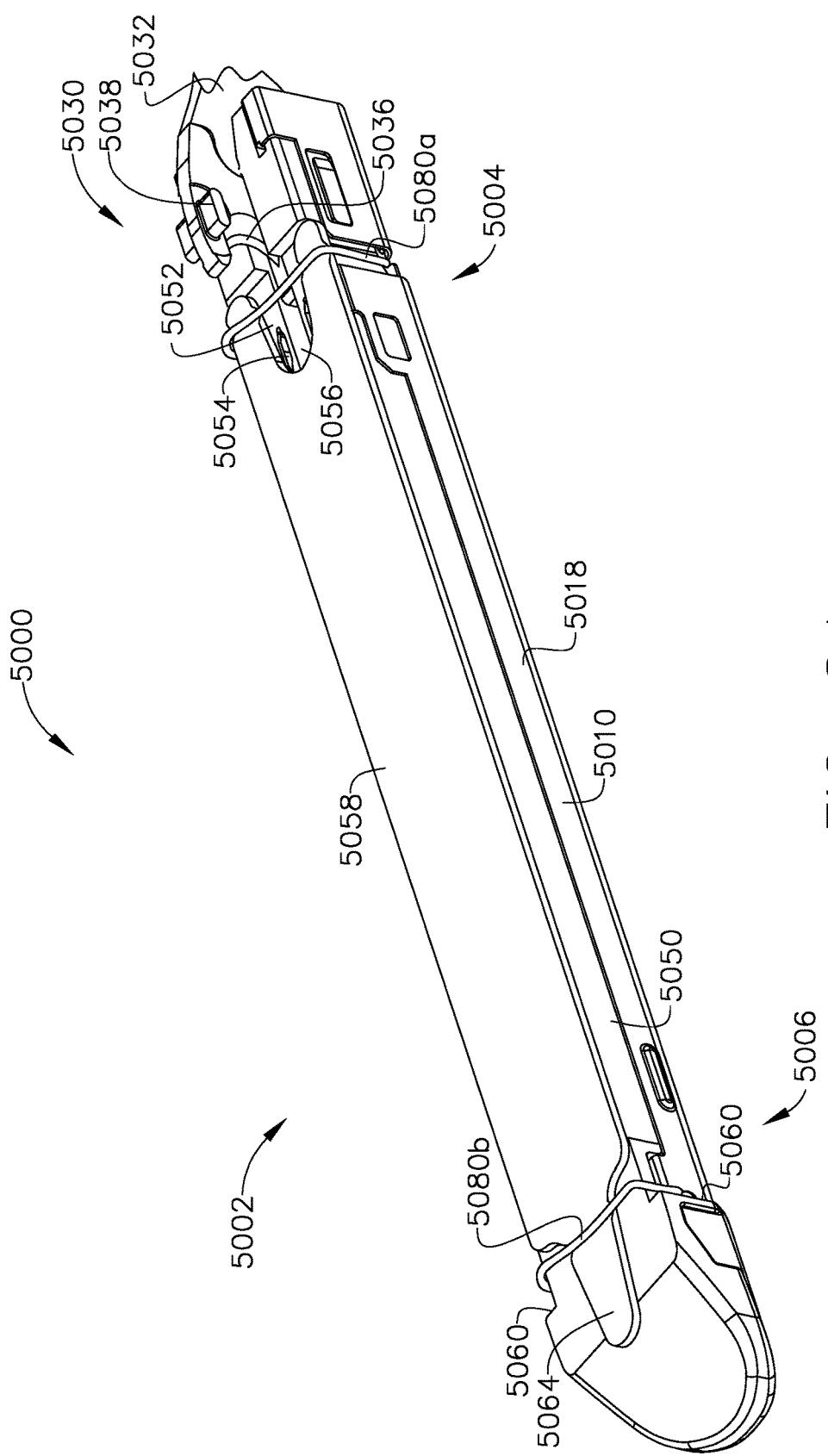
FIG. 84 is a perspective view of a jaw of an end effector assembly according to various embodiments of the present disclosure, depicting a tissue thickness compensator secured to a cartridge body by a proximal connector and by a distal connector, and further depicting a firing assembly in an unfired position.

Referring now to FIGS. 84-87, an end effector assembly 5000 can include a first jaw, illustrated elsewhere, and a second jaw 5002. In various embodiments, the second jaw 5002 can include a cartridge assembly that includes a fastener cartridge body 5050 and a tissue thickness compensator 5058 releasably secured to the fastener cartridge body 5050. Referring primarily to FIG. 84, the fastener cartridge body 5050 can have a cartridge deck 5052 and fastener cavities 5054 defined in the cartridge deck 5052. Further, the second jaw 5002 can include fasteners, such as surgical staples, for example, which can be removably positioned in the fastener cavities 5054. For example, a fastener can be ejectably positioned in each fastener cavity 5054 of the cartridge body 5050. In certain embodiments, the cartridge body 5050 can include a slot 5056, which can extend from a proximal portion 5004 of the second jaw 5002 toward a distal portion 5006 of the second jaw 5002. In various embodiments, a firing assembly 5030 can translate along the slot 5056 of the cartridge body 5050. For example, the firing assembly 5030 can translate within the slot 5056 during a firing stroke, and can eject the fasteners from the fastener cavities 5054 during the firing stroke.

Figure 29A:
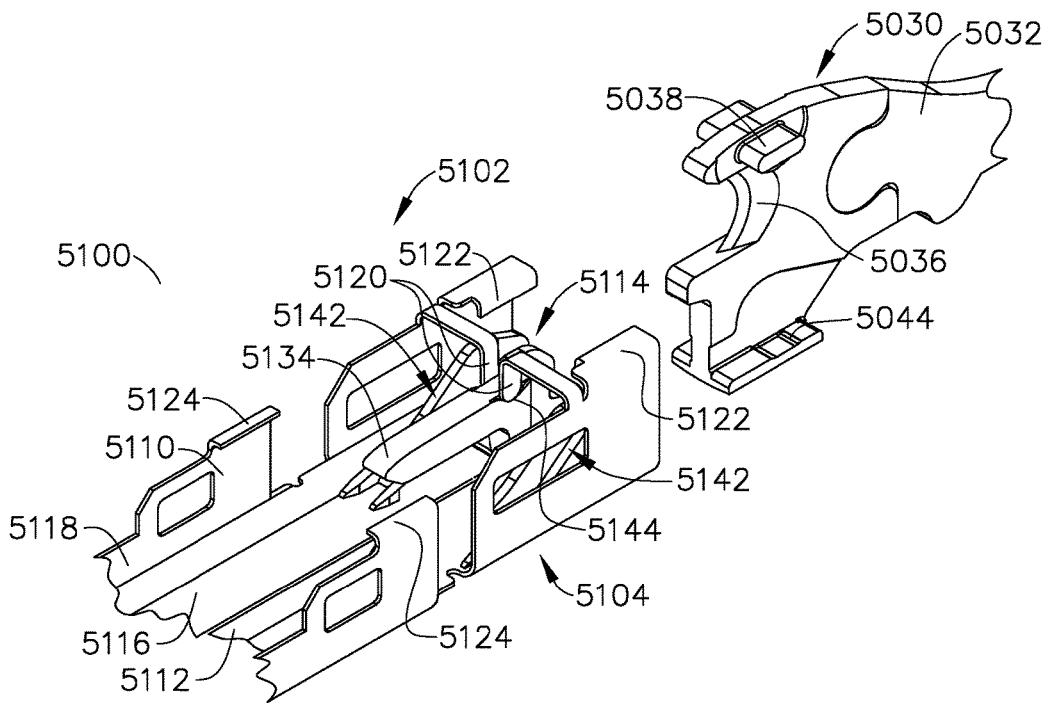
FIG. 29A is a partial, perspective view of a jaw of an end effector assembly with various elements removed therefrom according to various embodiments of the present disclosure, depicting a firing assembly in an unfired position, and further depicting a sled engaged with a release stop of an actuator.
Figure 29B:
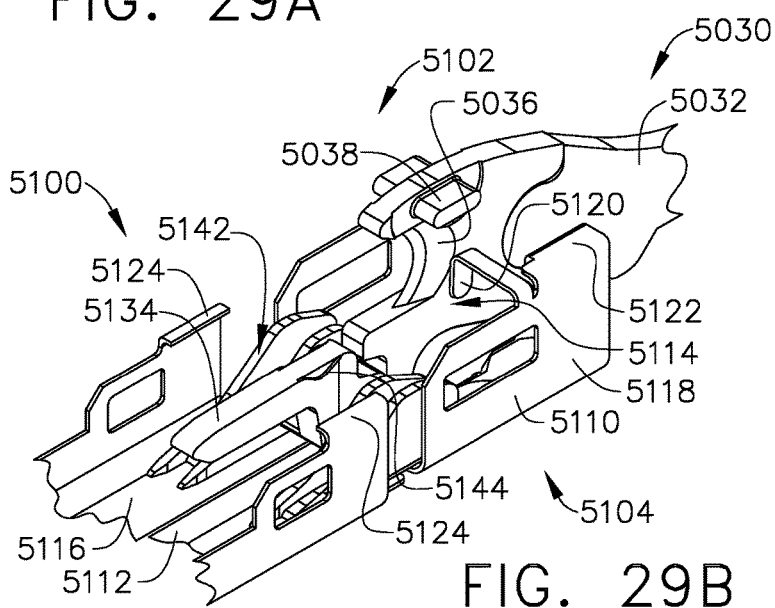
FIG. 29B is a partial, perspective view of the jaw of FIG. 29A with various elements removed therefrom, depicting the firing assembly in a partially fired position, and further depicting the sled disengaged from the release stop of the actuator.
Figure 30:
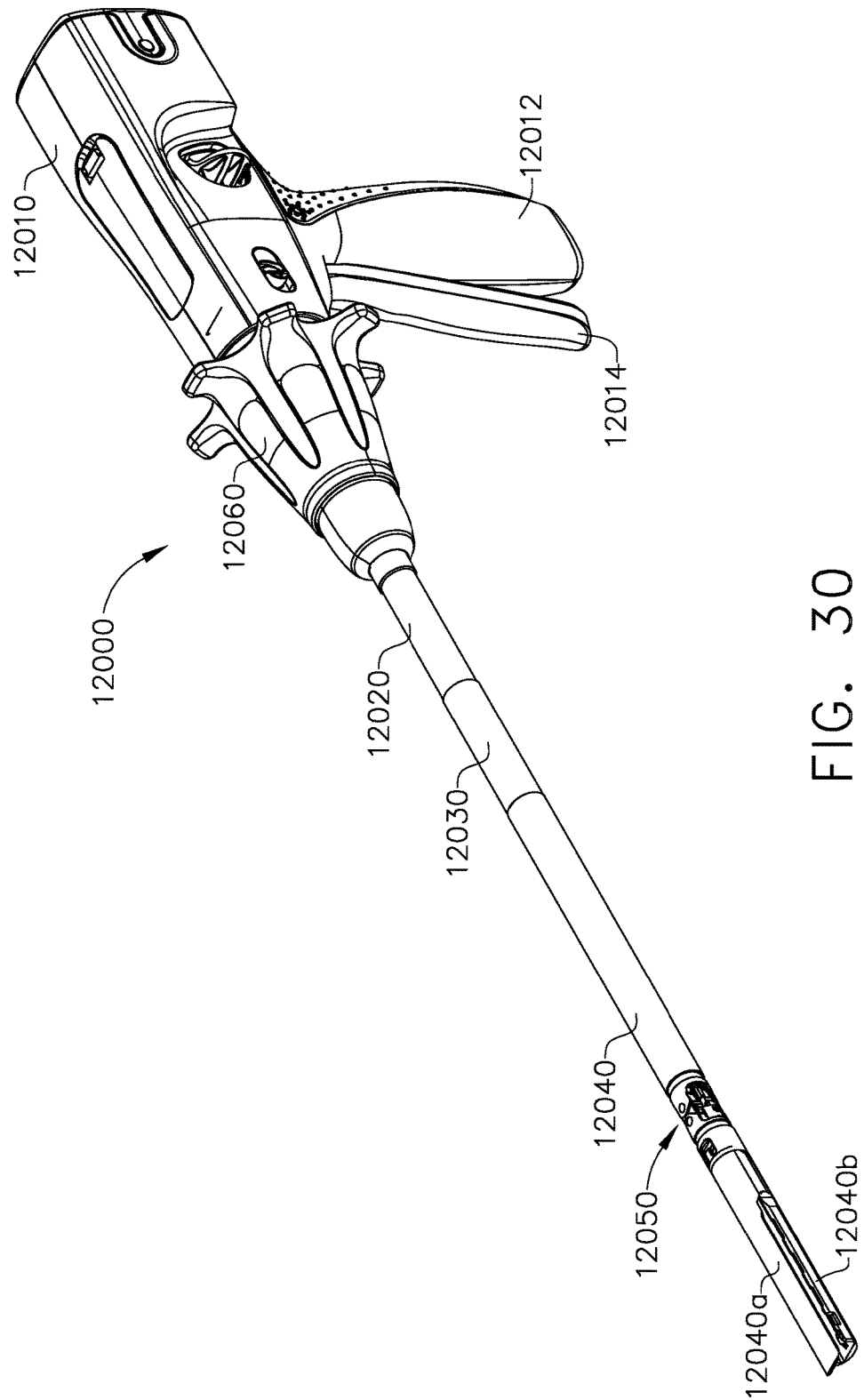
FIG. 30 is a perspective view of a surgical stapling instrument including a shaft and a detachable end effector.
Figure 31:
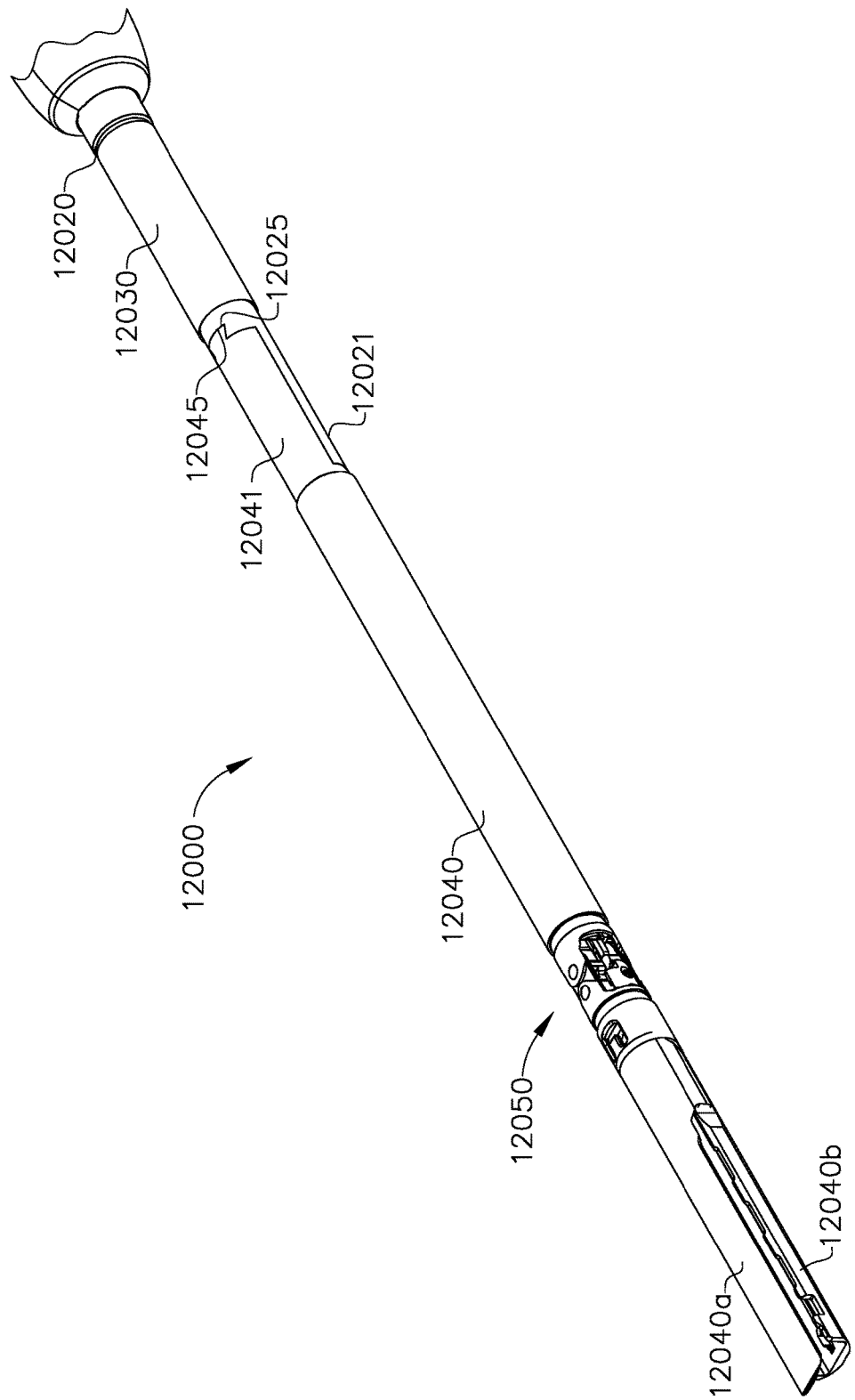
FIG. 31 is a partial perspective view of the shaft and the end effector of the surgical stapling instrument of FIG. 30.
Figure 32:
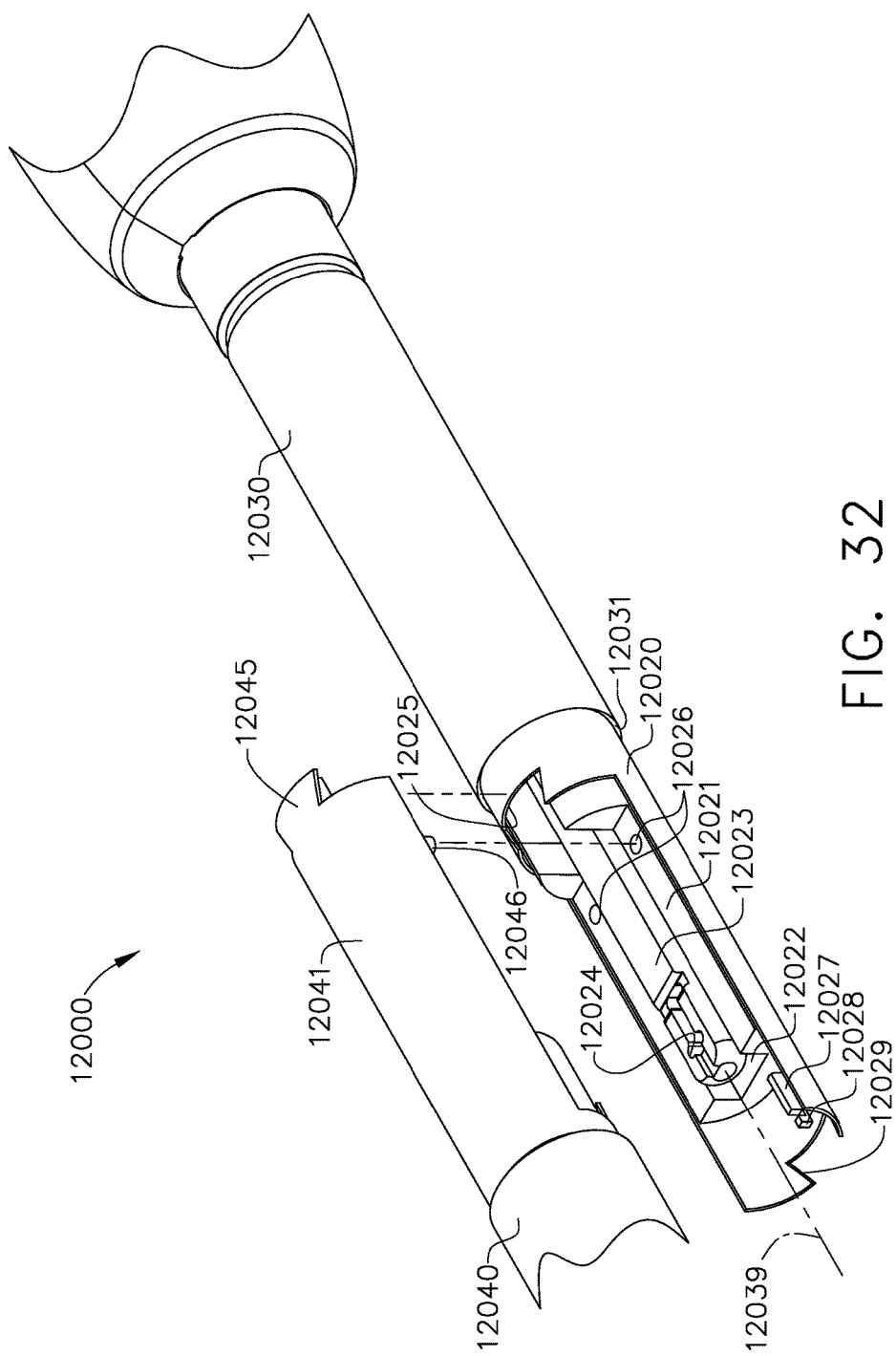
FIG. 32 is a partial perspective view of the end effector being assembled to the shaft of the surgical stapling instrument of FIG. 30.
Figure 33:
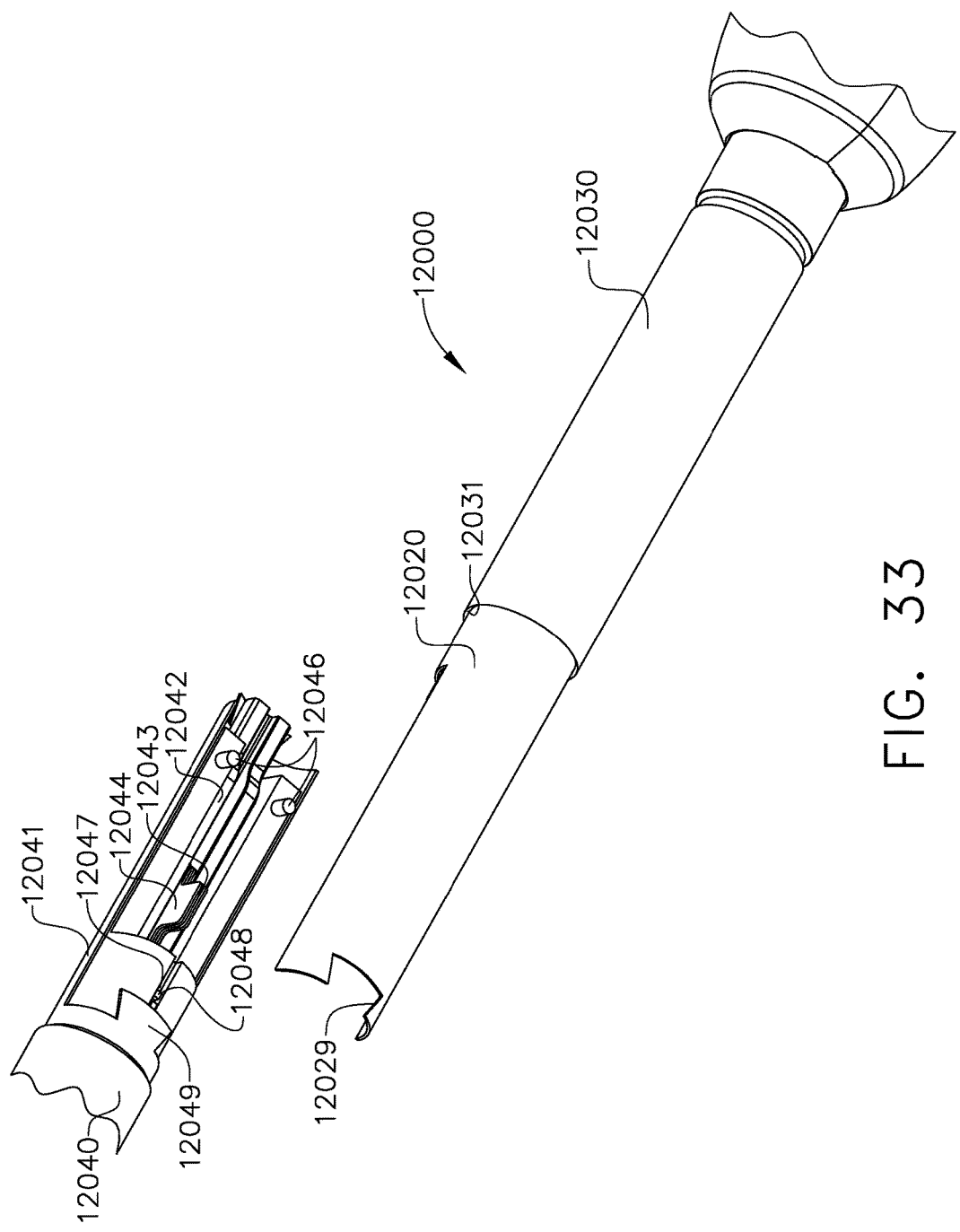
FIG. 33 is another partial perspective view of the end effector being assembled to the shaft of the surgical stapling instrument of FIG. 30.
Figure 34:
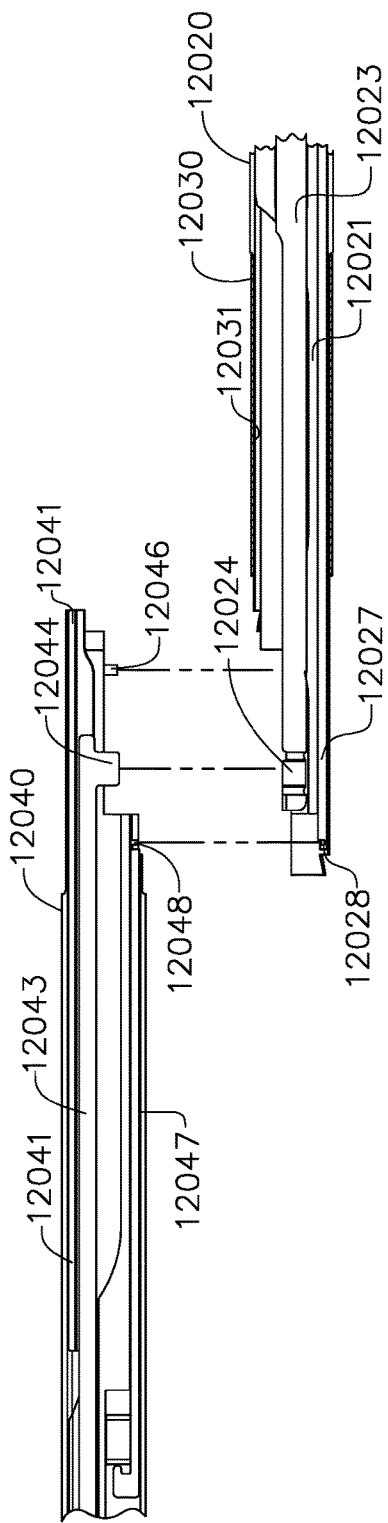
FIG. 34 is a partial cross-sectional elevational view illustrating the end effector uncoupled to the shaft of the surgical stapling instrument of FIG. 30.
Figure 35:
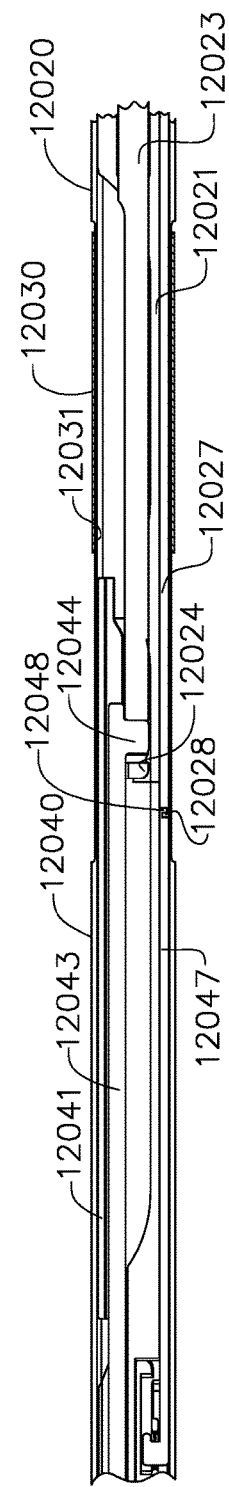
FIG. 35 is a partial cross-sectional elevational view illustrating the end effector coupled to the shaft of the surgical stapling instrument of FIG. 30, and further illustrating a slide collar in an open, unlocked position.
Figure 86:
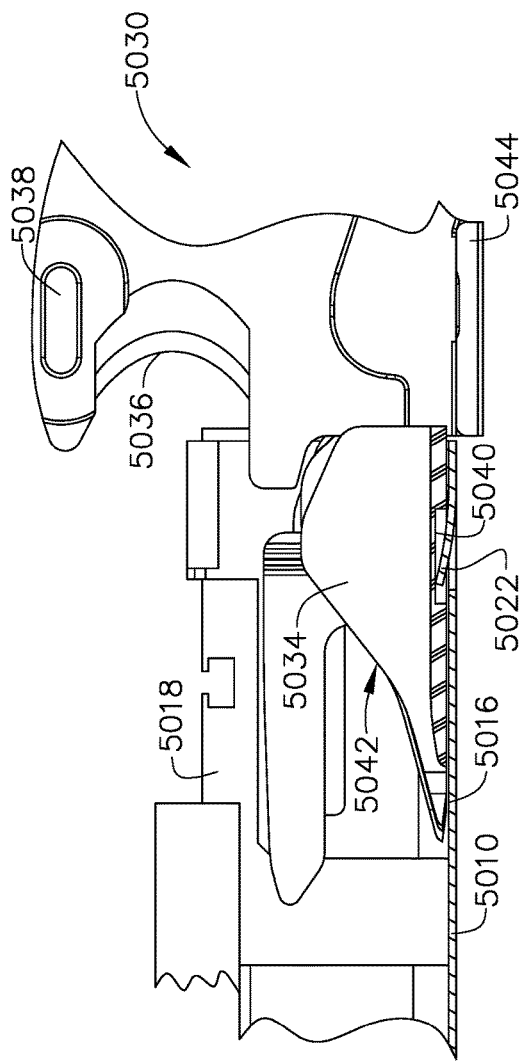
FIG. 86 is a partial, elevation view of the jaw of FIG. 84 with various elements removed therefrom, depicting a sled of the cartridge body engaged with a tab of the actuator of FIG. 85A.
Figure 87:
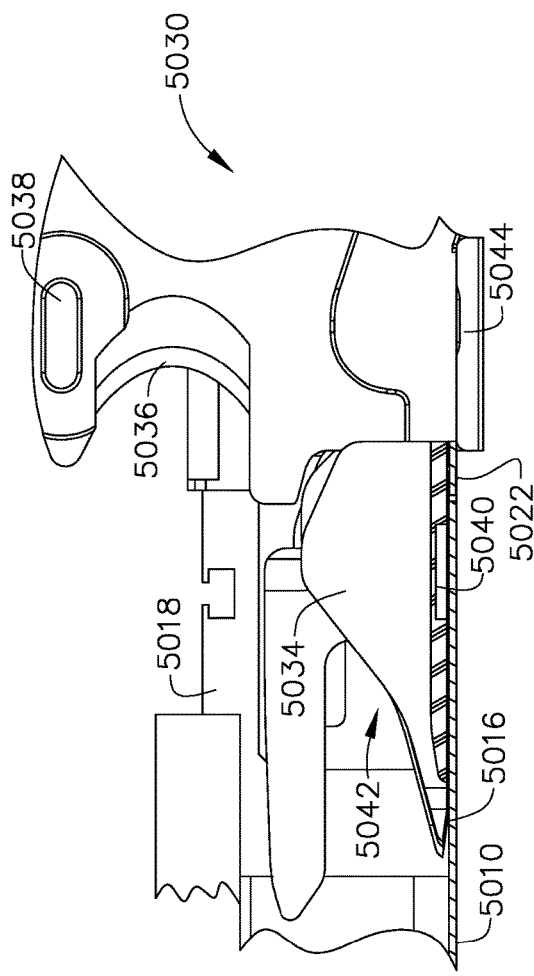
FIG. 87 is a partial, elevation view of the jaw of FIG. 84 with various elements removed therefrom, depicting the sled of the cartridge body disengaged from the tab of the actuator.

Referring primarily to FIGS. 84, 86 and 87, the firing assembly 5030 can include a firing bar (FIG. 84), a cutting edge 5036, a crossbar 5038, and a foot 5044 (FIGS. 86 and 87). The cutting edge 5036 can cut tissue and/or cut the tissue thickness compensator 5058 as the firing assembly 5030 is fired through the second jaw 5002 during a firing stroke. The crossbar 5038 can hold the first jaw relative to the cartridge body 5050, and the foot 5044 can hold the firing assembly 5030 relative to the cartridge body 5050, for example. In various embodiments, the crossbar 5038 and the foot 5044 can hold the cutting element 5036 perpendicular to the deck 5052 of the fastener cartridge 5050, for example. Referring primarily to FIGS. 29A and 29B, the firing assembly 5030 can engage a sled 5034 in the cartridge body 5050 during the firing stroke. The firing assembly 5030 can push the sled 5034 distally during the firing stroke to eject fasteners from the fastener cavities 5054, for example.

Referring primarily to FIG. 84, the tissue thickness compensator 5058 can be releasably secured to the cartridge body 5050 by at least one connector 5080*a*, 5080*b*. In certain embodiments, multiple connectors 5080*a*, 5080*b* can secure the tissue thickness compensator 5058 to the cartridge body 5050. For example, a proximal connector 5080*a* can secure the tissue thickness compensator 5058 to the cartridge body 5050 at the proximal portion 5004 of the second jaw 5002, and a distal connector 5080*b* can secure the tissue thickness compensator 5058 to the cartridge body 5050 at the distal portion 5006 of the second jaw 5002. In certain embodiments, additional connectors can secure the tissue thickness compensator 5058 to the cartridge body 5050. In such embodiments, the additional connectors can be spaced along at least a portion of the length of the cartridge body 5050, and can be positioned between the proximal connector 5080*a* and the distal connector 5080*b*, for example.

Still referring primarily to FIG. 84, the connectors 5080*a*, 5080*b* can hold the tissue thickness compensator 5058 relative to the cartridge body 5050. The tissue thickness compensator 5058 can be released from the cartridge body 5050 when the connectors 5080*a*, 5080*b* are broken, cut, dislodged or otherwise overcome. In certain embodiments, the firing assembly 5030 can overcome the connectors 5080*a*, 5080*b* as the firing assembly 5030 translates along the slot 5056 in the fastener cartridge 5050 during a firing stroke. During such a firing stroke, the firing assembly 5030 can cut tissue clamped between the first jaw and the second jaw 5002, and can also move the fasteners from the fastener cavities 5054 into the clamped tissue. In various embodiments, the firing assembly 5030 can push the sled 5034 (FIGS. 86 and 87) distally during the firing stroke. The sled 5034 can have a camming surface or ramp 5042, which can engage drivers in the fastener cavities 5054. When the ramp 5042 engages a driver, the ramp 5042 can push the driver toward the deck 5052 to eject the fastener from the fastener cavity 5054. Further, the firing assembly 5030 can cut the tissue thickness compensator 5058 and the connectors 5080*a*, 5080*b* during the firing stroke.

Referring primarily to FIG. 84, the cutting edge 5036 of the firing assembly 5030 can cut the proximal connector 5080*a* at or near the beginning of the firing stroke, for example, and can cut the distal connector 5080*b* at or near the end of the firing stroke, for example. In certain embodiments, the sled 5034 (FIGS. 86 and 87) can eject the fasteners from the fastener cavities 5054 after the cutting edge 5036 cuts the proximal connector 5080*a* and before the cutting edge 5036 cuts the distal connector 5080*b*. In such embodiments, if the firing assembly 5030 does not complete the firing stroke, the cutting edge 5036 of the firing assembly 5030 may stop before reaching the distal connector 5080*b*, and the tissue thickness compensator 5058 may remain secured to the cartridge body 5050 at the distal portion 5006 of the second jaw 5002. In certain embodiments, the tissue thickness compensator 5058 can remain secured to the cartridge body 5050 until the operator cuts or otherwise overcomes the distal connector 5080*b*. For example, the operator may introduce an additional surgical instrument and/or step in the surgical procedure to overcome the distal connector 5080*b*.

Referring still to FIGS. 84-87, in various embodiments, the second jaw 5002 can overcome the connectors 5080*a*, 5080*b* at or near the beginning of the firing stroke. In other words, an element of the second jaw 5002 can overcome the proximal connector 5080*a*, the distal connector 5080*b*, and any additional connectors therebetween at or near the beginning of the firing stroke. For example, the second jaw 5002 and/or the cartridge assembly can include an actuator 5010, which can overcome the distal connector 5080b before the fasteners are ejected from the fastener cavities. The actuator 5010 can overcome the distal connector 5080b and the tissue thickness compensator 5358 can be released from the cartridge body 5050 even when the firing stroke terminates prematurely, i.e., before the firing assembly 5030 reaches the distal portion 5006 of the second jaw 5002, for example. In various embodiments, the actuator 5010 can include a bottom side 5016 (FIGS. 85A-85C) and sidewalls 5018 (FIGS. 84 and 85D). The sidewalls 5018 can extend from the bottom side 5016 and around at least a portion of the cartridge body 5050. The bottom side 5016 and/or the sidewalls 5018 can extend past or around the fasteners positioned in the fastener cavities 5054. Further, the actuator 5010 can be moveably held relative to the cartridge body 5050. For example, the actuator 5010 can move from a pre-actuated position (FIG. 85A) to an actuated position (FIGS. 85B and 85D). In certain embodiments, the sidewalls 5018 of the actuator 5010 can engage slits in the cartridge body 5050, such that the actuator 5010 moves in the slits to slide relative to the cartridge body 5050. When the actuator 5010 moves relative to the cartridge body 5050, the actuator 5010 can slide relative to the fasteners positioned in fastener cavities 5054 of the cartridge body 5050. For example, the actuator 5010 can slide past and/or around the fasteners positioned in the fastener cavities 5054.

Figure 85C:
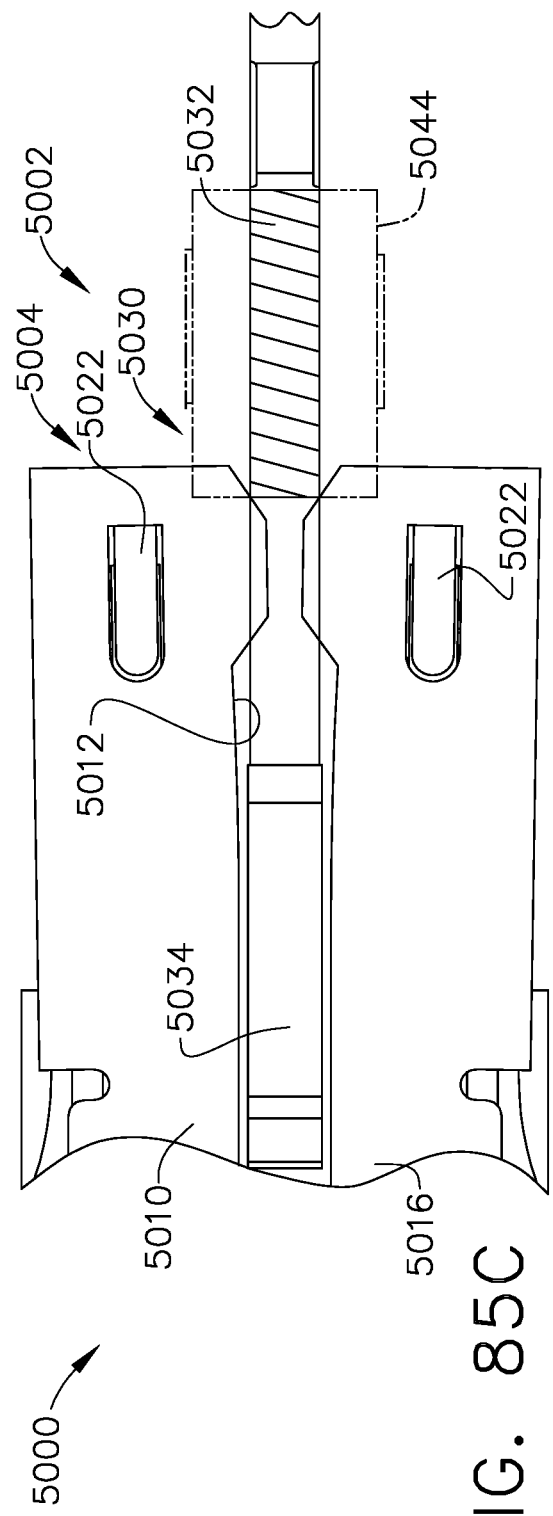
FIG. 85C is a detail view of the jaw of FIG. 85B.

Referring primarily to FIGS. 85A-85C, the actuator 5010 can include a slot 5012, which can extend from the proximal portion 5004 toward the distal portion 5006 of the second jaw 5002. The slot 5012 in the actuator 5010 can correspond to and/or be aligned with the slot 5056 (FIG. 84) in the cartridge body 5050, for example. Further, the firing assembly 5030 can translate along and/or within the slot 5012 in the actuator 5010 as the firing assembly 5030 translates along and/or within the slot 5056 in the cartridge body 5050 during the firing stroke. In various embodiments, the firing assembly 5030 can engage the actuator 5010 to move the actuator 5010 distally when the firing assembly 5030 is at or near the beginning of the firing stroke. In such embodiments, the firing assembly 5030 can actuate the actuator 5010 at the proximal portion 5004 of the second jaw 5002. When the actuator 5010 is actuated and moves distally, a distal end of the actuator 5010 can cut or otherwise overcome the distal connector 5080b, for example. In other words, proximal actuation of the actuator 5010 can effectuate distal release of the tissue thickness compensator 5058 from the cartridge body 5050. In various embodiments, the actuator 5010 can merely shift distally to overcome the distal connector 5080b. In at least one embodiment, the actuator 5010 can shift approximately 1 mm, for example, before overcoming the distal connector 5080b. In certain embodiments, the actuator 5010 can shift approximately 0.5 mm to approximately 5 mm, for example, before overcoming the distal connector 5080b.

Referring primarily to FIGS. 85A and 85B, the actuator 5010 can move from the pre-actuated position (FIG. 85A) to the actuated position (FIG. 85B) when the firing assembly 5030 moves between an unfired position and a partially fired position during part of the firing stroke. In various embodiments, the actuator 5010 can include a release stop, such as detent tabs 5022, for example. The progression of the firing element relative to the actuator 5010 can be paused by the detent tabs 5022. In other words, the detent tabs 5022 can temporarily halt the progression of the firing assembly 5030 relative to the actuator 5010. For example, while the actuator 5010 moves from the pre-actuated position toward the actuated position, the detent tabs 5022 can engage the sled 5034 and/or the firing assembly 5030 to hold the firing assembly 5030 relative to the actuator 5010, such that the actuator 5010 moves therewith. For example, referring primarily to FIGS. 86 and 87, the bottom side 5016 of the actuator 5010 can include a detent tab 5022, and the sled 5034 can include a recess or groove 5040. In various embodiments, the groove 5040 can receive the tab 5022 when the sled 5034 is positioned in the proximal portion 5004 of the second jaw 5002. For example, the groove 5040 can be aligned with the tab 5022 when the firing assembly 5030 moves from an unfired position to a fired position, and thus, when the actuator is pushed from a pre-actuated position (FIG. 85A) to an actuated positioned (FIG. 85B). In various embodiments, at least one tab 5022 can be positioned on either side of the slot 5012 (FIGS. 85A-85C) in the actuator 5010, and each tab 5022 can engage the sled 5034.

Referring primarily to FIG. 85A, the sled 5034 can engage the detent tabs 5022 as the firing assembly 5030 and sled 5034 translate along the slot 5056 (FIG. 84) during the firing stroke. For example, the detent tabs 5022 can engage the sled 5034 at or near the beginning of the firing stroke. In certain embodiments, the detent tabs 5022 can be near the proximal end of the actuator 5010, and the sled 4034 can engage the detent tabs 5022 upon the initiation of the firing stroke. When the firing bar 5032 is moved distally and the detent tabs 5022 are engaged with the recesses 5040 in the sled 5034 (FIGS. 86 and 87), the actuator 5010 can be driven and/or shifted distally. In certain embodiments, referring primarily to FIG. 85B, the actuator 5010 can move distally until it reaches a hard stop 5060 defined in the cartridge body 5050, for example. The hard stop 5060 can be at the distal portion 5006 of the second jaw 5002, and can prevent further distal movement of the actuator 5010, for example. In various embodiments, the actuator 5010 can abut the hard stop 5060 before the firing assembly 5030 ejects the fasteners from the fastener cavities 5054 of the cartridge body 5050 (FIG. 84). In some embodiments, the actuator 5010 can abut the hard stop 5060 as the firing assembly 5030 ejects at least one fastener from a fastener cavity 5054 and/or after the firing assembly 5030 has ejected at least one fastener from a fastener cavity 5054.

Figure 85D:
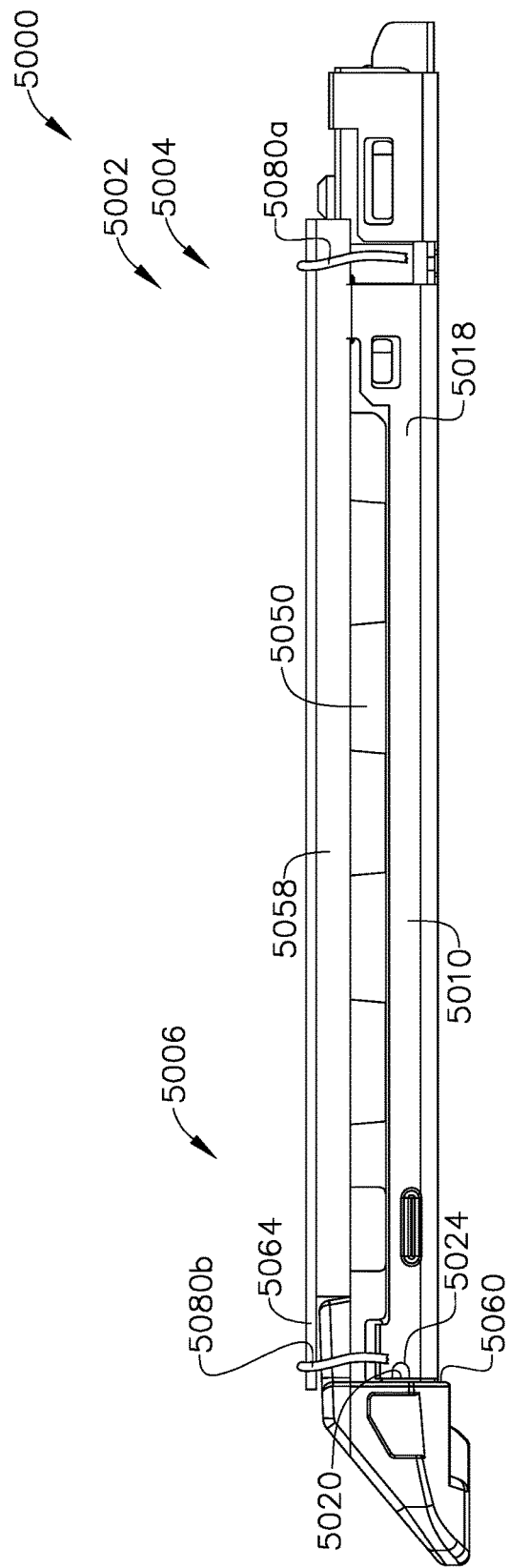
FIG. 85D is an elevation view of the jaw of FIG. 84, depicting the actuator in the actuated position, and further depicting the proximal and distal connectors broken.

Referring primarily to FIG. 85D, when the actuator 5010 is pushed distally by the sled 5034 and/or the firing assembly 5030, the actuator 5010 can cut or otherwise overcome the distal connector 5080b to release the tissue thickness compensator 5058 from the cartridge body 5050 at the distal portion 5006 of the second jaw 5002. In certain embodiments, the actuator 5010 can include a notch 5024 for receiving and holding the distal connector 5080b. The notch 5024 can hold the distal connector 5080b as the actuator 5010 shifts distally toward the hard stop 5060. Further, the actuator 5010 can include a cutting edge 5020, for example, along the notch 5024. In certain embodiments, when the actuator 5010 moves toward the hard stop 5060, the distal connector 5080b can be pushed between the hard stop 5060 and the cutting edge 5020 of the actuator 5010. In various embodiments, the cutting edge 5020 can cut the distal connector 5080b when the cutting edge 5020 is pushed into and/or toward the hard stop 5060. In such embodiments, the distal connector 5080b can be cut by the cutting edge 5020 of the actuator 5010 at or near the beginning of the firing stroke and before the fasteners are fired from the fastener cavities 5054 (FIG. 84). In some embodiments, the cutting edge 5020 can cut the distal connector 5080b as the firing assembly 5030 ejects at least one fastener from a fastener cavity 5054 and/or after the firing assembly 5030 has ejected at least one fastener from a fastener cavity 5054. In various embodiments, the actuator 5010 can overcome the distal connector 5080b without cutting it. For example, the actuator 5010 can dislodge or stretch the distal connector 5080b out of position such that the distal connector 5080b no longer holds the tissue thickness compensator 5058 relative to the cartridge body 5050.

In various embodiments, the proximal connector 5080a can be cut by a proximal cutting edge on the actuator 5010. Similarly, additional connectors along the length of the cartridge body 5050 can be cut or otherwise overcome by the actuator 5010 at or near the beginning of the firing stroke. Additionally or alternatively, the cutting edge 5036 of the firing assembly 5030 can cut or otherwise overcome the proximal connector 5080a and/or additional connectors. For example, the cutting edge 5036 of the firing assembly 5030 can cut the proximal connector 5080a and the cutting edge 5020 of the actuator 5010 can cut the distal connector 5080b before the fasteners are ejected from the fastener cavities 5054 of the cartridge body 5050 (FIG. 84).

Referring primarily to FIG. 87, the sled 5034 and/or the firing assembly 5030 can be configured to overcome the detent tabs 5022 of the actuator 5010. When the sled 5034 and/or the firing assembly 5030 overcome the detent tabs 5022, the firing assembly 5030 and the sled 5034 can move relative to the actuator 5010. For example, the firing assembly 5030 can push the sled 5034 distally to move the actuator 5010 distally until further distal movement of the actuator is prevented by the hard stop 5060 (FIGS. 85A, 85C, and 85D). Referring still to FIG. 87, when the actuator 5010 is blocked from further distal movement, the firing assembly 5030 can push the sled 5034 with sufficient force to deform, deflect, and/or dislodge the detent tabs 5022 from the recesses 5040 in the sled 5034. For example, the tabs 5022 can each comprise a cantilever which can flex downwardly out of engagement with the groove 5040 after a sufficient longitudinal force has been applied to the sled 5034. When the firing assembly 5030 pushes the sled 5034 out of engagement with the detent tabs 5022, the firing assembly 5030 and sled 5034 can move relative to the actuator 5010. In various embodiments, the detent tabs 5022 can be sufficiently rigid to withstand the force of the firing assembly 5030 as the actuator 5010 shifts distally toward the hard stop 5060, and can be sufficiently flexible to deflect when the actuator 5010 reaches the hard stop 5060 without requiring excessive force by a motor and/or operator. In various circumstances, the detent tabs 5022 can be configured to permit the firing bar 5032 to pass through the cartridge body 5050 after the force applied to detent tabs 5022 has exceeded a predetermined force.

Referring now to FIGS. 29A and 29B, an end effector assembly 5100 can include a first jaw, illustrated elsewhere, and a second jaw 5102. In various embodiments, the second jaw 5102 and/or a fastener cartridge assembly positionable therein can include an actuator 5110. The actuator 5110 can slide or shift relative to a fastener cartridge body, such as the fastener cartridge body 5050 (FIG. 84), for example, of the fastener cartridge assembly. Further, in certain embodiments, the actuator 5110 can include a bottom wall 5116 and sidewalls 5118, which can be positioned at least partially around the cartridge body 5050. The bottom wall 5116 and/or the sidewalls 5118 can extend past or around the fasteners positioned in the fastener cavities 5054 (FIG. 84) when the actuator is held relative to the cartridge body 5050. In various embodiments, the actuator 5110 can include a slot 5112 extending along at least a portion of the bottom wall 5116. Further, the sidewalls 5118 can include lips 5122 and/or lips 5124, which can slidably engage the cartridge body 5050. For example, the lips 5122 can extend around the cartridge body 5050 and into slits in the deck 5052 (FIG. 84) of the cartridge body 5050. Further, the lips 5124 can extend into slits along the side of the cartridge body 5050, for example. In various embodiments, the lips 5122, 5124 can slide within the slits as the actuator 5110 moves relative to the cartridge body 5050. In such embodiments, the lips can constrain and/or define the relative movement between the actuator 5110 and the cartridge body 5050, for example. When the actuator 5110 moves relative to the cartridge body 5050, the actuator 5110 can slide relative to the fasteners positioned in the fastener cavities 5054 of the cartridge body 5050. For example, the actuator 5110 can slide past or around the fasteners in the fastener cavities 5054.

Referring still to FIGS. 29A and 29B, the actuator 5110 can include a release stop, such as detent 5114, for example, at the proximal portion 5104 of the second jaw 5102, for example. Referring primarily to FIG. 29A, the detent 5114 can include a detent arm 5120 which can operably hold a sled 5134 of the cartridge body 5050 (FIG. 84). For example, the sled 5134 can include a groove 5144 and the detent arm 5120 can engage the groove 5144 to retain the sled 5134 relative to the actuator 5110. In various embodiments, the detent 5114 can have multiple detent arms 5120, which can be retained in grooves 5144 in the sled 5134. The detent arms 5120 can extend from opposite sides of the actuator 5110, for example, and the sled 5134 can be positioned intermediate the detent arms 5120, for example. In certain embodiments, the firing assembly 5030 can push against the sled 5134 and can shift the actuator 5110 distally while the detent arms 5120 are held in the grooves 5144 of the sled 5134 (FIG. 29A). The detent arms 5120 can be sufficiently rigid to hold the sled 5134 relative to the actuator 5110 as the actuator 5110 is pushed distally by the firing assembly 5030. Thereafter, the actuator 5110 can abut a hard stop, such as hard stop 5060 (FIGS. 84-85B and 85D), for example, which can prevent further distal movement of the actuator 5110.

Referring primarily to FIG. 29B, when the actuator 5010 abuts the hard stop 5060 (FIGS. 84-85B and 85D), the firing assembly 5030 can push the sled 5134 through the detent 5114. In other words, the firing assembly 5030 can force the sled 5134 to overcome the detent arms 5120. In such embodiments, the detent arms 5120 can be sufficiently flexible to flex out of engagement with the grooves 5144 of the sled 5134 and permit passage of the firing assembly 5030 between the detent arms 5120 and along the slot 5112 in the actuator 5110. Similar to the actuator 5010, the actuator 5110 can include an edge that can cut or otherwise overcome a distal connector, similar to distal connector 5080b (FIGS. 84 and 85D), for example, when the actuator 5110 is shifted distally by the firing assembly 5030. Thereafter, the firing assembly 5030 and the sled 5134 can translate along the slot 5112, and can eject fasteners from the fastener cavities 5054 in the cartridge body, for example. In various embodiments, the actuator 5110 can overcome the distal connector and/or additional connector(s) before a fastener is fired from the fastener cartridge 5050. In certain embodiments, the actuator 5110 can overcome the distal connector and/or additional connector(s) as at least one fastener is fired from a fastener cavity and/or after at least one fastener has been fired from a fastener cavity.

Figure 87A:
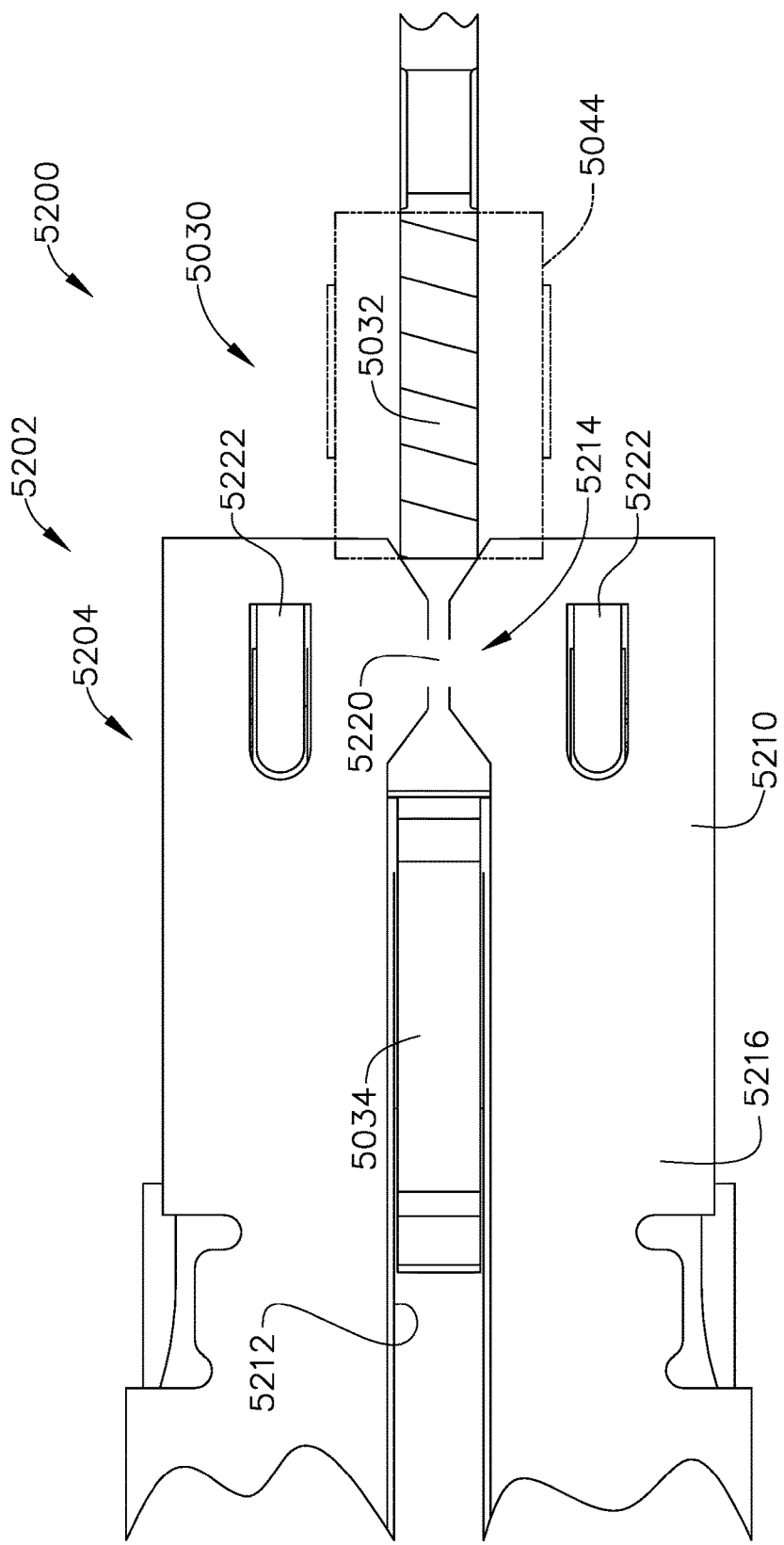
FIG. 87A is a partial, plan view of a jaw of an end effector assembly according to various embodiments of the present disclosure, depicting a firing bar of a firing assembly against a release stop of an actuator.
Figure 87B:
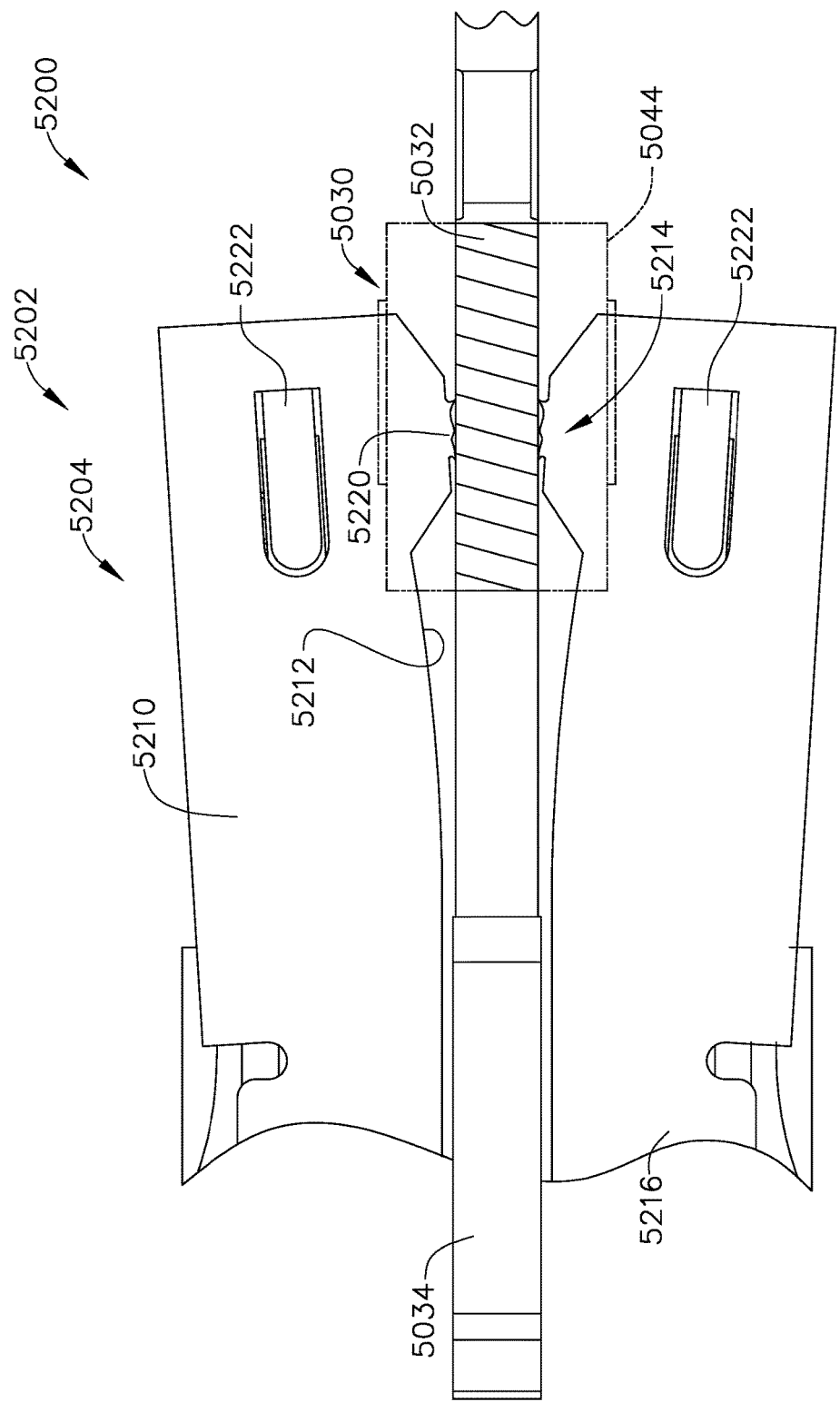
FIG. 87B is a partial, plan view of the jaw of FIG. 87A, depicting the firing bar of the firing assembly extending through the release stop of the actuator.

Referring now to FIGS. 87A and 87B, an end effector assembly 5200 can include a first jaw, illustrated elsewhere, and a second jaw 5202. In various embodiments, the second jaw 5202 and/or a fastener cartridge assembly can include an actuator 5210 that can slide relative to a fastener cartridge body, such as the fastener cartridge body 5050 (FIG. 84), for example. Further, in certain embodiments, the actuator 5210 can include a bottom wall 5216 and sidewalls. The sidewalls can be positioned at least partially around the cartridge body 5050, for example. The actuator 5210 can include a slot 5212 extending along at least a portion of the bottom wall 5216. Further, the actuator 5210 can be moveably held relative to the cartridge body 5050. When the actuator 5210 moves relative to the cartridge body 5050, the actuator 5210 can move relative to the fasteners positioned in the fastener cavities 5054 of the cartridge body 5050. For example, the actuator 5210 can slide past or around the fasteners positioned in the fastener cavities 5054.

In various embodiments, the firing assembly 5030 can translate along and/or within the slot 5212 during a firing stroke. Similar to the actuators 5010, 5110, the actuator 5210 can include a release stop 5214. In various embodiments, the release stop 5214 can include a frangible portion 5220, which can be a bridge across the slot 5212, for example. Referring primarily to FIG. 87A, the firing assembly 5030 can abut the release stop 5214 to push the actuator 5210 distally. Thereafter, the actuator 5210 can abut a hard stop, such as hard stop 5060 (FIGS. 84-85B and 85D), which can prevent further distal movement of the actuator 5210. Referring primarily to FIG. 87B, upon reaching the hard stop 5060, the firing assembly 5030 can break the frangible portion 5220 of the release stop 5214 to continue moving distally along the slot 5212 during the firing stroke. The frangible portion 5220 can be sufficiently rigid to withstand the force of the firing assembly 5030 as the actuator 5210 shifts distally toward the hard stop 5060 (FIG. 85D), and can be sufficiently frangible to break when the actuator 5210 reaches the hard stop 5060 without requiring excessive force by a motor and/or operator. In various embodiments, the actuator 5210 can overcome the distal connector 5080b and/or additional connector(s) before a fastener is fired from the fastener cartridge 5050. In certain embodiments, the actuator 5210 can overcome the distal connector and/or additional connector(s) as at least one fastener is fired from a fastener cavity and/or after at least one fastener has been fired from a fastener cavity.

Referring now to FIGS. 88 and 89, an end effector assembly 5300 can include a first jaw, illustrated elsewhere, and a second jaw 5302. In various embodiments, the second jaw 5302 can include a cartridge body 5350 and a tissue thickness compensator 5358 releasably secured to the cartridge body 5350. Similar to the second jaw 5002, the second jaw 5302 can include fasteners, such as surgical staples, for example, which can be removably positioned in fastener cavities in the cartridge body 5350. For example, a fastener can be ejectably positioned in each fastener cavity. In certain embodiments, the cartridge body 5350 can include a slot 5356 (FIG. 88), which can extend from a proximal portion 5304 toward a distal portion 5306 of the second jaw 5302. In various embodiments, the firing assembly 5030 can translate along the slot 5356 of the cartridge body 5350. The firing assembly 5030 can translate within the slot of the fastener cartridge 5350 during a firing stroke, and can eject the fasteners from the fastener cavities during the firing stroke, for example. The firing assembly 5030 can engage a sled 5334 (FIG. 89) in the cartridge body 5350 during the firing stroke, for example, and can push the sled 5334 distally during the firing stroke, for example. Furthermore, during the firing stroke, the firing assembly 5030 and/or an actuator 5310 can release the tissue thickness compensator 5358 from the cartridge body 5350.

Referring still to FIGS. 88 and 89, the tissue thickness compensator 5358 can include a body 5360, a proximal mount 5362 extending from the body 5360, and a distal mount 5364 extending from the body 5360. Referring primarily to FIG. 89, a pin 5366 can extend through the proximal mount 5362 into an opening 5356a in the cartridge body 5350, such that the pin 5366 releasably holds the tissue thickness compensator 5358 relative to the cartridge body 5350 at the proximal portion 5304 of the second jaw 5302, for example. The pin 5366 can be friction fit and/or snap-fit into the opening 5356a, for example. In certain embodiments, the pin 5366 can be held in the opening 5456a utilizing one or more adhesives, for example. In some embodiments, at least a portion of the cartridge body 5350 and/or pin 5366 can be welded, for example. In various embodiments, the tissue thickness compensator 5358 can include multiple proximal mounts 5362, which can be releasably secured to the cartridge body 5350 on either side or both sides of the slot 5356 (FIG. 88) in the cartridge body 5350. In certain embodiments, the distal mount 5364 can be secured to the cartridge body 5350 at the distal portion 5306 of the second jaw 5302, for example. The distal mount 5364 can be secured to the cartridge body 5350 via at least one adhesive between the distal mount 5364 and the cartridge body 5350, for example. Additionally or alternatively, the distal mount 5364 can be secured to the cartridge body 5350 by at least one pin and/or other fastener, for example.

Referring primarily to FIG. 89, the actuator 5310 can loop around the distal mount 5364 and can extend to the sled 5334 in the second jaw 5302. In various embodiments, the actuator 5310 can comprise a cable or cord, which can extend through the cartridge body 5350 and/or through a channel 5346 defined in the second jaw 5302 and/or in the sled 5334, for example. In various embodiments, distal movement of the sled 5334 can pull the actuator 5310 to break through the distal mount 5364 of the tissue thickness compensator 5358. For example, the actuator 5310 can have a first end 5316 secured to the sled 5334, a second end 5318 secured within the cartridge body 5350, and a loop 5320 between the first end 5316 and the second end 5318. The loop 5320 can loop around the distal mount 5364, for example. In various embodiments, the loop 5320 can wrap around the distal mount 5364 between the portion of the distal mount 5364 that is secured to the cartridge body 5350 and the body 5360 of the tissue thickness compensator 5358. In certain embodiments, the second end 5318 can be fixedly secured in the cartridge body 5350, such that when the first end 5316 moves, the loop 5320 tightens around the distal mount 5364. In various embodiments, the second jaw 5302 and/or the cartridge body 5350 can include buttons, pins, and/or castors, such as a first button 5312 and a second button 5314, for example. The actuator 5310 can wrap around the first button 5312 and the second button 5314, for example. The position of the buttons 5312, 5314 and the orientation of the actuator 5310 around the buttons 5312, 5314 can cause the loop 5320 of the actuator 5310 to tighten around the distal mount 5364 when the sled 5334 and the firing assembly 5330 move distally during a firing stroke. Further, as the loop 5320 tightens around the distal mount 5364, the loop 5320 can break through the distal mount 5364 to release the body 5360 of the tissue thickness compensator 5358 from the cartridge body 5350 at the distal portion 5306 of the second jaw 5302. As such, in view of the above, the distal mount 5364 can be disengaged during the beginning of the firing stroke.

In various embodiments, when the distal mount 5364 of the tissue thickness compensator 5358 is released from the cartridge body 5350, the pin 5366 securing the proximal mount 5362 of the tissue thickness compensator 5358 to the cartridge body 5350 can be released from the opening 5356 in the cartridge body 5350. For example, at or near the beginning of a stroke, the pin 5366 can be released from the opening 5356. The pin 5366 can be sheared and/or severed by the cutting edge 5036 of the firing assembly 5030, for example, and/or can be pushed and/or driven out of the opening 5356 by an element of the firing assembly 5030. In such embodiments, the tissue thickness compensator 5358 can be released from the cartridge body 5350 at or near the beginning of the firing stroke when both the proximal mount 5362 and the distal mount 5364 are released from the cartridge body 5350. In other words, the actuator 5310 can release the tissue thickness compensator 5358 from the cartridge body 5350 prior to the firing assembly 5030 and/or the sled 5334 ejecting the fasteners from the fastener cavities in the cartridge body 5350. In some embodiments, the firing assembly 5030 and/or the sled 5334 can eject at least one fastener from a fastener cavity before and/or while the actuator 5310 releases the tissue thickness compensator 5358 from the cartridge body 5350.

A fastener cartridge assembly can comprise a cartridge body comprising a plurality of fastener cavities and a slot. The fastener cartridge assembly can further comprise a plurality of fasteners, wherein each fastener is removably positioned in a fastener cavity. The fastener cartridge assembly can further comprise a firing element configured to move along the slot, a tissue thickness compensator releasably secured to the cartridge body, and a mount, wherein the mount secures the tissue thickness compensator to the cartridge body, and wherein the mount is positioned distal to a fastener of the plurality of fasteners. The fastener cartridge assembly can further comprise a cable between the firing element and the mount, wherein the cable is configured to break the mount when the firing element moves distally along the slot. The tissue thickness compensator can be released from the cartridge body when the cable breaks the mount. The cable can break the mount prior to the removal of the fasteners from the fastener cavities. The fastener cartridge assembly can further comprise a channel, wherein the cable extends through the channel.

Referring now to FIGS. 93A-93D, an end effector assembly 5600 can include a first jaw, illustrated elsewhere, and a second jaw 5602. In various embodiments, the second jaw 5602 can include a fastener cartridge body 5650 and a tissue thickness compensator 5658 releasably secured to the second jaw 5602 and/or to the fastener cartridge body 5650. In certain embodiments, the fastener cartridge body 5650 and the tissue thickness compensator 5658 releasably secured thereto can comprise a fastener cartridge assembly. Referring primarily to FIG. 93A, the cartridge body 5650 can have a cartridge deck 5652 and fastener cavities 5654 defined in the cartridge deck 5652. Further, the second jaw 5602 can include fasteners, such as surgical staples, for example, which can be removably positioned in the fastener cavities 5654. For example, a single fastener can be ejectably positioned in each fastener cavity 5654 of the cartridge body 5650. Still referring primarily to FIG. 93A, the cartridge body 5650 can include a ridge 5648 extending from the cartridge deck 5652. The ridge 5648 can extend around at least a portion of a fastener cavity 5654, for example. In various embodiments, when a fastener is positioned in a fastener cavity 5654, the tip of the fastener can protrude from the fastener cavity 5654. In such embodiments, the ridge 5648 positioned at least partially around the fastener cavity 5654 can support and/or guide the tip of the fastener when the fastener is ejected from the fastener cavity 5654. In certain embodiments, referring still to FIG. 93A, the cartridge body 5650 can include a slot 5656, which can extend from a proximal portion 5604 of the second jaw 5602 toward a distal portion 5606 of the second jaw 5602. In various embodiments, a firing assembly 5630 can translate along the slot 5656 of the cartridge body 5650. For example, the firing assembly 5630 can translate along the slot 5656 during a firing stroke, and can eject fasteners from the fastener cavities 5654 during the firing stroke.

Referring still to FIGS. 93A-93D, the firing assembly 5630 can include a firing bar 5632, a cutting edge 5636, a crossbar 5638, and a foot 5644. The cutting edge 5636 can cut tissue and/or cut the tissue thickness compensator 5658 as the firing assembly 5630 is fired through the second jaw 5602 during a firing stroke. The crossbar 5638 can engage a slot in the anvil of the first jaw to hold the firing assembly 5630 relative to the first jaw, and the foot 5644 can engage a slot in the second jaw 5602, such as the slot 5656 in the cartridge body 5650, for example, to hold the first jaw relative to the cartridge body 5650. In various embodiments, the crossbar 5638 and/or the foot 5644 can hold the cutting edge 5636 of the firing assembly 6530 perpendicular to the deck 5652 of the fastener cartridge 5650, for example. Referring primarily to FIGS. 93A and 93D, the firing assembly 5630 can engage a sled 5634 in the cartridge body 5650 during the firing stroke. The firing assembly 5630 can push the sled 5634 distally during the firing stroke to eject fasteners from the fastener cavities 5654, for example. In various embodiments, the sled 5634 can have a camming surface or ramp 5642, which can engage drivers and/or fasteners in the fastener cavities 5654, for example. When the ramp 5642 engages a driver, the ramp 5642 can push the driver toward the deck 5652 to eject the corresponding fastener from the fastener cavity 5654. Further, in various embodiments, the firing assembly 5630 can cut the tissue thickness compensator 5658 during the firing stroke.

Referring primarily to FIGS. 93A and 93B, the tissue thickness compensator 5658 can include a cartridge contacting surface 5662 (FIG. 93A) and a tissue contacting surface 5664 (FIG. 93B). The cartridge contacting surface 5662 can be positioned against the cartridge deck 5652 when the tissue thickness compensator 5658 is secured to the cartridge body 5650 (FIG. 93B), for example. Further, the tissue contacting surface 5664 can be positioned against tissue when tissue is clamped between the first jaw and the second jaw 5602, for example. Referring primarily to FIG. 93A, the tissue thickness compensator 5658 can include a mount 5660. In various embodiments, the mount 5660 can be a rectangular or triangular flap, for example, that can extend from the tissue thickness compensator 5658. Further, the mount 5660 can be a cutout portion of the tissue thickness compensator 5658, such that a space 5666 is left in the tissue thickness compensator 5658 that corresponds to the shape of the mount 5660. The mount 5660 can be aligned with the slot 5656 of the cartridge body 5650 when the tissue thickness compensator 5658 is positioned relative to the cartridge body 5650, for example. Further, the mount 5660 can extend into the slot 5656 when the cartridge contacting surface 5662 of the tissue thickness compensator 5658 is positioned adjacent to the deck 5652 of the cartridge body 5650. In various embodiments, the mount 5660 can be friction fit into the slot 5656 when the tissue thickness compensator 5658 is secured to the cartridge body 5650. The mount 5660 can hold at least a portion of the tissue thickness compensator 5658 relative to the cartridge body 5650. For example, when the mount 5660 is friction fit in the slot 5656, the cartridge contacting surface 5662 can be positioned against the deck 5652 of the cartridge body 5650.

In various embodiments, the tissue thickness compensator 5658 can include a plurality of mounts 5660, which can be aligned with the slot 5656 of the cartridge body 5650. For example, at least one mount 5660 can be positioned in the proximal portion 5604 of the second jaw 5602, and at least one mount 5660 can be positioned in the distal portion 5606 of the second jaw 5602. In various embodiments, the mounts 5660 can be spaced along at least a portion of the length of the tissue thickness compensator 5658. For example, the slot 5656 can be a longitudinal slot that extends from the proximal portion 5604 to the distal portion 5606 of the second jaw 5602. The mounts 5660 can be friction fit into the longitudinal slot 5656, for example, and can secure the tissue thickness compensator 5658 to the cartridge body 5650.

Referring primarily to FIGS. 93A and 93D, the sled 5634 can include a tongue 5640, which can project from the sled 5634 toward the distal portion 5606 of the jaw 5602. When the firing assembly 5630 pushes the sled 5634 during the firing stroke, the tongue 5640 can move along the slot 5656 in the cartridge body 5650. Referring primarily to FIG. 93D, the tongue 5640 can move along the slot 5656 adjacent to the cartridge contacting surface 5664 of the tissue thickness compensator 5658. Further, the tongue 5640 can move against the mounts 5660 that are positioned in the slot 5656. In various embodiments, the mounts 5660 can be deflectable. When the tongue 5640 pushes against the mounts 5660, the tongue 5640 can deflect the mounts 5660 into alignment, or at least substantial alignment, with the body of the tissue thickness compensator 5658. For example, when the tongue 5640 moves in the cartridge body 5650, the mounts 5660 can be sequentially deflected into the corresponding spaces 5666 defined in the tissue thickness compensator 5658. When the mounts 5660 are deflected out of the slot 5656, the tissue thickness compensator 5658 can be unsecured to and/or released from the cartridge body 5650. In various embodiments, another element of the sled 5634 and/or the firing assembly 5630 can deflect the mounts 5660 out of the slot 5656 to unsecure and/or release the tissue thickness compensator 5658 from the cartridge body 5650.

Figure 94:
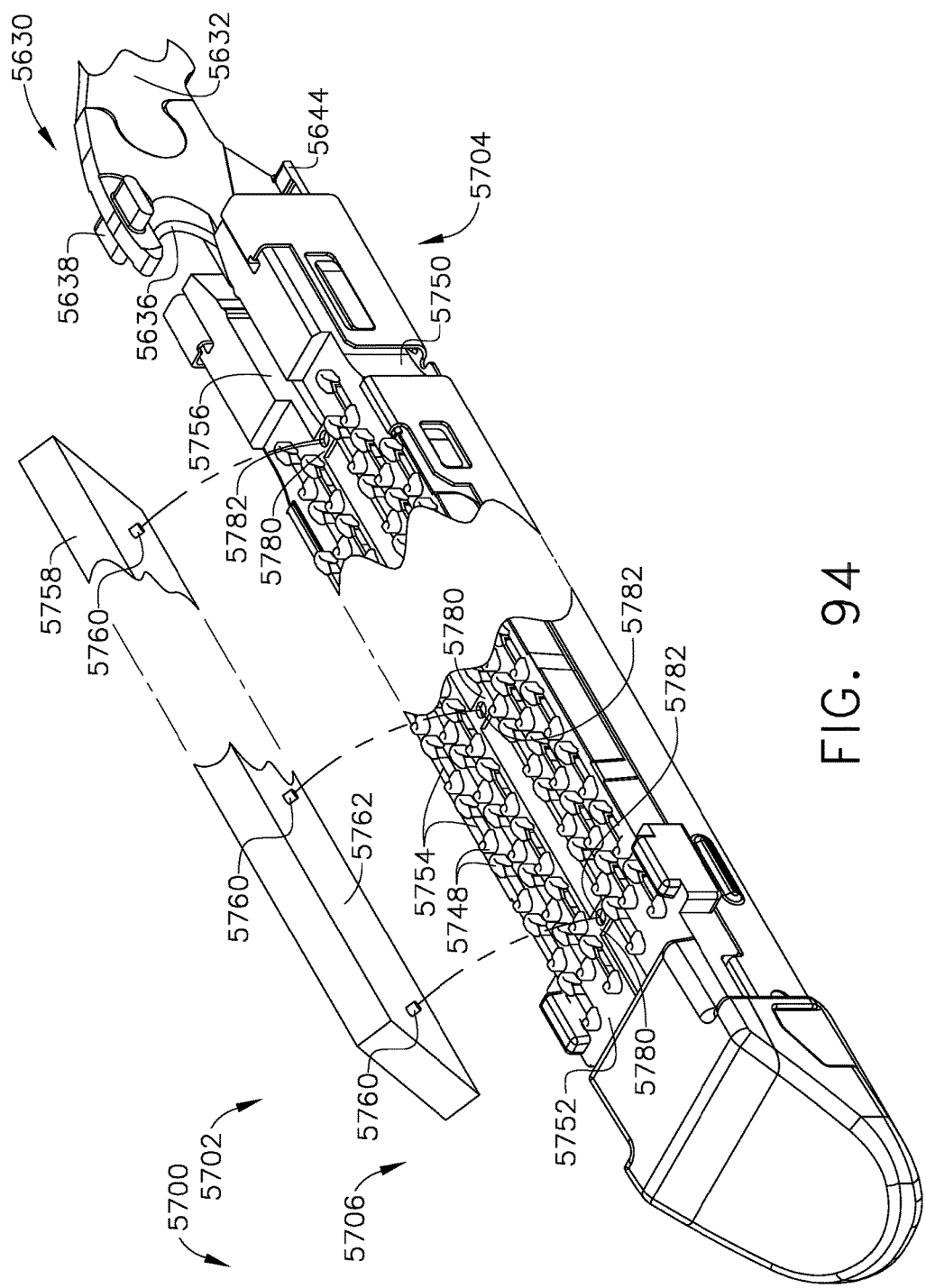
FIG. 94 is a partial, perspective view of a fastener cartridge assembly of an end effector assembly according to various embodiments of the present disclosure, depicting a tissue thickness compensator released from a cartridge body of the fastener cartridge assembly.

Referring now to FIG. 94, an end effector assembly 5700, similar to the end effector assembly 5600, can include a first jaw, illustrated elsewhere, and a second jaw 5702. In various embodiments, the second jaw 5702 can include a fastener cartridge body 5750 and a tissue thickness compensator 5758 releasably secured to the cartridge body 5750 and/or to the second jaw 5702. In certain embodiments, the fastener cartridge body 5750 and the tissue thickness compensator 5758 releasably secured thereto can comprise a fastener cartridge assembly, for example. Similar to the cartridge body 5650, the cartridge body 5750 can have a cartridge deck 5752, fastener cavities 5754 defined in the cartridge deck 5752 and for holding fasteners, ridges 5748 at least partially around the fastener cavities 5754, and/or a slot 5756 extending from a proximal portion 5704 of the second jaw 5702 toward a distal portion 5706 of the second jaw 5702. In various embodiments, the cartridge body 5750 can include a bridge 5780 traversing or extending across the slot 5756. The bridge 5780 can be a frangible and/or splitable bridge, for example. In certain embodiments, the bridge 5780 can be a thin, breakable portion, and can be a solid form absorbable material, such as PGA, PCL, PGA/PCL, PLA/PCL, and/or TMC, for example. The bridge 5780 can have an aperture 5782, which can extend at least partially through the bridge 5780.

Referring still to FIG. 94, in various embodiments, the firing assembly 5630 can translate along the slot 5756 of the cartridge body 5750. For example, the firing assembly 5630 can translate along the slot 5756 during a firing stroke, and can eject the fasteners from the fastener cavities 5754 during the firing stroke. The firing assembly 5630 can include the firing bar 5632, the cutting edge 5636, the crossbar 5638, and the foot 5644. The cutting edge 5636 can cut tissue and/or cut the tissue thickness compensator 5758 as the firing assembly 5630 is fired through the second jaw 5702 during a firing stroke. The crossbar 5638 can engage a slot in the anvil of the first jaw to hold the first jaw relative to the cartridge body 5750, and the foot 5644 can engage a slot in the second jaw 5702, such as the slot 5756 in the cartridge body 5750, for example, to hold the firing assembly 5630 relative to the second jaw 5702. In various embodiments, the crossbar 5638 and/or the foot 5644 can hold the cutting edge 5636 perpendicular to the deck 5752 of the fastener cartridge 5750, for example.

Referring still to FIG. 94, the tissue thickness compensator 5758 can include a cartridge contacting surface 5762 and a tissue contacting surface. The cartridge contacting surface 5762 can be positioned against the cartridge deck 5752 when the tissue thickness compensator 5758 is secured to the cartridge body 5750 and/or to the second jaw 5702, for example. Further, the tissue contacting surface can be positioned against tissue when tissue is clamped between the first jaw and the second jaw 5702, for example. In various embodiments, the tissue thickness compensator 5758 can include a mount 5760. The mount 5760 can be a protrusion, pin, tab, and/or post, for example, which can extend from cartridge contacting surface 5762 of the tissue thickness compensator 5758. The mount 5760 can be aligned, or at least substantially aligned, with the aperture 5782 of the bridge 5780 when the tissue thickness compensator 5758 is positioned relative to the cartridge body 5750, for example. Further, the mount 5760 can extend at least partially into the aperture 5782 when the cartridge contacting surface 5762 of the tissue thickness compensator 5758 is positioned adjacent to the deck 5752 of the cartridge body 5750. In various embodiments, the mount 5760 can be friction fit into the aperture 5782 when the tissue thickness compensator 5758 is secured to the cartridge body 5750. The mount 5760 can hold and/or secure the tissue thickness compensator 5758 relative to the cartridge body 5750 and/or to the second jaw 5702. For example, when the mount 5760 is friction fit in the aperture 5782 of the bridge 5780, the cartridge contacting surface 5762 can be positioned against the deck 5752 of the cartridge body 5750.

In various embodiments, the fastener cartridge 5750 can include a plurality of bridges 5780 extending across the slot 5756 of the cartridge body 5750. The bridges 5780 can be spaced along at least a portion of the length of the slot 5756, for example. For example, the slot 5756 can be a longitudinal slot that extends from the proximal portion 5704 to the distal portion 5706 of the second jaw 5702. Further, in various embodiments, the tissue thickness compensator 5758 can include a plurality of mounts 5760, which can be aligned with the bridges 5780 of the cartridge body 5750. For example, at least one mount 5760 can be positioned in the proximal portion 5704 of the second jaw 5702, and at least one mount 5760 can be positioned in the distal portion 5706 of the second jaw 5702 when the tissue thickness compensator 5758 is positioned relative to the cartridge body 5750. In various embodiments, the mounts 5760 can be spaced along at least a portion of the length of the tissue thickness compensator 5758. The mounts 5760 can be friction fit into the slot 5756, for example, and can secure the tissue thickness compensator 5758 to the cartridge body 5750 and/or to the second jaw 5702.

Referring still to FIG. 94, the cutting edge 5636 of the firing assembly 5630 can cut the tissue thickness compensator 5758 and/or tissue clamped between the first jaw and the second jaw 5702 of the end effector assembly 5700 when the firing assembly 5630 moves along the slot 5756 during a firing stroke. Further, the firing assembly 5630 can split the bridge 5780 when the firing assembly 5630 moves through the slot 5756. For example, the cutting edge 5636 of the firing assembly 5630 can break or cut the bridge 5780 when the firing assembly moves through the slot 5756. In various embodiments, the cutting edge 5636 can successively cut each bridge 5780 as the firing assembly 5630 moves in the slot 5756 during the firing stroke. When the bridges 5780 are cut or broken by the cutting edge 5636 the tissue thickness compensator 5758 can be unsecured to and/or released from the cartridge body 5750. In certain embodiments, the cutting edge 5636 can break or cut the mounts 5760 aligned therewith during a firing stroke. In various embodiments, another element of the sled and/or the firing assembly 5630 can break or cut the bridges 5780 to release the tissue thickness compensator 5758 from the cartridge body 5750.

Referring now to FIGS. 95 and 96, an end effector assembly 5800, similar to the end effector assembly 5600, can include a first jaw, illustrated elsewhere, and a second jaw 5802. In various embodiments, the second jaw 5802 can include a fastener cartridge body 5850 and a tissue thickness compensator 5858 releasably secured to the cartridge body 5850 and/or to the second jaw 5802. In certain embodiments, the fastener cartridge body 5850 and the tissue thickness compensator 5858 releasably secured thereto can comprise a fastener cartridge assembly. Similar to the cartridge body 5650, the cartridge body 5850 can have a cartridge deck 5852, fastener cavities 5854 defined in the cartridge deck 5852 configured to receive fasteners, a ridge 5848 positioned around at least a portion of a fastener cavity 5854, and a slot 5856, which can extend from a proximal portion 5804 of the second jaw 5802 toward a distal portion 5806 of the second jaw 5802. In various embodiments, the cartridge body 5850 can include a bridge 5880 traversing or extending at least partially across the slot 5856. The bridge 5880 can be a frangible and/or splitable bridge, for example. In certain embodiments, the bridge 5880 can include a first leg 5884 and a second leg 5886. Referring primarily to FIG. 96, the first leg 5884 can extend from a first side of the cartridge body 5850 into the slot 5856, for example, and the second leg 5886 can extend from a second side of the cartridge body 5850 into the slot 5856, for example. The first leg 5884 and the second leg 5886 can be angularly oriented relative to the axis of the slot 5856, and the first leg 5884 can be angularly oriented approximately 90 degrees relative to the second leg 5886, for example. In certain embodiments, the first leg 5884 and/or the second leg 5886 can deflectable. In various embodiments, the bridge 5880 can include a gap between the first leg 5884 and the second 5886, for example.

Referring still to FIGS. 95 and 96, in various embodiments, the firing assembly 5630 can translate along the slot 5856 of the cartridge body 5850. For example, the firing assembly 5630 can translate along the slot 5856 during a firing stroke, and can eject the fasteners from the fastener cavities 5854 during the firing stroke. The firing assembly 5630 can include the firing bar 5632, the cutting edge 5636, the crossbar 5638, and the foot 5644. The cutting edge 5636 can cut tissue and/or cut the tissue thickness compensator 5858 as the firing assembly 5630 is fired through the second jaw 5802 during a firing stroke. The crossbar 5638 can engage a slot in the anvil of the first jaw to hold the first jaw relative to the cartridge body 5850, and the foot 5644 can engage a slot in the second jaw 5802, such as the slot 5856 in the cartridge body 5850, for example, to hold the firing assembly 5630 relative to the second jaw 5802. In various embodiments, the crossbar 5638 and/or the foot 5644 can hold the cutting edge 5636 perpendicular to the deck 5852 of the fastener cartridge 5850, for example.

Referring still to FIGS. 95 and 96, the tissue thickness compensator 5858 can include a cartridge contacting surface 5862 and a tissue contacting surface. The cartridge contacting surface 5862 can be positioned against the cartridge deck 5852 when the tissue thickness compensator 5858 is secured to the cartridge body 5850 and/or to the second jaw 5802, for example. Further, the tissue contacting surface can be positioned against tissue when tissue is clamped between the first jaw and the second jaw 5802, for example. In various embodiments, the tissue thickness compensator 5858 can include a mount 5860. Similar to the mount 5760, the mount 5860 can be a protrusion, pin, tab, and/or post, for example, which can extend from the cartridge contacting surface 5862 of the tissue thickness compensator 5858. The mount 5860 can be aligned with the gap between the legs 5884, 5886 of the bridge 5880 when the tissue thickness compensator 5858 is positioned relative to the cartridge body 5850, for example. Further, the mount 5860 can be held by the legs 5884, 5886 of the bridge 5880 when the cartridge contacting surface 5862 of the tissue thickness compensator 5858 is positioned adjacent to the deck 5852 of the cartridge body 5850. In various embodiments, the mount 5860 can be friction fit into the gap between the legs 5884, 5886 when the tissue thickness compensator 5858 is secured to the cartridge body 5850. The mount-bridge engagement of the second jaw 5802 can hold the tissue thickness compensator 5858 relative to the cartridge body 5850. For example, when the mount 5860 is friction fit between the legs 5884, 5886 of the bridge 5880, the cartridge contacting surface 5862 can be held against the deck 5852 of the cartridge body 5850.

In various embodiments, referring primarily to FIG. 95, the fastener cartridge 5850 can include a plurality of bridges 5880 extending across the slot 5856 of the cartridge body 5850. The bridges 5880 can be spaced along at least a portion of the length of the slot 5856, for example. For example, the slot 5856 can be a longitudinal slot that extends from the proximal portion 5804 to the distal portion 5806 of the second jaw 5802. Further, in various embodiments, the tissue thickness compensator 5858 can include a plurality of mounts 5860, which can be aligned with the bridges 5880 of the cartridge body 5850. For example, at least one mount 5860 can be positioned in the proximal portion 5804 of the second jaw 5802, and at least one mount 5860 can be positioned in the distal portion 5806 of the second jaw 5802 when the tissue thickness compensator 5858 is positioned relative to the cartridge body 5850 and/or the second jaw 5802. In various embodiments, the mounts 5860 can be spaced along at least a portion of the length of the tissue thickness compensator 5858. The mounts 5860 can be friction fit into the bridges 5880, for example, and can secure the tissue thickness compensator 5858 to the cartridge body 5850.

Referring still to FIGS. 95 and 96, the cutting edge 5636 of the firing assembly 5630 can cut the tissue thickness compensator 5858 and/or the tissue clamped between the first jaw and the second jaw 5802 of the end effector assembly 5800 when the firing assembly 5630 moves along the slot 5856 during a firing stroke. Further, the firing assembly 5630 can split the bridge 5880 when the firing assembly 5630 moves through the slot 5856. For example, the cutting edge 5636 of the firing assembly 5630 can deflect and/or split the legs 5884, 5886 of the bridge 5880 when the firing assembly 5630 moves through the slot 5856. In various embodiments, the cutting edge 5636 can successively deflect the legs 5884, 5886 of each bridge 5880 to split each bridge 5880 as the firing assembly 5630 moves in the slot 5856 during the firing stroke. When the legs 5884, 5886 of a bridge 5880 are deflected by the cutting edge 5636, the bridge 5880 can release the corresponding mount 5860 of the tissue thickness compensator 5858. The tissue thickness compensator 5858 can be unsecured to and/or released from the cartridge body 5850 when each mount 5860 is released from each bridge 5880 along the length of the cartridge body 5850. In certain embodiments, the cutting edge 5636 can cut or break the mounts 5860 aligned therewith during a firing stroke. In various embodiments, another element of the sled and/or the firing assembly 5630 can split the bridges 5880 to release the tissue thickness compensator 5858 from the cartridge body 5850.

Figure 97:
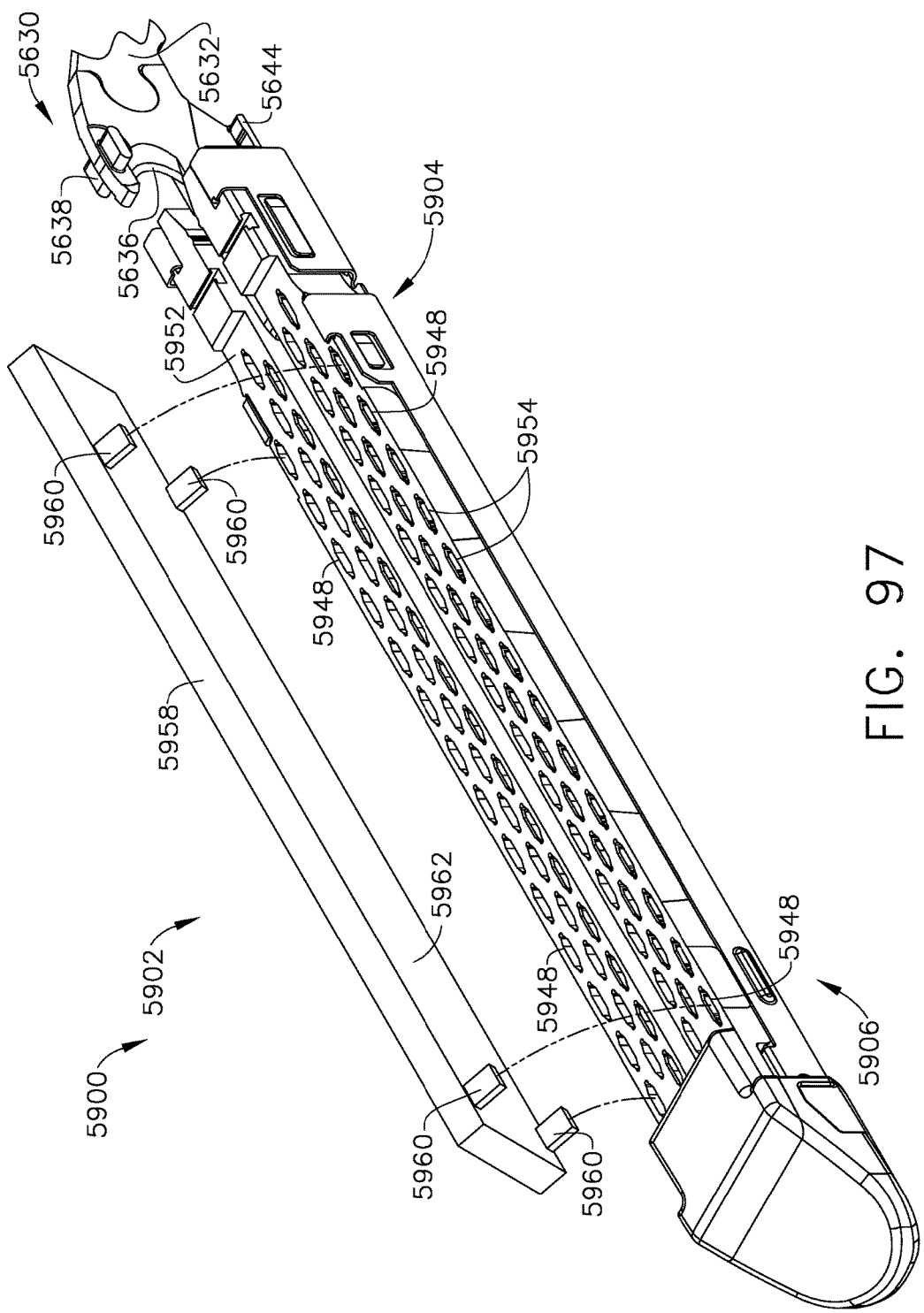
FIG. 97 is a perspective view of a fastener cartridge assembly of an end effector assembly according to various embodiments of the present disclosure, depicting a tissue thickness compensator released from a cartridge body of the fastener cartridge assembly.
Figure 98:
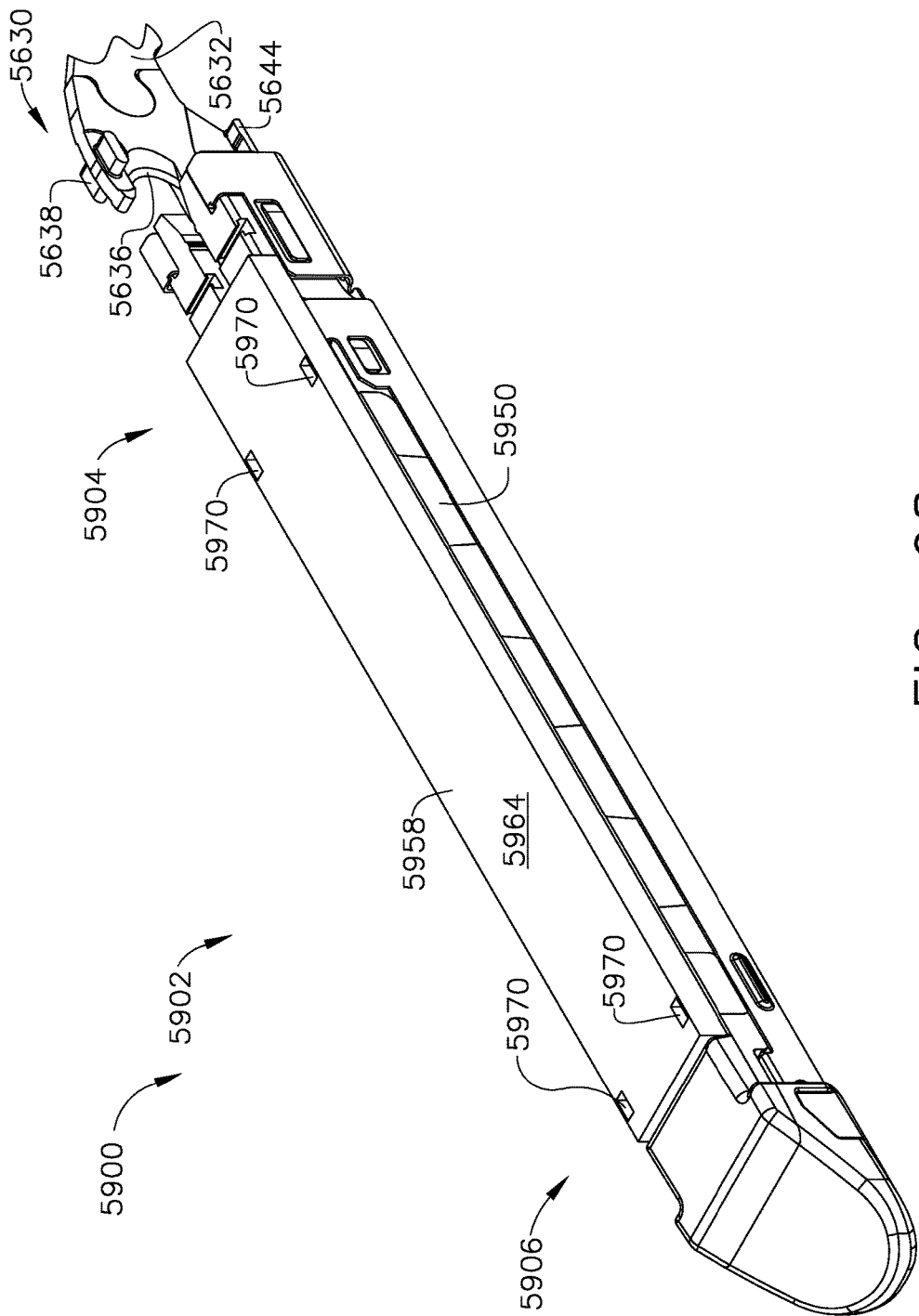
FIG. 98 is a perspective view of the fastener cartridge assembly of FIG. 97, depicting the tissue thickness compensator secured to the cartridge body of the fastener cartridge assembly.

Referring now to FIGS. 97-100, an end effector assembly 5900, similar to the end effector assembly 5600, can include a first jaw or anvil 5910 (FIGS. 99 and 100) and a second jaw 5902. In various embodiments, the second jaw 5902 can include a fastener cartridge body 5950 and a tissue thickness compensator 5958 releasably secured to the fastener cartridge body 5950 and/or to the second jaw 5902. In certain embodiments, the fastener cartridge body 5950 and the tissue thickness compensator 5958 releasably secured thereto can comprise a fastener cartridge assembly, for example. Referring primarily to FIG. 98, the fastener cartridge body 5950 can have a cartridge deck 5952 and cavities defined in the cartridge deck 5962. Mount cavities 5948 and/or fastener cavities 5954 can be defined in the cartridge deck 5952, for example. In various embodiments, the mount cavities 5948 and the fastener cavities 5954 can have the same or similar structure and/or geometry. The second jaw 5902 can include fasteners, such as surgical staples, for example, which can be removably positioned in the fastener cavities 5954. In certain embodiments, the cartridge body 5950 can include a slot 5956, which can extend from a proximal portion 5904 of the second jaw 5902 toward a distal portion 5906 of the second jaw 5902.

Referring still to FIGS. 97-100, in various embodiments, the firing assembly 5630 can translate along the slot 5956 of the cartridge body 5950 during a firing stroke, and can eject the fasteners from the fastener cavities 5954 during the firing stroke. The cutting edge 5636 can cut tissue and/or cut the tissue thickness compensator 5958 as the firing assembly 5630 is fired through the end effector assembly 5900 during the firing stroke. The crossbar 5638 can engage a slot 5912 in the anvil 5910 (FIGS. 99 and 100) to hold the first jaw relative to the cartridge body 5950, and the foot 5644 can engage a slot in the second jaw 5902, such as the slot 5956 in the cartridge body 5950, for example, to hold the firing assembly 5630 relative to the second jaw 5902. In various embodiments, the crossbar 5638 and/or the foot 5644 can hold the cutting edge 5636 perpendicular to the deck 5952 of the fastener cartridge 5950, for example.

Figure 99:
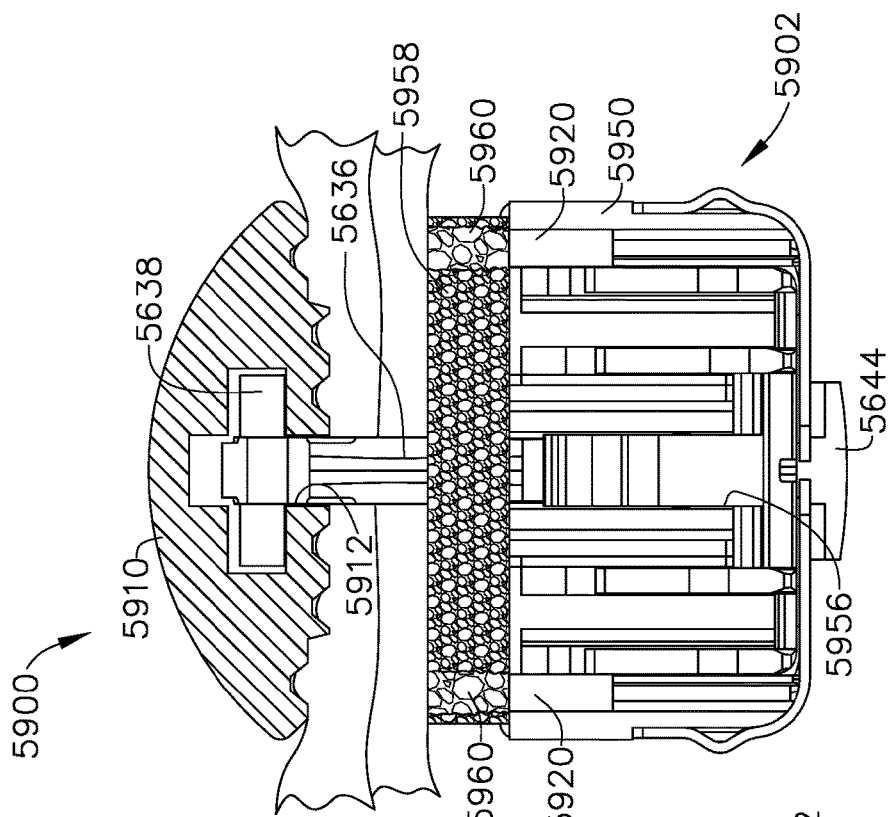
FIG. 99 is an elevational, cross-sectional view of the end effector assembly of FIG. 97, depicting the tissue thickness compensator secured to the cartridge body of the fastener cartridge assembly, and further depicting the end effector in an unclamped position.

Referring still to FIGS. 97-100, the tissue thickness compensator 5958 can include a cartridge contacting surface 5962 (FIG. 97) and a tissue contacting surface 5964 (FIGS. 98 and 99). The cartridge contacting surface 5962 can be positioned against the cartridge deck 5952 when the tissue thickness compensator 5958 is secured to the cartridge body 5950 and/or to the second jaw 5902, for example. Further, the tissue contacting surface 5964 can be positioned against tissue when tissue is clamped between the anvil 5910 and the second jaw 5902, for example. In various embodiments, the tissue thickness compensator 5958 can include a mount 5960. Similar to the mount 5760 and/or the mount 5860, for example, the mount 5960 can be a protrusion, pin, tab, and/or post, for example, which can extend from the cartridge contacting surface 5962 of the tissue thickness compensator 5958. In certain embodiments, the tissue thickness compensator 5958 can include a recess 5970, which can be adjacent to the mount 5960, for example. The recess 5970 can be vertically aligned with the mount 5970, for example. Referring primarily to FIG. 99, the recess 5970 can be defined in the tissue contacting surface 5964 of the tissue thickness compensator 5958, and can extend toward the mount 5960. In various embodiments, a thin piece of the tissue thickness compensator 5958 can be positioned between the recess 5970 and the mount 5960, for example.

The mount 5960 can be aligned with a mount cavity 5948 in the cartridge deck 5952 when the tissue thickness compensator 5958 is positioned relative to the cartridge body 5950, for example. Further, the mount 5960 can be positioned in the mount cavity 5948 when the cartridge contacting surface 5962 of the tissue thickness compensator 5958 is positioned adjacent to the deck 5952 of the cartridge body 5950. In various embodiments, the mount 5960 can be friction fit into the mount cavity 5948 when the tissue thickness compensator 5958 is secured to the cartridge body 5950. The friction fit engagement between the mount 5960 and the mount cavity 5948 can hold at least a portion of the tissue thickness compensator 5958 relative to the cartridge body 5950. For example, when the mount 5960 is friction fit in the mount cavity 5948, the cartridge contacting surface 5962 can be held against the deck 5952 of the cartridge body 5950.

Referring primarily to FIGS. 97 and 98, the fastener cartridge 5950 can include a plurality of mount cavities 5948 defined in the cartridge deck 5952. In certain embodiments, corresponding mount cavities 5948 can be defined in the cartridge deck 5952 on either side of the slot 5956. A first mount cavity 5948 can be defined on a first longitudinal side of the cartridge body 5950, for example, and a corresponding second mount cavity 5948 can be defined on a second longitudinal side of the cartridge body 5950, for example. A first pair of corresponding mount cavities 5948 can be positioned in the proximal portion 5904 of the second jaw 5902 and/or a second pair of corresponding mount cavities 5948 can be positioned in the distal portion 5906 of the second jaw 5902, for example. In various embodiments, fastener cavities 5954 can be positioned between the corresponding pairs of mount cavities 5948, i.e., closer to the slot 5956, and between the pair of mount cavities 5948 at the proximal portion 5904 of the second jaw 5902 and the pair of mount cavities 5948 at the distal portion 5906 of the second jaw 5902, i.e., in an intermediate portion of the cartridge body 5950. Further, in various embodiments, the tissue thickness compensator 5958 can include a plurality of mounts 5960, which can be aligned with the mount cavities 5948 of the cartridge body 5950. For example, at least one mount 5960 can be positioned in the proximal portion 5904 of the second jaw 5902, and at least one mount 5960 can be positioned in the distal portion 5906 of the second jaw 5902. In various embodiments, a pair of mounts 5960 can be positioned in the proximal portion 5904 of the second jaw 5902, and a pair of mounts 5960 can be positioned in the distal portion 5906 of the second jaw 5902. The mounts 5960 can be friction fit into mount cavities 5948, for example, and can secure at least a portion of the tissue thickness compensator 5958 to the cartridge body 5950.

Figure 100:
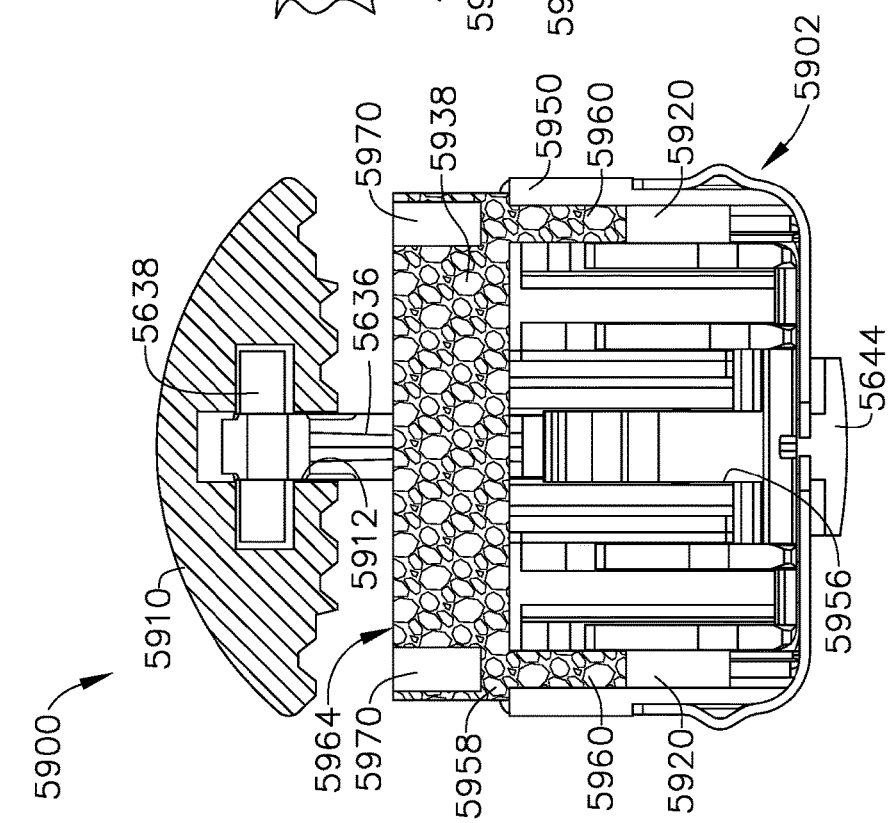
FIG. 100 is an elevational, cross-sectional view of the end effector assembly of FIG. 97, depicting the tissue thickness compensator unsecured to the cartridge body of the fastener cartridge assembly, and further depicting the end effector assembly in a clamped position.

Referring primarily to FIGS. 99 and 100, the mounts 5960 can be removed from the mount cavities 5948 during a firing stroke. In various embodiments, drivers 5920 movably positioned in the mount cavities 5948 can eject the mounts 5960 from the mount cavities 5948 during the firing stroke. For example, a driver 5920 can be positioned in each mount cavity 5948. During a firing stroke, an element of the firing assembly 5630 and/or a sled in the second jaw 5902 can engage the driver 5920 to move the driver 5920 toward the cartridge deck 5952 and/or toward the tissue thickness compensator 5958, for example. As the driver 5920 moves, the driver 5920 can push the mount 5960 positioned in the mount cavity 5948 toward the deck 5952 and/or toward the tissue thickness compensator 5958, for example. In various embodiments, the recess 5970 defined in the tissue thickness compensator 5958 that corresponds to the pushed mount 5960 can receive the pushed mount 5960. For example, the driver 5920 can push the mount 5960 into the recess 5970. The mount 5960 can be crushed, deformed and/or compressed into the recess 5970, for example. When the mounts 5960 are removed from the mount cavities 5960 during the firing stroke and pushed into the corresponding recesses 5970, the tissue thickness compensator 5958 can be unsecured and/or released from the cartridge body 5950.

Figure 63:
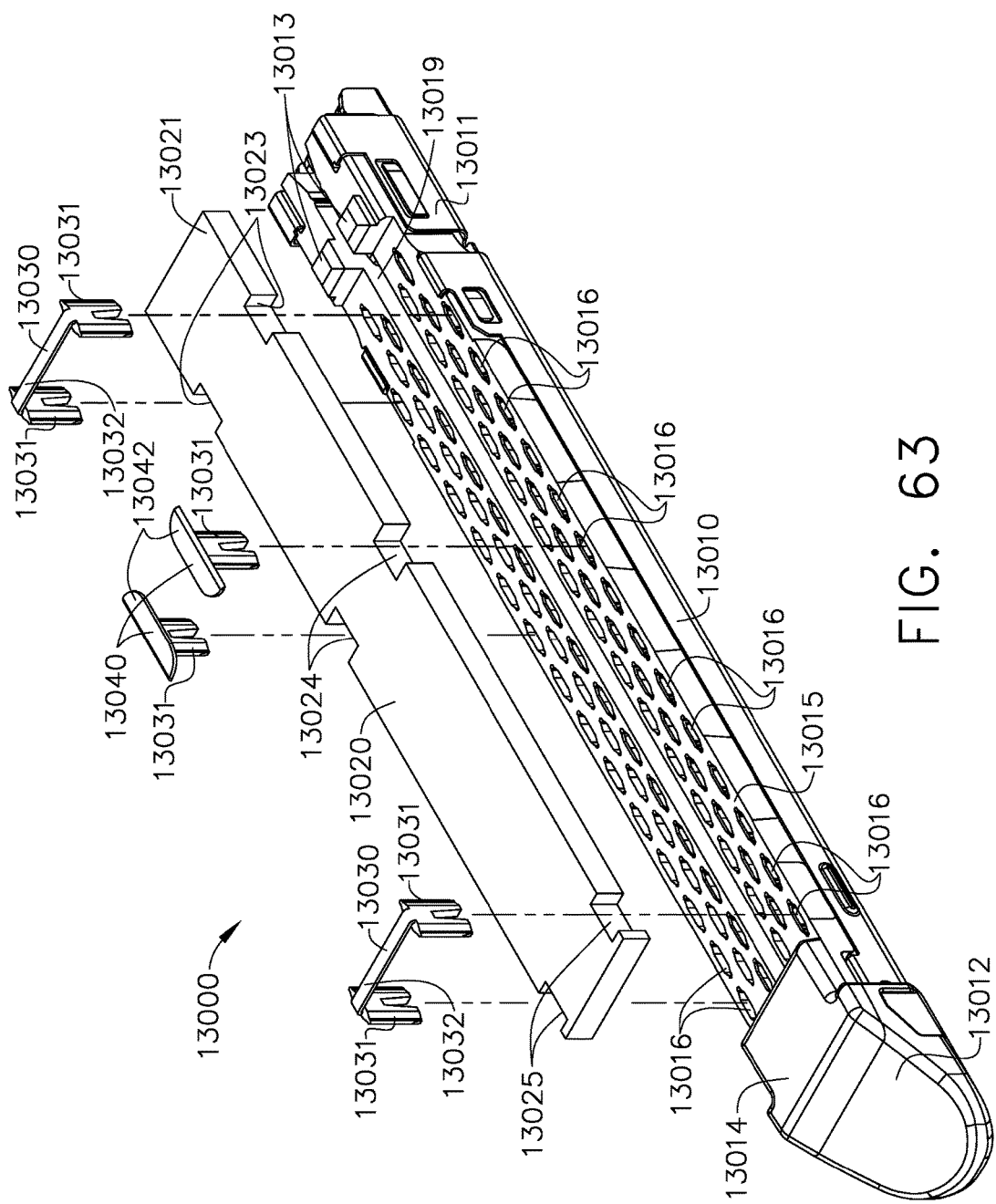
FIG. 63 is an exploded view of the staple cartridge of FIG. 62.

In various embodiments, referring now to FIGS. 62-66, a staple cartridge 13000 can comprise a cartridge body 13010, a tissue thickness compensator 13020, and a plurality of firable connectors configured to releasably hold the tissue thickness compensator 13020 to the cartridge body 13010, as described in greater detail further below. The cartridge body 13010 can comprise a proximal end 13011, a distal end 13012, and a deck 13015 configured to support the tissue thickness compensator 13020 thereon. The cartridge body 13010 can include one or more proximal stops 13013 extending therefrom which can be configured to block or resist the proximal movement of the tissue thickness compensator 13020. Similarly, the cartridge body 13010 can include one or more distal stops 13014 which can be configured to block or resist the distal movement of the tissue thickness compensator 13020. Referring primarily to FIG. 63, the cartridge body 13010 can further comprise a plurality of staple cavities 13016 defined therein. In various embodiments, the staple cartridge 13000 can comprise a plurality of connectors 13030 and 13040 configured to releasably hold the tissue thickness compensator 13020 to the cartridge body 13010. Each connector 13030, for example, can comprise a plurality of cavity plugs 13031, which are positionable in the staple cavities 13016, and a connecting bar 13032 extending between the cavity plugs 13031 and over the tissue thickness compensator 13020. The cavity plugs 13031, in at least one embodiment, can fit snugly within the staple cavities 13016. In certain embodiments, the cavity plugs 13031 can be press-fit and/or snap-fit into the staple cavities 13016. Each connector 13040, for example, can comprise a cavity plug 13031 and a head 13042 extending therefrom, wherein the head 13042 can at least partially extend over the tissue thickness compensator 13020. Referring again to FIG. 63, the tissue thickness compensator 13020 can comprise a set of proximal notches 13023 defined in the proximal end 13021 of the tissue thickness compensator 13020 configured to receive the cavity plugs 13031 extending from a proximal connector 13030, intermediate notches 13024 each configured to receive a cavity plug 13031 extending from intermediate connectors 13040, and a set of distal notches 13025 defined in the distal end 13022 of the tissue thickness compensator 13020 configured to receive the cavity plugs 13031 extending from a distal connector 13030, for example.

In use, a sled, or firing member, can be advanced distally through the staple cartridge 13000 to eject staples positioned within the staple cavities 13016. In various embodiments, the staple cavities 13016 comprising a staple positioned therein may not be plugged by a cavity plug 13031. In certain embodiments, the staple cavities having a cavity plug 13031 positioned therein may not have a staple positioned therein. In some embodiments, although not illustrated, a staple cavity may include a fastener and a cavity plug 13031 positioned therein. Referring again to FIGS. 65 and 66, the staple cartridge 13000 may further comprise a plurality of staple drivers 13050, for example, which support the staples in their unfired position. As the firing member, for example, is advanced distally through the staple cartridge, the firing member can lift the staple drivers 13050 and the staples upwardly, i.e., toward the deck 13015 of the cartridge body 13010 and toward an anvil positioned opposite the tissue thickness compensator 13020. Similarly, at least some of the staple drivers 13050 can contact and lift the cavity plugs 13031 positioned in some of the staple cavities 13016 upwardly toward the anvil. When the staples are lifted upwardly by the staple drivers 13050, the legs of the staples can pass through the tissue thickness compensator 13020, through tissue positioned between the tissue thickness compensator 13020 and the anvil, and contact the anvil positioned on the opposite side of the tissue. The staple drivers 13050 can then drive the staples against the anvil such that the staples are deformed to capture the tissue thickness compensator 13020 and the tissue therein. When the cavity plugs 13031 are lifted upwardly by the staple drivers 13050, the anvil may resist the upward movement of the cavity plugs 13031. In such circumstances, referring primarily to FIG. 63, the cavity plugs 13031 may deform, deflect, and/or break. In certain embodiments, the cavity plugs 13031 can include one or more notches, for example, which can induce the deformation, deflection, and/or breakage of the cavity plugs 13031 at a specific location therein. In various circumstances, the entirety, or at least substantial entirety, of the cavity plugs 13031 may be ejected from the staple cavities 13016 by the staple drivers 13050. At such point, the connectors 13030 and/or 13040 may no longer connect the tissue thickness compensator 13020 to the cartridge body 13010 and, as such, the cartridge body 13010 can be moved away the tissue thickness compensator 13020 that has been implanted against the tissue.

In use, further to the above, the firing member can be advanced from the proximal end 13011 toward the distal end 13012 of the staple cartridge 13000. The cartridge body 13010 can include a longitudinal slot 13019 configured to slidably receive at least a portion of the firing member therein. As the firing member is advanced distally, the firing member can eject the staples positioned in the proximal-most staples 13016 and, then, fire the proximal-most connector 13030. The firing of the proximal-most connector 13030 can release the proximal end 13021 of the tissue thickness compensator 13020 from the cartridge body 13010. In other embodiments, the firing member can fire the proximal-most connector prior to firing any staples. In any event, the firing member can be further advanced distally to eject staples from the staple cavities 13016 and then fire the intermediate connectors 13040. At such point, only the distal-most connector 13030 may remain which holds the tissue thickness compensator 13020 to the cartridge body 13010. Once the firing member has fired the distal-most connector 13030, the tissue thickness compensator 13020 may no longer be attached to the cartridge body 13010. The above-described sequence describes a staple cartridge which is fully or completely fired. Other circumstances can arise in which less than the entirety of the staples contained in the staple cartridge are fired. In such circumstances, some of the connectors holding the tissue thickness compensator 13020 to the cartridge body 13010 may not be fired. When the partial use of the staple cartridge 13000 is complete, the anvil may be opened and the cartridge body 13010 may be pulled away from the partially implanted tissue thickness compensator 13020. In such circumstances, the unfired connectors may be configured to slide out of the staple cavities 13016 even though they have not been fired. In any event, the connectors 13030 and 13040, for example, may be comprised of any suitable biocompatible and/or bioabsorbable material.

Further to the above, the firing member may include a cutting portion, such as a knife, for example, which can be configured to transect the tissue thickness compensator 13020 and the tissue as the firing member is advanced distally through the staple cartridge 13000. In such circumstances, the cutting portion can also be configured to transect the connecting bars 13032 of the connectors 13030.

Figure 101:
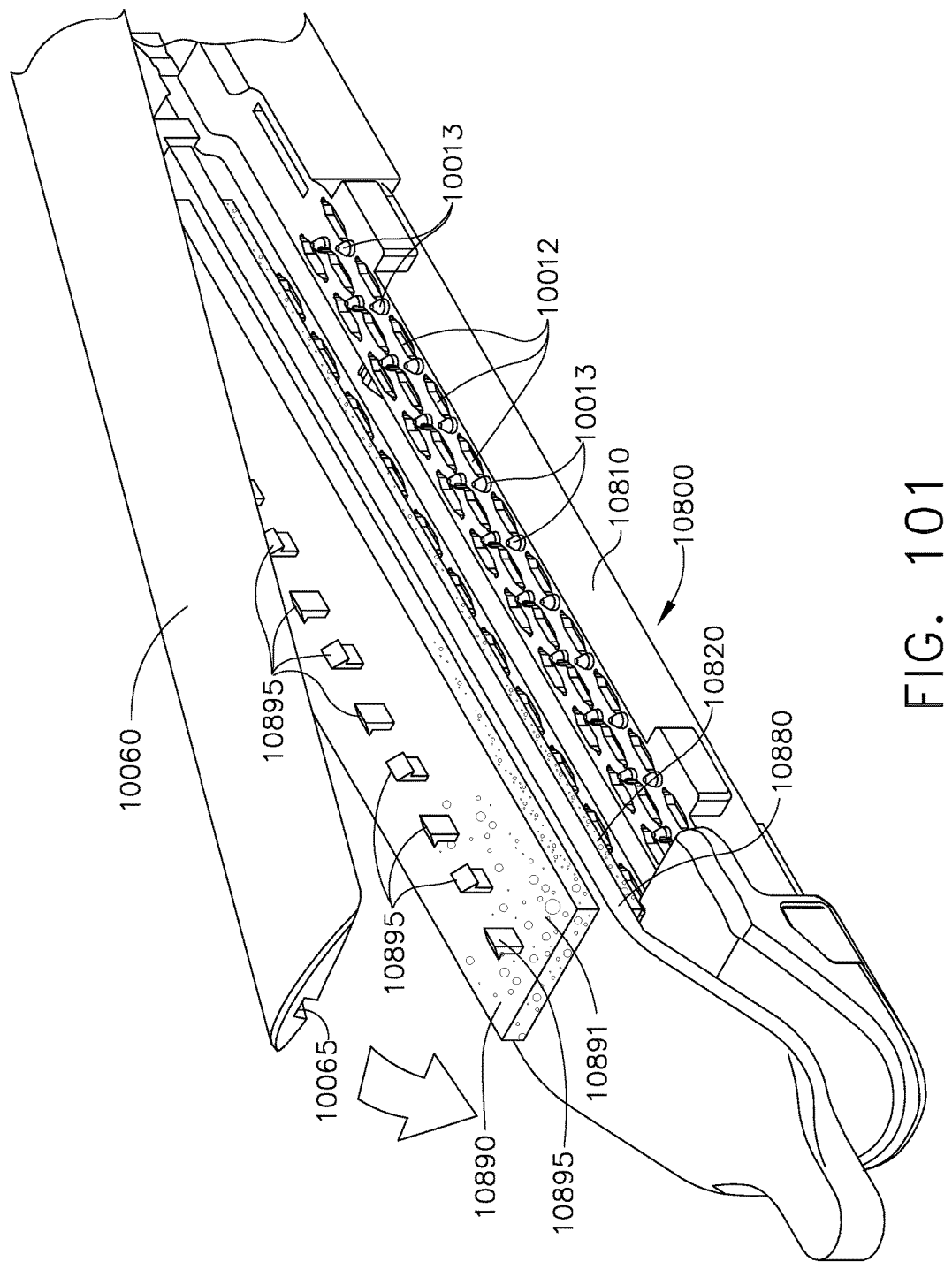
FIG. 101 is a perspective view of a staple cartridge applicator assembly comprising an upper tissue thickness compensator including a plurality of retention features extending therefrom and a staple cartridge comprising a lower tissue thickness compensator.

In various embodiments, referring now to FIGS. 101 and 102, a staple cartridge 10800 comprising a support portion 10810 and a tissue thickness compensator 10820 can be loaded into a staple cartridge channel with a staple cartridge applicator 10880, for example. Similar to the above, the staple cartridge applicator 10880 can also be configured to position an upper tissue thickness compensator 10890, for example, relative to an anvil, such as anvil 10060, for example, such that, when the anvil 10060 is closed, the anvil 10060 can contact and engage the tissue thickness compensator 10890. In at least one embodiment, the tissue thickness compensator 10890 can comprise a plurality of retention legs 10895 extending from the top surface 10891 of the tissue thickness compensator 10890 which can be configured to be engage the anvil 10060 and releasably retain the tissue thickness compensator 10890 to the anvil 10060. In at least one such embodiment, the legs 10895 can be arranged in a longitudinal row wherein each leg 10895 can comprise at least one foot configured to enter into and engage the knife slot 10065 defined in the anvil 10060. In certain embodiments, some of the feet of legs 10895 can extend in one direction while other feet can extend in another direction. In at least one embodiment, some of the feet can extend in opposite directions.

In any event, once the anvil 10060 has been engaged with the tissue thickness compensator 10890, referring now to FIGS. 102 and 103, the anvil 10060 can be reopened and the clinician can move the staple cartridge applicator 10880 away from the tissue thickness compensators 10820 and 10890. Thereafter, referring to FIG. 104, the upper tissue thickness compensator 10890 can be positioned on a first side of the targeted tissue and the tissue thickness compensator 10820, which can comprise a lower tissue thickness compensator, can be positioned on a second side of the tissue. After the tissue thickness compensators 10820 and 10890 have been suitably positioned, referring now to FIG. 105, a knife edge of a firing member, such as knife edge 10053, for example, can be advanced through the tissue and the tissue thickness compensators.

Figure 106:
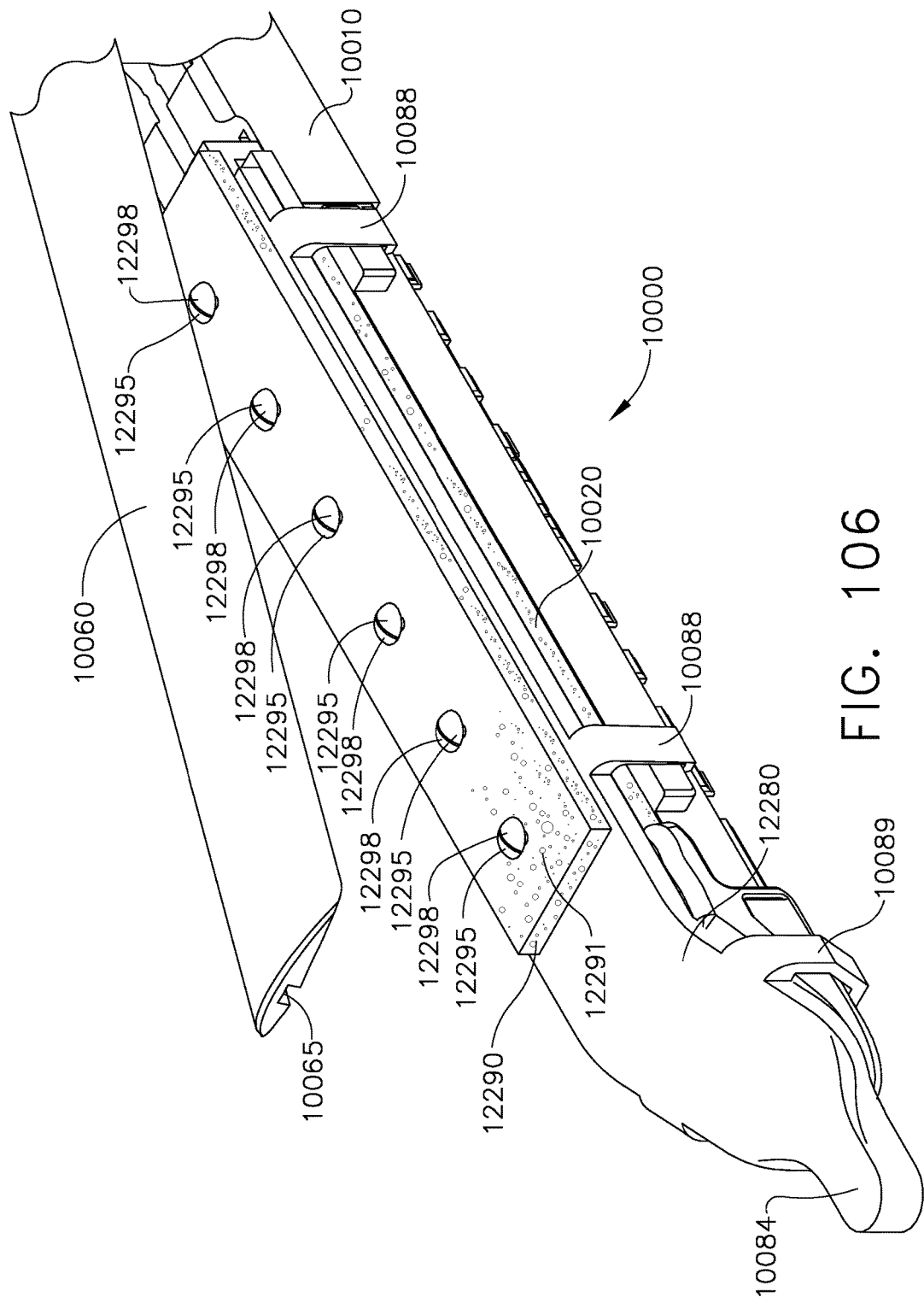
FIG. 106 is a perspective view of staple cartridge applicator assembly comprising an upper tissue thickness compensator configured to be attached to an anvil in accordance with at least one embodiment.

In various embodiments, referring now to FIG. 106, a staple cartridge applicator, such as applicator 12280, for example, can comprise a tissue thickness compensator 12290 detachably mounted thereto which can be, similar to the above, inserted into a staple cartridge channel, as illustrated in FIG. 106A, and engaged by the anvil 10060 when the anvil 10060 is moved into a closed position. The applicator 12280 may include a handle 10084 for positioning the compensator 12290 relative to a staple cartridge. In addition, the applicator 10084 may comprise a plurality of legs 10081 that may secure the compensator 12290 to the staple cartridge. In at least one such embodiment, the tissue thickness compensator 12290 can comprise a plurality of retention members 12295 extending upwardly from the top surface 12291 of the tissue thickness compensator 12290 wherein each retention member 12295 can comprise a plurality of flexible legs 12296 which can be configured to be inserted into the knife slot 10065 in the anvil 10060. Referring primarily to FIGS. 107 and 108, the flexible legs 12296 of each retention member 12295 can be separated by a gap 12298 such that, as the legs 12296 are inserted into the knife slot 10065, the legs 12296 can flex inwardly and then resiliently return outwardly once the enlarged feet of the flexible legs 12296 have passed through the knife slot 10065. In various embodiments, the enlarged feet of the flexible legs 12296 can flex behind opposing retention lips 12297 defined in the anvil 10060 and, as a result of the interaction of the legs 12296 and the lips 12297, the tissue thickness compensator 12290 can be retained to the anvil 10060. Thereafter, the staple cartridge applicator 12280 can be moved away from the tissue thickness compensator 12290, as illustrated in FIG. 106B. In use, once the tissue thickness compensator 12290 has been implanted against the tissue by staples deployed from staple cartridge 10000, for example, the anvil 10060 can be re-opened and, as the anvil 10060 is moved away from the implanted tissue thickness compensator 12290, the legs 12296 of the retention members 12995 can flex inwardly such that they can be pulled out of the knife slot 10065.

Figure 109:
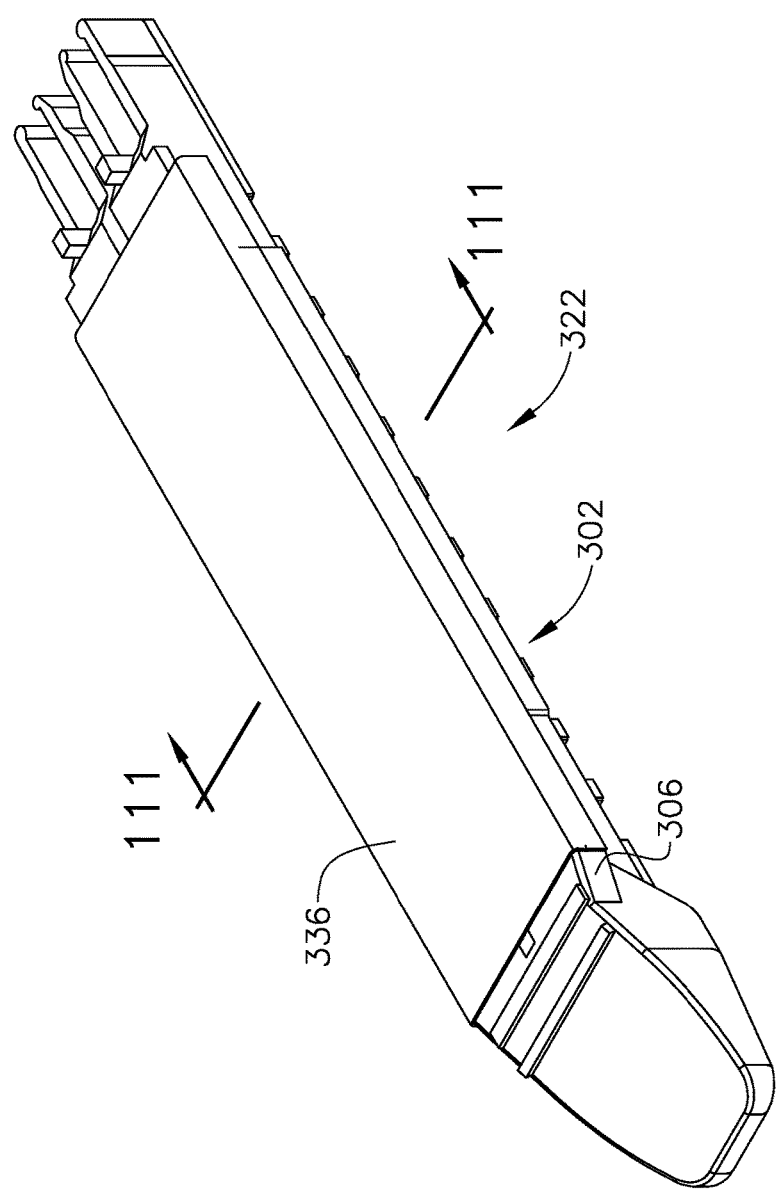
Figure 110:
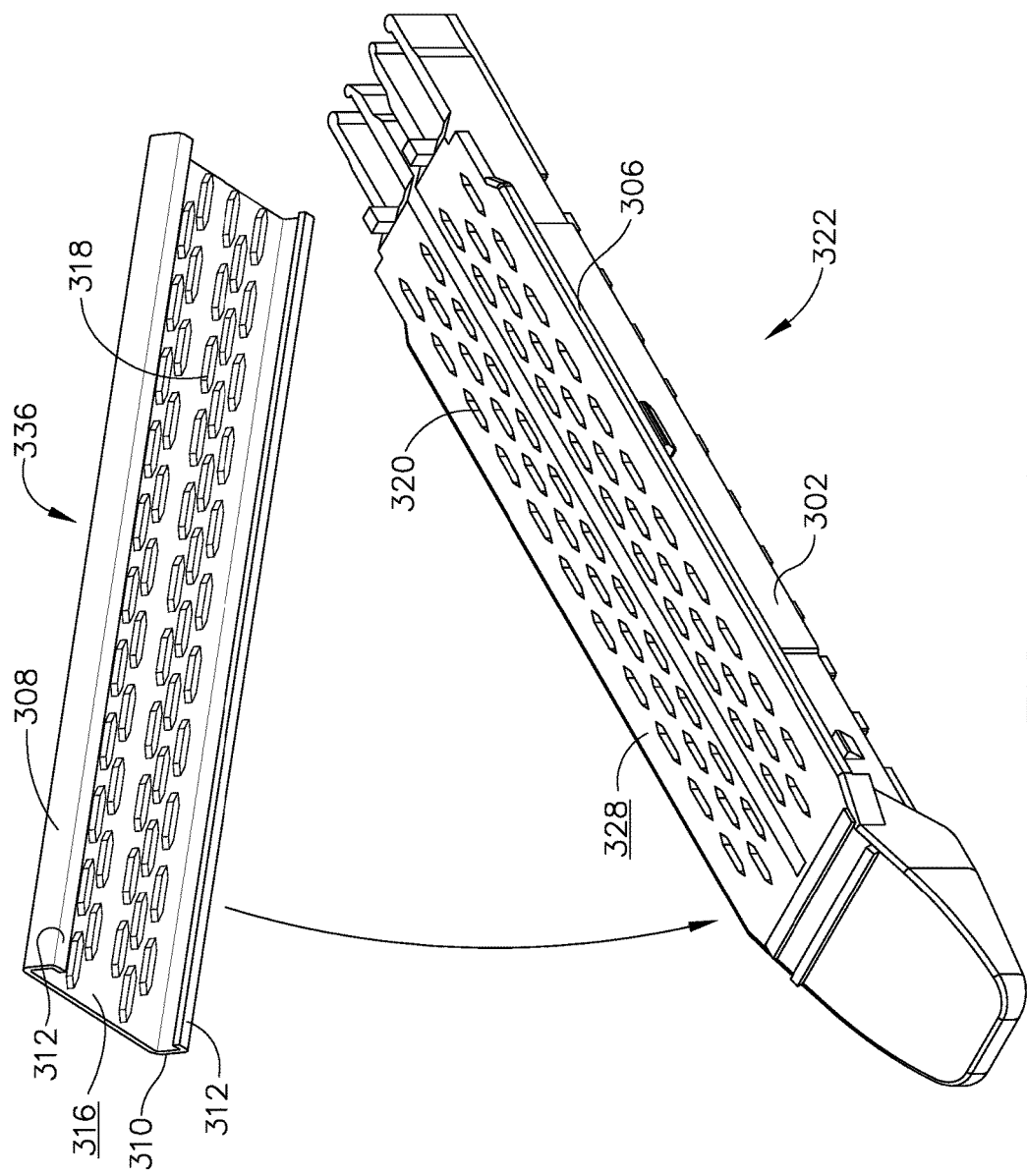
Figure 111:
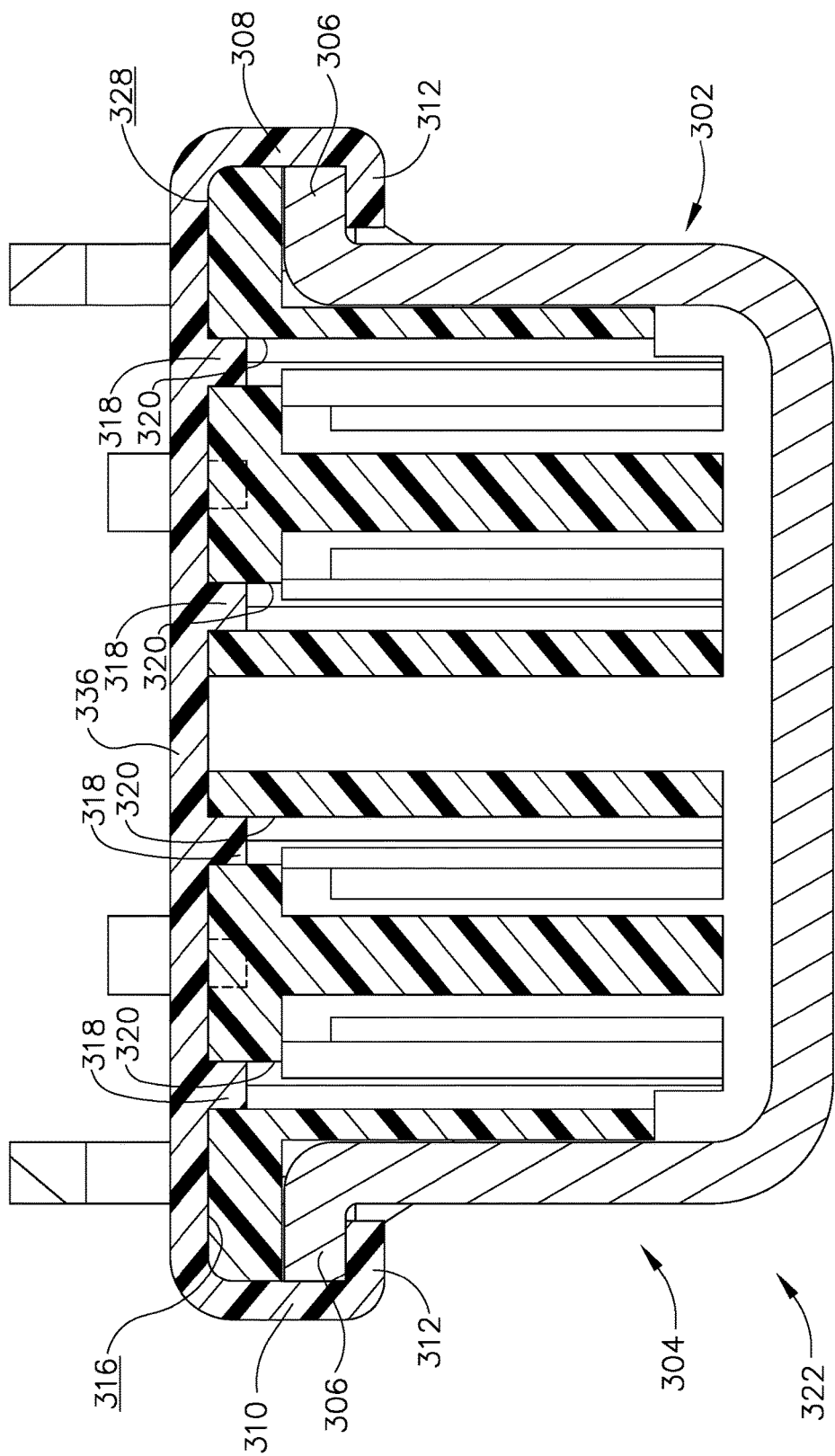

As outlined above, an end-effector assembly can include a staple cartridge, an anvil, and at least one piece of buttress material positioned intermediate the staple cartridge and the anvil. In at least one embodiment, referring now to FIGS. 109-111, a piece of buttress material, such as buttress material 336, can be configured to be snap-fit to at least one of staple cartridge 322 and/or an anvil (not illustrated) to releasably retain the piece of buttress material within the end effector. Referring to FIGS. 110 and 111, staple cartridge 322 can include first side wall 302 and second side wall 304, wherein at least one of the first and second side walls can include a lip 306 extending outwardly therefrom. In various embodiments, buttress material 336 can include first edge, or side, 308, second edge, or side, 310, and at least one lip 312 extending at least partially along the length of edges 308 and 310. In at least one embodiment, referring to FIG. 111, lips 312 can be configured to engage lips 306 in a snap-fit fashion in order to releasably retain buttress material 336 to staple cartridge 322.

Further to the above, referring to FIG. 111, buttress material 336 can include surface 316 which can be configured to be positioned adjacent to or against deck 328 of staple cartridge 322. In at least one embodiment, side edges 308 and 310 can comprise sidewalls which can extend in a perpendicular or transverse direction relative to surface 316. In such embodiments, lips 312 can extend from these sidewalls such that lips 312 can be interlocked behind lips 306 of staple cartridge 322. In various embodiments, lips 312 of buttress material 336 can be disengaged from lips 306 of staple cartridge 322 when the staples are deployed from staple cartridge 322. More particularly, when the staples are deployed, the staples can contact buttress material 336, apply an upward force to buttress material 336, and dislodge buttress material 336 from staple cartridge 322. Advantageously, as a result, buttress material 336 may be automatically disengaged from staple cartridge 322 when the staples are deployed therefrom and/or when the end-effector is opened as described above.

In various embodiments, referring to FIGS. 110 and 111, a piece of buttress material can include at least one member extending therefrom which can be configured to releasably retain the buttress material to one of a staple cartridge and/or an anvil. In at least one embodiment, member 318 can extend from buttress material 336 in a direction which is perpendicular or transverse to surface 316. In various embodiments, member 318 can be engaged with one of staple cavity 320, and/or an anvil pocket, in a friction-fit or press-fit manner to releasably retain the piece of buttress material to one of the staple cartridge and the anvil. Similar to the above, in various embodiments, staples deployed from staple cavities 320 can apply an upward force to buttress material 336 and disengage members 318 from staple cavities 320. In various embodiments, the staples can pierce members 318 and/or buttress material 336 to secure the buttress material to the tissue as outlined above.

Figure 112:
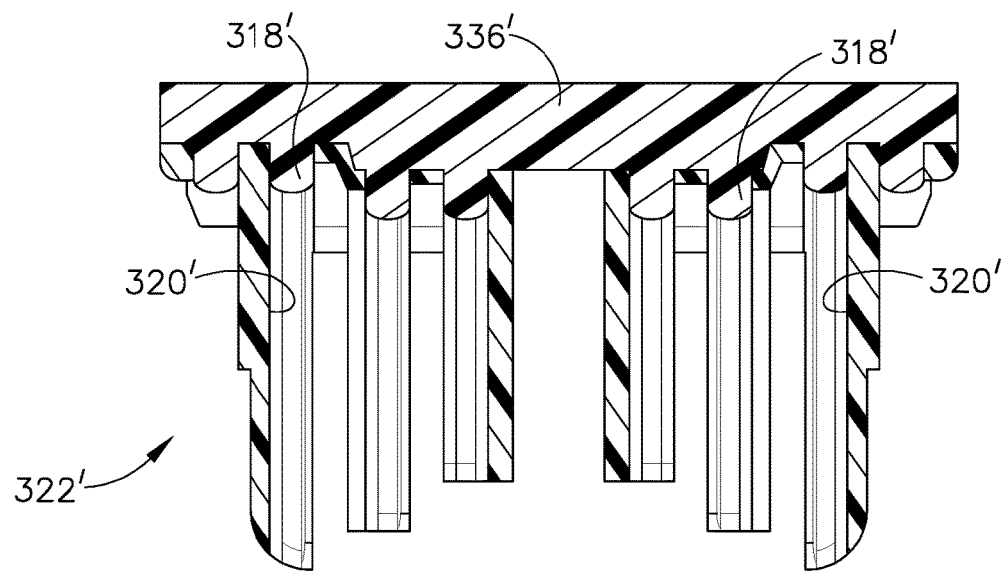
Figure 113:
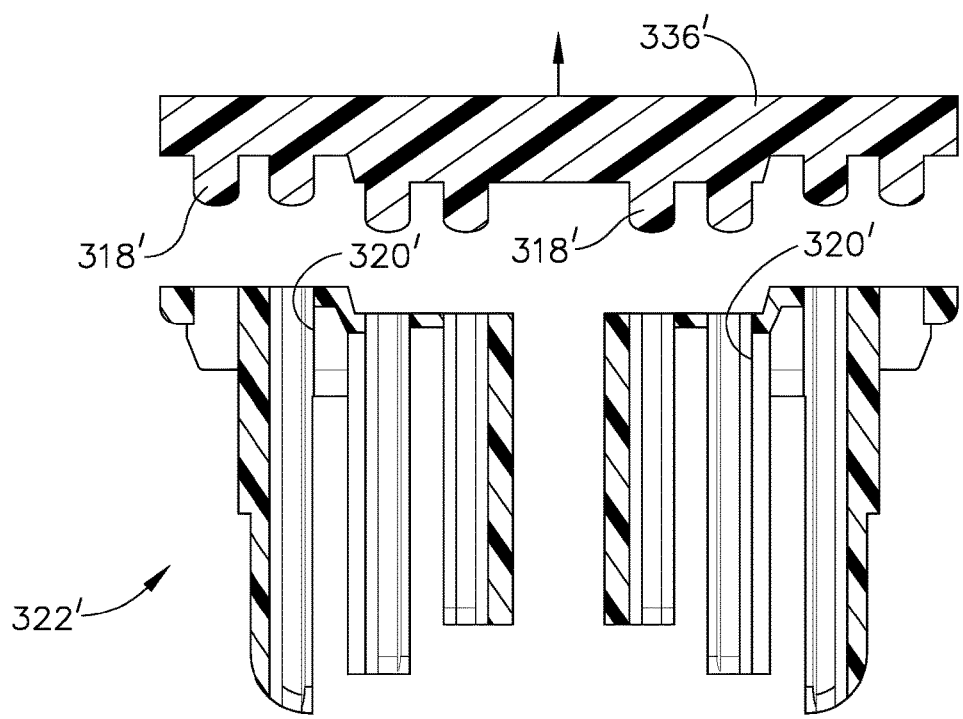

As illustrated in FIG. 110, a piece of buttress material can include more than one member, or projection, extending therefrom to retain a piece of buttress material to one of a staple cartridge and an anvil. In various embodiments, referring now to FIGS. 112 and 113, more than one member 318' can extend from piece of buttress material 336', for example. In at least one embodiment, members 318' can be can press-fit into staple cavities 320' of staple cartridge 322', and/or into anvil pockets of an anvil (not illustrated), such that the members can frictionally retain the piece of buttress material to the staple cartridge and/or the anvil as outlined above. As described in greater detail herein, a staple cartridge and/or anvil can include slots or apertures therein in addition to the staple cavities of the staple cartridge and the anvil pockets of the anvil for receiving projections, or retaining members, extending from a piece of buttress material.

Figure 114:
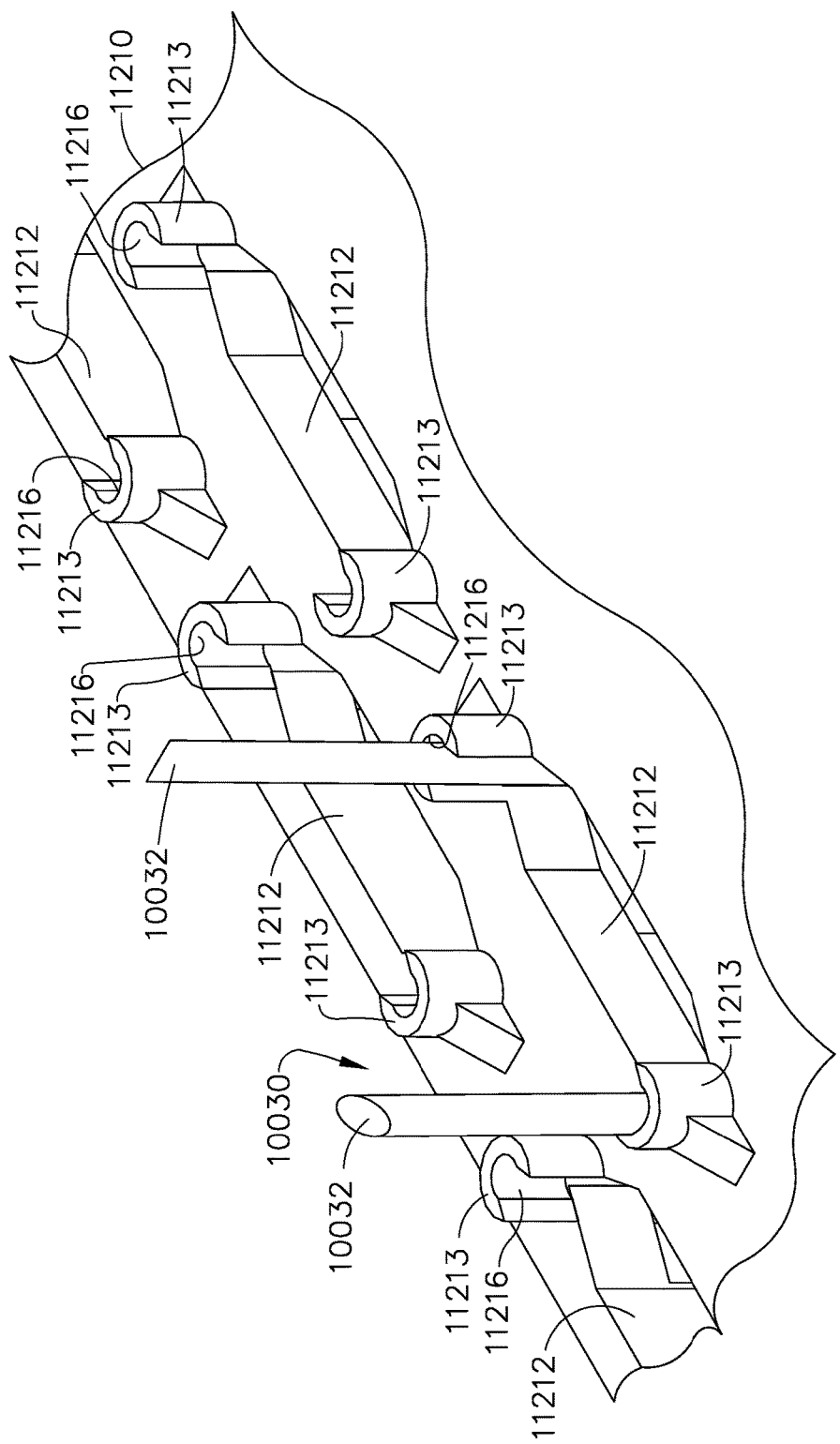

In certain embodiments, as described in greater detail below, a support portion can comprise retention features, which can be configured to progressively release a tissue thickness compensator from the support portion as the staples are progressively fired from the staple cartridge. Referring now to FIG. 114, a staple cartridge, such as staple cartridge 11200, for example, can comprise a support portion 11210 including retention features 11213 which can be configured to releasably hold a tissue thickness compensator 11220 (FIG. 115) to the support portion 11210. In various embodiments, the retention features 11213 can be positioned at the ends of each staple cavity 11212, for example, wherein each retention feature 11213 can comprise a guide groove 11216 defined therein which is configured to slidably receive a staple leg 10032 of a staple 10030. In such embodiments, both the staple legs 10032 and the retention features 11213 can be configured to releasably retain the tissue thickness compensator 11220 to the support portion 11210.

Figure 115:
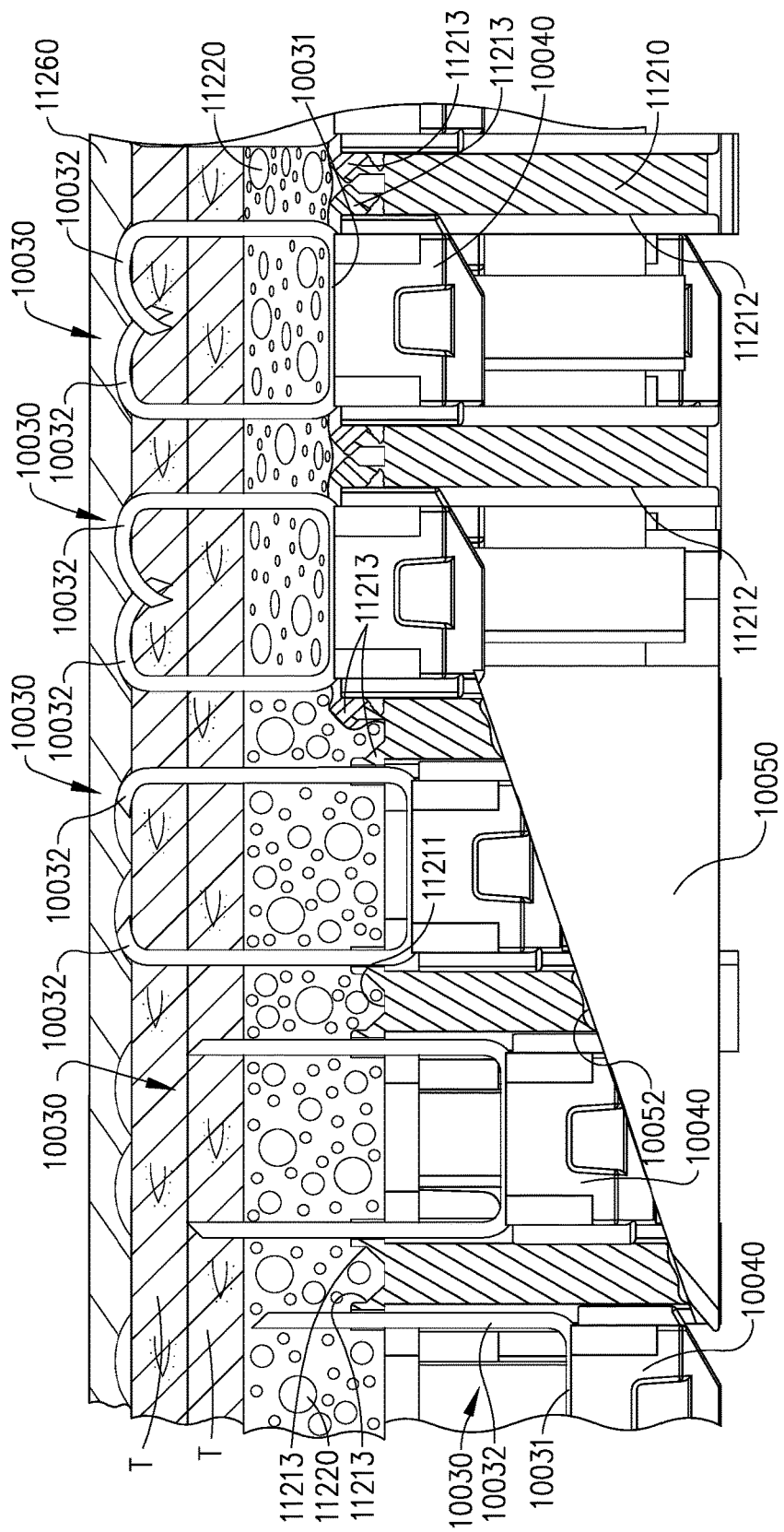

In use, referring now to FIG. 115, staple drivers 10040 contained within the support portion 11210 can be driven upwardly by a sled 10050, as described above, wherein the staple drivers 10040 can be configured to contact the retention features 11213, at least partially detach the retention features 11213 from the support portion 11210, and displace the retention features 11213 outwardly and away from the staples 10030 and the staple cavities 11212. When the retention features 11213 are detached from the support portion 11210 and/or displaced outwardly, the retention features 11213 may no longer be able to retain the tissue thickness compensator 11220 to the support portion 11210 and, as a result, the tissue thickness compensator 11220 can be released from the support portion 11210. Similar to the above, the tissue thickness compensator 11220 can be progressively released from the support portion 11210 as the staples 10030 are progressively ejected from the staple cartridge toward an anvil, such as anvil 11260, for example. In various embodiments, the staple drivers 10040 may contact the retention features 11213 when the top surfaces of the staple drivers 10040 become co-planar, or at least substantially co-planar, with the deck surface 11211 of the support portion 11210, for example. In such embodiments, the tissue thickness compensator 11220 may be released from the support portion 11210 at the same time as and/or just before the staples 10030 are formed to their fully-formed, or fully-fired, configuration.

Figure 116:
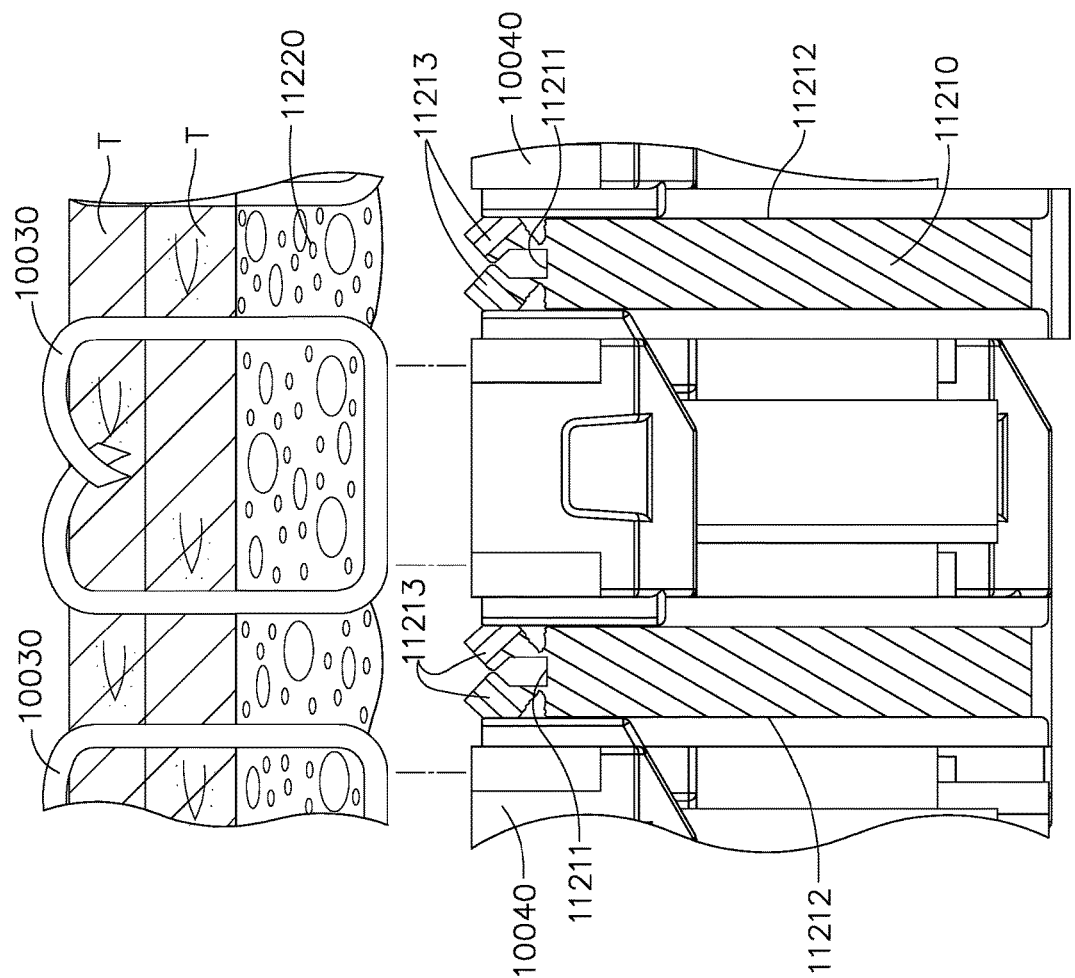

In at least one such embodiment, referring primarily to FIG. 116, the drivers 10040 can be overdriven such that they are pushed above the deck surface 11211 to fully form the staples 10030 and, during the process of being overdriven, break the retention features 11213 away from the support portion 11210. In various embodiments, referring again to FIG. 115, the retention features 11213 may extend over, or overhang, into the staple cavities 11212 prior to being detached or displaced outwardly such that the drivers 10040 can contact the retention features 11213 just as the drivers 10040 reach the deck surface 11211. In any event, once the tissue thickness compensator 11220 has been released from the support portion 11210, referring now to FIG. 116, the support portion 11210 can be moved away from the implanted tissue thickness compensator 11220.

Referring now to FIG. 117, a fastener cartridge assembly 6002 for use with an end effector assembly can include a cartridge body 6050 and a tissue thickness compensator 6058 releasably secured thereto. Similar to the cartridge body 5650, for example, the cartridge body 6050 can include a slot 6056 configured to guide a firing assembly and/or fastener cavities 6054 configured to removably retain fasteners in the cartridge body 6050. In various embodiments, the cartridge body 6050 can include a projection 6048, such as a post, mount, tab, and/or ridge, for example. The projection 6048 can extend from the cartridge deck of the cartridge body 6050 and into the tissue thickness compensator 6058 when the tissue thickness compensator 6058 is positioned relative to the cartridge deck. In various embodiments, the cartridge body 6050 can include a plurality of projections 6048 extending from the cartridge deck. The projections 6048 can be positioned along the length of the cartridge body 6050, for example, and can be positioned between adjacent fastener cavities 6054, for example.

Referring still the FIG. 117, in various embodiments, the tissue thickness compensator 6058 can be thermoformed around the projections 6048 of the tissue thickness compensator 6058. For example, the tissue thickness compensator 6058 can be positioned relative to the cartridge deck of the cartridge body 6050. Once positioned, the tissue thickness compensator 6058 can be heated to a sufficient temperature such that the tissue thickness compensator 6058 deforms to accommodate the shape of the cartridge deck, including the shape of the projections 6048 extending therefrom. The tissue thickness compensator 6058 can be locally heated, for example, and can reach a temperature near and/or approaching the glass transition temperature of the material comprising the tissue thickness compensator 6058, for example. The tissue thickness compensator can be heated to approximately 90 degrees C. to approximately 120 degrees C., for example. In certain embodiments, the tissue thickness compensator can be heated to approximately 75 degrees C. to approximately 150 degrees C., for example. Once the tissue thickness compensator 6058 has deformed to fit around the projections 6048, the heat source can be removed or reduced and the tissue thickness compensator 6058 can cool. The tissue thickness compensator 6058 can be subjected to the heightened temperature for approximately 2 seconds to approximately 5 seconds, for example, to attain sufficient deformation around the projections 6048. In other circumstances, the tissue thickness compensator 6058 can be subjected to the heightened temperature for approximately 1 second to approximately 10 seconds, for example, to attain sufficient deformation around the projections 6048. When cooling, the tissue thickness compensator 6058 can shrink closer toward and/or tighter around the projections 6048, for example. In various embodiments, the thermoformed tissue thickness compensator 6058 can prevent and/or limit lateral shifting and/or buckling of the tissue thickness compensator 6058 between fastener cavities 6054 and along the length of the cartridge body 6050.

Additionally or alternatively, the tissue thickness compensator 6058 can be thermoformed around at least a portion of a fastener removably positioned in a fastener cavity 6054. For example, the tissue thickness compensator 6058 can be thermoformed around the legs of staples extending above the cartridge deck. Referring still to FIG. 117, in various embodiments, the fastener cartridge assembly 6002 can include a cover or shell 6060 around at least a portion of the cartridge body 6050. The shell 6060 can extend around the bottom, sides, and/or cartridge deck of the cartridge body 6050, for example. The shell 6060 can be secured to the cartridge body 6050 by pins 6062, for example. Further, in various embodiments, the shell 6060 can include a metallic material, such as stainless steel 300 series, stainless steel 400 series, titanium, and/or medical grade aluminum, for example. The metallic shell 6060 can facilitate heat transfer in the cartridge body 6050 and/or the projections 6048 to improve the thermoforming effect, for example.

Referring now to FIG. 118, a fastener cartridge assembly 6102 for use with an end effector assembly can include a cartridge body 6150 and a tissue thickness compensator 6158 releasably secured thereto. Similar to the cartridge body 5650, the cartridge body 6150 can include a slot 6156 configured to guide a firing assembly, for example, and fastener cavities 6154 configured to removably hold fasteners in the cartridge body 6150, for example. The cartridge body 6150 can also include a ridge 6146, similar to the ridge 5648, extending from the cartridge deck 6152. The ridge 6146 can extend around at least a portion of a fastener cavity 6154, for example. In various embodiments, when a fastener is positioned in a fastener cavity 6154, the tip of the fastener can protrude from the fastener cavity 6148. In such embodiments, the ridge 6146 positioned at least partially around the fastener cavity 6154 can support and/or guide the tip of the fastener when the fastener is ejected from the fastener cavity 6154. In various embodiments, the cartridge body 6150 can include a plurality of ridges 6146 at least partially surrounding the fastener cavities 6154. For example, a ridge 6146 can extend around at least the proximal and/or distal ends of each fastener cavity 6154.

Referring still to FIG. 118, in various embodiments, the fastener cartridge assembly 6102 can include a cover or shell 6160, similar to shell 6060, for example, positioned around at least a portion of the cartridge body 6150. The shell 6160 can extend around the bottom and/or sides of the cartridge body 6150, for example, and can be secured to the cartridge body 6150 by pins 6162, for example. In various embodiments, the shell 6160 can include a projection 6148, such as a post, mount, tab, and/or ridge, for example. The projection 6148 can extend beyond the cartridge deck 6152 of the cartridge body 6150. In various embodiments, the projection 6148 can extend into the tissue thickness compensator 6158 when the tissue thickness compensator 6158 is positioned relative to the cartridge deck. In various embodiments, the shell 6160 can include a plurality of projections 6148 extending therefrom. The projections 6148 can be positioned along the length of the shell 6160, for example, and around the perimeter of the cartridge body 6150, for example.

Similar to the tissue thickness compensator 6058, the tissue thickness compensator 6158 can be thermoformed around the projections 6148 of the shell 6160. In various embodiments, the tissue thickness compensator 6158 can be wider than the shell 6160 such that a portion of the tissue thickness compensator 6158 extends beyond the perimeter of the cartridge body 6150. In such embodiments, the tissue thickness compensator 6158 can be thermoformed to the projections 6148 around the perimeter of the cartridge body 6150, for example. Additionally or alternatively, the tissue thickness compensator 6158 can be thermoformed to the ridges 6146 and/or to the staple legs extending from the fastener cavities 6154, for example. In various embodiments, the shell 6160 can include a metallic material, such as such as stainless steel 300 series, stainless steel 400 series, titanium, and/or medical grade aluminum, for example, to facilitate heat transfer and improve the thermoforming effect.

Referring now to FIGS. 119 and 120, an end effector assembly 6200 can include a first jaw or anvil 6210 and a second jaw 6202. The second jaw 6202 can include a cartridge body 6250 and a tissue thickness compensator 6258 releasably secured thereto. Similar to the cartridge body 5650, the cartridge body 6250 can include fastener cavities 6254 and fasteners, such as surgical staples, for example, which can be removably positioned therein. In various embodiments, a surgical staple 6290 can be positioned on a driver 6220 in a fastener cavity 6254. Referring primarily to FIG. 119, when the driver 6220 is in a pre-fired position, a portion of the staple 6290 can be positioned in the fastener cavity 6254. In various embodiments, the staple 6290 can include a base 6292 and legs 6294a, 6294b extending from the base 6292. The first leg 6294a can extend from a first end of the base 6292, for example, and a second leg 6294b can extend from a second end of the base 6292, for example. In various embodiments, when the driver 6220 is in a pre-fired position and the staple 6290 is in a pre-formed configuration, the base 6292 of the staple 6290 can be positioned in the fastener cavity 6254 and the legs 6294a, 6294b of the staple 6290 can extend from the fastener cavity 6254 into the tissue thickness compensator 6258.

In various embodiments, referring still to FIGS. 119 and 120, the staple legs 6294a, 6294b can include a barb between the base 6292 and the tips 6299a, 6299b of each staple leg 6294a, 6294b. The barb can be a sharp and/or pointed protrusion, such as a thorn, for example. In various embodiments, wire diameter of staples can be approximately 0.0069", approximately 0.0079", and/or approximately 0.0089", for example. The barb can be approximately 0.001", for example. In certain circumstances, the barb can be between approximately 0.0005" to approximately 0.003", for example. In certain embodiments, a first lower barb 6296a can be positioned on the first staple leg 6294a and a second lower barb 6296b can be positioned on the second staple leg 6294b. Lower barbs 6296a. 6296b can be positioned between the base 6292 and the tips 6299a, 6299b of the staple legs 6294a, 6294b. Further, a first upper barb 6298a can be positioned on the first staple leg 6294a and a second upper barb 6298b can be positioned on the second staple leg 6294b. Upper barbs 6298a, 6298b can be positioned between the lower barbs 6296a, 6296b and the tips 6299a, 6299b on the respective staple legs 6294a, 6294b. When the driver 6220 is in a pre-fired position and the staple 6290 is in a pre-formed configuration, at least one barb 6296a, 6296b, 6298a, 6298b of the staple 6290 can be positioned in the tissue thickness compensator 6258. In such embodiments, the barb 6296a, 6296b, 6298a, 6298b can grip and/or hold the tissue thickness compensator 6258 relative to the cartridge body 6250, for example. The barb 6296a, 6296b, 6298a, 6298b embedded in the tissue thickness compensator 6258 can prevent and/or limit lateral movement of the tissue thickness compensator 6258 relative to the cartridge deck, for example, and/or can prevent lifting of the tissue thickness compensator 6258 away from the cartridge deck, for example. Additionally or alternatively, in various embodiments, a barb can positioned at the tips 6299a, 6299b of the staple legs 6294a, 6294b.

Referring primarily to FIG. 120, when the driver 6220 moves to a fired position, the staple 6290 can be removed and/or ejected from the fastener cavity 6254. Further, the tissue thickness compensator 6258 and the tissue T can be clamped between the anvil 6210 and the cartridge body 6250 of the end effector assembly 6200. The staple forming pockets 6214 in the anvil 6210 can form the staple 6290 into a B-form, for example. Further, at least one barb 6296a, 6296b, 6298a, 6298b of the staple 6290 can engage the tissue clamped within the staple 6290, for example. The barb 6296a, 6296b, 6298a, 6298b can grip and/or hold the tissue T captured within the staple 6290.

Referring now to FIGS. 121-124, a fastener 6390 can be releasably held by a lock driver 6320 in a fastener cartridge 6350 (FIGS. 123 and 124) for use with an end effector assembly. In various embodiments, the fastener 6390 can include a base 6392 and legs 6394a, 6394b extending from the base 6392. The first leg 6394a can extend from a first end of the base 6392, for example, and a second leg 6394b can extend from a second end of the base 6392, for example. In certain embodiments, the lock driver 6320 can releasably hold the base 6392 of the fastener 6390. In various embodiments, the lock driver 6320 can include a catch 6340, which can releasably hook and/or hold the base 6392. The catch 6340 can be flexible, for example, and can flex to release the base 6392 of the fastener 6390, for example. In various embodiments, the lock driver 6320 and/or the catch 6340 can be comprised of plastic, such as Ultem, for example, with either glass filler or no glass filler such that the catch 6340 is sufficiently elastically and/or plastically deformed.

Referring primarily to FIGS. 123 and 124, the lock driver 6320 can be moveably positioned in a fastener cavity 6354 defined in the cartridge deck 6352 of the cartridge body 6350. The lock driver 6320 can move from a locked position (FIG. 123) to an unlocked position (FIG. 124) in the fastener cavity. A sled and/or driver in the cartridge body 6350 can engage the lock driver 6320 during a firing stroke to the move the lock driver 6320 from the locked position to the unlocked position. In various embodiments, the fastener 6390 can be secured to the lock driver 6320 when the lock driver 6320 is in the locked position, and can be released from the lock driver 6320 when the lock driver 6320 is moved to the unlocked position. When the lock driver 6320 moves from the locked position to the unlocked position, the fastener 6390 can be ejected from the fastener cavity 6354. A key 6353 adjacent to the fastener cavity 6354 can release the fastener 6390 from the lock driver 6320, for example. The key 6353 can be a lip extending inwardly from at least a portion of the rim of the fastener cavity 6354, for example. In various embodiments, the key 6353 can have a camming surface 6355. When the lock driver 6320 moves from the locked position to the unlocked position, a ledge 6344 of the catch 6340 can abut the camming surface 6355 of the key 6353. In such embodiments, as the catch 6340 moves against the camming surface 6355, the camming surface 6355 can flex the catch 6340, such that the hook 6342 releases the base 6392 of the fastener 6390. In various embodiments, the hook 6342 can rotate upwardly to release the base 6392. For example, the hook 6342 can rotate upwardly such that the opening of the hook 6342 is directed upward toward the tissue thickness compensator 6358, and such that the base 6392 can move upward through the opening and away from the lock driver 6320.

Referring still to FIGS. 123 and 124, a tissue thickness compensator 6358 can be releasably secured to the cartridge deck 6352 of the cartridge body 6350. When the lock driver 6320 is in the locked position (FIG. 123), the staple legs 6394a, 6394b can extend from the fastener cavity 6354 into the tissue thickness compensator 6358. The staple legs 6394a, 6394b can hold the tissue thickness compensator 6358 relative to the cartridge deck 6352, for example, and can prevent and/or limit lateral movement of the tissue thickness compensator 6358 relative to the cartridge deck 6352, for example. Further, when the lock driver 6320 moves to the unlocked position and the fastener 6390 is ejected from the fastener cavity 6354 (FIG. 124), the catch 6340 can release the base 6392 of the fastener 6390 such that the fastener 6390 can disengage the lock drivers 6320 and the cartridge body 6350. When the fasteners 6390 removably positioned in the fastener cavities 6354 are ejected from their respective fastener cavities 6354 and disengage the cartridge body 6350, the tissue thickness compensator 6858 can be unsecured to and/or released from the cartridge body 6350.

Referring now to FIGS. 125-129, an end effector assembly 6400 can include a first jaw and/or anvil 6410 (FIGS. 127-129) and a second jaw 6402. The second jaw 6402 can include a fastener cartridge body 6450 and a tissue thickness compensator 6458 releasably secured to the second jaw 6402 and/or to the tissue thickness compensator 6458. In certain embodiments, the fastener cartridge body 6450 and the tissue thickness compensator releasably secured thereto can comprise a fastener cartridge assembly, for example. In various embodiments, the cartridge body 6450 can include a cartridge deck 6452 and a slot 6456 extending through at least a portion of the cartridge body 6450. Cavities can be defined in the cartridge deck 6452 and into the cartridge body 6450. For example, fastener cavities 6454 can be defined in the cartridge deck 6452 and can receive fasteners 6490 (FIGS. 126A-129) therein. The fasteners 6490 can be removably positioned in the fastener cavities 6454. For example, a single fastener 6490 can be removably positioned in each fastener cavity 6454, and can be ejected from the fastener cavity 6454 during a firing stroke. Further, lock cavities 6448 can be defined in the cartridge deck 6452 and can receive locks 6440 therein. For example, a single lock 6440 can be moveably positioned in each lock cavity 6448, and can be moved from a locked position (FIGS. 127 and 128) to an unlocked position (FIG. 129) during the firing stroke.

Referring primarily to FIG. 126, the lock 6440 can include a base 6444 and a hook 6442 moveably positioned relative to the base 6444. For example, the hook 6442 can move within an aperture formed through at least a portion of the base 6444. The hook 6442 can receive and/or hold a connector 6480, for example. The hook 6442 can be comprised of liquid crystal polymer (LCP), Nylon, Ultem, polycarbonate, and/or ABS, for example. The connector 6480 can be a suture, for example. In certain embodiments, the connector can be comprised of PDS, PGA/PCL, PLLA/PCL, TMC/PCL, PGA and/or PCL, for example. In various embodiments, when the hook 6442 is embedded or partially embedded in the base 6444, the hook 6442 can constrain the connector 6480. The connector 6480 can be held between the hook 6442 and the base 6444, for example. When the hook 6442 is lifted or partially lifted out of the base 6444, the connector 6480 can be unconstrained by the hook 6442, for example, and can move out of engagement with the lock 6440, for example. In various embodiments, the connector 6480 can slide out of engagement with the lock 6440 when the hook 6442 is at least partially lifted out of the base 6444.

Referring primarily to FIG. 126A, the connector 6480 can extend from the tissue thickness compensator 6458. The tissue thickness compensator 6458 can be friction fit and/or thermoformed with the connector 6480, for example. In various embodiments, the connector 6480 can be threaded through the hook 6442 of the lock 6440 when the lock 6440 is in the unlocked position. As the connector 6480 is thread through the hook 6442, the tissue thickness compensator 6458 can move into position relative to the cartridge body 6450. For example, the tissue thickness compensator 6458 can be positioned on the cartridge deck 6452 of the cartridge body 6450. Referring primarily to FIG. 127, once the tissue thickness compensator 6458 is positioned relative to the cartridge body 6450, the lock 6440 can be moved from the unlocked position to a locked position. For example, the hook 6442 of the lock 6440 can be embedded or partially embedded in the base 6444 such that the lock 6440 encloses and/or constrains the connector 6480. In various embodiments, the lock 6440 and/or driver 6420 can include a spring, which can bias the lock 6440 into the unlocked position, for example. When in the locked position, the tissue thickness compensator 6458 can be secured to the cartridge body 6450 by the connector-lock engagement, for example.

Referring primarily to FIGS. 128 and 129, a key can move along at least a portion of the cartridge body 6450 during a firing stroke. The key can be a sled 6434 and/or an element of the firing assembly, for example. In various embodiments, the sled 6434 can engage the drivers in the cavities in the cartridge body 6450 during the firing stroke. The sled 6434 can push the drivers toward the cartridge deck 6452 and/or toward the tissue thickness compensator 6458 to eject fasteners from the fastener cavities 6454 and/or to move the locks 6440 from the locked position to the unlocked position. Referring primarily to FIG. 128, the sled 6434 can engage a driver 6420 in the lock cavity 6448 during the firing stroke. The sled 6434 can move the driver 6420 toward the cartridge deck 6452 and/or toward the tissue thickness compensator 6458. Further, referring primarily to FIG. 129, the driver 6420 can move the lock 6440 from the locked position to the unlocked position. For example, the driver 6420 can push the hook 6442 out of the base 6444. When the hook 6442 is lifted out of the base 6444, the connector can be unconstrained by the lock 6440. In such embodiments, the tissue thickness compensator 6458 can be unsecured to and/or released from the cartridge body 6450, for example.

Figure 67:
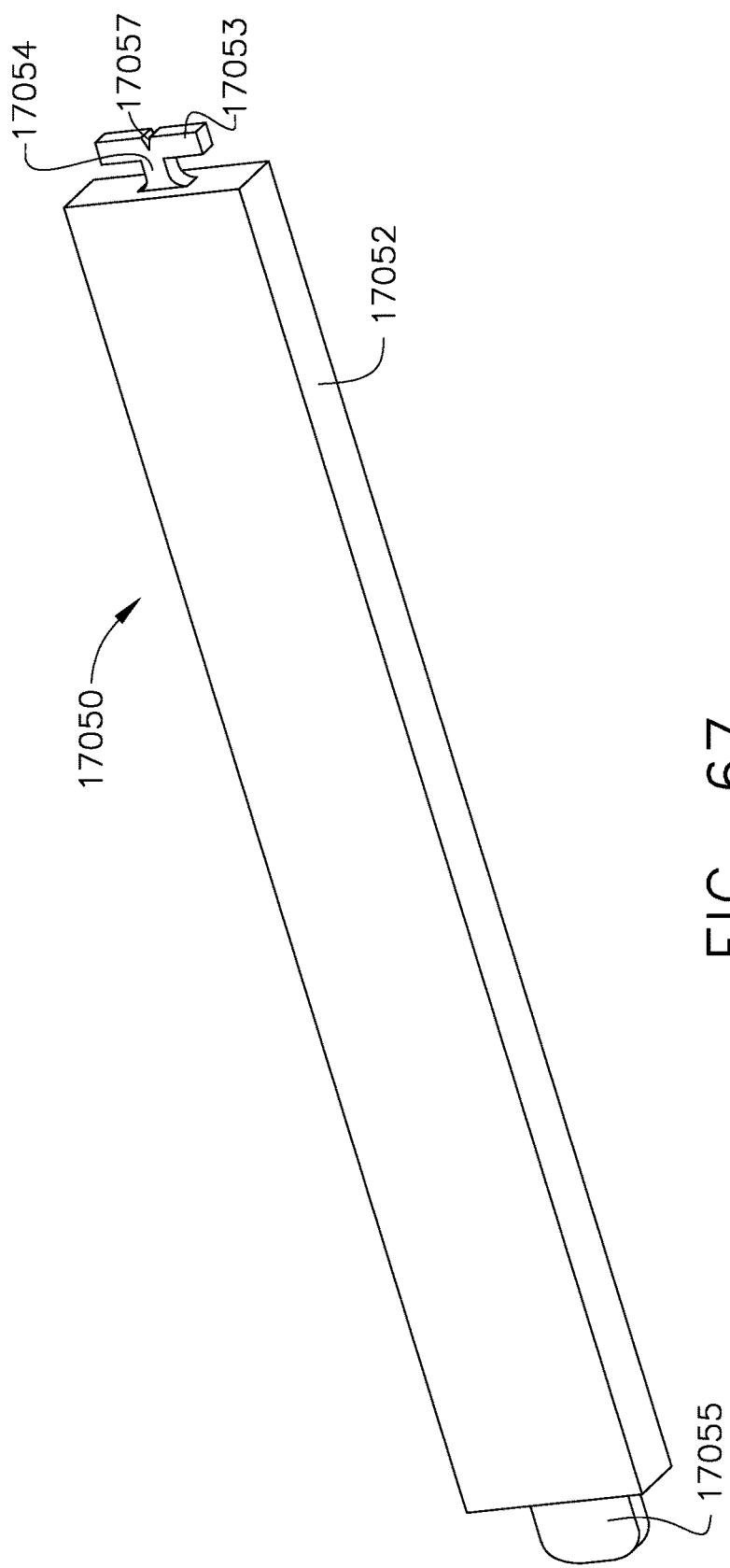
FIG. 67 is a perspective view of a tissue thickness compensator.
Figure 68:
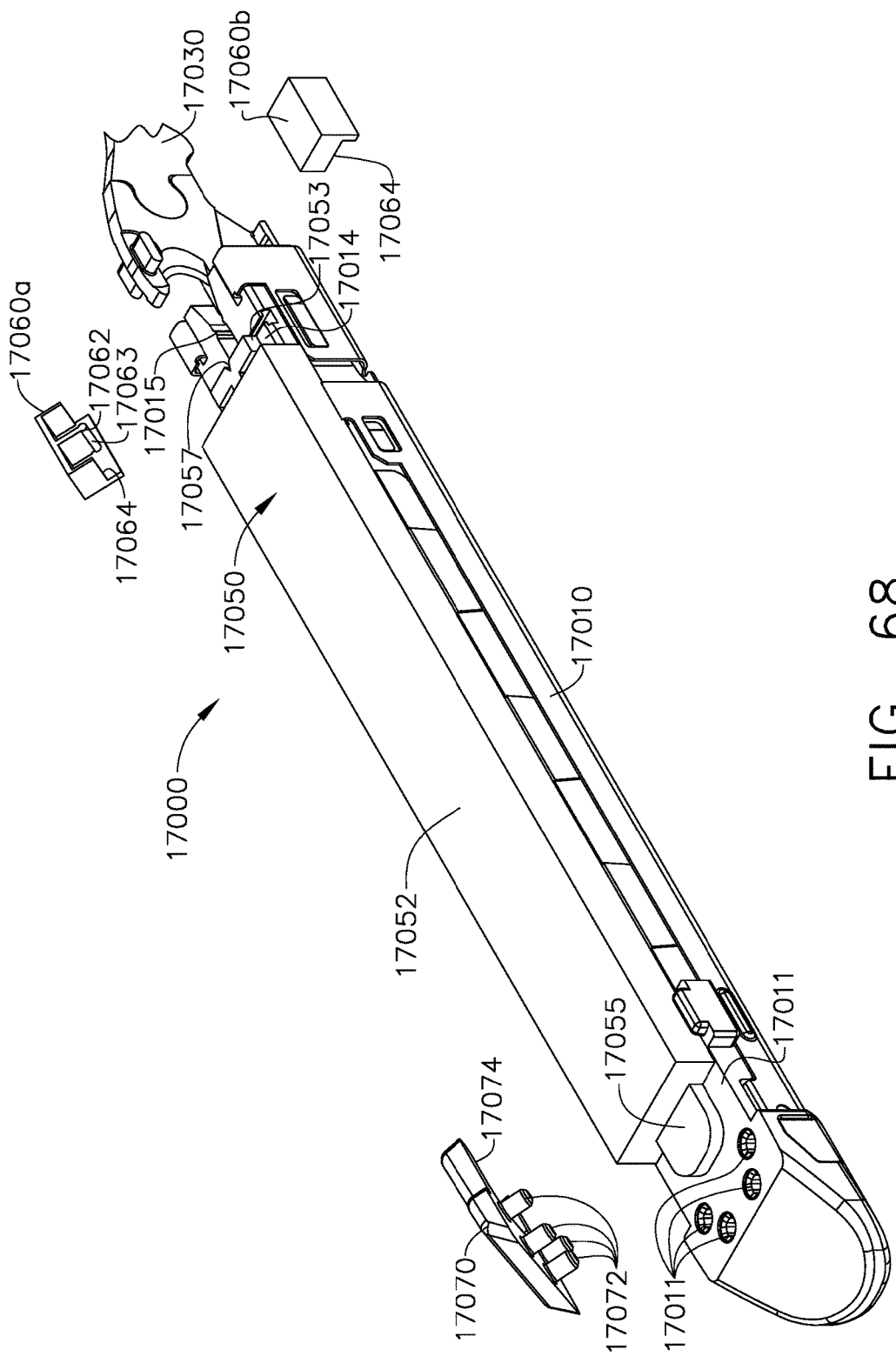
FIG. 68 is a perspective view of the tissue thickness compensator of FIG. 167 being assembled to a staple cartridge.

Referring now to FIG. 67, a tissue thickness compensator 17050, for example, can comprise a first portion 17052 and a second portion 17054 extending relative to the first portion 17052. The tissue thickness compensator 17050 can comprise part of a staple cartridge assembly. In some circumstances, the tissue thickness compensator 17050 can be attached to a cartridge body of the staple cartridge assembly. In certain circumstances, the tissue thickness compensator can be assembled to an anvil of a surgical stapling instrument. In either event, the first portion 17052 of the tissue thickness compensator 17050 can be compressible. In use, the first portion 17052 can be captured within staples ejected from the staple cartridge and can apply a compressive force to the tissue also captured within the staples. The second portion 17054 of the tissue thickness compensator 17050 can extend through the first portion 17052 wherein the second portion 17054 can comprise a proximal end 17053 and a distal end 17055 extending from the first portion 17052. As discussed in greater detail below, the second portion 17054 may be less flexible and/or more rigid than the first portion 17052. Referring now to FIG. 68, a staple cartridge assembly 17000 can comprise a cartridge body 17010 including a plurality of staple cavities defined therein and a plurality of staples at least partially stored within the staple cavities. As illustrated in FIG. 68, the tissue thickness compensator 17050 can be mounted to the cartridge body 17010.

Figure 69:
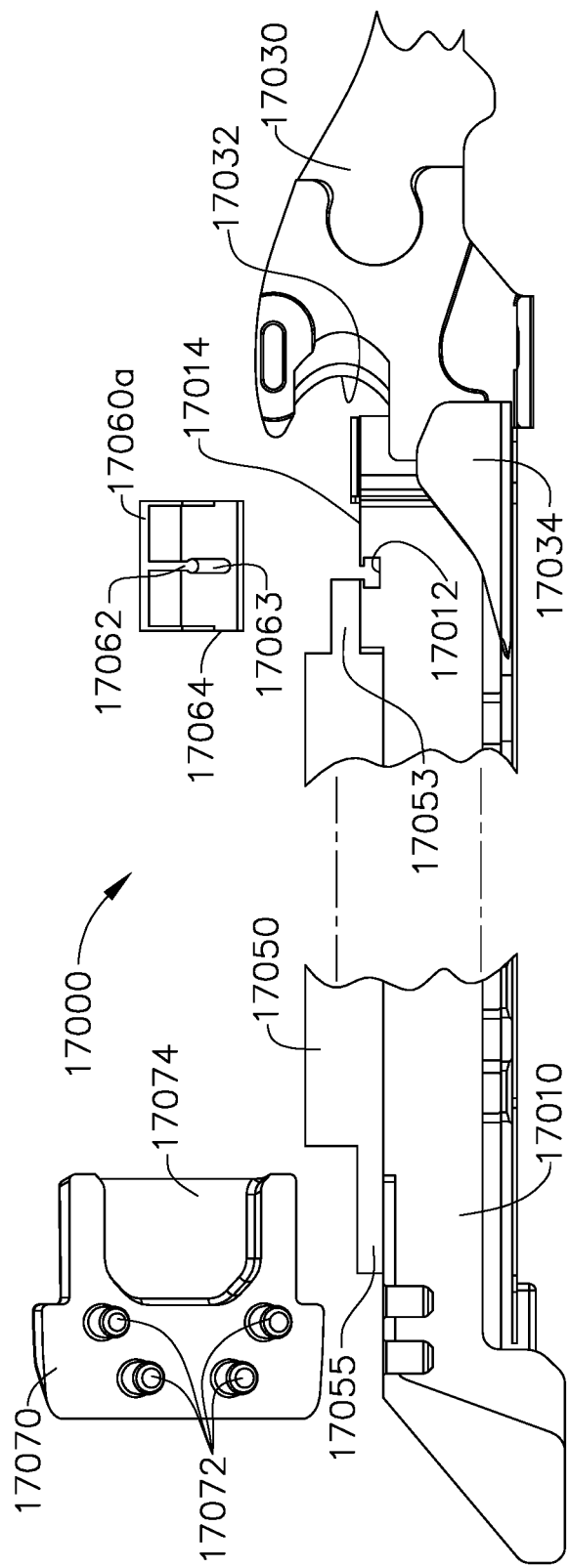
FIG. 69 is an exploded view of the tissue thickness compensator and the staple cartridge of FIG. 68.

The staple cartridge assembly 17000 can comprise a proximal mount 17060 configured to releasably hold the proximal end 17053 of the second portion 17054 to the cartridge body 17010 and a distal mount 17070 configured to releasably hold the distal end 17055 to the second portion 17054. The proximal mount 17060 can comprise a single component or more than one component. As illustrated in FIG. 68, the proximal mount 17060 can comprise a first mount portion 17060a and a second mount portion 17060b configured to at least partially capture and hold the second portion 17054 against the cartridge body 17010. Turning now to FIG. 69, each mount portion 17060a, 17060b can comprise a key 17062 which can be releasably secured within a key slot 17012 defined in the cartridge body 17010. Each key 17062 and key slot 17012 can be sized and configured such that the sidewalls of the key slot 17012 can apply a retention force to the key 17062 which resists the removal of the key 17062 from the key slot 17012. In various circumstances, the key 17062 can be releasably press-fit and/or snap-fit within the key slot 17012. In at least one circumstance, the key 17062 can comprise an enlarged end 17063 which can be releasably clamped between the sidewalls of the key slot 17012, for example. As illustrated in FIGS. 68 and 69, each mount portion 17060a, 17060b can comprise a window 17064 configured to at least partially receive the proximal end 17053 of the second portion 17054. In such circumstances, the sidewalls of the window 17064 can be configured to engage and compress the tissue thickness compensator 17030 against the deck 17014 of the cartridge body 17010. Furthermore, at least a portion of the second portion 17054 can be contained within the mount portions 17060a, 17060b.

Referring again to FIGS. 68 and 69, similar to the above, the distal mount 17070 can comprise a window 17074 which can be sized and configured to receive at least a portion of the distal end 17055 of the second portion 17054. Also similar to the above, the sidewalls of the window 17074 can be configured to engage and compress the tissue thickness compensator 17030 against the deck 17014 of the cartridge body 17010. Furthermore, at least a portion of the second portion 17054 can be contained within the mount portion 17070. The distal mount portion 17070 can comprise one or more pins 17072 extending therefrom which can be releasably secured within one or more pin apertures 17011 defined in the cartridge body 17010. Each pin 17070 and pin aperture 17011 can be sized and configured such that the sidewalls of the pin aperture 17011 can apply a retention force to the pin 17072 which resists the removal of the pin 17072 from the pin aperture 17011. In various circumstances, each pin 17072 can be releasably press-fit and/or snap-fit within a pin aperture 17011.

To assemble the staple cartridge 17000, in at least one circumstance, the tissue thickness compensator 17030 can be positioned against the deck 17014 of the cartridge body 17010 and the proximal mounts 17060 and the distal mount 17070 can then be assembled to cartridge body 17010. The mounts 17060, 17070 can be assembled to the cartridge body 17010 to capture or trap the tissue thickness compensator 17050 against the cartridge body 17010 as discussed above. As also discussed above, the mounts 17060, 17070 can be configured to capture and releasably retain the ends of the second portion 17074 to the cartridge body 17010. In certain circumstances, the proximal mounts 17060 and/or the distal mount 17070 can be configured to capture at least a portion of the first portion 17052 therein. While the tissue thickness compensator 17050 depicted in FIGS. 67-69 comprises two portions, various alternatives are envisioned in which a tissue thickness compensator can comprise more than two portions. For example, a tissue thickness compensator can comprise a compressible first portion 17052 and two or more rigid second portions 17054 extending therethrough. Also, for example, a tissue thickness compensator can comprise two or more compressible portions arranged in any suitable arrangement, such as in two or more layers, for example.

Once assembled, the staple cartridge 17000 can be assembled to a surgical stapler. In at least one circumstance, the staple cartridge 17000 can be removably retained with a channel defined in an end effector of the surgical stapler and then inserted into a surgical site within a patient. The proximal mounts 17060 and/or the distal mount 17070 can be configured to retain the tissue thickness compensator 17050 to the cartridge body 17010 while the staple cartridge 17000 is inserted into and/or manipulated within the surgical site. The second portion 17054 of the tissue thickness compensator 17050 can provide sufficient rigidity to the tissue thickness compensator 17050 such that the tissue thickness compensator 17050 does not become detached from the cartridge body 17010 until one or more of the proximal mounts 17060 and/or the distal mount 17070 is incised and/or detached from the cartridge body 17010, as discussed in greater detail below. Owing to the rigidity of the second portion 17054, in various circumstances, the attributes of the first portion 17052 of the tissue thickness compensator 17050 can be primarily or exclusively selected so as to provide the desired tissue compensation properties of the tissue thickness compensator 17050. In use, the second portion 17054 of the tissue thickness compensator 17050 can resist relative movement between the proximal end 17053 and the distal end 17055 and, in various circumstances, resist the movement of the proximal end 17053 and the distal end 17055 toward one another.

Once the staple cartridge 17000 has been suitably positioned, in various circumstances, a firing member 17030 can be advanced through the staple cartridge 17000 to deploy the staples removably positioned therein. The staple cartridge 17000 can include a movable member 17034 which can be advanced from a proximal end of the staple cartridge 17000 toward a distal end of the staple cartridge 17000 by the firing member 17030. The movable member 17034, further to the above, can be configured to lift the staples removably stored within the cartridge body 17010 between an unfired position and a fired position. The firing member 17030 can further comprise a cutting portion, such as knife 17032, for example, which can be configured to transect the tissue being stapled as the firing member 17030 is advanced distally through the staple cartridge 17000. The knife 17032 can also be configured to transect the tissue thickness compensator 17050 as the firing member 17030 is advanced distally through the staple cartridge 17000. Referring primarily to FIGS. 67 and 68, the proximal end 17053 of the second portion 17054 can be severed by the knife 17032. In at least one such embodiment, the tissue thickness compensator 17050 can be at least partially severed, or entirely severed, along a longitudinal axis at least partially defined by notch 17057 defined therein. As illustrated in FIG. 68, the notch 17057 can be aligned, or at least substantially aligned, with a longitudinal knife slot 17015 extending through the cartridge body 17010. Once the proximal end 17053 of the second portion 17054 has been at least partially transected by the knife 17032, the second portion 17054 can be at least partially released from, or can be releasable from, the proximal mounts 17060a, 17060b. In such circumstances, the tissue thickness compensator 17050 can become detached from the cartridge body 17010. For instance, the firing member 17030 may be at least partially advanced, or entirely advanced, through the staple cartridge 17000 to at least partially, or entirely, implant the tissue thickness compensator 17050 against the tissue and, owing to the at least partial transection of the tissue thickness compensator 17050, especially the second portion 17054, the tissue thickness compensator 17050 can be sufficiently flexible so as to slide out of the proximal mount portions 17060a, 17060b and the distal mount 17070. In use, in various circumstances, the firing member 17030 can be retracted to its proximal, or starting, position after the firing member 17030 has been at least partially fired and the tissue thickness compensator 17050 has been at least partially implanted wherein the cartridge body 17010 can then be pulled away from the implanted tissue thickness compensator 17050. For instance, if the cartridge body 17010 is pulled away from the tissue thickness compensator 17050 along the longitudinal axis, the at least partially transected tissue thickness compensator 17050 may be able to buckle longitudinally and the proximal and distal ends of the tissue thickness compensator 17050 may move toward one another, for example.

Figure 70:
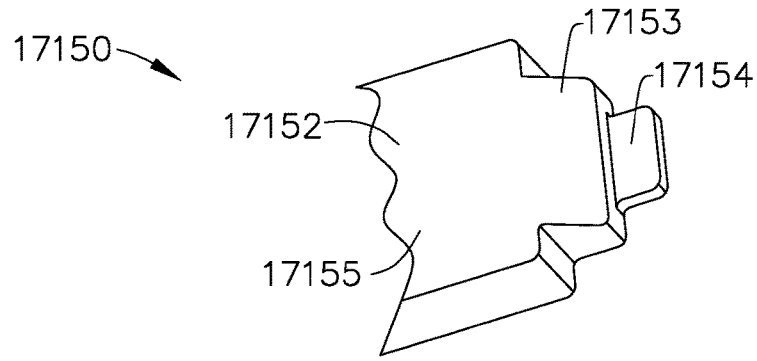
FIG. 70 is a detail view of a proximal end of a tissue thickness compensator.
Figure 71:
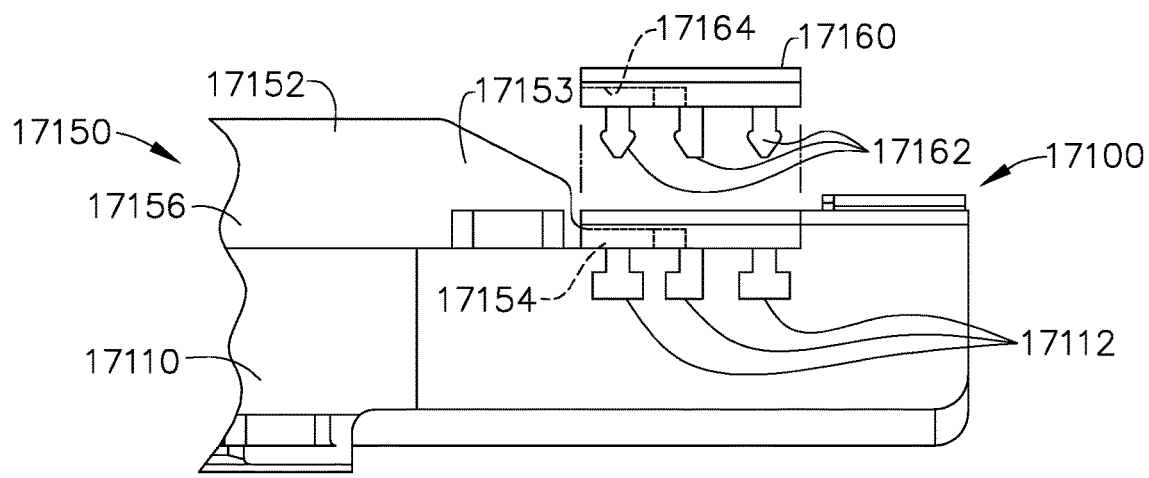
FIG. 71 is a partial elevational view of the tissue thickness compensator of FIG. 70 assembled to a staple cartridge.
Figure 72:
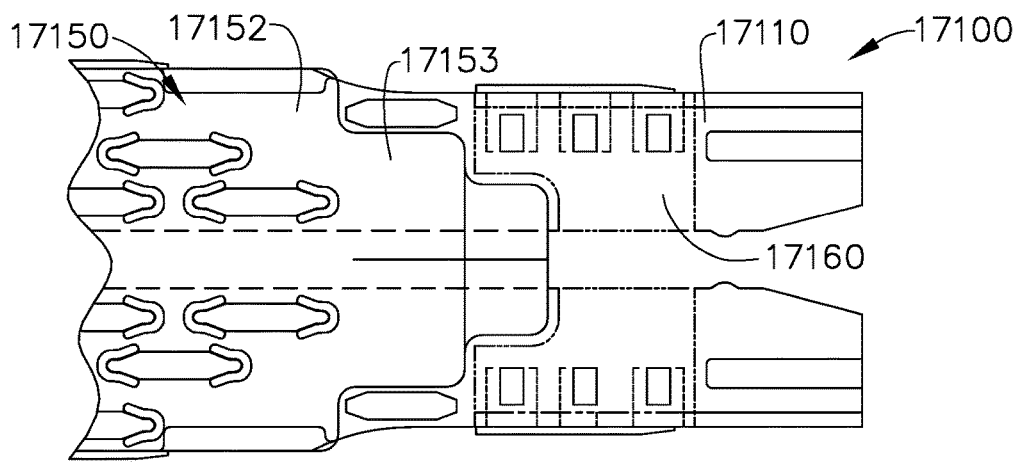
FIG. 72 is a plan view of the tissue thickness compensator and staple cartridge of FIG. 71.
Figure 75:
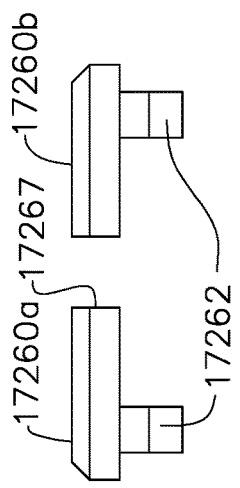
FIG. 75 is a rear view of the mount of FIG. 73.
Figure 74:
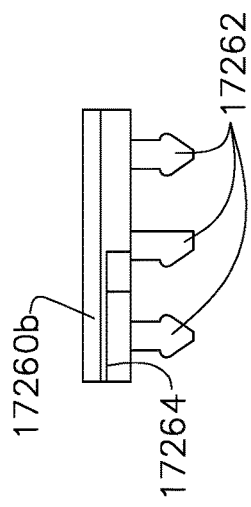
FIG. 74 is a side view of the mount of FIG. 73.
Figure 76:
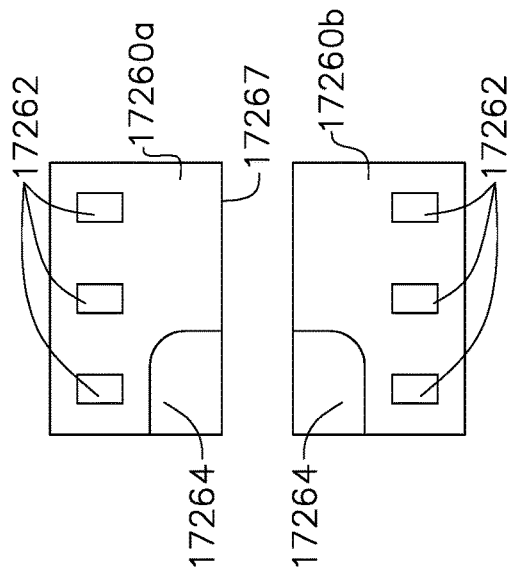
FIG. 76 is a bottom view of the mount of FIG. 73.
Figure 73:
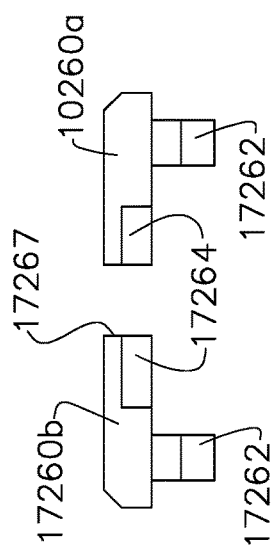
FIG. 73 is a front view of a mount for holding a tissue thickness compensator to a staple cartridge.

Referring now to FIGS. 70-72, a tissue thickness compensator 17150 can comprise a compressible portion 17152 and a mount portion 17154 extending through and/or extending from the compressible portion 17152. The compressible portion 17152 can comprise a proximal end 17153 which can include a thickness which is less than the thickness of the body portion 17156 of the tissue thickness compensator 17150. In at least one such embodiment, the proximal end 17153 can comprise a tapered portion, for example. Referring again to FIGS. 70-72, a staple cartridge assembly, such as staple cartridge 17100, for example, can include a proximal mount 17160 configured to releasably secure the mount portion 17154 of the tissue thickness compensator 17150 to a cartridge body 17010. Proximal mount 17160 can comprise one or more locks 17162 extending therefrom which can be received within one or more keyholes 10112 defined in the cartridge body 17110. In at least one such embodiment, each of the locks 17162 can comprise a leg and a foot extending from the leg wherein the leg can be configured to flex laterally as the lock 17162 is inserted into a keyhole 17112 and then resiliently return, or at least substantially return, to its unflexed configuration such that the foot can releasably engage, or move behind, a sidewall of the keyhole 17112. Similar to the above, the proximal mount 17160 can further comprise a cavity 17164 configured to receive the proximal mount portion 17154 of the tissue thickness compensator 17150. The cavity 17164 can be configured to compress the proximal mount portion 17154 against the deck of the cartridge body 17110 and hold the proximal end of the tissue thickness compensator 17150 in position. In various circumstances, a firing member, such as firing member 17030, for example, can be configured to incise the proximal mount 17160 as the firing member 17030 is being advanced to incise the tissue thickness compensator 17150. In at least one such circumstance, the incision of the proximal mount 17160 can release the tissue thickness compensator 17150 from the cartridge body 17110. Referring again to the embodiment depicted in FIG. 68, for example, the firing member 17030 can be configured to pass through a slot defined between the proximal mount portions 17060a, 17060b and, in at least some circumstances, pass through the proximal mount portions 17060a, 17060b without incising the same.

Referring now to FIGS. 73-76, further to the above, a proximal mount for releasably holding a tissue thickness compensator to a cartridge body can comprise first and second portions 17260a, 17260b which, when assembled to the cartridge body, can define a longitudinal gap or slot 17267 which can be sized and configured to permit the firing member 17030 to pass therebetween. Similar to the above, each of the first and second portions 17260a, 17260b can comprise a cavity 17264 configured to at least partially receive and hold a tissue thickness compensator in place. Also similar to the above, each of the first and second portions 17260a, 17260b can comprise locks 17262 extending therefrom which can be configured to engage the cartridge body.

As discussed above, a staple cartridge assembly can include a proximal mount or attachment portion configured to hold the proximal end of a tissue thickness compensator to the proximal end of a cartridge body and a distal mount or attachment portion configured to hold the distal end of the tissue thickness compensator to the distal end of the cartridge body. In certain other embodiments, a staple cartridge assembly may only comprise at least one proximal mount or at least one distal mount for holding the tissue thickness compensator to the cartridge body. Turning now to FIG. 147, a cartridge assembly 17300 can comprise a cartridge body 17310 and a tissue thickness compensator 17350, wherein the distal end of the tissue thickness compensator 17350 can comprise a distal end 17355 configured to be releasably mounted to the cartridge body 17310. In at least this embodiment, the distal end of the cartridge body 17310 can include lock apertures 17011 configured to receive and attach at least one distal mount to the cartridge body 17310. The reader will appreciate, at least with respect to this embodiment, that the cartridge assembly 17300 does not further include a proximal mount for mounting the proximal end of the tissue thickness compensator 17350 to the cartridge body 17310. In various circumstances, the distal end 17355 can be integrally formed with the body portion 17356 of the tissue thickness compensator 17350 or, alternatively, attached to the body portion 17356.

In various embodiments, referring now to FIGS. 156 and 157, a staple cartridge assembly, such as staple cartridge 10400, for example, can comprise a cartridge body 10410 including a distal end, or nose, 10419 which can be configured to releasably hold a tissue thickness compensator 10450 in position. Similar to the above, the tissue thickness compensator 10450 can comprise a first portion 10452 mounted to a second portion 10454, wherein the second portion 10454 can include a distal end 10455 configured to be releasably held by the nose 10419. In various circumstances, the nose 10419 and a deck 10414 of the cartridge body 10410 can define a slot 10418 therebetween configured to receive the distal end 10455. The nose 10419 can be comprised of a resilient material which can be sized and configured such that the nose 10419 is biased into engagement with the distal end 10455. In use, referring to FIG. 157, the nose 10419 can be sufficiently flexible so as to permit the tissue thickness compensator 10450 to slide out from underneath the nose 10419 when the cartridge body 10410 is moved away from the tissue thickness compensator 10450 after the tissue thickness compensator 10450 has been at least partially implanted. Turning now to FIG. 158, further to the above, the first layer 10452 can be comprised of a compressible foam which can be mounted to the second layer 10454. In various circumstances, one or more adhesives can be utilized to mount the first layer 10452 to the second layer 10454. The first layer 10452 can be mounted to the second layer 10454 such that the distal end 10455 and a notch 10457 defined in the distal end 10455 remain exposed. The first layer 10452 may be mounted to the second layer 10454 such that the first layer 10452 is centered laterally with respect to a longitudinal center axis 10459 defined by the second layer 10454.

As discussed above, a staple cartridge assembly can include a movable firing member at least partially stored therein which can be configured to lift staples stored within the staple cartridge assembly between unfired positions and fired positions. Turning now to FIGS. 159 and 160, a staple cartridge assembly 10500 can include a cartridge body 10510, a tissue thickness compensator 10550, and a movable firing member, or sled, 10034 slidably stored therein. The sled 10034 can include one or more ramps 10035 defined thereon which can be configured to lift the staples from their unfired positions to their fired positions in use. Prior to use, the sled 10034 can be releasably locked in position. In at least one such embodiment, the tissue thickness compensator 10550 can be configured to releasably hold the sled 10034 in a proximal position before the sled 10034 is advanced distally to eject the staples from the staple cartridge assembly 10500 and incise the tissue thickness compensator 10550. The tissue thickness compensator 10550 can comprise one or more tabs, or detents, 10557 extending therefrom which can releasably engage the sled 10034. For instance, the sled 10034 can include one or more recesses 10037 within which the detents 10557 can be positioned until a sufficient force is applied to the sled 10034 which can cause the sled 10034 to overcome the retention force applied to the sled 10034 by the detents 10557. In use, the detents 10557 can be configured to hold the sled 10034 in position until a longitudinal firing force applied to the sled 10034 in the distal direction exceeds a threshold force wherein, when the firing force exceeds the threshold force, the sled 10034 can slide distally and the detents 10557 can sufficiently flex, or otherwise deform, to permit the sled 10034 to slide thereby. In at least one embodiment, the detents 10557 can be positioned proximal to the staple cavities defined in the cartridge body 10510 and/or proximal to the staples stored within the cartridge body 10510 such that the sled 10034 can be releasably held in an unfired position which is proximal to the staples. Once the sled 10034 has been advanced distally, the sled 10034 can be advanced toward the staples. Further to the above, referring again to FIGS. 159 and 160, the cartridge body 10510 can include one or more retention slots 10517 which can be configured to receive at least a portion of the detents 10557. More particularly, in at least the illustrated embodiment, a retention slot 10517 defined in one side of the cartridge body 10510 can be aligned with a recess 10037 defined in a corresponding side of the sled 10034 when the sled 10034 is in its proximal, unfired position such that a detent 10557 can be concurrently positioned within the aligned retention slot 10517 and the recess 10037. In at least one such embodiment, the sidewalls of the retention slot 10517 defined in the cartridge body 10510 can support the detent 10557 and at least inhibit the detent 10557 from becoming prematurely dislodged from the recess 10037. As discussed above, the sled 10034 can be advanced distally such that the recess 10037 is no longer aligned with the detent 10557; however, in at least the illustrated embodiment, the detent 10557 may remain aligned with and/or positioned within the retention slot 10517 after the sled 10034 has been at least partially advanced. Referring primarily to FIG. 159, a first arrangement comprising a detent 10557, a sled recess 10037, and a cartridge retention slot 10517 can be arranged with respect to a first side of the sled 10034 and a second arrangement comprising a second detent 10557, a second sled recess 10037, and a second cartridge retention slot 10517 can be arranged with respect to a second, or opposite, side of the sled 10034.

Certain embodiments of staple cartridges can include a pliable layer, such as a tissue thickness compensator and/or a buttress material, for example, on a staple deck, wherein staples can arranged so that the tips of the unfired staples extend into the layer. In certain other embodiments, the pliable layer can comprise a compressible and/or crushable staple cartridge that is implantable in a patient and deforms and/or compresses when captured in the staples. The pliable layer and/or implantable staple cartridge can also deform and/or compress if a surgeon, nurse, technician, or other user ("user" or "users") inadvertently presses a thumb or other finger against the pliable layer or implantable staple cartridge, for example. Such deformation and/or compression can render the staple cartridge unusable.

Staple cartridge retainers are often supplied with retainers, which can assist the user in loading the staple cartridge into a surgical stapler. The retainer can also cover the staple deck and any pliable layer, thereby preventing the users from inadvertently compressing, crushing, and/or deforming the pliable layer. However, users sometimes prematurely remove the staple cartridge retainer prior to fully installing the staple cartridge into an end effector of a surgical stapler. By prematurely removing the retainer, the users can risk causing damage to the pliable layer.

FIGS. 164-167 illustrate an embodiment of a retainer 10000 that can be attached to a staple cartridge 10010. Referring to FIGS. 166 and 167, the staple cartridge 10010 can include a pliable layer 10020, such as a tissue thickness compensator and/or a buttress material, arranged on a staple deck 10011 of the staple cartridge 10010. As shown in FIG. 167, staples 10030 can extend from the staple cartridge 10010 into the exposed pliable layer 10020. If the retainer 10000 is prematurely removed, a user may inadvertently press on the pliable layer 10020 while pushing the staple cartridge 10010 into a staple cartridge channel of an end effector, thereby compressing and/or deforming the layer 10020.

FIGS. 168-173 illustrate an embodiment of a retainer 2600 that can be locked to a staple cartridge 2650 and that cannot be unlocked and removed from the staple cartridge 2650 until the staple cartridge 2650 is fully inserted into a staple cartridge channel 2670 of an end effector. As best illustrated in FIG. 168, a proximal end portion 2604 of the retainer 2600 can include movable cam portions 2616 with locking tabs 2626 extending from the movable cam portions 2616. The locking tabs 2626 extend into and engage a slot 2652, such as a knife slot, in the staple cartridge 2650. The engagement of the locking tabs 2626 within the slot 2652 releasably holds the retainer 2600 and the staple cartridge 2650 together. As explained in greater detail below, the locking tabs only disengage from the slot 2652 such that the retainer 2600 can be released and removed from the staple cartridge 2650 after the cam portions 2616 of the retainer 2616 engage a key in the staple cartridge channel 2670 that causes the cam portions 2616 to inwardly flex toward one another. Furthermore, in various embodiments, the cam portions 2616 can only engage the key if the staple cartridge 2650 is properly seated in the staple cartridge channel 2670.

As described above, in certain embodiments, the proximal end portion 2604 of the retainer 2600 can include cam portions 2616, each of which is attached to the body 2606 of the retainer 2600 by a neck 2624. The cam portions 2616 can be separated from one another by a gap 2622. The cam portions 2616 can flex inwardly in the direction of arrow I (shown in FIG. 172) when an inwardly-compressive force is applied and can resiliently flex outwardly in the direction of arrow O (shown in FIG. 170) about the necks 2624. A locking tab 2626 can extend from each cam portion 2618. As described in greater detail below, when arranged on a staple cartridge 2650, the locking tabs 2626 can extend into and releasably engage a slot 2652, such as a knife slot, in the staple cartridge 2650. Referring primarily to FIGS. 170 and 171, the cam portions can be biased in an outwardly flexed position such that lips 2628 extending from the locking tabs 2626 can engage ridges 2654 in the slot 2652 in the staple cartridge 2650. Biasing the cam portions 2616 in the outwardly flexed position can push the lips 2628 of the locking tabs 2626 into engagement with the ridges 2654 in the slot 2652 such that the retainer 2600 is locked to the staple cartridge 2650 absent an inwardly-compressive force from the key of the staple cartridge channel 2670.

Referring primarily to FIGS. 170-173, in various embodiments, the key of the staple cartridge channel 2670 can include interior walls of the staple cartridge channel 2670 that provide a progressively increasing inwardly-compressive force to the cam portions 2616 such that the cam portions 2616 can flex inwardly in the direction of arrow I (shown in FIG. 172) as the retainer 2600 and the staple cartridge 2650 are inserted into the staple cartridge channel 2670. For example, the staple cartridge channel 2670 can include first interior walls 2672 defining a first width that can accommodate the cam portions 2616 in their biased, outwardly-flexed position. The staple cartridge channel 2670 can include second interior walls 2676 defining a second width that can accommodate the cam portions 2616 in an inwardly-flexed position, as shown in FIG. 172. The staple cartridge channel 2670 can include intermediate interior walls 2674 positioned intermediate the first interior walls 2672 and the second interior walls 2676 that can transition from the first width to the second width. In use, the staple cartridge 2650 and the retainer 2600 are moved in a proximal direction relative to and toward the staple cartridge channel 2670 to be inserted into the staple cartridge channel 2670, indicated by arrow P in FIGS. 170 and 172. Referring primarily to FIGS. 170 and 171, as the staple cartridge 2650 and retainer 2600 are moved toward the staple cartridge channel 2670, rounded ends 2620 and outward-facing surfaces 2618 of the cam portions 2616 can engage the first walls 2672 of the staple cartridge channel 2670. As described above, in certain embodiments, the first walls 2672 can define a width that accommodates the cam portions 2616 in their biased, outwardly-flexed position. In various other embodiments, the first walls 2672 can define a width that accommodates the cam portions 2616 in a partially inwardly-flexed position, wherein the partial amount of inward flexing is sufficiently enough such that the lips 2628 of the locking tabs 2626 do not disengage from the ridges 2654 of the staple cartridge 2650 and the retainer 2600 becomes unlocked from the staple cartridge 2650. Referring now to FIGS. 172 and 173, as the staple cartridge 2650 and retainer 2600 continue to move proximally toward the staple cartridge channel 2670 in the direction of arrow P, the rounded ends 2620 and outward-facing surfaces 2618 engage the intermediate walls 2674 and then the second walls 2676. The intermediate walls 2674 and the second walls 2676 can provide a progressively increasing force that can cause the cam portions 2616 to flex progressively inward. Eventually, the cam portions 2616 will flex inwardly by an amount such that the lips 2628 of the locking tabs 2626 can be disengaged from the ridges 2654 in the slot 2652 of the staple cartridge 2650. When the locking tabs 2626 are disengaged from the ridges 2654, the retainer 2600 is unlocked from the staple cartridge 2650 such that the retainer 2600 can be removed from the staple cartridge 2650. In various embodiments, the cam portions 2616 flex inwardly so that the tabs 2626 disengage from the ridges 2654 only when the staple cartridge 2650 is fully inserted into the staple cartridge channel 2670.

In certain embodiments, a lockable retainer, such as retainer 2600 described above with reference to FIGS. 168-173, can also prevent a staple cartridge of a particular size from being inserted into an end effector that is intended for use with a staple cartridge of a different particular size. For example, the staple cartridge 2650 can comprise a datum surface 2632 that can engage a datum surface 2674 of the staple cartridge channel 2670. A first predetermined distance from the datum surface 2632 of the staple cartridge 2650 to the cam portions 2616 can correspond to a second predetermined distance between the datum surface 2674 of the staple cartridge channel 2670 and the walls 2672, 2674, and 2676 that comprise the key of the staple cartridge channel 2670. The first and second predetermined distances for a particularly-sized retainer and staple cartridge and for a staple cartridge channel intended for use with the particularly-sized staple cartridge can be different from the first and second predetermined distances for other differently-sized retainers, staple cartridges, and staple cartridge channels. Put differently, each size of staple cartridge, retainer, and staple cartridge channel can have a first predetermined distance and a second predetermined distance that is different from other sizes of staple cartridge, retainer, and staple cartridge channel. As a result, attempting to insert a staple cartridge and retainer into a incorrectly-sized staple cartridge channel can result in the cam portions of the retainer not engaging the walls of the staple cartridge channel and/or the datum surfaces of the staple cartridge and the staple cartridge channel not engaging. For example, the staple cartridge 2650 and the retainer 2600 can be arranged so that, when they are inserted into a correctly-sized staple cartridge channel, the cam portions 2616 can only engage the second walls 2676 of the staple cartridge channel 2670 such that the locking tabs 2626 disengage from the slot 2652 in the staple cartridge 2650 when the datum surfaces 2632 and 2674 engage one another. If the staple cartridge 2650 and the retainer 2600 are too short for the staple cartridge channel 2670, for example, then the cam portions 2616 may not reach the second walls 2676 such that the locking tabs 2626 can be disengaged from the slot 2552 in the staple cartridge 2650 when the datum surfaces 2632 and 2674 are engaged. As a result, the retainer 2600 would not be unlocked and removable from the staple cartridge 2650. Conversely, if the staple cartridge 2650 and the retainer 2600 are too long for the staple cartridge channel 2670, for example, then the cam portions 2616 engaging the second walls 2676 of the staple cartridge channel 2670 could prevent the datum surfaces 2632 and 2674 of the staple cartridge 2650 and the staple cartridge channel 2670, respectively, from engaging. As a result, the staple cartridge 2650 would not be completely seated in the staple cartridge channel 2670.

In addition to the locking tabs 2626 extending from the cam portions 2616, the retainer 2600 can also include a pair of proximal tabs 2612 arranged near a proximal end 2602 of the retainer 2600 and a pair of distal tabs 2610 arranged near a distal end 2604 of the retainer 2600. The proximal tabs 2608 and the distal tabs 2610 can extend from the body 2606 and can engage and releasably hold the staple cartridge 2650. In certain embodiments, the proximal tabs 2612 and the distal tabs 2610 can engage and hold the staple cartridge 2650 until the staple cartridge 2650 is fully seated in the staple cartridge channel 2670. Stated differently, the proximal tabs 2612 and/or the distal tabs 2610 can serve as another lock that prevents the retainer 2600 from being removed from the staple cartridge 2650 before the staple cartridge 2650 is completely seated in the staple cartridge channel 2670.

Referring primarily to FIG. 168, each proximal tab 2612 can include a proximal lip 2614 and each distal tab 2610 can include a distal lip 2610. Each proximal lip 2614 can include an inward-facing angled surface 2615 and each distal lip 2610 can include an inward-facing angled surface 2611. The proximal lips 2614 and the distal lips 2610 can engage and releasably hold lateral sides of the staple cartridge 2650. When the staple cartridge 2650 and the retainer 2600 are inserted into the staple cartridge channel 2670, the inward-facing angled surfaces 2611 and 2615 can engage edges 2672 and 2678 of the staple cartridge channel 2670. The edges 2672 and 2678 of the staple cartridge channel 2670 can flex outwardly the proximal tabs 2612 and/or the distal tabs 2610 such that the proximal lips 2614 and the distal lips 2610 disengage from the lateral sides of the staple cartridge 2650. When the proximal lips 2614 and the distal lips 2610 are disengaged, the retainer 2600 can be released and removed from the staple cartridge 2650.

Referring to FIGS. 174-180, the end effector 12 of a surgical instrument, for example, can be configured to receive an end effector insert 28010. In various embodiments, the end effector insert 28010 can comprise a compensator body 28012 and at least one clip 28014*a*, 28014*b*. In various embodiments, the end effector insert 28010 can comprise a proximal clip 28014*b* at the proximal end of the compensator body 28012 and a distal clip 28014*a* at the distal end of the compensator body 28012, for example. Referring primarily to FIG. 177, the distal clip 28014*a* can be secured to the anvil 25060 of the end effector 12 at or near the distal end of the anvil 25060. For example, the distal clip 28014*a* can be substantially aligned with and/or partially positioned within the longitudinal slot 25062 of the anvil 25060. Referring primarily to FIG. 178, the proximal clip 28014*b* can be secured to a staple cartridge 25000 in the lower jaw 25070 of the end effector 12 (FIG. 179). The proximal clip 28014*b* can be secured to the staple cartridge 25000 at or near the proximal end of the staple cartridge 25000. For example, the proximal clip 28014*b* can be substantially aligned with and/or positioned within a longitudinal slot 25004 in the staple cartridge 25000.

Referring now to FIGS. 179 and 180, the end effector insert 28010 can be inserted into the end effector 12 of a surgical instrument. In various embodiments, at least a portion of the end effector insert 28010, such as the compensator body 28012, distal clips 28014*a*, and/or proximal clip 28014*b*, can be deformable and/or resilient, for example. When the end effector insert 28010 is inserted into the end effector 12, the distal and/or the proximal clips 28014*a*, 28014*b* can bend or flex. When the clips 28014*a*, 28014*b* are flexed, for example, the clips 28014*a*, 28014*b* can seek to return to their initial, undeformed configuration and can generate a corresponding springback or restoring force, for example. In various embodiments, when the end effector insert 28010 is positioned within the end effector 12, the end effector insert 28010 can apply a spring load to the end effector 12. In some embodiments, the end effector insert 28010 can be solid or substantially solid such that an operator can grasp the insert 28010 when the operator is inserting the end effector insert 28010 and staple cartridge 25000 into the end effector 12.

In some embodiments, the end effector insert 28010 can be removed from the end effector 12 prior to cutting and/or fastening operations of the end effector 12. In other embodiments, the end effector insert 28010 can remain positioned in the end effector 12 during cutting and/or firing operations. For example, the end effector insert 28010 can be transected by the cutting element 25052 as staples are fired from their staples cavities 25002 (FIG. 178) in the staple cartridge 25000. In various embodiments, the end effector insert 28010 can comprise a tissue thickness compensation material, similar to at least one of the tissue thickness compensators described herein. For example, the end effector insert 28010 can comprise a polymeric composition, such as a bioabsorbable, biocompatible elastomeric polymer, for example. The end effector insert 28010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the end effector insert 28010 can comprise at least one therapeutic agent such as a pharmaceutically active agent or medicament.

Referring still to FIGS. 174-180, the end effector insert 28010 can be releasably attached to the end effector 12 and/or to the anvil 25060 and/or the staple cartridge 25000 of the end effector 12. The proximal clip 28014*b* can be releasably secured to the staple cartridge 25000 (FIG. 178), for example, and the distal clip 28014*a* can be releasably secured to the anvil 25060 (FIG. 177), for example. In various embodiments, the proximal clip 28014*b* can be aligned with and/or retained within the slot 25004 of the staple cartridge 25000. Further, in certain embodiments, the distal clip 28014*a* can be aligned with and/or retained within the slot 25062 of the anvil 25060. Referring primarily to FIG. 179, in certain embodiments, the proximal clip 28014*b* can be releasably secured to the staple cartridge 25000 before the staple cartridge 25000 is positioned in the lower jaw 25070 (FIG. 179). As the staple cartridge 25000 and the attached end effector insert 28010 are moved toward and/or into the end effector 12 and/or the lower jaw 25070, the distal clip 28014*a* can be moved into alignment with the slot 25062 in the anvil 25060, for example. In various embodiments, when the staple cartridge 25000 and the end effector insert 28010 are positioned in the end effector 12 (FIG. 180), the distal clip 28014*a* can releasably engage the anvil 25060. The distal clip 28014*a* can slide into the slot 25062 in the anvil 25060, for example. In various embodiments, the distal clip 28014*a* can be positioned relative to the anvil 25060 before or while the proximal clip 28014*b* is positioned relative to the staple cartridge 25000.

When the end effector insert 28010 is releasably secured within the end effector 12, for example by the proximal clip 28014*b* and the distal clip 28014*a* as described herein, the end effector insert 28010 can be held in tension in the end effector 12. Stated differently, the proximal clip 28014*b* secured relative to the staple cartridge 25000 in the lower jaw 25070 can exert a pulling force along the end effector insert 28010 and on the distal clip 28014*a* secured relative to the anvil 25060, for example. In various embodiments, the tension between the proximal clip 28015*b* and the distal clip 28014*a* can help to hold the end effector insert 28010 in the end effector 12.

In various embodiments, when the staple cartridge 25000 and end effector insert 28010 are positioned in the end effector 12, the proximal clip 28014*b* can be positioned intermediate the unfired sled 25056 (FIG. 178) and the staple cartridge 25000. For example, the unfired sled 25056 can be proximal to the proximal clip 28013*b*. In certain embodiments, during a firing stroke, the sled 25056 can move distally past the proximal clip 28014*b*, and can deflect the proximal clip 28014*b*, for example. In various embodiments, when the sled 25056 deflects the proximal clip 28014*b* during the firing stroke, the proximal clip 28014*b* can be released from the slot 25004 in the staple cartridge 25000. In certain embodiments, the sled 25056 and/or an element of the firing bar 25050 (illustrated elsewhere) can release the proximal clip 28014*b* from the staple cartridge 25000. Further, when the proximal clip 28014*b* is released from the staple cartridge 25000, the tension in the end effector insert 28010 can be at least partially relieved. In the absence of a pulling force exerted on the distal clip 28014*a*, the distal clip 28014*a* can release from the anvil 25060. Accordingly, the end effector insert 28010 can be released from the end effector 12 and, for example, can remain in the patient's tissue after the end effector 12 has been removed from the patient.

In certain embodiments, a proximal end of an anvil-attachable layer, such as a tissue thickness compensator and/or a buttress material, for example, can be releasably attached to a proximal end of a staple cartridge for alignment with and attachment to an anvil of an end effector into which the staple cartridge can be inserted. Generally, the anvil-attachable layer can be arranged relative to an anvil-facing side of a staple cartridge. For example, the anvil-attachable layer can be arranged on a staple deck of the staple cartridge and/or can be arranged on a staple deck layer. A proximal end of the anvil-attachable layer can be attached to a proximal end of the staple cartridge or a proximal end of the staple deck layer. After the staple cartridge is inserted into the end effector of the surgical stapler, the anvil of the surgical stapler can be closed against the anvil-attachable layer such that the layer becomes attached to the anvil. When the anvil is reopened, the anvil-attachable layer, now attached to the anvil, can move with the anvil and away from the staple cartridge. In various circumstances, as the attached layer moves with the anvil, the attached layer can pivot about its proximal end that is attached to the staple cartridge and/or the staple cartridge layer. In various other circumstances, as the attached layer moves with the anvil, the proximal end of the layer can detach from the staple cartridge. The surgical stapler, with the anvil-attachable layer attached to the anvil, can now cut and staple patient tissue. The anvil-attachable layer can also be cut by the surgical stapler and captured by the staples. After the anvil-attachable layer and patient tissue are captured by the staples, the surgical stapler can be removed from the patient. In various embodiments in which the anvil-attachable layer is still attached to the staple cartridge, the surgical stapler can be pulled free from the layer, breaking the attachment between the layer and the staple cartridge.

FIGS. 181 and 182 illustrate an embodiment of a staple cartridge assembly 2400 comprising an anvil-attachable layer 2414. The anvil-attachable layer 2414 can comprise a tissue thickness compensator and/or a buttress material, for example. A proximal end 2416 of the anvil-attachable layer 2414 can be attached to a proximal end 2418 of a staple cartridge body 2402. In various embodiments, the staple cartridge assembly 2400 can include a staple cartridge layer 2412, such as a tissue thickness compensator and/or a buttress material, for example, arranged on a staple deck of the staple cartridge body 2402. A cartridge pan 2404 can at least partially surround the staple cartridge body 2402 and can be comprised of a metal material, for example. The staple cartridge body 2402 can include a surface 2406 and grooves 2408 defined in the surface 2406 at a proximal end 2418 of the cartridge body 2402. Referring to FIG. 181, in order to attach the anvil-attachable layer 2414 to the staple cartridge body 2402, a proximal end portion 2416 of the anvil-attachable layer 2414 can be positioned over the grooves 2408. Then, as shown in FIG. 182, tabs 2410 extending from the cartridge pan 2404 can be deformed such that they extend into the grooves 2408, capturing the proximal end portion 2416 of the anvil-attachable layer 2414 in the grooves 2408 between the side walls of the grooves 2408 and the tabs 2410, for example. The tabs 2410 can also capture the anvil-attachable layer 2414 between bottoms of the grooves 2408 and the tabs 2410, for example.

In use, the staple cartridge assembly 2400 shown in FIG. 182, can be inserted into a staple cartridge channel of an end effector of a surgical stapler. Then, an anvil of the end effector can be closed against the anvil-attachable layer 2414. The anvil-attachable layer 2414 can be arranged on the staple cartridge body 2402 such that the layer 2414 is properly aligned with the anvil when the staple cartridge assembly 2400 is inserted into the staple cartridge channel 2400 and the anvil is then closed. In various embodiments, an anvil-facing surface 2415 of the anvil-attachable layer 2414 can include an adhesive that can adhere to a surface of the anvil and/or one or more attachment features that engage the anvil to attach the anvil-attachable layer 2414 to the anvil. For example, the anvil-facing surface 2415 can include one or more protrusions extending therefrom that can engage a knife slot of the anvil. After the anvil-attachable layer 2414 has been attached to the anvil, the anvil can be returned to an open position with the anvil-attachable layer 2414 attached thereto. The portion of the anvil-attachable layer 2414 attached to the anvil can pivot about the proximal end 2416 of the layer 2414 that is attached to the staple cartridge body 2402 to enable the layer 2414 to move with the anvil. Now, the surgical stapler can comprise a staple cartridge layer 2412 aligned on the staple cartridge body 2402 and the anvil-attachable layer 2414 attached to and aligned with the anvil.

When the staple cartridge layer 2412 aligned with the staple cartridge body 2402 and the anvil-attachable layer 2414 attached to and aligned with the anvil, the surgical stapler is prepared for use to cut and staple patient tissue. The staple cartridge body 2402 and the staple cartridge layer 2412 can be positioned on one side of the patient tissue and the anvil and anvil-attachable layer 2414 can be positioned on an opposite side of the patient tissue. The attachment of the anvil-attachable layer 2414 to the anvil and to the staple cartridge body 2402 can stabilize the anvil-attachable layer 2414 relative to the anvil while the stapler is being positioned against the patient tissue. When the surgical stapler is properly positioned relative to patient tissue, the anvil can be closed, capturing the tissue between the staple cartridge body 2402 and the staple cartridge layer 2412 on one side of the tissue and the anvil and the anvil-attachable layer 2414 on a second opposing side of the tissue.

After the anvil is closed with patient tissue captured between the staple cartridge body 2402 and the staple cartridge layer 2412 on one side and the anvil and anvil-attachable layer 2414 on the other side, the surgical stapler can be fired. For example, a staple driver can be advanced in a distal direction through staple driver slots 2422 in the staple cartridge body 2402 to fire and form staples that are stored in the staple cartridge. The fired and formed staples can capture the staple cartridge layer 2412, the anvil-attachable layer 2414, and the patient tissue therebetween. Also, a cutting blade can be advanced in the distal direction through a knife slot 2420 in the cartridge body 2402 and a knife slot in the anvil. The cutting blade can sever the staple cartridge layer 2412, the anvil-attachable layer 2414, and the patient tissue therebetween as the cutting blade is advanced. In various embodiments, the staple driver and the cutting blade can be advanced simultaneously. In various circumstances, the staple driver can lead the cutting blade such that the staples are fired and formed before the cutting blade severs the patient tissue, the staple cartridge layer 2412, and the anvil-attachable layer 2414.

After the staple cartridge layer, the anvil-attachable layer 2414, and the patient tissue therebetween have been captured by the staples and cut by the cutting blade, the anvil can be reopened. When the anvil is reopened, the anvil-attachable layer 2414 that is now attached to the staple cartridge layer 2412 and the patient tissue by the staples can be detached from the anvil. For example, as the anvil is opened and/or as the surgical stapler is removed from the patient, the anvil-attachable layer 2414 can be held in place by the staples and the patient tissue, such that the layer 2414 can be pulled away from an adhesive and/or attachment feature, for example, that is holding the layer 2414 to the anvil. Furthermore, the proximal end 2416 of the anvil-attachable layer 2414 can be pulled away from the staple cartridge body 2402 in order to be detached from the proximal end 2416 of the staple cartridge body 2402. For example, in various circumstances, the portions of the proximal end 2416 of the anvil-attachable layer 2414 captured between the grooves 2408 in the cartridge body 2402 and the tabs 2410 of the cartridge pan 2404 can be pulled out from between the tabs 2410 and the grooves 2408. In various other circumstances, the anvil-attachable layer 2414 can be torn away from portions of the anvil-attachable layer 2414 that are captured between the grooves 2408 and the tabs 2410 of the cartridge pan 2404. For example, the portion of the anvil-attachable layer 2414 captured between the grooves 2408 and the tabs 2410 can be distressed by the tabs 2410 pressing into the portion of the layer 2414 in order to reduce the force required to tear the remaining portion of the layer 2414 and/or to define locations where the layer 2414 will tear. For example, the tabs 2410 extending into the anvil-adjustable layer 2414 may partially score, cut, and/or perforate the layer 2414, for example. After the staple cartridge layer 2412 is detached from the staple cartridge body 2402 and the anvil-attachable layer 2414 is detached from the staple cartridge body 2402 and the anvil, the surgical stapler can be removed from the patient, leaving the layers 2412 and 2414 implanted in the patient. The layers 2412 and 2414 can bolster the lines of staples and/or can compress to different thicknesses in different staples to provide at least a minimum amount of compression to patient tissue captured by the staples, for example.

Still referring to FIGS. 181 and 182, in various embodiments, the anvil attachable layer 2414 can be detached from the staple cartridge body 2402 after the layer 2414 is attached to the anvil and the anvil is reopened. As described above, after the staple cartridge assembly 2400 is inserted into a staple cartridge channel and an anvil is closed on the anvil-attachable layer 2414, the layer 2414 can be attached to an anvil by an adhesive and/or attachment feature on an anvil-facing surface 2415 of the layer 2414. When the anvil is reopened, the anvil-attachable layer 2414 can move with the anvil away from the staple cartridge body 2402. In various circumstances, movement of the anvil and the anvil-attachable layer 2414 away from the staple cartridge body 2402 can pull the portions of the layer 2414 captured between the tabs 2410 of the cartridge pan 2404 and the grooves 2408 in the cartridge body 2402 out from between the tabs 2410 and the grooves 2408 such that the proximal end 2416 of the layer 2414 can also move with the anvil.

FIGS. 183 and 184 illustrate another embodiment comprising a staple cartridge assembly 2450 that includes an anvil-attachable layer 2464 attachable to a staple cartridge body 2452. In this embodiment, a proximal end 2466 of the anvil-attachable layer 2464 is attached to surfaces 2472 on attachment portions 2470 that can extend from a surface 2456 of the cartridge body 2452. The proximal end 2466 of the anvil-attachable layer 2464 can be attached to the surfaces 2472 by adhesives, ultrasonic welding, thermal welding, and/or heat staking, for example. In various embodiments, the staple cartridge assembly 2450 can include a staple cartridge layer 2462 arranged on the staple cartridge body 2462. In such embodiments, the attachment portions 2470 can extend from the surface 2456 of the cartridge body 2452 such that the surfaces 2472 are approximately level with an anvil-facing surface 2467 of the staple cartridge layer 2462. As a result, the anvil-attachable layer 2464 can lie substantially flat across the anvil-facing surface 2467 of the staple cartridge layer 2462 and the surfaces 2472. In various circumstances, similar to the embodiments described above with respect to FIGS. 181 and 182, after the staple cartridge assembly 2450 is inserted into a staple cartridge channel of an end effector, an anvil of the end effector can be closed in order to make contact with an anvil-facing side 2465 of the anvil-attachable layer 2464. An adhesive and/or attachment features on the anvil-facing side 2465 of the anvil-attachable layer 2464 can attach the anvil-attachable layer 2464 to the anvil. Then, when the anvil is reopened, the anvil-attachable layer 2464 can pivot about the proximal end 2466 attached to the surfaces 2472.

Similar to the embodiments described above with respect to FIGS. 181 and 182, the staple cartridge layer 2462, the anvil-attachable layer 2464, and patient tissue therebetween can be cut and stapled together. Then, the anvil of the surgical stapler is reopened and/or the surgical stapler is removed from the patient, the anvil-attachable layer 2464 can be detached from the anvil and the staple cartridge layer 2462 can be detached from the staple cartridge body 2452. Also, the proximal end 2466 of the anvil-attachable layer 2464 can detach from the adhesive and/or other attachment to the surfaces 2472 such that the anvil-attachable layer 2464 can be implanted in the patient.

Still referring to FIGS. 183 and 184, in various embodiments, when the anvil is reopened after the anvil-attachable layer 2464 is attached thereto, the proximal end 2466 of the anvil-attachable layer 2464 can detach from the surfaces 2472. For example, the proximal end 2466 of the anvil-attachable layer 2464 can also be attached to the anvil. When the anvil and attached anvil-attachable layer 2464 move in a direction away from the staple cartridge body 2452 and/or the staple cartridge layer 2462, the proximal end 2466 of the layer 2464 can be pulled and detach from the surfaces 2472. In such embodiments, the anvil-attachable layer 2464 can be detached from the staple cartridge before the staple cartridge layer 2464, the anvil-attachable layer 2464, and patient tissue therebetween are cut and stapled.

FIGS. 185 and 186 illustrate another embodiment comprising a staple cartridge assembly 2500 that includes a staple cartridge layer 2506 and an anvil-attachable layer 2510. In the embodiment shown in FIGS. 185 and 186, the anvil-attachable layer 2510 is attached to the staple cartridge layer 2506 instead of to the staple cartridge body 2502. The staple cartridge layer 2506 and the anvil-attachable layer 2510 each can comprise a tissue thickness compensator and/or a buttress material, for example. The anvil-attachable layer 2510 can include a first proximal tab portion 2512 extending from a proximal end 2508 of the layer 2510. The first proximal tab portion 2512 can be attached to a proximal end surface 2516 of the staple cartridge layer 2506. For example, the first proximal tab portion 2512 can be glued, welded, and/or overmolded onto the proximal end surface 2516 of the staple cartridge layer 2506. In certain embodiments, the anvil-attachable layer 2510 can include a second proximal tab portion 2514 extending from the first proximal tab portion 2512. The second proximal tab portion 2514 can be attached to a bottom surface 2518 of the staple cartridge layer 2506 by gluing, welding, and/or overmolding, for example.

Similar to the embodiments described above with reference to FIGS. 181-184, after the staple cartridge assembly 2500 is inserted into a staple cartridge channel of an end effector of a surgical stapler and when an anvil of the end effector is closed on the anvil-attachable layer 2510, an anvil-facing surface 2511 of the anvil-attachable layer 2510 can be attached to the anvil by an adhesive and/or by attachment features. When the anvil is reopened, the anvil-attachable layer 2510 can move away from the staple cartridge layer 2506 and the staple cartridge body 2502 with the anvil. In various circumstances, the anvil-attachable layer 2510 can pivot about the first tab portion 2512 as the anvil reopens. After the anvil-attachable layer 2510 is attached to the anvil, the end effector can be closed on patient tissue such that the staple cartridge body 2502 and staple cartridge layer 2506 are positioned on a first side of the patient tissue and the anvil and anvil-attachable layer 2510 are positioned on a second opposing side of the patient tissue. As described above with reference to FIGS. 181 and 182, a cutting blade can be advanced through a knife slot 2520 in the cartridge body 2502 and a staple driver can be advanced through a staple driver slot 2422 in the cartridge body 2502. Referring primarily to FIG. 185, in certain embodiments, the first tab portion 2512 and the second tab portion 2514 of the anvil-attachable layer can by aligned with the knife slot 2512. As the cutting blade is advanced through the knife slot 2520, the cutting blade can sever the first tab portion 2512 and the second tab portion 2514. In various circumstances, the severing of the first tab portion 2512 and the second tab portion 2514 by the cutting blade can detach the first tab portion 2512 and the second tab portion 2514 from the staple cartridge layer 2506. After the cutting blade and the staple driver have been advanced and the staple cartridge layer 2506, the anvil-attachable layer 2510, and patient tissue therebetween have been cut and stapled, the anvil may be reopened such that the anvil-attachable layer 2510 separates from the anvil and the staple cartridge layer 2506 separates from the staple cartridge body 2502. As noted above, the anvil-attachable layer 2510 in the embodiment of FIGS. 185 and 186 is attached to the staple cartridge layer 2506 and not to the staple cartridge body 2502. Thus, no action is needed to separate the anvil-attachable layer 2510 from the staple cartridge body 2502. Furthermore, the first tab portion 2512 and/or the second tab portion 2514 of the anvil-attachable layer 2510 can remain attached to the staple cartridge layer 2506 since both layers are captured by staples and are implantable in the patient. For example, if the cutting blade does not detach the first tab portion 2512 and the second tab portion 2514 from the staple cartridge layer 2506, then the staple cartridge layer 2506 and the anvil-attachable layer 2510 will be attached to each other inside of the patient by the formed staples and by the first and second tab portions 2512 and 2514.

Still referring to FIGS. 185 and 186, in various embodiments, after the staple cartridge assembly 2500 has been inserted in to the staple cartridge channel and the anvil-attachable layer 2510 has been attached to the anvil, the first tab portion 2512 and the second tab portion 2514 can detach from the staple cartridge layer 2506 when the anvil is reopened and the anvil and anvil-attachable layer 2510 move away from the staple cartridge layer 2506. For example, the anvil and the anvil-attachable layer 2510 attached thereto can pull the first tab portion 2512 and the second tab portion 2514 away from the staple cartridge layer 2506 such that the first tab portion 2512 and the second tab portion 2514 detach from the staple cartridge layer 2506.

FIGS. 187 and 188 illustrate another embodiment comprising an anvil-attachable layer 2550 for use with a surgical stapler. As explained below, a proximal end portion 2554 of the anvil-attachable layer 2550 is attachable to a proximal end portion of a staple cartridge for insertion into an end effector of the surgical stapler and for alignment and attachment to an anvil of the end effector. A body 2552 of the anvil-attachable layer 2550 can be detached from the staple cartridge by a cutting blade of the surgical stapler at the beginning of the stroke of the cutting blade. For example, the cutting blade 2570 shown in FIG. 188 can detach the anvil-attachable layer 2550 from the staple cartridge before any patient tissue is cut and before any portion of the body 2552 of the anvil-attachable layer 2550 has been captured by staples.

Referring primarily to FIG. 187, the anvil-attachable layer 2550 can include a body 2552 and a proximal end portion 2554. The proximal end portion 2554 includes attachment features 2556 that can attach to a proximal end portion of a staple cartridge. For example, the attachment features 2556 can include adhesives, welds, and/or heat staking. The attachment feature 2556 can also comprise a portion captured between a slot in a staple cartridge and a tab of a cartridge pan, as described above with respect to FIGS. 181 and 182, for example. The anvil-attachable layer 2550 can be attached to and aligned with the staple cartridge such staple cavities of the staple cartridge are aligned with the body 2552 of the layer 2550. Put differently, when staples from the staple cartridge have been fired, the staples will capture the body 2552 of the anvil-attachable layer 2550. Similar to the embodiments described above with reference to FIGS. 181-186, a staple cartridge assembly that includes the anvil-attachable layer 2550 attached to a staple cartridge can be inserted into a staple cartridge channel of an end effector of a surgical stapler. An anvil of the end effector can close on an anvil-facing surface 2553 of the anvil-attachable layer 2550. The anvil-facing surface 2553 can include an adhesive and/or attachment features that releasably attach the anvil-attachable layer 2550 to the anvil when the anvil is closed on the anvil-facing surface 2553. When the anvil is reopened, the anvil-attachable layer 2550 can pivot about the attachment features 2556 to move with the anvil. Similar to the embodiments described above with reference to FIGS. 181-186, the staple cartridge can include a staple cartridge layer, such as a tissue thickness compensator and/or a buttress material, for example.

The anvil-attachable layer 2550 can comprise a first lateral side 2566 and a second lateral side 2568. The first lateral side 2566 and the second later side 2568 can define a midline 2564 therebetween. In certain embodiments, the anvil-attachable layer 2550 can be attached to and aligned with the anvil of the end effector such that the midline 2564 is aligned with a knife slot in the anvil and a knife slot in the staple cartridge. The body 2552 of the anvil-attachable layer 2550 can include a first lateral slit 2558 positioned near a proximal end and extending from the first lateral side 2566 and past the midline 2564. The body 2552 of the anvil-attachable layer 2550 also can include a second lateral slit 2560 positioned proximally relative to the first lateral slit 2558 extending from the second lateral side 2568 and past the midline 2564. The first lateral slit 2558 and the second lateral slit 2560 can define a connector portion 2562 therebetween that can connect the body 2552 of the anvil-attachable layer 2550 to the proximal end portion 2554 of the layer 2550.

Referring primarily to FIG. 188, after the anvil-attachable layer 2550 is releasably attached to the anvil of the end effector, the end effector can be closed on patient tissue such that the anvil and the anvil-attachable layer 2550 are on one side of the tissue and the staple cartridge and/or the staple cartridge layer is on an opposite side of the tissue. Then, a cutting blade 2570 can be advanced through a knife slot in the cartridge, such as knife slot 2418 shown in FIGS. 181-185, for example, and a knife slot in the anvil. The midline 2564 of the anvil-attachable layer 2550 can be aligned with the knife slots such that the cutting blade 2570 progressively cuts the anvil-attachable layer 2550 along the midline. As the cutting blade advances through the anvil-attachable layer 2550 in a distal direction indicated by arrow D, a cutting edge 2572 of the cutting blade 2570 first cuts the proximal end portion 2554 of the layer 2550 before then cutting through the connector portion 2562, separating the body 2552 of the layer 2550 from the proximal end portion 2554 of the layer 2550. Finally, the cutting blade 2570 cuts through the body 2552 of the anvil-attachable layer 2550. After the cutting blade 2570 has advanced through the anvil-attachable layer 2550, the layer is divided in four pieces. The body 2552 of the anvil-attachable layer 2550 is detached from the proximal portion 2554 of the layer 2550. Furthermore, the body 2552 of the anvil-attachable layer 2550 is divided into two pieces 2580 and 2582 and the proximal portion 2554 of the layer 2550 is divided into two pieces 2586 and 2588.

In various circumstances, a surgeon using a surgical stapler may not completely fire the stapler. For example, referring to FIG. 188, the surgeon may only advance the cutting blade 2570 and the staple driver halfway through the body 2552 of the anvil-attachable layer 2550. Continuing the example, the body 2552 of the anvil-attachable layer 2550 is released from the staple cartridge at the beginning of the cutting stroke of the cutting blade 2570 when the blade 2570 severs the connector portion 2560 of the layer 2550. The cutting blade 2570 will then be advanced to cut along the midline 2564 along approximately half the length of the body 2552 of the anvil-attachable layer 2550. Likewise, a staple driver can advance to fire and form staples in patient tissue and in the half of the body 2552 of the layer 2550 that is cut by the cutting blade 2570. The remaining half of the body 2552 of the anvil-attachable layer 2550 is not cut and is not captured by staples. The cutting blade 2570 and the staple driver can then be retracted and the anvil can be reopened. When the anvil is reopened, the portion of the body 2552 of the anvil-attachable layer 2550 that is captured by the staples and attached to patient tissue can detach from the anvil. As described above, the connector portion 2560 connecting the body 2552 of the anvil-attachable layer 2550 to the proximal end portion 2554 can be severed before any staples are fired and before the cutting blade 2570 severs any patient tissue or any portion of the body 2552 of the layer 2550. Therefore, the body 2552 of the layer 2550 is already free from the staple cartridge. When the surgical stapler is removed from the patient, the portion of the body 2552 of the anvil-attachable layer 2550 that is captured by patient tissue can pull the remainder of the body 2552 away from the anvil. As this example describes, the anvil-attachable layer 2550 can accommodate an incomplete firing of the surgical stapler because the connector portion 2560 of the anvil-attachable layer 2550 can be cut by the cutting blade 2570 before any staples from a staple cartridge are fired and formed in the body 2552 of the layer 2550.

The embodiments described with reference to FIGS. 181-186 can also accommodate an incomplete firing of a surgical stapler. In each instance, a cutting blade of the surgical stapler is not needed to separate the anvil-attachable layer from the staple cartridge. In the embodiments described with reference to FIGS. 181-184, the anvil-attachable layers can be pulled free from their attachments to the staple cartridge body after a partial firing the surgical instrument. In the embodiments described with reference to FIGS. 185 and 186, the anvil-attachable layer is attached to a staple cartridge layer instead of being attached to the staple cartridge. As described above, the staple cartridge layer and the anvil-attachable layer are both implantable in the patient. Thus, whether the surgical instrument is completely fired has no bearing on separating the anvil-attachable layers in the embodiments described with reference to FIGS. 181-186 from a staple cartridge in a surgical stapler.

In various circumstances, a surgeon can use a second surgical instrument to detach the anvil-attachable layers, described above with reference to FIGS. 181-184, from a staple cartridge. For example, in various circumstances, the surgical stapler is used on delicate tissue, such as lung tissue, the surgeon may want to avoid tugging on the tissue that can result from pulling the surgical stapler free from the anvil-attachable layer. In such circumstances, the surgeon can introduce another surgical instrument, such as a grasping tool, to hold the stapled patient tissue and anvil-attachable layer stationary while the surgical stapler is removed from the patient. In the various embodiments of anvil-attachable layers described above with reference to FIGS. 185-188, a surgeon may not need a second surgical tool to detach the anvil-attachable layer from the surgical stapler. Referring again to the embodiments described with reference to FIGS. 185 and 186, the anvil-attachable layer 2510 is attached to a staple cartridge layer 2506 that is also implanted in the patient. There is no attachment of the anvil-attachable layer to the staple cartridge in the surgical stapler. Therefore, the patient tissue does not need to be tugged or pulled to separate the anvil-attachable layer from the staple cartridge when the stapler is removed from the patient. Referring again to the embodiments described with reference to FIGS. 187 and 188, the body 2552 of the anvil-attachable layer 2550 is mechanically detached from the surgical stapler by a cutting blade 2570 at the beginning of the stroke of the cutting blade. Again, there is no attachment of the body 2552 of the anvil-attachable layer 2550 to the staple cartridge in the surgical stapler when the surgical stapler is ready for removal from the patient after cutting and stapling patient tissue. Therefore, the patient tissue does not need to be tugged or pulled to separate the body 2552 of the anvil-attachable layer 2550 from the staple cartridge when the stapler is removed from the patient.

Referring primarily to FIGS. 189-190, a compensator 27120 for a sleeve 27110 can comprise a body 27122 having a longitudinal protrusion 27124 that extends along at least a portion of the body 27122. The longitudinal protrusion 27124 can define a longitudinal path along the midline of the body 27122, for example. In various embodiments, the longitudinal protrusion 27124 can be received by a longitudinal slot in an anvil when the sleeve 27110 is positioned on the anvil. Referring primarily to FIG. 191, the longitudinal protrusion 27124 can comprise a rounded projection. For example, the cross-section of the longitudinal protrusion 27124 can form an arc and/or partial ring. In other embodiments, the longitudinal protrusion 27124 can comprise an angular and/or stepped projection. The compensator 27120 can further comprise an edge 27126, which can be straight, bent, fluted, wavy, and/or zigzagged, for example. In various embodiments, the edge 27126 can comprise gaps 27128 that can be configured to receive the catch extensions extending from the anvil when the assembled sleeve 27110 is positioned on the anvil.

As outlined herein, a layer, such as a tissue thickness compensator, for example, can be implanted against tissue by one or more fasteners ejected from a staple cartridge. As also outlined herein, in various circumstances, the entirety of a staple line can capture at least a portion of the layer against the tissue. For instance, the proximal-most staples in a staple line can capture at least a portion of the layer therein while the distal-most staples in the staple line can also capture at least a portion of the layer therein. In certain circumstances, a proximal portion of the layer can extend proximally with respect to the proximal-most staples in the staple line and/or a distal portion of the layer can extend distally with respect to the distal-most staples in the staple line. In use, a series of layers can be implanted. In at least one such circumstance, the layers can be implanted consecutively along a cut line. In some circumstances, the layers can be implanted such that one layer partially overlaps another layer. For instance, the distal end of a first implanted layer can overlap with the proximal end of a second implanted layer. Likewise, the distal end of the second implanted layer can overlap with a proximal end of a third layer, and so forth. As a result, certain fasteners may capture a portion of two or more layers therein. The presence of two or more layers captured within a staple can increase the pressure applied to the tissue captured within the staple and/or increase the rigidity of the tissue, especially when several adjacent staples have captured more than one layer. Referring now to FIGS. 192-194, as described in greater detail below, a tissue thickness compensator 11050 can comprise a proximal end 11053 and a distal end 11055 wherein the proximal end 11053 and/or the distal end 11055 can comprise one or more strain relief portions which can reduce the rigidity of the tissue thickness compensator 11050 and the rigidity of the tissue being stapled.

Referring again to FIGS. 192-194, the distal end 11055 of the tissue thickness compensator 11050 can comprise one or more slots 11058 defined therein. The slots 11058 can comprise cuts and/or notches, for example, defined in the tissue thickness compensator 11050. The slots 11058 can define projections, or tabs, 11056 which can be configured to at least partially move and/or flex relative to one another and/or the body portion of the tissue thickness compensator 11050. Stated another way, the slots 11058 can provide localized strain relief to the tissue thickness compensator 11050 and the underlying tissue. In certain circumstances, the tabs 11056 of a first tissue thickness compensator 11050 can be overlapped with a proximal end 11053 of a second tissue thickness compensator 11050. In various circumstances, the slots 11058 can permit the first tissue thickness compensator 11050 and the second tissue thickness compensator to pivot relative to one another. In certain circumstances, referring primarily to FIG. 194, the tabs 11056 of a first tissue thickness compensator 11050 can be overlapped with the tabs 11056 of a second tissue thickness compensator 11050. In various circumstances, the slots 11058 in the overlapped distal ends 11055 can further reduce the rigidity within the underlying tissue. Although the illustrated embodiment of tissue thickness compensator 11050 only comprises an arrangement of tabs 11057 and slots 11058 on one end thereof, a tissue thickness compensator may comprise an arrangement of tabs 11057 and slots 11058 on both ends thereof, for example.

In certain embodiments, further to the above, each tab 11056 can comprise a tapered profile. For instance, each tab 11056 can comprise a base attached to the body of the tissue thickness compensator 11050 having a base width and a free end on the opposite end thereof having an end width, wherein the base width can be wider than the end width. In certain embodiments, the end width can be wider than the base width. Referring primarily to FIG. 194, an end 11055 can comprise a plurality of tabs 11056 having different configurations. For instance, the tabs 11056 can have different lengths. As illustrated in FIG. 194, an end-most tab 11056a can have a first length, a second tab 11056b can have a second length which is longer than the first length, a third tab 10056c can have a third length which is longer than the second length, a fourth tab 10056d can have a fourth length which is longer than the third length, a fifth tab 10056e can have a fifth length which is longer than the fourth length, and a sixth tab 10056f can have a sixth length which is longer than the fifth length, for example. In such an embodiment, the tabs 10056 can become progressively shorter toward the distal end of the tissue thickness compensator 10050. In other embodiments, the lengths of the tabs 10056 can be arranged in any other suitable arrangement.

In various circumstances, further to the above, a layer can comprise edges which define the perimeter of the layer. These edges may be straight, substantially straight, linear, and/or substantially linear, in certain circumstances. In some such circumstances, the layer edges may impinge on and/or otherwise affect the surrounding tissue. Also, in some such circumstances, the edges may be rigid and may rigidly support the tissue. In effect, certain portions of the tissue may be unsupported by the layer which are adjacent to other portions of the tissue which are rigidly supported by the layer without transition therebetween. Referring to FIGS. 192-194 once again, the perimeter of the tissue thickness compensator 11050 can include a contoured configuration which can provide a region of transitional rigidity to the underlying tissue. The perimeter of the tissue thickness compensator 11050 can comprise a plurality of notches or recesses 11059 defined therein which can define tabs 11057. Similar to the above, the tabs 11057 can extend from the body of the tissue thickness compensator 11050 and can move relative thereto. Also similar to the above, each tab 11057 can comprise a base end attached to the body of the tissue thickness compensator 11050 and free end which is movable relative to the base end. In certain circumstances, the free end of a tab 11057 can have a width which is narrower than the width of the base end of the tab 11057 while, in other circumstances, the free end of a tab 11057 can have a width which is wider than the width of the base end of the tab 11057. The tabs 11057 can comprise any suitable configuration such as a semi-circular, or an at least partially arcuate, configuration, for example. As a result of the above, the tissue underlying and/or fastened to the body portion of the tissue thickness compensator 11050 can be rigidly supported by the body portion, the tissue underlying and/or fastened to the tabs 11057 can be less than rigidly supported by the tabs 11057, and the tissue adjacent to the tabs 11057, but not underlying the tabs 11057, may be unsupported by the tissue thickness compensator 11050.

Referring now to FIGS. 195 and 196, a staple cartridge assembly 11100 can comprise a cartridge body 11110 and a tissue thickness compensator 11150 attached to the cartridge body 11110. The cartridge assembly 11100 can further comprise one or more attachment members 11160 configured to releasably hold the tissue thickness compensator 11150 to the cartridge body 11110. In at least one circumstance, each attachment member can comprise a strap which extends around the cartridge body 11110 and the tissue thickness compensator 11150. In use, further to the above, a firing member 10030 can be advanced through the staple cartridge 11100 to incise the tissue thickness compensator 11150, fire the staples at least partially stored in the cartridge body 11110, and sever the attachment members 11160. The tissue thickness compensator 11150 can comprise a first, or proximal, end 11157 and a second, or distal, end 11155. The distal end 11155 can comprise an elongate projection 11156 extending from a body portion 11153 of the tissue thickness compensator 11150. As illustrated in FIG. 195, the elongate projection 11156 can extend distally with respect to the distal-most attachment member 11160. In at least the illustrated embodiment, the cartridge body 11110 can comprise a deck 11113 within which staple cavities of the cartridge body 11110 can be defined. In various circumstances, the body 11153 of the tissue thickness compensator 11150 can be configured and arranged such that it covers the deck 11113 and the staple cavities defined in the cartridge body 11110. In at least some circumstances, as also illustrated in FIG. 195, the elongate projection 11156 can extend distally from the deck 11113 and extend distally with respect to the staple cavities defined in the deck 11113.

In use, further to the above, the tissue thickness compensator 11150 can be fastened to tissue and can provide tissue thickness compensation properties, as described herein. Similar to the above, the tissue underlying the tissue thickness compensator 11150 may be rigidly supported by the tissue thickness compensator 11150 and the staples securing the same whereas the tissue surrounding the tissue thickness compensator 11150 may be unsupported by the tissue thickness compensator 11150 and may be flexible. In such circumstances, the tissue between the flexible unsupported tissue and the rigidly supported tissue underlying the tissue thickness compensator 11150, i.e., the transition tissue, can undergo an undesirable amount of strain. Such strain may negatively impact the transition tissue. For instance, when a tissue thickness compensator is secured to pulmonary, or lung, tissue, for example, the tissue immediately surrounding the perimeter of the tissue thickness compensator, i.e., the perimeter tissue, may tear in certain circumstances, especially the perimeter tissue adjacent to and/or surrounding the distal end of the tissue thickness compensator, i.e., the end perimeter tissue. The distal projection 11156 of the tissue thickness compensator 11150, however, can support the end perimeter tissue. Stated another way, the distal projection 11156 can provide transitional support to the end perimeter tissue. Such transitional support can be less than the support provided by the body of the tissue thickness compensator 11150 and can mitigate the change in strain between the unsupported tissue and the fully supported tissue underlying the tissue thickness compensator 11150. In various circumstances, the distal projection 11156 can provide an enlarged area in which force can be transmitted between the unstapled tissue and the stapled tissue. The distal projection 11156 can be configured to flex and move with the unsupported tissue and the tissue thickness compensator 11150. In various circumstances, the distal projection 11156 can move relative to the body portion of the tissue thickness compensator 11150 and/or the unsupported tissue.

The tissue thickness compensator 11150, referring again to FIGS. 195 and 196, can further comprise a notch 11157 defined in the proximal end 11153 thereof. The notch 11157 can be defined between two distally extending projections 11158. The notch 11157 can comprise any suitable shape, such as a parabolic shape, for example. Similar to the above, the distally extending projections 11158 can provide transitional support to the proximal end perimeter tissue. Such transitional support can be less than the support provided by the body of the tissue thickness compensator 11150 and can mitigate the change in strain between the unsupported tissue and the fully supported tissue underlying the tissue thickness compensator 11150. In various circumstances, the proximal projections 11158 can provide an enlarged area in which force can be transmitted between the unstapled tissue and the stapled tissue. The proximal projections 11158 can be configured to flex and move with the unsupported tissue and the tissue thickness compensator 11150. In various circumstances, the proximal projections 11158 can move relative to the body portion of the tissue thickness compensator 11150, each other, and/or the unsupported tissue. Various alternative embodiments are envisioned in which more than two projections extend from the proximal end and/or distal end of a tissue thickness compensator.

As illustrated in FIG. 196, two or more tissue thickness compensators 11150 can be implanted in an end-to-end manner along a path. In such circumstances, the distal end 11155 of a first tissue thickness compensator 11150 can overlap with the proximal end 11153 of a second tissue thickness compensator 11150. Similarly the distal end 11155 of the second tissue thickness compensator 11150 can overlap with the proximal end 11153 of a third tissue thickness compensator 11150. In various circumstances, the distal projection 11156 of the first tissue thickness compensator 11150 can be aligned, or at least substantially aligned, with the recess 11157 of the second tissue thickness compensator 11150. Also, in various embodiments, the distal projection 11156 and the proximal recess 11558 can be sized and configured such that they have substantially the same size and/or shape. In various circumstances, a distal projection 11156 can be configured to be positioned within a proximal recess 11157 of an adjacent tissue thickness compensator 11150.

Turning now to FIGS. 293 and 294, an end effector of a surgical stapling instrument can comprise a first jaw including a cartridge channel 11390 configured to receive a staple cartridge 11300 therein and a second jaw including an anvil 11391. Similar to the above, the staple cartridge 11300 can comprise a cartridge body 11310 and a tissue thickness compensator 11350. The staple cartridge 11300 can further comprise a tissue abutment member 11355 attached thereto. The tissue abutment member 13555, in various circumstances, can be removably attached to the cartridge body 11310. In addition to or in lieu of being removably attached to the cartridge body 11310, the tissue abutment member 11355 can be attached to the tissue thickness compensator 11350. In at least one such embodiment, the tissue abutment member 11355 may be releasably secured to the tissue thickness compensator 11350. In use, similar to the above, fasteners may be deployed from the cartridge body 11310 to secure the tissue thickness compensator 11350 to tissue T captured between the tissue thickness compensator 11350 and the anvil 11391. In various circumstances, fasteners may not penetrate the tissue abutment member 11355. In certain other circumstances, fasteners may penetrate and capture at least a portion of the tissue abutment member. 11355 therein and secure the tissue abutment member 11355 to the tissue T. In either event, similar to the above, at least a portion of the tissue abutment member 11355 can be configured to provide transitional support between the unsupported tissue and the tissue underlying the tissue thickness compensator 11350 which is rigidly supported by the fasteners. The tissue abutment member 11355 can comprise any suitable shape, such as tongue-shaped, for example. In at least one embodiment, the tissue abutment member 11355 can comprise one or more notches 11358 which can define tabs 11356 therebetween. Once the tissue thickness compensator 11350 has been positioned against and secured to the tissue T, the tissue abutment member 11355 can be configured to flex relative to the tissue thickness compensator 11350 and provide support to the tissue adjacent the distal end of the tissue thickness compensator 11350. In various circumstances, the tissue abutment member 11355 can flex relative to the tissue thickness compensator 11350 and the tabs 11356 can flex relative to each other, the body of the tissue abutment member 11355, and/or the tissue thickness compensator 11350, for example.

Referring again to FIGS. 293 and 294, at least a portion of the tissue abutment member 11355 can overlap the tissue thickness compensator 11350. In various circumstances, such a portion of the tissue abutment member 11355 can be attached to the tissue thickness compensator 11350 by one or more adhesives, for example. In certain circumstances, at least a portion of the tissue abutment member 11355 can overlap one or more staple cavities defined in the cartridge body 11310 such that the staples ejected from such staple cavities can capture at least a portion of the tissue abutment member 11355 therein and secure the tissue abutment member 11355 to the tissue. At least a portion of the tissue abutment member 11355 can overlap a nose 11311 of the cartridge body 11310. In various circumstances, such a portion of the tissue abutment member 11355 can be attached to the nose 11311 by one or more adhesives, for example. In other circumstances, such a portion of the tissue abutment member 11355 may not be attached to the nose 11311. Referring primarily to FIG. 294, at least a portion of the tissue abutment member 11355 can overlap a distal portion 11312 of the nose 11311. In various circumstances, such a portion of the tissue abutment member 11355 may not be attached to the distal portion 11312 of the nose 11311. In at least some circumstances, a gap can be defined between the tissue abutment member 11355. At least a portion of the tissue abutment member 11355 can extend freely from the nose 11311 of the cartridge body 11310. In such embodiments, the tissue abutment member 11355 can comprise a cantilever.

In use, further to the above, the staple cartridge 11300 can be positioned on a first side of the tissue T and the anvil 11391 can be positioned on the second side. The anvil 11391 can then be pivoted toward the staple cartridge 11300 about a pivot 11392 defined in a shaft 11393 of a surgical stapling instrument. Once the anvil 11391 and the staple cartridge 11300 have been suitably positioned, the staples contained within the cartridge body 11310 can be ejected therefrom, penetrate the tissue thickness compensator 11350, and secure the tissue thickness compensator 11350 to the tissue T. Thereafter, the anvil 11391 can be opened and the end effector can be moved away from the tissue T. In such circumstances, the cartridge body 11310 can be pulled away from the tissue thickness compensator 11350 thereby leaving the tissue thickness compensator 11350 behind. Concurrently, the tissue abutment member 11355 can detach from the staple cartridge 11300 with the tissue thickness compensator 11350. To the extent that the tissue abutment member 11355 is attached to the tissue thickness compensator 11350, the tissue thickness compensator 11350 can hold the tissue abutment member 11355 against the tissue. In various circumstances, the tissue abutment member 11355 can be biased against the tissue T by the tissue thickness compensator 11350. When the tissue moves, expands, and/or flexes, for example, the tissue abutment member 11355 can flexibly support the underlying tissue T and distribute forces, stresses, and/or strains over a large area.

Referring again to FIGS. 293 and 294, the end effector of a surgical instrument can comprise a tissue abutment member, such as tissue abutment member 11395, for example, attached to the anvil 11391. In various circumstances, the tissue abutment member 11395 can be the same as, or at least substantially the same as, the tissue abutment member 11355. In at least one circumstance, the tissue abutment member 11395 can comprise notches 11398 defined between tabs 11396. In use, the tissue abutment member 11395 can be attached to the anvil 11391 utilizing one or more adhesives, for example, wherein the tissue abutment member 11395 can be positioned against the tissue T when the anvil 11391 is positioned relative to the tissue T and then closed. When the anvil 11391 is reopened after the staples have been fired from the staple cartridge, the tissue abutment member 11395 can detach from the anvil 11391 and remain attached to the tissue T. In various circumstances, at least a portion of the tissue abutment member 11395 can be captured within the staples ejected from the cartridge body 11310, for example. In at least some such circumstances, the tissue abutment member 11395 can at least partially overlap, or extend over, staple cavities defined in the anvil 11391. In some circumstances, one or more adhesives, such as activatable adhesives, for example, can be located on the tissue-contacting surfaces of the tissue abutment member 11395 such that the tissue abutment member 11395 adheres to the tissue T. In any event, referring primarily to FIG. 294, one or both of the tissue abutment member 11355 and the tissue abutment member 11395 may be utilized to flexibly support the tissue T. In embodiments where both the tissue abutment member 11355 and the tissue abutment member 11395 are utilized, the tissue abutment members 11355 and 11395 may be comprised of the same material, or different materials. The tissue abutment members 11355 and 11395 may comprise the same shape and configuration, or different shapes and configurations. The tissue abutment members 11355 and 11395 may also comprise the same thickness, or different thicknesses. Such properties of the tissue abutment members 11355 and 11395 can be selected so as to provide a desired support profile to the tissue positioned therebetween. For instance, such properties may be selected such that one of the tissue thickness compensators 11355 and 11395 is more rigid than the other. Concurrently, such properties may be selected such that one of the tissue thickness compensators 11355 and 11395 is more flexible than the other.

In various circumstances, a tissue thickness compensator can comprise a plurality of layers. For instance, a tissue thickness compensator can comprise a first layer and a second layer. Such layers can be comprised of the same materials, or different materials. Some layers can be configured to provide different properties to the tissue thickness compensator. For instance, a tissue thickness compensator can comprise a compressible first layer that provides tissue thickness compensation properties and a more rigid second layer which can support the first layer. Referring primarily to FIGS. 197 and 198, a tissue thickness compensator 11250 can comprise a first layer 11251 and a second layer 11252. The second layer 11252 can be compressible and can provide tissue thickness compensation properties. The first layer 11251 can be rigid and can support the second layer 11252. The second layer 11252 can be positioned against and/or attached to a cartridge body 11210, for example. In certain circumstances, the first layer 11251 can comprise a longitudinal channel 11253 extending along the length thereof which can be sized and configured to be releasably retained in a longitudinal knife slot 11215 defined in the cartridge body 11210. In various circumstances, the second layer 11252 can be secured to the first layer 11251 and held in place by the first layer 11251.

Referring again to FIGS. 197 and 198, compensator 11250 may comprise a plurality of layers. In addition, an outer periphery 11218 of the second layer 11252 may be at least partially extended beyond an outer periphery 11220 of the first layer 11251. Furthermore, the first layer 11251 and the second layer 11252 may comprise different degrees of stiffness. For example, the second layer 11252 may be configured to be more flexible than the first layer 11251. This arrangement may provide tissue thickness compensator 11250 with a sufficiently rigid inner region, comprised from the first layer 11251 and the second layer 11252, which may be suitable to provide adequate support for staples 11260, and a sufficiently flexible outer region, comprised from the second layer 11252, which may be suitable to provide sufficient flexibility to soften the impact upon tissue T, for example, during and/or after the capturing of the tissue T and the tissue thickness compensator 11250 by the staples 11260. Layers 11251 and 11252 can be joined together, for example, by an adhesive. Other attachment means for attaching the first layer 11251 to the second layer 11252 are contemplated within the scope of the current disclosure.

Further to the above, the first layer 11251 may include an inner portion 11254 and an outer portion 11256 at least partially surrounding the inner portion 11254, wherein the outer portion 11256 may be configured to be more flexible than the inner portion 11254. For example, the outer portion 11254 may comprise a plurality of slits 11210 which may increase the flexibility of the outer portion 11254. Furthermore, as described above, the second layer 11252 may be configured to be more flexible than the first layer 11251. This arrangement may provide tissue thickness compensator 11250 with three regions of different rigidity including a first inner region having the most rigidity, the inner region being comprised of inner portion 11254 of the first layer 11251 and the second layer 11252, a middle region having an intermediate rigidity, the middle region being comprised of outer portion 11256 of first layer 11251 and the second layer 11252, and a third outer region having the least rigidity, the third region being comprised solely of the second layer 11252.

The second layer 11252 of tissue thickness compensator 11250 can comprise a woven structure which may include a plurality of fibers which may be woven into the woven structure. The woven structure may provide the second layer 11252 with sufficient flexibility to soften the impact upon tissue T, for example, during and/or after the capturing of the tissue T and the tissue thickness compensator 11250 by staples 11260. Furthermore, the outer periphery 11218 can be comprised of fibers which can provide an atraumatic tissue contacting surface to minimize impact upon tissue T, as described above. The woven structure and fibers can be comprised of biocompatible materials. Furthermore, the woven structure and/or fibers can be comprised from a bioabsorbable material such as PLLA, PGA, PCL, and/or combinations thereof, for example.

Referring to FIGS. 199-201, a staple cartridge channel can be configured to receive a staple cartridge 1060 which can comprise a cartridge body 1062, a cartridge deck 1064, and a support 1065. In addition, a tissue thickness compensator such as, for example, tissue thickness compensator 1100 may be removably positioned against or adjacent cartridge deck 1064, as illustrated in FIG. 199.

Referring again to FIGS. 199-201, a tissue thickness compensator may be configured to be absorbed after implantation in a patient. The absorption process may initially reduce the tissue thickness compensator into smaller pieces which may include rough edges that may have undesirable effects on surrounding tissue T. To mitigate these effects, tissue thickness compensator 1100 may be at least partially assembled from a plurality of pieces 1140, which each may have atraumatic outer peripheries and may be joined together to form a single structure, as illustrated in FIG. 201. Pieces 1140 can be joined to form tissue thickness compensator 1100 in a manner such that the absorption process may first reduce tissue thickness compensator 1100 into pieces 1140 thereby minimizing the presence of rough edges. For example, pieces 1140 may comprise circular profiles and may be joined together by thermal bonding to form tissue thickness compensator 1100. Other profiles and other means for joining pieces 1140 are contemplated within the scope of the present disclosure. In one example, pieces 1140 can be joined together by an adhesive 1143 (See FIG. 200) configured to be absorbed faster than pieces 1140 to allow separation of the pieces 1140 in an initial stage of the absorption process. As illustrated in FIG. 200, pieces 1140 can be arranged in an overlapping array wherein an end portion of one of the pieces 1140 may overlap with an end portion of another one of the pieces 1140 such that the two end portions of the pieces 1140 are releasably attached to each other, for example, by an adhesive. Under certain circumstances, pieces 1140 can be arranged in another overlapping array wherein one of the pieces 1140 can be positioned over and releasably attached to a plurality of pieces 1140, as illustrated in FIG. 201.

Referring to FIGS. 202-204, as described above, a tissue thickness compensator may be configured to be absorbed after implantation in a patient and the absorption process may initially reduce the tissue thickness compensator into random smaller pieces. Guiding the absorption process to yield small pieces with atraumatic outer edges can be achieved, as described above, by starting with small pieces having atraumatic outer edges. Another approach may include modifying the tissue thickness compensator in such a manner that allows its separation into smaller pieces having atraumatic peripheries in an initial stage of the absorption process. For example, as illustrated in FIG. 202, a tissue thickness compensator 1200 may comprise a pattern such as pattern 1212, for example, which can be molded or carved into the tissue thickness compensator 1200 to yield, for example, a plurality of circular shaped portions 1210. The portions 1210 may be defined by reducing the thickness of tissue thickness compensator 1200 along circumferences 1214 of the circular shaped portions 1210, as illustrated in the cross-sectional view in FIG. 202A. In result, a faster absorption along the circumferences 1214 of circular shaped portions 1210 may occur which may lead to a separation of the circular shaped portions 1210 from each other in an initial stage of the absorption process. Patterns comprising portions with other geometrical shapes with atraumatic outer peripheries are contemplated within the scope of the current disclosure. For example, as illustrated in FIG. 203, tissue thickness compensator 1200' may comprise a pattern 1216 comprising portions 1218 which may include profiles that extend longitudinally in a wave-like profile along a length of tissue thickness compensator 1200'. In another example, as illustrated in FIG. 204, tissue thickness compensator 1200" may comprise a pattern 1220 which may include hexagonal shaped portions 1222.

Referring to FIG. 205, as described above, a tissue thickness compensator, such as tissue thickness compensator 1250, may be captured along with tissue T by staples, such as staples 1002, for example, and may be configured to be reduced into atraumatic pieces, such as pieces 1226, for example, in an initial stage of the absorption process after implantation in a patient. Upon separation, pieces 1226 can move and/or slide relative to each other which may impact surrounding tissue T. To minimize relative motion between pieces 1226, fired staples 1002 can be spatially arranged onto tissue thickness compensator 1250 such that a staple 1002 may capture multiple pieces 1226, as illustrated in FIG. 205. This may also aid in maintaining tissue thickness compensator 1250 in a substantially singular structure even after pieces 1226 are separated from each other in the initial stage of the absorption process. As such, the tissue thickness compensator 1250 may continue to provide support for tissue T captured by staples 1002 after pieces 1226 are separated from each other in the initial stage of the absorption process.

Further to the above, referring now to FIG. 206, yet another approach can be taken to guide the absorption process of a tissue thickness compensator to yield small pieces with atraumatic outer edges. For example, as illustrated in FIG. 206, a tissue thickness compensator such as tissue thickness compensator 1300 may comprise a plurality of slits 1310 which can be strategically positioned to improve the flexibility of tissue thickness compensator 1300, as described above. In addition, slits 1310 may partially divide tissue thickness compensator 1300 into a plurality of portions 1312 which may separate from each other during an initial stage of the absorption process. Slits 1312 can reduce the width of tissue thickness compensator 1300 along outer peripheries 1314 of portions 1312, as illustrated in FIG. 206. This reduction in width may lead to faster absorption along the outer peripheries 1314 of portions 1312, which can result in reducing tissue thickness compensator 1300 into separate portions 1312 during the initial stage of the absorption process.

Referring to FIGS. 207A and 207B an end effector of a surgical stapling instrument can comprise a first jaw and a second jaw, wherein at least one of the first jaw and the second jaw can be configured to be moved relative to the other. In certain embodiments, the end effector can comprise a first jaw including a staple cartridge channel 1010 and a second jaw including an anvil 1012 (FIG. 207B), wherein the anvil 1012 can be pivoted toward and/or away from the staple cartridge channel 1010, for example. The staple cartridge channel 1010 can be configured to receive a staple cartridge 1020, for example, which can be removably retained within the staple cartridge channel 1010. Other embodiments may include staple cartridges that are not readily removable from the cartridge channel 1010. The staple cartridge 1020 can comprise a cartridge body 1022, a cartridge deck 1024, and a layer 1000 wherein, as illustrated in FIG. 207A, layer 1000 may be removably positioned against or adjacent cartridge deck 1024.

Similar to other embodiments described herein, referring again to FIGS. 207A and 207B, the cartridge body 1022 can comprise a plurality of staple cavities 1026 and a staple 1002 positioned within each staple cavity 1026. Also similar to other embodiments described herein, the staples 1002 can be supported by staple drivers 1028 positioned within the cartridge body 1022 wherein a sled and/or firing member, for example, can be advanced through the staple cartridge 1020 to lift the staple drivers 1028 upwardly within the staple cavities 1026 and eject the staples 1002 from the staple cavities 1026, as illustrated in FIG. 207B. Tissue T and/or layer 1000 can be captured by staples 1002, as illustrated in FIG. 207B, as staples 1002 are ejected from the staples cavities 1026.

Layer 1000 may be comprised of a biocompatible material. In addition, layer 1000 can be comprised of a bioabsorbable material such as PLLA, PGA, PCL, and/or combinations thereof, for example. In at least one embodiment, layer 1000 can comprise a tissue thickness compensator which may include internal compression features designed to compensate for tissue T thickness when layer 1000 and tissue T are captured by staples 1002, as described above.

Referring again to FIG. 207B, layer 1000 can include a tissue contacting surface 1003 which can be configured to reduce slippage between the layer 1000 and the tissue T positioned thereagainst. Pressure exerted against the tissue T in contact with the tissue contacting surface 1003 may depend in part on the contact area between the tissue T and the tissue contacting surface 1003. Since pressure is reversibly proportional to area, reducing the contact area may yield higher pressure against the tissue T and in turn may yield better slippage protection. The tissue contacting surface 1003 may include a plurality of cleats 1030 comprising small contact areas, wherein the cleats 1030 may reduce slippage between the layer 1000 and the tissue T positioned thereagainst. Layer 1000 can be manufactured with cleats 1030, for example, by compression molding techniques. Alternatively, cleats 1030 can be formed onto tissue contacting surface 1003 after layer 1000 is manufactured, for example, by laser and/or chemical etching techniques which may yield a plurality of protruding structures. Furthermore, cleats 1030 may comprise micrometer and/or nanometer scale structures formed onto tissue contacting surface 1003 using, for example, photolithography techniques which may generally use a pre-fabricated photomask as a master from which a final pattern of micrometer and/or nanometer scale cleats can be derived. Other techniques for forming micrometer and/or nanometer scale cleats 1030 can be utilized and are contemplated within the scope of the current disclosure. In one example, electron beam lithography can be utilized to create cleats 1030.

Referring now to FIGS. 207C-224, cleats 1030 can comprise a plurality of shapes. For example, as illustrated in FIG. 207C, tissue contacting surface 1003 may include pillar-shaped cleats 1038 which may include square and/or rectangle bases and substantially perpendicular sides extending generally away from tissue contacting surface 1003. In addition, pillar-shaped cleats 1038 may terminate at generally narrow top portions, or tips 1040, as illustrated in cross-sectional view in FIG. 208. Furthermore, tissue contacting surface 1003 may include cone-shaped cleats 1032, as illustrated in FIG. 218, pyramid-shaped cleats 1034, as illustrated in FIG. 219, and/or dome-shaped cleats 1042, as illustrated in FIG. 211. The pyramid-shaped cleats 1034 may include square and/or triangular bases and sloping sides that may extend generally away from tissue contacting surface 1003 and terminate at top portions 1036, as illustrated in the cross-sectional view in FIG. 220.

Cleats 1030 can be spatially arranged onto tissue contacting surface 1003 in a predetermined pattern or array. For example, cleats 1030 can be spatially arranged onto tissue contacting surface 1003 in multiple rows which may extend longitudinally along a length of surface 1003 in parallel to each other. Cleats 1030 can also be spatially arranged in circles. For example, cleats 1030 can be arranged in concentric circles. Alternatively, cleats 1030 can be randomly positioned onto tissue contacting surface 1003.

Further to the above, tissue contacting surface 1003 may include cleats 1030 comprising multiple shapes, multiple heights, and/or multiple spatial arrangements to provide various degrees of slippage protection along various regions of the tissue contacting surface 1003. For example, greater slippage protection may be needed at and/or around regions of tissue contacting surface 1003 where staples 1002 are configured to penetrate and capture tissue T.

Referring to FIGS. 209, 210, and 215-217, layer 1000 may comprise linear protrusions 1044 which can be disposed onto the tissue contacting surface 1003. Linear protrusions 1044 may extend longitudinally. For example, linear protrusions 1044 may extend in parallel with each other, along a length of the layer 1000, as illustrated in FIG. 209. Alternatively, linear protrusions 1044 may extend along a width of the layer 1000, as illustrated in FIG. 215. Furthermore, longitudinal and transverse linear protrusions 1044 may cross paths. For example, as illustrated in FIG. 217, a first pattern 1046 of the linear protrusions 1044 may extend in parallel in a first direction on tissue contacting surface 1003, and a second pattern 1048 of linear protrusions 1044 may extend in parallel in a second direction on tissue contacting surface 1003, wherein the first direction can be perpendicular, or substantially perpendicular, to the second direction. Furthermore, linear protrusions 1044 may comprise substantially uniform cross-sectional areas, as illustrated in FIG. 210. Alternatively, linear protrusions 1044 may comprise different cross-sectional areas (not shown). In certain circumstances, the first pattern 1046 and the second pattern 1048 may be continuous or intermittent.

Further to the above, layer 1000 may include non-linear protrusions which can be disposed onto the tissue contacting surface 1003 alone or in combination with linear protrusions 1044. Furthermore, linear protrusions 1044 and/or the non-linear protrusions can be disposed onto the tissue contacting surface 1003 in combination with cleats 1030 to produce a desired degree of slippage protection.

Referring to FIGS. 213 and 214, layer 1000 may comprise a plurality of depressions 1050 which can be carved into the tissue contacting surface 1003, as illustrated in FIG. 223. Depressions 1050 may comprise substantially uniform socket shapes, as illustrated in FIG. 224. Alternatively, depressions 1050 may comprise different depths which may provide various degrees of slippage protection along various regions of the tissue contacting surface 1003. Generally, a greater depth of a particular depression may yield a greater flexibility of the region where the depression lies and a greater collapsibility of such region. Furthermore, as discussed above with respect to Cleats 1030, depressions 1050 may comprise a plurality of shapes and/or spatial arrangements. In addition, layer 1000 may comprise combinations of depressions 1050 and cleats 1030 spatially arranged on tissue contacting surface 1003. In certain circumstances, cleats 1030 and depressions 1050 may be arranged in alternating patterns.

Referring again to FIGS. 223 and 224, layer 1000 may comprise linear depressions 1052 which, similar to linear protrusions 1044 (described above), may extend longitudinally, for example in parallel with each other, along a length of the layer 1000, as illustrated in FIG. 223. Furthermore, layer 1000 may comprise combinations of linear depressions 1052 and linear protrusions 1044 spatially arranged onto tissue contacting surface 1003, for example in an alternating pattern. Furthermore, referring now to FIGS. 221 and 222, the combinations of linear depressions 1052 and linear protrusions 1044 can be arranged in a corrugated pattern 1054, as illustrated in FIG. 221.

Referring now to FIGS. 244-246, a tissue thickness compensator, such as compensator 22320, for example, can comprise a plurality of first cavities 22322*a* and a plurality of second cavities 22322*b* which can be aligned with staple forming pockets 22062*a* and 22062*b*, respectively. Referring primarily to FIG. 245, the staple forming pockets 22062*a* and 22062*b* may be defined in separate stepped surfaces on the anvil 22060. More particularly, the forming pockets 22062*a* can be defined in first surfaces 22069*a* of anvil 22060 and the forming pockets 22062*b* can be defined in second surfaces 22069*b* wherein the first surfaces 22069*a* can be positioned offset, or higher, with respect to the second surfaces 22069*b*, for example. The first cavities 22322*a* of the tissue thickness compensator 22320 can be larger than the second cavities 22322*b* wherein, in at least one such embodiment, the first cavities 22322*a* can extend higher than the second cavities 22322*b*. As a result of the above, the first cavities 22322*a* can extend upwardly into the first staple forming pockets 22062*a* while, concurrently, the second cavities 22322*b* can extend upwardly into the second staple forming pockets 22062*b*. The first cavities 22322*a* and/or the second cavities 22322*b* can be configured to contain a medicament.

Further to the above, the first cavities 22322*a* can be arranged in certain rows while the second cavities 22322*b* can be arranged in different rows. The cavities 22322*a* and/or the cavities 22322*b* can be configured to fit snugly within staple forming pockets 22062*a* and/or 22062*b*, respectively. Furthermore, the compensator 22320 can be assembled to the anvil 22060 such that the second layer 22327 of the compensator 22320 is positioned against the second surfaces 22069*b* of the anvil 22060. Referring now to FIGS. 247 and 248, the compensator 22320 can be positioned adjacent to the anvil 22060 such that the compensator 22320 can abut the anvil 22060 when the anvil 22060 is displaced toward the staple cartridge 22000 to compress the tissue T therebetween.

Referring now to FIGS. 224A and 224B, similar to the above, layer 1000 can also be positioned adjacent to the anvil 1012 such that the layer 1000 can abut the anvil 1012 when the anvil 1012 is displaced toward the staple cartridge 1020 to compress the tissue T therebetween. Also similar to the above, the layer 1000 may be captured by staples 1002 as staples 1002 are ejected from the staple cavities 1026 by staple drivers 1028. In particular, as illustrated in FIGS. 224A and 224B, staples 1002 may each comprise a base 1060, a first deformable member 1062 comprising a first tip 1063 and a second deformable member 1064 comprising a second tip 1065 which, along with the first tip 1063, may penetrate through layer 1000 to reach their respective forming pockets 1066 and 1068 as staples 1002 are ejected from the staple cavities 1026 by staple drivers 1028. In addition, tips 1063 and 1065 may each penetrate through layer 1000 a second time as the tips 1063 and 1065 are guided on a return path out of the forming pockets 1066 and 1068, respectively.

Referring again to FIG. 224A, layer 1000 may include portions 1070 which may comprise a reduced thickness relative to the remainder of the layer 1000. For example, as illustrated in FIG. 224A, layer 1000 may comprise a substantially uniform thickness "A" and portions 1070 may comprise a thickness smaller than thickness "A." In addition, layer 1000 can be aligned with staple cartridge 1020 such that upon firing staples 1002 the tips 1063 and 1065 of staples 1002 may penetrate through tissue T and the full thickness "A" of layer 1000 as the tips 1063 and 1065 of the deformable members 1062 and 1064 travel toward the respective pockets 1066 and 1068 and may penetrate through the reduced thickness of portions 1070 as they are guided out of the pockets 1066 and 1068, respectively. The reduced thickness of portions 1070 may improve the repiercing of tips 1063 and 1065 into the tissue T on the return paths of tips 1063 and 1065 from pockets 1066 and 1068, respectively.

Referring now to FIG. 224B, layer 1000 may comprise protrusions 1080 which may comprise an increased thickness relative to the remainder of the layer 1000. For example, as illustrated in FIG. 224B, layer 1000 may comprise a substantially uniform thickness "A" and protrusions 1080 may comprise a thickness "A-FB" greater than thickness "A". Layer 1000 can be aligned with staple cartridge 1020 such that upon firing staples 1002 the tips 1063 and 1065 of staples 1002 may penetrate through tissue T and the thickness "A" of layer 1000 as the tips 1063 and 1065 of the deformable members 1062 and 1064 travel toward the respective pockets 1066 and 1068. In addition, tips 1063 and 1065 of staples 1002 may penetrate through the thickness "A" of layer 1000 as they are guided out of the pockets 1066 and 1068 respectively thereby wrapping, or substantially wrapping, deformable members 1062 and 1064 at least partially around protrusions 1080. In other words, tissue T and protrusions 1080 may be captured between each of deformable members 1062 and 1064 and bases 1060 of staples 1002. Further to the above, protrusions 1080 can be arranged in rows and can be configured to fit snugly within the staple forming pockets of anvil 1020. For example, as illustrated in FIG. 224B, protrusions 1080 can comprise curved profiles which can be configured for mating engagement with forming pockets 1066 and 1068.

As described above, certain embodiments of surgical staplers may include a layer, such as a buttress material and/or a tissue thickness compensator, arranged on a surface of an anvil of the end effector. The layer can be susceptible to movement and/or misalignment. For example, the layer may be moved relative to the anvil if the layer is dragged across patient tissue while a surgeon positions the surgical stapler prior to stapling tissue. In certain embodiments, the layer can include releasable retention features for attaching the layer to the anvil so that the layer remains aligned with the anvil until after the surgical stapler is fired. In certain embodiments, the releasable retention features can be implantable in the patient.

In certain embodiments, referring now to FIGS. 225-227, an anvil-attachable layer 33420, such as a buttress material and/or a tissue thickness compensator, can comprise a shell 33426, a cavity 33424 defined in the shell 33426, and a core 33425 positioned within the cavity 33424. In at least one such embodiment, the shell 33426 can comprise a film body formed from a continuous extruded shape and the core 33425 can comprise a fibrous medicament core, such as ORC, for example. In at least one embodiment, the shell 33426 can comprise one or more flexible legs 33423 which can be configured to extend into a knife slot 22063 defined in the anvil 22060 and releasably retain the anvil-attachable layer 33420 to the anvil 22060.

In certain other embodiments, referring to FIGS. 244-248, an anvil-attachable layer 22320, such as a buttress material and/or a tissue thickness compensator, can be attached to an anvil 22060. In at least one embodiment, the anvil-attachable layer 22320 can include cavities 22322a and/or cavities 22322b that can be configured to fit snugly within staple forming pockets 22062a and/or 22062b, respectively. The snug fit can releasably retain the anvil-attachable layer 22320 relative to the anvil 22060. In certain embodiments, the anvil-attachable layer 22320 can be assembled to the anvil 22060 such that a second layer 22327 of the anvil-attachable layer 22320 is positioned against the second surfaces 22069b of the anvil 22060. In certain other embodiments, referring now to FIGS. 247 and 248, the anvil-attachable layer 22320 can be positioned adjacent to the anvil 22060 such that the anvil-attachable layer 22320 can abut the anvil 22060 when the anvil 22060 is displaced toward the staple cartridge 22000 to compress the tissue T therebetween.

Referring to FIGS. 228-234, a retainer can be used to align and attach an anvil-attachable layer to an anvil of an end effector. Referring primarily to FIGS. 229 and 230, an anvil-attachable layer 2030 can include a body 2034 and a protrusion 2036 extending from the body 2034. Referring to FIGS. 231-234, the protrusion 2036 can engage a slot 2048, such as a knife slot, in an anvil 2042 of an end effector. In certain embodiments, the protrusion 2036 can be wider than the slot 2048 such that the protrusion 2036 is compressed when inserted into the slot 2048. In certain embodiments, the protrusion 2036 can be deformed such that it bulges outwardly and presses against surfaces of the slot 2048. A compressive force between the protrusion 2036 and the slot 2048 can provide a retention force that holds the anvil-attachable layer 2030 relative to the anvil 2042.

The anvil-attachable layer 2030 can be releasably attached to a retainer 2000. The retainer 2000 can align the anvil-attachable layer 2030 with the anvil 2042 and attach the anvil-attachable layer 2030 to the anvil 2042. Embodiments of the retainer 2000 can include a cover 2006 and tabs 2008, 2010 (tab 2010 illustrated in FIGS. 228-230) extending therefrom. As illustrated in FIGS. 229 and 230, the tabs can engage and releasably hold a staple cartridge 2020 to the retainer 2000. The retainer also can include a grip portion 2002 extending from the cover 2006 that a user may grasp to insert the retainer 2000, the staple cartridge 2020, and the anvil-attachable layer 2030 into a staple cartridge channel 2040 of an end effector.

The retainer 2000 can also include tabs 2014 that extend from the cover 2006. In certain embodiments, the retainer 2000 can include two tabs 2014, one tab extending from each lateral side of the cover 2006. As can be best seen in FIG. 228, each tab 2014 can include an inward-facing groove 2016 and an inward-facing angled surface 2018. Referring to FIGS. 229 and 230, lateral edges of the anvil-attachable layer 2030 can engage the grooves 2016 in the tabs 2014. When the anvil-attachable layer 2030 is engaged in the slots 2016 of the retainer 2000, in various embodiments, the anvil-attachable layer 2030 and the cover 2006 of the retainer 2000 can define a gap therebetween. The anvil-attachable layer 2030 can be arranged on the retainer 2000 such that the protrusion 2036 of the layer 2030 extends away from the retainer 2000. As best seen in FIGS. 228 and 231, the retainer 2000 can also include a raised ridge 2022 extending from the cover 2006. As best shown in FIG. 231, the raised ridge 2022 of the retainer 2000 can be aligned with the protrusion 2036 of the anvil-attachable layer 2030.

In use, a surgeon, nurse, clinician or other user, can insert the staple cartridge 2020 into the staple cartridge channel 2040 of the end effector, close the anvil on the retainer to release the anvil-attachable layer from the retainer and attach the layer to the anvil, and then remove the retainer from the end effector. Referring primarily to FIGS. 231-234, the user can grasp the retainer 2000 by the grip portion 2002 and insert the staple cartridge 2020 into a staple cartridge channel 2040 of the end effector. As the staple cartridge 2020 is being inserted into the staple cartridge channel 2040, tabs 2008 of the retainer 2000 can engage the staple cartridge channel 2040 of the end effector. FIG. 231 illustrates the staple cartridge 2020 loaded into the staple cartridge channel 2040 with the retainer 2000 and anvil-attachable layer 2030 on top of the staple cartridge 2020. As also illustrated in FIG. 231, the anvil 2042 of the end effector is positioned above the anvil-attachable layer 2030 and the retainer 2000. Referring now to FIG. 232, the anvil 2042 can be moved toward the retainer 2000 and the anvil-attachable layer 2030. As the anvil 2042 is moved, a surface 2044 of the anvil 2042 can contact the body 2034 of the anvil-attachable layer 2030. Furthermore, a slot 2046, such as a knife slot, of the anvil 2042 can engage the ridge 2036 of the anvil-attachable layer 2030. Also, as the anvil 2042 is moved toward the staple cartridge 2020, lateral edges 2050 of the anvil 2042 can engage the inward-facing angled surfaces 2018 of the film-holding tabs 2014, pushing the tabs 2014 outward such that the inward-facing grooves 2016 move away from the lateral edges of the anvil-attachable layer 2030.

Continued movement of the anvil 2042 toward the anvil-attachable layer 2030 can push the anvil-attachable layer 2030 toward the cover 2006 of the retainer 2000. Also, as the anvil 2042 continues to move toward the staple cartridge 2020, the raised ridge 2022 of the retainer 2000 can support the protrusion 2036 of the anvil-attachable layer 2034 as it engages the slot 2046 of the anvil 2042. As described above, the raised ridge 2022 of the retainer 2000 can deform the protrusion 2036 of the anvil-attachable layer 2030 such that the exterior dimensions of the protrusion 2036 of the anvil-attachable layer 2030 extend outwardly. Put differently, as the ridge 2036 of the anvil-attachable layer 2030 enters the slot 2046 of the anvil 2042, the raised ridge 2022 of the retainer 2000 can press into the anvil-attachable layer 2030 under the protrusion 2036, causing the protrusion 2036 to bulge out and/or expand into the slot 2046 of the anvil 2042. The resulting contact between the expanded protrusion 2036 and the slot 2046 can hold the ridge 2036 of the anvil-attachable layer 2030 within the slot 2046. The slot 2046 can include lips 2048 that can capture at least a portion of the protrusion 2036, further retaining the protrusion 2036 within the slot 2046 of the anvil 2042.

Referring now to FIG. 233, when the anvil 2042 is moved away from the retainer 2000, the anvil-attachable layer 2030 is carried away from the retainer 2000 with the anvil 2042. As illustrated in FIG. 234, after the anvil 2042 and the anvil-attachable layer 2030 have moved away from the retainer 2000, the retainer 2000 can be removed from the end effector, leaving the anvil-attachable layer 2030 and the staple cartridge 2020 in the end effector.

Referring again to FIGS. 229 and 230, in certain embodiments, a proximal end 2032 of the anvil-attachable layer 2030 can be attached to the staple cartridge 2020. For example, the anvil-attachable layer 2030 may be attached to the staple cartridge 2020 by adhesive, tack welding, and/or heat staking. In various embodiments, the anvil-attachable layer 2030 can detach from the staple cartridge 2020 after the anvil-attachable layer 2030 is attached to the anvil 2042 and the anvil is reopened. In various other embodiments, the anvil-attachable layer 2030 can remain attached to the staple cartridge 2020 until after the staples in the staple cartridge have been fired and the anvil-attachable layer 2030 is captured within the fired staples.

FIG. 235 illustrates the anvil-attachable layer 2030 separate from the retainer 2000. FIGS. 236 and 237 illustrate other embodiments of anvil-attachable layers. FIG. 236 illustrates an embodiment of an anvil-attachable layer 2060 that includes a body 2064 and discrete protrusions 2062 extending therefrom. FIG. 237 illustrates another embodiment of an anvil-attachable layer 2070 that includes a body 2074 with discrete protrusions 2072 extending therefrom. For example, each discrete protrusion 2072 can include a peg 2073 extending from the body of the anvil-attachable layer 2070 and a cap 2075 extending from the peg 2073. In certain embodiments, the cap 2075 can have larger dimensions than the peg 2073 so that the cap extends over the lateral edges 2048 in the slot 2046 in the anvil 2042 when the protrusions 2072 are inserted into the slot 2046.

Referring now to FIGS. 238-243, various embodiments of anvil-attachable layers can include one or more deployable attachment features that can be formed in the body of the anvil-attachable layer. FIGS. 238-240 illustrate an embodiment of an anvil-attachable layer 2080 that includes a body 2082 and an array of deployable attachment features 2084 formed in the body 2082. Each deployable attachment feature 2084 can be formed in the body 2082 by forming apertures 2085 in the body 2082. Each deployable attachment feature 2084 can include a longitudinal portion 2086 attached to the body 2082 and a lateral portion 2088 attached to the longitudinal portion 2086. In various embodiments, the longitudinal portion 2086 can be attached to the body 2082 by a hinge 2087. The aperture 2085 surrounding each deployable attachment feature 2084 and the hinge 2087 can permit movement of the deployable attachment features 2084 between an undeployed configuration and a deployed configured, described in greater detail below. In various other embodiments, the hinge 2087 can be absent. In such embodiments, the deployable attachment features 2084 can be bent about the longitudinal portions 2086, for example, to move between the undeployed configuration and the deployed configuration.

FIG. 238 illustrates the deployable attachment features 2084 in an undeployed configuration, wherein each of the deployable attachment features 2084 lies substantially in a plane defined by the body 2082 of the anvil-attachable layer 2084. FIG. 239 illustrates the deployable attachment features 2084 in a deployed configuration, wherein each deployable attachment feature 2084 extends out of the plane defined by the body 2082 of the anvil-attachable layer 2080. For example, the deployable attachment features 2084 can rotate about the hinges 2087 to extend out of the plane defined by the body 2082. As illustrated in FIG. 240, the deployable attachment features 2084 can be deployed into a slot 2046 of an anvil 2042. When deployed, the longitudinal portion 2086 of the deployable attachment feature 2084 can extend into the slot 2046 of the anvil 2042 and the lateral portion 2088 can extend further into the slot 2046. In various circumstances, the lateral portion 2088 of the deployable attachment feature 2084 can engage a lip 2048 in the slot 2046 to provide for stronger retention between the anvil-attachable layer 2080 and the anvil 2042. Furthermore, engagement between the lateral portion 2088 of the deployable attachment feature 2084 and the lip 2048 in the slot 2046 can prevent the deployable attachment feature 2084 from returning to the undeployed position. In certain embodiments, the longitudinal portion 2086 of each deployable attachment feature 2084 can be shorter than a narrow portion 2047 of the slot 2046. In such embodiments, the longitudinal portion 2086 can be under tension when the lateral portion 2088 engages the lip 2048 in the slot 2046. The tension in the lateral portion 2088 can hold the body 2082 of the anvil-attachable layer 2080 snugly against the anvil 2042.

The body 2082 and the deployable attachment features 2084 may be formed from a unitary body. Then, the apertures 2085 can be formed in the body 2082 by, for example, cutting the apertures 2085 into the body 2082. The apertures 2085 can be cut by a stamping tool, a cutting blade, a laser, or any other suitable means. In various other embodiments, the anvil-attachable layer 2080 and the apertures 2085 can be formed in a mold. In certain embodiments, the apertures 2085 can include a gap between the body 2082 and a deployable attachment feature 2084. In certain other embodiments, the apertures 2085 do not provide for a gap between the body 2082 and the deployable attachment features 2084. In various embodiments, the hinge 2087 can be formed by thinning or scoring the anvil-attachable layer 2080 between the body 2082 and the longitudinal portion 2086, for example. In various other embodiments, the hinges provide no change in thickness between the body 2082 and the longitudinal portions 2086 of the deployable attachment features 2084.

FIGS. 238-240, described above, illustrate an embodiment of an anvil-attachable layer 2080 wherein the deployable attachment features 2084 each include a lateral portion 2088 that includes a circular portion. The lateral portion can include other suitable shapes, including but not limited to triangles, ovals, and polygons. For example, FIGS. 241-243 illustrate an embodiment of an anvil-attachable layer 2090 wherein the deployable attachment features 2094 each include a lateral portion 2098 that has a rectangular cross-section. Each deployable attachment feature 2094 can be attached to the body 2092 by a hinge 2097.

In certain embodiments, the body and deployable attachment features of an anvil-attachable layer can comprise a flexible and/or a resilient material. For example, referring again to FIGS. 238-240, the body 2082 and deployable attachment features 2084 of anvil-attachable layer 2080 can comprise a flexible and/or a resilient material. As another example, referring to FIGS. 241-243, the body 2092 and deployable attachment features 2094 of anvil-attachable layer 2090 can comprise a flexible and/or a resilient material. Referring to the anvil-attachable layer 2080 of FIGS. 238-240, when each deployable attachment feature 2084 is deployed into a slot 2046, such as a knife slot, of an anvil 2042, the lateral portion 2088 can flex and/or deform to pass through a narrow portion 2047 of the slot 2046. Then, as the lateral portion 2088 extends past the lips 2048 of the slot 2046 and into to a wide portion 2049 of the slot 2046, the lateral portion 2088 can return to an unflexed and/or undeformed shape. As the lateral portion 2088 returns to the unflexed and/or undeformed shape, the lateral portion 2088 can extend laterally into the wide portion 2049 of the slot 2046. After the lateral portion 2088 extends laterally into the wide portion 2049 of the slot 2046, the narrow portion 2047 of the slot 2046 can provide an interference fit that inhibits the lateral portion 2088 from being readily pulled out of the slot 2046. Stated differently, to be pulled out of the slot 2046, the lateral portion 2088 must flex and/or deform again to fit through the narrow portion 2047 of the slot 2046. In various embodiments, the lateral portion 2088 and/or the narrow portion 2047 of the slot 2046 can be sized so that a pulling force required to pull the deployable attachment feature 2084 out of the slot can be large enough so that the anvil-attachable layer 2080 is not displaced from the anvil 2042 while the anvil 2042 is positioned relative to patient tissue. However, the pulling force can be small enough such that the anvil-attachable layer 2080 can pull away from the anvil after the anvil-attachable layer 2080 is captured by staples.

In various embodiments, a cutting blade of a surgical stapler can sever the deployable attachment features of an anvil-attachable layer. Referring to FIG. 240, a cutting blade can travel through the slot 2046 of the anvil 2042. The cutting blade can cut each deployable attachment feature 2084 substantially in half. The halves of each deployable attachment features 2084 can be easily pulled out of the slot 2046 when the anvil-attachable layer 2080 is removed from the anvil 2042 after the staples are fired.

For anvil-attachable layers that include deployable attachment features, such as the anvil-attachable layers disclosed in FIGS. 238-243, a retainer can be used to align the anvil-attachable layer with an anvil and to deploy the deployable attachment features into a slot in the anvil. FIGS. 251-254 illustrate a retainer 19700 that first installs a staple cartridge 19690 into a staple cartridge channel 19740 and then presses an anvil-attachable layer 2056 against an anvil 19720. The retainer 19700 includes a first portion 2052 and a second portion 2054, wherein the first portion 2052 is movable relative to the second portion 2054 in the directions indicated by arrows Q and S (shown in FIGS. 253 and 254, respectively). The first portion 2052 can include a cam that includes anti-lobes 19646 and 19647 and lobes 19642 and 19643. The second portion can include cam protrusions 19614 and 19616 that engage the cam of the first portion 2052. As illustrated in FIGS. 251 and 252, when the retainer 19700 is being inserted into the end effector, the cam protrusions 19614 and 19616 engage the anti-lobes 16646 and 16647 of the cam of the first portion 2052. Referring now to FIGS. 253 and 254, after the staple cartridge has been seated in a staple cartridge channel 19740 of the end effector, the first portion 2052 can move in the direction of arrow Q relative to the second portion 2054. Moving the first portion 2052 in the direction of arrow Q causes the cam protrusions 19614 and 19616 to engage the lobes 19642 and 19643 of the cam of the first portion 2052. The lobes 19642 and 19643 push the cam protrusions 19614 and 19616 apart, thereby pushing the anvil-attachable layer 2056 into contact with the anvil 19720.

Referring now to FIGS. 255-258, in certain embodiments, a retainer can install a staple cartridge in a staple cartridge channel, arrange an anvil-attachable layer on an anvil, and deploy deployable attachment features of the anvil-attachable layer into engagement with the anvil. Referring to FIGS. 256 and 257, embodiments of a retainer 2110 can include a grip portion 2112, a staple-cartridge-facing portion 2114, and an anvil-facing portion 2118. The staple-cartridge-facing portion 2114 and the anvil-facing portion 2118 can be spaced apart and arranged at an angle relative to one another by a support 2116. As can best be seen in FIG. 258, the staple-cartridge-facing portion 2114 and the anvil-facing portion 2118 can be arranged at an angle similar to the angle between the staple cartridge channel 2160 and the anvil 2150 when the anvil 2150 is in a fully-open position. The staple-cartridge-facing portion 2114 can include first clips 2124 and second clips 2126 extending therefrom. The first clips 2114 can engage and releasably hold a staple cartridge 2140 to the retainer 2110, as illustrated in FIG. 255. The second clips 2126 can engage a staple cartridge channel 2160 of an end effector, such that the retainer 2110 is releasably held to the staple cartridge channel 2160. The anvil-facing portion 2118 can include a clip 2120 that holds an anvil-attachable layer, such as the anvil-attachable layer 2080 illustrated in FIGS. 238-240, relative to the anvil surface 2118. The anvil-facing portion 2118 can also include discrete protrusions 2122 that are positioned relative to locations of the deployable attachment features 2084 of the anvil-attachable layer 2080. As illustrated in FIG. 255, when the anvil-attachable layer 2080 is loaded onto the anvil-facing portion 2118 of the retainer 2110, the anvil-attachable layer 2080 can rest on top of the discrete protrusions 2122.

Referring to FIG. 258, in certain embodiments, as the retainer 2110 is being inserted into the end effector and the staple cartridge 2140 is being seated in the staple cartridge channel 2160, the anvil-attachable layer 2080 can make contact with the anvil 2150. Once the anvil-attachable layer 2080 is in contact with the anvil 2150, the retainer 2110 and staple cartridge 2140 can continue to move relative to the anvil 2150 until the staple cartridge 2140 is fully seated. In such embodiments, the anvil-facing portion 2118 of the retainer 2110 can be moved toward and be pushed against the anvil-attachable layer 2080 such that the discrete protrusions 2122 extending from the anvil-facing portion 2118 of the retainer 2110 can push the deployable attachment features 2084 in the layer 2080 into a deployed configuration, described above in connection with FIGS. 238-243. In various embodiments, each discrete protrusion 2122 of the anvil-facing portion 2118 of the retainer 2110 can include an angled face 2123 that can engage the deployable attachment features 2084. As the retainer 2110 continues to be moved relative to the anvil 2150 and the anvil-attachable later 2080, the angled surfaces 2123 can be progressively engaged with the deployable attachment features 2084 until the deployable attachment features 2084 have rotated about the hinges 2087 and are deployed in the slot 2152 of the anvil 2150. As illustrated in FIG. 258, the angled surface 2123 of the discrete protrusions 2122 can support both the longitudinal portion 2086 and the lateral portion 2088 of each deployable attachment feature such that both the longitudinal portion 2086 and the lateral portion 2088 deploy in to the slot 2152 of the anvil 2150.

In certain other embodiments, the retainer 2110 may completely seat the staple cartridge 2140 in the staple cartridge channel 2160 without the anvil-attachable layer 2080 contacting the anvil 2150. In such embodiments, after the staple cartridge 2140 is completely seated in the staple cartridge channel 2160, the anvil 2150 can be moved from a fully-open position toward a closed position so that the anvil 2150 contacts the anvil-attachable layer 2080 and the discrete protrusions 2122 deploy the deployable attachment features 2084 into the slot 2052 of the anvil 2050.

FIGS. 259-262 illustrate another embodiment of a retainer 2170. The retainer 2170 can include a staple-cartridge-facing portion 2174 and an anvil-facing portion 2178 spaced apart and arranged at an angle to one another by a support 2190. The staple-cartridge-facing portion 2174 can engage and releasably hold a staple cartridge 2140. The staple-cartridge-facing portion 2174 can also engage and releasably hold a staple cartridge channel 2160 of an end effector. An anvil-attachable layer, such as anvil-attachable layer 2080, described above with reference to FIGS. 238-240, can be arranged on the anvil-facing portion 2178. As illustrated in greater detail in FIGS. 261 and 262, the anvil-facing portion 2178 can include apertures 2182 that can be aligned with the deployable attachment features 2084 of the anvil-attachable layer 2080 arranged on the anvil-facing portion 2178. Each aperture 2182 can include a cam 2202 arranged therein. Each cam 2202 can be attached to the anvil-facing portion 2178 by a flexible member 2204 such that the cam 2202 can rotate about the flexible member 2204 out of the aperture 2182 and into contact with the deployable attachment feature 2084. Each cam 2202 can include a curved surface 2203 that can progressively deploy the deployable attachment feature 2084 into a slot 2152 in the anvil 2150. Referring to FIG. 261, as the cam begins to be moved out of the aperture 2182 and into contact with the deployable attachment feature 2084, the curved surface 2203 of the cam 2202 will first make contact with the lateral portion 2088 of the deployable attachment feature 2084 such that the lateral portion 2088 is deployed into the slot 2152 of the anvil 2150. Now referring to FIG. 262, as the cam 2202 continues to be moved out of the aperture 2182, the curved surface 2203 of the cam 2202 can contact the longitudinal portion 2086 of the deployable attachment feature 2086 such that the lateral portion 2086 is also deployed into the slot 2152 of the anvil 2150.

The support 2190 between the staple-cartridge-facing portion 2174 and the anvil-facing portion 2178 can include a stationary portion 2194 and a moveable portion 2196. The moveable portion 2196 can be operably coupled to a button 2192 that a user can push to move the moveable portion 2196 relative to the stationary portion 2194. The moveable portion 2196 of the support 2190 can include a series of cam surfaces 2206 that can engage the cam portions 2202 to push the cam portions 2202 out of the apertures 2182. When the moveable portion 2196 is moved proximally relative to the stationary portion 2194, the cam surfaces 2206 can displace the cams 2202 out of the apertures 2182 and into contact with the deployable attachment features 2084 of the film 2080, as described above.

In certain embodiments, the movable portion 2196 of the support 2190 can be biased in a distal position relative to the stationary portion 2194, as illustrated in FIG. 259. For example, a spring or the like may be arranged between the stationary portion 2194 and the moveable portion 2196. The spring can bias the movable portion 2196 of the support 2190 in a distal position relative to the stationary portion 2194. In various embodiments, the biasing force can be sufficiently high such that forces required to seat the staple cartridge 2140 in the staple cartridge channel 2160 will not overcome the biasing force. As a result, the deployable attachment features 2084 are less likely to be deployed by the cams 2202 if forces required to completely seat the staple cartridge 2140 in the staple cartridge channel 2160 are inadvertently applied to the button 2192.

In various embodiments in which an anvil-attachable layer is releasably retained to an anvil of a surgical stapler, the anvil-attachable layer can include additional features to stabilize patient tissue relative to the layer and to the anvil. Referring now to FIGS. 249 and 250, anvil-attachable layers 22320a and 22320b are illustrated in a position between an anvil 22060 and patient tissue T. Embodiments of the anvil-attachable layers 22320a and 22320b can include protrusions 2078 extending from the body on a side facing the patient tissue T. The protrusions 2078 can push into or pierce the tissue T, providing grip between the tissue T and the anvil-attachable layers 22320a and 22320b. The grip can prevent the tissue from slipping relative to the anvil-attachable layers 22320a and 22320b.

In various embodiments, the retention features may be separated from the anvil-attachable layer after a surgical stapler in which the layer is installed has been fired. In such embodiments, the retention features can be attached to one or more tethers. The tethers can be attached to the surgical stapler or to another object outside of the patient so that the retention features can be removed from the patient by pulling on the tethers after the stapler has been fired.

In various embodiments, the tissue thickness compensator may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam can have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In certain embodiments, a tissue thickness compensator could be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or haemostatic behavior. Further, the gradient could be also compositional with a varying bioabsorption profile. A short term absorption profile may be preferred to address hemostasis while a long term absorption profile may address better tissue healing without leakages.

Examples of non-synthetic polymers include, but are not limited to, lypholized polysaccharide, glycoprotein, elastin, proteoglycan, gelatin, collagen, and oxidized regenerated cellulose (ORC). Examples of synthetic absorbable polymers include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxylkanoate (PHA), a copolymer of glycolide and ε-caprolactone (PGCL), a copolymer of glycolide and -trimethylene carbonate, poly(glycerol sebacate) (PGS), polydioxanone, poly(orthoesters), polyanhydrides, polysaccharides, poly(ester-amides), tyrosine-based polyarylates, tyrosine-based polyiminocarbonates, tyrosine-based polycarbonates, poly(D,L-lactide-urethane), poly(B-hydroxybutyrate), poly(E-caprolactone), polyethyleneglycol (PEG), poly[bis(carboxylatophenoxy) phosphazene], poly(amino acids), pseudo-poly(amino acids), absorbable polyurethanes, and combinations thereof.

In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of c-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of c-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and ε-caprolactone. In another embodiment, the elastomeric copolymer is a copolymer of lactide and ε-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-ε-caprolactone) copolymer (poliglecaprolactone 25), commercially available from Ethicon, Inc. under the trade designation MONOCRYL, for example.

Examples of synthetic non-absorbable polymers include, but are not limited to, foamed polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise a greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example. According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, a tissue thickness compensator may be releasably attached to a staple cartridge and/or anvil by a flowable attachment portion. The flowable attachment portion may be operatively associated with the staple cartridge and/or anvil. In various embodiments, a flowable attachment portion may be provided between the tissue thickness compensator and the staple cartridge and/or anvil. In various embodiments, at least a portion of an outer surface of the tissue thickness compensator may comprise the flowable attachment portion. In various embodiments, an adhesive laminate may comprise the tissue thickness compensator and flowable attachment portion. The adhesive laminate may comprise a base layer comprising the tissue thickness compensator and an adhesive layer on at least a portion of a surface of the base layer comprising the flowable attachment portion. The adhesive laminate may comprise a tissue contacting surface comprising the tissue thickness compensator and an opposing surface comprising the flowable attachment portion. The adhesive laminate may releasably attach the adhesive laminate to a staple cartridge and/or anvil.

In various embodiments, a flowable attachment portion may comprise a flowable polymeric composition, such as a pressure sensitive adhesive ("PSA"), for example. An effective amount of the PSA may be applied to the tissue thickness compensator to provide adequate cohesive strength to produce the desired adhesion properties to the staple cartridge and/or anvil. PSAs may be characterized by one or more of the following properties: (1) aggressive and permanent tack; (2) adherence with no more than finger pressure; (3) sufficient ability to hold onto an adherend; and (4) sufficient cohesive strength to be removed cleanly from the adherend. In various embodiments, the flowable attachment portion may flow when pressure, heat, and/or stress are applied thereto. Such pressure and/or stress may be applied directly by hand and/or by a device, such as, for example, a mechanical device, and may be a manual process and/or an automated process.

In various embodiments, the flowable attachment portion may be responsive to a temperature change and/or a pressure change. In various embodiments, the flowable attachment portion may flow from a first position to a second position when heat and/or pressure are applied thereto. In various embodiments, the flowable attachment portion may be flowable at body temperature (37° C.) and/or room temperature (25° C.). In various embodiments, the flowable attachment portion may be flowable at body temperature (37° C.) but not at room temperature (25° C.). In various embodiments, the flowable attachment portion may be responsive to a temperature change such that the flowable attachment portion is in the first position when the tissue thickness compensator is at a first temperature and in the second position when the tissue thickness compensator is at a second temperature. In various embodiments, the second temperature may be greater than the first temperature. In various embodiments, the first temperature may be room temperature and the second temperature may be body temperature. In various embodiments, the flowable attachment portion may be responsive to a pressure change such that the flowable attachment portion is in the first position when the tissue thickness compensator is at a first pressure and in the second position when the tissue thickness compensator at a second pressure. In various embodiments, the second pressure may be greater than the first pressure. In various embodiments, the first pressure may be atmospheric pressure and the second pressure may be finger pressure. In various embodiments, the flowable attachment portion may flow from a first position when at room temperature and/or atmospheric pressure to a second position when at body temperature and/or under pressure. In various embodiments, the flowable attachment portion may flow from a first (unstressed) position to the second position when pressure and/or stress are applied thereto.

In various embodiments, the flowable attachment portion may flow into a void in the staple cartridge and/or anvil. In various embodiments, the flowable attachment portion may flow when heat and/or pressure are applied thereto and extend over at least a portion of the surface of the staple cartridge and/or anvil lacking the flowable attachment portion and/or fill at least a portion of a void in the staple cartridge and/or anvil, such as, for example, a slot and/or a staple cavity. In various embodiments, the flowable attachment portion may flow in-vivo to fill at least a portion of a void in the staple cartridge and/or anvil. In various embodiments, the flowable attachment portion may flow such that the flowable attachment portion comprises a complementary shape to the at least a portion of the void in the staple cartridge and/or anvil. In various embodiments, the flowable polymeric composition may flow to fill at least a portion of a slot and/or staple cavity in the anvil. In various embodiments, the flowable attachment portion may flow into the void when pressure is applied thereto and take the shape of the void. Without wishing to be bound to any particular theory, it is believed that the filling at least a portion of a void in the staple cartridge and/or anvil with the flowable attachment portion may improve the attachment of the tissue thickness compensator to the staple cartridge and/or anvil.

In various embodiments, a flowable attachment portion, such as, for example, the PSA, may be responsive to a change in temperature and/or a change in pressure to move between a first position and/or a first profile and a second position and/or a second profile. In various embodiments, the flowable attachment portion may have a first position spaced away from the staple cartridge and/or anvil. In various embodiments, the flowable attachment portion may be configured to penetrate a void in the staple cartridge and/or anvil and/or fill at least a portion of the void in the staple cartridge and/or anvil when the flowable attachment portion is in the second position. As described herein, the flowable attachment portion may take the shape of the void such that the flowable attachment portion comprises a profile complementary to the void when the flowable attachment portion is in the second profile. In various embodiments, the first position and/or first profile may be spaced from the staple cartridge and/or anvil, and the second position and/or second profile may contact the staple cartridge and/or anvil. In various embodiments, the first position and/or first profile may comprise a neutral (original) profile when at room temperature and/or atmospheric pressure and the second position and/or second profile may comprise a complementary profile to the void in the staple cartridge and/or anvil when at body temperature and/or under pressure. The profile of the flowable attachment portion may flow to achieve a complementary shape and/or dimension of the void in the staple cartridge and/or anvil.

In various embodiments, a method of bonding a tissue thickness compensator to a substrate, such as, for example, a staple cartridge and/or an anvil, may generally comprise providing a tissue thickness compensator; applying a flowable attachment portion, such as a pressure sensitive adhesive, for example, to at least a portion of a surface of the tissue thickness compensator; and contacting the flowable attachment portion and the substrate. In various embodiments, the method of bonding a tissue thickness compensator to a substrate may comprise applying pressure to at least one of the tissue thickness compensator and substrate. The flowable attachment portion may flow from a first position on an outer surface of the tissue thickness compensator to a second position further comprising an outer surface and/or inner surface of the substrate. The flowable attachment portion may come into contact with the substrate causing adhesion of the tissue thickness compensator to the substrate. In various embodiments, the flowable attachment portion may bond the tissue thickness compensator to the substrate. In various embodiments, the flowable attachment portion may flow into at least one void in the substrate, such as, for example, a slot and/or staple cavity. In various embodiments, the flowable attachment portion may fill at least a portion of the at least one void in the substrate when in the second position.

In various embodiments, a method of attaching a tissue thickness compensator to a substrate, such as, for example, a staple cartridge and/or an anvil, may generally comprise applying at least one discrete bead and/or strip of a flowable polymeric composition, such as a pressure sensitive adhesive, for example, to a surface of the tissue thickness compensator; contacting the substrate and the at least one discrete bead and/or strip of the flowable polymeric composition; and pressing one of the substrate and at least one discrete bead and/or strip of flowable polymeric composition into the other of the substrate and at least one discrete bead and/or strip of flowable polymeric composition to releasably attach the tissue thickness compensator to the substrate. In various embodiments, the method of attaching a tissue thickness compensator to a substrate may comprise applying the at least one discrete bead and/or strip of flowable polymeric composition to the substrate at a perimeter and/or central axis of the tissue thickness compensator at an expected location of the substrate. In various embodiments, the method of attaching a tissue thickness compensator to a substrate may comprise applying the at least one discrete bead and/or strip of flowable polymeric composition in a longitudinal direction and/or lateral direction on the tissue thickness compensator.

In various embodiments, the method of attaching a tissue thickness compensator to a substrate may comprise applying the at least one discrete bead and/or strip of flowable polymeric composition in a pattern and/or an amount that is preselected based at least in part on expected loads on the tissue thickness compensator. The patterns and amount of the flowable polymeric composition to be applied may be selected to withstand the stresses, e.g., shear stress, associated with a clinician's manipulation of the medical device. The patterns and amount of the flowable polymeric composition to be applied may be preferably selected to balance loads on the flowable polymeric composition due to the clinician's manipulation with ease of application and/or conservation of the flowable polymeric composition. In addition, the composition of the flowable polymeric composition may be considered when selecting the patterns and amount of the flowable polymeric composition to apply.

In various embodiments, the flowable attachment portion may partially adhere the tissue thickness compensator to the staple cartridge and/or anvil and/or fully partially adhere the tissue thickness compensator to the staple cartridge and/or anvil. A fully adhered tissue thickness compensator may include a full layer of the flowable polymeric composition, such as, for example, a pressure sensitive adhesive, between the tissue thickness compensator and the substrate. A fully adhered tissue thickness compensator may lack a portion of the tissue thickness compensator free of the flowable polymeric composition. A partially adhered tissue thickness compensator may include an effective amount of the flowable polymeric composition between the tissue thickness compensator and substrate that includes at least a portion of the tissue thickness compensator free of the flowable polymeric composition. A partially adhered tissue thickness compensator may exert a greater shear stress on the flowable polymeric composition relative to a fully adhered tissue thickness compensator. Therefore, the shear properties of the flowable polymeric composition and/or the amount and patterns of the flowable polymeric composition may be selected to withstand the expected manipulation of the medical device by the clinician.

In various embodiments, the flowable polymeric composition may be applied to the tissue thickness compensator in one of a continuous pattern and a discontinuous pattern. In various embodiments, a continuous pattern of flowable polymeric composition may comprise a discrete strip of flowable polymeric composition applied to at least a portion of the tissue thickness compensator. In various embodiments, a continuous pattern of flowable polymeric composition may comprise a continuous bead of flowable polymeric composition disposed along at least a portion of the central axis of the tissue thickness compensator in the longitudinal direction and/or at least a portion of a perimeter of the tissue thickness compensator. The flowable polymeric composition may be applied in various other patterns and configurations on the substrate, such as, for example, a crisscrossed pattern or other diagonal patterns, in a continuous full sheet or layer, or in any other design to achieve the desired adhesive properties. In various embodiments, the continuous pattern of flowable polymeric composition may be applied along an inner periphery and/or outer periphery of the tissue thickness compensator. In various embodiments, the continuous pattern of flowable polymeric composition may be applied along an inner periphery of the tissue thickness compensator to be positioned along a central longitudinal axis of the substrate when attached thereto. In various embodiments, the continuous pattern of flowable polymeric composition may be applied along an inner periphery of the tissue thickness compensator to be aligned with at least one void in the substrate, such as a slot and/or staple cavity, for example, when attached thereto. In various embodiments, the continuous pattern of flowable polymeric composition may be applied along an outer periphery of the tissue thickness compensator to be positioned along an outer perimeter of the substrate when attached thereto. In various embodiments, the flowable polymeric composition may be applied to the tissue thickness compensator to leave an inner portion and/or a peripheral border on the substrate that is free of flowable polymeric composition.

In various embodiments, a discontinuous pattern of flowable polymeric composition may comprise a plurality of discrete beads and/or strips of flowable polymeric composition spaced apart from each other on the substrate. In various embodiments, at least a portion of the plurality of beads and/or strips of flowable polymeric composition may be compressed together when pressure and/or stress is applied. In various embodiments, the compressed plurality of beads and/or strips of flowable polymeric composition may form a continuous pattern of flowable polymeric composition. In various embodiments, a partially adhered tissue thickness compensator may comprise a plurality of discrete beads and/or strips of flowable polymeric composition on a surface of the tissue thickness compensator spaced apart from each other such that at least a portion of the tissue thickness compensator comprises free space lacking the flowable polymeric composition when pressure is applied. The free space may comprise a portion of the tissue thickness compensator in which the beads and/or strips of flowable polymeric composition do not contact each other and/or a portion of the tissue thickness compensator in which the beads and/or strips of flowable polymeric composition are not applied. In various embodiments, the free space may comprise an inner portion and/or a peripheral border on the substrate.

In various embodiments, the method of attaching the tissue thickness compensator to the substrate may comprise applying at least one discrete strip of flowable polymeric composition to the tissue thickness compensator. In various embodiments, a discrete strip of flowable polymeric composition may extend along a portion of the central longitudinal axis of the tissue thickness compensator. In at least one embodiment, a discrete strip of flowable polymeric composition may be applied along a portion of the tissue thickness compensator aligned with at least one void in the substrate, such as a slot and/or staple cavity. In various embodiments, the method of attaching the tissue thickness compensator to the substrate may comprise applying a plurality of parallel discrete strips of flowable polymeric composition to the tissue thickness compensator. In various embodiments, two discrete strips of flowable polymeric composition may extend in the longitudinal direction along opposing side edges of the tissue thickness compensator. In at least one embodiment, each of the two discrete strips of flowable polymeric composition may applied along a portion of the tissue thickness compensator aligned with at least one void in the substrate, such as a slot and/or staple cavities, for example. In various embodiments, the distance between the strips and/or side edge may be preselected such that the flowable polymeric composition may flow into at least one void in the substrate, such as, for example, at least one staple cavity in an anvil, when attached thereto.

In various embodiments, the distance between the plurality of parallel discrete strips of flowable polymeric composition and/or side edge may be preselected to one of fully adhere the tissue thickness compensator to the substrate and partially adhere the tissue thickness compensator to the substrate. In various embodiments, a width of the strip may be at least 1 mm, for example. In various embodiments, a width of the strip may be between approximately 0.5 mm and approximately 1.5 mm, for example. In various embodiments, a width of the strip may be between approximately 1.0 mm and approximately 1.25 mm, for example. In various embodiments, a width of a gap between the adhesive strips and/or side edge may be at least 1 mm, for example. In various embodiments, the distance between the strips and/or side edge may be preselected to partially adhere the tissue thickness compensator to the substrate with an adhesive to empty space ratio preselected based on expected loads on the tissue thickness compensator. In various embodiments, the adhesive to empty space ratio may be 1:10 to 10:1, such as, for example, 1:1, 1:2, 1:3, 1:4, 1:5, and 2:3

In various embodiments, a minimum of 0.25 mm of the PSA substrate may be needed to be flowable, for example. In various embodiments, the PSA substrate can comprise a thickness between approximately 1.25 mm and approximately 1.50 mm, for example. In certain embodiments, the PSA substrate can comprise a thickness between approximately 0.5 mm and approximately 0.75 mm, for example.

As described herein, in various embodiments, the flowable attachment portion may comprise a flowable polymeric composition. The flowable polymeric composition may comprise a pressure sensitive adhesive. The flowable attachment portion may comprise a pressure sensitive adhesive laminate. In various embodiments, the flowable attachment portion may comprise an adhesive laminate comprising the tissue thickness compensator and flowable polymeric composition. The polymeric composition may comprise one or more synthetic polymers and/or one or more natural polymers. The polymeric composition may be bioabsorbable, biocompatible and/or biodegradable. Examples of natural polymers include, but are not limited to, lypholized polysaccharide, glycoprotein, elastin, proteoglycan, gelatin, collagen, fibrin, fibronectin, fibrinogen, elastin, serum albumin, hemoglobin, ovalbumin, and oxidized regenerated cellulose (ORC) and combinations thereof. Examples of polysaccharides include, but are not limited to, hyaluronic acid, chondroitin sulfate, hydroxyethyl starch, hydroxyethyl cellulose, hydroxypropylcellulose, carboxyetyl-cellulose, chitan/chitosan, agarose and alginate, and combinations thereof. Examples of synthetic polymers include, but are not limited to, poly(lactic acid) (PLA), poly(L-lactic acid) (PLLA), polycaprolactone (PCL), polyglycolic acid (PGA), poly (glycolic acid) poly (hydroxybutyrate), poly (phosphazine), polyester, poly(trimethylene carbonate) (TMC), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), polydioxanone, poly(orthoesters), polyanhydrides, polyacrylamides, polysaccharides, poly(ester-amides), tyrosine-based polyarylates, tyrosine-based polyiminocarbonates, tyrosine-based polycarbonates, poly (D,L-lactide-urethane), poly(B-hydroxybutyrate), poly(E-caprolactone), polyethyleneglycol (PEG), polyethylene oxide, poly[bis(carboxylatophenoxy) phosphazene], poly (amino acids), pseudo-poly(amino acids), absorbable polyurethanes, polyhydroxyethylmethylacrylate, poly-vinylpyrrolidone, polyvinyl alcohol, polyacrylic acid, polyacetate, polycaprolactone, polypropelene, nylon and combinations thereof.

In various embodiments, the flowable polymeric composition may comprise a copolymer of ε-caprolactone and glycolide (PCL/PGA). In various embodiments, the flowable polymeric composition may comprise from about 50% to about 90% by weight of the polymeric composition of PGA and about 50% to about 10% by weight of the polymeric composition of PCL, for example. In various embodiments, the flowable polymeric composition may comprise from about 50% to about 75% by weight of the polymeric composition of PGA and about 50% to about 25% by weight of the polymeric composition of PCL, for example. In various embodiments, the flowable polymeric composition may comprise from about 50% to about 60% by weight of the polymeric composition of PGA and about 50% to about 40% by weight of the polymeric composition of PCL, for example. In at least one embodiment, the flowable polymeric composition may comprise about 70% by weight of polymeric composition of PGA and about 30% by weight of the polymeric composition of PCL, for example. In at least one embodiment, the flowable polymeric composition may comprise about 64% by weight of polymeric composition of PGA and about 36% by weight of the polymeric composition of PCL, for example.

In various embodiments, the flowable polymeric composition may comprise a copolymer of ε-caprolactone and lactide, including L-lactide, D-lactide blends thereof and lactic acid copolymers. In various embodiments, the flowable polymeric composition may comprise a mole ratio of PCL to PGA from 30:70 to 70:30, such as, for example, 35:65 to 65:35, 45:55 to 35:65, and 50:50. In various embodiments, the amount of ε-caprolactone may be from 30 and 45 mole percent with the balance being glycolide, such as, for example, 35 to 40 mole percent ε-caprolactone with the balance being glycolide. In various embodiments, the PSA may comprise a 36:64 (mol/mol) [poly(ε-caprolactone-co-glycolide)] copolymer. In various embodiments, the flowable polymeric composition may comprise a copolymer of p-dioxanone (1,4-dioxan-2-one) and lactide, including L-lactide, D-lactide and lactic acid. In various embodiments, the flowable polymeric composition may comprise a mole ratio of p-dioxanone to lactide of from 40:60 to 60:40. In various embodiments, the flowable polymeric composition may comprise a copolymer of ε-caprolactone and p-dioxanone. In various embodiments, the flowable polymeric composition may comprise a mole ratio of ε-caprolactone to p-dioxanone of from 30:70 to 70:30.

In various embodiments, the tissue thickness compensator and flowable attachment portion may comprise one of a same polymeric composition and a different polymeric composition. In various embodiments, the tissue thickness compensator and flowable attachment portion may each comprise the same bioabsorbable material, such as, for example, a copolymer of ε-caprolactone and glycolide (PCL/PGA). In various embodiments, the tissue thickness compensator and flowable attachment portion may differ in at least one characteristic selected from composition, modulus, elongation, inherent viscosity, crystallinity, and bioabsorption. In various embodiments, the tissue thickness compensator and flowable attachment portion may comprise the same copolymer that differs in at least one characteristic selected from composition, modulus, elongation, inherent viscosity, crystallinity, and bioabsorption. For example, the tissue thickness compensator and flowable attachment portion may each comprise a PCL/PGA copolymer that differs in the weight percent of ε-caprolactone and glycolide and/or mole ratio of ε-caprolactone to glycolide. In at least one embodiment, the tissue thickness compensator may comprise about 50% by weight of polymeric composition of PGA and about 50% by weight of the polymeric composition of PCL, and the flowable attachment portion may comprise about 64% by weight of polymeric composition of PGA and about 36% by weight of the polymeric composition of PCL. In at least one embodiment, the tissue thickness compensator may comprise a PCL/PGA copolymer having a mole ratio of ε-caprolactone to glycolide of 50:50 and the flowable attachment portion may comprise a PCL/PGA copolymer having a mole ratio of ε-caprolactone to glycolide of 36:64.

In various embodiments, a concentration of ε-caprolactone in the pressure sensitive adhesive and a concentration of ε-caprolactone in the tissue thickness compensator may differ by at least 1 weight percent by weight of the polymeric compositions, respectively. In various embodiments, a concentration of ε-caprolactone in the pressure sensitive adhesive and a concentration of ε-caprolactone in the tissue thickness compensator may differ by at least 5 weight percent. In various embodiments, a concentration of ε-caprolactone in the pressure sensitive adhesive and a concentration of ε-caprolactone in the tissue thickness compensator may differ by at least 10 weight percent. In various embodiments, a concentration of ε-caprolactone in the pressure sensitive adhesive and a concentration of ε-caprolactone in the tissue thickness compensator may differ by at least 15 weight percent. In various embodiments, a concentration of ε-caprolactone in the pressure sensitive adhesive and a concentration of ε-caprolactone in the tissue thickness compensator may differ by 1 to 15 weight percent. In various embodiments, a concentration of ε-caprolactone in the pressure sensitive adhesive and a concentration of ε-caprolactone in the tissue thickness compensator may differ by 10 to 15 weight percent. In various embodiments, a concentration of ε-caprolactone in the pressure sensitive adhesive and a concentration of ε-caprolactone in the tissue thickness compensator may differ by 14 weight percent. In various embodiments, a concentration of ε-caprolactone in the pressure sensitive adhesive may differ from a concentration of ε-caprolactone in the tissue thickness compensator as described above such that a concentration of ε-caprolactone in the pressure sensitive adhesive may be one of greater than and less than a concentration of ε-caprolactone in the tissue thickness compensator.

In various embodiments, a concentration of polyglycolic acid in the pressure sensitive adhesive and a concentration of polyglycolic acid in the tissue thickness compensator may differ by at least 1 weight percent. In various embodiments, a concentration of polyglycolic acid in the pressure sensitive adhesive and a concentration of polyglycolic acid in the tissue thickness compensator may differ by at least 5 weight percent. In various embodiments, a concentration of polyglycolic acid in the pressure sensitive adhesive and a concentration of polyglycolic acid in the tissue thickness compensator may differ by at least 10 weight percent. In various embodiments, a concentration of polyglycolic acid in the pressure sensitive adhesive and a concentration of polyglycolic acid in the tissue thickness compensator may differ by at least 15 weight percent. In various embodiments, a concentration of polyglycolic acid in the pressure sensitive adhesive and a concentration of polyglycolic acid in the tissue thickness compensator may differ by at least 20 weight percent. In various embodiments, a concentration of polyglycolic acid in the pressure sensitive adhesive and a concentration of polyglycolic acid in the tissue thickness compensator may differ by 1 to 20 weight percent. In various embodiments, a concentration of polyglycolic acid in the pressure sensitive adhesive and a concentration of polyglycolic acid in the tissue thickness compensator may differ by 15 to 20 weight percent. In various embodiments, a concentration of polyglycolic acid in the pressure sensitive adhesive and a concentration of polyglycolic acid in the tissue thickness compensator may differ by 16 weight percent. In various embodiments, a concentration of polyglycolic acid in the pressure sensitive adhesive may differ from a concentration of polyglycolic acid in the tissue thickness compensator as described above such that a concentration of polyglycolic acid in the pressure sensitive adhesive may be one of greater than and less than a concentration of polyglycolic acid in the tissue thickness compensator.

In various embodiments, a concentration of ε-caprolactone in the pressure sensitive adhesive and a concentration of ε-caprolactone in the tissue thickness compensator may differ by at least 1 mole percent. In various embodiments, a concentration of ε-caprolactone in the pressure sensitive adhesive and a concentration of ε-caprolactone in the tissue thickness compensator may differ by at least 5 mole percent. In various embodiments, a concentration of ε-caprolactone in the pressure sensitive adhesive and a concentration of ε-caprolactone in the tissue thickness compensator may differ by at least 10 mole percent. In various embodiments, a concentration of ε-caprolactone in the pressure sensitive adhesive and a concentration of ε-caprolactone in the tissue thickness compensator may differ by at least 15 mole percent. In various embodiments, a concentration of ε-caprolactone in the pressure sensitive adhesive and a concentration of ε-caprolactone in the tissue thickness compensator may differ by 1 to 15 mole percent. In various embodiments, a concentration of ε-caprolactone in the pressure sensitive adhesive and a concentration of ε-caprolactone in the tissue thickness compensator may differ by 10 to 15 mole percent. In various embodiments, a concentration of ε-caprolactone in the pressure sensitive adhesive and a concentration of ε-caprolactone in the tissue thickness compensator may differ by 14 mole percent. In various embodiments, a concentration of ε-caprolactone in the pressure sensitive adhesive may differ from a concentration of ε-caprolactone in the tissue thickness compensator as described above such that a concentration of ε-caprolactone in the pressure sensitive adhesive may be one of greater than and less than a concentration of ε-caprolactone in the tissue thickness compensator.

In various embodiments, a concentration of polyglycolic acid in the pressure sensitive adhesive and a concentration of polyglycolic acid in the tissue thickness compensator may differ by at least 1 mole percent. In various embodiments, a concentration of polyglycolic acid in the pressure sensitive adhesive and a concentration of polyglycolic acid in the tissue thickness compensator may differ by at least 5 mole percent. In various embodiments, a concentration of polyglycolic acid in the pressure sensitive adhesive and a concentration of polyglycolic acid in the tissue thickness compensator may differ by at least 10 mole percent. In various embodiments, a concentration of polyglycolic acid in the pressure sensitive adhesive and a concentration of polyglycolic acid in the tissue thickness compensator may differ by at least 15 mole percent. In various embodiments, a concentration of polyglycolic acid in the pressure sensitive adhesive and a concentration of polyglycolic acid in the tissue thickness compensator may differ by at least 20 mole percent. In various embodiments, a concentration of polyglycolic acid in the pressure sensitive adhesive and a concentration of polyglycolic acid in the tissue thickness compensator may differ by 1 to 20 mole percent. In various embodiments, a concentration of polyglycolic acid in the pressure sensitive adhesive and a concentration of polyglycolic acid in the tissue thickness compensator may differ by 15 to 20 mole percent. In various embodiments, a concentration of polyglycolic acid in the pressure sensitive adhesive and a concentration of polyglycolic acid in the tissue thickness compensator may differ by 16 mole percent. In various embodiments, a concentration of polyglycolic acid in the pressure sensitive adhesive may differ from a concentration of polyglycolic acid in the tissue thickness compensator as described above such that a concentration of polyglycolic acid in the pressure sensitive adhesive may be one of greater than and less than a concentration of polyglycolic acid in the tissue thickness compensator.

In various embodiments, the polymeric compositions may comprise additional optional components to further improve the processability of the compositions and/or mechanical characteristics and other characteristics, such as tackiness, resistance to ageing by light, oxygen and heat, and visual appearance, for example. Such optional components may include other copolymers that can be included in the polymeric composition to achieve a desired property, such as, for example, to increase adhesion or compatibility with the substrate. In various embodiments, the additional optional components may include, but are not limited to, other polymers or copolymers, fillers, cross-linkers, tackifiers, plasticizers, pigments, dyes, antioxidants, colorants and stabilizers. In various embodiments, the polymeric composition may comprise a tackifier included in a finite amount of at least 0.1, at least 2, or at least 5 up to 10, 25, or 50 weight percent, based on the total weight of polymeric composition. In various embodiments, the polymeric composition may comprise a plasticizer included in a finite amount of at least 0.1, at least 2, or at least 5 up to 10, 25, or 50 weight percent, based on the total weight of polymeric composition.

In various embodiments, the flowable attachment portion may comprise a flowable (plastically deformable) polymeric composition. In various embodiments, the flowable polymeric composition may normally tacky at room temperature (e.g., 20° C. to 25° C.) and releasably adhere to a variety of substrates using only moderate pressure, such as finger pressure, for example, to form the bond to attach to the substrate. In various embodiments, the flowable polymeric composition may be a solid up to 40° C., up to 45° C., up to 50° C., up to 55° C., and/or up to 60° C. In various embodiments, the flowable polymeric composition may melt without degradation at greater than 40° C., greater than 45° C., greater than 50° C., greater than 55° C., greater than 60° C., and/or greater than 120° C. In various embodiments, the flowable polymeric composition may melt without degradation up to 600° C., up to 500° C., up to 400° C., up to 300° C., up to 240° C., and/or up to 180° C. In various embodiments, the flowable polymeric composition may melt without degradation from 40.1° C. to 600° C., 120° C. to 240° C., and/or 180° C.

In various embodiments, the flowable polymeric composition may be characterized by an inherent viscosity in a 0.1 g/dL hexafluoroisopropanol solution at 25° C. from 0.6 to 4.0 dL/g, 0.8 to 3.2 g/dL, 1.0 to 2.4 g/dL, and/or 1.6 g/dL. In various embodiments, the flowable polymeric composition may not comprise a gel.

In various embodiments, the flowable polymeric composition may be characterized by one or more of the following properties: a percent crystallinity of less than about 25 percent, a percent crystallinity of less than about 15 percent, and a percent crystallinity from 15 to 25 percent; a percent elongation greater than about 200, a percent elongation greater than about 500, and a percent elongation from about 200 to about 500; and a modulus less than about 40,000 psi, a modulus less than about 20,000 psi, and a modulus from about 20,000 to about 40,000 psi.

In various embodiments, the flowable attachment portion may comprise one of a strip, tape, roll of tape, sheet, and film attached to a surface and/or edge of the tissue thickness compensator. In various embodiments, the flowable attachment portion may comprise a pressure sensitive tape comprising an adhesive and a backing. In various embodiments, the backing may comprise one of a flexible backing material and an inflexible backing material. Examples of flexible backing materials include, but are not limited to plastic films such as polypropylene, polyethylene, polyvinyl chloride, polyester (polyethylene terephthalate), polycarbonate, polymethyl(meth)acrylate (PMMA), cellulose acetate, cellulose triacetate, and ethyl cellulose. Foam backings may be used. Examples of inflexible backing materials include, but are not limited to, metal, metalized polymeric film, indium tin oxide coated glass and polyester, PMMA plate, polycarbonate plate, glass, or ceramic sheet material. In various embodiments, the pressure sensitive tape may comprise a release liner. In various embodiments, the pressure sensitive tape may be applied by removing the release liner thereby exposing the adhesive.

In various embodiments, the flowable attachment portion may be applied to the tissue thickness compensator using conventional coating techniques, such as, for example, roller coating, flow coating, dip coating, spin coating, spray coating, knife coating, and die coating. In various embodiments, the flowable attachment portion may have an initial thickness from approximately 1.25 mm to approximately 1.50 mm, for example. In some embodiments, the flowable attachment portion may have an initial thickness from approximately 0.5 mm to approximately 0.75 mm, for example. In various embodiments, the flowable attachment portion may have a final thickness of at least 0.25 mm, for example, when pressure is applied thereto.

In various embodiments, referring to FIG. 263, the flowable attachment portion 30000 may comprise a continuous strip centrally disposed in a longitudinal direction along a portion of the central axis of the tissue thickness compensator 30010. The width of the strip may be at least 1 mm, for example. The width of the strip can be between approximately 0.5 mm and approximately 1.5 mm, for example. The width of the strip can be between approximately 1.0 mm and approximately 1.25 mm, for example. The first position of the flowable attachment portion 30000 may be spaced away from the anvil 30020 and the first profile of the flowable attachment portion 30000 may comprise a neutral (original) profile. As shown in FIG. 264, the flowable attachment portion 30000 may be aligned with a void 30025 in the anvil 30020, such as a centrally disposed slot, for example. As shown in FIG. 265, the flowable attachment portion 30000 may flow into the slot 30025 and come into securing engagement with the anvil 30020 when a threshold level of pressure is applied to the flowable attachment portion 30000. The flowable attachment portion 30000 may fill at least a portion of the slot 30025 such that the flowable attachment portion 30000 may take the shape of the slot 30025. The second position of the flowable attachment portion 30000 may contact the anvil 30020 and the second profile of the flowable attachment 30000 portion may comprise a complementary profile to the slot 30025. The flowable attachment portion 30000 may releasably attach the tissue thickness compensator 30010 to the anvil 30020.

In various embodiments, referring to FIG. 266, the flowable attachment portion 30000 may comprise two continuous strips parallel to each other and disposed in a longitudinal direction along a portion of the tissue thickness compensator 30010. The width of the strip may be at least 1 mm, for example. The width of the strip can be between approximately 0.5 mm and approximately 1.5 mm, for example. The width of the strip can be between approximately 1.0 mm and approximately 1.25 mm, for example. The two discrete strips may be spaced apart from the central axis and side edges of the tissue thickness compensator 30010. The width of a gap between the each strip may be at least 1 mm, for example, and the width of a gap between the each strip and side edge may be at least 1 mm, for example. The adhesive to empty space ratio may be between approximately 1:4 and approximately 1:2, for example. The adhesive to empty space ratio may be at least 1:10, for example. In various circumstances, the adhesive to empty space ratio may be zero. A constant layer across the entire surface may be desirable, in some circumstances. The first position of the flowable attachment portion 30000 may be spaced away from the anvil 30020 and the first profile of the flowable attachment portion 30000 may comprise a neutral (original) profile. As shown in FIG. 267, the flowable attachment portion 30000 may be aligned with the staple forming cavities 30030, for example. As shown in FIG. 268, the flowable attachment portion 30000 may flow into the staple cavities 30030 and come into securing engagement with the anvil 30020 when a threshold level of pressure, such as finger pressure, for example, is applied to the flowable attachment portion 30000. The flowable attachment portion 30000 may fill at least a portion of the staple cavity 30030 such that the flowable attachment portion 30000 may take the shape of the staple cavity 30030. At least a portion of the staple cavities 30030 may be free of the flowable attachment portion 30000. The second position of the flowable attachment portion 30000 may contact the anvil 30020 and the second profile of the flowable attachment portion 30000 may comprise a complementary profile to the staple cavities 30030. The flowable attachment portion 30000 may releasably attach the tissue thickness compensator 30000 to the anvil 30020.

In various embodiments, referring now to FIGS. 269-273, a staple cartridge 30100 comprising a support portion 30102 and a tissue thickness compensator 30110 can be loaded into a staple cartridge channel with a staple cartridge applicator 30140, for example. In various embodiments, an applicator 30140 can be configured to position an upper tissue thickness compensator 30110 relative to an anvil 30120 in addition to positioning a staple cartridge 30100 within a staple cartridge channel. The applicator 30140 can comprise latch arms 30141 which can be releasably engaged with lock projections extending from a support portion 30102 of the staple cartridge 30100 such that the applicator 30140 can be maintained in position over a tissue thickness compensator 30110 of the staple cartridge 30100. In various embodiments, the upper tissue thickness compensator 30110 can be removably attached to the applicator 30140 such that the anvil 30120 of a surgical instrument can be closed onto the applicator 30140, engage the tissue thickness compensator 30110, and detach from the tissue thickness compensator 30110 from the applicator 30140. In various embodiments, the tissue thickness compensator 30110 and/or the anvil 30120 can comprise one or more retention features which can be configured to releasably hold the tissue thickness compensator 30110 to the anvil. In various embodiments, the retention features may comprise an adhesive sheet and/or an adhesive tab 30112.

Figure 271:
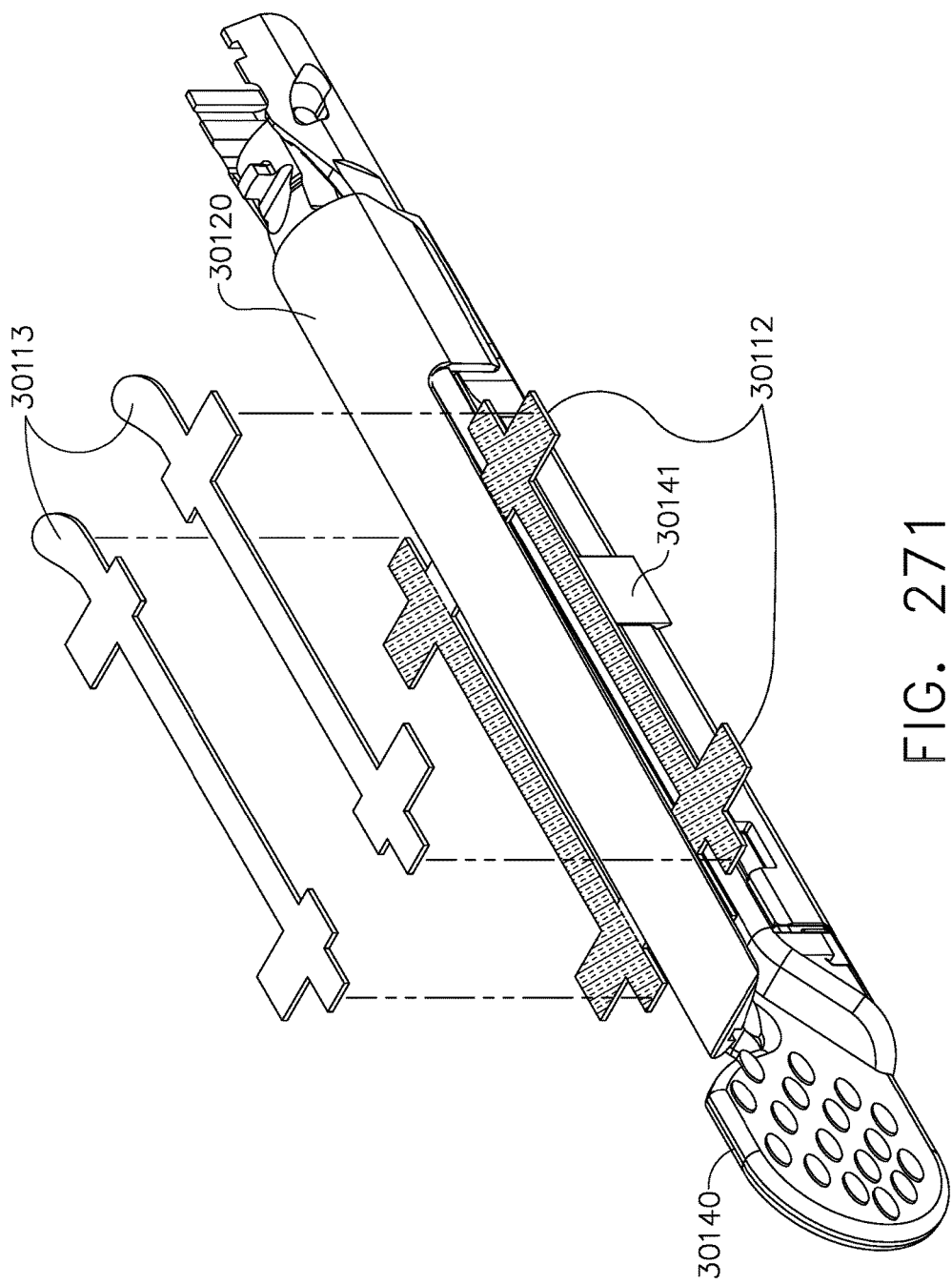
Figure 272:
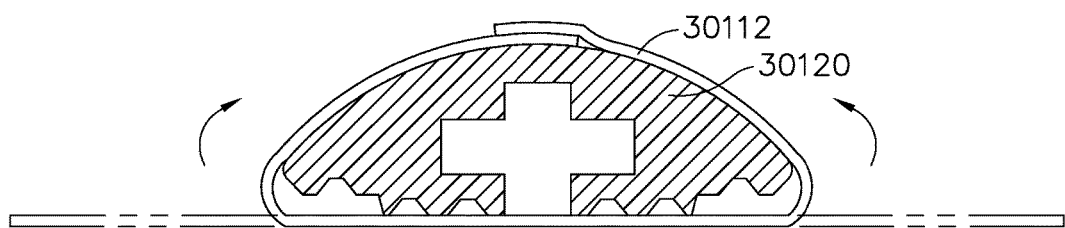
Figure 273:
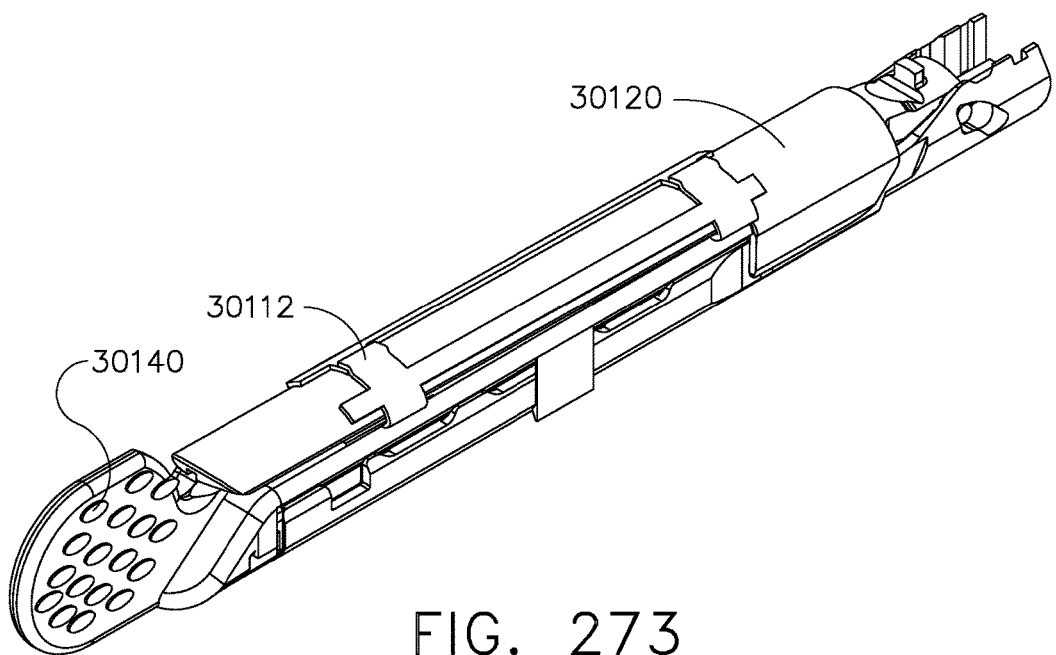

In various embodiments, the adhesive sheet and/or an adhesive tab may be integrally formed from a portion of the tissue thickness compensator 30110. In various embodiments, the tissue thickness compensator 30110 may comprise at least one adhesive tab 30112 along an edge of the tissue thickness compensator 30110. The adhesive tab 30112 may comprise a release liner 30113. Referring to FIG. 271, the anvil 30120 may be moved to a closed position to engage the tissue thickness compensator 30110. The release liner 30113 may be removed to expose an adhesive surface of the adhesive tab 30112. Referring to FIGS. 272 and 273, a first end of the adhesive tab 30112 may be secured to the anvil and a second end of the adhesive tab 30112 may be secured to the anvil to releasably attach the tissue thickness compensator 30110 to the anvil. The adhesive tab 30112 may be pulled distally to detach the tissue thickness compensator 30110 from the applicator 30140. Thereafter, the anvil and the staple cartridge 30100 can be positioned relative to the tissue that is to be stapled and/or incised. The clinician may pull the adhesive tab 30112 to detach the tissue thickness compensator 30110 from the anvil.

Referring to FIGS. 284-288, in various embodiments, the tissue thickness compensator 30210 may comprise at least one adhesive tab 30212 along a distal edge of the tissue thickness compensator 30210. The adhesive tab 30212 may comprise a release liner 30213. As described herein, a staple cartridge applicator 30240 can be configured to position an upper tissue thickness 30210 compensator relative to an anvil 30220. The release liner 30213 may be removed to expose an adhesive surface of the adhesive tab 30212. The adhesive tab 30212 may be folded over and secured to the anvil 30220 to releasably attach the tissue thickness compensator 30210 to the anvil 30220. The adhesive tab 30212 may be pulled distally to detach the tissue thickness compensator 30210 from the applicator 30240. Thereafter, the anvil 30220 and the staple cartridge 30200 can be positioned relative to the tissue that is to be stapled and/or incised. Referring to FIGS. 289-290, in use, a staple-deploying sled can be advanced distally through the staple cartridge by a firing member that can advance a knife edge 30211 through the tissue thickness compensator 30210 in order to incise at least a portion of the adhesive tab 30212 and progressively detach the tissue thickness compensator 30210 from the anvil 30220. The clinician may pull the remainder of the adhesive tab 30212 from the anvil 30220 before reloading a new staple cartridge 30200.

Figure 274:
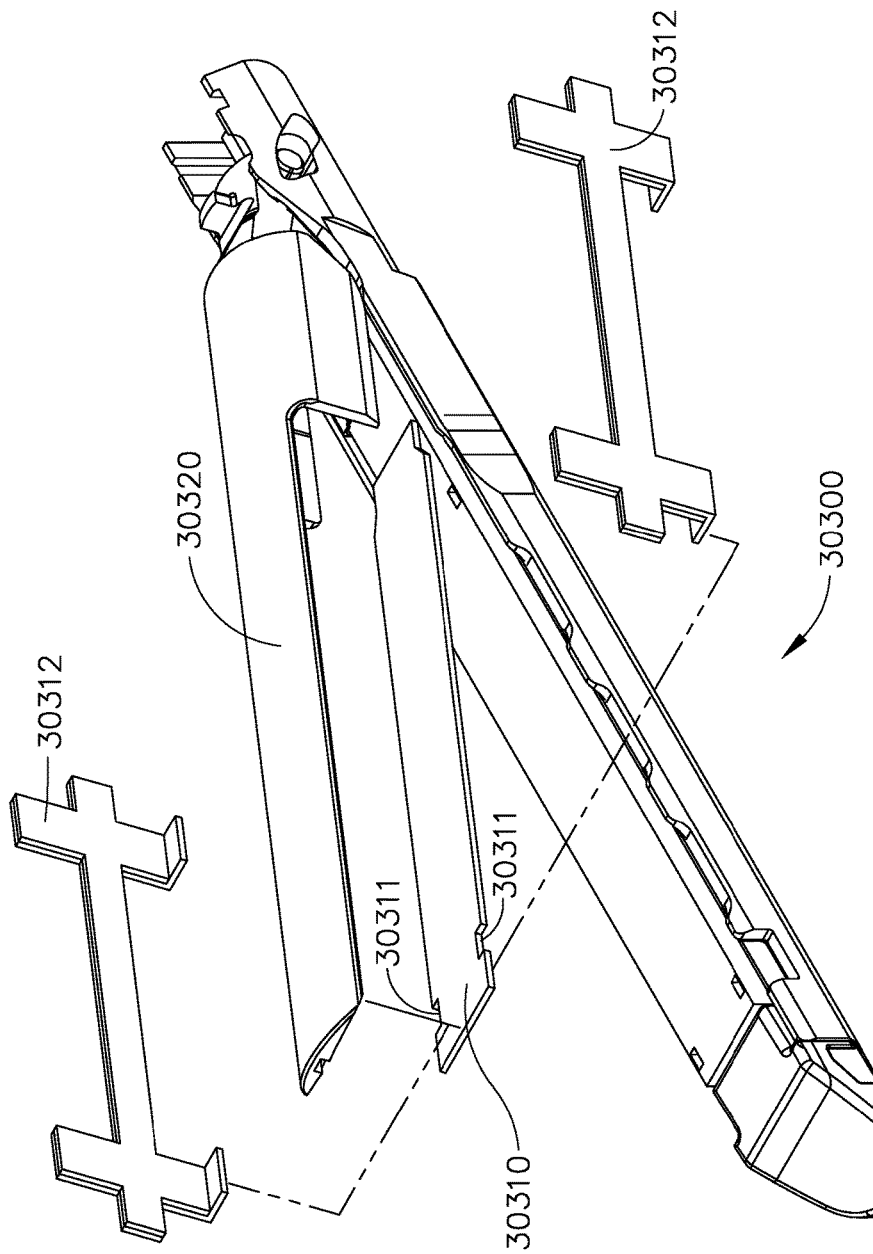
Figure 275:
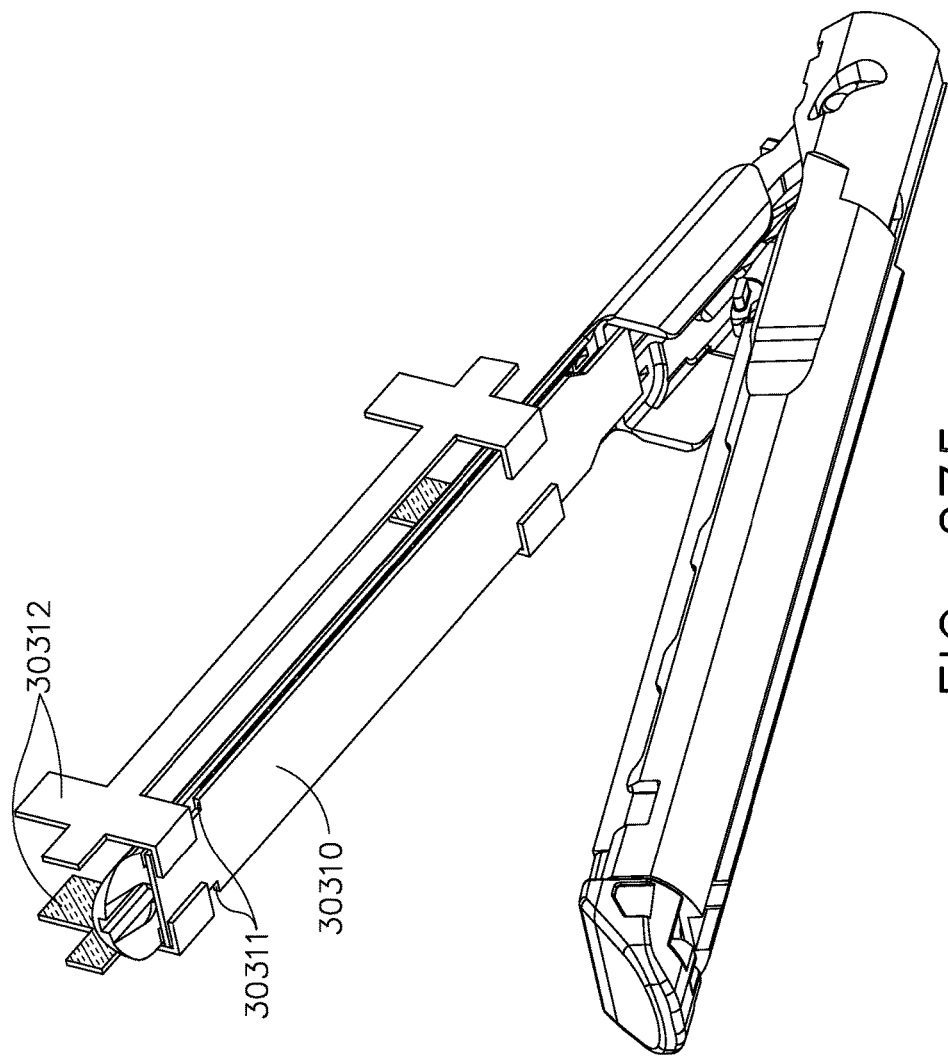
Figure 276:
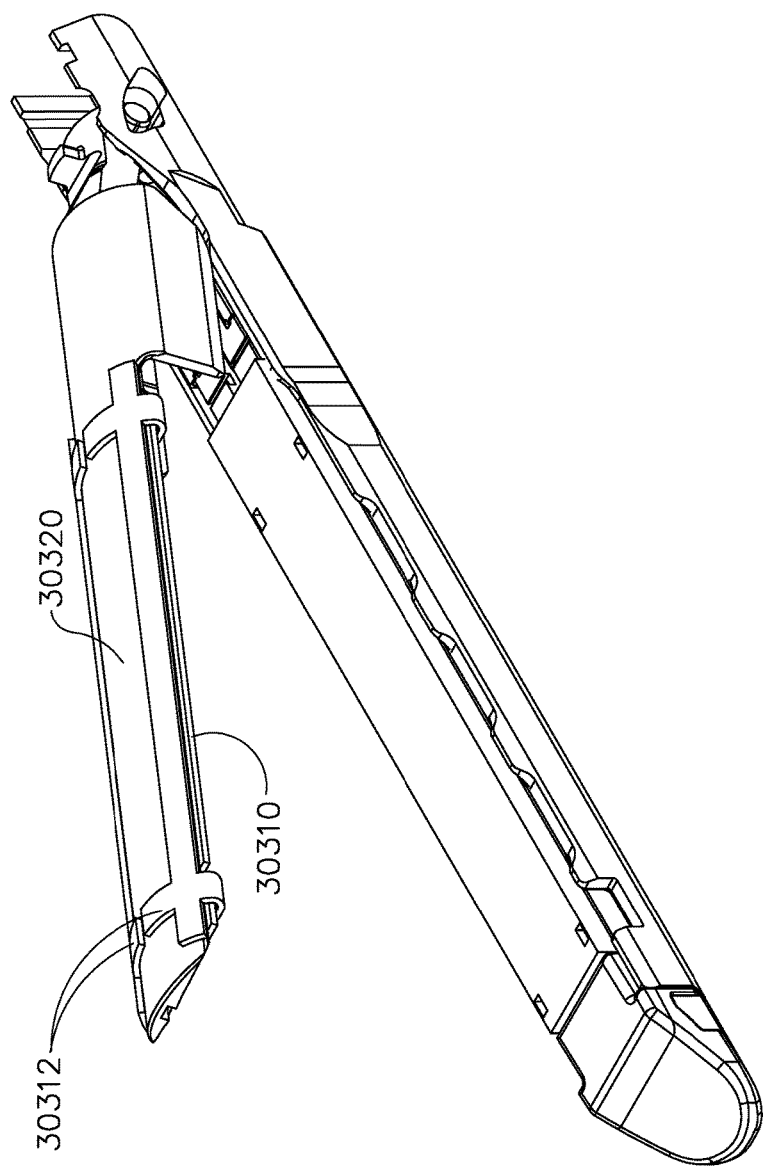
Figure 277:
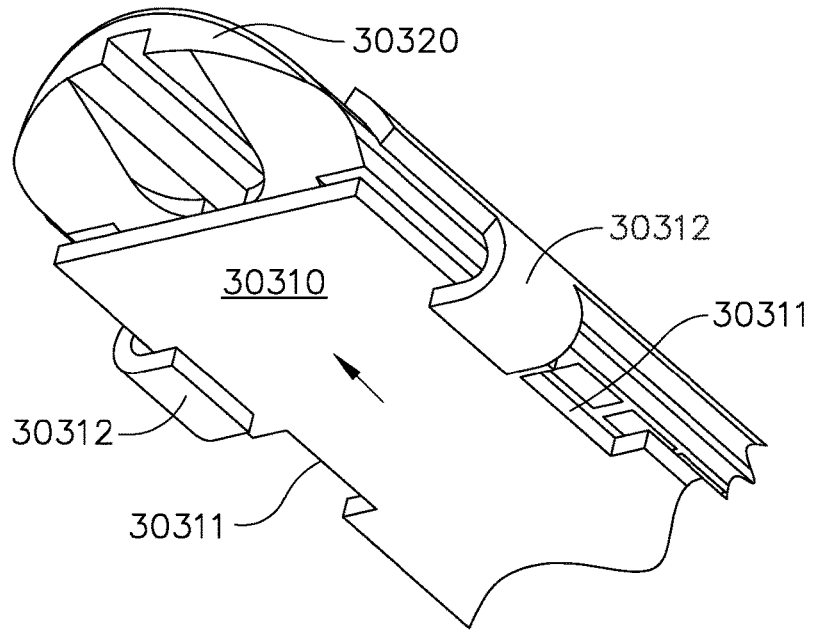

In various embodiments, the adhesive sheet and/or an adhesive tab may be separate from the tissue thickness compensator. Referring to FIGS. 274-276, in at least one embodiment, an adhesive tab 30312 (see also FIGS. 288 and 292) may be provided between the staple cartridge 30300 and tissue thickness compensator 30310. The tissue thickness compensator 30310 may comprise a notch 30311 configured and dimensioned coordinate with the adhesive tab 30312 to releasably retain the tissue thickness compensator 30310 to the anvil 30320. A first end of the adhesive tab 30312 may be secured to the tissue thickness compensator 30310 adjacent the notch 30311 and a second end of the adhesive tab 30312 may be secured to the anvil 30320. As shown in FIG. 277, the adhesive tab 30312 is not engaging the notch 30311. Thereafter, the anvil 30320 and the staple cartridge 30300 can be positioned relative to the tissue T that is to be stapled and/or incised.

Figure 278:
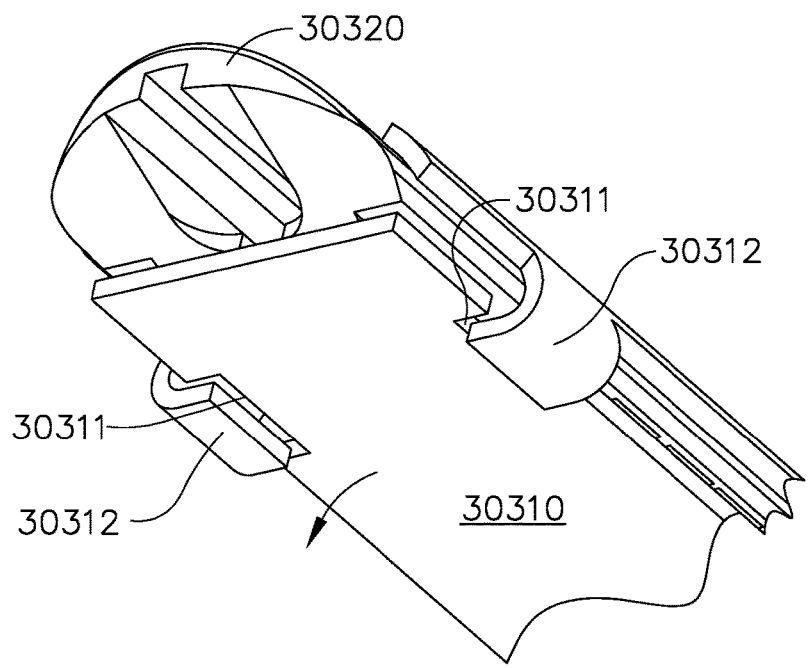
Figure 279:
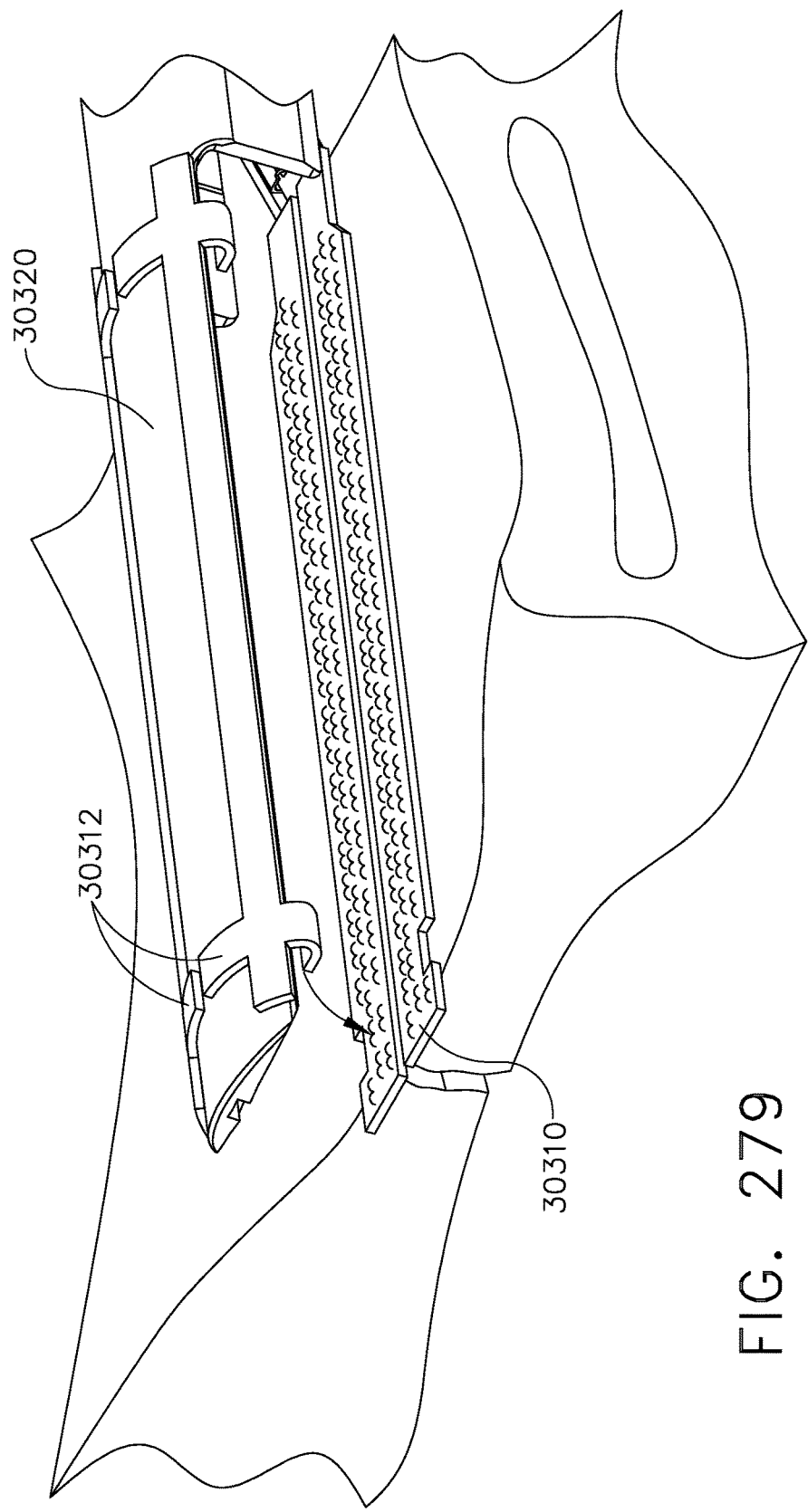
Figure 280:
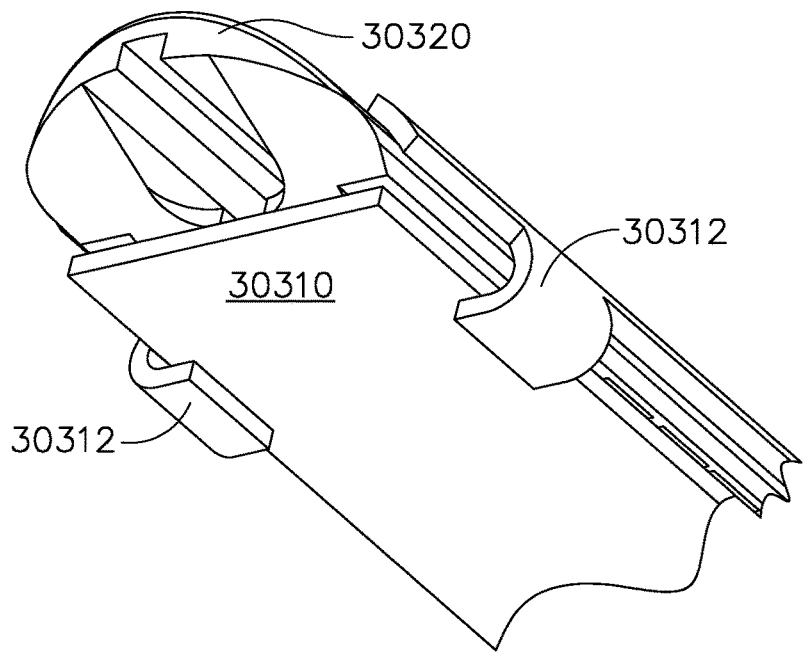
Figure 281:
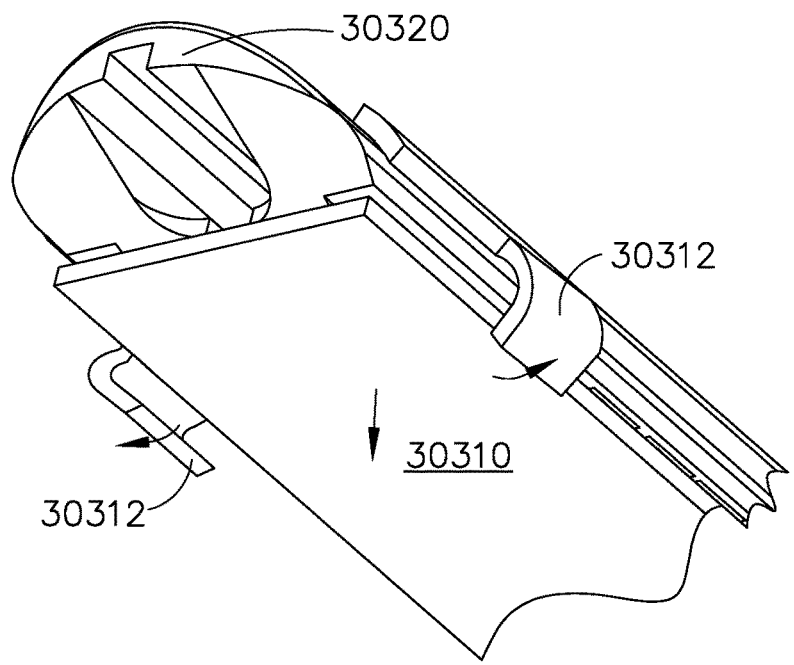
Figure 282:
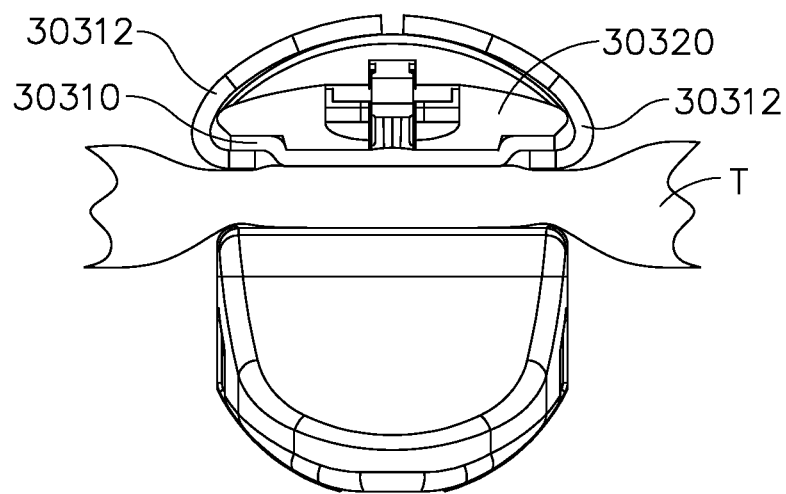
Figure 283:
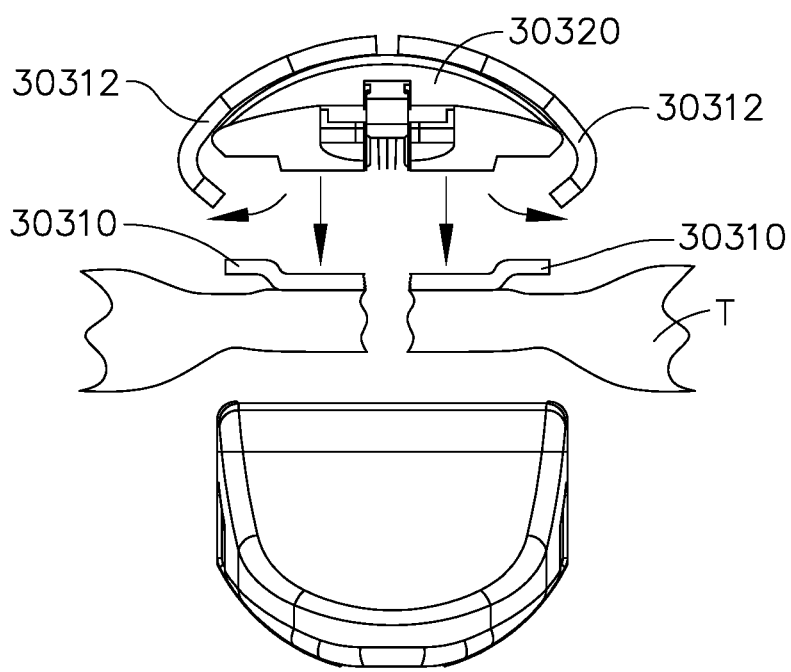
Figure 284:
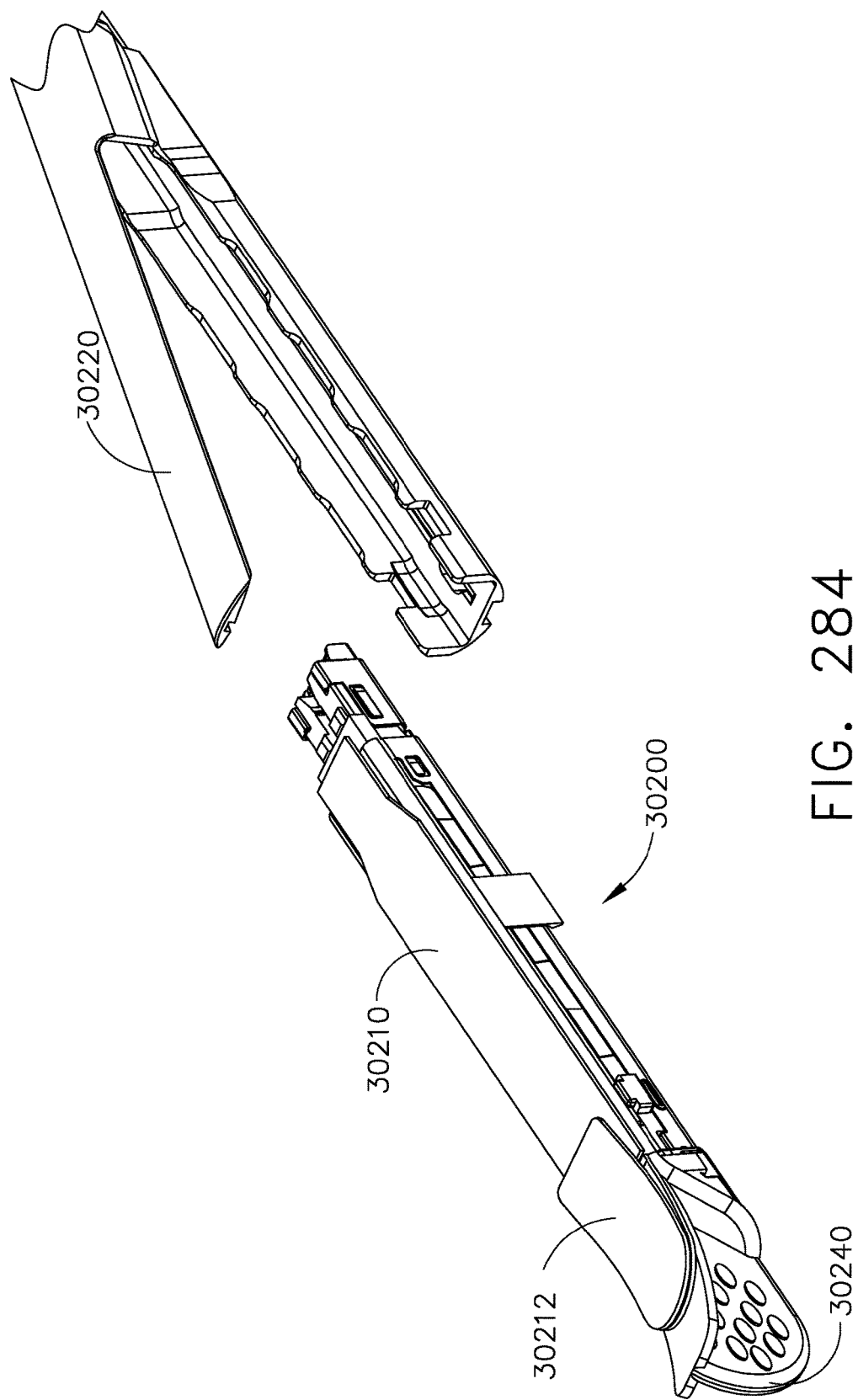
Figure 285:
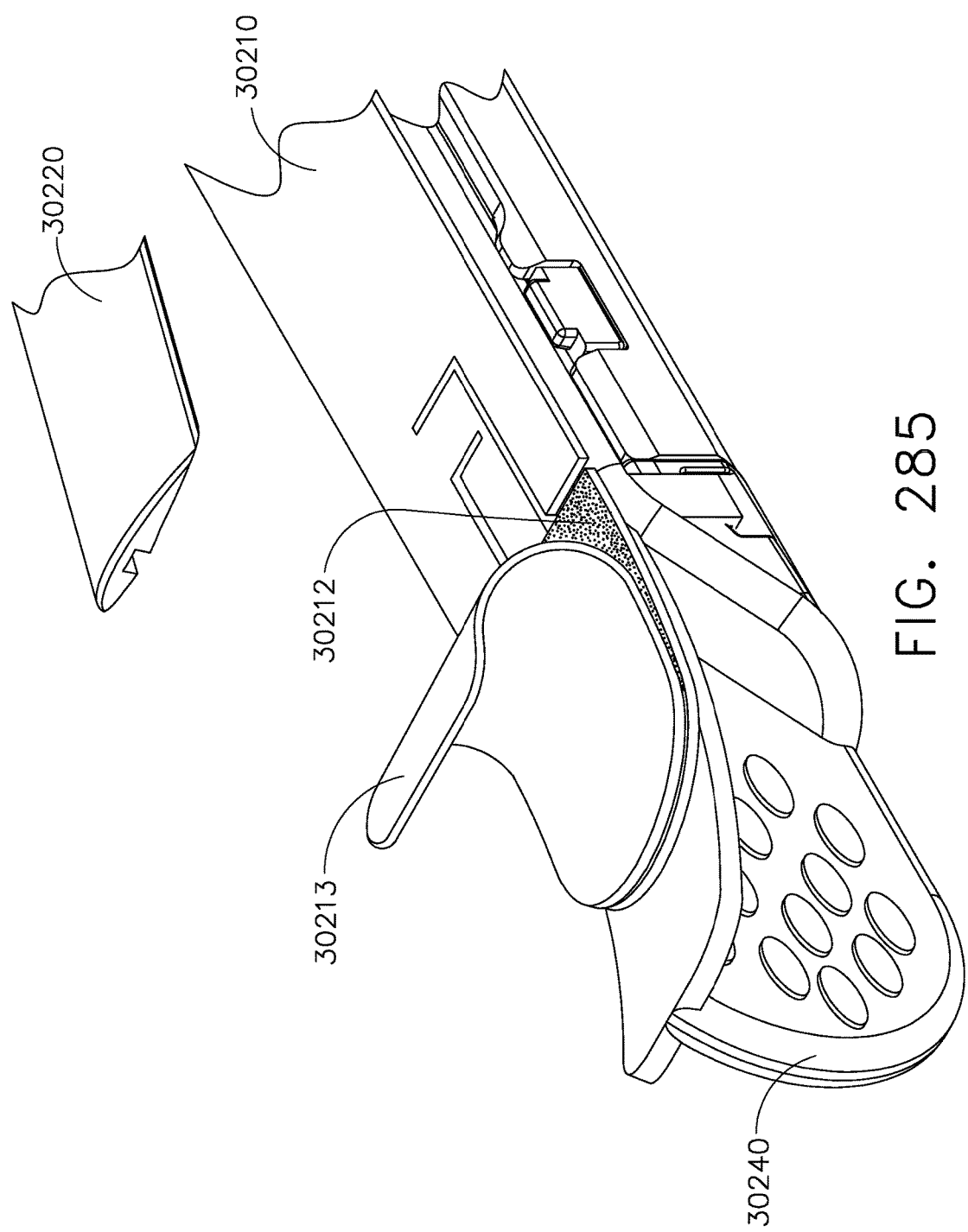
Figure 288:
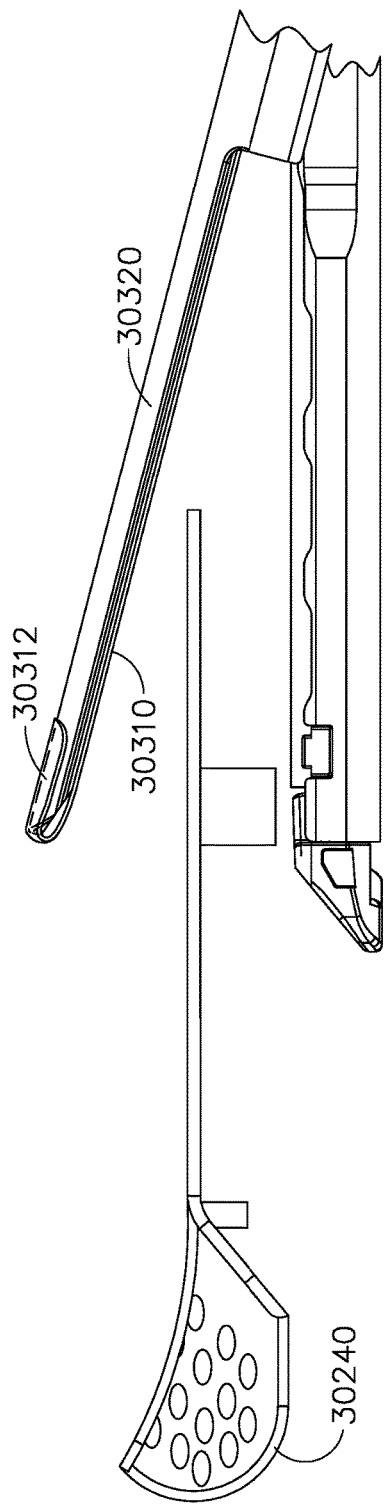
Figure 292:
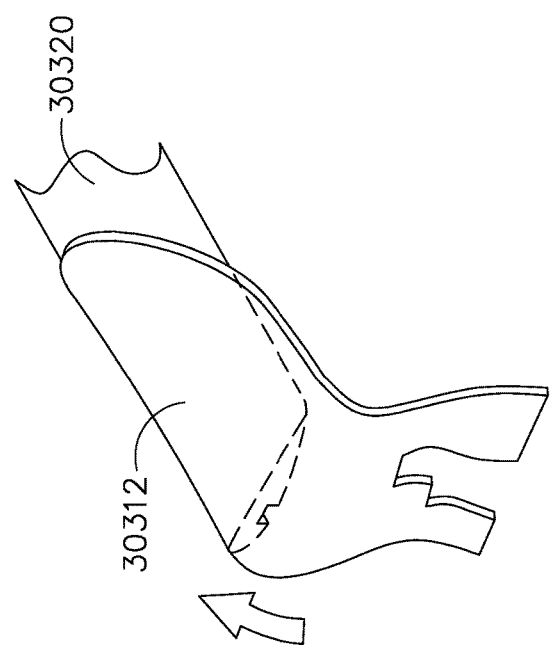

As described above, in use, a staple-deploying sled can be advanced distally through the staple cartridge by a firing member in order to eject the staples from the staple cartridge, as outlined above. As the staples are deformed, each staple can capture a portion of the tissue thickness compensator against the top surface of the tissue. At the same time, the firing member can advance a knife edge through the tissue thickness compensator 30310, wherein, in at least one embodiment, the knife edge can be advanced through the tissue thickness compensator 30310 to move the tissue thickness compensator 30310 distally and align the adhesive tab 30312 and notch 30311, as shown in FIGS. 277-279, in order to incise the tissue thickness compensator 30310 and detach the tissue thickness compensator 30310 from the anvil 30320. In various embodiments, as the staples are moved from their unfired positions to their fired positions by the staple drivers, as discussed above, the tissue thickness compensator 30310 lacking a notch may move downwardly, as shown in FIGS. 280 and 281, to disengage the adhesive tabs 30312 and detach the tissue thickness compensator 30310 from the anvil 30320. After the staples have been deployed, the anvil 30320 can be re-opened and moved away from the implanted tissue thickness compensator 30310, as shown in FIG. 283. The reader will appreciate, upon comparing FIGS. 282 and 283, that the tissue thickness compensator 30310 can be fastened to the tissue T and incised by the cutting member, as discussed above.

In various embodiments, the flowable attachment portion may be applied by removing the first release liner from the first adhesive tab thereby exposing the flowable attachment portion comprising a pressure sensitive adhesive, for example. The first adhesive tab may be rolled down or otherwise pressed onto the outer surface of the substrate. Next, the second release liner may be removed from the second adhesive tab thereby exposing the PSA. The second adhesive tab may be pressed onto the outer surface of the substrate and/or first adhesive tab. Once the PSA has been applied to the tissue thickness compensator, it is placed in contact with the staple cartridge and/or anvil. The PSA may secure the tissue thickness compensator to the substrate.

Various embodiments described herein are described in the context of staples removably stored within staple cartridges for use with surgical stapling instruments. In some circumstances, staples can include wires which are deformed when they contact an anvil of the surgical stapler. Such wires can be comprised of metal, such as stainless steel, for example, and/or any other suitable material. Such embodiments, and the teachings thereof, can be applied to embodiments which include fasteners removably stored with fastener cartridges for use with any suitable fastening instrument.

Various embodiments described herein are described in the context of tissue thickness compensators attached to, and/or for use with, staple cartridges and/or fastener cartridges. Such tissue thickness compensators can be utilized to compensate for variations in tissue thickness from one end of a staple cartridge to another, or for variations in tissue thickness captured within one staple, or fastener, as compared to another. Such tissue thickness compensators can also be utilized to compensate for variations in tissue thickness from one side of a staple cartridge to another. Such embodiments, and the teachings thereof, can be applied to embodiments which include a layer, or layers, of material attached to, and/or for use with, staple cartridges and/or fastener cartridges. A layer can include buttress material.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A staple cartridge, comprising:
   a cartridge body comprising a laterally sloped deck and staple cavities;
   staples at least partially positioned within said staple cavities;
   a layer attached to said deck, wherein said layer at least partially extends over said staple cavities, and wherein said layer is positioned adjacent to said laterally sloped deck;
   a clamping mechanism configured to releasably secure said layer to said cartridge body, said clamping mechanism comprising:
      a clamp portion; and
      a retention portion moveable between an engaged configuration wherein said retention portion is engaged with said layer and positioned above said deck and a disengaged configuration wherein said retention portion is disengaged from said layer and positioned lower than said deck; and
   a firing assembly movable through said cartridge body to eject said staples from said staple cavities during a firing stroke of said firing assembly, wherein said firing assembly is configured to engage said retention portion to transition said retention portion into said disengaged configuration during said firing stroke.

2. The staple cartridge of claim 1, wherein said firing stroke comprises an end position, wherein said firing assembly is configured to eject all of said staples from said staple cavities before reaching said end position, and wherein said firing assembly is configured to release said layer before reaching said end position.

3. The staple cartridge of claim 1, wherein said firing stroke comprises an end position, wherein said firing assembly is configured to eject all of said staples from said staple cavities before reaching said end position, and wherein said firing assembly is configured to release said layer upon reaching said end position.

4. The staple cartridge of claim 1, wherein said staples comprise different unformed heights, and wherein said staples comprise different formed heights.

5. The staple cartridge of claim 1, wherein said layer comprises a tissue thickness compensator.

6. A staple cartridge, comprising:
- a cartridge body comprising a laterally sloped deck and staple cavities;
- staples at least partially positioned within said staple cavities;
- a layer attached to said deck, wherein said layer at least partially extends over said staple cavities, and wherein said layer is positioned adjacent said laterally sloped deck;
- a retention pin engaged with said layer to secure said layer to said cartridge body, wherein said retention pin is moveable between a first configuration wherein said retention pin is engaged with said layer and positioned above said deck and a second configuration wherein said retention pin is separated from said layer and positioned below said deck; and
- a firing member movable through said cartridge body to eject said staples from said staple cavities during a firing stroke of said firing member, wherein said firing member is configured to engage said retention pin to transition said retention pin into said second configuration during said firing stroke to release said layer from said cartridge body.

7. The staple cartridge of claim 6, wherein said firing stroke comprises an end position, wherein said firing member is configured to eject all of said staples from said staple cavities before reaching said end position, and wherein said firing member is configured to release said layer before reaching said end position.

8. The staple cartridge of claim 6, wherein said firing stroke comprises an end position, wherein said firing member is configured to eject all of said staples from said cartridge body before reaching said end position, and wherein said firing member is configured to release said layer upon reaching said end position.

9. The staple cartridge of claim 6, wherein said staples comprise different unformed heights, and wherein said staples comprise different formed heights.

10. The staple cartridge of claim 6, wherein said layer comprises a tissue thickness compensator.

11. The staple cartridge of claim 6, further comprising a biasing member configured to bias said retention pin into engagement with said layer, and wherein said firing member is configured to overcome said biasing member during said firing stroke.

12. An end effector of a surgical instrument, said end effector comprising:
- an anvil; and
- a staple cartridge, comprising:
  - a cartridge body comprising a laterally stepped deck and staple cavities;
  - staples at least partially positioned within said staple cavities;
  - a layer attached to said deck, wherein said layer at least partially extends over said staple cavities;
  - an anchor configured to releasably secure said layer to said cartridge body, said anchor comprising:
    - a clamp portion; and
    - a retention portion moveable between an engaged configuration wherein said retention portion is engaged with said layer and positioned above said deck and a disengaged configuration wherein said retention portion is disengaged from said layer and positioned lower than said deck; and
  - a firing member movable through said cartridge body to eject said staples from said staple cavities during a firing stroke of said firing member, wherein said anchor is engageable by said firing member during said firing stroke to release said layer such that said firing member is configured to transition said retention portion into said disengaged configuration during said firing stroke.

13. The end effector of claim 12, wherein said staple cartridge is movable relative to said anvil to capture tissue therebetween.

14. The end effector of claim 13, wherein said staples comprise different unformed heights, and wherein said staples comprise different formed heights.

* * * * *